US006818447B1

(12) United States Patent
Pavco et al.

(10) Patent No.: US 6,818,447 B1
(45) Date of Patent: Nov. 16, 2004

(54) METHOD AND REAGENT FOR THE TREATMENT OF DISEASES OR CONDITIONS RELATED TO LEVELS OF VASCULAR ENDOTHELIAL GROWTH FACTOR RECEPTOR

(75) Inventors: Pamela Pavco, Lafayette, CO (US); James McSwiggen, Boulder, CO (US); Daniel Stinchcomb, Boulder, CO (US); Jaime Escobedo, Alamo, CA (US)

(73) Assignee: Sirna Therapeutics, Inc., Boulder, CO (US)

( * ) Notice: Subject to any disclaimer, the term of this patent is extended or adjusted under 35 U.S.C. 154(b) by 159 days.

(21) Appl. No.: 09/685,664

(22) Filed: Oct. 10, 2000

Related U.S. Application Data

(63) Continuation of application No. 08/584,040, filed on Jan. 11, 1996, now Pat. No. 6,346,398.
(60) Provisional application No. 60/005,974, filed on Oct. 26, 1995.

(51) Int. Cl.$^7$ .......................... C12N 5/02; C12N 15/00; C12P 19/34; C07H 21/04
(52) U.S. Cl. .................. 435/325; 536/24.5; 435/91.31; 435/320.1
(58) Field of Search .............................. 536/23.1, 24.5, 536/24.3, 24.33, 24.31; 435/6, 325, 375, 320.1, 91.31; 514/44

(56) References Cited

U.S. PATENT DOCUMENTS

| 4,987,071 A | 1/1991 | Cech et al. |
|---|---|---|
| 5,334,711 A | 8/1994 | Sproat et al. |
| 5,359,051 A | 10/1994 | Cook et al. |
| 5,496,698 A | * 3/1996 | Draper et al. |
| 5,851,999 A | * 12/1998 | Ullrich et al. |

FOREIGN PATENT DOCUMENTS

| EP | 0360257 | 3/1990 |
|---|---|---|
| WO | WO 9103162 | 3/1991 |
| WO | WO 9207065 | 9/1991 |
| WO | WO 9323569 | 4/1993 |
| WO | WO 9315187 | 8/1993 |
| WO | WO 9323057 | 11/1993 |
| WO | WO 9402595 | 2/1994 |
| WO | WO 9411499 | 5/1994 |
| WO | WO9411499 | 5/1994 |
| WO | WO 9421679 | 9/1994 |
| WO | WO9421791 | 9/1994 |
| WO | WO9504142 | 2/1995 |
| WO | WO 9504142 | 2/1995 |
| WO | WO 9504818 | 2/1995 |
| WO | WO 9513380 | 5/1995 |
| WO | WO 9521868 | 8/1995 |
| WO | WO 9523225 | 8/1995 |
| WO | WO9700957 | 1/1997 |
| WO | WO9904819 | 2/1999 |

OTHER PUBLICATIONS

Andrea D. Branch, TIBS 32—Feb. 1998, pp. 45–50.*
Jim Haseloff et al., NATURE, vol. 334, Aug. 18, 1988, pp. 585–591.*
Usman et al., "Chemical modification of hammerhead ribozymes: activity and nuclease resistance," *Nucleic Acids Syposium Series* 31:163–164 (1994).
International Search Report, PCT/US96/17480.
Aiello et al., "Vascular Endothelial Growth Factor in Ocular Fluid of Patients with Diabetic Retinopathy and Other Retinal Disorders" *New Engl. J. Med.* 331:1480–1487 (1994).
Berkman et al., "Expression of the Vascular Permeability Factor/Vascular Endothelial Growth Factor Gene in Central Nervous System Neoplasms" *J. Clini. Invest.* 91:153–159 (1993).
Burger et al., "Expermental Corneal Neovascularization: Biomicroscopic, Angiographic, and Morphologic Correlation" *Cornea* 4:35–41 (1985).
Detmar et al., "Overexpression of Vascular Permeability Factor/Vascular Endothelial Growth Factor and Its Receptors in Psoriasis" *J. Exp. Med.* 180:1141–1146 (1994).
Fava et al., "Vascular Permeability Factor/Endothelial Growth Factor (VPF/VEGF): Accumulation and Expression in Human Synovial Fluids and Rheumatoid Synovial Tissue" *J. Exp. Med.* 180:341–346 (1994).
Ferrara, "Vascular Endothelial Growth Factor" *Trends Cardiovas, Med.* 3:244–250 (1993).
Folkman, "Tumor Angiogenesis" *Adv. Cancer, Res.* 43:175–203 (1985).
Fong, et al., "Role of the Flt–1 receptor tyrosine kinase in regulating the assembly of vascular endothelium" *Nature* 376:66–70 (1995).
Gitay–Goren et al., "The Binding of Vascular Endothelial Growth Factor to Its Receptors Is Dependent on Cell Surface–associated Heparin–like Molecules" *J. Biol. Chem.* 267:6093–6098 (1992).
Grant et al., "Insulin–like growth factor I acts as an angiogenic agent in rabbit cornea and retina: comparative studies with basic fibroblast growth factor" *Diabetologia* 36:282–291 (1993).
Koch et al., "Vascualr Endothelial Growth Factor" *J. Immunol.* 152:4149–4155 (1994).
Lepri, et al., "Effect of Low Molecular Weight Heparan Sulphate on Angiogenesis in the Rat Cornea After Chemical Cauterization" *J. Ocular Pharmacol.* 10:273–280 (1994).

(List continued on next page.)

Primary Examiner—Sean McGarry
Assistant Examiner—Janet L Epps-Ford
(74) Attorney, Agent, or Firm—McDonnell Boehnen Hulbert & Berghoff LLP

(57) ABSTRACT

The present invention relates to nucleic acid molecules which modulate the synthesis, expression and/or stability of an mRNA encoding one or more receptors of vascular endothelial growth factor.

12 Claims, 22 Drawing Sheets

OTHER PUBLICATIONS

Matthews et al., "A receptor tyrosine kinase cDNA isolated from a population of enriched primitive hematopoietic cells and exhibiting close genetic linkage to c–kit" *Prior. Natl. Acad. Sci., USA*, 88:9026–9030 (1991).

Millauer et al., "Glioblastoma growth inhibited in vivo by a dominant–negative Flk–1 mutant" *Nature* 367:576–579 (1994).

Miller et al., "Vascular Endothelial Growth Factor/Vascular Permeability Factor Is Temporally and Spatially Correlated with Ocular Angiogenesis in a Primate Model" *Am. J. Pathol.* 145:574–584 (1994).

Neufeld et al., "Vascular Endothelial Growth Factor and its Receptors" *Prog. Growth Factor Res.* 5:89–97 (1994).

O'Reilly et al., "Angiostatin: A Novel Angiogenesis Inhibitor That Mediates the Suppression of Metastases by a Lewis Lung Carcinoma" *Cell* 79:315–328 (1994).

Ormerod et al., "Effects of Altering the Eicosanoid Precursor Pool on Neovascularization and Inflammation in the Alkali–burned Rabbit Cornea" *Am. J. Pathol.* 137:1243–1252 (1990).

Pandey et al., "Role of B61, the Ligand for the Eck Receptor Tyrosine Kinase, in TNF–α—Induced Angiogenesis" *Science* 268:567–569 (1995).

Passaniti et al., "Methods in Labortory Investigation, A simple, Quantitative Method of Assessing Angiogenesis and Antiangiogenic Agents Using Reconstituted Basement Membrane, Heparin, and Fibroblast Growth Factor" *Lab. Invest.* 67: 519–528 (1992).

Pierce et al., "Vascular endothelial growth factor/vascular permeability factor expression ina mouse model of retinal neovascularization" *Proc. Natl. Acad. SCi. USA.* 92:905–909 (1995).

Plouët et al., "Isolation and characterization of a newly identified endothelial cell mitogen produced by AtT–20 cells" *EMBO J.* 8:3801–3806 (1989).

Senger et al., "Vascular permeability factor (VPF, VEGF) in tumor biology" *Cancer and Metas. Rev.* 12:303–324 (1993).

Shalaby et al., "Failure of blood–island formation and vasculogenesis in Flk–1–deficient mice" *Nature* 376:62–66 (1995).

Shibuya et al., "Nucleotide sequence and expression of a novel human receptor–type tyrosine kinase gene (flt) closely related to the fms family" *Oncogene* 5:519–524 (1990).

Shweiki et al, "Patterns of Expression of Vascular Endothelial Growth Factor (VEGF) and VEGF Receptors in Mice Suggest a Role in Hormonally Regulated Angiogenesis" *J. Clin. Invest.* 91:2235–2243 (1993).

Takahashi et al., "Markedly Increased Amounts of Messenger RNAs for Vascular Endothelial Growth Factor and Placenta Growth Factor in Renal Cell Carcinoma Associated with Angiogenesis" *Cancer Res.* 54: 4233–4237 (1994).

Takeshita et al., "Therapeutic Angiogenesis, A single Intraarterial Bolus of Vascular Endothelial Growth Factor Augments Revascularization in a Rabbit Ischemic Hind Limb Model" *J. Clin. Invest.* 93:662–670 (1994).

Terman et al., "Identification of a new endothelial cell growth factor receptor tyrosine kinase" *Oncogene* 6:1677–1683 (1991).

Usman et al., "Exploiting the chemical synthesis of RNA," *TIBS* 17:334–339 (1992).

Vaisman et al., "Characterization of the Receptors of Vascular Endothelial Growth Factor" *J. Bio. Chem.* 265:19461–19466 (1990).

Zieche et al., "Angiogenesis Can Be Stimulated or Repressed In vivo by a Change in GM3:GD3 Ganglioside Ratio" *Lab. Invest.* 67:711–715 (1992).

Beigelman et al., "Chemical Modification of Hammerhead Ribozymes," *J. Biol. Chem.* 270:25702–25708 (1995).

Carter, "Adeno–Associated Virus Vectors," *Curr. Opi. Biotech.* 3:533–539 (1992).

Chen et al., "Multitarget–Ribozyme Directed To Cleave at up to Nine Highly Conserved HIV–1 env RNA Regions Inhibits HIV–1 Replication Potential Effectiveness Against Most Presently Sequenced HIV–1 Isolates," *Nucleic Acids Research* 20:4581–4589 (1992).

Chowrira et al., "Extensive Phosphorotioate Substitution Yields Highly Active and Nuclease–Resistant Hairpin Ribozymes," *Nucleic Acids Res.*, 20:2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Collins et al., "Reaction Conditions and Kinetics of Self–Cleavage of a Ribozyme Derived From Neurospora VS RNA," *Biochemisry* 32:2795–2799 (1993).

Dropulic et al., "Functional Characterization of a U5 Ribozyme: Intracellular Suppression of Human Immunodeficiency Virus Type I Expression," *Journal of Virology*, 66:1432–1441 (1992).

Duval–Valentin et al., "Specific inhibition of transcription by triple helix–forming oligonucletides," *Proc. Natl. Acad. Sci. USA* 89:504 (1992).

Egholm et al., "PNA hybridizes to complementary oligonucleotides obeying the Watson–Crick hydrogen–bonding rules," *Nature* 365:566–568 (1993).

Elroy–Stein et al., "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Folkman et al., "Angiogenesis," *J. Biol. Chem.* 267:10931–10934 (1992).

Folkman, "What is the Evidence that Tumors are Angiogenesis Dependent?" Journal of the National Cancer Institute 82:4–6 (1990).

Gao et al., "Cytoplasmic Expression of a Reporter Gene by Co–Delivery of T7 RNA Polymerase and T7 Promoter Sequence with Cationic Liposomes," *Nucleic Acids Res* 21:2867–2872 (1993).

Guerrier–Tekada et al., "The RNA Moiety of Ribonuclease P Is the Catalytic Subunit of the Enzyme," *Cell* 35:849–857 (1983).

Hampel et al., "Hairpin' Catalytic RNA Model: Evidence for Helices and Sequence Requirement for Substrate RNA," *Nucleic Acids Res.* 18:299 (1990).

Hampel et al., "RNA Catalytic Properties of the Mimimum a(–)sTRSV Sequence," *Biochemistry* 28:4929–4399 (1989).

Izant et al., "Constitutive and Conditional Suppression of Exogenous and Endogeneous Genes by Anti–Sense RNA," *Science* 229:345–352 (1985).

Jaeger et al., "Improved Predictions of Secondary Structures for RNA," *Proc. Natl. Acad. Sci. USA*, 86:7706–7710 (1989).

Jellinek et al., "Inhibition of Receptor Binding by High–Affinity RNA Ligands to Vascular Endothelial Growth Factor," *Biochemistry* 33:10450–10456 (1994).

Kashani–Sabet et al., "Reversal of the Malignant Phenotype by an Anti ras Ribozyme," *Antisense Research and Development.*, 2:3–15 (1992).

Kim et al., "Inhibition of vascular endothelial growth factor–induced angiogenesis suppresses tumour growth in vivo," *Nature* 362:841–844 (1993).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Lieber et al., "Stable High–Level Gene Expression in Mammalian Cells by T7 Phage RNA Polymerase," *Methods Enzymol.*, 217:47–66 (1993).

Lisziewics et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. USA* 90:8000–8004 (1993).

McGarry et al., "Inhibition of heat shock protein synthesis by heat–inducible antisense RNA," *Proc. Natl. Acad. Sci. USA* 83:399–403 (1986).

Millauer et al., "High Affinity VEGF Binding and Developmental Expression Suggest Flk–1 as a Major Regulator of Vasculogenesis and Angiogenesis," *Cell* 72:835–846 (1993).

Milligan et al., "Synthesis of Small RNAs Using T7 RNA Polymerase," *Methods Enzymol*, 180:51–62 (1989).

Ohkawa et al., "Activities of HIV–RNA Targeted Ribozymes Transcribed From a 'Shot–Gun' Type Ribozyme–trimming Plasmid," *Nucleic Acids Symp. Serv.*, 27:15–16 (1992).

Ojwang et al., "Inhibition of Human Immunodeficiency Virus Type 1 Expression by a Hairpin Ribozyme," *Proc. N atl. Acad. Sci. USA* 89:10802–10806 (1992).

Perrault et al., "Mixed Deoxyribo– and Ribo–Oligonucleotides with Catalytic Activity," *Nature* 344:565–567 (1990).

Perrotta et al., "Cleavage of Oligoribonucleotides by a Rybozyme Derived from the Hepatitis δ Virus RNA Sequence," *Biochemistry* 31:16–21 (1992).

Pieken et al., "Kinetic Characterication of Ribonuclease–Resistant 2'–Modified Hammerhead Ribozymes," *Science* 253:314–317 (1991).

Plate et al., "Vascular endothelial growth factor is potential tumor angiogenesis factor in human gilomas in vivo," *Nature* 359:845–848 (1992).

Rossi et al., "Ribozymes as Anti–HIV–1 Therapeutic Agents: Principles, Applications, and Problems," *Aids Research and Human Retroviruses* 8:183–189 (1992).

Sarver et al., "Ribozymes as Potential Anti–HIV–1 Therapeutic Agents," *Science* 247:1222–1225 (1990).

Saville et al., "A Site–Specific Self–Cleavage Reaction Performed by a Novel RNA In Neurospora Mitochondria," *Cell* 61:685–696 (1990).

Saville et al.,*Proc. Natl. Acad. Sci. USA* 88:8826–8830 (1991).

Scanlon et al., *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucleic Acids Res.* 18:5433–5441 (1990).

Stein et al., "Antisense Oligonucleotides as Therapeutic Agents—Is the Bullet Really Magical?" *Science* 261:1004–1288 (1993).

Taira et al., "Construction of a novel RNA–transcript–trimming plasmid which can be used both in vitro in plce of run–off and (G)–free transcriptions and in vivo as multi–sequences transcription vectors," *Nucleic Acids Res.*, 19:5125–5130 (1991).

Thompson et al., "Improved accumulation and activity of ribozymes expressed from a tRNA–based RNA polymerase III promoter," *Nucleic Acids Res.* 23:2259–2268 (1995).

Torrence et al., "Targeting RNA for degradation with a (2'–5') oligoadenylate–antisense chimera," *Proc. Natl. Acad. Sci. USA* 90:1300–1304 (1993).

Usman et al., "Automated Chemical Synthesis of Long Oligoriibonucleotides Using 2'–O–Silylated Ribonycleoside 3'–O–Phosphoramidites on a Controlled–Pore Glass Support: Synthesis of a 43–Nucleotide Sequence Similar to the 3'–Half Molecule of a *Escherichia coli* Formylmethoionine tRNA," *J. Am. Chem. Soc.*, 109:7845–7854 (1987).

Usman et al., "Chemical modification of hammerhead Ribozymes: activity and nuclease resistance," *Nucleic Acids Symp. Ser.* 31:163–164 (1994).

Usman et al., "Exploiting the chemical synthesis of RNA" *TIBS.* 17:334–339 (1992).

Ventura et al., "Activation of HIV–Specific Ribozyme Activity by Self–Cleavage" *Nucleic Acids Res.*, 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of VIrology* 65:5531–5534 (1991).

Wincott et al., "Synthesis, deprotection, analysis and purification of RNA and ribozymes," *Nucleic Acids Research* 23:2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.*, 10:4529–4537 (1990).

International Search Report, PCT/US02/17674, filed May 29, 2002.

Parry et al. 1999. "Bioactivity of anti–angiogenic ribozymes targeting Flt–1 and KDR mRNA," *Nucleic Acid Res.* 27:2569–77.

* cited by examiner

Figure 1: Hammerhead Ribozyme

Figure 2. Hammerhead Ribozyme Substrate Motifs

Figure 3: Hairpin Ribozyme

Figure 4: Hepatitis Delta Virus Ribozyme (SEQ ID NO 8219)

Figure 5. Neurospora vs Ribozyme

Figure 6
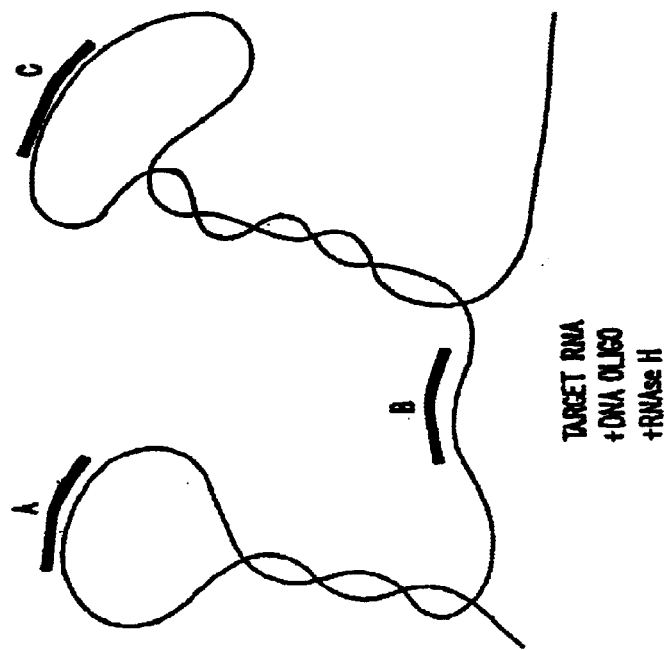
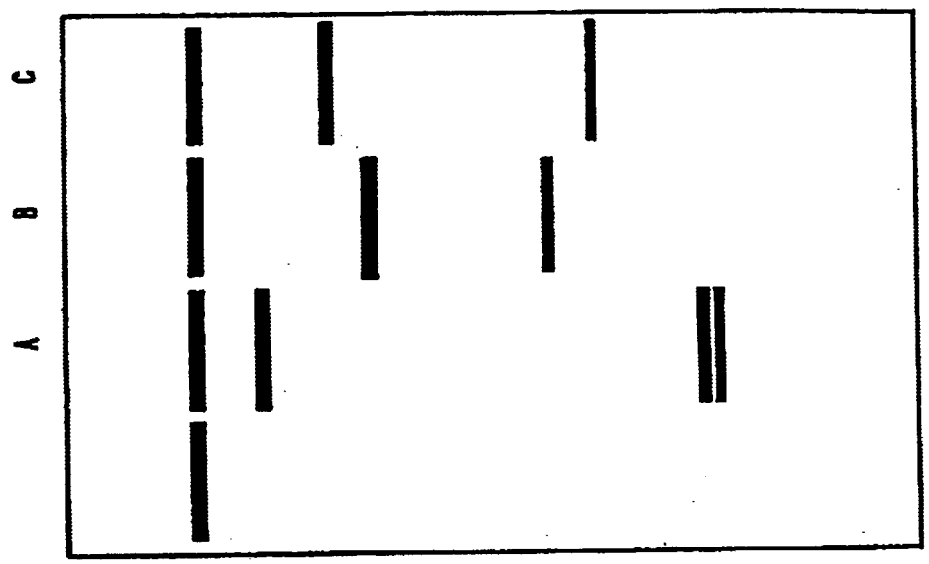

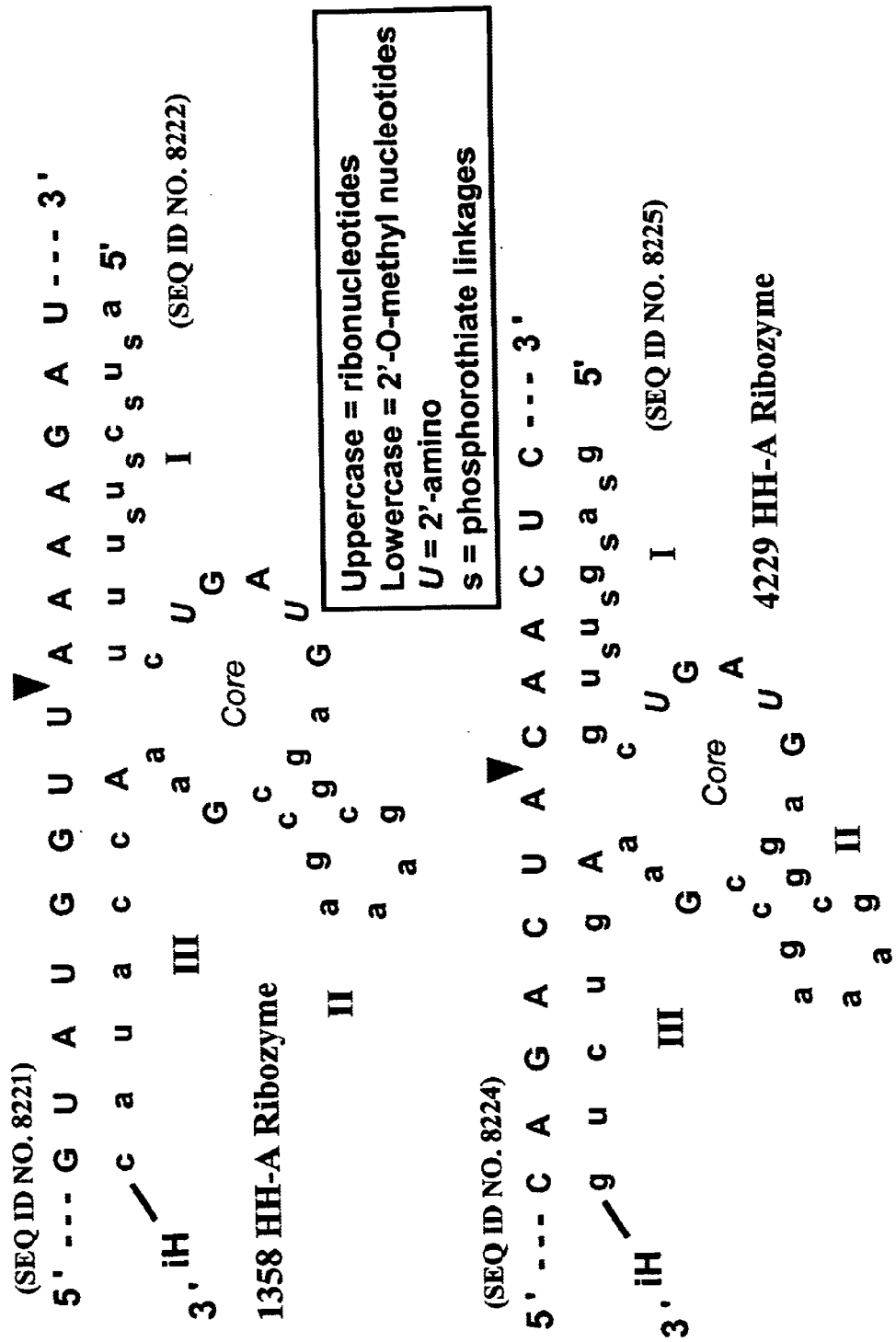

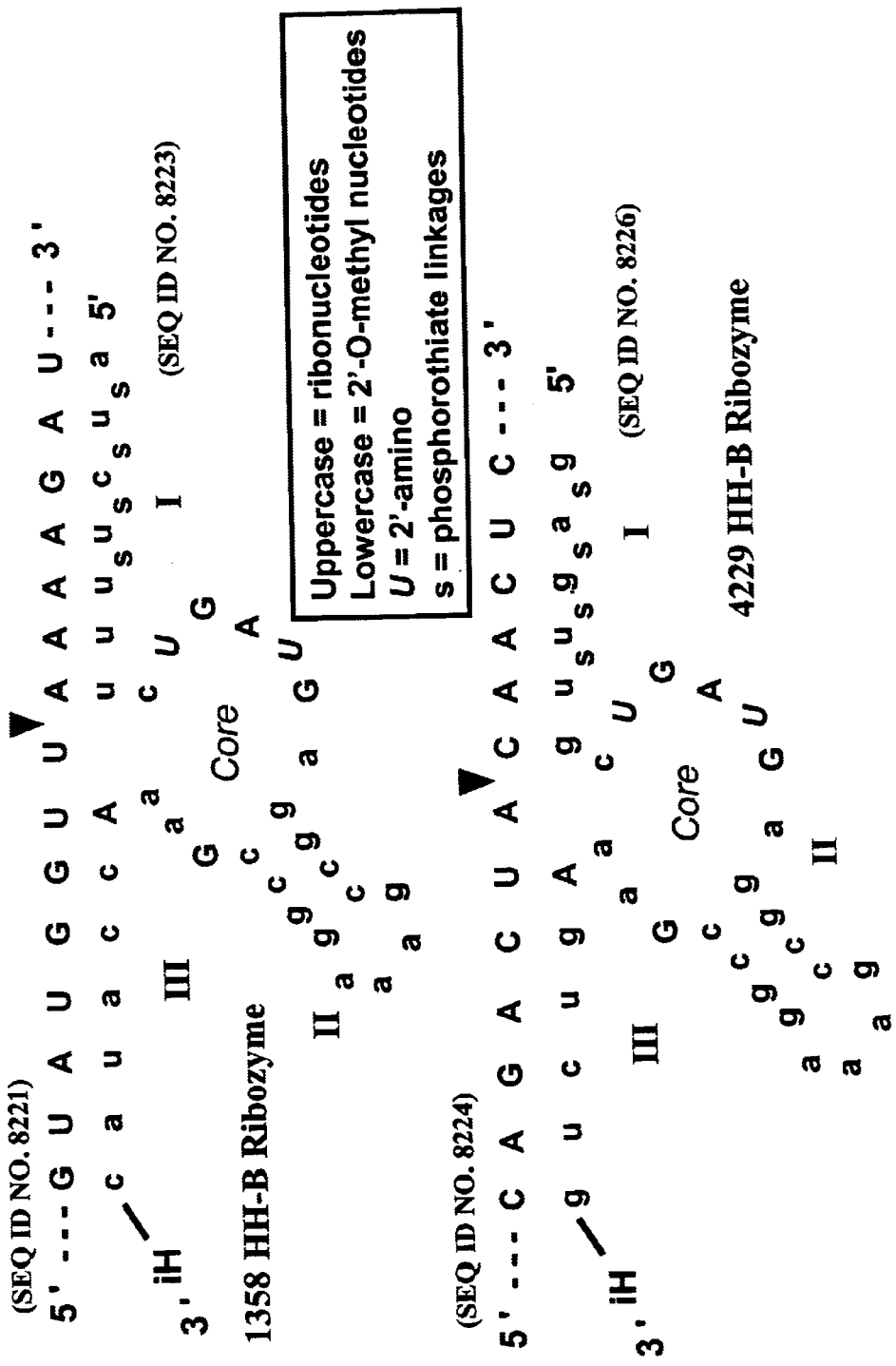
Figure 11A2: Hammerhead Ribozymes Targeted Against flt-1 RNA

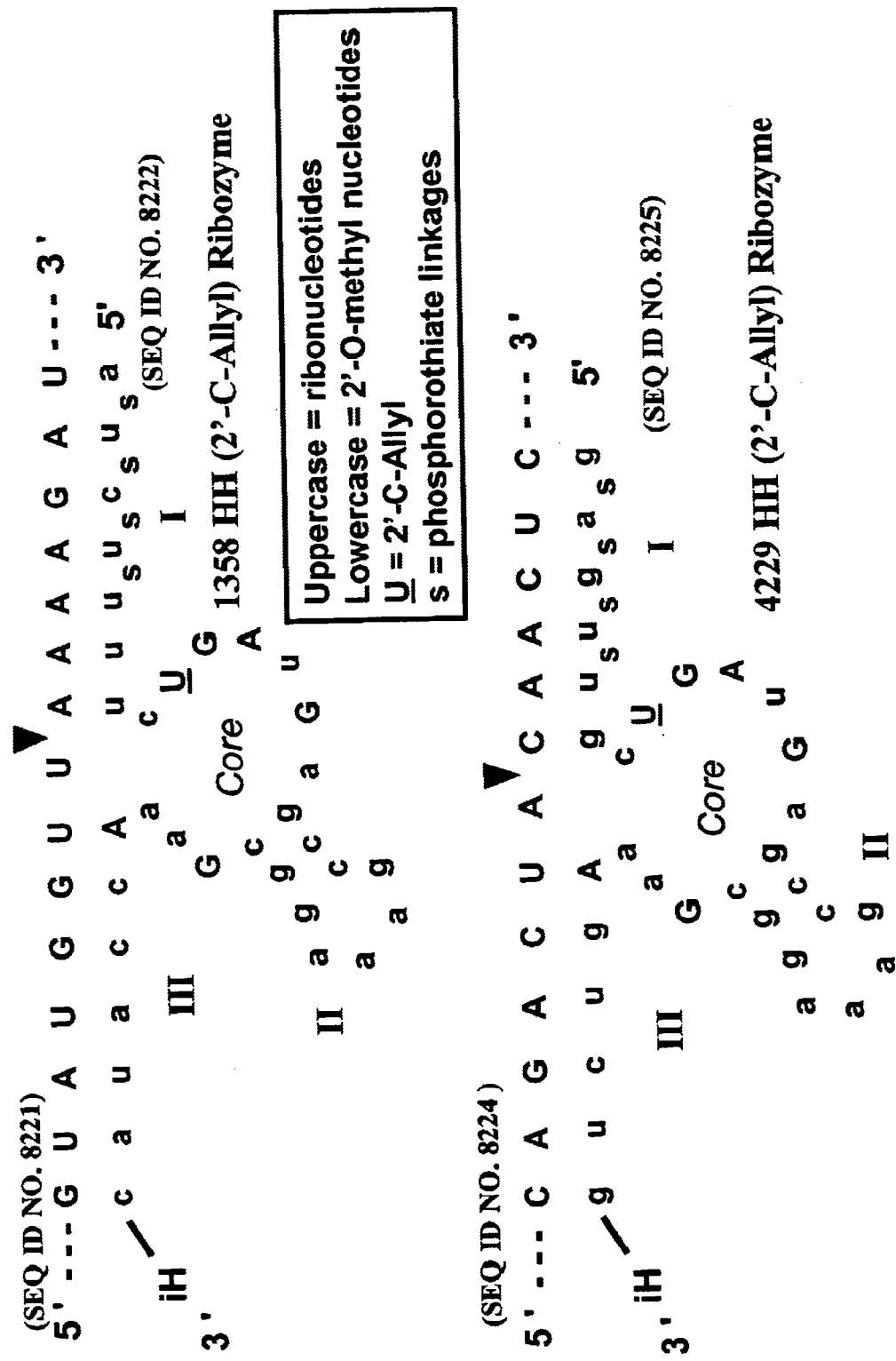
Figure 12A1: Hammerhead Ribozymes Targeted Against flt-1 RNA

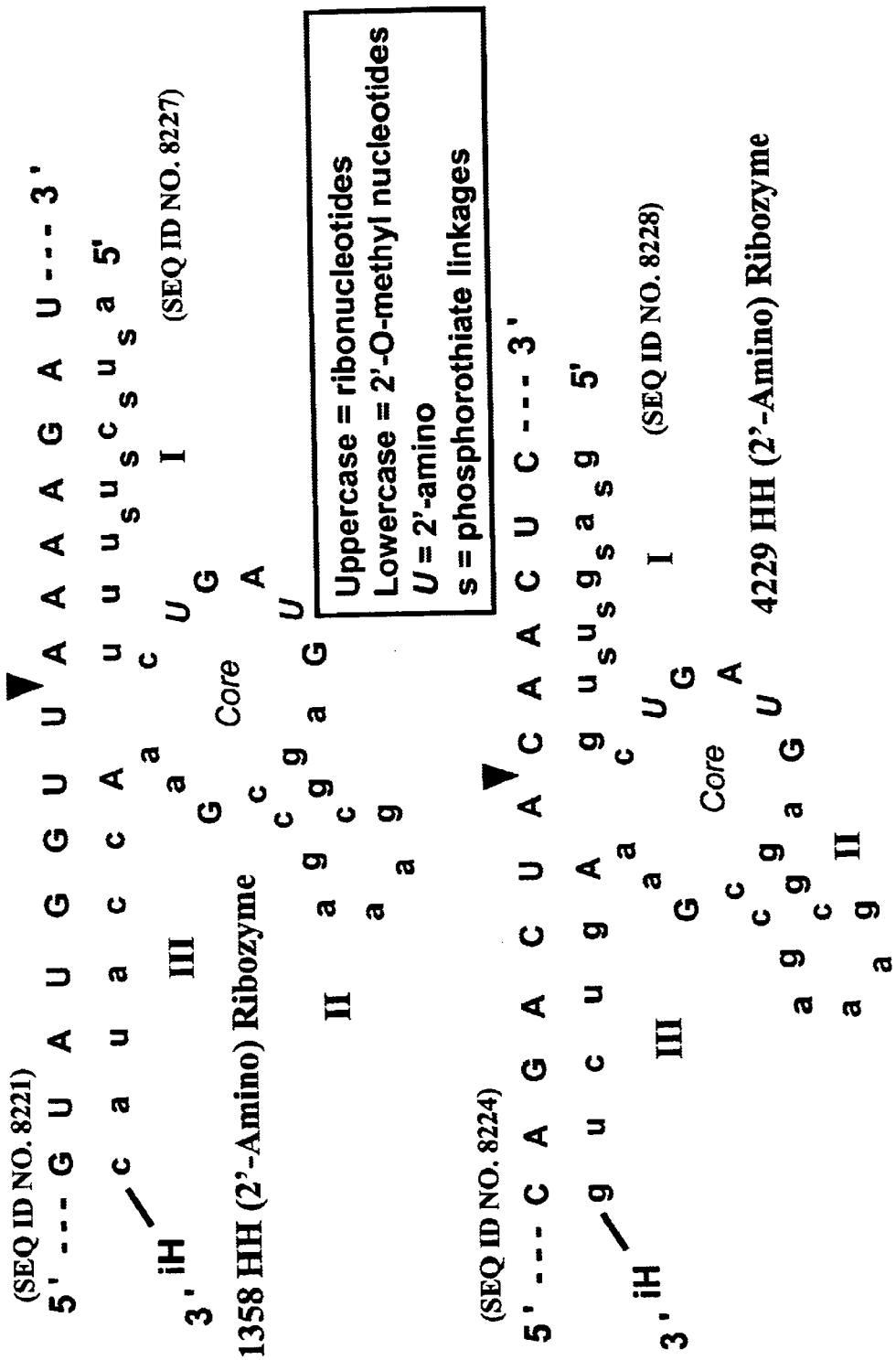
Figure 12A2: Hammerhead Ribozymes Targeted Against flt-1 RNA

METHOD AND REAGENT FOR THE TREATMENT OF DISEASES OR CONDITIONS RELATED TO LEVELS OF VASCULAR ENDOTHELIAL GROWTH FACTOR RECEPTOR

This application is a continuation of U.S. patent application Ser. No. 08/584,040, filed Jan. 11, 1996, now U.S. Pat. No. 6,346,398, which claims the benefit of U.S. Patent Application No. 60/005,974, filed Oct. 26, 1995, both of which are hereby incorporated by reference.

This application is a continuation-in-part of Pavco et al., U.S. Serial No. 60/005,974 all of which is hereby incorporated by reference herein (including drawings).

BACKGROUND OF THE INVENTION

The Sequence Listing file named "MBHB00,876-K SequenceListing.txt" (2,337,188 bytes in size) submitted on Compact Disc-Recordable (CD-R) medium ("010706_1627") in compliance with 37 C.F.R. §1.52(e) is incorporated herein by reference.

This invention relates to methods and reagents for the treatment of diseases or conditions relating to the levels of expression of vascular endothelial growth factor (VEGF) receptor(s).

The following is a discussion of relevant art, none of which is admitted to be prior art to the present invention.

VEGF, also referred to as vascular permeability factor (VPF) and vasculotropin, is a potent and highly specific mitogen of vascular endothelial cells (for a review see Ferrara, 1993 *Trends Cardiovas. Med.* 3, 244; Neufeld et al., 1994 *Prog. Growth Factor Res.* 5, 89). VEGF induced neovascularization is implicated in various pathological conditions such as tumor angiogenesis, proliferative diabetic retinopathy, hypoxia-induced angiogenesis, rheumatoid arthritis, psoriasis, wound healing and others.

VEGF, an endothelial cell-specific mitogen, is a 34–45 kDa glycoprotein with a wide range of activities that include promotion of angiogenesis, enhancement of vascular-permeability and others. VEGF belongs to the platelet-derived growth factor (PDGF) family of growth factors with approximately 18% homology with the A and B chain of PDGF at the amino acid level. Additionally, VEGF contains the eight conserved cysteine residues common to all growth factors belonging to the PDGF family (Neufeld et al., supra). VEGF protein is believed to exist predominantly as disulfide-linked homodimers; monomers of VEGF have been shown to be inactive (Plouet et al., 1989 *EMBO J.* 8, 3801).

VEGF exerts its influence on vascular endothelial cells by binding to specific high-affinity cell surface receptors. Covalent cross-linking experiments with $^{125}$I-labeled VEGF protein have led to the identification of three high molecular weight complexes of 225, 195 and 175 kDa presumed to be VEGF and VEGF receptor complexes (Vaisman et al., 1990 *J. Biol. Chem.* 265, 19461). Based on these studies VEGF-specific receptors of 180, 150 and 130 kDa molecular mass were predicted. In endothelial cells, receptors of 150 and the 130 kDa have been identified. The VEGF receptors belong to the superfamily of receptor tyrosine kinases (RTKs) characterized by a conserved cytoplasmic catalytic kinase domain and a hydrophylic kinase sequence. The extracellular domains of the VEGF receptors consist of seven immunoglobulin-like domains that are thought to be involved in VEGF binding functions.

The two most abundant and high-affinity receptors of VEGF are flt-1 (fms-like tyrosine kinase) cloned by Shibuya et al., 1990 *Oncogene* 5, 519 and KDR (kinase-insert-domain-containing receptor) cloned by Terman et al., 1991 *Oncogene* 6, 1677. The murine homolog of KDR, cloned by Mathews et al., 1991, *Proc. Natl. Acad. Sci.*, USA, 88, 9026, shares 85% amino acid homology with KDR and is termed as flk-1 (fet al liver kinase-1). Recently it has been shown that the high-affinity binding of VEGF to its receptors is modulated by cell surface-associated heparin and heparin-like molecules (Gitay-Goren et al., 1992 *J. Biol. Chem.* 267, 6093).

VEGF expression has been associated with several pathological states such as tumor angiogenesis, several forms of blindness, rheumatoid arthritis, psoriasis and others. Following is a brief summary of evidence supporting the involvement of VEGF in various diseases:

1) Tumor Angiogenesis

Increased levels of VEGF gene expression have been reported in vascularized and edema-associated brain tumors (Berkman et al., 1993 *J. Clini. Invest.* 91, 153). A more direct demostration of the role of VEGF in tumor angiogenesis was demonstrated by Jim Kim et al., 1993 *Nature* 362,841 wherein, monoclonal antibodies against VEGF were successfully used to inhibit the growth of rhabdomyosarcoma glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576).

2) Ocular Diseses

Aiello et al., 1994 *New Engl. J. Med.* 331, 1480, showed that the ocular fluid, of a majority of patients suffering from diabetic retinopathy and other retinal disorders, contains a high concentration of VEGF. Miller et al., 1994 *Am. J. Pathol.* 145, 574, reported elevated levels of VEGF mRNA in patients suffering from retinal ischemia. These observations support a direct role for VEGF in ocular diseases.

3) Psoriasis

Detmar et al., 1994 *J. Exp. Med.* 180, 1141 reported that VEGF and its receptors were over-expressed in psoriatic skin and psoriatic dermal microvessels, suggesting that VEGF plays a significant role in psoriasis.

4) Rheumatoid Arthritis

Immunohistochemistry and in situ hybridization studies on tissues from the joints of patients suffering from rheumatoid arthritis show an increased level of VEGF and its receptors (Fava et al., 1994 *J. Exp. Med.* 180, 341). Additionally, Koch et al., 1994 *J. Immunol.* 152, 4149, found that VEGF-specific antibodies were able to significantly reduce the mitogenic activity of synovial tissues from patients suffering from rheumatoid arthritis. These observations support a direct role for VEGF in rheumatoid arthritis.

In addition to the above data on pathological conditions involving excessive angiogenesis, a number of studies have demonstrated that VEGF is both necessary and sufficient for neovascularization. Takashita et al., 1995 *J. Clin. Invest.* 93, 662, demonstrated that a single injection of VEGF augmented collateral vessel development in a rabbit model of ischemia. VEGF also can induce neovascularization when injected into the cornea. Expression of the VEGF gene in CHO cells is sufficient to confer tumorigenic potential to the cells. Kim et al., supra and Millauer et al., supra used monoclonal antibodies against VEGF or a dominant negative form of flk-1 receptor to inhibit tumor-induced neovascularization.

During development, VEGF and its receptors are associated with regions of new vascular growth (Millauer et al. 1993 *Cell* 72, 835; Shalaby et al., 1993 *J. Clin. Invest.* 91, 2235). Furthermore. transgenic mice lacking either of the VEGF receptors are defective in blood vessel formation, infact these mouse do not survive; flk-1 appears to be required for differentiation of endothelial cells, while flt-1 appears to be required at later stages of vessel formation (Shalaby et al., 1995 Nature 376, 62; Fung et al., 1995 Nature 376, 66). Thus, these receptors must be present to properly signal endothelial cells or their precursors to respond to vascularization-promoting stimuli.

All of the conditions listed above, involve extensive vascularization. This hyper-stimulation of endothelial cells may be alleviated by VEGF antagonists. Thus most of the therapeutic efforts for the above conditions have concentrated on finding inhibitors of the VEGF protein.

Kim et al., 1993 Nature 362, 841 have been successful in inhibiting VEGF-induced tumor growth and angiogenesis in nude mice by treating the mice with VEGF-specific monoclonal antibody.

Koch et al., 1994 J. Immunol. 152, 4149 showed that the mitogenic activity of microvascular endothelial cells found in rheumatoid arthritis (RA) synovial tissue explants and the chemotactic property of endothelial cells from RA synovial fluid can be neutralized significantly by treatment with VEGF-specific antibodies.

Ullrich et al., International PCT Publication No. WO 94/11499 and Millauer et al., 1994 Nature 367, 576 used a soluble form of flk-1 receptor (dominant-negative mutant) to prevent VEGF-mediated tumor angiogenesis in immunodeficient mice.

Kendall and Thomas, International PCT Publication No. WO 94/21679 describe the use of naturally occuring or recombinantly-engineered soluble forms of VEGF receptors to inhibit VEGF activity.

Robinson, International PCT Publication No. WO 95/04142 describes the use of antisense oligonucleotides targeted against VEGF RNA to inhibit VEGF expression.

Jellinek et al., 1994 Biochemistry 33, 10450 describe the use of VEGF-specific high-affinity RNA aptamers to inhibit the binding of VEGF to its receptors.

Rockwell and Goldstein, International PCT Publication No. WO 95/21868, describe the use of anti-VEGF receptor monoclonal antibodies to neutralize the the effect of VEGF on endothelial cells.

SUMMARY OF THE INVENTION

The invention features novel nucleic acid-based techniques [e.g., enzymatic nucleic acid molecules (ribozymes), antisense nucleic acids, 2–5A antisense chimeras, triplex DNA, antisense nucleic acids containing RNA cleaving chemical groups (Cook et al., U.S. Pat. No. 5,359,051)] and methods for their use to down regulate or inhibit the expression of receptors of VEGF (VEGF–R).

In a preferred embodiment, the invention features use of one or more of the nucleic acid-based techniques to inhibit the expression of flt-1 and/or flk-1/KDR receptors.

By "inhibit" it is meant that the activity of VEGF–R or level of mRNAs or equivalent RNAs encoding VEGF–R is reduced below that observed in the absence of the nucleic acid. In one embodiment, inhibition with ribozymes preferably is below that level observed in the presence of an enzymatically inactive RNA molecule that is able to bind to the same site on the mRNA, but is unable to cleave that RNA. In another embodiment, inhibition with antisense oligonucleotides is preferably below that level observed in the presence of for example, an oligonucleotide with scrambled sequence or with mismatches.

By "enzymatic nucleic acid molecule" it is meant an RNA molecule which has complementarity in a substrate binding region to a specified gene target, and also has an enzymatic activity which is active to specifically cleave target RNA. That is, the enzymatic RNA molecule is able to intermolecularly cleave RNA and thereby inactivate a target RNA molecule. This complementary regions allow sufficient hybridization of the enzymatic RNA molecule to the target RNA and thus permit cleavage. One hundred percent complementarity is preferred, but complementarity as low as 50–75%. may also be useful in this invention. By "equivalent" RNA to VEGF–R is meant to include those naturally occurring RNA molecules in various animals, including human, mice, rats, rabbits, primates and pigs.

By "antisense nucleic acid" it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review see Stein and Cheng, 1993 Science 261, 1004).

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 Proc. Natl. Acad. Sci. USA 90, 1300).

By "triplex DNA" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504).

By "gene" it is meant a nucleic acid that encodes an RNA.

By "complementarity" it is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general. enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in VEGF–R mRNAs represent a novel therapeutic approach to treat tumor angiogenesis, ocular diseases, rhuematoid arthritis, psoriasis and others. Applicant indicates that ribozymes are able to inhibit the activity of VEGF-R (specifically flt-1 and flk-1/KDR) and that the catalytic activity of the ribozymes is required for their inhibitory effect. Those of ordinary skill in the art will find that it is clear from the examples described that other ribozymes that cleave VEGF-R mRNAs may be readily designed and are within the invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *AIDS Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemisty* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding VEGF-R proteins (specifically flt-1 and flk-1/KDR) such that specific treatment of a disease or condition can be provided with either one or several enzymatic nucleic acids. Such enzymatic nucleic acid molecules can be delivered exogenously to specific tissue or cellular targets as required. Alternatively, the ribozymes can be expressed from DNA and/or RNA vectors that are delivered to specific cells.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41: Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225; Thompson et al., 1995 *Nucleic Acids Res.* 23, 2259). Those skilled in the art realize that any nucleic acid can me expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856).

Such nucleic acids are useful for the prevention of the diseases and conditions discussed above, and any other diseases or conditions that are related to the levels of VEGF-R(specifically flt-1 and flk-1/KDR) in a cell or tissue.

By "related" is meant that the reduction of VEGF-R (specifically flt-1 and flk-1/KDR) RNA levels and thus reduction in the level of the respective protein will relieve, to some extent, the symptoms of the disease or condition.

Ribozymes are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II to IX. Examples of such ribozymes also are shown in Tables II to IX. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target RNA molecules and inhibit VEGF-R (specifically flt-1 and flk-1/KDR) activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

DESCRIPTION OF THE PREFERRED EMBODIMENTS

First the drawings will be described briefly.

Drawings

Figure 1:
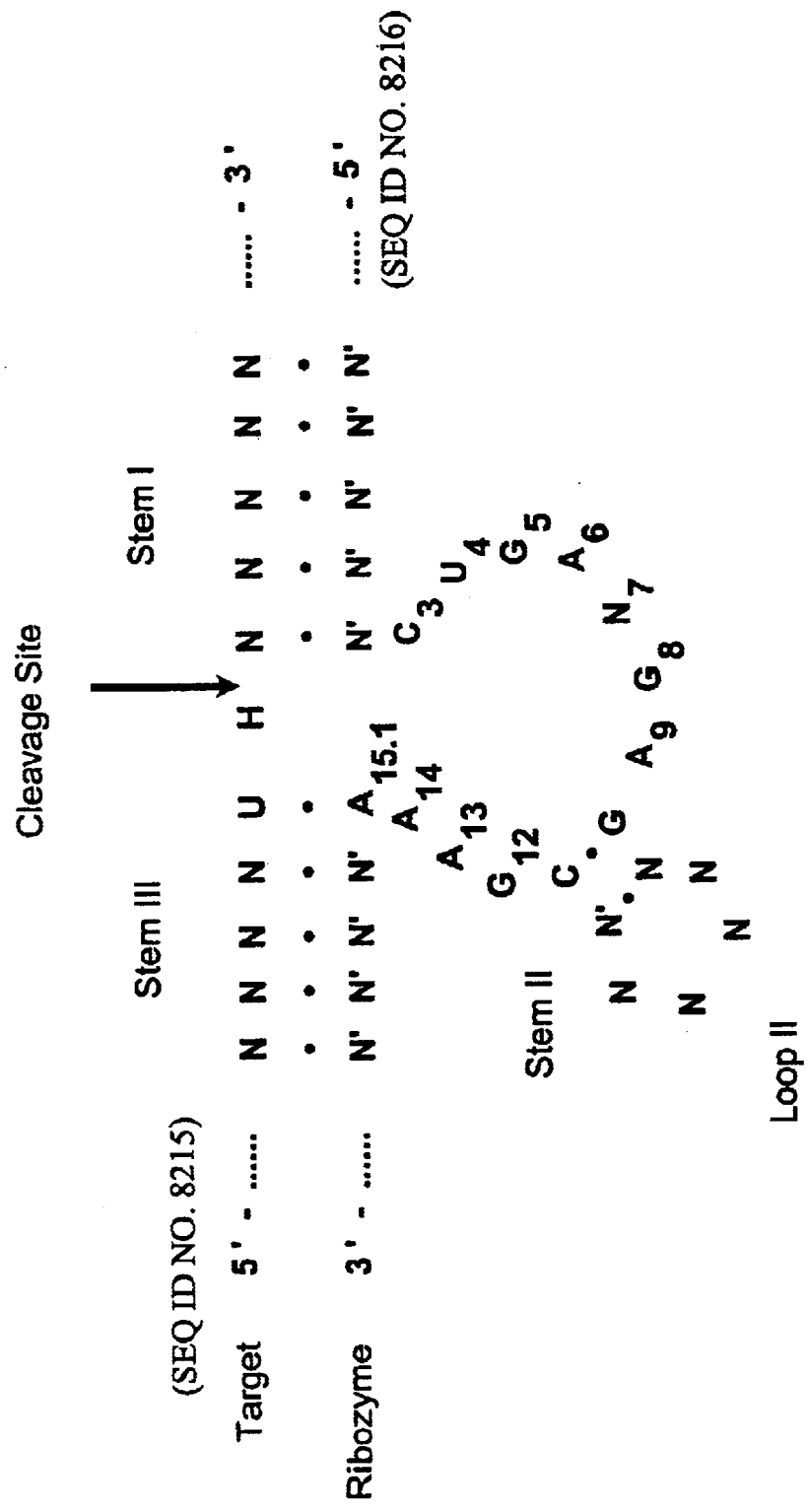
FIG. 1 is a diagrammatic representation of the hammerhead ribozyme domain known in the art. Stem II can be $\geq 2$ base-pair long. (SEQ ID NO: 8215–8216)
Figure 2:
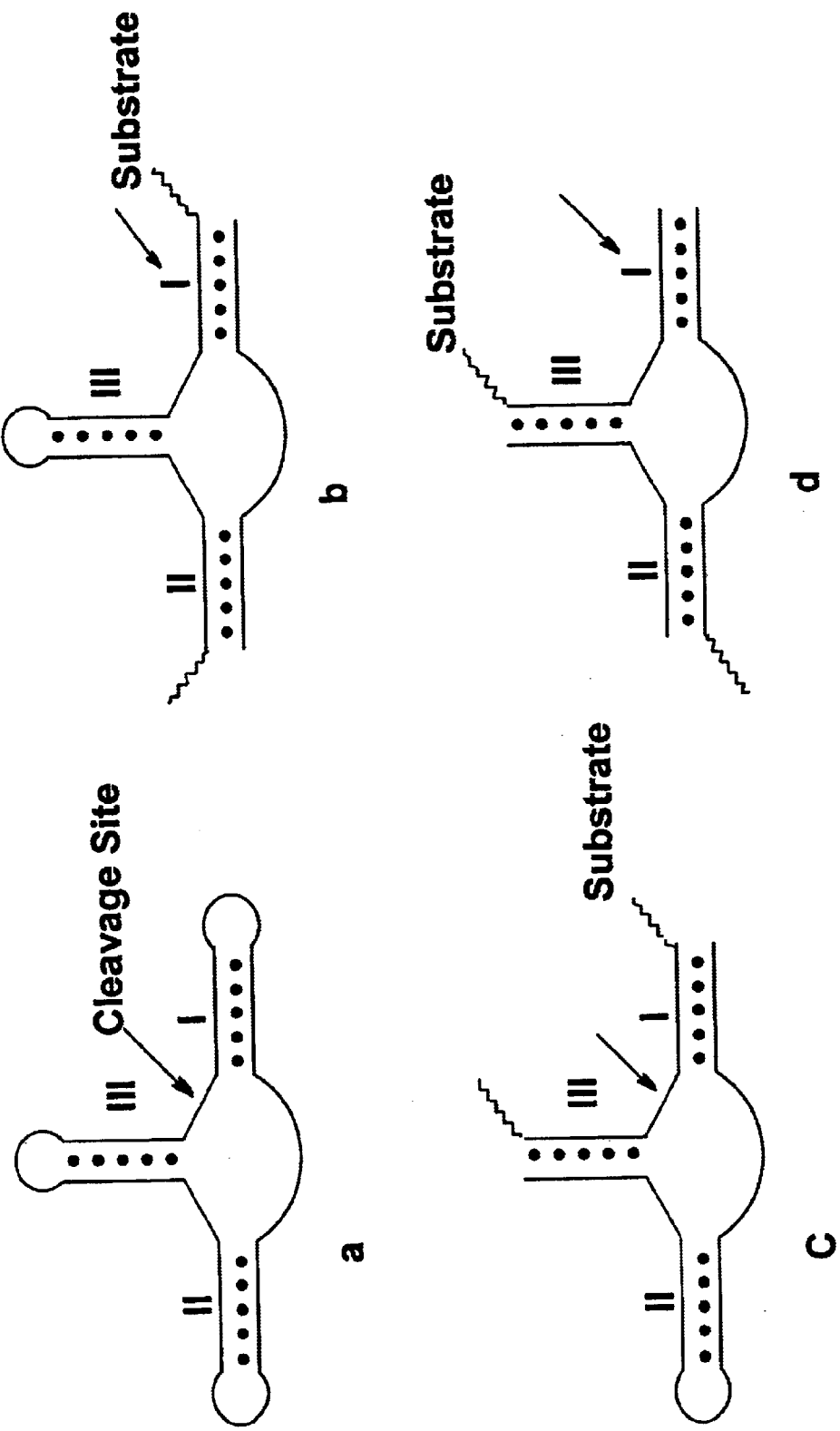
FIG. 2a is a diagrammatic representation of the hammerhead ribozyme domain known in the art.
FIG. 2b is a diagrammatic representation of the hammerhead ribozyme as divided by Uhlenbeck (1987, Nature, 327, 596–600) into a substrate and enzyme portion.
FIG. 2c is a similar diagram showing the hammerhead divided by Haseloff and Gerlach (1988, Nature, 334, 585–591) into two portion.

FIG. 2d is a similar diagram showing the hammerhead divided by Jeffries and Symons (1989, Nucl. Acids. Res., 17, 1371–1371) into two portions.

Figure 3:
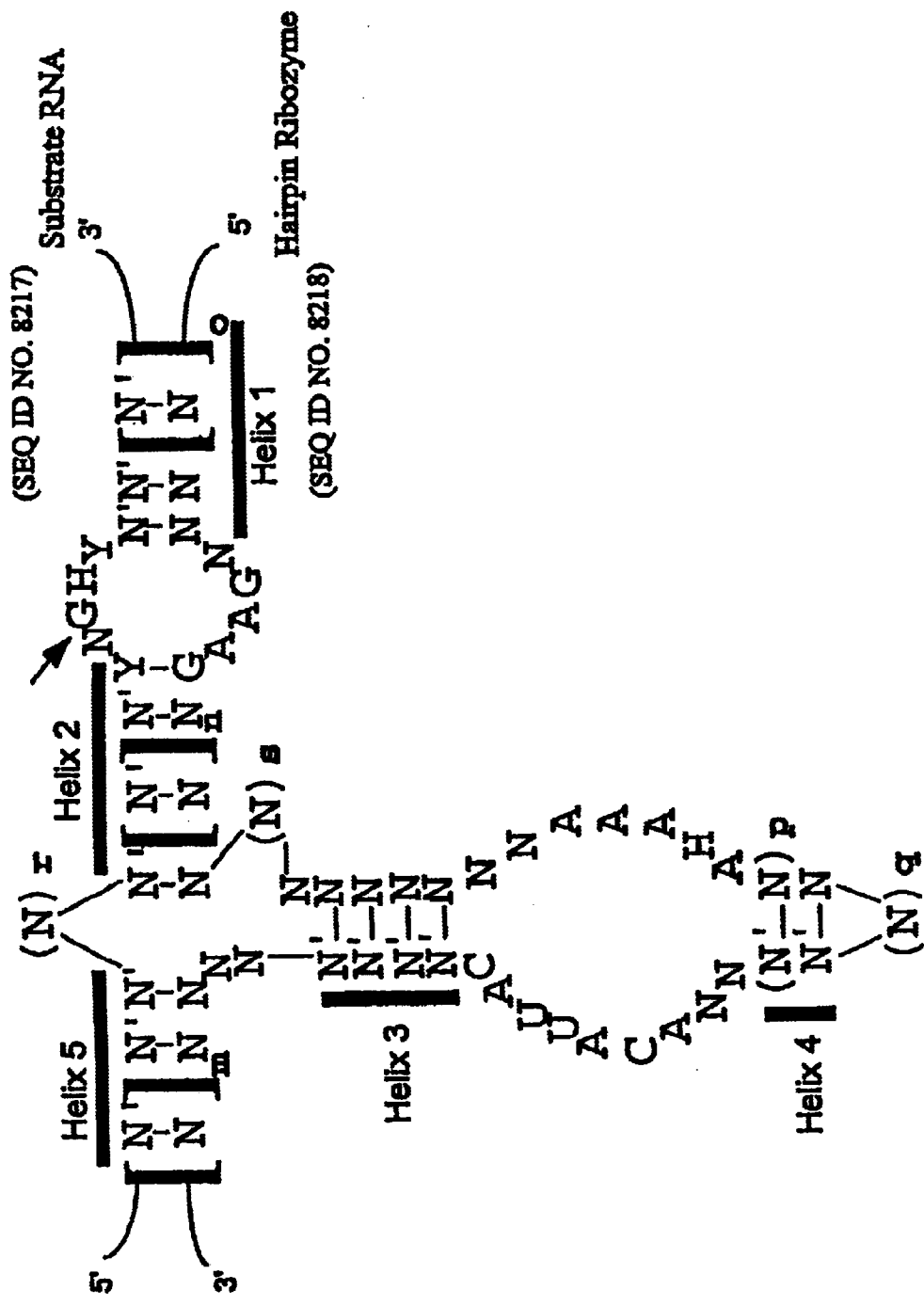

FIG. 3 is a diagramatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases. i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base, and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "_" refers to a covalent bond. (SEQ ID NO: 8217–8218)

Figure 4:
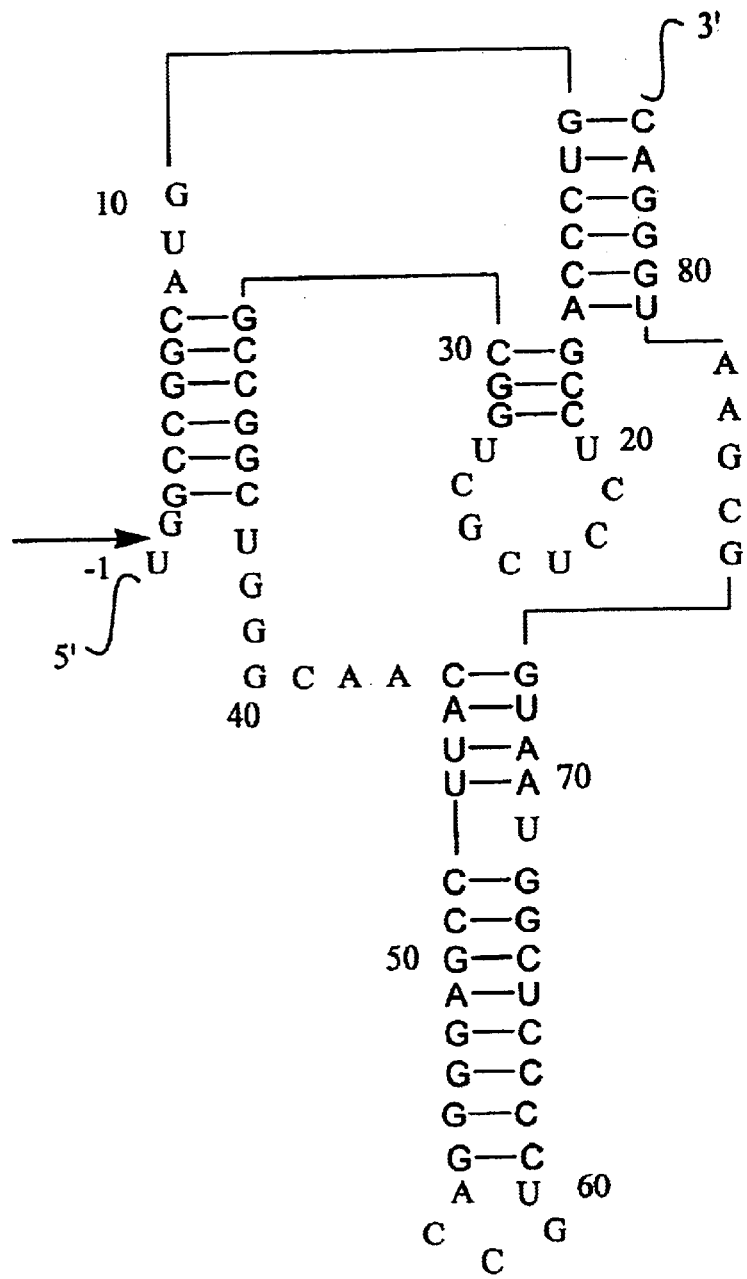

FIG. 4 is a representation of the general structure of the hepatitis delta virus ribozyme domain known in the art. (SEQ ID NO: 8219)

Figure 5:
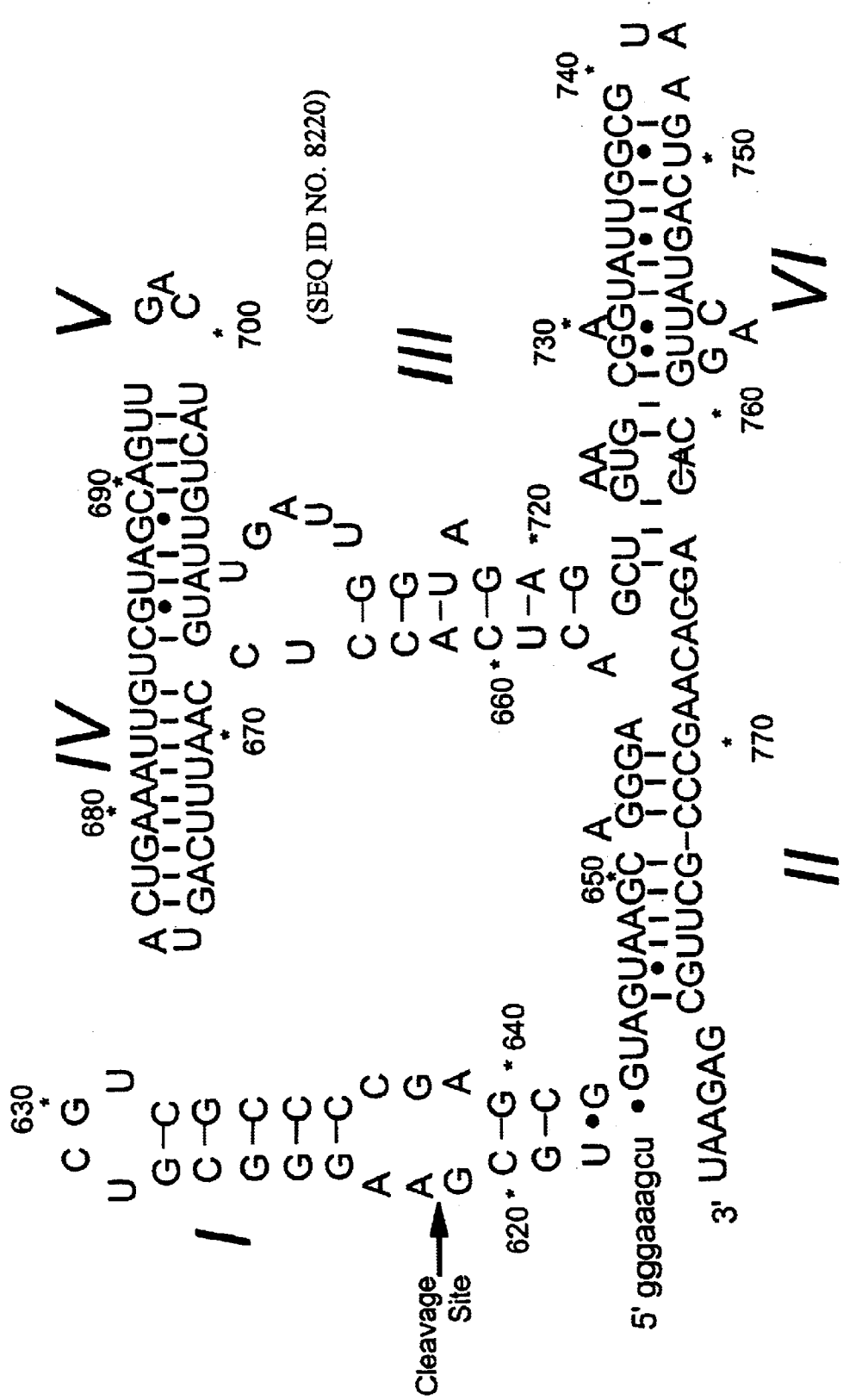

FIG. 5 is a representation of the general structure of the VS RNA ribozyme domain. (SEQ ID NO: 8220)

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
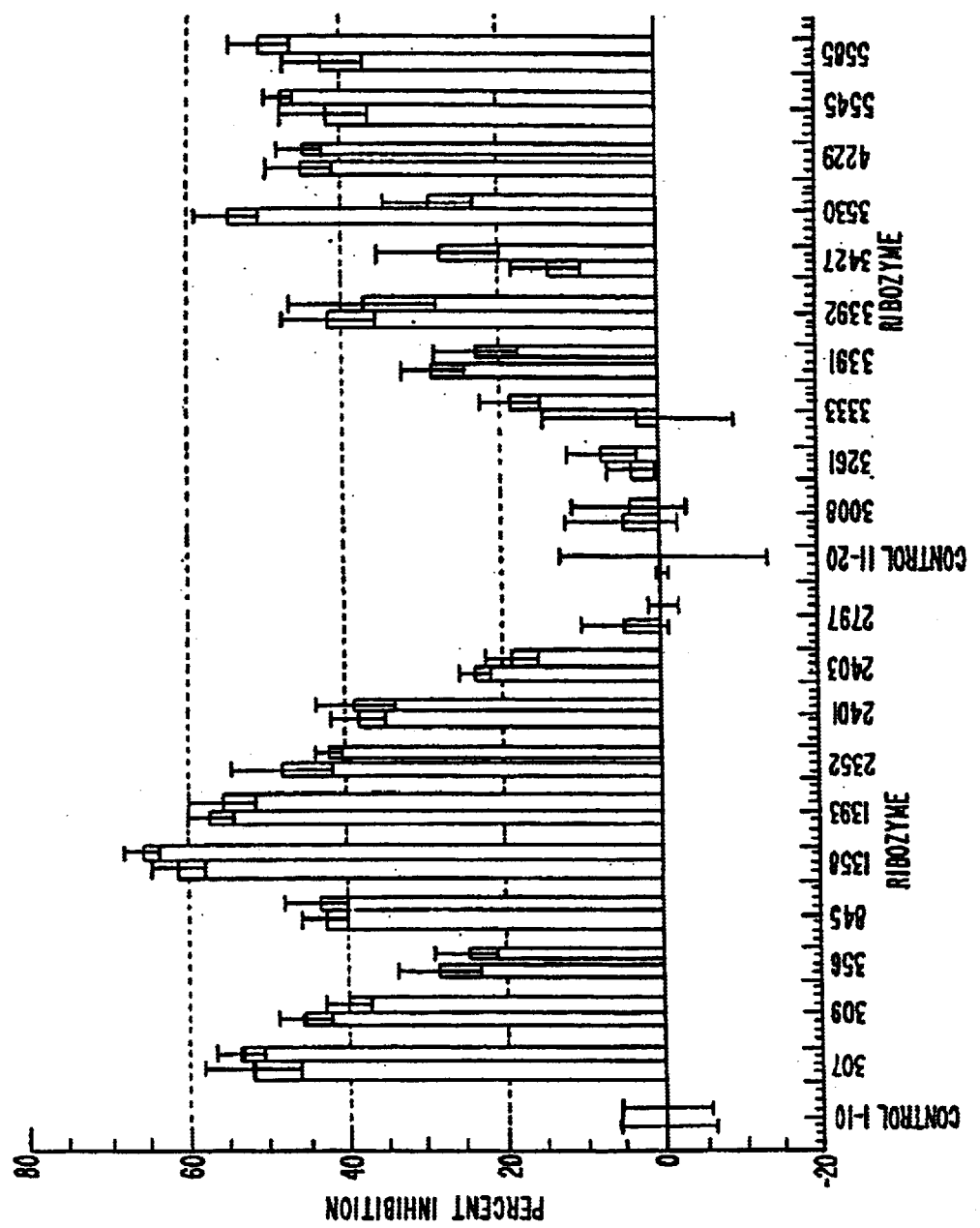

FIG. 7 shows the effect of hammerhead ribozymes targeted against flt-1 receptor on the binding of VEGF to the surface of human microvascular endothelial cells. Sequences of the ribozymes used are shown in Table II; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The results of two separate experiments are shown as separate bars for each set. Each bar represents the average of triplicate samples. The standard deviation is shown with error bars. For the flt-1 data, 500 nM ribozyme (3:1 charge ratio with LipofectAMINE®) was used. Control 1–10 is the control for ribozymes 307–2797, control 11–20 is the control for ribozymes 3008–5585. The Control 1–10 and Control 11–20 represent the treatment of cells with LipofectAMINE® alone without any ribozymes.

Figure 8:
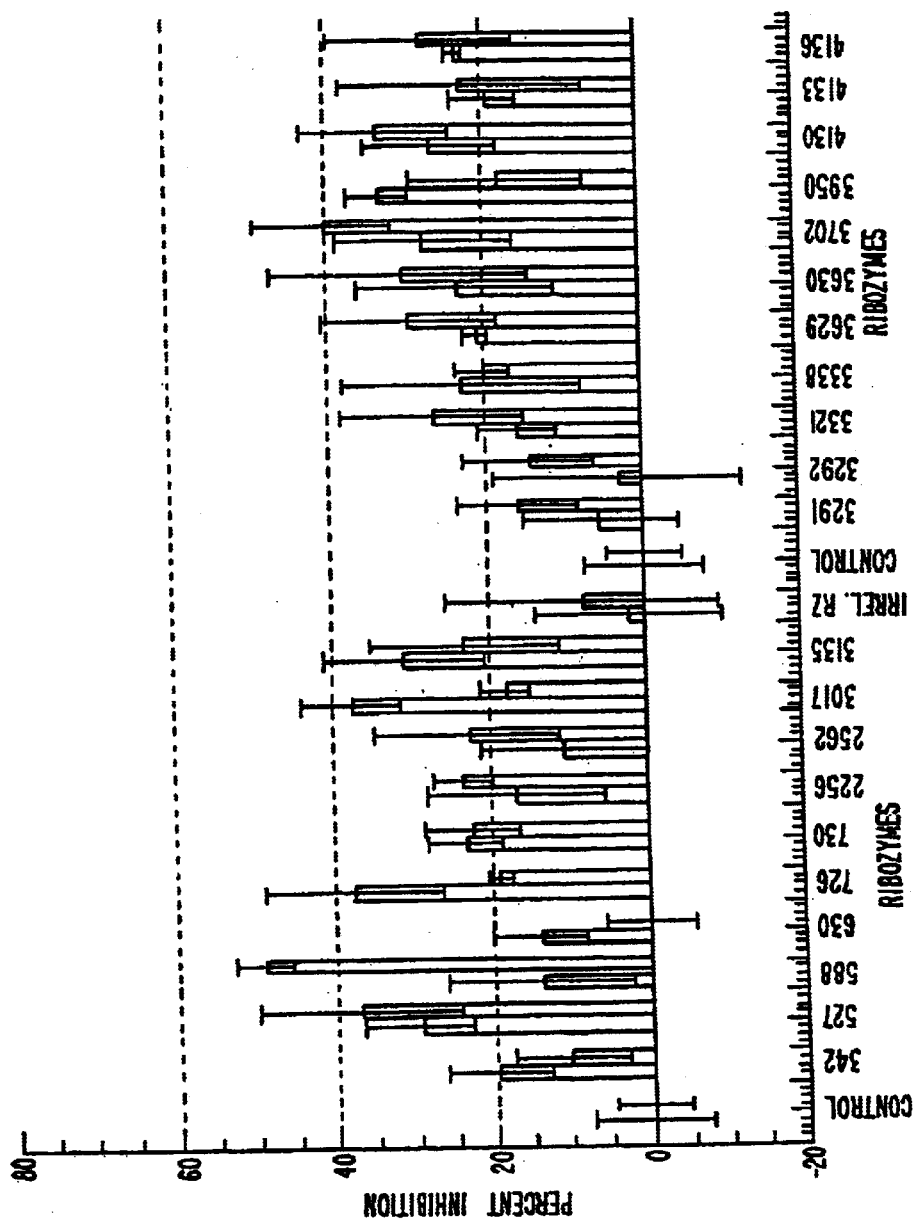

FIG. 8 shows the effect of hammerhead ribozymes targeted against KDR receptor on the binding of VEGA to KDR on the surface of human microvascular endothelial cells. Sequences of the ribozymes used are shown in Table IV; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The Control 1–10 and Control 11–20 represent the treatment of cells with LipofectAMINE®) alone without any ribozymes. Irrel. RZ, is a control experiment wherein the cells are treated with a non-KDR-targeted ribozyme complexed with Lipofectamine®. 200 nM ribozyme (3:1 charge ratio with LipofectAMINE(®) was used. In addition to the KDR-targeted ribozymes, the effect on VEGF binding of a ribozyme targeted to an irrelevant mRNA (irrel. RZ) is also shown. Because the affinity of KDR for VEGF is about 10-fold lower than the affinity of flt-1 for VEGF, a higher concentration of VEGF was used in the binding assay.

Figure 9:
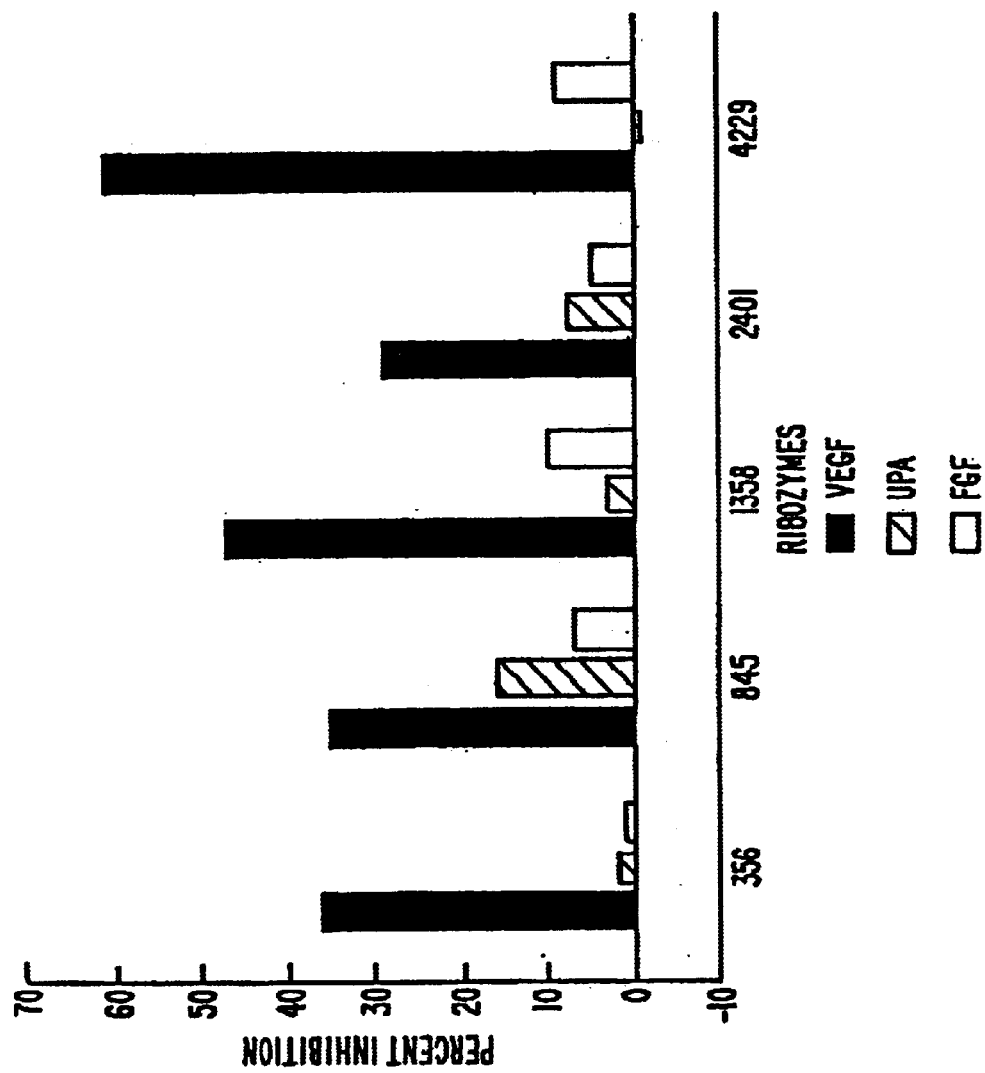

FIG. 9 shows the specificity of hammerhead ribozymes targeted against flt-1 receptor. Inhibition of the binding of VEGF, urokinase plasminogen activator (UPA) and fibroblast growth factor (FGF) to their corresponding receptors as a function of anti-FLT ribozymes is shown. The sequence and description of the ribozymes used are as described under FIG. 7 above. The average of triplicate samples is given; percent inhibition as calculated below.

Figure 10:
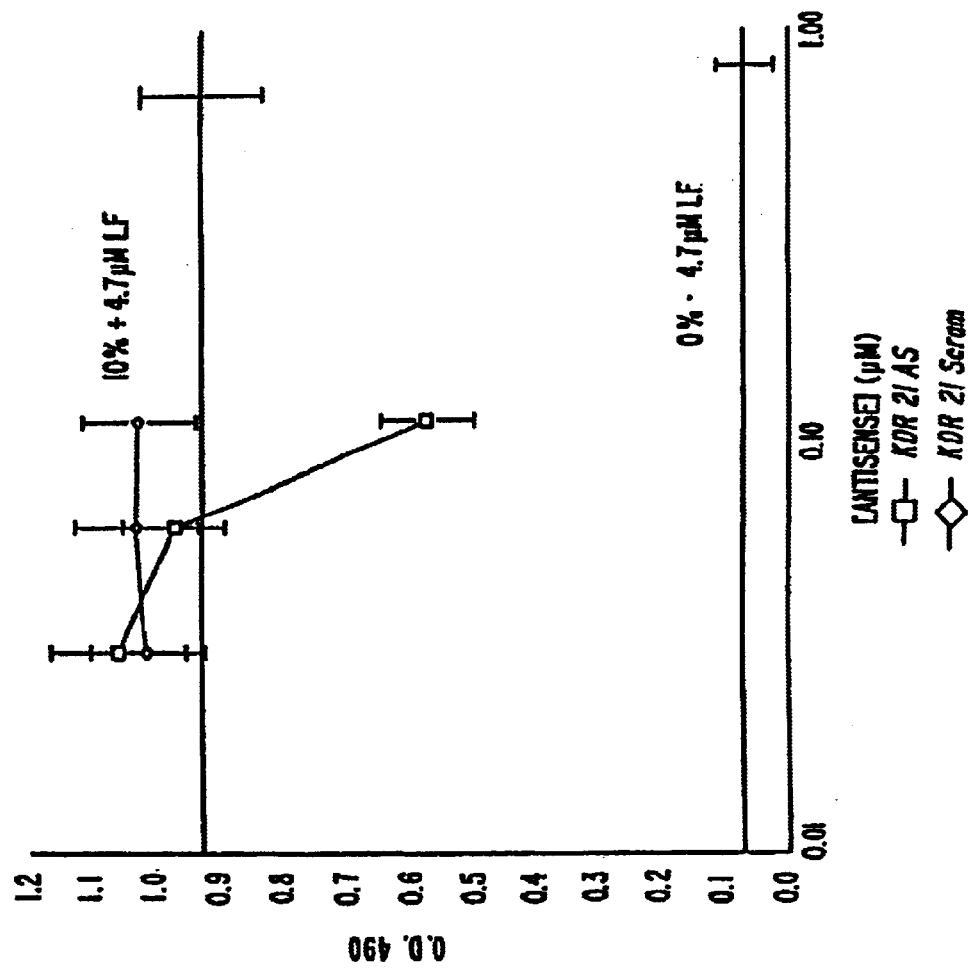

FIG. 10 shows the inhibition of the proliferation of Human aortic endothelial cells (HAEC) mediated by phosphorothioate antisense oligodeoxynucleotides targeted against human KDR receptor RNA. Cell proliferation (O.D. 490) as a function of antisense oligodeoxynucleotide concentration is shown. KDR 21AS represents a 21 nt phosphorothioate antisense oligodeoxynucleotide targeted against KDR RNA. KDR 21 Scram represents a 21 nt phosphorothioate oligodeoxynucleotide having a scrambled sequence. LF represents the lipid carrier Lipofectin.

FIGS. 11A1–11C shows in vitro cleavage of flt-1 RNA by hammerhead ribozymes. A1–A2) diagrammatic representation of hammerhead ribozymes targeted against flt-1 RNA. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose (designated as 3'-iH). 1358 HH-A and 4229 HH-A contain 3 base-paired stem II region. 1358 HH-B and 4229 HH-B contain 4 base-paired stem II region. B (SEQ ID NO: 8221–8222, 8224–8226) and C) show in vitro cleavage kinetics of HH ribozymes targeted against sites 1358 and 4229 within the flt-1 RNA.

FIGS. 12A1–12B shows inhibition of human microvascular endothelial cell proliferation mediated by anti-flt-1 hammerhead ribozymes. A) Diagrammatic representation of hammerhead (HH) ribozymes targeted against sites 1358 and 4229 within the the flt-1 RNA. B) Graphical representation of the inhibition of cell proliferation mediated by 1358HH and 4229HH ribozymes.(SEQ ID NO: 8221–8222, 8224–8225, 8228)

Figure 13:
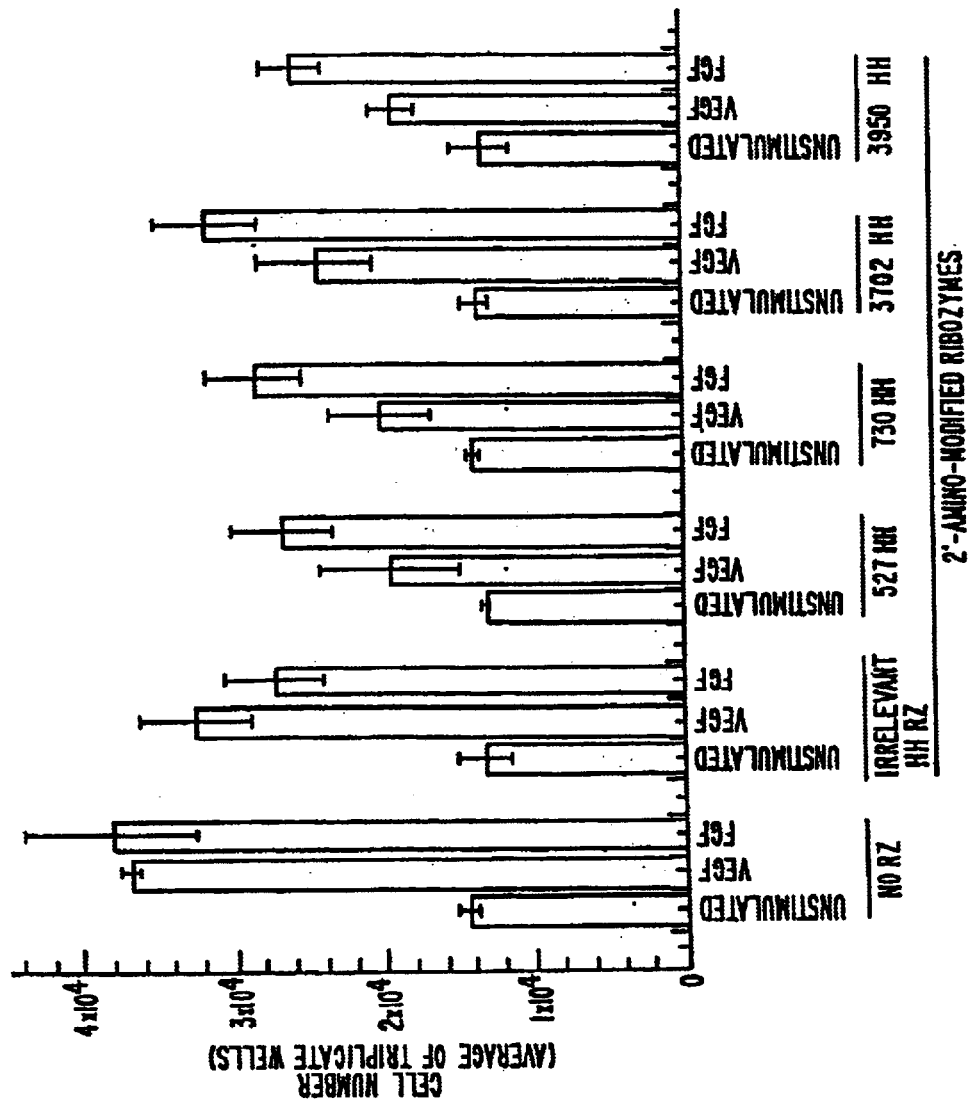

FIG. 13 shows inhibition of human microvascular endothelial cell proliferation mediated by anti-KDR hammerhead ribozymes. The figure is a graphical representation of the inhibition of cell proliferation mediated by hammerhead ribozymes targeted against sites 527, 730, 3702 and 3950 within the KDR RNA. Irrelevant HH RZ is a hammerhead ribozyme targeted to an irrelevant target. All of these ribozymes, including the Irrelevant HH RZ, were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 14:
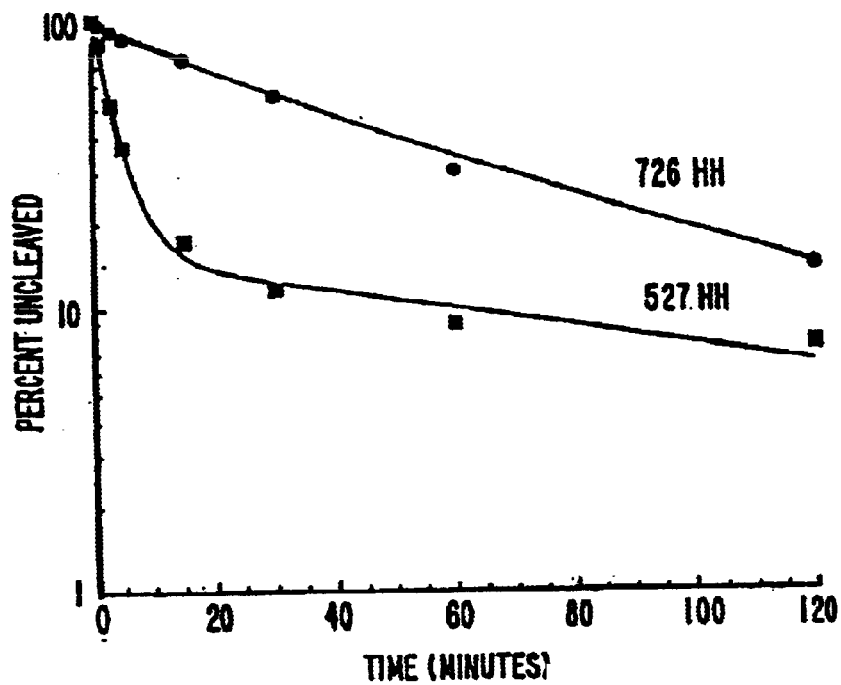

FIG. 14 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 726 HH and 527 HH contain 4 base-paired stem II region. Percent in vitro cleavage kinetics as a function of time of HH ribozymes targeted against sites 527 and 726 within the KDR RNA is shown.

Figure 15:
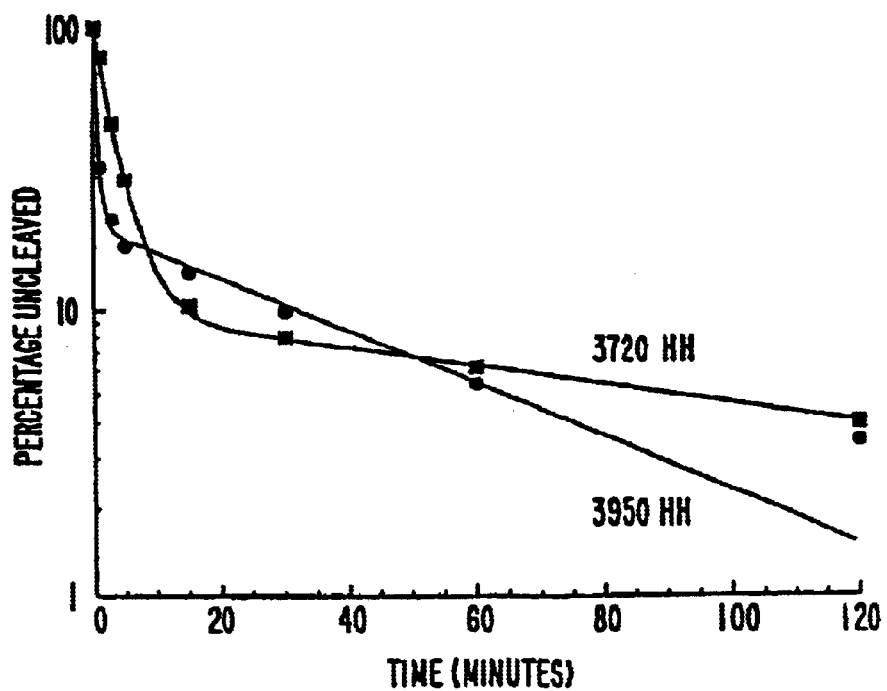

FIG. 15 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 3702 HH and 3950 HH contain 4 base-paired stem II region. Percent in vitro cleavage kinetics as a function of time of HH ribozymes targeted against sites 3702 and 3950 within the KDR RNA is shown.

Figure 16:
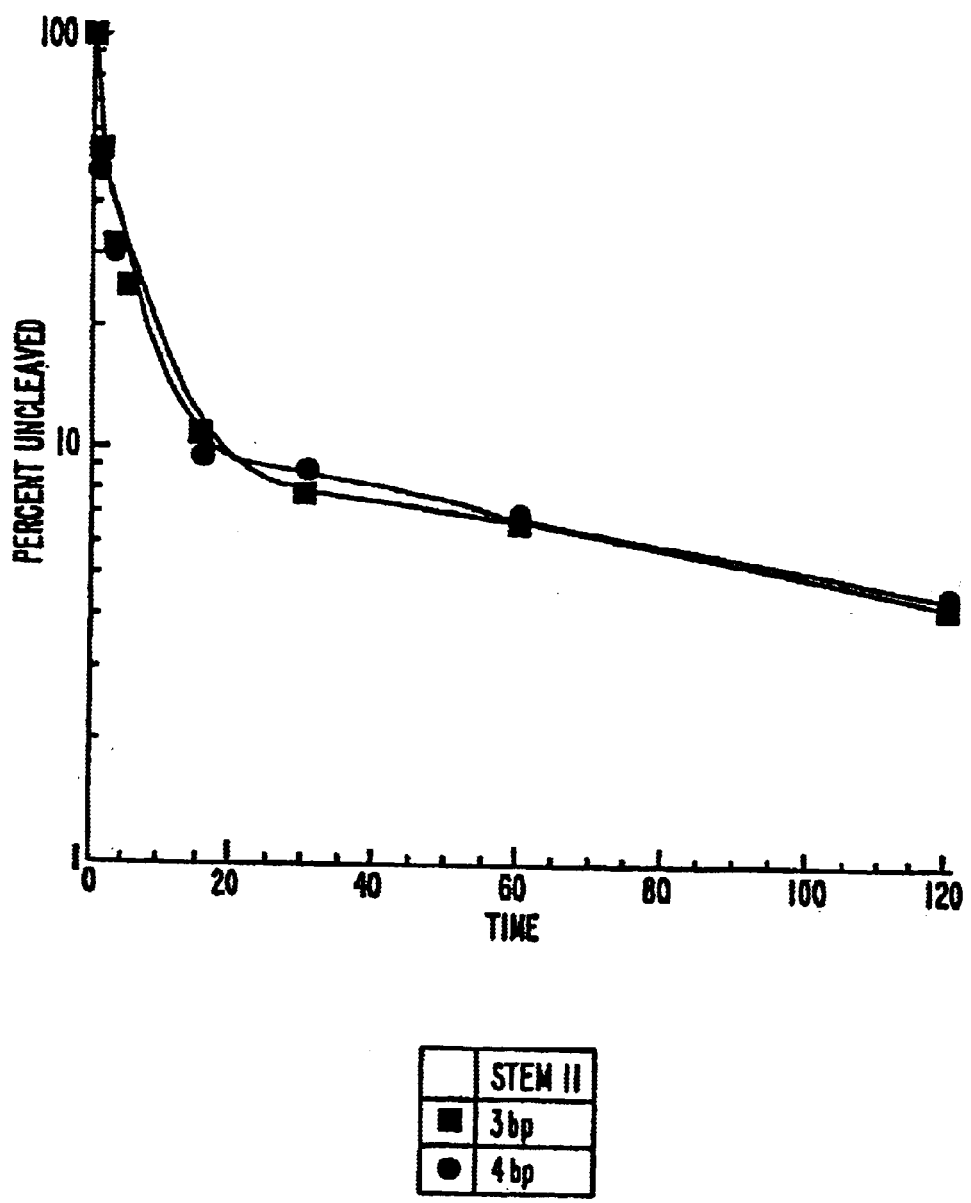

FIG. 16 shows in vitro cleavage of RNA by hammerhead ribozymes that are targeted to sites that are conserved between flt-1 and KDR RNA. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). FLT/KDR-I HH ribozyme was synthesized with either a 4 base-paired or a 3 base-paired stem II region. FLT/KDR-I HH can cleave site 3388 within flt-1 RNA and site 3151 within KDR RNA. Percent in vitro cleavage kinetics as a function of time of HH ribozymes targeted against sites 3702 and 3950 within the KDR RNA is shown.

Figure 17:
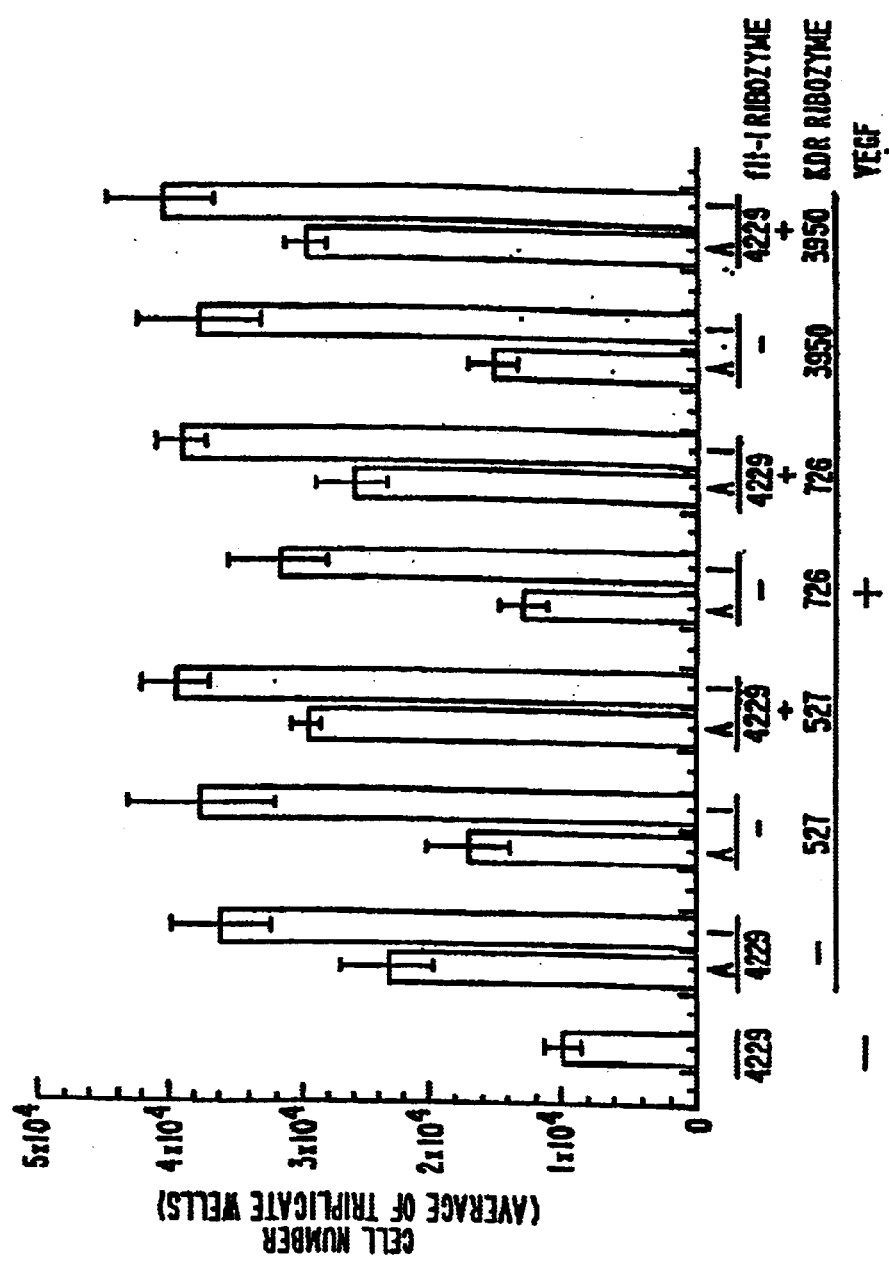

FIG. 17 shows inhibition of human microvascular endothelial cell proliferation mediated by anti-KDR and anti-flt-1 hammerhead ribozymes. The figure is a graphical representation of the inhibition of cell proliferation mediated by hammerhead ribozymes targeted against sites KDR sites –527, 726 or 3950 or flt-1 site 4229. The figure also shows enhanced inhibition of cell proliferation by a combination of flt-1 and KDR hammerhead ribozymes. 4229+527, indicates the treatment of cells with both the flt 4229 and the KDR 527 ribozymes. 4229+726, indicates the treatment of cells with both the flt 4229 and the KDR 726 ribozymes. 4229+3950, indicates the treatment of cells with both the flt 4229 and the KDR 3950 ribozymes. VEGF –, indicates the basal level of cell proliferation in the absence of VEGF. A, indicates catalytically active ribozyme; I, indicates catalytically inactive ribozyme. All of these ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 18:
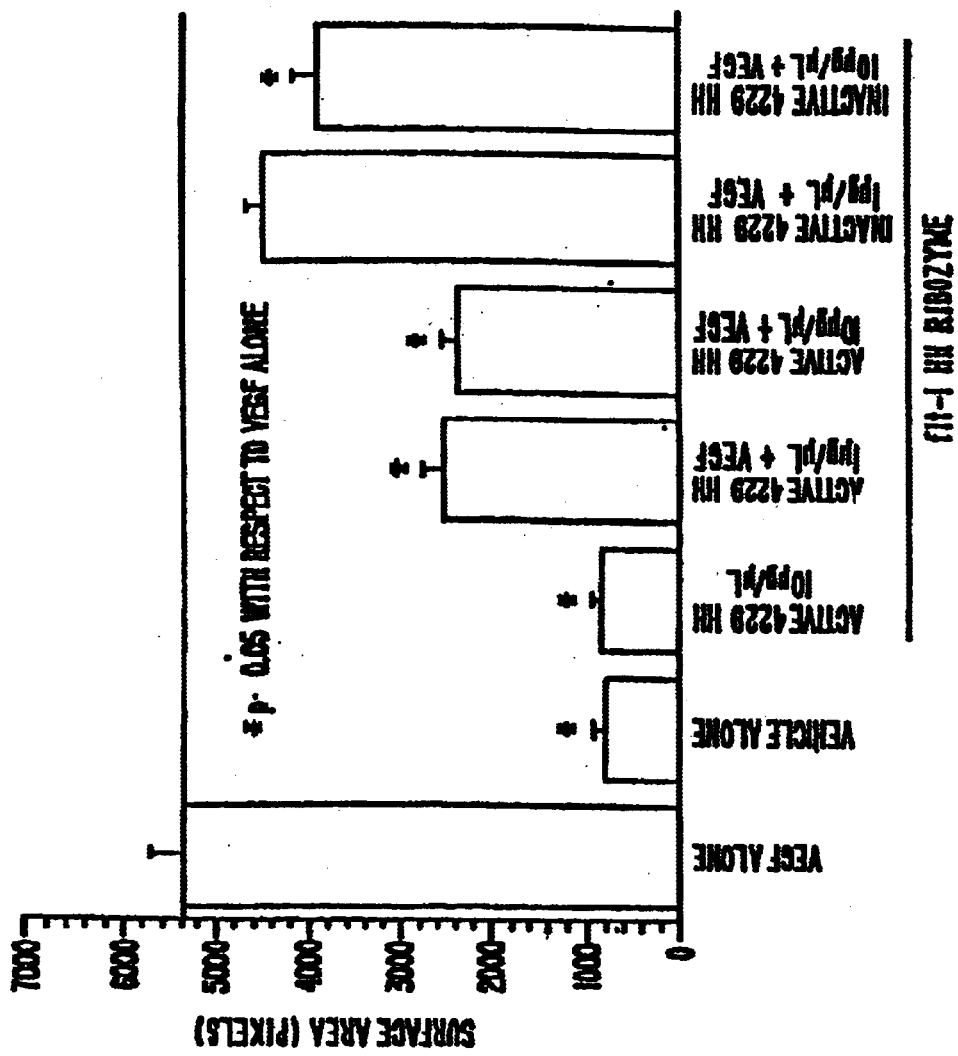

FIG. 18 shows the inhibition of VEGF-induced angiogenesis in rat cornea mediated by anti-flt-1 hammerhead ribozyme. All of these ribozymes were chemically modified such that the ribozyme consists of ribose residues at five positions; U4 position contains 2'-C-allyl modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH). A decrease in the Surface Area corresponds to a reduction in angiogenesis. VEGF alone, corresponds to treatment of the cornea with VEGF and no ribozymes. Vehicle alone, corresponds to the treatment of the cornea with the carrier alone and no VEGF. This control gives a basal level of Surface Area. Active 4229 HH, corresponds to the treatment of cornea with the flt-1 4229 HH ribozyme in the absence of any VEGF. This control also gives a basal level of Surface Area. Active 4229 HH+VEGF, corresponds to the co-treatment of cornea with the flt-1 4229 HH ribozyme and VEGF. Inactive 4229 HH+VEGF, corresponds to the co-treatment of cornea with a catalytically inactive version of 4229 HH ribozyme and VEGF.

RIBOZYMES

Ribozymes of this invention block to some extent VEGF-R (specifically flt-1 and flk-1/KDR) production and can be used to treat disease or diagnose such disease. Ribozymes will be delivered to cells in culture, to cells or tissues in animal models of angiogenesis and/or RA and to human cells or tissues ex vivo or in vivo. Ribozyme cleavage of VEGF–R RNAs (specifically RNAs that encode flt-1 and flk-1/KDR) in these systems may alleviate disease symptoms.

Target Sites

Targets for useful ribozymes can be determined as disclosed in Draper et al., International PCT Publication No. WO 95/13380, and hereby incorporated by reference herein in totality. Other examples include the following PCT applications which concern inactivation of expression of disease-related genes: WO 95/23225, WO 95/13380, WO 94/02595, incorporated by reference herein. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human and mouse flt-1, KDR and/or flk-1 mRNAs were screened for optimal ribozyme target sites using a computer folding algorithm. Hammerhead or hairpin ribozyme cleavage sites were identified. These sites are shown in Tables II to IX (all sequences are 5' to 3' in the tables; X can be any base-paired sequence, the actual sequence is not relevant here). The nucleotide base position is noted in the Tables as that site to be cleaved by the designated type of ribozyme. While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and cleave target RNA in a sequence-specific manner. The ribozymes were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity.

Referring to FIG. 6, mRNA is screened for accessible cleavage sites by the method described generally in Draper et al., PCT WO93/23569, hereby incorporated by reference herein. Briefly, DNA oligonucleotides complementary to potential hammerhead or hairpin ribozyme cleavage sites were synthesized. A polymerase chain reaction is used to generate substrates for T7 RNA polymerase transcription from human and mouse flt-1, KDR and/or flk-1 cDNA clones. Labeled RNA transcripts are synthesized in vitro from the templates. The oligonucleotides and the labeled transcripts were annealed, RNAseH was added and the mixtures were incubated for the designated times at 37° C. Reactions are stopped and RNA separated on sequencing polyacrylamide gels. The percentage of the substrate cleaved is determined by autoradiographic quantitation using a PhosphorImaging system. From these data, hammerhead or hairpin ribozyme sites are chosen as the most accessible.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table XI outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer : detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of $EtOH:MeCN:H_2O/3:1:1$, vortexed and the supernatant was then added to the first supernatant. The combined supernatants, containing the oligoribonucleotide, were dried to a white powder.

The base-deprotected oligoribonucleotide was resuspended in anhydrous TEA.HF/NMP solution (250 μL of a solution of 1.5 mL N-methyl-pyrrolidinone, 750 μL TEA and 1.0 mL TEA3.HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for G5 and a U for A14 (numbering from Hertel, K. J., et al., 1992, Nucleic Acids Res., 20, 3252). The average stepwise coupling yields were >98% (Wincott et al., 1995 Nucleic Acids Res. 23, 2677–2684).

Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51).

All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 TIBS 17, 34; Usman et al., 1994 Nucleic Acids Symp. Ser. 31, 163). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 Wincott et al., Supra, the totality of which is hereby incorporated herein by reference) and are resuspended in water.

The sequences of the ribozymes that are chemically synthesized, useful in this study, are shown in Tables II to IX. Those in the art will recognize that these sequences are representative only of many more such sequences where the enzymatic portion of the ribozyme (all but the binding arms) is altered to affect activity. Stem-loop IV sequence of hairpin ribozymes listed in for example Table III (5'-CACGUUGUG-3') can be altered (substitution, deletion, and/or insertion) to contain any sequence, provided a minimum of two base-paired stem structure can form. The sequences listed in Tables II to IX may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No.

WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; Rossi et al., International Publication No. WO 91/03162; Beigelman et al., 1995 J. Biol Chem. in press; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

Sullivan, et al., supra, describes the general methods for delivery of enzymatic RNA molecules. Ribozymes may be administered to cells by a variety of methods known to those familiar to the art, including, but not restricted to, encapsulation in liposomes. by iontophoresis, or by incorporation into other vehicles. such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et aL, supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 Proc. Natl. Acad. Sci. U S A, 87, 6743–7; Gao and Huang 1993 Nucleic Acids Res., 21, 2867–72; Lieber et al., 1993 Methods Enzymol., 217, 47–66; Zhou et al., 1990 Mol. Cell. Biol., 10, 4529–37; Thompson et al., 1995 supra). Several investigators have demonstrated that ribozymes expressed from such promoters can function in mammalian cells (e.g. Kashani-Sabet et al., 1992 Antisense Res. Dev., 2, 3–15; Ojwang et al., 1992 Proc. Natl. Acad. Sci. U S A, 89,10802–6; Chen et al., 1992 Nucleic Acids Res., 20, 4581–9; Yu et al., 1993 Proc. Natl. Acad. Sci. U S A, 90, 6340–4; L'Huillier et al., 1992 EMBO J. 11, 4411–8; Lisziewicz et al., 1993 Proc. Natl. Acad. Sci. U. S. A., 90, 8000–4; Thompson et al., 1995 Nucleic Acids Res. 23, 2259). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves RNAs that encode flt-1, KDR and/or flk-1 are inserted into a plasmid DNA vector or an adenovirus or adeno-associated virus DNA viral vector or a retroviral RNA vector. Viral vectors have been used to transfer genes and lead to either transient or long term gene expression (Zabner et aL, 1993 Cell 75, 207; Carter, 1992 Curr. Opi. Biotech. 3, 533). The adenovirus, AAV or retroviral vector is delivered as recombinant viral particles. The DNA may be delivered alone or complexed with vehicles (as described for RNA above). The recombinant adenovirus or AAV or retroviral particles are locally administered to.,the site of, treatment, e.g., through incubation or inhalation in vivo or by direct application to cells or tissues ex vivo. Retroviral vectors have also been used to express ribozymes in mammalian cells (Ojwang et al., 1992 supra; Thompson et al., 1995 supra).

flt-1, KDR and/or flk-1 are attractive nucleic acid-based therapeutic targets by several criteria. The interaction between VEGF and VEGF-R is well-established. Efficacy can be tested in well-defined and predictive animal models. Finally, the disease conditions are serious and current therapies are inadequate. Whereas protein-based therapies would inhibit VEGF activity nucleic acid-based therapy provides a direct and elegant approach to directly modulate flt-1, KDR and/or flk-1 expression.

Because flt-1 and KDR mRNAs are highly homologous in certain regions, some ribozyme target sites are also homologous (see Table X). In this case, a single ribozyme will target both flt-1 and KDR mRNAs. At partially homologous sites, a single ribozyme can sometimes be designed to accomodate a site on both mRNAs by including G/U basepairing. For example, if there is a G present in a ribozyme target site in KDR mRNA at the same position there is an A in the flt-1 ribozyme target site, the ribozyme can be synthesized with a U at the complementary position and it will bind both to sites. The advantage of one ribozyme that targets both VEGF-R mRNAs is clear, especially in cases where both VEGF receptors may contribute to the progression of angiogenesis in the disease state.

"Angiogenesis" refers to formation of new blood vessels which is an essential process in reproduction, development and wound repair. "Tumor angiogenesis" refers to the induction of the growth of blood vessels from surrounding tissue into a solid tumor. Tumor growth and tumor metastasis are dependent on angiogenesis (for a review see Folkman, 1985 supra; Folkman 1990 J. Natl. Cancer Inst., 82, 4; Folkman and Shing, 1992 J. Biol. Chem. 267, 10931).

Angiogenesis plays an important role in other diseases such as arthritis wherein new blood vessels have been shown to invade the joints and degrade cartilage (Folkman and Shing, supra).

"Retinopathy" refers,to inflammation of the retina and/or degenerative condition of the retina which may lead to occlusion of the retina and eventual blindness. In "diabetic retinopathy" angiogenesis causes the capillaries in the retina to invade the vitreous resulting in bleeding and blindness which is also seen in neonatal retinopathy (for a review see Folkman, 1985 supra; Folkman 1990 supra; Folkman and Shing, 1992 supra).

EXAMPLE 1 flt-1, KDR and/or flk-1 Ribozymes

By engineering ribozyme motifs applicant has designed several ribozymes directed against flt-1, KDR and/or flk-1 encoded mRNA sequences. These ribozymes were synthesized with modifications that improve their nuclease resistance (Beigelman et al., 1995 *J Biol. Chem.* 270, 25702) and enhance their activity in cells. The ability of ribozymes to cleave target sequences in vitro was evaluated essentially as described in Thompson et al., PCT Publication No. WO 93/23057; Draper et al., PCT Publication No. WO 95/04818.

EXAMPLE 2

Effect of Ribozymes on the Binding of VEGF to flt-1, KDR and/or flk-1 Receptors Several common human cell lines are available that express endogenous flt-1, KDR and/or flk-1, flt-1, KDR and/or flk-1 can be detected easily with monoclonal antibodies. Use of appropriate fluorescent reagents and fluorescence-activated cell-sorting (FACS) will permit direct quantitation of surface flt-1, KDR and/or flk-1 on a cell-by-cell basis. Active ribozymes are expected to directly educe flt-1, KDR and/or flk-1 expression and thereby reduce VEGF binding to the cells. In this example, human umbelical cord microvascular endothelial cells were used.

Cell Preparation

Plates are coated with 1.5% gelatin and allowed to stand for one hour. Cells (e.g., microvascular endothelial cells derived from human umbilical cord vein) are plated at 20,000 cells/well (24 well plate) in 200 µl growth media and incubated overnight (~1 doubling) to yield ~40,000 cells (75–80% confluent).

Ribozyme Treatment

Media is removed from cells and the cells are washed two times with 300 µl 1×PBS: $Ca^{2+}$: $Mg^{2+}$ mixture. A complex of 200–500 nM ribozyme and LipofectAMINE® (3:1 lipid:phosphate ratio) in 200 µl OptiMEM® (5% FBS) was added to the cells. The cells are incubated for 6 hr (equivalent to 2–3 VEGF–R turnovers).

$^{125}I$ VEGF Binding Assay

The assay is carried out on ice to inhibit internalization of VEGF during the experiment. The media containing the ribozyme is removed from the cells and the cells are washed twice with with 300 µl 1×PBS: $Ca^{2+}$: $Mg^{2+}$ mixture containing 1% BSA. Appropriate $^{125}I$ VEGF solution (100,000 cpm/well, +/−10 × cold 1×PBS, 1% BSA) was applied to the cells. The cells are incubated on ice for 1 h. $^{125}I$ VEGF-containing solution is removed and the cells are washed three times with with 300 µl 1×PBS: $Ca^{2+}$: $Mg^{2+}$ mixture containing 1% BSA. To each well 300 µl of 100 mM Tris-HCl, pH 8.0, 0.5% Triton X-100 was added and the the mixture was incubated for 2 min. The $^{125}I$ VEGF-binding was quantitated using standard scintillation counting techniques. Percent inhibition was calculated as follows:

$$Percent\ Inhibition = \frac{cpm^{125}|VEGF\ bound\ by\ the\ ribozyme\text{-}treated\ samples}{cpm^{125}|VEGF\ bound\ by\ the\ Control\ sample} \times 100$$

EXAMPLE 3

Effect of Hammerhead Ribozymes Targeted Against flt-1 Receptor on the Binding of VEGF Hammerhead ribozymes targeted to twenty sites within flt-1 RNA were synthesized as described above. Sequence of the ribozymes used are shown in Table II; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, 3' end of the ribozyme contains a 3'-3' linked inverted abasic ribose.

Referring to FIG. 7, the effect of hammerhead ribozymes targeted against flt-1 receptor on the binding of VEGF to flt-1 on the surface of human microvascular endothelial cells is shown. The majority of the ribozymes tested were able to inhibit the expression of flt-1 and thereby were able to inhibit the binding of VEGF.

In order to determine the specificity of ribozymes targeted against flt-1 RNA, the effect of five anti-flt-1 ribozymes on the binding of VEGF, UPA (urokinase plasminogen activator) and FGF (fibroblast growth factor) to their corresponding receptors were assayed. As shown in FIG. 9, there was significant inhibition of VEGF binding to its receptors on cells treated with anti-flt-1 ribozymes. There was no specific inhibition of the binding of UPA and FGF to their corresponding receptors. These data strongly suggest that anti-flt-1 ribozymes specifically cleave flt-1 RNA and not RNAs encoding the receptors for UPA and FGF, resulting in the inhibition of flt-1 receptor expression on the surface of the cells. Thus the ribozymes are responsible for the inhibition of VEGF binding but not the binding of UPA and FGF.

EXAMPLE 4

Effect of Hammerhead Ribozymes Targeted Against KDR Receptor on the Binding of VEGF Hammerhead ribozymes targeted to twenty one sites within KDR RNA were synthesized as described above. Sequence of the ribozymes used are shown in Table IV; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose.

Referring to FIG. 8, the effect of hammerhead ribozymes targeted against KDR receptor on the binding of VEGF to KDR on the surface of human microvascular endothelial cells is shown. A majority of the ribozymes tested were able to inhibit the expression of KDR and thereby were able to inhibit the binding of VEGF. As a control, the cells were treated with a ribozyme that is not targeted towards KDR RNA (irrel. RZ); there was no specific inhibition of VEGF binding. The results from this control experiment strongly suggest that the inhibition of VEGF binding observed with anti-KDR ribozymes is a ribozyme-mediated inhibition.

EXAMPLE 5

Effect of Ribozymes Targeted Against VEGF Receptors on Cell Proliferation

Cell Preparation 24-well plates are coated with 1.5% gelatin (porcine skin 300 bloom). After 1 hr, excess gelatin is washed off of the plate. Microvascular endothelial cells are plated at 5,000 cells/well (24 well plate) in 200 µl growth media. The cells are allowed to grow for ~18 hr (~1 doubling) to yield ~10,000 cells (25–30% confluent).

Ribozyme Treatment

Media is removed from the cells, and the cells are washed two times with 300 µl 1×PBS: $Ca^{2+}$: $Mg^{2+}$ mixture.

For anti-flt-1 HH ribozyme experiment (FIG. 12) a complex of 500 nM ribozyme; 15 µM LFA (3:1 lipid:phosphate ratio) in 200 µl OptiMEM (5% FCS) media was added to the cells. Incubation of cells is carried out for 6 hr (equivalent to 2–3 VEGF receptor turnovers).

For anti-KDR HH ribozyme experiment (FIG. 13) a complex of 200 nM ribozyme; 5.25 µM LFA (3:1 lipid:phosphate ratio) in 200 µl OptiMEM (5% FCS) media was added to the cells. Incubation of cells is carried out for 3 hr.

Proliferation

After three or six hours, the media is removed from the cells and the cells are washed with 300 µl 1×PBS: $Ca^{2+}$: $Mg^{2+}$ mixture. Maintenance media (contains dialyzed 10% FBS) +/−VEGF or basic FGF at 10 ng/ml is added to the cells. The cells are incubated for 48 or 72 h. The cells are trypsinized and counted (Coulter counter). Trypan blue is added on one well of each treatment as control.

Figure 12B:
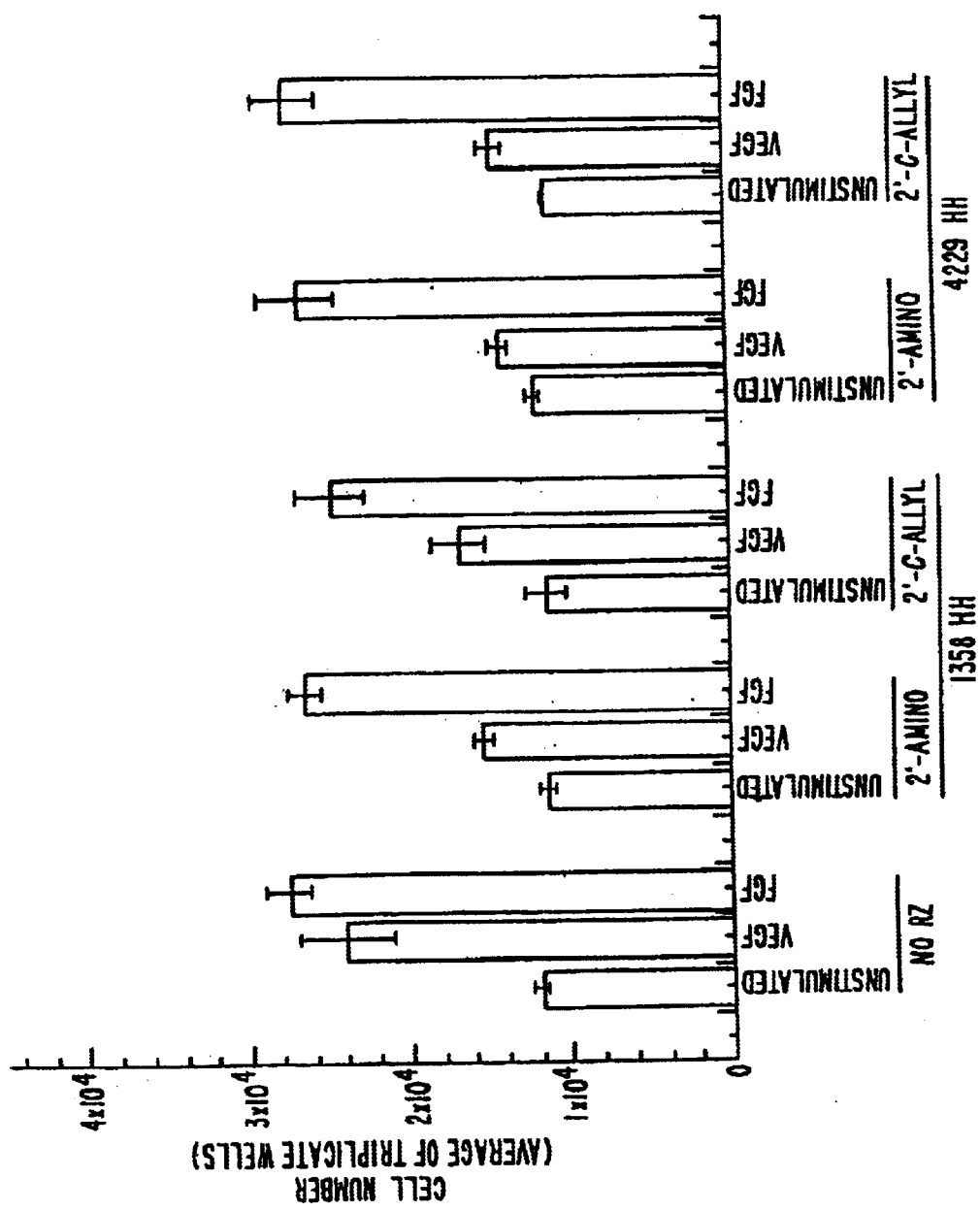

As shown in FIG. 12B, VEGF and basic FGF can stimulate human microvascular endothelial cell proliferation. However, treatment of cells with 1358 HH or 4229 HH ribozymes, targeted against flt-1 mRNA, results in a significant decrease in the ability of VEGF to stimulate endothelial cell proliferation. These ribozymes do not inhibit the FGF-mediated stimulation of endothelial cell proliferation.

Human microvascular endothalial cells were also treated with hammerhead ribozymes targeted against sites 527, 730, 3702 or 3950 within the KDR mRNA. As shown in FIG. 13, all four ribozymes caused significant inhibition of VEGF-mediated induction of cell proliferation. No significant inhibition of cell proliferation was observed when the cells were treated with a hammerhead ribozyme targeted to an irrelevant RNA. Additionally, none of the ribozymes inhibited FGF-mediated stimulation of cell proliferation.

These results strongly suggest that hammerhead ribozymes targeted against either flt-1 or KDR mRNA can specifically inhibit VEGF-mediated induction of endothelial cell proliferation.

EXAMPLE 6

Effect of Antisense Oligonucleotides Targeted Against VEGF Receptors on Cell Proliferation (Calorimetric Assay)

Following are some of the reagents used in the proliferation assay:

Cells

Human aortic endothelial cells (HAEC) from Clonetics®. Cells at early passage are preferably used.

Uptake Medium

EBM (from Clonetics®);1% L-Glutamine;20 mM Hepes;No serum;No antibiotics.

Growth Medium

EGM (from Clonetics®);FBS to 20%;1% L-Glutamine; 20 mM Hepes.

Cell Plating 96-well tissue culture plates are coated with 0.2% gelatin (50 µl/well). The gelatin is incubated in the wells at room temperature for 15–30 minutes. The gelatin is removed by aspiration and the wells are washed with PBS:$Ca^{2+}$: $Mg^{2+}$ mixture. PBS mixture is left in the wells until cells are ready to be added. HAEC cells were detached by trypsin treatment and resuspended at $1.25 \times 10^4$/ml in growth medium. PBS is removed from plates and 200 µl of cells (i.e. $2.5 \times 10^3$ cells/well) are added to each well. The cells are allowed to grow for 48 hours before the proliferation assay.

Assay

Growth medium is removed from the wells. The cells are washed twice with PBS:$Ca^{2+}$: $Mg^{2+}$ mixture without antibiotics. A formulation of lipid/antisense oligonucleotide (antisense oligonucleotide is used here as a non-limiting example) complex is added to each well (100 µl/well) in uptake medium. The cells are incubated for 2–3 hours at 37° C. in $CO_2$ incubator. After uptake, 100 µl/well of growth medium is added (gives final FBS concentration of 10%). After approximately 72 hours, 40 µl MTS® stock solution (made as described by manufacturer) was added to each well and incubated at 37° C. for 1–3 hours, depending on the color development. (For this assay, 2 hours was sufficient). The intensity of color formation was determined on a plate reader at 490 nM.

Phosphorothioate-substituted antisense oligodeoxynucleotides were custom synthesized by The Midland Certified Reagent Company®, Midland, Tex. Following non-limiting antisense oligodeoxynucleotides targeted against KDR RNA were used in the proliferation assay:

KDR 21 AS: 5'-GCA GCA CCT TGC TCT
    CCA TCC-3'     (SEQ ID NO. 8230)

SCRAMBLED CONTROL: 5'-CTG CCA ACT TCC CAT GCC
    TGC-3'     (SEQ ID NO. 8231)

As shown in FIG. 10, proliferation of HAEC cells are specifically inhibited by increasing concentrations of the phosphorothioate anti-KDR-antisense oligodeoxynucleotide. The scrambled antisense oligonucleotide is not expected to bind the KDR RNA and therefore is not expected to inhibit KDR expression. As expected, there is no detectable inhibition of proliferation of HAEC cells treated with a phosphorothioate antisense oligonucleotide with scrambled sequence.

EXAMPLE 7

In vitro Cleavage of flt-1 RNA by Hammerhead Ribozymes

Referring to FIG. 11A, hammerhead ribozymes (HH) targeted against sites 1358 and 4229 within the flt-1 RNA were synthesized as described above.

RNA Cleavage Assay In vitro

Substrate RNA was 5' end-labeled using [$\gamma$-$^{32}$P] ATP and T4 polynucleotide kinase (US Biochemicals). Cleavage reactions were carried out under ribozyme "excess" conditions. Trace amount (≦1 nM) of 5' end-labled substrate and 40 nM unlabeled ribozyme were denatured and renatured separately by heating to 90° C. for 2 min and snap-cooling on ice for 10–15 min. The ribozyme and substrate were incubated, separately, at 37° C. for 10 min in a buffer containing 50 mM Tris-HCl and 10 mM MgCl$_2$. The reaction was initiated by mixing the ribozyme and substrate solutions and incubating at 37° C. Aliquots of 5 µl are taken at regular intervals of time and the reaction is quenched by mixing with equal volume of 2×formamide stop mix. The samples are resolved on 20% denaturing polyacrylamide gels. The results were quantified and percentage of target RNA, cleaved is plotted as a function of time.

Figure 11B:
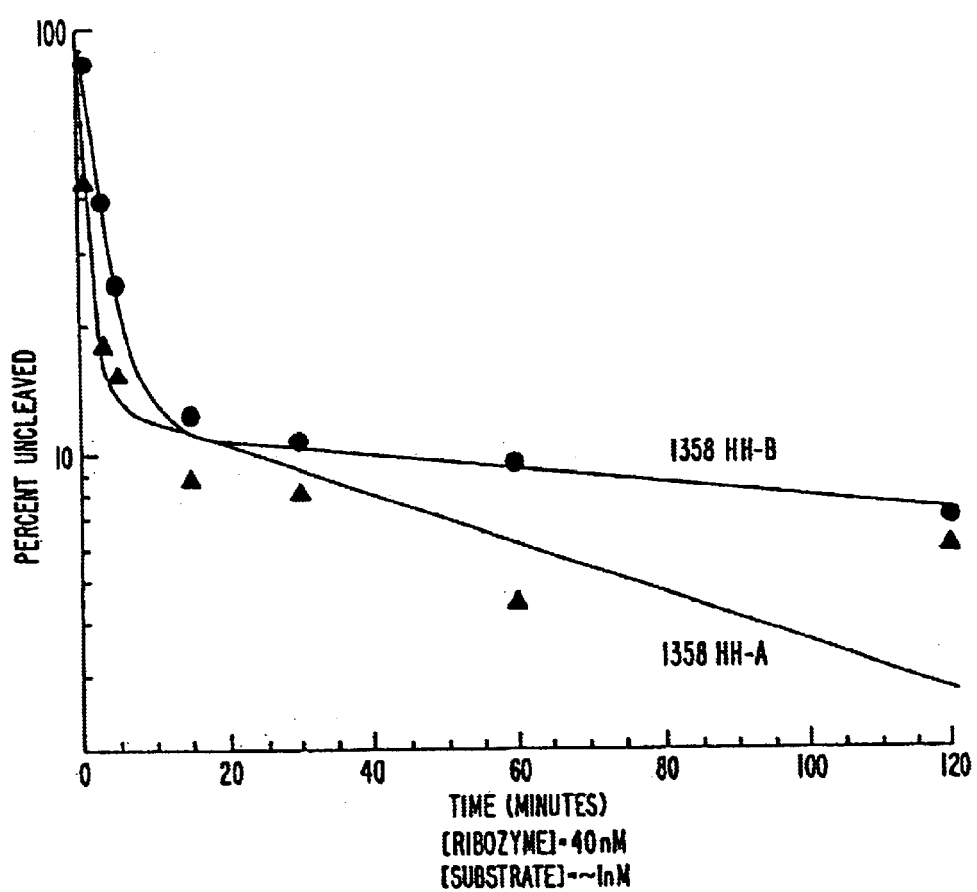
Figure 11C:
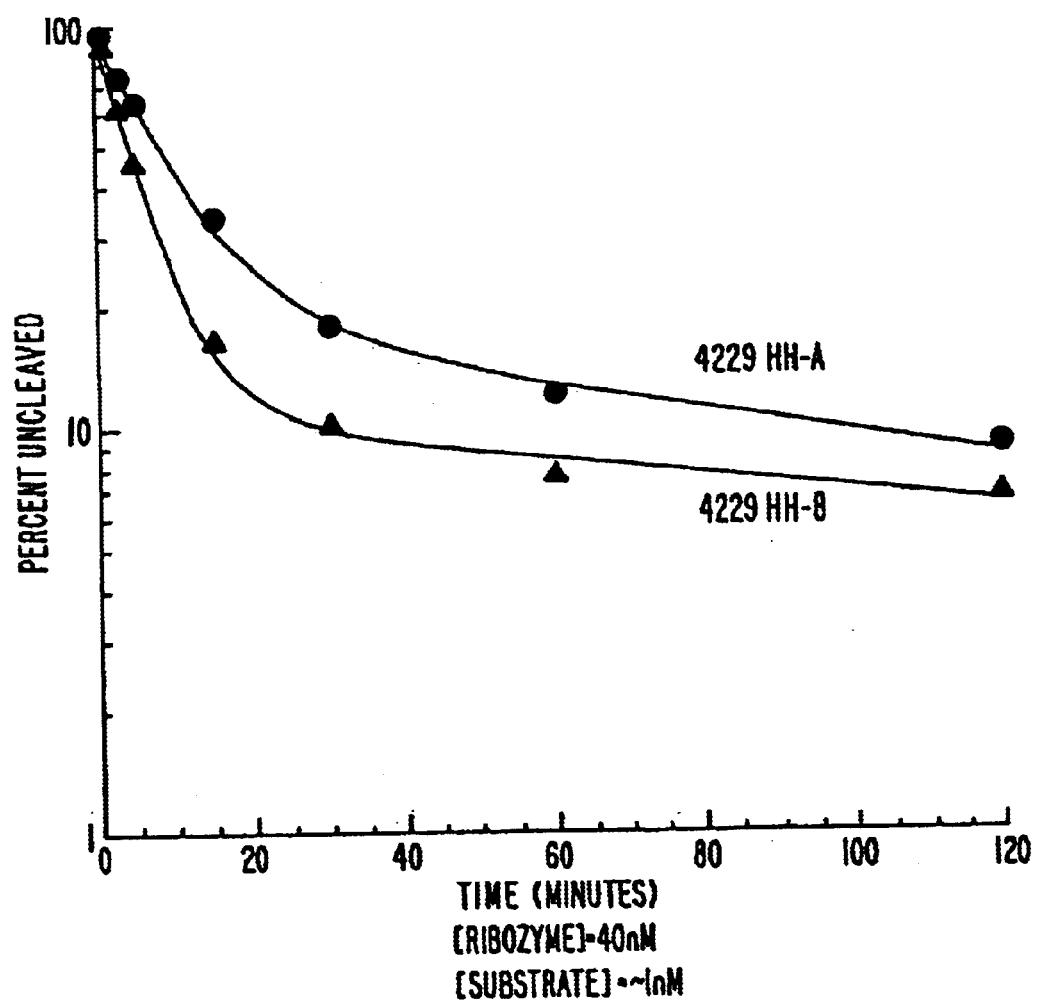

Referring to FIGS. 11B and 11C, hammerhead ribozymes targeted against sites 1358 and 4229 within the flt-1 RNA are capable of cleaving target RNA efficiently in vitro.

EXAMPLE 8

In vitro Cleavage of KDR RNA by Hammerhead Ribozymes

In this non-limiting example, hammerhead ribozymes targeted against sites 726, 527, 3702 and 3950 within KDR RNA were synthesized as described above. RNA cleavage reactions were carried out in vitro essentially as described under Example 7.

Referring to FIGS. 14 and 15, all four ribozymes were able to cleave their cognate target RNA efficiently in a sequence-specific manner.

EXAMPLE 9

In vitro Cleavage of RNA by Hammerhead Ribozymes Targeted Against Cleavage Sites that Are Homologous Between KDR and flt-1 mRNA Because flt-1 and KDR mRNAs are highly homologous in certain regions, some ribozyme target sites are also homologous (see Table X). In this case, a single ribozyme will target both flt-1 and KDR mRNAs. Hammerhead ribozyme (FLT/KDR-1) targeted against one of the homologous sites between flt-1 and KDR (flt-1 site 3388 and KDR site 3151) was synthesized as described above. Ribozymes with either a 3 bp stem II or a 4 bp stem II were synthesized. RNA cleavage reactions were carried out in vitro essentially as described under Example 7.

Referring to FIG. 16, FLT/KDR-I ribozyme with either a 3 or a 4 bp stem II was able to cleave its target RNA efficiently in vitro.

EXAMPLE 10

Effect of Multiple Ribozymes Targeted Against Both flt-1 and KDR RNA on Cell Proliferation Since both flt-1 and KDR receptors of VEGF are involved in angiogenesis, the inhibition of the expression of both of these genes may be an effective approach to inhibit angiogenesis.

Human microvascular endothalial cells were treated with hammerhead ribozymes targeted against sites flt-1 4229 alone, KDR 527 alone, KDR 726 alone, KDR 3950 alone. flt-1 4229+KDR 527, flt-1 4229+KDR 726 or flt-1 4229+KDR 3950. As shown in FIG. 17, all the combinations of active ribozymes (A) caused significant inhibition of VEGF-mediated induction of cell proliferation. No significant inhibition of cell proliferation was observed when the cells were treated with a catalytically inactive (I) hammerhead ribozymes. Additionally, cells treated with ribozymes targeted against both flt-1 and KDR RNAs—flt-1 4229+KDR 527; flt-1 4229+KDR 726; flt-1 4229+KDR 3950, were able to cause a greater inhibition of VEGF-mediated induction of cell proliferation when compared with individual ribozymes targeted against either flt-1 or KDR RNA (see flt-1 4229 alone; KDR 527 alone; KDR 726 alone; KDR 3950 alone). This strongly suggests that treatment of cells with multiple ribozymes may be a more effective means of inhibition of gene expression.

Animal Models

There are several animal models in which the anti-angiogenesis effect of nucleic acids of the present invention, such as ribozymes, directed against VEGF-R mRNAs can be tested. Typically a corneal model has been used to study angiogenesis in rat and rabbit since recruitment of vessels can easily be followed in this normally avascular tissue (Pandey et al., 1995 *Science* 268: 567–569). In these models, a small Teflon or Hydron disk pretreated with an angiogenesis factor (e.g. bFGF or VEGF) is inserted into a pocket surgically created in the cornea. Angiogenesis is monitored 3 to 5 days later. Ribozymes directed against VEGF-R mRNAs would be delivered in the disk as well, or dropwise to the eye over the time course of the experiment. In another eye model, hypoxia has been shown to cause both increased expression of VEGF and neovascularization in the retina (Pierce et al., 1995 *Proc. Natl. Acad. Sci.* USA. 92: 905–909; Shweiki et aL, 1992 *J. Clin. Invest.* 91: 2235–2243).

In human glioblastomas, it has been shown that VEGF is at least partially responsible for tumor angiogenesis (Plate et al., 1992 *Nature* 359, 845). Animal models have been developed in which glioblastoma cells are implanted subcutaneously into nude mice and the progress of tumor growth and angiogenesism is studied (Kim et al., 1993 supra; Millauer et al., 1994 supra).

Another animal model that addresses neovascularization involves Matrigel, an extract of basement membrane that becomes a solid gel when injected subcutaneously (Passaniti et al., 1992 *Lab. Invest.* 67: 519–528). When the Matrigel is supplemented with angiogenesis factors such as VEGF, vessels grow into the Matrigel over a period of 3 to 5 days and angiogenesis can be assessed. Again, ribozymes directed against VEGF-R mRNAs would be delivered in the Matrigel.

Several animal models exist for screening of anti-angiogenic agents. These include corneal vessel formation following corneal injury (Burger et al., 1985 *Cornea* 4: 35–41; Lepri, et al., 1994 *J. Ocular Pharmacol.* 10: 273–280; Ormerod et al., 1990 *Am. J. Pathol.* 137: 1243–1252) or intracorneal growth factor implant (Grant et al., 1993 *Diabetologia* 36: 282–291; Pandey et al. 1995 supra; Zieche et al., 1992 *Lab. Invest.* 67: 711–715), vessel growth into Matrigel matrix containing growth factors (Passaniti et al., 1992 supra), female reproductive organ neovascularization following hormonal manipulation (Shweiki et al., 1993 *Clin. Invest.* 91: 2235–2243), several models involving inhibition of tumor growth in highly vascularized solid tumors (O'Reilly et aL, 1994 *Cell* 79: 315–328; Senger et al., 1993 *Cancer and Metas. Rev.* 12: 303–324; Takahasi et al., 1994 *Cancer Res.* 54: 4233–4237; Kim et al., 1993 supra), and transient hypoxia-induced neovascularization in the mouse retina (Pierce et al., 1995 *Proc. Natl. Acad. Sci.* USA. 92: 905–909).

The cornea model, described in Pandey et al. supra, is the most common and well characterized anti-angiogenic agent efficacy screening model. This model involves an avascular tissue into which vessels are recruited by a stimulating agent (growth factor, thermal or alkalai burn, endotoxin). The corneal model would utilize the intrastromal corneal implantation of a Teflon pellet soaked in a VEGF-Hydron solution to recruit blood vessels toward the pellet which can be quantitated using standard microscopic and image analysis techniques. To evaluate their anti-angiogenic efficacy, ribozymes are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al. supra) is a non-tissue model which utilizes Matrigel, an extract of basement membrane (Kleinman et al., 1986) or Millipore® filter disk, which can be impregnated wvith growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk would be used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk are avascular; however, it is not tissue. In the Matrigel or Millipore® filter disk model, ribozymes are administered within the matrix of the Matrigel or Millipore® filter disk to test their anti-angiogenic efficacy. Thus, delivery issues in this model, as with delivery of ribozymes by Hydron-coated Teflon pellets in the rat cornea model, may be less problematic due to the homogeneous presence of the ribozyme within the respective matrix.

These models offer a distinct advantage over several other angiogenic models listed previously. The ability to use VEGF as a pro-angiogenic stimulus in both models is highly desirable since ribozymes will target only VEGFr mRNA. In other words, the involvement of other non-specific types of stimuli in the cornea and Matrigel models is not advantageous from the standpoint of understanding the pharmacologic mechanism by which the anti-VEGFr mRNA ribozymes produce their effects. In addition, the models will allow for testing the specificity of the anti-VEGFr mRNA ribozymes by using either a- or bFGF as a pro-angiogenic factor. Vessel recruitment using FGF should not be affected in either model by anti-VEGFr mRNA ribozymes. Other models of angiogenesis including vessel formation in the female reproductive system using hormonal manipulation (Shweiki et al., 1993 supra); a variety of vascular solid tumor models which involve indirect correltations with angiogenesis (O'Reilly et al., 1994 supra; Senger et al., 1993 supra; Takahasi et al., 1994 supra; Kim et al., 1993 supra); and retinal neovascularization following transient hypoxia (Pierce et al., 1995 supra) were not selected for efficacy screening due to their non-specific nature, although there is a correlation between VEGF and angiogenesis in these models.

Other model systems to study tumor angiogenesis is reviewed by Folkman, 1985 Adv. Cancer. Res., 43, 175.

flt-1, KDR and/or flk-1 protein levels can be measured clinically or experimentally by FACS analysis. flt-1, KDR and/or flk-1 encoded mRNA levels will be assessed by Northern analysis, RNase-protection, primer extension analysis and/or quantitative RT-PCR. Ribozymes that block flt-1, KDR and/or flk-1 protein encoding mRNAs and therefore result in decreased levels of flt-1, KDR and/or flk-1 activity by more than 20% in vitro will be identified.

Ribozymes and/or genes encoding them are delivered by either free delivery, liposome delivery, cationic lipid delivery, adeno-associated virus vector delivery, adenovirus vector delivery, retrovirus vector delivery or plasmid vector delivery in these animal model experiments (see above).

Patients can be treated by locally administering nucleic acids targeted against VEGF–R by direct injection. Routes of administration may include, but are not limited to, intravascular, intramuscular, subcutaneous, intraarticular, aerosol inhalation, oral (tablet, capsule or pill form), topical, systemic, ocular, intraperitoneal and/or intrathecal delivery.

EXAMPLE 11

Ribozyme-mediated Inhibition of Angiogenesis In vivo

The purpose of this study was to assess the anti-angiogenic activity of hammerhead ribozymes targeted against flt-1 4229 site in the rat cornea model of VEGF induced angiogenesis (see above). These ribozymes have either active or inactive catalytic core and either bind and cleave or just bind to VEGF–R mRNA of the flt-1 subtype. The active ribozymes, that are able to bind and cleave the target RNA, have been shown to inhibit ($^{125}$I-labeled) VEGF binding in cultured endothelial cells and produce a dose-dependent decrease in VEGF induced endothelial cell proliferation in these cells (see Examples 3–5 above). The catalytically inactive forms of these ribozymes, wherein the ribozymes can only bind to the RNA but cannot catalyze RNA cleavage, fail to show these characteristics. The ribozymes and VEGF were co-delivered using the filter disk method: Nitrocellulose filter disks (Millipore®) of 0.057 diameter were immersed in appropriate solutions and were surgically implanted in rat cornea as described by Pandey et al., supra. This delivery method has been shown to deliver rhodamine-labeled free ribozyme to scleral cells and, in all likelihood cells of the pericorneal vascular plexus. Since the active ribozymes show cell culture efficacy and can be delivered to the target site using the disk method, it is essential that these ribozymes be assessed for in vivo anti-angiogenic activity.

The stimulus for angiogenesis in this study was the treatment of the filter disk with 30 μM VEGF which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The ribozymes was co-adminstered with VEGF on a disk in two different ribozyme concentrations. One concern with the simultaneous administration is that the ribozymes will not be able to inhibit angiogenesis since VEGF receptors can be stimulated. However, we have observed that in low VEGF doses, the neovascular response reverts to normal suggesting that the VEGF stimulus is essential for maintaining the angiogenic response. Blocking the production of VEGF receptors using simultaneous administration of anti-VEGF–R mRNA ribozymes could attenuate the normal neovascularization induced by the filter disk treated with VEGF.

MATERIALS AND METHODS
1. Stock Hammerhead Ribozyme Solutions
   a. flt-1 4229 (786 µM)—Active
   b. flt-1 4229 (736 µM)—Inactive
2. Experimantal Solutions/groups

| Group 1 | Solution 1 | Control VEGF solution: 30 µM in 82 mM Tris base |
| Group 2 | Solution 2 | flt-1 4229 (1 µg/µL) in 30 µM VEGF/82 mM Tris base |
| Group 3 | Solution 3 | flt-1 4229 (10 µg/µL) in 30 µM VEGF/82 mM Tris base |
| Group 4 | Solution 4 | No VEGF, flt-1 4229 (10 µg/µL) in 82 mM Tris base |
| Group 5 | Solution 5 | No VEGF, No ribozyme in 82 mM Tris base |

10 eyes per group, 5 animals (Since they have similar molecular weights, the molar concentrations should be essentially similar).

Each solution (VEGF and RIBOZYMES) were prepared as a 2× solution for 1:1 mixing for final concentrations above, with the exception of solution 1 in which VEGF was 2× and diluted with ribozyme diluent (sterile water).

3. VEGF Solutions

The 2×VEGF solution (60 µM) was prepared from a stock of 0.82 µg/µL in 50 mM Tris base. 200 µL of VEGF stock was concentrated by speed vac to a final volume of 60.8 µL, for a final concentration of 2.7 µg/µL or 60 µM. Six 10 µL aliquots was prepared for daily mixing. 2× solutions for VEGF and Ribozyme was stored at 4° C. until the day of the surgery. Solutions were mixed for each day of surgery. Original 2× solutions was prepared on the day before the first day of the surgery.

4. Surgical Solutions

Anesthesia
   stock ketamine hydrochloride 100 mg/mL
   stock xylazine hydrochloride 20 mg/mL
   stock acepromazine 10 mg/mL Final Anesthesia Solution
   50 mg/mL ketamine, 10 mg/mL xylazine, and 0.5 mg/mL acepromazine 5% povidone iodine for opthalmic surgical wash
   2% lidocaine (sterile) for opthalmic administration (2 drops per eye)
   sterile 0.9% NaCl for opthalmic irrigation 5. Surgical Methods Standard surgical procedure as described in Pandey et al, supra. Filter disks were incubated in 1 µL of each solution for approximately 30 minutes prior to implantation.

5. Experimental Protocol

The animal cornea were treated with the treatment groups as described above. Animals were allowed to recover for 5 days after treatment with daily observation (scoring 0–3). On the fifth day animals were euthanized and digital images of each eye was obtained for quantitaion using Image Pro Plus. Quantitated neovascular surface area were analyzed by ANOVA followed by two post-hoc tests including Dunnets and Tukey-Kramer tests for significance at the 95% confidence level. Dunnets provide information on the significance between the differences within the means of treatments vs. controls while Tukey-Kramer provide information on the significance of differences within the means of each group.

Results are graphically represented in FIG. 18. As shown in the figure, flt-1 4229 active hammerhead ribozyme at both concentrations was effective at inhibiting angiogenesis while the inactive ribozyme did not show any significant reduction in angiogenesis. A statistically signifiant reduction in neovascular surface area was observed only with active ribozymes. This result clearly shows that the ribozymes are capable of significantly inhibiting angiogenesis in vivo. Specifically, the mechanism of inhibition appears to be by the binding and cleavage of target RNA by ribozymes.

Diagnostic Uses

Ribozymes of this invention may be used as diagnostic tools to examine genetic drift and mutations within diseased cells or to detect the presence of flt-1, KDR and/or flk-1 RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with flt-1, KDR and/or flk-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., flt-1, KDR and/or flk-1) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

TABLE II

Human flt1 VEGF Receptor-Hammerhead Ribozyme and Substrate Sequence

| Pos | Substrate | Seq ID No | HH Ribozyme | Seq ID No |
|---|---|---|---|---|
| 10 | CGGACACUC CUCUCGGC | 1 | GCCGAGAG CUGAUGAGGNNNNNNNNCCGAA AGUGUCCG | 4157 |
| 13 | ACACUCCUC UCGGCUCC | 2 | GGAGCCGA CUGAUGAGGNNNNNNNNCCGAA AGGAGUGU | 4158 |
| 15 | ACUCCUCUC GGCUCCUC | 3 | GAGGAGCC CUGAUGAGGNNNNNNNNCCGAA AGAGGAGU | 4159 |
| 20 | UCUCGGCUC CUCCCCGG | 4 | CCGGGGAG CUGAUGAGGNNNNNNNNCCGAA AGCCGAGA | 4160 |
| 23 | CGGCUCCUC CCCGGCAG | 5 | CUGCCGGG CUGAUGAGGNNNNNNNNCCGAA AGGAGCCG | 4161 |
| 43 | CGGCGGCUC GGAGCGGG | 6 | CCCGCUCC CUGAUGAGGNNNNNNNNCCGAA AGCCGCCG | 4162 |
| 54 | AGCGGGCUC CGGGGCUC | 7 | GAGCCCCG CUGAUGAGGNNNNNNNNCCGAA AGCCCGCU | 4163 |
| 62 | CCGGGGCUC GGGUGCAG | 8 | CUGCACCC CUGAUGAGGNNNNNNNNCCGAA AGCCCCGG | 4164 |
| 97 | GCGAGGAUU ACCCGGGG | 9 | CCCCGGGU CUGAUGAGGNNNNNNNNCCGAA AUCCUCGC | 4165 |
| 98 | CGAGGAUUA CCCGGGGA | 10 | UCCCCGGG CUGAUGAGGNNNNNNNNCCGAA AAUCCUCG | 4166 |
| 113 | GAAGUGGUU GUCUCCUG | 11 | CAGGAGAC CUGAUGAGGNNNNNNNNCCGAA ACCACUUC | 4167 |
| 116 | GUGGUUGUC UCCUGGCU | 12 | AGCCAGGA CUGAUGAGGNNNNNNNNCCGAA ACAACCAC | 4168 |
| 118 | GGUUGUCUC CUGGCUGG | 13 | CCAGCCAG CUGAUGAGGNNNNNNNNCCGAA AGACAACC | 4169 |
| 145 | CGGGCGCUC AGGGCGCG | 14 | CGCGCCCU CUGAUGAGGNNNNNNNNCCGAA AGCGCCCG | 4170 |
| 185 | GACGGACUC UGGCGGCC | 15 | GGCCGCCA CUGAUGAGGNNNNNNNNCCGAA AGUCCGUC | 4171 |
| 198 | GGCCGGGUC GUUGGCCG | 16 | CGGCCAAC CUGAUGAGGNNNNNNNNCCGAA ACCCGGCC | 4172 |
| 201 | CGGGUCGUU GGCCGGGG | 17 | CCCCGGCC CUGAUGAGGNNNNNNNNCCGAA ACGACCCG | 4173 |
| 240 | GGCCGCGUC GCGCUCAC | 18 | GUGAGCGC CUGAUGAGGNNNNNNNNCCGAA ACGCGGCC | 4174 |
| 246 | GUCGCGCUC ACCAUGGU | 19 | ACCAUGGU CUGAUGAGGNNNNNNNNCCGAA AGCGCGAC | 4175 |
| 255 | ACCAUGGUC AGCUACUG | 20 | CAGUAGCU CUGAUGAGGNNNNNNNNCCGAA ACCAUGGU | 4176 |
| 260 | GGUCAGCUA CUGGGACA | 21 | UGUCCCAG CUGAUGAGGNNNNNNNNCCGAA AGCUGACC | 4177 |
| 276 | ACCGGGGUC CUGGCGUG | 22 | CACACGCC CUGAUGAGGNNNNNNNNCCGAA ACCCCGGU | 4178 |
| 294 | GCGCUGCUC AGCUGUCU | 23 | AGACAGCU CUGAUGAGGNNNNNNNNCCGAA AGCAGCGC | 4179 |
| 301 | UCAGCUGUC UGCUUCUC | 24 | GAGAAGCA CUGAUGAGGNNNNNNNNCCGAA ACAGCUGA | 4180 |
| 306 | UGUCGCUU CUCACAGG | 25 | CCUGUGAG CUGAUGAGGNNNNNNNNCCGAA AGCAGACA | 4181 |
| 307 | GUCUGCUUC UCACAGGA | 26 | UCCUGUGA CUGAUGAGGNNNNNNNNCCGAA AAGCAGAC | 4182 |
| 309 | CUGCUUCUC ACAGGAUC | 27 | GAUCCUGU CUGAUGAGGNNNNNNNNCCGAA AGAAGCAG | 4183 |
| 317 | CACAGGAUC UAGUUCAG | 28 | CUGAACUA CUGAUGAGGNNNNNNNNCCGAA AUCCUGUG | 4184 |
| 319 | CAGGAUCUA GUUCAGGU | 29 | ACCUGAAC CUGAUGAGGNNNNNNNNCCGAA AGAUCCUG | 4185 |
| 322 | GAUCUAGUU CAGGUUCA | 30 | UGAACCUG CUGAUGAGGNNNNNNNNCCGAA ACUAGAUC | 4186 |
| 323 | AUCUAGUUC AGGUUCAA | 31 | UUGAACCU CUGAUGAGGNNNNNNNNCCGAA AACUAGAU | 4187 |
| 328 | GUUCAGGUU CAAAAUUA | 32 | UAAUUUUG CUGAUGAGGNNNNNNNNCCGAA ACCUGAAC | 4188 |
| 329 | UUCAGGUUC AAAAUUAA | 33 | UUAAUUUU CUGAUGAGGNNNNNNNNCCGAA AACCUGAA | 4189 |
| 335 | UUCAAAAUU AAAAGAUC | 34 | GAUCUUUU CUGAUGAGGNNNNNNNNCCGAA AUUUUGAA | 4190 |
| 336 | UCAAAAUUA AAAGAUCC | 35 | GGAUCUUU CUGAUGAGGNNNNNNNNCCGAA AAUUUUGA | 4191 |
| 343 | UAAAAGAUC CUGAACUG | 36 | CAGUUCAG CUGAUGAGGNNNNNNNNCCGAA AUCUUUUA | 4192 |
| 355 | AACUGAGUU AAAAGGC | 37 | GCCUUUUA CUGAUGAGGNNNNNNNNCCGAA ACUCAGUU | 4193 |
| 356 | ACUGAGUUU AAAAGGCA | 38 | UGCCUUUU CUGAUGAGGNNNNNNNNCCGAA AACUCAGU | 4194 |
| 357 | CUGAGUUUA AAAGGCAG | 39 | GUGCCUUU CUGAUGAGGNNNNNNNNCCGAA AAACUCAG | 4195 |
| 375 | CAGCACAUC AUGCAAGC | 40 | GCUUGCAU CUGAUGAGGNNNNNNNNCCGAA AUGUGCUG | 4196 |
| 400 | CACUGCAUC UCCAAUGC | 41 | GCAUUGGA CUGAUGAGGNNNNNNNNCCGAA AUGCAGUG | 4197 |
| 402 | CUGCAUCUC CAAUGCAG | 42 | CUGCAUUG CUGAUGAGGNNNNNNNNCCGAA AGAUGCAG | 4198 |
| 427 | CAGCCCAUA AAUGGUCU | 43 | AGACCAUU CUGAUGAGGNNNNNNNNCCGAA AUGGGCUG | 4199 |
| 434 | UAAAUGGUC UUUGCCUG | 44 | CAGGCAAA CUGAUGAGGNNNNNNNNCCGAA ACCAUUUA | 4200 |
| 436 | AAUGGUCUU UGCCUGAA | 45 | UUCAGGCA CUGAUGAGGNNNNNNNNCCGAA AGACCAUU | 4201 |
| 437 | AUGGUCUUU GCCUGAAA | 46 | UUUCAGGC CUGAUGAGGNNNNNNNNCCGAA AAGACCAU | 4202 |
| 454 | UGGGAGUA ACUAAAUC | 47 | GCUUUCCU CUGAUGAGGNNNNNNNNCCGAA ACUCACCA | 4203 |
| 477 | CUGAGCAUA ACUAAAUC | 48 | GAUUUAGU CUGAUGAGGNNNNNNNNCCGAA AUGCUCAG | 4204 |
| 481 | GCAUAACUA AAUCUGCC | 49 | GGCAGAUU CUGAUGAGGNNNNNNNNCCGAA AGUUAUGC | 4205 |
| 485 | AACUAAAUC UGCCUGUG | 50 | CACAGGCA CUGAUGAGGNNNNNNNNCCGAA AUUUAGUU | 4206 |
| 512 | CAAACAAUU CUGCAGUA | 51 | UACUGCAG CUGAUGAGGNNNNNNNNCCGAA AUUGUUUG | 4207 |
| 513 | AAACAAUUC UGCAGUAC | 52 | GUACUGCA CUGAUGAGGNNNNNNNNCCGAA AAUUGUUU | 4208 |
| 520 | UCUGCAGUA CUUUAACC | 53 | GGUUAAAG CUGAUGAGGNNNNNNNNCCGAA ACUGCAGA | 4209 |
| 523 | GCAGUACUU UAACCUUG | 54 | CAAGGUUA CUGAUGAGGNNNNNNNNCCGAA AGUACUGC | 4210 |
| 524 | CAGUACUUU AACCUUGA | 55 | UCAAGGUU CUGAUGAGGNNNNNNNNCCGAA AAGUACUG | 4211 |
| 525 | AGUACUUUA ACCUUGAA | 56 | UUCAAGGU CUGAUGAGGNNNNNNNNCCGAA AAAGUACU | 4212 |
| 530 | UUUAACCUU GAACACAG | 57 | CUGUGUUC CUGAUGAGGNNNNNNNNCCGAA AGGUUAAA | 4213 |
| 541 | ACACAGCUC AAGCAAAC | 58 | GUUUGCUU CUGAUGAGGNNNNNNNNCCGAA AGCUGUGU | 4214 |
| 560 | CACUGGCUU CUACAGCU | 59 | AGCUGUAG CUGAUGAGGNNNNNNNNCCGAA AGCCAGUG | 4215 |
| 561 | ACUGGCUUC UACAGCUG | 60 | CAGCUGUA CUGAUGAGGNNNNNNNNCCGAA AAGCCAGU | 4216 |
| 563 | UGGCUUCUA CAGCUGCA | 61 | UGCAGCUG CUGAUGAGGNNNNNNNNCCGAA AGAAGCCA | 4217 |
| 575 | CUGCAAAUA UCUAGCUG | 62 | CAGCUAGA CUGAUGAGGNNNNNNNNCCGAA AUUUGCAG | 4218 |
| 577 | GCAAAUAUC UAGCUGUA | 63 | UACAGCUA CUGAUGAGGNNNNNNNNCCGAA AUAUUUGC | 4219 |
| 579 | AAAUAUCUA GCUGUACC | 64 | GGUACAGC CUGAUGAGGNNNNNNNNCCGAA AGAUAUUU | 4220 |
| 585 | CUAGCUGUA CCUACUUC | 65 | GAAGUAGG CUGAUGAGGNNNNNNNNCCGAA ACAGCUAG | 4221 |
| 589 | CUGUACCUA CUUCAAAG | 66 | CUUUGAAG CUGAUGAGGNNNNNNNNCCGAA AGGUACAG | 4222 |
| 592 | UACCUACUU CAAAGAAG | 67 | CUUCUUUG CUGAUGAGGNNNNNNNNCCGAA AGUAGGUA | 4223 |
| 593 | ACCUACUUC AAAGAAGU | 68 | UCUUCUUU CUGAUGAGGNNNNNNNNCCGAA AAGUAGGU | 4224 |
| 614 | AACAGAAUC UGCAAUCU | 69 | AGAUUGCA CUGAUGAGGNNNNNNNNCCGAA AUUCUGUU | 4225 |
| 621 | UCUGCAAUC UAUAUAUU | 70 | AAUAUAUA CUGAUGAGGNNNNNNNNCCGAA AUUGCAGA | 4226 |
| 623 | UGCAAUCUA UAUAUUUA | 71 | UAAAUAUA CUGAUGAGGNNNNNNNNCCGAA AGAUUGCA | 4227 |
| 625 | CAAUCUAUA UAUUUAUU | 72 | AAUAAAUA CUGAUGAGGNNNNNNNNCCGAA AUAGAUUG | 4228 |
| 627 | AUCUAUAUA UUUAUUAG | 73 | CUAAUAAA CUGAUGAGGNNNNNNNNCCGAA AUAUAGAU | 4229 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 629 | CUAUAUAUU UAUUAGUG | 74 | CACUAAUA CUGAUGAGGNNNNNNNNCCGAA AUAUAUAG | 4230 |
| 630 | UAUAUAUUU AUUAGUGA | 75 | UCACUAAU CUGAUGAGGNNNNNNNNCCGAA AAUAUAUA | 4231 |
| 631 | AUAUAUUUA UUAGUGAU | 76 | AUCACUAA CUGAUGAGGNNNNNNNNCCGAA AAAUAUAU | 4232 |
| 633 | AUAUUUAUU AGUGAUAC | 77 | GUAUCACU CUGAUGAGGNNNNNNNNCCGAA AUAAAUAU | 4233 |
| 634 | UAUUUAUUA GUGAUACA | 78 | UGUAUCAC CUGAUGAGGNNNNNNNNCCGAA AAUAAAUA | 4234 |
| 640 | UUAGUGAUA CAGGUAGA | 79 | UCUACCUG CUGAUGAGGNNNNNNNNCCGAA AUCACUAA | 4235 |
| 646 | AUACAGGUA GACCUUUC | 80 | GAAAGGUC CUGAUGAGGNNNNNNNNCCGAA ACCUGUAU | 4236 |
| 652 | GUAGACCUU UCGUAGAG | 81 | CUCUACGA CUGAUGAGGNNNNNNNNCCGAA AGGUCUAC | 4237 |
| 653 | UAGACCUUU CGUAGAGA | 82 | UCUCUACG CUGAUGAGGNNNNNNNNCCGAA AAGGUCUA | 4238 |
| 654 | AGACCUUUC GUAGAGAU | 83 | AUCUCUAC CUGAUGAGGNNNNNNNNCCGAA AAAGGUCU | 4239 |
| 657 | CCUUUCGUA GAGAUGUA | 84 | UACAUCUC CUGAUGAGGNNNNNNNNCCGAA ACGAAAGG | 4240 |
| 665 | AGAGAUGUA CAGUGAAA | 85 | UUUCACUG CUGAUGAGGNNNNNNNNCCGAA ACAUCUCU | 4241 |
| 675 | AGUGAAAUC CCCGAAAU | 86 | AUUUCGGG CUGAUGAGGNNNNNNNNCCGAA AUUUCACU | 4242 |
| 684 | CCCGAAAUU AUACACAU | 87 | AUGUGUAU CUGAUGAGGNNNNNNNNCCGAA AUUUCGGG | 4243 |
| 685 | CCGAAAUUA UACACAUG | 88 | CAUGUGUA CUGAUGAGGNNNNNNNNCCGAA AAUUUCGG | 4244 |
| 687 | GAAAUUAUA CACAUGAC | 89 | GUCAUGUG CUGAUGAGGNNNNNNNNCCGAA AUAAUUUC | 4245 |
| 711 | AGGGAGCUC GUCAUUCC | 90 | GGAAUGAC CUGAUGAGGNNNNNNNNCCGAA AGCUCCCU | 4246 |
| 714 | GAGCUCGUC AUUCCCUG | 91 | CAGGGAAU CUGAUGAGGNNNNNNNNCCGAA ACGAGCUC | 4247 |
| 717 | CUCGUCAUU CCCUGCCG | 92 | CGGCAGGG CUGAUGAGGNNNNNNNNCCGAA AUGACGAG | 4248 |
| 718 | UCGUCAUUC CCUGCCGG | 93 | CCGGCAGG CUGAUGAGGNNNNNNNNCCGAA AAUGACGA | 4249 |
| 729 | UGCCGGGUU ACGUCACC | 94 | GGUGACGU CUGAUGAGGNNNNNNNNCCGAA ACCCGGCA | 4250 |
| 730 | GCCGGGUUA CGUCACCU | 95 | AGGUGACG CUGAUGAGGNNNNNNNNCCGAA AACCCGGC | 4251 |
| 734 | GGUUACGUC ACCUAACA | 96 | UGUUAGGU CUGAUGAGGNNNNNNNNCCGAA ACGUAACC | 4252 |
| 739 | CGUCACCUA ACAUCACU | 97 | AGUGAUGU CUGAUGAGGNNNNNNNNCCGAA AGGUGACG | 4253 |
| 744 | CCUAACAUC ACUGUUAC | 98 | GUAACAGU CUGAUGAGGNNNNNNNNCCGAA AUGUUAGG | 4254 |
| 750 | AUCACUGUU ACUUUAAA | 99 | UUUAAAGU CUGAUGAGGNNNNNNNNCCGAA ACAGUGAU | 4255 |
| 751 | UCACUGUUA CUUUAAAA | 100 | UUUUAAAG CUGAUGAGGNNNNNNNNCCGAA AACAGUGA | 4256 |
| 754 | CUGUUACUU UAAAAAAG | 101 | CUUUUUUA CUGAUGAGGNNNNNNNNCCGAA AGUAACAG | 4257 |
| 755 | UGUUACUUU AAAAAGU | 102 | ACUUUUUU CUGAUGAGGNNNNNNNNCCGAA AAGUAACA | 4258 |
| 756 | GUUACUUUA AAAAGUU | 103 | AACUUUUU CUGAUGAGGNNNNNNNNCCGAA AAAGUAAC | 4259 |
| 764 | AAAAAGUU UCCACUUG | 104 | CAAGUGGA CUGAUGAGGNNNNNNNNCCGAA ACUUUUUU | 4260 |
| 765 | AAAAGUUU CCACUUGA | 105 | UCAAGUGG CUGAUGAGGNNNNNNNNCCGAA AACUUUUU | 4261 |
| 766 | AAAGUUUC CACUUGAC | 106 | GUCAAGUG CUGAUGAGGNNNNNNNNCCGAA AAACUUUU | 4262 |
| 771 | UUUCCACUU GACACUUU | 107 | AAAGUGUC CUGAUGAGGNNNNNNNNCCGAA AGUGGAAA | 4263 |
| 778 | UUGACACU UGAUCCCU | 108 | AGGGAUCA CUGAUGAGGNNNNNNNNCCGAA ACGUGUCAA | 4264 |
| 779 | UGACACUUU GAUCCCUG | 109 | CAGGGAUC CUGAUGAGGNNNNNNNNCCGAA AAGUGUCA | 4265 |
| 783 | ACUUUGAUC CCUGAUGG | 110 | CCAUCAGG CUGAUGAGGNNNNNNNNCCGAA AUCAAAGU | 4266 |
| 801 | AAACGCAUA AUCUGGGA | 111 | UCCCAGAU CUGAUGAGGNNNNNNNNCCGAA AUGCGUUU | 4267 |
| 804 | CGCAUAAUC UGGGACAG | 112 | CUGUCCCA CUGAUGAGGNNNNNNNNCCGAA AUUAUGCG | 4268 |
| 814 | GGGACAGUA GAAAGGGC | 113 | GCCCUUUC CUGAUGAGGNNNNNNNNCCGAA ACUGUCCC | 4269 |
| 824 | AAAGGGCUU CAUCAUAU | 114 | AUAUGAUG CUGAUGAGGNNNNNNNNCCGAA AGCCCUUU | 4270 |
| 825 | AAGGGCUUC AUCAUAUC | 115 | GAUAUGAU CUGAUGAGGNNNNNNNNCCGAA AAGCCCUU | 4271 |
| 828 | GGCUUCAUC AUAUCAAA | 116 | UUUGAUAU CUGAUGAGGNNNNNNNNCCGAA AUGAAGCC | 4272 |
| 831 | UUCAUCAUA UCAAAUGC | 117 | GCAUUUGA CUGAUGAGGNNNNNNNNCCGAA AUGAUGAA | 4273 |
| 833 | CAUCAUAUC AAAUGCAA | 118 | UUGCAUUU CUGAUGAGGNNNNNNNNCCGAA AUAUGAUG | 4274 |
| 845 | UGCAACGUA CAAAGAAA | 119 | UUUCUUUG CUGAUGAGGNNNNNNNNCCGAA ACGUUGCA | 4275 |
| 855 | AAAGAAAUA GGGCUCU | 120 | AGAAGCCC CUGAUGAGGNNNNNNNNCCGAA AUUUCUUU | 4276 |
| 861 | AUAGGGCUU CUGACCUG | 121 | CAGGUCAG CUGAUGAGGNNNNNNNNCCGAA AGCCCUAU | 4277 |
| 862 | UAGGGCUUC UGACCUGU | 122 | ACAGGUCA CUGAUGAGGNNNNNNNNCCGAA AAGCCCUA | 4278 |
| 882 | GCAACAGUC AAUGGGCA | 123 | UGCCCAUU CUGAUGAGGNNNNNNNNCCGAA ACUGUUGC | 4279 |
| 892 | AUGGGCAUU UGUAUAAG | 124 | CUUAUACA CUGAUGAGGNNNNNNNNCCGAA AUGCCCAU | 4280 |
| 893 | UGGGCAUUU GUAUAAGA | 125 | UCUUAUAC CUGAUGAGGNNNNNNNNCCGAA AAUGCCCA | 4281 |
| 896 | GCAUUUGUA UAAGACAA | 126 | UUGUCUUA CUGAUGAGGNNNNNNNNCCGAA ACAAAUGC | 4282 |
| 898 | AUUUGUAUA AGACAAAC | 127 | GUUUGUCU CUGAUGAGGNNNNNNNNCCGAA AUACAAAU | 4283 |
| 908 | GACAAACUA UCUCACAC | 128 | GUGUGAGA CUGAUGAGGNNNNNNNNCCGAA AGUUUGUC | 4284 |
| 910 | CAAACUAUC UCACACAU | 129 | AUGUGUGA CUGAUGAGGNNNNNNNNCCGAA AUAGUUUG | 4285 |
| 912 | AACUAUCUC ACACAUCG | 130 | CGAUGUGU CUGAUGAGGNNNNNNNNCCGAA AGAUAGUU | 4286 |
| 919 | UCACACAUC GACAAACC | 131 | GGUUUGUC CUGAUGAGGNNNNNNNNCCGAA AUGUGUGA | 4287 |
| 931 | AAACCAAUA CAAUCAUA | 132 | UAUGAUUG CUGAUGAGGNNNNNNNNCCGAA AUUGGUUU | 4288 |
| 936 | AAUACAAUC AUAGUCCA | 133 | ACAUCUAC CUGAUGAGGNNNNNNNNCCGAA AUUGUAUU | 4289 |
| 939 | ACAAUCAUA GUGUCCA | 134 | UGGACAUC CUGAUGAGGNNNNNNNNCCGAA AUGAUUGU | 4290 |
| 945 | AUAGUGUC CAAAUAAG | 135 | CUUAUUUG CUGAUGAGGNNNNNNNNCCGAA ACAUCUAU | 4291 |
| 951 | GUCCAAAUA AGCACACC | 136 | GGUGUGCU CUGAUGAGGNNNNNNNNCCGAA AUUUGGAC | 4292 |
| 969 | CGCCCAGUC AAAUUACU | 137 | AGUAAUUU CUGAUGAGGNNNNNNNNCCGAA ACUGGGCG | 4293 |
| 974 | AGUCAAAUU ACUUAGAG | 138 | CUCUAAGU CUGAUGAGGNNNNNNNNCCGAA AUUUGACU | 4294 |
| 975 | GUCAAAUUA CUUAGAGG | 139 | CCUCUAAG CUGAUGAGGNNNNNNNNCCGAA AAUUUGAC | 4295 |
| 978 | AAAUUACUU AGAGGCCA | 140 | UGGCCUCU CUGAUGAGGNNNNNNNNCCGAA AGUAAUUU | 4296 |
| 979 | AAUUACUUA GAGGCCAU | 141 | AUGGCCUC CUGAUGAGGNNNNNNNNCCGAA AAGUAAUU | 4297 |
| 988 | GAGGCCAUA CUCUUGUC | 142 | GACAAGAG CUGAUGAGGNNNNNNNNCCGAA AUGGCCUC | 4298 |
| 991 | GCCAUACUC UUGUCCUC | 143 | GAGGACAA CUGAUGAGGNNNNNNNNCCGAA AGUAUGGC | 4299 |
| 993 | CAUACUCUU GUCCUCAA | 144 | UUGAGGAC CUGAUGAGGNNNNNNNNCCGAA AGAGUAUG | 4300 |
| 996 | ACUCUUGUC CUCAAUUG | 145 | CAAUUGAG CUGAUGAGGNNNNNNNNCCGAA ACAAGAGU | 4301 |
| 999 | CUUGUCCUC AAUUGUAC | 146 | GUACAAUU CUGAUGAGGNNNNNNNNCCGAA AGGACAAG | 4302 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1003 | UCCUCAAUU GUACUGCU | 147 | AGCAGUAC CUGAUGAGGNNNNNNNNCCGAA AUUGAGGA | 4303 |
| 1006 | UCAAUUGUA CUGCUACC | 148 | GGUAGCAG CUGAUGAGGNNNNNNNNCCGAA ACAAUUGA | 4304 |
| 1012 | GUACUGCUA CCACUCCC | 149 | GGGAGUGG CUGAUGAGGNNNNNNNNCCGAA AGCAGUAC | 4305 |
| 1018 | CUACCACUC CCUUGAAC | 150 | GUUCAAGG CUGAUGAGGNNNNNNNNCCGAA AGUGGUAG | 4306 |
| 1022 | CACUCCCUU GAACACGA | 151 | UCGUGUUC CUGAUGAGGNNNNNNNNCCGAA AGGGAGUG | 4307 |
| 1035 | ACGAGAGUU CAAAUGAC | 152 | GUCAUUUG CUGAUGAGGNNNNNNNNCCGAA ACUCUCGU | 4308 |
| 1036 | CGAGAGUUC AAAUGACC | 153 | GGUCAUUU CUGAUGAGGNNNNNNNNCCGAA AACUCUCG | 4309 |
| 1051 | CCUGGAGUU ACCCUGAU | 154 | AUCAGGGU CUGAUGAGGNNNNNNNNCCGAA ACUCCAGG | 4310 |
| 1052 | CUGGAGUUA CCCUGAUG | 155 | CAUCAGGG CUGAUGAGGNNNNNNNNCCGAA AACUCCAG | 4311 |
| 1069 | AAAAAAAUA AGAGAGCU | 156 | AGCUCUCU CUGAUGAGGNNNNNNNNCCGAA AUUUUUUU | 4312 |
| 1078 | AGAGAGCUU CCGUAAGG | 157 | CCUUACGG CUGAUGAGGNNNNNNNNCCGAA AGCUCUCU | 4313 |
| 1079 | GAGAGCUUC CGUAAGGC | 158 | GCCUUACG CUGAUGAGGNNNNNNNNCCGAA AAGCUCUC | 4314 |
| 1083 | GCUUCCGUA AGGCGACG | 159 | CGUCGCCU CUGAUGAGGNNNNNNNNCCGAA ACGGAAGC | 4315 |
| 1095 | CGACGAAUU GACCAAAG | 160 | CUUUGGUC CUGAUGAGGNNNNNNNNCCGAA AUUCGUCG | 4316 |
| 1108 | AAAGCAAUU CCCAUGCC | 161 | GGCAUGGG CUGAUGAGGNNNNNNNNCCGAA AUUGCUUU | 4317 |
| 1109 | AAGCAAUUC CCAUGCCA | 162 | UGGCAUGG CUGAUGAGGNNNNNNNNCCGAA AAUUGCUU | 4318 |
| 1122 | GCCAACAUA UUCUACAG | 163 | CUGUAGAA CUGAUGAGGNNNNNNNNCCGAA AUGUUGGC | 4319 |
| 1124 | CAACAUAUU CUACAGUG | 164 | CACUGUAG CUGAUGAGGNNNNNNNNCCGAA AUAUGUUG | 4320 |
| 1125 | AACAUAUUC UACAGUGU | 165 | ACACUGUA CUGAUGAGGNNNNNNNNCCGAA AAUAUGUU | 4321 |
| 1127 | CAUAUUCUA CAGUGUUC | 166 | GAACACUG CUGAUGAGGNNNNNNNNCCGAA AGAAUAUG | 4322 |
| 1134 | UACAGUGUU CUUACUAU | 167 | AUAGUAAG CUGAUGAGGNNNNNNNNCCGAA ACACUGUA | 4323 |
| 1135 | ACAGUGUUC UUACUAUU | 168 | AAUAGUAA CUGAUGAGGNNNNNNNNCCGAA AACACUGU | 4324 |
| 1137 | AGUGUUCUU ACUAUUGA | 169 | UCAAUAGU CUGAUGAGGNNNNNNNNCCGAA AGAACACU | 4325 |
| 1138 | GUGUUCUUA CUAUUGAC | 170 | GUCAAUAG CUGAUGAGGNNNNNNNNCCGAA AAGAACAC | 4326 |
| 1141 | UUCUUACUA UUGACAAA | 171 | UUUGUCAA CUGAUGAGGNNNNNNNNCCGAA AGUAAGAA | 4327 |
| 1143 | CUUACUAUU GACAAAAU | 172 | AUUUUGUC CUGAUGAGGNNNNNNNNCCGAA AUAGUAAG | 4328 |
| 1173 | AAAGGACUU AUACUUUG | 173 | CAAAGUAU CUGAUGAGGNNNNNNNNCCGAA AGUCCUUU | 4329 |
| 1174 | AAGGACUUU AUACUUGU | 174 | ACAAGUAU CUGAUGAGGNNNNNNNNCCGAA AAGUCCUU | 4330 |
| 1175 | AGGACUUUA UACUUGUC | 175 | GACAAGUA CUGAUGAGGNNNNNNNNCCGAA AAAGUCCU | 4331 |
| 1177 | GACUUUAUA CUUGUCGU | 176 | ACGACAAG CUGAUGAGGNNNNNNNNCCGAA AUAAAGUC | 4332 |
| 1180 | UUUAUACUU GUCGUGUA | 177 | UACACGAC CUGAUGAGGNNNNNNNNCCGAA AGUAUAAA | 4333 |
| 1183 | AUACUUGUC GUGUAAGG | 178 | CCUUACAC CUGAUGAGGNNNNNNNNCCGAA ACAAGUAU | 4334 |
| 1188 | UGUCGUGUA AGGAGUGG | 179 | CCACUCCU CUGAUGAGGNNNNNNNNCCGAA ACACGACA | 4335 |
| 1202 | UGGACCAUC AUUCAAAU | 180 | AUUUGAAU CUGAUGAGGNNNNNNNNCCGAA AUGGUCCA | 4336 |
| 1205 | ACCAUCAUU CAAAUCUG | 181 | CAGAUUUG CUGAUGAGGNNNNNNNNCCGAA AAUGAUGGU | 4337 |
| 1206 | CCAUCAUUC AAAUCUGU | 182 | ACAGAUUU CUGAUGAGGNNNNNNNNCCGAA AAUGAUGG | 4338 |
| 1211 | AUUCAAAUC UGUUAACA | 183 | UGUUAACA CUGAUGAGGNNNNNNNNCCGAA AUUUGAAU | 4339 |
| 1215 | AAAUCUGUU AACACCUC | 184 | GAGGUGUU CUGAUGAGGNNNNNNNNCCGAA ACAGAUUU | 4340 |
| 1216 | AAUCUGUUA ACACCUCA | 185 | UGAGGUGU CUGAUGAGGNNNNNNNNCCGAA AACAGAUU | 4341 |
| 1223 | UAACCCUC AGUGCAUA | 186 | UAUGCACU CUGAUGAGGNNNNNNNNCCGAA AGGUGUUA | 4342 |
| 1231 | CAGUGCAUA UAUAUGAU | 187 | AUCAUAUA CUGAUGAGGNNNNNNNNCCGAA AUGCACUG | 4343 |
| 1233 | GUGCAUAUA UAUGAUAA | 188 | UUAUCAUA CUGAUGAGGNNNNNNNNCCGAA AUAUGCAC | 4344 |
| 1235 | GCAUAUAUA UGAUAAGG | 189 | CUUUAUCA CUGAUGAGGNNNNNNNNCCGAA AUAUAUGC | 4345 |
| 1240 | UAUAUGAUA AGCAUUC | 190 | GAAUGCUU CUGAUGAGGNNNNNNNNCCGAA AUCAUAUA | 4346 |
| 1247 | UAAAGCAUU CAUCACUG | 191 | CAGUGAUG CUGAUGAGGNNNNNNNNCCGAA AUGCUUUA | 4347 |
| 1248 | AAAGCAUUC AUCACUGU | 192 | ACAGUGAU CUGAUGAGGNNNNNNNNCCGAA AAUGCUUU | 4348 |
| 1251 | GCAUUCAUC ACUGUGAA | 193 | UUCACAGU CUGAUGAGGNNNNNNNNCCGAA AUGAAUGC | 4349 |
| 1264 | UGAAACAUC GAAAACAG | 194 | CUGUUUUC CUGAUGAGGNNNNNNNNCCGAA AUGUUUCA | 4350 |
| 1281 | CAGGUGCUU GAAACCGU | 195 | ACGGUUUC CUGAUGAGGNNNNNNNNCCGAA AGCACCUG | 4351 |
| 1290 | GAAACCGUA GCUGGCAA | 196 | UUGCCAGC CUGAUGAGGNNNNNNNNCCGAA ACGGUUUC | 4352 |
| 1304 | CAAGCGGUC UUACCGGC | 197 | GCCGGUAA CUGAUGAGGNNNNNNNNCCGAA ACCGCUUG | 4353 |
| 1306 | AGCGGUCUU ACCGGCUC | 198 | GAGCCGGU CUGAUGAGGNNNNNNNNCCGAA AGACCGCU | 4354 |
| 1307 | GCGGUCUUA CCGGCUCU | 199 | AGAGCCGG CUGAUGAGGNNNNNNNNCCGAA AAGACCGC | 4355 |
| 1314 | UACCGGCUC UCUAUGAA | 200 | UUCAUAGA CUGAUGAGGNNNNNNNNCCGAA AGCCGGUA | 4356 |
| 1316 | CCGGCUCUC UAUGAAAG | 201 | CUUUCAUA CUGAUGAGGNNNNNNNNCCGAA AGAGCCGG | 4357 |
| 1318 | GGCUCUCUA UGAAAGUG | 202 | CACUUUCA CUGAUGAGGNNNNNNNNCCGAA AGAGAGCC | 4358 |
| 1334 | GAAGGCAUU UCCCUCGC | 203 | GCGAGGGA CUGAUGAGGNNNNNNNNCCGAA AUGCCUUC | 4359 |
| 1335 | AAGGCAUUU CCCUCGCC | 204 | GGCGAGGG CUGAUGAGGNNNNNNNNCCGAA AAUGCCUU | 4360 |
| 1336 | AGGCAUUUC CCUCGCCG | 205 | CGGCGAGG CUGAUGAGGNNNNNNNNCCGAA AAAUGCCU | 4361 |
| 1340 | AUUUCCCUC GCCGGAAG | 206 | CUUCCGGC CUGAUGAGGNNNNNNNNCCGAA AGGGAAAU | 4362 |
| 1350 | CCGGAAGUU GUAUGGUU | 207 | AACCAUAC CUGAUGAGGNNNNNNNNCCGAA ACUUCCGG | 4363 |
| 1353 | GAAGUUGUA UGGUUAAA | 208 | UUUAACCA CUGAUGAGGNNNNNNNNCCGAA ACAACUUC | 4364 |
| 1358 | UGUAUGGUU AAAGAUG | 209 | CAUCUUUU CUGAUGAGGNNNNNNNNCCGAA ACCAUACA | 4365 |
| 1359 | GUAUGGUUA AAGAUGG | 210 | CCAUCUUU CUGAUGAGGNNNNNNNNCCGAA AACCAUAC | 4366 |
| 1370 | AGAUGGGUU ACCUGCGA | 211 | UCGCAGGU CUGAUGAGGNNNNNNNNCCGAA ACCCAUCU | 4367 |
| 1371 | GAUGGGUUA CCUGCGAC | 212 | GUCGCAGG CUGAUGAGGNNNNNNNNCCGAA AACCCAUC | 4368 |
| 1388 | UGAGAAAUC UGCUCGCU | 213 | AGCGAGCA CUGAUGAGGNNNNNNNNCCGAA AUUUCUCA | 4369 |
| 1393 | AAUCUGCUC GCUAUUUG | 214 | CAAAUAGC CUGAUGAGGNNNNNNNNCCGAA AGCAGAUUU | 4370 |
| 1397 | UGCUCGCUA UUUGACUC | 215 | GAGUCAAA CUGAUGAGGNNNNNNNNCCGAA AGCGAGCA | 4371 |
| 1399 | CUCGCUAUU UGACUCGU | 216 | ACGAGUCA CUGAUGAGGNNNNNNNNCCGAA AUAGCGAG | 4372 |
| 1400 | UCGCUAUUU GACUCGUG | 217 | CACGAGUC CUGAUGAGGNNNNNNNNCCGAA AAUAGCGA | 4373 |
| 1405 | AUUUGACUC GUGGCUAC | 218 | GUAGCCAC CUGAUGAGGNNNNNNNNCCGAA AGUCAAAU | 4374 |
| 1412 | UCGUGGCUA CUCGUUAA | 219 | UUAACGAG CUGAUGAGGNNNNNNNNCCGAA AGCCACGA | 4375 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1415 | UGGCUACUC GUUAAUUA | 220 | UAAUUAAC CUGAUGAGGNNNNNNNNCCGAA AGUAGCCA | 4376 |
| 1418 | CUACUCGUU AAUUAUCA | 221 | UGAUAAUU CUGAUGAGGNNNNNNNNCCGAA ACGAGUAG | 4377 |
| 1419 | UACUCGUUA AUUAUCAA | 222 | UUGAUAAU CUGAUGAGGNNNNNNNNCCGAA AACGAGUA | 4378 |
| 1422 | UCGUUAAUU AUCAAGGA | 223 | UCCUUGAU CUGAUGAGGNNNNNNNNCCGAA AUUAACGA | 4379 |
| 1423 | CGUUAAUUA UCAAGGAC | 224 | GUCCUUGA CUGAUGAGGNNNNNNNNCCGAA AAUUAACG | 4380 |
| 1425 | UUAAUUAUC AAGGACGU | 225 | ACGUCCUU CUGAUGAGGNNNNNNNNCCGAA AUAAUUAA | 4381 |
| 1434 | AAGGACGUA ACUGAAGA | 226 | UCUUCAGU CUGAUGAGGNNNNNNNNCCGAA ACGUCCUU | 4382 |
| 1456 | CAGGGAAUU AUACAAUC | 227 | GAUUGUAU CUGAUGAGGNNNNNNNNCCGAA AUUCCCUG | 4383 |
| 1457 | AGGGAAUUA UACAAUCU | 228 | AGAUUGUA CUGAUGAGGNNNNNNNNCCGAA AAUUCCCU | 4384 |
| 1459 | GGAAUUAUA CAAUCUUG | 229 | CAAGAUUG CUGAUGAGGNNNNNNNNCCGAA AUAAUUCC | 4385 |
| 1464 | UAUACAAUC UUGCUGAG | 230 | CUCAGCAA CUGAUGAGGNNNNNNNNCCGAA AUUGUAUA | 4386 |
| 1466 | UACAAUCUU GCUGAGCA | 231 | UGCUCAGC CUGAUGAGGNNNNNNNNCCGAA AGAUUGUA | 4387 |
| 1476 | CUGAGCAUA AAACAGUC | 232 | GACUGUUU CUGAUGAGGNNNNNNNNCCGAA AUGCUCAG | 4388 |
| 1484 | AAACAGUC AAAUGUGU | 233 | ACACAUUU CUGAUGAGGNNNNNNNNCCGAA ACUGUUUU | 4389 |
| 1493 | AAAUGUGUU UAAAAACC | 234 | GGUUUUUA CUGAUGAGGNNNNNNNNCCGAA ACACAUUU | 4390 |
| 1494 | AAUGUGUUU AAAAACCU | 235 | AGGUUUUU CUGAUGAGGNNNNNNNNCCGAA AACACAUU | 4391 |
| 1495 | AUGUGUUUA AAAACCUC | 236 | GAGGUUUU CUGAUGAGGNNNNNNNNCCGAA AAACACAU | 4392 |
| 1503 | AAAAACCUC ACUGCCAG | 237 | GUGGCAGU CUGAUGAGGNNNNNNNNCCGAA AGGUUUUU | 4393 |
| 1513 | CUGCCACUC UAAUUGUC | 238 | GACAAUUA CUGAUGAGGNNNNNNNNCCGAA AGUGGCAG | 4394 |
| 1515 | GCCACUCUA AUUGUCAA | 239 | UUGACAAU CUGAUGAGGNNNNNNNNCCGAA AGAGUGGC | 4395 |
| 1518 | ACUCUAAUU GUCAAUGU | 240 | ACAUUGAC CUGAUGAGGNNNNNNNNCCGAA AUUAGAGU | 4396 |
| 1521 | CUAAUUGUC AAUGUGAA | 241 | UUCACAUU CUGAUGAGGNNNNNNNNCCGAA ACAAUUAG | 4397 |
| 1539 | CCCCAGAUU UACGAAAA | 242 | UUUUCGUA CUGAUGAGGNNNNNNNNCCGAA AUCUGGGG | 4398 |
| 1540 | CCCAGAUUU ACGAAAAG | 243 | CUUUUCGU CUGAUGAGGNNNNNNNNCCGAA AAUCUGGG | 4399 |
| 1541 | CCAGAUUUA CGAAAAGG | 244 | CCUUUUCG CUGAUGAGGNNNNNNNNCCGAA AAAUCUGG | 4400 |
| 1556 | GGCCGUGUC AUCGUUUC | 245 | GAAACGAU CUGAUGAGGNNNNNNNNCCGAA ACACGGCC | 4401 |
| 1559 | CGUGUCAUC GUUUCCAG | 246 | CUGGAAAC CUGAUGAGGNNNNNNNNCCGAA AUGACACG | 4402 |
| 1562 | GUCAUCGUU CCAGACC | 247 | GGUCUGGA CUGAUGAGGNNNNNNNNCCGAA ACGAUGAC | 4403 |
| 1563 | UCAUCGUUU CCAGACCC | 248 | GGGUCUGG CUGAUGAGGNNNNNNNNCCGAA AACGAUGA | 4404 |
| 1564 | CAUCGUUUC CAGACCCG | 249 | CGGGUCUG CUGAUGAGGNNNNNNNNCCGAA AAACGAUG | 4405 |
| 1576 | ACCCGGCUC UCUACCCA | 250 | UGGGUAGA CUGAUGAGGNNNNNNNNCCGAA AGCCGGGU | 4406 |
| 1578 | CCGGCUCUC UACCCACU | 251 | AGUGGGUA CUGAUGAGGNNNNNNNNCCGAA AGAGCCGG | 4407 |
| 1580 | GGCUCUCUA CCCACUGG | 252 | CCAGUGGG CUGAUGAGGNNNNNNNNCCGAA AGAGAGCC | 4408 |
| 1602 | AGACAAAUC CUGACUUG | 253 | CAAGUCAG CUGAUGAGGNNNNNNNNCCGAA AUUUGUCU | 4409 |
| 1609 | UCCUGACUU GUACGGCA | 254 | UGCCGUAC CUGAUGAGGNNNNNNNNCCGAA AGUCAGGA | 4410 |
| 1612 | UGACUUGUA CCGCAUAU | 255 | AUAUGCGG CUGAUGAGGNNNNNNNNCCGAA ACAAGUCA | 4411 |
| 1619 | UACCGCAUA UGGUAUCC | 256 | GGAUACCA CUGAUGAGGNNNNNNNNCCGAA AUGCGGUA | 4412 |
| 1624 | CAUAUGGUA UCCCUCAA | 257 | UUGAGGGA CUGAUGAGGNNNNNNNNCCGAA ACCAUAUG | 4413 |
| 1626 | UAUGGUAUC CCUACACC | 258 | GGUUGAGG CUGAUGAGGNNNNNNNNCCGAA AUACCAUA | 4414 |
| 1630 | GUAUCCCUC AACCUACA | 259 | UGUAGGUU CUGAUGAGGNNNNNNNNCCGAA AGGGAUAC | 4415 |
| 1636 | CUCAACCUA CAAUCAAG | 260 | CUUGAUUG CUGAUGAGGNNNNNNNNCCGAA AGGUUGAG | 4416 |
| 1641 | CCUACAAUC AAGUGGUU | 261 | AACCACUU CUGAUGAGGNNNNNNNNCCGAA AUUGUAGG | 4417 |
| 1649 | CAAGUGGUU CUGGCACC | 262 | GGUGCCAG CUGAUGAGGNNNNNNNNCCGAA ACCACUUG | 4418 |
| 1650 | AAGUGGUUC UGGCACCC | 263 | GGGUGCCA CUGAUGAGGNNNNNNNNCCGAA AACCACUU | 4419 |
| 1663 | ACCCCUGUA ACCAUAAU | 264 | AUUAUGGU CUGAUGAGGNNNNNNNNCCGAA ACAGGGGU | 4420 |
| 1669 | GUAACCAUA AUCAUUCC | 265 | GGAAUGAU CUGAUGAGGNNNNNNNNCCGAA AUGGUUAC | 4421 |
| 1672 | ACCAUAAUC AUUCCGAA | 266 | UUCGGAAU CUGAUGAGGNNNNNNNNCCGAA AUUAUGGU | 4422 |
| 1675 | AUAAUCAUU CCGAAGCA | 267 | UGCUUCGG CUGAUGAGGNNNNNNNNCCGAA AUGAUUAU | 4423 |
| 1676 | UAAUCAUUC CGAAGCAA | 268 | UUGCUUCG CUGAUGAGGNNNNNNNNCCGAA AAUGAUUA | 4424 |
| 1694 | GUGUGACUU UGUUCCA | 269 | UGGAACAA CUGAUGAGGNNNNNNNNCCGAA AGUCACAC | 4425 |
| 1695 | UGUGACUUU GUUCCAAU | 270 | UUGGAACA CUGAUGAGGNNNNNNNNCCGAA AAGUCACA | 4426 |
| 1696 | GUGACUUUG UUCCAAU | 271 | AUUGGAAC CUGAUGAGGNNNNNNNNCCGAA AAAGUCAC | 4427 |
| 1699 | ACUUUGUU CCAAUAAU | 272 | AUUAUUGG CUGAUGAGGNNNNNNNNCCGAA ACAAAAGU | 4428 |
| 1700 | CUUUUGUUC CAAUAAUG | 273 | CAUUAUUG CUGAUGAGGNNNNNNNNCCGAA AACAAAAG | 4429 |
| 1705 | GUUCCAAUA AUGAAGAG | 274 | CUCUUCAU CUGAUGAGGNNNNNNNNCCGAA AUUGGAAC | 4430 |
| 1715 | UGAAGAGUC UUUAUCC | 275 | GGAUAAGA CUGAUGAGGNNNNNNNNCCGAA ACUCUUCA | 4431 |
| 1718 | AGAGUCCUU UAUCCUGG | 276 | CCAGGAUA CUGAUGAGGNNNNNNNNCCGAA AGGACUCU | 4432 |
| 1719 | GAGUCCUUU AUCCUGGA | 277 | UCCAGGAU CUGAUGAGGNNNNNNNNCCGAA AAGGACUC | 4433 |
| 1720 | AGUCCUUUA UCCUGGAU | 278 | AUCCAGGA CUGAUGAGGNNNNNNNNCCGAA AAAGGACU | 4434 |
| 1722 | UCCUUUAUC CUGGAUGC | 279 | GCAUCCAG CUGAUGAGGNNNNNNNNCCGAA AUAAAGGA | 4435 |
| 1755 | AACAGAAUU GAGAGCAU | 280 | AUGCUCUC CUGAUGAGGNNNNNNNNCCGAA AUUCUGUU | 4436 |
| 1764 | GAGAGCAUC ACUCAGCG | 281 | CGCUGAGU CUGAUGAGGNNNNNNNNCCGAA AUGCUCUC | 4437 |
| 1768 | GCAUCACUC AGCGCAUG | 282 | CAUGCGCU CUGAUGAGGNNNNNNNNCCGAA AGUGAUGC | 4438 |
| 1782 | AUGGCAAUA AUAGAAGG | 283 | CCUUCUAU CUGAUGAGGNNNNNNNNCCGAA AUUGCCAU | 4439 |
| 1785 | GCAAUAAUA GAAGGAAA | 284 | UUUCCUUC CUGAUGAGGNNNNNNNNCCGAA AUUAUUGC | 4440 |
| 1798 | GAAAGAAUA AGAUGGCU | 285 | AGCCAUCU CUGAUGAGGNNNNNNNNCCGAA AUUCUUUC | 4441 |
| 1807 | AGAUGGCUA GCACCUUG | 286 | CAAGGUGC CUGAUGAGGNNNNNNNNCCGAA AGCCAUCU | 4442 |
| 1814 | AGCACCUU GGUGGCUA | 287 | CCACACCA CUGAUGAGGNNNNNNNNCCGAA AGGUGCUA | 4443 |
| 1818 | ACCUUGGUU GUGGCUGA | 288 | UCAGCCAC CUGAUGAGGNNNNNNNNCCGAA ACCAAGGU | 4444 |
| 1829 | GCUGACUC UAGAAUUU | 289 | AAAUUCUA CUGAUGAGGNNNNNNNNCCGAA AGUCAGCC | 4445 |
| 1831 | CUGACUCUA GAAUUUCU | 290 | AGAAAUUC CUGAUGAGGNNNNNNNNCCGAA AGAGUCAG | 4446 |
| 1836 | UCUAGAAUU UCUGGAAU | 291 | AUUCCAGA CUGAUGAGGNNNNNNNNCCGAA AUUCUAGA | 4447 |
| 1837 | CUAGAAUUU CUGGAAUC | 292 | GAUUCCAG CUGAUGAGGNNNNNNNNCCGAA AAUUCUAG | 4448 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1838 | UAGAAUUUC UGGAAUCU | 293 | AGAUUCCA CUGAUGAGgnnnnnnnnCCGAA AAAUUCUA | 4449 |
| 1845 | UCUGGAAUC UACAUUUG | 294 | CAAAUGUA CUGAUGAGgnnnnnnnnCCGAA AUUCCAGA | 4450 |
| 1847 | UGGAAUCUA CAUUUGCA | 295 | UGCAAAUG CUGAUGAGgnnnnnnnnCCGAA AGAUUCCA | 4451 |
| 1851 | AUCUACAUU UGCAUAGC | 296 | GCUAUGCA CUGAUGAGgnnnnnnnnCCGAA AUGUAGAU | 4452 |
| 1852 | UCUACAUUU GCAUAGCU | 297 | AGCUAUGC CUGAUGAGgnnnnnnnnCCGAA AAUGUAGA | 4453 |
| 1857 | AUUUGCAUA GCUUCCAA | 298 | UUGGAAGC CUGAUGAGgnnnnnnnnCCGAA AUGCAAAU | 4454 |
| 1861 | GCAUAGCUU CCAAUAAA | 299 | UUUAUUGG CUGAUGAGgnnnnnnnnCCGAA AGCUAUGC | 4455 |
| 1862 | CAUAGCUUC CAAUAAAG | 300 | CUUUAUUG CUGAUGAGgnnnnnnnnCCGAA AAGCUAUG | 4456 |
| 1867 | CUUCCAAUA AAGUUGGG | 301 | CCCAACUU CUGAUGAGgnnnnnnnnCCGAA AUUGGAAG | 4457 |
| 1872 | AAUAAAGUU GGGACUGU | 302 | ACAGUCCC CUGAUGAGgnnnnnnnnCCGAA ACUUUAUU | 4458 |
| 1893 | AGAAACAUA AGCUUUUA | 303 | UAAAAGCU CUGAUGAGgnnnnnnnnCCGAA AUGUUUCU | 4459 |
| 1898 | CAUAAGCUU UUAUAUCA | 304 | UGAUAUAA CUGAUGAGgnnnnnnnnCCGAA AGCUUAUG | 4460 |
| 1899 | AUAAGCUUU UAUAUCAC | 305 | GUGAUAUA CUGAUGAGgnnnnnnnnCCGAA AAGCUUAU | 4461 |
| 1900 | UAAGCUUUU AUAUCACA | 306 | UGUGAUAU CUGAUGAGgnnnnnnnnCCGAA AAAGCUUA | 4462 |
| 1901 | AAGCUUUUA UAUCACAG | 307 | CUGUGAUA CUGAUGAGgnnnnnnnnCCGAA AAAAGCUU | 4463 |
| 1903 | GCUUUUAUA UCACAGAU | 308 | AUCUGUGA CUGAUGAGgnnnnnnnnCCGAA AUAAAAGC | 4464 |
| 1905 | UUUUAUAUC ACAGAUGU | 309 | ACAUCUGU CUGAUGAGgnnnnnnnnCCGAA AUAUAAAA | 4465 |
| 1925 | AAAUGGGUU UCAUGUUA | 310 | UAACAUGA CUGAUGAGgnnnnnnnnCCGAA ACCCAUUU | 4466 |
| 1926 | AAUGGGUUU CAUGUUAA | 311 | UUAACAUG CUGAUGAGgnnnnnnnnCCGAA AACCCAUU | 4467 |
| 1927 | AUGGGUUUC AUGUUAAC | 312 | GUUAACAU CUGAUGAGgnnnnnnnnCCGAA AAACCCAU | 4468 |
| 1932 | UUUCAUGUU AACUUGGA | 313 | UCCAAGUU CUGAUGAGgnnnnnnnnCCGAA ACAUGAAA | 4469 |
| 1933 | UUCAUGUUA ACUUGGAA | 314 | UUCCAAGU CUGAUGAGgnnnnnnnnCCGAA AACAUGAA | 4470 |
| 1937 | UGUUAACUU GGAAAAAA | 315 | UUUUUUCC CUGAUGAGgnnnnnnnnCCGAA AGUUAACA | 4471 |
| 1976 | GAAACUGUC UUGCACAG | 316 | CUGUGCAA CUGAUGAGgnnnnnnnnCCGAA ACAGUUUC | 4472 |
| 1978 | AACUGUCUU GCACAGUU | 317 | AACUGUGC CUGAUGAGgnnnnnnnnCCGAA AGACAGUU | 4473 |
| 1986 | UGCACAGUU AACAAGUU | 318 | AACUUGUU CUGAUGAGgnnnnnnnnCCGAA ACUGUGCA | 4474 |
| 1987 | GCACAGUUA ACAAGUUC | 319 | GAACUUGU CUGAUGAGgnnnnnnnnCCGAA AACUGUGC | 4475 |
| 1994 | UAACAAGUU CUUAUACA | 320 | UGUAUAAG CUGAUGAGgnnnnnnnnCCGAA ACUUGUUA | 4476 |
| 1995 | AACAAGUUC UUAUACAG | 321 | CUGUAUAA CUGAUGAGgnnnnnnnnCCGAA AACUUGUU | 4477 |
| 1997 | CAAGUUCUU AUACAGAG | 322 | CUCUGUAU CUGAUGAGgnnnnnnnnCCGAA AGAACUUG | 4478 |
| 1998 | AAGUUCUUA UACAGAGA | 323 | UCUCUGUA CUGAUGAGgnnnnnnnnCCGAA AAGAACUU | 4479 |
| 2000 | GUUCUUAUA CAGAGACG | 324 | CGUCUCUG CUGAUGAGgnnnnnnnnCCGAA AUAAGAAC | 4480 |
| 2010 | AGAGACGUU ACUUGGAU | 325 | AUCCAAGU CUGAUGAGgnnnnnnnnCCGAA ACGUCUCU | 4481 |
| 2011 | GAGACGUUA CUUGGAUU | 326 | AAUCCAAG CUGAUGAGgnnnnnnnnCCGAA AACGUCUC | 4482 |
| 2014 | ACGUUACUU GGAUUUUA | 327 | UAAAAUCC CUGAUGAGgnnnnnnnnCCGAA AGUAACGU | 4483 |
| 2019 | ACUUGGAUU UUACUGCG | 328 | CGCAGUAA CUGAUGAGgnnnnnnnnCCGAA AUCCAAGU | 4484 |
| 2020 | CUUGGAUUU UACUGCGG | 329 | CCGCAGUA CUGAUGAGgnnnnnnnnCCGAA AAUCCAAG | 4485 |
| 2021 | UUGGAUUUU ACUGCGGA | 330 | UCCGCAGU CUGAUGAGgnnnnnnnnCCGAA AAAUCCAA | 4486 |
| 2022 | UGGAUUUUA CUGCGGAC | 331 | GUCCGCAG CUGAUGAGgnnnnnnnnCCGAA AAAAUCCA | 4487 |
| 2034 | CGGACAGUU AAUAACAG | 332 | CUGUUAUU CUGAUGAGgnnnnnnnnCCGAA ACUGUCCG | 4488 |
| 2035 | GGACAGUUA AUAACAGA | 333 | UCUGUUAU CUGAUGAGgnnnnnnnnCCGAA AACUGUCC | 4489 |
| 2038 | CAGUUAAUA ACAGAACA | 334 | UGUUCUGU CUGAUGAGgnnnnnnnnCCGAA AUUAACUG | 4490 |
| 2054 | AAUGCACUA CAGUAUUA | 335 | UAAUACUG CUGAUGAGgnnnnnnnnCCGAA AGUGCAUU | 4491 |
| 2059 | ACUACAGUA UUAGCAAG | 336 | CUUGCUAA CUGAUGAGgnnnnnnnnCCGAA ACUGUAGU | 4492 |
| 2061 | UACAGUAUU AGCAAGCA | 337 | UGCUUGCU CUGAUGAGgnnnnnnnnCCGAA AUACUGUA | 4493 |
| 2062 | ACAGUAUUA GCAAGCAA | 338 | UUGCUUGC CUGAUGAGgnnnnnnnnCCGAA AAUACUGU | 4494 |
| 2082 | AUGGCCAUC ACUAAGGA | 339 | UCCUUAGU CUGAUGAGgnnnnnnnnCCGAA AUGGCCAU | 4495 |
| 2086 | CCAUCACUA AGGAGCAC | 340 | GUGCUCCU CUGAUGAGgnnnnnnnnCCGAA AGUGAUGG | 4496 |
| 2096 | GGAGCACUC CAUCACUC | 341 | GAGUGAUG CUGAUGAGgnnnnnnnnCCGAA AGUGCUCC | 4497 |
| 2100 | CACUCCAUC ACUCUUAA | 342 | UUAAGAGU CUGAUGAGgnnnnnnnnCCGAA AUGGAGUG | 4498 |
| 2104 | CCAUCACUC UUAAUCUU | 343 | AAGAUUAA CUGAUGAGgnnnnnnnnCCGAA AGUGAUGG | 4499 |
| 2106 | AUCACUCUU AAUCUUAC | 344 | GUAAGAUU CUGAUGAGgnnnnnnnnCCGAA AGAGUGAU | 4500 |
| 2107 | UCACUCUUA AUCUUACC | 345 | GGUAAGAU CUGAUGAGgnnnnnnnnCCGAA AAGAGUGA | 4501 |
| 2110 | CUCUUAAUC UUACCAUC | 346 | GAUGGUAA CUGAUGAGgnnnnnnnnCCGAA AUUAAGAG | 4502 |
| 2112 | CUUAAUCUU ACCAUCAU | 347 | AUGAUGGU CUGAUGAGgnnnnnnnnCCGAA AGAUUAAG | 4503 |
| 2113 | UUAAUCUUA CCAUCAUG | 348 | CAUGAUGG CUGAUGAGgnnnnnnnnCCGAA AAGAUUAA | 4504 |
| 2118 | CUUACCAUC AUGAAUGU | 349 | ACAUUCAU CUGAUGAGgnnnnnnnnCCGAA AUGGUAAG | 4505 |
| 2127 | AUGAAUGUU CCCUGCA | 350 | UGCAGGGA CUGAUGAGgnnnnnnnnCCGAA ACAUUCAU | 4506 |
| 2128 | UGAAUGUUU CCCUGCAA | 351 | UUGCAGGG CUGAUGAGgnnnnnnnnCCGAA AACAUUCA | 4507 |
| 2129 | GAAUGUUUC CCUGCAAG | 352 | CUUGCAGG CUGAUGAGgnnnnnnnnCCGAA AAACAUUC | 4508 |
| 2140 | UGCAAGAUU CAGGCACC | 353 | GGUGCCUG CUGAUGAGgnnnnnnnnCCGAA AUCUUGCA | 4509 |
| 2141 | GCAAGAUUC AGGCACCU | 354 | AGGUGCCU CUGAUGAGgnnnnnnnnCCGAA AAUCUUGC | 4510 |
| 2150 | AGGCACCUA UGCCUGCA | 355 | UGCAGGCA CUGAUGAGgnnnnnnnnCCGAA AGGUGCCU | 4511 |
| 2172 | AGGAAUGUA UACACAGG | 356 | CCUGUGUA CUGAUGAGgnnnnnnnnCCGAA ACAUUCCU | 4512 |
| 2174 | GAAUGUAUA CACAGGGG | 357 | CCCCUGUG CUGAUGAGgnnnnnnnnCCGAA AUACAUUC | 4513 |
| 2190 | GAAGAAAUC UCCAGAA | 358 | UUCUGGAG CUGAUGAGgnnnnnnnnCCGAA AUUUCUUC | 4514 |
| 2193 | GAAAUCCUC CAGAAGAA | 359 | UUCUUCUG CUGAUGAGgnnnnnnnnCCGAA AGGAUUUC | 4515 |
| 2208 | AAAGAAAUU ACAACGA | 360 | CUGAUUGU CUGAUGAGgnnnnnnnnCCGAA AUUUCUUU | 4516 |
| 2209 | AAGAAAUUA CAAUCAGA | 361 | UCUGAUUG CUGAUGAGgnnnnnnnnCCGAA AAUUUCUU | 4517 |
| 2214 | AUUACAAUC AGAGAUCA | 362 | UGAUCUCU CUGAUGAGgnnnnnnnnCCGAA AUUGUAAU | 4518 |
| 2221 | UCAGAGAUC AGGAAGCA | 363 | UGCUUCCU CUGAUGAGgnnnnnnnnCCGAA AUCUCUGA | 4519 |
| 2234 | AGCACCAUA CCUCCUGC | 364 | GCAGGAGG CUGAUGAGgnnnnnnnnCCGAA AUGGUGCU | 4520 |
| 2238 | CCAUACCUC CUGCGAAA | 365 | UUUCGCAG CUGAUGAGgnnnnnnnnCCGAA AGGUAUGG | 4521 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 2250 | CGAAACCUC AGUGAUCA | 366 | UGAUCACU CUGAUGAGgNNNNNNNNCCGAA AGGUUUCG | 4522 |
| 2257 | UCAGUGAUC ACACAGUG | 367 | CACUGUGU CUGAUGAGgNNNNNNNNCCGAA AUCACUGA | 4523 |
| 2271 | GUGGCCAUC AGCAGUUC | 368 | GAACUGCU CUGAUGAGgNNNNNNNNCCGAA AUGGCCAC | 4524 |
| 2278 | UCAGCAGUU CCACCACU | 369 | AGUGGUGG CUGAUGAGgNNNNNNNNCCGAA ACUGCUGA | 4525 |
| 2279 | CAGCAGUUC CACCACUU | 370 | AAGUGGUG CUGAUGAGgNNNNNNNNCCGAA AACUGCUG | 4526 |
| 2287 | CCACCACUU UAGACUGU | 371 | ACAGUCUA CUGAUGAGgNNNNNNNNCCGAA AGUGGUGG | 4527 |
| 2288 | CACCACUUU AGACUGUC | 372 | GACAGUCU CUGAUGAGgNNNNNNNNCCGAA AAGUGGUG | 4528 |
| 2289 | ACCACUUUA GACUGUCA | 373 | UGACAGUC CUGAUGAGgNNNNNNNNCCGAA AAAGUGGU | 4529 |
| 2296 | UAGACUGUC AUGCUAAU | 374 | AUUAGCAU CUGAUGAGgNNNNNNNNCCGAA ACAGUCUA | 4530 |
| 2302 | GUCAUGCUA AUGGUGUC | 375 | GACACCAU CUGAUGAGgNNNNNNNNCCGAA AGCAUGAC | 4531 |
| 2310 | AAUGGUGUC CCCGAGCC | 376 | GGCUCGGG CUGAUGAGgNNNNNNNNCCGAA ACACCAUU | 4532 |
| 2320 | CCGAGCCUC AGAUCACU | 377 | AGUGAUCU CUGAUGAGgNNNNNNNNCCGAA AGGCUCGG | 4533 |
| 2325 | CCUCAGAUC ACUUGGUU | 378 | AACCAAGU CUGAUGAGgNNNNNNNNCCGAA AUCUGAGG | 4534 |
| 2329 | AGAUCACUU GGUUUAAA | 379 | UUUAAACC CUGAUGAGgNNNNNNNNCCGAA AGUGAUCU | 4535 |
| 2333 | CACUUGGUU UAAAAACA | 380 | UGUUUUUA CUGAUGAGgNNNNNNNNCCGAA ACCAAGUG | 4536 |
| 2334 | ACUUGGUUU AAAAACAA | 381 | UUGUUUUU CUGAUGAGgNNNNNNNNCCGAA AACCAAGU | 4537 |
| 2335 | CUUGGUUUA AAACAAC | 382 | GUUGUUUU CUGAUGAGgNNNNNNNNCCGAA AAACCAAG | 4538 |
| 2352 | CACAAAAUA CAACAAGA | 383 | UCUUGUUG CUGAUGAGgNNNNNNNNCCGAA AUUUUGUG | 4539 |
| 2370 | CCUGGAAUU AUUUUAGG | 384 | CCUAAAAU CUGAUGAGgNNNNNNNNCCGAA AUUCCAGG | 4540 |
| 2371 | CUGGAAUUA UUUUAGGA | 385 | UCCUAAAA CUGAUGAGgNNNNNNNNCCGAA AAUUCCAG | 4541 |
| 2373 | GGAAUUAUU UUAGGACC | 386 | GGUCCUAA CUGAUGAGgNNNNNNNNCCGAA AUAAUUCC | 4542 |
| 2374 | GAAUUAUUU UAGGACCA | 387 | UGGUCCUA CUGAUGAGgNNNNNNNNCCGAA AAUAAUUC | 4543 |
| 2375 | AAUUAUUUU AGGACCAG | 388 | CUGGUCCU CUGAUGAGgNNNNNNNNCCGAA AAAUAAUU | 4544 |
| 2376 | AUUAUUUUA GGACCAGG | 389 | CCUGGUCC CUGAUGAGgNNNNNNNNCCGAA AAAAUAAU | 4545 |
| 2399 | CACGCUGUU UAUUGAAA | 390 | UUUCAAUA CUGAUGAGgNNNNNNNNCCGAA ACAGCGUG | 4546 |
| 2400 | ACGCUGUUU AUUGAAAG | 391 | CUUUCAAU CUGAUGAGgNNNNNNNNCCGAA AACAGCGU | 4547 |
| 2401 | CGCUGUUUA UUGAAGA | 392 | UCUUUCAA CUGAUGAGgNNNNNNNNCCGAA AAACAGCG | 4548 |
| 2403 | CUGUUUAUU GAAAGAGU | 393 | ACUCUUUC CUGAUGAGgNNNNNNNNCCGAA AUAAACAG | 4549 |
| 2412 | GAAAGAGUC ACAGAAGA | 394 | UCUUCUGU CUGAUGAGgNNNNNNNNCCGAA ACUCUUUC | 4550 |
| 2433 | GAAGGUGUC UAUCACUG | 395 | CAGUGAUA CUGAUGAGgNNNNNNNNCCGAA ACACCUUC | 4551 |
| 2435 | AGGUGUCUA UCACUGCA | 396 | UGCAGUGA CUGAUGAGgNNNNNNNNCCGAA AGACACCU | 4552 |
| 2437 | GUGUCUAUC ACUGCAAA | 397 | UUUGCAGU CUGAUGAGgNNNNNNNNCCGAA AUAGACAC | 4553 |
| 2465 | GAAGGGCUC UGUGGAAA | 398 | UUUCCACA CUGAUGAGgNNNNNNNNCCGAA AGCCCUUC | 4554 |
| 2476 | UGGAAAGUU CAGCAUAC | 399 | GUAUGCUG CUGAUGAGgNNNNNNNNCCGAA ACUUUCCA | 4555 |
| 2477 | GGAAAGUUC AGCAUACC | 400 | GGUAUGCU CUGAUGAGgNNNNNNNNCCGAA AACUUUCC | 4556 |
| 2483 | UUCAGCAUA CCUCACUG | 401 | CAGUGAGG CUGAUGAGgNNNNNNNNCCGAA AUGCUGAA | 4557 |
| 2487 | GCAUACCUC ACUGUUCA | 402 | UGAACAGU CUGAUGAGgNNNNNNNNCCGAA AGGUAUGC | 4558 |
| 2493 | CUCACUGUU CAAGGAAC | 403 | GUUCCUUG CUGAUGAGgNNNNNNNNCCGAA ACAGUGAG | 4559 |
| 2494 | UCACUGUUC AAGGAACC | 404 | GGUUCCUU CUGAUGAGgNNNNNNNNCCGAA AACAGUGA | 4560 |
| 2504 | AGGAACCUC GGACAAGU | 405 | ACUUGUCC CUGAUGAGgNNNNNNNNCCGAA AGGUUCCU | 4561 |
| 2513 | GGACAAGUC UAAUCUGG | 406 | CCAGAUUA CUGAUGAGgNNNNNNNNCCGAA ACUUGUCC | 4562 |
| 2515 | ACAAGUCUA AUCUGGAG | 407 | CUCCAGAU CUGAUGAGgNNNNNNNNCCGAA AGACUUGU | 4563 |
| 2518 | AGUCUAAUC UGGAGCCA | 408 | CAGCUCCA CUGAUGAGgNNNNNNNNCCGAA AUUAGACU | 4564 |
| 2529 | GAGCUGAUC ACUCUAAC | 409 | GUUAGAGU CUGAUGAGgNNNNNNNNCCGAA AUCAGCUC | 4565 |
| 2533 | UGAUCACUC UAACAUGC | 410 | GCAUGUUA CUGAUGAGgNNNNNNNNCCGAA AGUGAUCA | 4566 |
| 2535 | AUCACUCUA ACAUGCAC | 411 | GUGCAUGU CUGAUGAGgNNNNNNNNCCGAA AGAGUGAU | 4567 |
| 2560 | CUGCGACUC UCAGCUGG | 412 | CCAGAUGA CUGAUGAGgNNNNNNNNCCGAA AGUCGCAG | 4568 |
| 2562 | GCGACUCUC UUCUGGCU | 413 | AGCCAGAA CUGAUGAGgNNNNNNNNCCGAA AGAGUCGC | 4569 |
| 2564 | GACUCUCUU CUGGCUCC | 414 | GGAGCCAG CUGAUGAGgNNNNNNNNCCGAA AGAGAGUC | 4570 |
| 2565 | ACUCUCUUC UGGCUCCU | 415 | AGGAGCCA CUGAUGAGgNNNNNNNNCCGAA AAGAGAGU | 4571 |
| 2571 | UUCUGGCUC CUAUUAAC | 416 | GUUAAUAG CUGAUGAGgNNNNNNNNCCGAA AGCCAGAA | 4572 |
| 2574 | UGGCUCCUA UUAACCCU | 417 | AGGGUUAA CUGAUGAGgNNNNNNNNCCGAA AGGAGCCA | 4573 |
| 2576 | GCUCCUAUU AACCCUCC | 418 | GGAGGGUU CUGAUGAGgNNNNNNNNCCGAA AUAGGAGC | 4574 |
| 2577 | CUCCUAUUA ACCCUCCU | 419 | AGGAGGGU CUGAUGAGgNNNNNNNNCCGAA AAUAGGAG | 4575 |
| 2583 | UUAACCCUC CUAUCCG | 420 | CGGAUAAG CUGAUGAGgNNNNNNNNCCGAA AGGGUUAA | 4576 |
| 2586 | ACCCUCCUU AUCCGAAA | 421 | UUUCGGAU CUGAUGAGgNNNNNNNNCCGAA AGGAGGGU | 4577 |
| 2587 | CCCUCCUUA UCCGAAAA | 422 | UUUUCGGA CUGAUGAGgNNNNNNNNCCGAA AAGGAGGG | 4578 |
| 2589 | CUCCUUAUC CGAAAAAU | 423 | AUUUUUCG CUGAUGAGgNNNNNNNNCCGAA AUAAGGAG | 4579 |
| 2606 | GAAAAGGUC UUCUUCUG | 424 | CAGAAGAA CUGAUGAGgNNNNNNNNCCGAA ACCUUUUC | 4580 |
| 2608 | AAAGGUCUU CUUCUGAA | 425 | UUCAGAAG CUGAUGAGgNNNNNNNNCCGAA AGACCUUU | 4581 |
| 2609 | AAGGUCUUC UUCUGAAA | 426 | UUUCAGAA CUGAUGAGgNNNNNNNNCCGAA AAGACCUU | 4582 |
| 2611 | GGUCUUCUU CUGAAAUA | 427 | UAUUUCAG CUGAUGAGgNNNNNNNNCCGAA AGAAGACC | 4583 |
| 2612 | GUCUUCUUC UGAAAUAA | 428 | UUAUUUCA CUGAUGAGgNNNNNNNNCCGAA AAGAAGAC | 4584 |
| 2619 | UCUGAAAUA AAGACUGA | 429 | UCAGUCUU CUGAUGAGgNNNNNNNNCCGAA AUUUCAGA | 4585 |
| 2630 | GACUGACUA CCUAUCAA | 430 | UUGAUAGG CUGAUGAGgNNNNNNNNCCGAA AGUCAGUC | 4586 |
| 2634 | GACUACCUA UCAAUUAU | 431 | AUAAUUGA CUGAUGAGgNNNNNNNNCCGAA AGGUAGUC | 4587 |
| 2636 | CUACCUAUC AAUUAUAA | 432 | UUAUAAUU CUGAUGAGgNNNNNNNNCCGAA AUAGGUAG | 4588 |
| 2640 | CUAUCAAUU AUAAUGGA | 433 | UCCAUUAU CUGAUGAGgNNNNNNNNCCGAA AUUGAUAG | 4589 |
| 2641 | UAUCAAUUA UAAUGGAC | 434 | GUCCAUUA CUGAUGAGgNNNNNNNNCCGAA AAUUGAUA | 4590 |
| 2643 | UCAAUUAUA AUGGACCC | 435 | GGGUCCAU CUGAUGAGgNNNNNNNNCCGAA AUAAUUGA | 4591 |
| 2661 | GAUGAAGUU CCUUUGGA | 436 | UCCAAAGG CUGAUGAGgNNNNNNNNCCGAA ACUUCAUC | 4592 |
| 2662 | AUGAAGUUC CUUUGGAU | 437 | AUCCAAAG CUGAUGAGgNNNNNNNNCCGAA AACUUCAU | 4593 |
| 2665 | AAGUUCCUU GGAUGAG | 438 | CUCAUCCA CUGAUGAGgNNNNNNNNCCGAA AGGAACUU | 4594 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 2666 | AGUUCCUUU GGAUGAGC | 439 | GCUCAUCC CUGAUGAGGNNNNNNNNCCGAA AAGGAACU | 4595 |
| 2688 | GAGCGGCUC CCUUAUGA | 440 | UCAUAAGG CUGAUGAGGNNNNNNNNCCGAA AGCCGCUC | 4596 |
| 2692 | GGCUCCCUU AUGAUGCC | 441 | GGCAUCAU CUGAUGAGGNNNNNNNNCCGAA AGGGAGCC | 4597 |
| 2693 | GCUCCCUUA UGAUGCCA | 442 | UGGCAUCA CUGAUGAGGNNNNNNNNCCGAA AAGGGAGC | 4598 |
| 2714 | GUGGGAGUU UGCCCGGG | 443 | CCCGGGCA CUGAUGAGGNNNNNNNNCCGAA ACUCCCAC | 4599 |
| 2715 | UGGGAGUUU GCCCGGGA | 444 | UCCCGGGC CUGAUGAGGNNNNNNNNCCGAA AACUCCCA | 4600 |
| 2730 | GAGAGACUU AAACUGGG | 445 | CCCAGUUU CUGAUGAGGNNNNNNNNCCGAA AGUCUCUC | 4601 |
| 2731 | AGAGACUUA AACUGGGC | 446 | GCCCAGUU CUGAUGAGGNNNNNNNNCCGAA AAGUCUCU | 4602 |
| 2744 | GGGCAAAUC ACUUGGAA | 447 | UUCCAAGU CUGAUGAGGNNNNNNNNCCGAA AUUUGCCC | 4603 |
| 2748 | AAAUCACUU GGAAGAGG | 448 | CCUCUUCC CUGAUGAGGNNNNNNNNCCGAA AGUGAUUU | 4604 |
| 2761 | GAGGGCUUU UGGAAAA | 449 | UUUUCCAA CUGAUGAGGNNNNNNNNCCGAA AGCCCCUC | 4605 |
| 2762 | AGGGGCUUU UGGAAAAG | 450 | CUUUUCCA CUGAUGAGGNNNNNNNNCCGAA AAGCCCCU | 4606 |
| 2763 | GGGGCUUUU GGAAAAGU | 451 | ACUUUUCC CUGAUGAGGNNNNNNNNCCGAA AAAGCCCC | 4607 |
| 2775 | AAAGUGGUU CAAGCAUC | 452 | GAUGCUUG CUGAUGAGGNNNNNNNNCCGAA ACCACUUU | 4608 |
| 2776 | AAGUGGUUC AAGCAUCA | 453 | UGAUGCUU CUGAUGAGGNNNNNNNNCCGAA AACCACUU | 4609 |
| 2783 | UCAAGCAUC AGCAUUUG | 454 | CAAAUGCU CUGAUGAGGNNNNNNNNCCGAA AUGCUUGA | 4610 |
| 2789 | AUCAGCAUU UGGCAUUA | 455 | UAAUGCCA CUGAUGAGGNNNNNNNNCCGAA AUGCUGAU | 4611 |
| 2790 | UCAGCAUUU GGCAUUAA | 456 | UUAAUGCC CUGAUGAGGNNNNNNNNCCGAA AAUGCUGA | 4612 |
| 2796 | UUUGGCAUU AAGAAAUC | 457 | GAUUUCUU CUGAUGAGGNNNNNNNNCCGAA AUGCCAAA | 4613 |
| 2797 | UUGGCAUUA AGAAAUCA | 458 | UGAUUUCU CUGAUGAGGNNNNNNNNCCGAA AAUGCCAA | 4614 |
| 2804 | UAAGAAAUC ACCUACGU | 459 | ACGUAGGU CUGAUGAGGNNNNNNNNCCGAA AUUUCUUA | 4615 |
| 2809 | AAUCACCUA CGUGCCGG | 460 | CCGGCACG CUGAUGAGGNNNNNNNNCCGAA AGGUGAUU | 4616 |
| 2864 | CAGCGAGUA CAAAGCUC | 461 | GAGCUUUG CUGAUGAGGNNNNNNNNCCGAA ACUCGCUG | 4617 |
| 2872 | ACAAAGCUC UGAUGACU | 462 | AGUCAUCA CUGAUGAGGNNNNNNNNCCGAA AGCUUUGU | 4618 |
| 2886 | ACUGAGCUA AAAAUCUU | 463 | AAGAUUUU CUGAUGAGGNNNNNNNNCCGAA AGCUCAGU | 4619 |
| 2892 | CUAAAAAUC UUGACCCA | 464 | UGGGUCAA CUGAUGAGGNNNNNNNNCCGAA AUUUUUAG | 4620 |
| 2894 | AAAAAUCUU GACCCACA | 465 | UGUGGGUC CUGAUGAGGNNNNNNNNCCGAA AGAUUUUU | 4621 |
| 2904 | ACCCACAUU GGCCACCA | 466 | UGGUGGCC CUGAUGAGGNNNNNNNNCCGAA AUGUGGGU | 4622 |
| 2914 | GCCACCAUC UGAACGUG | 467 | CACGUUCA CUGAUGAGGNNNNNNNNCCGAA AUGGUGGC | 4623 |
| 2925 | AACGUGGUU AACCUGCU | 468 | AGCAGGUU CUGAUGAGGNNNNNNNNCCGAA ACCACGUU | 4624 |
| 2926 | ACGUGGUUA ACCUGCGU | 469 | CAGCAGGU CUGAUGAGGNNNNNNNNCCGAA AACCACGU | 4625 |
| 2962 | GAGGGCCUC UGAUGGUG | 470 | CACCAUCA CUGAUGAGGNNNNNNNNCCGAA AGGCCCUC | 4626 |
| 2973 | AUGGUGAUU GUUGAAUA | 471 | UAUUCAAC CUGAUGAGGNNNNNNNNCCGAA AUCACCAU | 4627 |
| 2976 | GUGAUUGUU GAAUACUG | 472 | CAGUAUUC CUGAUGAGGNNNNNNNNCCGAA ACAAUCAC | 4628 |
| 2981 | UGUUGAAUA CUGCAAAU | 473 | AUUUGCAG CUGAUGAGGNNNNNNNNCCGAA AUUCAACA | 4629 |
| 2990 | CUGCAAAUA UGGAAAUC | 474 | GAUUUCCA CUGAUGAGGNNNNNNNNCCGAA AUUUGCAG | 4630 |
| 2998 | AUGGAAAUC UCUCCAAC | 475 | GUUGGAGA CUGAUGAGGNNNNNNNNCCGAA AUUUCCAU | 4631 |
| 3000 | GGAAAUCUC UCCAACUA | 476 | UAGUUGGA CUGAUGAGGNNNNNNNNCCGAA AGAUUUCC | 4632 |
| 3002 | AAAUCUCUC CAACUACC | 477 | GGUAGUUG CUGAUGAGGNNNNNNNNCCGAA AGAGAUUU | 4633 |
| 3008 | CUCCAACUA CCUCAAGA | 478 | UCUUGAGG CUGAUGAGGNNNNNNNNCCGAA AGUUGGAG | 4634 |
| 3012 | AACUACCUC AAGAGCAA | 479 | UUGCUCUU CUGAUGAGGNNNNNNNNCCGAA AGGUAGUU | 4635 |
| 3029 | ACGUGACUU AUUUUUUC | 480 | GAAAAAAU CUGAUGAGGNNNNNNNNCCGAA AGUCACGU | 4636 |
| 3030 | CGUGACUUA UUUUUCU | 481 | AGAAAAAA CUGAUGAGGNNNNNNNNCCGAA AAGUCACG | 4637 |
| 3032 | UGACUUAUU UUUCUCA | 482 | UGAGAAAA CUGAUGAGGNNNNNNNNCCGAA AUAAGUCA | 4638 |
| 3033 | GACUUAUUU UUUCUCAA | 483 | UUGAGAAA CUGAUGAGGNNNNNNNNCCGAA AAUAAGUC | 4639 |
| 3034 | ACUUAUUUU UUCUCAAC | 484 | GUUGAGAA CUGAUGAGGNNNNNNNNCCGAA AAAUAAGU | 4640 |
| 3035 | CUUAUUUUU UCUCAACA | 485 | UGUUGAGA CUGAUGAGGNNNNNNNNCCGAA AAAAUAAG | 4641 |
| 3036 | UUAUUUUUU CUCAACAA | 486 | UUGUUGAG CUGAUGAGGNNNNNNNNCCGAA AAAAAUAA | 4642 |
| 3037 | UAUUUUUUC UCAACAAG | 487 | CUUGUUGA CUGAUGAGGNNNNNNNNCCGAA AAAAAAUA | 4643 |
| 3039 | UUUUUUCUC AACAAGGA | 488 | UCCUUGUU CUGAUGAGGNNNNNNNNCCGAA AGAAAAAA | 4644 |
| 3057 | GCAGCACUA CACAUGGA | 489 | UCCAUGUG CUGAUGAGGNNNNNNNNCCGAA AGUGCUGC | 4645 |
| 3070 | UGGAGCCUA AGAAAGAA | 490 | UUCUUUCU CUGAUGAGGNNNNNNNNCCGAA AGGCUCCA | 4646 |
| 3120 | CCAAGACUA GAUAGCGU | 491 | ACGCUAUC CUGAUGAGGNNNNNNNNCCGAA AGUCUUGG | 4647 |
| 3124 | GACUAGAUA GCGUCACC | 492 | GGUGACGC CUGAUGAGGNNNNNNNNCCGAA AUCUAGUC | 4648 |
| 3129 | GAUAGCGUC ACCAGCAG | 493 | CUGCUGGU CUGAUGAGGNNNNNNNNCCGAA ACGCUAUC | 4649 |
| 3146 | CGAAAGCUU GCGAGCGG | 494 | AGCUCGCA CUGAUGAGGNNNNNNNNCCGAA AGCUUUCG | 4650 |
| 3147 | GAAAGCUUU GCGAGCUC | 495 | GAGCUCGC CUGAUGAGGNNNNNNNNCCGAA AAGCUUUC | 4651 |
| 3155 | UGCGAGCUC CGGCUUUC | 496 | GAAAGCCG CUGAUGAGGNNNNNNNNCCGAA AGCUCGCA | 4652 |
| 3161 | CUCCGGCUU UCAGGAAG | 497 | CUUCCUGA CUGAUGAGGNNNNNNNNCCGAA AGCCGGAG | 4653 |
| 3162 | UCCGGCUUU CAGGAAGA | 498 | UCUUCCUG CUGAUGAGGNNNNNNNNCCGAA AAGCCGGA | 4654 |
| 3163 | CCGGCUUUC AGGAAGAU | 499 | AUCUUCCU CUGAUGAGGNNNNNNNNCCGAA AAAGCCGG | 4655 |
| 3172 | AGGAAGAUA AAAGUCUG | 500 | CAGACUUU CUGAUGAGGNNNNNNNNCCGAA AUCUUCCU | 4656 |
| 3178 | AUAAAGUC UGAGUGAU | 501 | AUCACUCA CUGAUGAGGNNNNNNNNCCGAA ACUUUUAU | 4657 |
| 3189 | AGUGAUGUU GAGGAAGA | 502 | UCUUCCUC CUGAUGAGGNNNNNNNNCCGAA ACAUCACU | 4658 |
| 3205 | AGGAGGAUU CUGACGGU | 503 | ACCGUCAG CUGAUGAGGNNNNNNNNCCGAA AUCCUCCU | 4659 |
| 3206 | GGAGGAUUC UGACGGUU | 504 | AACCGUCA CUGAUGAGGNNNNNNNNCCGAA AAUCCUCC | 4660 |
| 3214 | CUGACGGUU UCUACAAG | 505 | CUUGUAGA CUGAUGAGGNNNNNNNNCCGAA ACCGUCAG | 4661 |
| 3215 | UGACGGUUU CUACAAGG | 506 | CCUUGUAG CUGAUGAGGNNNNNNNNCCGAA AACCGUCA | 4662 |
| 3216 | GACGGUUUC UACAAGGA | 507 | UCCUUGUA CUGAUGAGGNNNNNNNNCCGAA AAACCGUC | 4663 |
| 3218 | CGGUUUCUA CAAGGAGC | 508 | GCUCCUUG CUGAUGAGGNNNNNNNNCCGAA AGAAACCG | 4664 |
| 3231 | GAGCCCAUC ACUAUGGA | 509 | UCCAUAGU CUGAUGAGGNNNNNNNNCCGAA AUGGGCUC | 4665 |
| 3235 | CCAUCACUA UGGAAGAU | 510 | AUCUUCCA CUGAUGAGGNNNNNNNNCCGAA AGUGAUGG | 4666 |
| 3244 | UGGAAGAUC UGAUUUCU | 511 | AGAAAUCA CUGAUGAGGNNNNNNNNCCGAA AUCUUCCA | 4667 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 3249 | GAUCUGAUU UCUUACAG | 512 | CUGUAAGA CUGAUGAGGNNNNNNNNCCGAA AUCAGAUC | 4668 |
| 3250 | AUCUGAUUU CUUACAGU | 513 | ACUGUAAG CUGAUGAGGNNNNNNNNCCGAA AAUCAGAU | 4669 |
| 3251 | UCUGAUUUC UUACAGUU | 514 | AACUGUAA CUGAUGAGGNNNNNNNNCCGAA AAAUCAGA | 4670 |
| 3253 | UGAUUUCUU ACAGUUUU | 515 | AAAACUGU CUGAUGAGGNNNNNNNNCCGAA AGAAAUCA | 4671 |
| 3254 | GAUUUCUUA CAGUUUUC | 516 | GAAAACUG CUGAUGAGGNNNNNNNNCCGAA AAGAAAUC | 4672 |
| 3259 | CUUACAGUU UUCAAGUG | 517 | CACUUGAA CUGAUGAGGNNNNNNNNCCGAA ACUGUAAG | 4673 |
| 3260 | UUACAGUUU UCAAGUGG | 518 | CCACUUGA CUGAUGAGGNNNNNNNNCCGAA AACUGUAA | 4674 |
| 3261 | UACAGUUUU CAAGUGGC | 519 | GCCACUUG CUGAUGAGGNNNNNNNNCCGAA AAACUGUA | 4675 |
| 3262 | ACAGUUUUC AAGUGGCC | 520 | GGCCACUU CUGAUGAGGNNNNNNNNCCGAA AAAACUGU | 4676 |
| 3284 | CAUGGAGUU CCUGUCUU | 521 | AAGACAGG CUGAUGAGGNNNNNNNNCCGAA ACUCCAUG | 4677 |
| 3285 | AUGGAGUUC CUGUCUUC | 522 | GAAGACAG CUGAUGAGGNNNNNNNNCCGAA AACUCCAU | 4678 |
| 3290 | GUUCCUGUC UUCCAGAA | 523 | UUCUGGAA CUGAUGAGGNNNNNNNNCCGAA ACAGGAAC | 4679 |
| 3292 | UCCUGUCUU CCAGAAAG | 524 | CUUUCUGG CUGAUGAGGNNNNNNNNCCGAA AGACAGGA | 4680 |
| 3293 | CCUGUCUUC CAGAAAGU | 525 | ACUUUCUG CUGAUGAGGNNNNNNNNCCGAA AAGACAGG | 4681 |
| 3306 | AAGUGCAUU CAUCGGGA | 526 | UCCCGAUG CUGAUGAGGNNNNNNNNCCGAA AUGCACUU | 4682 |
| 3307 | AGUGCAUUC AUCGGGAC | 527 | GUCCCGAU CUGAUGAGGNNNNNNNNCCGAA AAUGCACU | 4683 |
| 3310 | GCAUUCAUC GGGACCUG | 528 | CAGGUCCC CUGAUGAGGNNNNNNNNCCGAA AUGAAUGC | 4684 |
| 3333 | AGAAACAUU CUUUAUCU | 529 | GAUAAAGA CUGAUGAGGNNNNNNNNCCGAA AUGUUUCU | 4685 |
| 3334 | GAAACAUUC UUUAUCUG | 530 | AGAUAAAA CUGAUGAGGNNNNNNNNCCGAA AAUGUUUC | 4686 |
| 3336 | AACAUUCUU UAUCUGA | 531 | UCAGAUAA CUGAUGAGGNNNNNNNNCCGAA AGAAUGUU | 4687 |
| 3337 | ACAUUCUUU AUCUGAG | 532 | CUCAGAUA CUGAUGAGGNNNNNNNNCCGAA AAGAAUGU | 4688 |
| 3338 | CAUUCUUUU AUCUGAGA | 533 | UCUCAGAU CUGAUGAGGNNNNNNNNCCGAA AAAGAAUG | 4689 |
| 3339 | AUUCUUUUA UCUGAGAA | 534 | UUCUCAGA CUGAUGAGGNNNNNNNNCCGAA AAAAGAAU | 4690 |
| 3341 | UCUUUUAUC UGAGAACA | 535 | UGUUCUCA CUGAUGAGGNNNNNNNNCCGAA AUAAAAGA | 4691 |
| 3363 | GUGAAGAUU GUGAUUU | 536 | AAAUCACA CUGAUGAGGNNNNNNNNCCGAA AUCUUCAC | 4692 |
| 3364 | UGAAGAUUU GUGAUUUU | 537 | AAAAUCAC CUGAUGAGGNNNNNNNNCCGAA AAUCUUCA | 4693 |
| 3370 | UUUGUGAUU UGGCCUU | 538 | AAGGCCAA CUGAUGAGGNNNNNNNNCCGAA AUCACAAA | 4694 |
| 3371 | UUGUGAUUU GGCCUUG | 539 | CAAGGCCA CUGAUGAGGNNNNNNNNCCGAA AAUCACAA | 4695 |
| 3372 | UGUGAUUUG GCCUUGC | 540 | GCAAGGCC CUGAUGAGGNNNNNNNNCCGAA AAAUCACA | 4696 |
| 3378 | UUUGGCCUU GCCCGGGA | 541 | UCCCGGGC CUGAUGAGGNNNNNNNNCCGAA AGGCCAAA | 4697 |
| 3388 | CCCGGGAUA UUUAUAAG | 542 | CUUAUAAA CUGAUGAGGNNNNNNNNCCGAA AUCCCGGG | 4698 |
| 3390 | CGGGAUAUU UAUAAGAA | 543 | UUCUUAUA CUGAUGAGGNNNNNNNNCCGAA AUAUCCCG | 4699 |
| 3391 | GGGAUAUUU AUAAGAAC | 544 | GUUCUUAU CUGAUGAGGNNNNNNNNCCGAA AAUAUCCC | 4700 |
| 3392 | GGAUAUUUA UAAGAACC | 545 | GGUUCUUA CUGAUGAGGNNNNNNNNCCGAA AAAAUAUCC | 4701 |
| 3394 | AUAUUUAUA AGAACCCC | 546 | GGGGUUCU CUGAUGAGGNNNNNNNNCCGAA AUAAAAUAU | 4702 |
| 3406 | ACCCCGAUU AUGUGAGA | 547 | UCUCACAU CUGAUGAGGNNNNNNNNCCGAA AUCGGGGU | 4703 |
| 3407 | CCCCGAUUA UGUGAGAA | 548 | UUCUCACA CUGAUGAGGNNNNNNNNCCGAA AAUCGGGG | 4704 |
| 3424 | AAGGAGAUA CUCGACUU | 549 | AAGUCGAG CUGAUGAGGNNNNNNNNCCGAA AUCUCCUU | 4705 |
| 3427 | GAGAUACUC GACUUCCU | 550 | AGGAAGUC CUGAUGAGGNNNNNNNNCCGAA AGUAUCUC | 4706 |
| 3432 | ACUCGACUU CCUCUGAA | 551 | UUCAGAGG CUGAUGAGGNNNNNNNNCCGAA AGUCGAGU | 4707 |
| 3433 | CUCGACUUC CUCUGAAA | 552 | UUUCAGAG CUGAUGAGGNNNNNNNNCCGAA AAGUCGAG | 4708 |
| 3436 | GACUUCCUC UGAAAUGG | 553 | CCAUUUCA CUGAUGAGGNNNNNNNNCCGAA AGGAAGUC | 4709 |
| 3451 | GGAUGGCUC CCGAAUCU | 554 | AGAUUCGG CUGAUGAGGNNNNNNNNCCGAA AGCCAUCC | 4710 |
| 3458 | UCCCGAAUC UAUCUUUG | 555 | CAAAGAUA CUGAUGAGGNNNNNNNNCCGAA AUUCGGGA | 4711 |
| 3460 | CCGAAUCUA UCUUUGAC | 556 | GUCAAAGA CUGAUGAGGNNNNNNNNCCGAA AGAUUCGG | 4712 |
| 3462 | GAAUCUAUC UUUGACAA | 557 | UUGUCAAA CUGAUGAGGNNNNNNNNCCGAA AUAGAUUC | 4713 |
| 3464 | AUCUAUCUU UGACAAAA | 558 | UUUUGUCA CUGAUGAGGNNNNNNNNCCGAA AGAUAGAU | 4714 |
| 3465 | UCUAUCUUU GACAAAAU | 559 | AUUUUGUC CUGAUGAGGNNNNNNNNCCGAA AAGAUAGA | 4715 |
| 3474 | GACAAAAUC UACAGCAC | 560 | GUGCUGUA CUGAUGAGGNNNNNNNNCCGAA AUUUUGUC | 4716 |
| 3476 | CAAAAUCUA CAGCACCA | 561 | UGGUGCUG CUGAUGAGGNNNNNNNNCCGAA AGAUUUUG | 4717 |
| 3500 | CGUGGGUC UUACGGAG | 562 | CUCCGUAA CUGAUGAGGNNNNNNNNCCGAA ACCACACG | 4718 |
| 3502 | UGGGUCUU ACGGAGUA | 563 | UACUCCGU CUGAUGAGGNNNNNNNNCCGAA AGACCACA | 4719 |
| 3503 | GUGGUCUUA CGGAGUAU | 564 | AUACUCCG CUGAUGAGGNNNNNNNNCCGAA AAGACCAC | 4720 |
| 3510 | UACGGAGUA UUGCUGUG | 565 | CACAGCAA CUGAUGAGGNNNNNNNNCCGAA ACUCCGUA | 4721 |
| 3512 | CGGAGUAUU GCUGUGGG | 566 | CCCACAGC CUGAUGAGGNNNNNNNNCCGAA AUACUCCG | 4722 |
| 3525 | UGGGAAAUC UUCCCUU | 567 | AAGGGAAG CUGAUGAGGNNNNNNNNCCGAA AUUUCCCA | 4723 |
| 3527 | GGAAAUCUU CUCCUUAG | 568 | CUAAGGAG CUGAUGAGGNNNNNNNNCCGAA AGAUUUCC | 4724 |
| 3528 | GAAAUCUUC UCCUUAGG | 569 | CCUAAGGA CUGAUGAGGNNNNNNNNCCGAA AAGAUUUC | 4725 |
| 3530 | AAUCUUCUC CUUAGGUG | 570 | CACCUAAG CUGAUGAGGNNNNNNNNCCGAA AGAAGAUU | 4726 |
| 3533 | CUUCUCCUU AGGGGGAAG | 571 | ACCCACCU CUGAUGAGGNNNNNNNNCCGAA AGGAGAAG | 4727 |
| 3534 | UUCUCCUUA GGUGGGUC | 572 | GACCCACC CUGAUGAGGNNNNNNNNCCGAA AAGGAGAA | 4728 |
| 3542 | AGGUGGGUC UCCAUACC | 573 | GGUAUGGA CUGAUGAGGNNNNNNNNCCGAA ACCCACCU | 4729 |
| 3544 | GUGGGUCUC CAUACCCA | 574 | UGGGUAUG CUGAUGAGGNNNNNNNNCCGAA AGACCCAC | 4730 |
| 3548 | GUCUCCAUA CCCAGGAG | 575 | CUCCUGGG CUGAUGAGGNNNNNNNNCCGAA AUGGAGAC | 4731 |
| 3558 | CCAGGAGUA CAAAUGGA | 576 | UCCAUUUG CUGAUGAGGNNNNNNNNCCGAA ACUCCUGG | 4732 |
| 3575 | UGAGGACUU UGCAGUC | 577 | GACUGCAA CUGAUGAGGNNNNNNNNCCGAA AGUCCUCA | 4733 |
| 3576 | GAGGACUUU GCAGUCG | 578 | CGACUGCA CUGAUGAGGNNNNNNNNCCGAA AAGUCCUC | 4734 |
| 3577 | AGGACUUUG CAGUCGC | 579 | GCGACUGC CUGAUGAGGNNNNNNNNCCGAA AAAGUCCU | 4735 |
| 3583 | UUUGCAGUC GCCUGAGG | 580 | CCUCAGGC CUGAUGAGGNNNNNNNNCCGAA ACUGCAAA | 4736 |
| 3613 | UGAGAGCUC CUGAGUAC | 581 | GUACUCAG CUGAUGAGGNNNNNNNNCCGAA AGCUCUCA | 4737 |
| 3620 | UCCUGAGUA CUCUACUC | 582 | GAGUAGAG CUGAUGAGGNNNNNNNNCCGAA ACUCAGGA | 4738 |
| 3623 | UGAGUACUC UACUCCUG | 583 | CAGGAGUA CUGAUGAGGNNNNNNNNCCGAA AGUACUCA | 4739 |
| 3625 | AGUACUCUA CUCCUGAA | 584 | UUCAGGAG CUGAUGAGGNNNNNNNNCCGAA AGAGUACU | 4740 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 3628 | ACUCUACUC CUGAAAUC | 585 | GAUUUCAG CUGAUGAGgNNNNNNNNCCGAA AGUAGAGU | 4741 |
| 3636 | CCUGAAAUC UAUCAGAU | 586 | AUCUGAUA CUGAUGAGgNNNNNNNNCCGAA AUUUCAGG | 4742 |
| 3638 | UGAAAUCUA UCAGAUCA | 587 | UGAUCUGA CUGAUGAGgNNNNNNNNCCGAA AGAUUUCA | 4743 |
| 3640 | AAAUCUAUC AGAUCAUG | 588 | CAUGAUCU CUGAUGAGgNNNNNNNNCCGAA AUAGAUUU | 4744 |
| 3645 | UAUCAGAUC AUGCUGGA | 589 | UCCAGCAU CUGAUGAGgNNNNNNNNCCGAA AUCUGAUA | 4745 |
| 3689 | GCCAAGAUU UGCAGAAC | 590 | GUUCUGCA CUGAUGAGgNNNNNNNNCCGAA AUCUUGGC | 4746 |
| 3690 | CCAAGAUUU GCAGAACU | 591 | AGUUCUGC CUGAUGAGgNNNNNNNNCCGAA AAUCUUGG | 4747 |
| 3699 | GCAGAACUU GUGGAAAA | 592 | UUUUCCAC CUGAUGAGgNNNNNNNNCCGAA AGUUCUGC | 4748 |
| 3711 | GAAAAACUA GGUGAUUU | 593 | AAAUCACC CUGAUGAGgNNNNNNNNCCGAA AGUUUUUC | 4749 |
| 3718 | UAGGUGAUU UGCUUCAA | 594 | UUGAAGCA CUGAUGAGgNNNNNNNNCCGAA AUCACCUA | 4750 |
| 3719 | AGGUGAUUU GCUUCAAG | 595 | CUUGAAGC CUGAUGAGgNNNNNNNNCCGAA AAUCACCU | 4751 |
| 3723 | GAUUUGCUU CAAGCAAA | 596 | UUUGCUUG CUGAUGAGgNNNNNNNNCCGAA AGCAAAUC | 4752 |
| 3724 | AUUUGCUUC AAGCAAAU | 597 | AUUUGCUU CUGAUGAGgNNNNNNNNCCGAA AAGCAAAU | 4753 |
| 3735 | GCAAAUGUA CAACAGGA | 598 | UCCUGUUG CUGAUGAGgNNNNNNNNCCGAA ACAUUUGC | 4754 |
| 3748 | AGGAUGGUA AAGACUAC | 599 | GUAGUCUU CUGAUGAGgNNNNNNNNCCGAA ACCAUCCU | 4755 |
| 3755 | UAAAGACUA CAUCCCAA | 600 | UUGGGAUG CUGAUGAGgNNNNNNNNCCGAA AGUCUUUA | 4756 |
| 3759 | GACUACAUC CCAAUCAA | 601 | UUGAUUGG CUGAUGAGgNNNNNNNNCCGAA AUGUAGUC | 4757 |
| 3765 | AUCCCAAUC AAUGCCAU | 602 | AUGGCAUU CUGAUGAGgNNNNNNNNCCGAA AUUGGGAU | 4758 |
| 3774 | AAUGCCAUA CUGACAGG | 603 | CCUGUCAG CUGAUGAGgNNNNNNNNCCGAA AUGGCAUU | 4759 |
| 3787 | CAGGAAAUA GUGGGUUU | 604 | AAACCCAC CUGAUGAGgNNNNNNNNCCGAA AUUUCCUG | 4760 |
| 3794 | UAGUGGGUU UACAUACU | 605 | AGUAUGUA CUGAUGAGgNNNNNNNNCCGAA ACCCACUA | 4761 |
| 3795 | AGUGGGUUU ACAUACUC | 606 | GAGUAUGU CUGAUGAGgNNNNNNNNCCGAA AACCCACU | 4762 |
| 3796 | GUGGGUUUA CAUACUCA | 607 | UGAGUAUG CUGAUGAGgNNNNNNNNCCGAA AAACCCAC | 4763 |
| 3800 | GUUUACAUA CUCAACUC | 608 | GAGUUGAG CUGAUGAGgNNNNNNNNCCGAA AUGUAAAC | 4764 |
| 3803 | UACAUACUC AACUCCUG | 609 | CAGGAGUU CUGAUGAGgNNNNNNNNCCGAA AGUAUGUA | 4765 |
| 3808 | ACUCAACUC CUGCCUUC | 610 | GAAGGCAG CUGAUGAGgNNNNNNNNCCGAA AGUUGAGU | 4766 |
| 3815 | UCCUGCCUU CUCUGAGG | 611 | CCUCAGAG CUGAUGAGgNNNNNNNNCCGAA AGGCAGGA | 4767 |
| 3816 | CCUGCCUUC UCUGAGGA | 612 | UCCUCAGA CUGAUGAGgNNNNNNNNCCGAA AAGGCAGG | 4768 |
| 3818 | UGCCUUCUC UGAGGACU | 613 | AGUCCUCA CUGAUGAGgNNNNNNNNCCGAA AGAAGGCA | 4769 |
| 3827 | UGAGGACUU CUUCAAGG | 614 | CCUUGAAG CUGAUGAGgNNNNNNNNCCGAA AGUCCUCA | 4770 |
| 3828 | GAGGACUUC UUCAAGGA | 615 | UCCUUGAA CUGAUGAGgNNNNNNNNCCGAA AAGUCCUC | 4771 |
| 3830 | GGACUUCUU CAAGGAAA | 616 | UUUCCUUG CUGAUGAGgNNNNNNNNCCGAA AGAAGUCC | 4772 |
| 3831 | GACUUCUUC AAGGAAAG | 617 | CUUUCCUU CUGAUGAGgNNNNNNNNCCGAA AAGAAGUC | 4773 |
| 3841 | AGGAAAGUA UUUCAGCU | 618 | AGCUGAAA CUGAUGAGgNNNNNNNNCCGAA ACUUUCCU | 4774 |
| 3843 | GAAAGUAUU UCAGCUCC | 619 | GGAGCUGA CUGAUGAGgNNNNNNNNCCGAA AUACUUUC | 4775 |
| 3844 | AAAGUAUUU CAGCUCCG | 620 | CGGAGCUG CUGAUGAGgNNNNNNNNCCGAA AAUACUUU | 4776 |
| 3845 | AAGUAUUUC AGCUCCGA | 621 | UCGGAGCU CUGAUGAGgNNNNNNNNCCGAA AAAUACUU | 4777 |
| 3850 | UUUCAGCUC CGAAGUUU | 622 | AAACUUCG CUGAUGAGgNNNNNNNNCCGAA AGCUGAAA | 4778 |
| 3857 | UCCGAAGUU UAAUUCAG | 623 | CUGAAUUA CUGAUGAGgNNNNNNNNCCGAA ACUUCGGA | 4779 |
| 3858 | CCGAAGUUU AAUUCAGG | 624 | CCUGAAUU CUGAUGAGgNNNNNNNNCCGAA AACUUCGG | 4780 |
| 3859 | CGAAGUUUA AUUCAGGA | 625 | UCCUGAAU CUGAUGAGgNNNNNNNNCCGAA AAACUUCG | 4781 |
| 3862 | AGUUUAAUU CAGGAAGC | 626 | GCUUCCUG CUGAUGAGgNNNNNNNNCCGAA AUUAAACU | 4782 |
| 3863 | GUUUAAUUC AGGAAGCU | 627 | AGCUUCCU CUGAUGAGgNNNNNNNNCCGAA AAUUAAAC | 4783 |
| 3872 | AGGAAGCUC UGAUGAUG | 628 | CAUCAUCA CUGAUGAGgNNNNNNNNCCGAA AGCUUCCU | 4784 |
| 3882 | GAUGAUGUC AGAUAUGU | 629 | ACAUAUCU CUGAUGAGgNNNNNNNNCCGAA ACAUCAUC | 4785 |
| 3887 | UGUCAGAUA UGUAAAUG | 630 | CAUUUACA CUGAUGAGgNNNNNNNNCCGAA AUCUGACA | 4786 |
| 3891 | AGAUAUGUA AAUGCUUU | 631 | AAAGCAUU CUGAUGAGgNNNNNNNNCCGAA ACAUAUCU | 4787 |
| 3898 | UAAAUGCUU UCAAGUUC | 632 | GAACUUGA CUGAUGAGgNNNNNNNNCCGAA AGCAUUUA | 4788 |
| 3899 | AAAUGCUUU CAAGUUCA | 633 | UGAACUUG CUGAUGAGgNNNNNNNNCCGAA AAGCAUUU | 4789 |
| 3900 | AAUGCUUUC AAGUUCAU | 634 | AUGAACUU CUGAUGAGgNNNNNNNNCCGAA AAAGCAUU | 4790 |
| 3905 | UUUCAAGUU CAUGAGCC | 635 | GGCUCAUG CUGAUGAGgNNNNNNNNCCGAA ACUUGAAA | 4791 |
| 3906 | UUCAAGUUC AUGAGCCU | 636 | AGGCUCAU CUGAUGAGgNNNNNNNNCCGAA AACUUGAA | 4792 |
| 3924 | GAAAGAAUC AAAACCUU | 637 | AAGGUUUU CUGAUGAGgNNNNNNNNCCGAA AUUCUUUC | 4793 |
| 3932 | CAAAACCUU UGAAGAAC | 638 | GUUCUUCA CUGAUGAGgNNNNNNNNCCGAA AGGUUUUG | 4794 |
| 3933 | AAAACCUUU GAAGAACU | 639 | AGUUCUUC CUGAUGAGgNNNNNNNNCCGAA AAGGUUUU | 4795 |
| 3942 | GAAGAACUU UUACCGAA | 640 | UUCGGUAA CUGAUGAGgNNNNNNNNCCGAA AGUUCUUC | 4796 |
| 3943 | AAGAACUUU UACCGAAU | 641 | AUUCGGUA CUGAUGAGgNNNNNNNNCCGAA AAGUUCUU | 4797 |
| 3944 | AGAACUUUU ACCGAAUG | 642 | CAUUCGGU CUGAUGAGgNNNNNNNNCCGAA AAAGUUCU | 4798 |
| 3945 | GAACUUUUA CCGAAUGC | 643 | GCAUUCGG CUGAUGAGgNNNNNNNNCCGAA AAAAGUUC | 4799 |
| 3959 | UGCCACCUC CAUGUUGG | 644 | CAAACAUG CUGAUGAGgNNNNNNNNCCGAA AGGUGGCA | 4800 |
| 3965 | CUCCAUGUU UGAUGACU | 645 | AGUCAUCA CUGAUGAGgNNNNNNNNCCGAA ACAUGGAG | 4801 |
| 3966 | UCCAUGUUU GAUGACUA | 646 | UAGUCAUC CUGAUGAGgNNNNNNNNCCGAA AACAUGGA | 4802 |
| 3974 | UGAUGACUA CCAGGGCG | 647 | CGCCCUGG CUGAUGAGgNNNNNNNNCCGAA AGUCAUCA | 4803 |
| 3994 | GCAGCACUC UGGCCUGG | 648 | CCAGGCCA CUGAUGAGgNNNNNNNNCCGAA AGUGCUGC | 4804 |
| 3998 | CACUCUGUU GGCCUCUC | 649 | GAGAGGCC CUGAUGAGgNNNNNNNNCCGAA ACAGAGUG | 4805 |
| 4004 | GUUGGCCUC UCCCAUGC | 650 | GCAUGGGA CUGAUGAGgNNNNNNNNCCGAA AGGCCAAC | 4806 |
| 4006 | UGGCCUCUC CAUGCUG | 651 | CAGCAUGG CUGAUGAGgNNNNNNNNCCGAA AGAGGCCA | 4807 |
| 4022 | GAAGCCUUG CACCGGA | 652 | UCCAGGUG CUGAUGAGgNNNNNNNNCCGAA AGCGCUUC | 4808 |
| 4023 | AAGCGCUUC ACCGGAC | 653 | GUCCAGGU CUGAUGAGgNNNNNNNNCCGAA AAGCGCUU | 4809 |
| 4052 | CAAGGCCUC GCUCAAGA | 654 | UCUUGAGC CUGAUGAGgNNNNNNNNCCGAA AGGCCUUG | 4810 |
| 4056 | GCCUCGCUC AAGAUUGA | 655 | UCAAUCUU CUGAUGAGgNNNNNNNNCCGAA AGCGAGGC | 4811 |
| 4062 | CUCAAGAUU GACUUGAG | 656 | CUCAAGUC CUGAUGAGgNNNNNNNNCCGAA AUCUUGAG | 4812 |
| 4067 | GAUUGACUU GAGAGUAA | 657 | UUACUCUC CUGAUGAGgNNNNNNNNCCGAA AGUCAAUC | 4813 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4074 | UUGAGAGUA ACCAGUAA | 658 | UUACUGGU CUGAUGAGGNNNNNNNNCCGAA ACUCUCAA | 4814 |
| 4081 | UAACCAGUA AAAGUAAG | 659 | CUUACUUU CUGAUGAGGNNNNNNNNCCGAA ACUGGUUA | 4815 |
| 4087 | GUAAAAGUA AGGAGUCG | 660 | CGACUCCU CUGAUGAGGNNNNNNNNCCGAA ACUUUUAC | 4816 |
| 4094 | UAAGGAGUC GGGGCUGU | 661 | ACAGCCCC CUGAUGAGGNNNNNNNNCCGAA ACUCCUUA | 4817 |
| 4103 | GGGGCUGUC UGAUGUCA | 662 | UGACAUCA CUGAUGAGGNNNNNNNNCCGAA ACAGCCCC | 4818 |
| 4110 | UCUGAUGUC AGCAGGCC | 663 | GGCCUGCU CUGAUGAGGNNNNNNNNCCGAA ACAUCAGA | 4819 |
| 4123 | GGCCCAGUU UCUGCCAU | 664 | AUGGCAGA CUGAUGAGGNNNNNNNNCCGAA ACUGGGCC | 4820 |
| 4124 | GCCCAGUUU CUGCCAUU | 665 | AAUGGCAG CUGAUGAGGNNNNNNNNCCGAA AACUGGGC | 4821 |
| 4125 | CCCAGUUUC UGCCAUUC | 666 | GAAUGGCA CUGAUGAGGNNNNNNNNCCGAA AAACUGGG | 4822 |
| 4132 | UCUGCCAUU CCAGCUGU | 667 | ACAGCUGG CUGAUGAGGNNNNNNNNCCGAA AUGGCAGA | 4823 |
| 4133 | CUGCCAUUC CAGCUGUG | 668 | CACAGCUG CUGAUGAGGNNNNNNNNCCGAA AAUGGCAG | 4824 |
| 4149 | GGGCACGUC AGCGAAGG | 669 | CCUUCGCU CUGAUGAGGNNNNNNNNCCGAA ACGUGCCC | 4825 |
| 4169 | GCGCAGGUU CACCUACG | 670 | CGUAGGUG CUGAUGAGGNNNNNNNNCCGAA ACCUGCGC | 4826 |
| 4170 | CGCAGGUUC ACCUACGA | 671 | UCGUAGGU CUGAUGAGGNNNNNNNNCCGAA AACCUGCG | 4827 |
| 4175 | GUUCACCUA CGACCACG | 672 | CGUGGUCG CUGAUGAGGNNNNNNNNCCGAA AGGUGAAC | 4828 |
| 4203 | AGGAAAAUC GCGUGCUG | 673 | CAGCACGC CUGAUGAGGNNNNNNNNCCGAA AUUUUCCU | 4829 |
| 4214 | GUGCUGCUC CCCGCCCC | 674 | GGGGCGGG CUGAUGAGGNNNNNNNNCCGAA AGCAGCAC | 4830 |
| 4229 | CCCAGACUA CAACUCGG | 675 | CCGAGUUG CUGAUGAGGNNNNNNNNCCGAA AGUCUGGG | 4831 |
| 4235 | CUACAACUC GGUGGUCC | 676 | GGACCACC CUGAUGAGGNNNNNNNNCCGAA AGUUGUAG | 4832 |
| 4242 | UCGGUGGUC CUGUACUC | 677 | GAGUACAG CUGAUGAGGNNNNNNNNCCGAA ACCACCGA | 4833 |
| 4247 | GGUCCUGUA CUCCACCC | 678 | GGGUGGAG CUGAUGAGGNNNNNNNNCCGAA ACAGGACC | 4834 |
| 4250 | CCUGUACUC CACCCCAC | 679 | GUGGGGUG CUGAUGAGGNNNNNNNNCCGAA AGUACAGG | 4835 |
| 4263 | CCACCCAUC UAGAGUUU | 680 | AAACUCUA CUGAUGAGGNNNNNNNNCCGAA AUGGGUGG | 4836 |
| 4265 | ACCCAUCUA GAGUUUGA | 681 | UCAAACUC CUGAUGAGGNNNNNNNNCCGAA AGAUGGGU | 4837 |
| 4270 | UCUAGAGUU UGACACGA | 682 | UCGUGUCA CUGAUGAGGNNNNNNNNCCGAA ACUCUAGA | 4838 |
| 4271 | CUAGAGUUU GACACGAA | 683 | UUCGUGUC CUGAUGAGGNNNNNNNNCCGAA AACUCUAG | 4839 |
| 4284 | CGAAGCCUU AUUUCUAG | 684 | CUAGAAAU CUGAUGAGGNNNNNNNNCCGAA AGGCUUCG | 4840 |
| 4285 | GAAGCCUUA UUUCUAGA | 685 | UCUAGAAA CUGAUGAGGNNNNNNNNCCGAA AAGGCUUC | 4841 |
| 4287 | AGCCUUAUU UCUAGAAG | 686 | CUUCUAGA CUGAUGAGGNNNNNNNNCCGAA AUAAGGCU | 4842 |
| 4288 | GCCUUAUUU CUAGAAGC | 687 | GCUUCUAG CUGAUGAGGNNNNNNNNCCGAA AAUAAGGC | 4843 |
| 4289 | CCUUAUUUC UAGAAGCA | 688 | UGCUUCUA CUGAUGAGGNNNNNNNNCCGAA AAAUAAGG | 4844 |
| 4291 | UUAUUUCUA GAAGCACA | 689 | UGUGCUUC CUGAUGAGGNNNNNNNNCCGAA AGAAAUAA | 4845 |
| 4305 | ACAUGUGUA UUUAUACC | 690 | GGUAUAAA CUGAUGAGGNNNNNNNNCCGAA ACACAUGU | 4846 |
| 4307 | AUGUGUAUU UAUACCCC | 691 | GGGGUAUA CUGAUGAGGNNNNNNNNCCGAA AUACACAU | 4847 |
| 4308 | UGUGUAUUU AUACCCCA | 692 | GGGGUAUA CUGAUGAGGNNNNNNNNCCGAA AAUACACA | 4848 |
| 4309 | GUGUAUUUA UACCCCAG | 693 | UGGGGGUA CUGAUGAGGNNNNNNNNCCGAA AAAUACAC | 4849 |
| 4311 | GUAUUUAUA CCCCAGGG | 694 | CCUGGGGG CUGAUGAGGNNNNNNNNCCGAA AUAAAUAC | 4850 |
| 4325 | AGGAAACUA GCUUUUGC | 695 | GCAAAAGC CUGAUGAGGNNNNNNNNCCGAA AGUUUCCU | 4851 |
| 4329 | AACUAGCUU UGCCAGUU | 696 | ACUGGCAA CUGAUGAGGNNNNNNNNCCGAA AGCUAGUU | 4852 |
| 4330 | ACUAGCUUU UGCCAGUA | 697 | UACUGGCA CUGAUGAGGNNNNNNNNCCGAA AAGCUAGU | 4853 |
| 4331 | CUAGCUUUU GCCAGUAU | 698 | AUACUGGC CUGAUGAGGNNNNNNNNCCGAA AAAGCUAG | 4854 |
| 4338 | UUGCCAGUA UUAUGCAU | 699 | AUGCAUAA CUGAUGAGGNNNNNNNNCCGAA ACUGGCAA | 4855 |
| 4340 | GCCAGUAUU AUGCAUAU | 700 | AUAUGCAU CUGAUGAGGNNNNNNNNCCGAA AAUACUGGC | 4856 |
| 4341 | CCAGUAUUA UGCAUAUA | 701 | UAUAUGCA CUGAUGAGGNNNNNNNNCCGAA AAUACUGG | 4857 |
| 4347 | UUAUGCAUA UAAGUUUA | 702 | AACUUAUA CUGAUGAGGNNNNNNNNCCGAA AUGCAUAA | 4858 |
| 4349 | AUGCAUAUA UAAGUUUA | 703 | UAAACUUA CUGAUGAGGNNNNNNNNCCGAA AUAUGCAU | 4859 |
| 4351 | GCAUAUAUA AGUUUACA | 704 | UGUAAACU CUGAUGAGGNNNNNNNNCCGAA AUAUAUGC | 4860 |
| 4355 | AUAUAAGUU UACACCUU | 705 | AAGGUGUA CUGAUGAGGNNNNNNNNCCGAA ACUUAUAU | 4861 |
| 4356 | UAUAAGUUU ACACCUUU | 706 | AAAGGUGU CUGAUGAGGNNNNNNNNCCGAA AACUUAUA | 4862 |
| 4357 | AUAAGUUUA CACCUUUA | 707 | UAAAGGUG CUGAUGAGGNNNNNNNNCCGAA AAACUUAU | 4863 |
| 4363 | UUACACCUU UAUCUUUC | 708 | GAAAGAUA CUGAUGAGGNNNNNNNNCCGAA AGGUGUAA | 4864 |
| 4364 | UACACCUUU AUCUUUCC | 709 | GGAAAGAU CUGAUGAGGNNNNNNNNCCGAA AAGGUGUA | 4865 |
| 4365 | ACACCUUUA UCUUUCCA | 710 | UGGAAAGA CUGAUGAGGNNNNNNNNCCGAA AAAGGUGU | 4866 |
| 4367 | ACCUUUAUC UUCCAUG | 711 | CAUGGAAA CUGAUGAGGNNNNNNNNCCGAA AUAAAGGU | 4867 |
| 4369 | CUUUAUCUU UCCAUGGG | 712 | CCCAUGGA CUGAUGAGGNNNNNNNNCCGAA AGAUAAAG | 4868 |
| 4370 | UUUAUCUUU CCAUGGGA | 713 | UCCCAUGG CUGAUGAGGNNNNNNNNCCGAA AAGAUAAA | 4869 |
| 4371 | UUAUCUUUC CAUGGGAG | 714 | CUCCCAUG CUGAUGAGGNNNNNNNNCCGAA AAAGAUAA | 4870 |
| 4389 | CAGCUGCUU UUGUGAU | 715 | AUCACAAA CUGAUGAGGNNNNNNNNCCGAA AGCAGCUG | 4871 |
| 4390 | AGCUGCUUU UUGUGAUU | 716 | AAUCACAA CUGAUGAGGNNNNNNNNCCGAA AAGCAGCU | 4872 |
| 4391 | GCUGCUUUU UGUGAUUU | 717 | AAAUCACA CUGAUGAGGNNNNNNNNCCGAA AAAGCAGC | 4873 |
| 4392 | CUGCUUUUU GUGAUUUU | 718 | AAAAUCAC CUGAUGAGGNNNNNNNNCCGAA AAAAGCAG | 4874 |
| 4398 | UUUGUGAUU UUUUAAUU | 719 | AUUAAAAA CUGAUGAGGNNNNNNNNCCGAA AUCACAAA | 4875 |
| 4399 | UUGUGAUUU UUUAAUAU | 720 | UAUUAAAA CUGAUGAGGNNNNNNNNCCGAA AAUCACAA | 4876 |
| 4400 | UGUGAUUUU UUAAUAGU | 721 | CUAUUAAA CUGAUGAGGNNNNNNNNCCGAA AAAUCACA | 4877 |
| 4401 | GUGAUUUUU UAAUAGUU | 722 | ACUAUUAA CUGAUGAGGNNNNNNNNCCGAA AAAAUCAC | 4878 |
| 4402 | UGAUUUUUU AAUAGUG | 723 | CACUAUUA CUGAUGAGGNNNNNNNNCCGAA AAAAAUCA | 4879 |
| 4403 | GAUUUUUUU AAUAGUGC | 724 | GCACUAUU CUGAUGAGGNNNNNNNNCCGAA AAAAAAUC | 4880 |
| 4404 | AUUUUUAAUA GUGCUUUU | 725 | AGCACUAU CUGAUGAGGNNNNNNNNCCGAA AAAAAAAU | 4881 |
| 4407 | UUUUUAAUA GUGCUUUU | 726 | AAAAGCAC CUGAUGAGGNNNNNNNNCCGAA AUUAAAAA | 4882 |
| 4413 | AUAGUGCUU UUUUUUUU | 727 | AAAAAAAA CUGAUGAGGNNNNNNNNCCGAA AGCACUAU | 4883 |
| 4414 | UAGUGCUUU UUUUUUUU | 728 | AAAAAAAA CUGAUGAGGNNNNNNNNCCGAA AAGCACUA | 4884 |
| 4415 | AGUGCUUUU UUUUUUUG | 729 | CAAAAAAA CUGAUGAGGNNNNNNNNCCGAA AAAGCACU | 4885 |
| 4416 | GUGCUUUUU UUUUUUGA | 730 | UCAAAAAA CUGAUGAGGNNNNNNNNCCGAA AAAAGCAC | 4886 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4417 | UGCUUUUUU UUUUUGAC | 731 | GUCAAAAA CUGAUGAGGNNNNNNNNCCGAA AAAAAGCA | 4887 |
| 4418 | GCUUUUUUU UUUUGACU | 732 | AGUCAAAA CUGAUGAGGNNNNNNNNCCGAA AAAAAAGC | 4888 |
| 4419 | GUUUUUUUU UUUGACUA | 733 | UAGUCAAA CUGAUGAGGNNNNNNNNCCGAA AAAAAAAG | 4889 |
| 4420 | UUUUUUUUU UUGACUAA | 734 | UUAGUCAA CUGAUGAGGNNNNNNNNCCGAA AAAAAAAA | 4890 |
| 4421 | UUUUUUUUU UGACUAAC | 735 | GUUAGUCA CUGAUGAGGNNNNNNNNCCGAA AAAAAAAA | 4891 |
| 4422 | UUUUUUUUU GACUAACA | 736 | UGUUAGUC CUGAUGAGGNNNNNNNNCCGAA AAAAAAAA | 4892 |
| 4427 | UUUUGACUA ACAAGAAU | 737 | AUUCUUGU CUGAUGAGGNNNNNNNNCCGAA AGUCAAAA | 4893 |
| 4438 | AAGAAUGUA ACUCCAGA | 738 | UCUGGAGU CUGAUGAGGNNNNNNNNCCGAA ACAUUCUU | 4894 |
| 4442 | AUGUAACUC CAGAUAGA | 739 | UCUAUCUG CUGAUGAGGNNNNNNNNCCGAA AGUUACAU | 4895 |
| 4448 | CUCCAGAUA GAGAAAUA | 740 | UAUUUCUC CUGAUGAGGNNNNNNNNCCGAA AUCUGGAG | 4896 |
| 4456 | AGAGAAAUA GUGACAAG | 741 | CUUGUCAC CUGAUGAGGNNNNNNNNCCGAA AUUUCUCU | 4897 |
| 4476 | AGAACACUA CUGCUAAA | 742 | UUUAGCAG CUGAUGAGGNNNNNNNNCCGAA AGUGUUCU | 4898 |
| 4482 | CUACUGCUA AAUCCUCA | 743 | UGAGGAUU CUGAUGAGGNNNNNNNNCCGAA AGCAGUAG | 4899 |
| 4486 | UGCUAAAUC CUCAUGUU | 744 | AACAUGAG CUGAUGAGGNNNNNNNNCCGAA AUUUAGCA | 4900 |
| 4489 | UAAAUCCUC AUGUUACU | 745 | AGUAACAU CUGAUGAGGNNNNNNNNCCGAA AGGAUUUA | 4901 |
| 4494 | CCUCAUGUU ACUCAGUG | 746 | CACUGAGU CUGAUGAGGNNNNNNNNCCGAA ACAUGAGG | 4902 |
| 4495 | CUCAUGUUA CUCAGUGU | 747 | ACACUGAG CUGAUGAGGNNNNNNNNCCGAA AACAUGAG | 4903 |
| 4498 | AUGUUACUC AGUGUACU | 748 | CUAACGUG CUGAUGAGGNNNNNNNNCCGAA AGUAACAU | 4904 |
| 4504 | CUCAGUGUU AGAGAAAU | 749 | AUUUCUCU CUGAUGAGGNNNNNNNNCCGAA ACACUGAG | 4905 |
| 4505 | UCAGUGUUA GAGAAAUC | 750 | GAUUUCUC CUGAUGAGGNNNNNNNNCCGAA AACACUGA | 4906 |
| 4513 | AGAGAAAUC CUUCCUAA | 751 | UUAGGAAG CUGAUGAGGNNNNNNNNCCGAA AUUUCUCU | 4907 |
| 4516 | GAAAUCCUU CCUAAACC | 752 | GGUUUAGG CUGAUGAGGNNNNNNNNCCGAA AGGAUUUC | 4908 |
| 4517 | AAAUCCUUC CUAAACCC | 753 | GGGUUUAG CUGAUGAGGNNNNNNNNCCGAA AAGGAUUU | 4909 |
| 4520 | UCCUUCCUA AACCCAAU | 754 | AUUGGGUU CUGAUGAGGNNNNNNNNCCGAA AGGAAGGA | 4910 |
| 4533 | CAAUGACUU CCCUGCUC | 755 | GAGCAGGG CUGAUGAGGNNNNNNNNCCGAA AGUCAUUG | 4911 |
| 4534 | AAUGACUUC CCUGCUCC | 756 | GGAGCAGG CUGAUGAGGNNNNNNNNCCGAA AAGUCAUU | 4912 |
| 4541 | UCCCUGCUC CAACCCCC | 757 | GGGGGUUG CUGAUGAGGNNNNNNNNCCGAA AGCAGGGA | 4913 |
| 4557 | CGCCACCUC AGGGCACG | 758 | CGUGCCCU CUGAUGAGGNNNNNNNNCCGAA AGGUGGCG | 4914 |
| 4576 | GGACCAGUU UGAUUGAG | 759 | CUCAAUCA CUGAUGAGGNNNNNNNNCCGAA ACUGGUCC | 4915 |
| 4577 | GACCAGUUU GAUUGAGG | 760 | CCUCAAUC CUGAUGAGGNNNNNNNNCCGAA AACUGGUC | 4916 |
| 4581 | AGUUUGAUU GAGGAGCU | 761 | AGCUCCUC CUGAUGAGGNNNNNNNNCCGAA AUCAAACU | 4917 |
| 4598 | GCACUGAUC ACCCAAUG | 762 | CAUUGGGU CUGAUGAGGNNNNNNNNCCGAA AUCAGUGC | 4918 |
| 4610 | CAAUGCAUC ACGUACCC | 763 | GGGUACGU CUGAUGAGGNNNNNNNNCCGAA AUGCAUUG | 4919 |
| 4615 | CAUCACGUA CCCCACUG | 764 | CAGUGGGG CUGAUGAGGNNNNNNNNCCGAA ACGUGAUG | 4920 |
| 4664 | AAGCCCGUU AGCCCCAG | 765 | CUGGGGCU CUGAUGAGGNNNNNNNNCCGAA ACGGGCUU | 4921 |
| 4665 | AGCCCGUUA GCCCCAGG | 766 | CCUGGGGC CUGAUGAGGNNNNNNNNCCGAA AACGGGCU | 4922 |
| 4678 | CAGGGGAUC ACUGGCUG | 767 | CAGCCAGU CUGAUGAGGNNNNNNNNCCGAA AUCCCCUG | 4923 |
| 4700 | AGCAACAUC UCGGGAGU | 768 | ACUCCCGA CUGAUGAGGNNNNNNNNCCGAA AUGUUGCU | 4924 |
| 4702 | CAACAUCUC GGGAGUCC | 769 | GGACUCCC CUGAUGAGGNNNNNNNNCCGAA AGAUGUUG | 4925 |
| 4709 | UCGGGAGUC CUCUAGCA | 770 | UGCUAGAG CUGAUGAGGNNNNNNNNCCGAA ACUCCCGA | 4926 |
| 4712 | GGAGUCCUC UAGCAGGC | 771 | GCCUGCUA CUGAUGAGGNNNNNNNNCCGAA AGGACUCC | 4927 |
| 4714 | AGUCCUCUA GCAGGCCU | 772 | AGGCCUGC CUGAUGAGGNNNNNNNNCCGAA AGAGGACU | 4928 |
| 4723 | GCAGGCCUA AGACAUGU | 773 | ACAUGUCU CUGAUGAGGNNNNNNNNCCGAA AGGCCUGC | 4929 |
| 4802 | GAAAGAAUU UGAGACGC | 774 | GCGUCUCA CUGAUGAGGNNNNNNNNCCGAA AUUCUUUC | 4930 |
| 4803 | AAAGAAUUU GAGACGCA | 775 | UGCGUCUC CUGAUGAGGNNNNNNNNCCGAA AAUUCUUU | 4931 |
| 4840 | ACGGGCUC AGCAAUGC | 776 | GCAUUGCU CUGAUGAGGNNNNNNNNCCGAA AGCCCCGU | 4932 |
| 4852 | AAUGCCAUU UCAGUGGC | 777 | GCCACUGA CUGAUGAGGNNNNNNNNCCGAA AUGGCAUU | 4933 |
| 4853 | AUGCCAUUU CAGUGGCU | 778 | AGCCACUG CUGAUGAGGNNNNNNNNCCGAA AAUGGCAU | 4934 |
| 4854 | UGCCAUUUC AGUGGCUU | 779 | AAGCCACU CUGAUGAGGNNNNNNNNCCGAA AAAUGGCA | 4935 |
| 4862 | CAGUGGCUU CCCAGCUC | 780 | GAGCUGGG CUGAUGAGGNNNNNNNNCCGAA AGCCACUG | 4936 |
| 4863 | AGUGGCUUC CCAGCUCU | 781 | AGAGCUGG CUGAUGAGGNNNNNNNNCCGAA AAGCCACU | 4937 |
| 4870 | UCCCAGCUC UGACCCUU | 782 | AAGGGUCA CUGAUGAGGNNNNNNNNCCGAA AGCUGGGA | 4938 |
| 4878 | CUGACCCUU CUACAUUU | 783 | AAAUGUAG CUGAUGAGGNNNNNNNNCCGAA AGGGUCAG | 4939 |
| 4879 | UGACCCUUC UACAUUUG | 784 | CAAAUGUA CUGAUGAGGNNNNNNNNCCGAA AAGGGUCA | 4940 |
| 4881 | ACCCUUCUA CAUUUGAG | 785 | CUCAAAUG CUGAUGAGGNNNNNNNNCCGAA AGAAGGGU | 4941 |
| 4885 | UUCUACAUU UGAGGGCC | 786 | GGCCCUCA CUGAUGAGGNNNNNNNNCCGAA AUGUAGAA | 4942 |
| 4886 | UCUACAUUU GAGGGCCC | 787 | GGGCCCUC CUGAUGAGGNNNNNNNNCCGAA AAUGUAGA | 4943 |
| 4929 | GGGGACAUU UCUGGAU | 788 | AUCCAGAA CUGAUGAGGNNNNNNNNCCGAA AUGUCCCC | 4944 |
| 4930 | GGGACAUUU CUGGAUU | 789 | AAUCCAGA CUGAUGAGGNNNNNNNNCCGAA AAUGUCCC | 4945 |
| 4931 | GGACAUUUC UGGAUUC | 790 | GAAUCCAG CUGAUGAGGNNNNNNNNCCGAA AAAUGUCC | 4946 |
| 4932 | GACAUUUCU GGAUUCU | 791 | AGAAUCCA CUGAUGAGGNNNNNNNNCCGAA AAAAUGUC | 4947 |
| 4938 | UUCUGGAUU CUGGGAGG | 792 | CCUCCCAG CUGAUGAGGNNNNNNNNCCGAA AUCCAGAA | 4948 |
| 4939 | UCUGGAUUC UGGGAGGC | 793 | GCCUCCCA CUGAUGAGGNNNNNNNNCCGAA AAUCCAGA | 4949 |
| 4963 | GGACAAAUA UCUUUUUGG | 794 | AAAAAAGA CUGAUGAGGNNNNNNNNCCGAA AUUUGUCC | 4950 |
| 4965 | ACAAAUAUC UUUUUGG | 795 | CCAAAAAA CUGAUGAGGNNNNNNNNCCGAA AUAUUUGU | 4951 |
| 4967 | AAAUAUCUU UUUGGAA | 796 | UUCCAAAA CUGAUGAGGNNNNNNNNCCGAA AGAUAUUU | 4952 |
| 4968 | AAUAUCUUU UUGGAAC | 797 | GUUCCAAA CUGAUGAGGNNNNNNNNCCGAA AAGAUAUU | 4953 |
| 4969 | AUAUCUUUU UUGGAACU | 798 | AGUUCCAA CUGAUGAGGNNNNNNNNCCGAA AAAGAUAU | 4954 |
| 4970 | UAUCUUUUU UGGAACUA | 799 | UAGUUCCA CUGAUGAGGNNNNNNNNCCGAA AAAAGAUA | 4955 |
| 4971 | AUCUUUUUU GGAACUAA | 800 | UUAGUUCC CUGAUGAGGNNNNNNNNCCGAA AAAAAGAU | 4956 |
| 4978 | UUGGAACUA AAGCAAAU | 801 | AUUUGCUU CUGAUGAGGNNNNNNNNCCGAA AGUUCCAA | 4957 |
| 4987 | AAGCAAAUU UUAGACCU | 802 | AGGUCUAA CUGAUGAGGNNNNNNNNCCGAA AUUUGCUU | 4958 |
| 4988 | AGCAAAUUU UAGACCUU | 803 | AAGGUCUA CUGAUGAGGNNNNNNNNCCGAA AAUUUGCU | 4959 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4989 | GCAAAUUUU AGACCUUU | 804 | AAAGGUCU CUGAUGAGGNNNNNNNNCCGAA AAAUUUGC | 4960 |
| 4990 | CAAAUUUUA GACCUUUA | 805 | UAAAGGUC CUGAUGAGGNNNNNNNNCCGAA AAAAUUUG | 4961 |
| 4996 | UUAGACCUU UACCUAUG | 806 | CAUAGGUA CUGAUGAGGNNNNNNNNCCGAA AGGUCUAA | 4962 |
| 4997 | UAGACCUUU ACCUAUGG | 807 | CCAUAGGU CUGAUGAGGNNNNNNNNCCGAA AAGGUCUA | 4963 |
| 4998 | AGACCUUUA CCUAUGGA | 808 | UCCAUAGG CUGAUGAGGNNNNNNNNCCGAA AAAGGUCU | 4964 |
| 5002 | CUUUACCUA UGGAAGUG | 809 | CACUUCCA CUGAUGAGGNNNNNNNNCCGAA AGGUAAAG | 4965 |
| 5013 | GAAGUGGUU CUAUGUCC | 810 | GGAGAUAG CUGAUGAGGNNNNNNNNCCGAA ACCACUUC | 4966 |
| 5014 | AAGUGGUUC UAUGUCCA | 811 | UGGACAUA CUGAUGAGGNNNNNNNNCCGAA AACCACUU | 4967 |
| 5016 | GUGGUUCUA UGUCCAUU | 812 | AAUGGACA CUGAUGAGGNNNNNNNNCCGAA AGAACCAC | 4968 |
| 5020 | UUCUAUGUC CAUUCUCA | 813 | UGAGAAUG CUGAUGAGGNNNNNNNNCCGAA ACAUAGAA | 4969 |
| 5024 | AUGUCCAUU CUCAUUCG | 814 | CGAAUGAG CUGAUGAGGNNNNNNNNCCGAA AUGGACAU | 4970 |
| 5025 | UGUCCAUUC UCAUUCGU | 815 | ACGAAUGA CUGAUGAGGNNNNNNNNCCGAA AAUGGACA | 4971 |
| 5027 | UCCAUUCUC AUUCGUGG | 816 | CCACGAAU CUGAUGAGGNNNNNNNNCCGAA AGAAUGGA | 4972 |
| 5030 | AUUCUCAUU CGUGGCAU | 817 | AUGCCACG CUGAUGAGGNNNNNNNNCCGAA AUGAGAAU | 4973 |
| 5031 | UUCUCAUUC GUGGCAUG | 818 | CAUGCCAC CUGAUGAGGNNNNNNNNCCGAA AAUGAGAA | 4974 |
| 5041 | UGGCAUGUU UUGAUUUG | 819 | CAAAUCAA CUGAUGAGGNNNNNNNNCCGAA ACAUGCCA | 4975 |
| 5042 | GGCAUGUUU UGAUUUGU | 820 | ACAAAUCA CUGAUGAGGNNNNNNNNCCGAA AACAUGCC | 4976 |
| 5043 | GCAUGUUUU GAUUUGUA | 821 | UACAAAUC CUGAUGAGGNNNNNNNNCCGAA AAACAUGC | 4977 |
| 5047 | GUUUGAUUU GUAGCAC | 822 | GUGCUACA CUGAUGAGGNNNNNNNNCCGAA AUCAAAAC | 4978 |
| 5048 | UUUUGAUUU GUAGCACU | 823 | AGUGCUAC CUGAUGAGGNNNNNNNNCCGAA AAUCAAAA | 4979 |
| 5051 | UGAUUUGUA GCACUGAG | 824 | CUCAGUGC CUGAUGAGGNNNNNNNNCCGAA ACAAAUCA | 4980 |
| 5069 | GUGGCACUC AACUCUGA | 825 | UCAGAGUU CUGAUGAGGNNNNNNNNCCGAA AGUGCCAC | 4981 |
| 5074 | ACUCAACUC UGAGCCCA | 826 | UGGGCUCA CUGAUGAGGNNNNNNNNCCGAA AGUUGAGU | 4982 |
| 5084 | GAGCCCAUA CUUUUGGC | 827 | GCCAAAAG CUGAUGAGGNNNNNNNNCCGAA AUGGGCUC | 4983 |
| 5087 | CCCAUACUU UUGGCUCC | 828 | GGAGCCAA CUGAUGAGGNNNNNNNNCCGAA AGUAUGGG | 4984 |
| 5088 | CCAUACUUU UGGCUCCU | 829 | AGGAGCCA CUGAUGAGGNNNNNNNNCCGAA AAGUAUGG | 4985 |
| 5089 | CAUACUUUU GGCUCCUC | 830 | GAGGAGCC CUGAUGAGGNNNNNNNNCCGAA AAAGUAUG | 4986 |
| 5094 | UUUUGGCUC CUCUAGUA | 831 | UACUAGAG CUGAUGAGGNNNNNNNNCCGAA AGCCAAAA | 4987 |
| 5097 | UGGCUCCUC UAGUAAGA | 832 | UCUUACUA CUGAUGAGGNNNNNNNNCCGAA AGGAGCCA | 4988 |
| 5099 | GCUCCUCUA GUAAGAUG | 833 | CAUCUUAC CUGAUGAGGNNNNNNNNCCGAA AGAGGAGC | 4989 |
| 5102 | CCUCUAGUA AGAUGCAC | 834 | GUGCAUCU CUGAUGAGGNNNNNNNNCCGAA ACUAGAGG | 4990 |
| 5119 | UGAAAACUU AGCCAGAG | 835 | CUCUGGCU CUGAUGAGGNNNNNNNNCCGAA AGUUUUCA | 4991 |
| 5120 | GAAAACUUA GCCAGAGU | 836 | ACUCUGGC CUGAUGAGGNNNNNNNNCCGAA AAGUUUUC | 4992 |
| 5129 | GCCAGAGUU AGGUUGUC | 837 | GACAACCU CUGAUGAGGNNNNNNNNCCGAA ACUCUGGC | 4993 |
| 5130 | CCAGAGUUA GGUUGUCU | 838 | AGACAACC CUGAUGAGGNNNNNNNNCCGAA AACUCUGG | 4994 |
| 5134 | AGUUAGGUU GUCCCAG | 839 | CUGGAGAC CUGAUGAGGNNNNNNNNCCGAA ACCUAACU | 4995 |
| 5137 | UAGGUUGUC UCCAGGCC | 840 | GGCCUGGA CUGAUGAGGNNNNNNNNCCGAA ACAACCUA | 4996 |
| 5139 | GGUUGUCUC CAGGCCAU | 841 | AUGGCCUG CUGAUGAGGNNNNNNNNCCGAA AGACAACC | 4997 |
| 5156 | GAUGGCCUU ACACUGAA | 842 | UUCAGUGU CUGAUGAGGNNNNNNNNCCGAA AGGCCAUC | 4998 |
| 5157 | AUGGCCUUA CACUGAAA | 843 | UUUCAGUG CUGAUGAGGNNNNNNNNCCGAA AAGGCCAU | 4999 |
| 5170 | GAAAAUGUC ACAUUCUA | 844 | UAGAAUGU CUGAUGAGGNNNNNNNNCCGAA ACAUUUUC | 5000 |
| 5175 | UGUCACAUU CUAUUUUG | 845 | CAAAAUAG CUGAUGAGGNNNNNNNNCCGAA AUGUGACA | 5001 |
| 5176 | GUCACAUUC UAUUUUGG | 846 | CCAAAAUA CUGAUGAGGNNNNNNNNCCGAA AAUGUGAC | 5002 |
| 5178 | CACAUUCUA UUUUGGGU | 847 | ACCCAAAA CUGAUGAGGNNNNNNNNCCGAA AGAAUGUG | 5003 |
| 5180 | CAUUCUAUU UUGGGUAU | 848 | AUACCCAA CUGAUGAGGNNNNNNNNCCGAA AUAGAAUG | 5004 |
| 5181 | AUUCUAUUU UGGGUAUU | 849 | AAUACCCA CUGAUGAGGNNNNNNNNCCGAA AAUAGAAU | 5005 |
| 5182 | UUCUAUUUU GGGUAUUA | 850 | UAAUACCC CUGAUGAGGNNNNNNNNCCGAA AAAAUAGAA | 5006 |
| 5187 | UUUUGGGUA UUAAUAUA | 851 | UAUAUUAA CUGAUGAGGNNNNNNNNCCGAA ACCCAAAA | 5007 |
| 5189 | UUGGGUAUU AAUAUAUA | 852 | UAUAUAUU CUGAUGAGGNNNNNNNNCCGAA AUACCCAA | 5008 |
| 5190 | UGGGUAUUA AUAUAUAG | 853 | CUAUAUAU CUGAUGAGGNNNNNNNNCCGAA AAUACCCA | 5009 |
| 5193 | GUAUUAAUA UAUAGUCC | 854 | GGACUAUA CUGAUGAGGNNNNNNNNCCGAA AUUAAUAC | 5010 |
| 5195 | AUUAAUAUA UAGUCCAG | 855 | CUGGACUA CUGAUGAGGNNNNNNNNCCGAA AUAUUAAU | 5011 |
| 5197 | UAAUAUAUA GUCCAGAC | 856 | GUCUGGAC CUGAUGAGGNNNNNNNNCCGAA AUAUAUUA | 5012 |
| 5200 | UAUAUAGUC CAGACACU | 857 | AGUGUCUG CUGAUGAGGNNNNNNNNCCGAA ACUAUAUA | 5013 |
| 5209 | CAGACACUU AACUCAAU | 858 | AUUGAGUU CUGAUGAGGNNNNNNNNCCGAA AGUGUCUG | 5014 |
| 5210 | AGACACUUA ACUCAAUU | 859 | AAUUGAGU CUGAUGAGGNNNNNNNNCCGAA AAGUGUCU | 5015 |
| 5214 | ACUUAACUC AAUUUCUU | 860 | AAGAAAUU CUGAUGAGGNNNNNNNNCCGAA AGUUAAGU | 5016 |
| 5218 | AACUCAAUU UCUUGGUA | 861 | UACCAAGA CUGAUGAGGNNNNNNNNCCGAA AUUGAGUU | 5017 |
| 5219 | ACUCAAUUU CUUGGUAU | 862 | AUACCAAG CUGAUGAGGNNNNNNNNCCGAA AAUUGAGU | 5018 |
| 5220 | CUCAAUUUC UUGGUAUU | 863 | AAUACCAA CUGAUGAGGNNNNNNNNCCGAA AAAUUGAG | 5019 |
| 5222 | CAAUUUCUU GGUAUUAU | 864 | AUAAUACC CUGAUGAGGNNNNNNNNCCGAA AGAAAUUG | 5020 |
| 5226 | UUCUUGGUA UUAUCUG | 865 | CAGAAUAA CUGAUGAGGNNNNNNNNCCGAA ACCAAGAA | 5021 |
| 5228 | CUUGGUAUU AUUCUGUU | 866 | AACAGAAU CUGAUGAGGNNNNNNNNCCGAA AUACCAAG | 5022 |
| 5229 | UUGGUAUUA UUCUGUUU | 867 | AAACAGAA CUGAUGAGGNNNNNNNNCCGAA AAUACCAA | 5023 |
| 5231 | GGUAUUAUU CUGUUUUG | 868 | CAAAACAG CUGAUGAGGNNNNNNNNCCGAA AUAAUACC | 5024 |
| 5232 | GUAUUAUUC UGUUUUGC | 869 | GCAAAACA CUGAUGAGGNNNNNNNNCCGAA AAUAAUAC | 5025 |
| 5236 | UAUUCUGUU UUGCACAG | 870 | CUGUGCAA CUGAUGAGGNNNNNNNNCCGAA ACAGAAUA | 5026 |
| 5237 | AUUCUGUUU UGCACAGU | 871 | ACUGUGCA CUGAUGAGGNNNNNNNNCCGAA AACAGAAU | 5027 |
| 5238 | UUCUGUUUU GCACAGUU | 872 | AACUGUGC CUGAUGAGGNNNNNNNNCCGAA AAACAGAA | 5028 |
| 5246 | UGCACAGUU AGUUGUGA | 873 | UCACAACU CUGAUGAGGNNNNNNNNCCGAA ACUGUGCA | 5029 |
| 5247 | GCACAGUUA GUUGUGAA | 874 | UUCACAAC CUGAUGAGGNNNNNNNNCCGAA AACUGUGC | 5030 |
| 5250 | CAGUUAGUU GUGAAAGA | 875 | UCUUUCAC CUGAUGAGGNNNNNNNNCCGAA ACUAACUG | 5031 |
| 5284 | AAUGCAGUC UGAGGAG | 876 | CUCCUCAG CUGAUGAGGNNNNNNNNCCGAA ACUGCAUU | 5032 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5296 | AGGAGAGUU UUCUCCAU | 877 | AUGGAGAA CUGAUGAGGNNNNNNNNCCGAA ACUCUCCU | 5033 |
| 5297 | GGAGAGUUU UCUCCAUA | 878 | UAUGGAGA CUGAUGAGGNNNNNNNNCCGAA AACUCUCC | 5034 |
| 5298 | GAGAGUUUU CUCCAUAU | 879 | AUAUGGAG CUGAUGAGGNNNNNNNNCCGAA AAACUCUC | 5035 |
| 5299 | AGAGUUUUC UCCAUAUC | 880 | GAUAUGGA CUGAUGAGGNNNNNNNNCCGAA AAAACUCU | 5036 |
| 5301 | AGUUUUCUC CAUAUCAA | 881 | UUGAUAUG CUGAUGAGGNNNNNNNNCCGAA AGAAAACU | 5037 |
| 5305 | UUCUCCAUA UCAAAACG | 882 | CGUUUUGA CUGAUGAGGNNNNNNNNCCGAA AUGGAGAA | 5038 |
| 5307 | CUCCAUAUC AAAACGAG | 883 | CUCGUUUU CUGAUGAGGNNNNNNNNCCGAA AUAUGGAG | 5039 |
| 5336 | AAAAAGGUC AAUAAGGU | 884 | ACCUUAUU CUGAUGAGGNNNNNNNNCCGAA ACCUUUUU | 5040 |
| 5340 | AGGUCAAUA AGGUCAAG | 885 | CUUGACCU CUGAUGAGGNNNNNNNNCCGAA AUUGACCU | 5041 |
| 5345 | AAUAAGGUC AAGGGAAA | 886 | CUUCCCUU CUGAUGAGGNNNNNNNNCCGAA ACCUUAUU | 5042 |
| 5361 | GACCCCGUC UCUAUACC | 887 | GGUAUAGA CUGAUGAGGNNNNNNNNCCGAA ACGGGGUC | 5043 |
| 5363 | CCCCGUCUC UAUACCAA | 888 | UUGGUAUA CUGAUGAGGNNNNNNNNCCGAA AGACGGGG | 5044 |
| 5365 | CCGUCUCUA UACCAACC | 889 | GGUUGGUA CUGAUGAGGNNNNNNNNCCGAA AGAGACGG | 5045 |
| 5367 | GUCUCUAUA CCAACCAA | 890 | UUGGUUGG CUGAUGAGGNNNNNNNNCCGAA AUAGAGAC | 5046 |
| 5382 | AAACCAAUU CACCAACA | 891 | UGUUGGUG CUGAUGAGGNNNNNNNNCCGAA AUUGGUUU | 5047 |
| 5383 | AACCAAUUC ACCAACAC | 892 | GUGUUGGU CUGAUGAGGNNNNNNNNCCGAA AAUUGGUU | 5048 |
| 5395 | AACACAGUU GGACCCA | 893 | UGGGUCCC CUGAUGAGGNNNNNNNNCCGAA ACUGUGUU | 5049 |
| 5417 | CAGGAAGUC AGUCACGU | 894 | ACGUGACU CUGAUGAGGNNNNNNNNCCGAA ACUUCCUG | 5050 |
| 5421 | AAGUCAGUC ACGUUUCC | 895 | GGAAACGU CUGAUGAGGNNNNNNNNCCGAA ACUGACUU | 5051 |
| 5426 | AGUCACGUU UCCUUUUC | 896 | GAAAAGGA CUGAUGAGGNNNNNNNNCCGAA ACGUGACU | 5052 |
| 5427 | GUCACGUUU CCUUUUCA | 897 | UGAAAAGG CUGAUGAGGNNNNNNNNCCGAA AACGUGAC | 5053 |
| 5428 | UCACGUUUC CUUUUCAU | 898 | AUGAAAAG CUGAUGAGGNNNNNNNNCCGAA AAACGUGA | 5054 |
| 5431 | CGUUCCUU UUCAUUUA | 899 | UAAAUGAA CUGAUGAGGNNNNNNNNCCGAA AGGAAACG | 5055 |
| 5432 | GUUUCCUUU UCAUUUAA | 900 | UUAAAUGA CUGAUGAGGNNNNNNNNCCGAA AAGGAAAC | 5056 |
| 5433 | UUUCCUUUU CAUUUAAU | 901 | AUUAAAUG CUGAUGAGGNNNNNNNNCCGAA AAAGGAAA | 5057 |
| 5434 | UUCCUUUUC AUUUAAUG | 902 | CAUUAAAU CUGAUGAGGNNNNNNNNCCGAA AAAAGGAA | 5058 |
| 5437 | CUUUUCAUU UAAUGGGG | 903 | CCCCAUUA CUGAUGAGGNNNNNNNNCCGAA AUGAAAAG | 5059 |
| 5438 | UUUUCAUUU AAUGGGGA | 904 | UCCCCAUU CUGAUGAGGNNNNNNNNCCGAA AAUGAAAA | 5060 |
| 5439 | UUUCAUUUA AUGGGGAU | 905 | AUCCCCAU CUGAUGAGGNNNNNNNNCCGAA AAAUGAAA | 5061 |
| 5448 | AUGGGGAUU CCACUAUC | 906 | GAUAGUGG CUGAUGAGGNNNNNNNNCCGAA AUCCCCAU | 5062 |
| 5449 | UGGGGAUUC CACUAUCU | 907 | AGAUAGUG CUGAUGAGGNNNNNNNNCCGAA AAUCCCCA | 5063 |
| 5454 | AUUCCACUA UCUCACAC | 908 | GUGUGAGA CUGAUGAGGNNNNNNNNCCGAA AGUGGAAU | 5064 |
| 5456 | UCCACUAUC UCACACUA | 909 | UAGUGUGA CUGAUGAGGNNNNNNNNCCGAA AUAGUGGA | 5065 |
| 5458 | CACUAUCUC ACACUAAU | 910 | AUUAGUGU CUGAUGAGGNNNNNNNNCCGAA AGAUAGUG | 5066 |
| 5464 | CUCACACUA AUCUGAAA | 911 | UUUCAGAU CUGAUGAGGNNNNNNNNCCGAA AGUGUGAG | 5067 |
| 5467 | ACACUAAUC UGAAAGGA | 912 | UCCUUUCA CUGAUGAGGNNNNNNNNCCGAA AUUAGUGU | 5068 |
| 5489 | AAGAGCAUU AGCUGGCG | 913 | CGCCAGCU CUGAUGAGGNNNNNNNNCCGAA AUGCUCUU | 5069 |
| 5490 | AGAGCAUUA GCUGGCGC | 914 | GCGCCAGC CUGAUGAGGNNNNNNNNCCGAA AAUGCUCU | 5070 |
| 5501 | UGGCGCAUA UUAAGCCA | 915 | GUGCUUAA CUGAUGAGGNNNNNNNNCCGAA AUGCGCCA | 5071 |
| 5503 | GCGCAUAUU AAGCACUU | 916 | AAGUGCUU CUGAUGAGGNNNNNNNNCCGAA AUAUGCGC | 5072 |
| 5504 | CGCAUAUUA AGCACUUU | 917 | AAAGUGCU CUGAUGAGGNNNNNNNNCCGAA AAUAUGCG | 5073 |
| 5511 | UAAGCACUU AAGCUCC | 918 | GGAGCUUA CUGAUGAGGNNNNNNNNCCGAA AGUGCUUA | 5074 |
| 5512 | AAGCACUUU AAGCUCCU | 919 | AGGAGCUU CUGAUGAGGNNNNNNNNCCGAA AAGUGCUU | 5075 |
| 5513 | AGCACUUUA AGCUCCUU | 920 | AAGGAGCU CUGAUGAGGNNNNNNNNCCGAA AAAGUGCU | 5076 |
| 5518 | UUUAAGCUC CUUGAGUA | 921 | UACUCAAG CUGAUGAGGNNNNNNNNCCGAA AGCUUAAA | 5077 |
| 5521 | AAGCUCCUU GAGUAAAA | 922 | UUUUACUC CUGAUGAGGNNNNNNNNCCGAA AGGAGCUU | 5078 |
| 5526 | CCUUGAGUA AAAGGUG | 923 | CACCUUUU CUGAUGAGGNNNNNNNNCCGAA ACUCAAGG | 5079 |
| 5537 | AAGGUGGUA UGUAAUUU | 924 | AAAUUACA CUGAUGAGGNNNNNNNNCCGAA ACCACCUU | 5080 |
| 5541 | UGGUAUGUA AUUUAUGC | 925 | GCAUAAAU CUGAUGAGGNNNNNNNNCCGAA ACAUACCA | 5081 |
| 5544 | UAUGUAAUU UAUGCAAG | 926 | CUUGCAUA CUGAUGAGGNNNNNNNNCCGAA AUUACAUA | 5082 |
| 5545 | AUGUAAUUU AUGCAAGG | 927 | CCUUGCAU CUGAUGAGGNNNNNNNNCCGAA AAUUACAU | 5083 |
| 5546 | UGUAAUUUA UGCAAGGU | 928 | ACCUUGCA CUGAUGAGGNNNNNNNNCCGAA AAAUUACA | 5084 |
| 5555 | UGCAAGGUA UUUCUCCA | 929 | UGGAGAAA CUGAUGAGGNNNNNNNNCCGAA ACCUUGCA | 5085 |
| 5557 | CAAGGUAUU UCUCCAGU | 930 | ACUGGAGA CUGAUGAGGNNNNNNNNCCGAA AUACCUUG | 5086 |
| 5558 | AAGGUAUUU CUCCAGUU | 931 | AACUGGAG CUGAUGAGGNNNNNNNNCCGAA AAUACCUU | 5087 |
| 5559 | AGGUAUUUC UCCAGUUG | 932 | CAACUGGA CUGAUGAGGNNNNNNNNCCGAA AAAUACCU | 5088 |
| 5561 | GUAUUUCUC CAGUUGGG | 933 | CCCAACUG CUGAUGAGGNNNNNNNNCCGAA AGAAAUAC | 5089 |
| 5566 | UCUCCAGUU GGGACUCA | 934 | UGAGUCCC CUGAUGAGGNNNNNNNNCCGAA ACUGGAGA | 5090 |
| 5573 | UUGGGACUC AGGAUAUU | 935 | AAUAUCCU CUGAUGAGGNNNNNNNNCCGAA AGUCCCAA | 5091 |
| 5579 | CUCAGGAUA UUAGUUAA | 936 | UUAACUAA CUGAUGAGGNNNNNNNNCCGAA AUCCUGAG | 5092 |
| 5581 | CAGGAUAUU AGUUAAUG | 937 | CAUUAACU CUGAUGAGGNNNNNNNNCCGAA AUAUCCUG | 5093 |
| 5582 | AGGAUAUUA GUUAAUGA | 938 | UCAUUAAC CUGAUGAGGNNNNNNNNCCGAA AAUAUCCU | 5094 |
| 5585 | AUAUUAGUU AAUGAGCC | 939 | GGCUCAUU CUGAUGAGGNNNNNNNNCCGAA ACUAAUAU | 5095 |
| 5586 | UAUUAGUUA AUGAGCCA | 940 | UGGCUCAU CUGAUGAGGNNNNNNNNCCGAA AACUAAUA | 5096 |
| 5596 | UGAGCCAUC ACUAGAAG | 941 | CUUCUAGU CUGAUGAGGNNNNNNNNCCGAA AUGGCUCA | 5097 |
| 5600 | CCAUCACUA GAAGAAAA | 942 | UUUUCUUC CUGAUGAGGNNNNNNNNCCGAA AGUGAUGG | 5098 |
| 5615 | AAGCCCAUU UCAACUG | 943 | CAGUUGAA CUGAUGAGGNNNNNNNNCCGAA AUGGGCUU | 5099 |
| 5616 | AGCCCAUUU CAACUGCU | 944 | GCAGUUGA CUGAUGAGGNNNNNNNNCCGAA AAUGGGCU | 5100 |
| 5617 | GCCCAUUUC AACUGCUU | 945 | AGCAGUUG CUGAUGAGGNNNNNNNNCCGAA AAAUGGGC | 5101 |
| 5618 | CCCAUUUUC AACUGCUU | 946 | AAGCAGUU CUGAUGAGGNNNNNNNNCCGAA AAAAUGGG | 5102 |
| 5626 | CAACUGCUU UGAAACUU | 947 | AAGUUUCA CUGAUGAGGNNNNNNNNCCGAA AGCAGUUG | 5103 |
| 5627 | AACUGCUUU GAAACUUG | 948 | CAAGUUUC CUGAUGAGGNNNNNNNNCCGAA AAGCAGUU | 5104 |
| 5634 | UUGAAACUU GCCUGGGG | 949 | CCCCAGGC CUGAUGAGGNNNNNNNNCCGAA AGUUUCAA | 5105 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5644 | CCUGGGGUC UGAGCAUG | 950 | CAUGCUCA CUGAUGAGGNNNNNNNNCCGAA ACCCCAGG | 5106 |
| 5661 | AUGGGAAUA GGGAGACA | 951 | UGUCUCCC CUGAUGAGGNNNNNNNNCCGAA AUUCCCAU | 5107 |
| 5674 | GACAGGGUA GGAAAGGG | 952 | CCCUUUCC CUGAUGAGGNNNNNNNNCCGAA ACCCUGUC | 5108 |
| 5688 | GGGCGCCUA CUCUUCAG | 953 | CUGAAGAG CUGAUGAGGNNNNNNNNCCGAA AGGCGCCC | 5109 |
| 5691 | CGCCUACUC UUCAGGGU | 954 | ACCCUGAA CUGAUGAGGNNNNNNNNCCGAA AGUAGGCG | 5110 |
| 5693 | CCUACUCUU CAGGGUCU | 955 | AGACCCUG CUGAUGAGGNNNNNNNNCCGAA AGAGUAGG | 5111 |
| 5694 | CUACUCUUC AGGGUCUA | 956 | UAGACCCU CUGAUGAGGNNNNNNNNCCGAA AAGAGUAG | 5112 |
| 5700 | UUCAGGGUC UAAAGAUC | 957 | GAUCUUUA CUGAUGAGGNNNNNNNNCCGAA ACCCUGAA | 5113 |
| 5702 | CAGGGUCUA AAGAUCAA | 958 | UUGAUCUU CUGAUGAGGNNNNNNNNCCGAA AGACCCUG | 5114 |
| 5708 | CUAAAGAUC AAGGGGGC | 959 | GCCCCUUG CUGAUGAGGNNNNNNNNCCGAA AUCUUUAG | 5115 |
| 5719 | GUGGGCCUU GGAUCGCU | 960 | AGCGAUCC CUGAUGAGGNNNNNNNNCCGAA AGGCCCAC | 5116 |
| 5724 | CCUUGGAUC GCUAAGCU | 961 | AGCUUAGC CUGAUGAGGNNNNNNNNCCGAA AUCCAAGG | 5117 |
| 5728 | GGAUCGCUA AGCUGGCU | 962 | AGCCAGCU CUGAUGAGGNNNNNNNNCCGAA AGCGAUCC | 5118 |
| 5737 | AGCUGGCUC UGUUUGAU | 963 | AUCAAACA CUGAUGAGGNNNNNNNNCCGAA AGCCAGCU | 5119 |
| 5741 | GGCUCUGUU UGAUGCUA | 964 | UAGCAUCA CUGAUGAGGNNNNNNNNCCGAA ACAGAGCC | 5120 |
| 5742 | GCUCUGUUU GAUGCUAU | 965 | AUAGCAUC CUGAUGAGGNNNNNNNNCCGAA AACAGAGC | 5121 |
| 5749 | UUGAUGCUA UUUAUGCA | 966 | UGCAUAAA CUGAUGAGGNNNNNNNNCCGAA AGCAUCAA | 5122 |
| 5751 | GAUGCUAUU UAUGCAAG | 967 | CUUGCAUA CUGAUGAGGNNNNNNNNCCGAA AUAGCAUC | 5123 |
| 5752 | AUGCUAUUU AUGCAAGU | 968 | ACUUGCAU CUGAUGAGGNNNNNNNNCCGAA AAUAGCAU | 5124 |
| 5753 | UGCUAUUUA UGCAAGUU | 969 | AACUUGCA CUGAUGAGGNNNNNNNNCCGAA AAAUAGCA | 5125 |
| 5761 | AUGCAAGUU AGGGUCUA | 970 | UAGACCCU CUGAUGAGGNNNNNNNNCCGAA ACUUGCAU | 5126 |
| 5762 | UGCAAGUUA GGGUCUAU | 971 | AUAGACCC CUGAUGAGGNNNNNNNNCCGAA AACUUGCA | 5127 |
| 5767 | GUUAGGGUC UAUGUAUU | 972 | AAUACAUA CUGAUGAGGNNNNNNNNCCGAA ACCCUAAC | 5128 |
| 5769 | UAGGGUCUA UGUAUUUA | 973 | UAAAUACA CUGAUGAGGNNNNNNNNCCGAA AGACCCUA | 5129 |
| 5773 | GUCUAUGUA UUUAGGAU | 974 | AUCCUAAA CUGAUGAGGNNNNNNNNCCGAA ACAUAGAC | 5130 |
| 5775 | CUAUGUAUU UAGGAUGC | 975 | GCAUCCUA CUGAUGAGGNNNNNNNNCCGAA AUACAUAG | 5131 |
| 5776 | UAUGUAUUU AGGAUGCG | 976 | CGCAUCCU CUGAUGAGGNNNNNNNNCCGAA AAAUACAUA | 5132 |
| 5777 | AUGUAUUUA GGAUGCGC | 977 | GCGCAUCC CUGAUGAGGNNNNNNNNCCGAA AAAUACAU | 5133 |
| 5788 | AUGCGCCUA CUCUUCAG | 978 | CUGAAGAG CUGAUGAGGNNNNNNNNCCGAA AGGCGCAU | 5134 |
| 5791 | CGCCUACUC UUCAGGGU | 954 | ACCCUGAA CUGAUGAGGNNNNNNNNCCGAA AGUAGGCG | 5110 |
| 5793 | CCUACUCUU CAGGGUCU | 955 | AGACCCUG CUGAUGAGGNNNNNNNNCCGAA AGAGUAGG | 5111 |
| 5794 | CUACUCUUC AGGGUCUA | 956 | UAGACCCU CUGAUGAGGNNNNNNNNCCGAA AAGAGUAG | 5112 |
| 5800 | UUCAGGGUC UAAAGAUC | 957 | GAUCUUUA CUGAUGAGGNNNNNNNNCCGAA ACCCUGAA | 5113 |
| 5802 | CAGGGUCUA AAGAUCAA | 958 | UUGAUCUU CUGAUGAGGNNNNNNNNCCGAA AGACCCUG | 5114 |
| 5808 | CUAAAGAUC AAGGGGGC | 959 | GCCCCUUG CUGAUGAGGNNNNNNNNCCGAA AUCUUUAG | 5115 |
| 5819 | GUGGGCCUU GGAUCGCU | 960 | AGCGAUCC CUGAUGAGGNNNNNNNNCCGAA AGGCCCAC | 5116 |
| 5824 | CCUUGGAUC GCUAAGCU | 961 | AGCUUAGC CUGAUGAGGNNNNNNNNCCGAA AUCCAAGG | 5117 |
| 5828 | GGAUCGCUA AGCUGGCU | 962 | AGCCAGCU CUGAUGAGGNNNNNNNNCCGAA AGCGAUCC | 5118 |
| 5837 | AGCUGGCUC UGUUUGAU | 963 | AUCAAACA CUGAUGAGGNNNNNNNNCCGAA AGCCAGCU | 5119 |
| 5841 | GGCUCUGUU UGAUGCUA | 964 | UAGCAUCA CUGAUGAGGNNNNNNNNCCGAA ACAGAGCC | 5120 |
| 5842 | GCUCUGUUU GAUGCUAU | 965 | AUAGCAUC CUGAUGAGGNNNNNNNNCCGAA AACAGAGC | 5121 |
| 5849 | UUGAUGCUA UUUAUGCA | 966 | UGCAUAAA CUGAUGAGGNNNNNNNNCCGAA AGCAUCAA | 5122 |
| 5851 | GAUGCUAUU UAUGCAAG | 967 | CUUGCAUA CUGAUGAGGNNNNNNNNCCGAA AUAGCAUC | 5123 |
| 5852 | AUGCUAUUU AUGCAAGU | 968 | ACUUGCAU CUGAUGAGGNNNNNNNNCCGAA AAUAGCAU | 5124 |
| 5853 | UGCUAUUUA UGCAAGUU | 969 | AACUUGCA CUGAUGAGGNNNNNNNNCCGAA AAAUAGCA | 5125 |
| 5861 | AUGCAAGUU AGGGUCUA | 970 | UAGACCCU CUGAUGAGGNNNNNNNNCCGAA ACUUGCAU | 5126 |
| 5862 | UGCAAGUUA GGGUCUAU | 971 | AUAGACCC CUGAUGAGGNNNNNNNNCCGAA AACUUGCA | 5127 |
| 5867 | GUUAGGGUC UAUGUAUU | 972 | AAUACAUA CUGAUGAGGNNNNNNNNCCGAA ACCCUAAC | 5128 |
| 5869 | UAGGGUCUA UGUAUUUA | 973 | UAAAUACA CUGAUGAGGNNNNNNNNCCGAA AGACCCUA | 5129 |
| 5873 | GUCUAUGUA UUUAGGAU | 974 | AUCCUAAA CUGAUGAGGNNNNNNNNCCGAA ACAUAGAC | 5130 |
| 5875 | CUAUGUAUU UAGGAUGU | 979 | ACAUCCUA CUGAUGAGGNNNNNNNNCCGAA AUACAUAG | 5135 |
| 5876 | UAUGUAUUU AGGAUGUC | 980 | GACAUCCU CUGAUGAGGNNNNNNNNCCGAA AAAUACAUA | 5136 |
| 5877 | AUGUAUUUA GGAUGUCU | 981 | AGACAUCC CUGAUGAGGNNNNNNNNCCGAA AAAUACAU | 5137 |
| 5884 | UAGGAUGUC UGCACCUU | 982 | AAGGUGCA CUGAUGAGGNNNNNNNNCCGAA ACAUCCUA | 5138 |
| 5892 | CUGCACCUU CUGCAGCC | 983 | GGCUGCAG CUGAUGAGGNNNNNNNNCCGAA AGGUGCAG | 5139 |
| 5893 | UGCACCUUC UGCAGCCA | 984 | UGGCUGCA CUGAUGAGGNNNNNNNNCCGAA AAGGUGCA | 5140 |
| 5904 | CAGCCAGUC AGAAGCUG | 985 | CAGCUUCU CUGAUGAGGNNNNNNNNCCGAA ACUGGCUG | 5141 |
| 5930 | CAGUGGAUU GCUGCUUC | 986 | GAAGCAGC CUGAUGAGGNNNNNNNNCCGAA AUCCACUG | 5142 |
| 5937 | UUGCUGCUU CUUGGGGA | 987 | UCCCCAAG CUGAUGAGGNNNNNNNNCCGAA AGCAGCAA | 5143 |
| 5938 | UGCUGCUUC UUGGGGAG | 988 | CUCCCCAA CUGAUGAGGNNNNNNNNCCGAA AAGCAGCA | 5144 |
| 5940 | CUGCUUCUU GGGGAGAA | 989 | UUCUCCCC CUGAUGAGGNNNNNNNNCCGAA AGAAGCAG | 5145 |
| 5953 | AGAAGAGUA UGCUUCCU | 990 | AGGAAGCA CUGAUGAGGNNNNNNNNCCGAA ACUCUUCU | 5146 |
| 5958 | AGUAUGCUU CCUUUUAU | 991 | AUAAAAGG CUGAUGAGGNNNNNNNNCCGAA AGCAUACU | 5147 |
| 5959 | GUAUGCUUC CUUUUAUC | 992 | GAUAAAAG CUGAUGAGGNNNNNNNNCCGAA AAGCAUAC | 5148 |
| 5962 | UGCUUCCUU UUAUCCAU | 993 | AUGGAUAA CUGAUGAGGNNNNNNNNCCGAA AGGAAGCA | 5149 |
| 5963 | GCUUCCUUU UAUCCAUG | 994 | CAUGGAUA CUGAUGAGGNNNNNNNNCCGAA AAGGAAGC | 5150 |
| 5964 | CUUCCUUUU AUCCAUGU | 995 | ACAUGGAU CUGAUGAGGNNNNNNNNCCGAA AAAGGAAG | 5151 |
| 5965 | UUCCUUUUA UCCAUGUA | 996 | UACAUGGA CUGAUGAGGNNNNNNNNCCGAA AAAAGGAAG | 5152 |
| 5967 | CCUUUUAUC CAUGUAAU | 997 | AUUACAUG CUGAUGAGGNNNNNNNNCCGAA AUAAAAGG | 5153 |
| 5973 | AUCCAUGUA AUUUAACU | 998 | AGUUAAAU CUGAUGAGGNNNNNNNNCCGAA ACAUGGAU | 5154 |
| 5976 | CAUGUAAUU UAACUGUA | 999 | UACAGUUA CUGAUGAGGNNNNNNNNCCGAA AUUACAUG | 5155 |
| 5977 | AUGUAAUUU AACUGUAG | 1000 | CUACAGUU CUGAUGAGGNNNNNNNNCCGAA AAUUACAU | 5156 |
| 5978 | UGUAAUUUA ACUGUAGA | 1001 | UCUACAGU CUGAUGAGGNNNNNNNNCCGAA AAAUUACA | 5157 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5984 | UUAACUGUA GAACCUGA | 1002 | UCAGGUUC CUGAUGAGGNNNNNNNNCCGAA ACAGUUAA | 5158 |
| 5996 | CCUGAGCUC UAAGUAAC | 1003 | GUUACUUA CUGAUGAGGNNNNNNNNCCGAA AGCUCAGG | 5159 |
| 5998 | UGAGCUCUA AGUAACCG | 1004 | CGGUUACU CUGAUGAGGNNNNNNNNCCGAA AGAGCUCA | 5160 |
| 6002 | CUCUAAGUA ACCGAAGA | 1005 | UCUUCGGU CUGAUGAGGNNNNNNNNCCGAA ACUUAGAG | 5161 |
| 6015 | AAGAAUGUA UGCCUCUG | 1006 | CAGAGGCA CUGAUGAGGNNNNNNNNCCGAA ACAUUCUU | 5162 |
| 6021 | GUAUGCCUC UGUUCUUA | 1007 | UAAGAACA CUGAUGAGGNNNNNNNNCCGAA AGGCAUAC | 5163 |
| 6025 | GCCUCUGUU CUUAUGUG | 1008 | CACAUAAG CUGAUGAGGNNNNNNNNCCGAA ACAGAGGC | 5164 |
| 6026 | CCUCUGUUC UUAUGUGC | 1009 | GCACAUAA CUGAUGAGGNNNNNNNNCCGAA AACAGAGG | 5165 |
| 6028 | UCUGUUCUU AUGUGCCA | 1010 | UGGCACAU CUGAUGAGGNNNNNNNNCCGAA AGAACAGA | 5166 |
| 6029 | CUGUUCUUA UGUGCCAC | 1011 | GUGGCACA CUGAUGAGGNNNNNNNNCCGAA AAGAACAG | 5167 |
| 6040 | UGCCACAUC CUUGUUUA | 1012 | UAAACAAG CUGAUGAGGNNNNNNNNCCGAA AUGUGGCA | 5168 |
| 6043 | CACAUCCUU GUUUAAAG | 1013 | CUUUAAAC CUGAUGAGGNNNNNNNNCCGAA AGGAUGUG | 5169 |
| 6046 | AUCCUUGUU UAAAGGCU | 1014 | AGCCUUUA CUGAUGAGGNNNNNNNNCCGAA ACAAGGAU | 5170 |
| 6047 | UCCUUGUUU AAAGGCUC | 1015 | GAGCCUUU CUGAUGAGGNNNNNNNNCCGAA AACAAGGA | 5171 |
| 6048 | CCUUGUUUA AAGGCUCU | 1016 | AGAGCCUU CUGAUGAGGNNNNNNNNCCGAA AAACAAGG | 5172 |
| 6055 | UAAAGGCUC UCUGUAUG | 1017 | CAUACAGA CUGAUGAGGNNNNNNNNCCGAA AGCCUUUA | 5173 |
| 6057 | AAGGCUCUC UGUAUGAA | 1018 | UUCAUACA CUGAUGAGGNNNNNNNNCCGAA AGAGCCUU | 5174 |
| 6061 | CUCUCUGUA UGAAGAGA | 1019 | UCUCUUCA CUGAUGAGGNNNNNNNNCCGAA ACAGAGAG | 5175 |
| 6079 | GGGACCGUC AUCAGCAC | 1020 | GUGCUGAU CUGAUGAGGNNNNNNNNCCGAA ACGGUCCC | 5176 |
| 6082 | ACCGUCAUC AGCACAUU | 1021 | AAUGUGCU CUGAUGAGGNNNNNNNNCCGAA AUGACGGU | 5177 |
| 6090 | CAGCACAUU CCCUAGUG | 1022 | CACUAGGG CUGAUGAGGNNNNNNNNCCGAA AUGUGCUG | 5178 |
| 6091 | AGCACAUUC CCUAGUGA | 1023 | UCACUAGG CUGAUGAGGNNNNNNNNCCGAA AAUGUGCU | 5179 |
| 6095 | CAUUCCCUA GUGAGCCU | 1024 | AGGCUCAC CUGAUGAGGNNNNNNNNCCGAA AGGGAAUG | 5180 |
| 6104 | GUGAGCCUA CUGGCUCC | 1025 | GGAGCCAG CUGAUGAGGNNNNNNNNCCGAA AGGCUCAC | 5181 |
| 6111 | UACUGGCUC CUGGCAGC | 1026 | GCUGCCAG CUGAUGAGGNNNNNNNNCCGAA AGCCAGUA | 5182 |
| 6124 | CAGCGGCUU UUGUGGAA | 1027 | UUCCACAA CUGAUGAGGNNNNNNNNCCGAA AGCCGCUG | 5183 |
| 6125 | AGCGGCUUU UGUGGAAG | 1028 | CUUCCACA CUGAUGAGGNNNNNNNNCCGAA AAGCCGCU | 5184 |
| 6126 | GCGGCUUUU GUGGAAGA | 1029 | UCUUCCAC CUGAUGAGGNNNNNNNNCCGAA AAAGCCGC | 5185 |
| 6137 | GGAAGACUC ACUAGCCA | 1030 | UGGCUAGU CUGAUGAGGNNNNNNNNCCGAA AGUCUUCC | 5186 |
| 6141 | GACUCACUA GCCAGAAG | 1031 | CUUCUGGC CUGAUGAGGNNNNNNNNCCGAA AGUGAGUC | 5187 |
| 6166 | GGGACAGUC CUCUCCAC | 1032 | GUGGAGAG CUGAUGAGGNNNNNNNNCCGAA ACUGUCCC | 5188 |
| 6169 | ACAGUCCUC UCCACCAA | 1033 | UUGGUGGA CUGAUGAGGNNNNNNNNCCGAA AGGACUGU | 5189 |
| 6171 | AGUCCUCUC CACCAAGA | 1034 | UCUUGGUG CUGAUGAGGNNNNNNNNCCGAA AGAGGACU | 5190 |
| 6181 | ACCAAGAUC UAAAUCCA | 1035 | UGGAUUUA CUGAUGAGGNNNNNNNNCCGAA AUCUUGGU | 5191 |
| 6183 | CAAGAUCUA AAUCCAAA | 1036 | UUUGGAUU CUGAUGAGGNNNNNNNNCCGAA AGAUCUUG | 5192 |
| 6187 | AUCUAAAUC CAAACAAA | 1037 | UUUGUUUG CUGAUGAGGNNNNNNNNCCGAA AUUUAGAU | 5193 |
| 6204 | AGCAGGCUA GAGCCAGA | 1038 | UCUGGCUC CUGAUGAGGNNNNNNNNCCGAA AGCCUGCU | 5194 |
| 6226 | GGACAAAUC UUUGUUGU | 1039 | ACAACAAA CUGAUGAGGNNNNNNNNCCGAA AUUUGUCC | 5195 |
| 6228 | ACAAAUCUU UGUUGUUC | 1040 | GAACAACA CUGAUGAGGNNNNNNNNCCGAA AGAUUUGU | 5196 |
| 6229 | CAAAUCUUU GUUGUUCC | 1041 | GGAACAAC CUGAUGAGGNNNNNNNNCCGAA AAGAUUUG | 5197 |
| 6232 | AUCUUUGUU GUUCCUCU | 1042 | AGAGGAAC CUGAUGAGGNNNNNNNNCCGAA ACAAAGAU | 5198 |
| 6235 | UUUGUUGUU CCUCUUCU | 1043 | AGAAGAGG CUGAUGAGGNNNNNNNNCCGAA ACAACAAA | 5199 |
| 6236 | UUGUUGUUC CUCUUCUU | 1044 | AAGAAGAG CUGAUGAGGNNNNNNNNCCGAA AACAACAA | 5200 |
| 6239 | UUGUUCCUC UUCUUUAC | 1045 | GUAAAGAA CUGAUGAGGNNNNNNNNCCGAA AGGAACAA | 5201 |
| 6241 | GUUCCUCUU CUUUACAC | 1046 | GUGUAAAG CUGAUGAGGNNNNNNNNCCGAA AGAGGAAC | 5202 |
| 6242 | UUCCUCUUC UUUACACA | 1047 | UGUGUAAA CUGAUGAGGNNNNNNNNCCGAA AAGAGGAA | 5203 |
| 6244 | CCUCUUCUU UACACAUA | 1048 | UAUGUGUA CUGAUGAGGNNNNNNNNCCGAA AGAAGAGG | 5204 |
| 6245 | CUCUUCUUU ACACAUAC | 1049 | GUAUGUGU CUGAUGAGGNNNNNNNNCCGAA AAGAAGAG | 5205 |
| 6246 | UCUUCUUUA CACAUACG | 1050 | CGUAUGUG CUGAUGAGGNNNNNNNNCCGAA AAAGAAGA | 5206 |
| 6252 | UUACACAUA CGCAAACC | 1051 | GGUUUGCG CUGAUGAGGNNNNNNNNCCGAA AUGUGUAA | 5207 |
| 6280 | CUGGCAAUU UUAUAAAU | 1052 | AUUUAUAA CUGAUGAGGNNNNNNNNCCGAA AUUGCCAG | 5208 |
| 6281 | UGGCAAUUU UAUAAAUC | 1053 | GAUUUAUA CUGAUGAGGNNNNNNNNCCGAA AAUUGCCA | 5209 |
| 6282 | GGCAAUUUU AUAAAUCA | 1054 | UGAUUUAU CUGAUGAGGNNNNNNNNCCGAA AAAUUGCC | 5210 |
| 6283 | GCAAUUUUA UAAAUCAG | 1055 | CUGAUUUA CUGAUGAGGNNNNNNNNCCGAA AAAAUUGC | 5211 |
| 6285 | AAUUUUAUA AAUCAGGU | 1056 | ACCUGAUU CUGAUGAGGNNNNNNNNCCGAA AUAAAAUU | 5212 |
| 6289 | UUAUAAAUC AGGUAACU | 1057 | AGUUACCU CUGAUGAGGNNNNNNNNCCGAA AUUUAUAA | 5213 |
| 6294 | AAUCAGGUA ACUGGAAG | 1058 | CUUCCAGU CUGAUGAGGNNNNNNNNCCGAA ACCUGAUU | 5214 |
| 6308 | AAGGAGGUU AAACUCAG | 1059 | CUGAGUUU CUGAUGAGGNNNNNNNNCCGAA ACCUCCUU | 5215 |
| 6309 | AGGAGGUUA AACUCAGA | 1060 | UCUGAGUU CUGAUGAGGNNNNNNNNCCGAA AACCUCCU | 5216 |
| 6314 | GUUAAACUC AGAAAAAA | 1061 | UUUUUUCU CUGAUGAGGNNNNNNNNCCGAA AGUUUAAC | 5217 |
| 6331 | GAAGACCUC AGUCAAUU | 1062 | AAUUGACU CUGAUGAGGNNNNNNNNCCGAA AGGUCUUC | 5218 |
| 6335 | ACCUCAGUC AAUUCUCU | 1063 | AGAGAAUU CUGAUGAGGNNNNNNNNCCGAA ACUGAGGU | 5219 |
| 6339 | CAGUCAAUU CUCUACUU | 1064 | AAGUAGAG CUGAUGAGGNNNNNNNNCCGAA AUUGACUG | 5220 |
| 6340 | AGUCAAUUC UCUACUUU | 1065 | AAAGUAGA CUGAUGAGGNNNNNNNNCCGAA AAUUGACU | 5221 |
| 6342 | UCAAUUCUC UACUUUUU | 1066 | AAAAAGUA CUGAUGAGGNNNNNNNNCCGAA AGAAUUGA | 5222 |
| 6344 | AAUUCUCUA CUUUUUUU | 1067 | AAAAAAAG CUGAUGAGGNNNNNNNNCCGAA AGAGAAUU | 5223 |
| 6347 | UCUCUACUU UUUUUUUU | 1068 | AAAAAAAA CUGAUGAGGNNNNNNNNCCGAA AGUAGAGA | 5224 |
| 6348 | CUCUACUUU UUUUUUUU | 1069 | AAAAAAAA CUGAUGAGGNNNNNNNNCCGAA AAGUAGAG | 5225 |
| 6349 | UCUACUUUU UUUUUUUU | 1070 | AAAAAAAA CUGAUGAGGNNNNNNNNCCGAA AAAGUAGA | 5226 |
| 6350 | CUACUUUUU UUUUUUUU | 1071 | AAAAAAAA CUGAUGAGGNNNNNNNNCCGAA AAAAGUAG | 5227 |
| 6351 | UACUUUUUU UUUUUUUU | 1072 | AAAAAAAA CUGAUGAGGNNNNNNNNCCGAA AAAAAGUA | 5228 |
| 6352 | ACUUUUUUU UUUUUUUU | 1073 | AAAAAAAA CUGAUGAGGNNNNNNNNCCGAA AAAAAAGU | 5229 |
| 6353 | CUUUUUUUU UUUUUUUU | 1074 | AAAAAAAA CUGAUGAGGNNNNNNNNCCGAA AAAAAAAG | 5230 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6354 | UUUUUUUUU UUUUUUUC | 1075 | GAAAAAAA CUGAUGAGgnnnnnnnnCCGAA AAAAAAAA | 5231 |
| 6355 | UUUUUUUUU UUUUUUCC | 1076 | GGAAAAAA CUGAUGAGgnnnnnnnnCCGAA AAAAAAAA | 5232 |
| 6356 | UUUUUUUUU UUUUUCCA | 1077 | UGGAAAAA CUGAUGAGgnnnnnnnnCCGAA AAAAAAAA | 5233 |
| 6357 | UUUUUUUUU UUUUCCAA | 1078 | UUGGAAAA CUGAUGAGgnnnnnnnnCCGAA AAAAAAAA | 5234 |
| 6358 | UUUUUUUUU UUUCCAAA | 1079 | UUUGGAAA CUGAUGAGgnnnnnnnnCCGAA AAAAAAAA | 5235 |
| 6359 | UUUUUUUUU UUCCAAAU | 1080 | AUUUGGAA CUGAUGAGgnnnnnnnnCCGAA AAAAAAAA | 5236 |
| 6360 | UUUUUUUUU UCCAAAUC | 1081 | GAUUUGGA CUGAUGAGgnnnnnnnnCCGAA AAAAAAAA | 5237 |
| 6361 | UUUUUUUUU CCAAAUCA | 1082 | UGAUUUGG CUGAUGAGgnnnnnnnnCCGAA AAAAAAAA | 5238 |
| 6362 | UUUUUUUUC CAAAUCAG | 1083 | CUGAUUUG CUGAUGAGgnnnnnnnnCCGAA AAAAAAAA | 5239 |
| 6368 | UUCCAAAUC AGAUAAUA | 1084 | UAUUAUCU CUGAUGAGgnnnnnnnnCCGAA AUUUGGAA | 5240 |
| 6373 | AAUCAGAUA AUAGCCCA | 1085 | UGGGCUAU CUGAUGAGgnnnnnnnnCCGAA AUCUGAUU | 5241 |
| 6376 | CAGAUAAUA GCCCAGCA | 1086 | UGCUGGGC CUGAUGAGgnnnnnnnnCCGAA AUUAUCUG | 5242 |
| 6388 | CAGCAAAUA GUGAUAAC | 1087 | GUUAUCAC CUGAUGAGgnnnnnnnnCCGAA AUUUGCUG | 5243 |
| 6394 | AUAGUGAUA ACAAAUAA | 1088 | UUAUUUGU CUGAUGAGgnnnnnnnnCCGAA AUCACUAU | 5244 |
| 6401 | UAACAAAUA AAACCUUA | 1089 | UAAGGUUU CUGAUGAGgnnnnnnnnCCGAA AUUUGUUA | 5245 |
| 6408 | UAAAACCUU AGCUGUUC | 1090 | GAACAGCU CUGAUGAGgnnnnnnnnCCGAA AGGUUUUA | 5246 |
| 6409 | AAAACCUUA GCUGUUCA | 1091 | UGAACAGC CUGAUGAGgnnnnnnnnCCGAA AAGGUUUU | 5247 |
| 6415 | UUAGCUGUU CAUGCUAU | 1092 | AAGACAUG CUGAUGAGgnnnnnnnnCCGAA ACAGCUAA | 5248 |
| 6416 | UAGCUGUUC AUGUCUUG | 1093 | CAAGACAU CUGAUGAGgnnnnnnnnCCGAA AACAGCUA | 5249 |
| 6421 | GUUCAUGUC UUGAUUUC | 1094 | GAAAUCAA CUGAUGAGgnnnnnnnnCCGAA ACAUGAAC | 5250 |
| 6423 | UCAUGUCUU GAUUUCAA | 1095 | UUGAAAUC CUGAUGAGgnnnnnnnnCCGAA AGACAUGA | 5251 |
| 6427 | GUCUUGAUU UCAAUAAU | 1096 | AUUAUUGA CUGAUGAGgnnnnnnnnCCGAA AUCAAGAC | 5252 |
| 6428 | UCUUGAUUU CAAUAAUU | 1097 | AAUUAUUG CUGAUGAGgnnnnnnnnCCGAA AAUCAAGA | 5253 |
| 6429 | CUUGAUUUC AAUAAUUA | 1098 | UAAUUAUU CUGAUGAGgnnnnnnnnCCGAA AAAUCAAG | 5254 |
| 6433 | AUUUCAAUA AUUAAUUC | 1099 | GAAUUAAU CUGAUGAGgnnnnnnnnCCGAA AUUGAAAU | 5255 |
| 6436 | UCAAUAAUU AAUUCUUA | 1100 | UAAGAAUU CUGAUGAGgnnnnnnnnCCGAA AUUAUUGA | 5256 |
| 6437 | CAAUAAUUA AUUCUUAA | 1101 | UUAAGAAU CUGAUGAGgnnnnnnnnCCGAA AAUUAUUG | 5257 |
| 6440 | UAAUUAAUU CUUAAUCA | 1102 | UGAUUAAG CUGAUGAGgnnnnnnnnCCGAA AUUAAUUA | 5258 |
| 6441 | AAUUAAUUC UUAAUCAU | 1103 | AUGAUUAA CUGAUGAGgnnnnnnnnCCGAA AAUUAAUU | 5259 |
| 6443 | UUAAUUCUU AAUCAUUA | 1104 | UAAUGAUU CUGAUGAGgnnnnnnnnCCGAA AGAAUUAA | 5260 |
| 6444 | UAAUUCUUA AUCAUUAA | 1105 | UUAAUGAU CUGAUGAGgnnnnnnnnCCGAA AAGAAUUA | 5261 |
| 6447 | UUCUUAAUC AUUAAGAG | 1106 | CUCUUAAU CUGAUGAGgnnnnnnnnCCGAA AUUAAGAA | 5262 |
| 6450 | UUAAUCAUU AAGAGACC | 1107 | GGUCUCUU CUGAUGAGgnnnnnnnnCCGAA AUGAUUAA | 5263 |
| 6451 | UAAUCAUUA AGAGACCA | 1108 | UGGUCUCU CUGAUGAGgnnnnnnnnCCGAA AAUGAUUA | 5264 |
| 6461 | GAGACCAUA AUACUCCC | 1109 | GUAUUUAC CUGAUGAGgnnnnnnnnCCGAA AUGGUCUC | 5265 |
| 6464 | ACCAUAAUA AAUACUCC | 1110 | GGAGUAUU CUGAUGAGgnnnnnnnnCCGAA AUUAUGGU | 5266 |
| 6468 | UAAUAAAUA CUCCUUUU | 1111 | AAAAGGAG CUGAUGAGgnnnnnnnnCCGAA AUUUAUUA | 5267 |
| 6471 | UAAAUACUC CUUUUCAA | 1112 | UUGAAAAG CUGAUGAGgnnnnnnnnCCGAA AGUAUUUA | 5268 |
| 6474 | AUACUCCUU UCAAGAGA | 1113 | CUCUUGAA CUGAUGAGgnnnnnnnnCCGAA AGGAGUAU | 5269 |
| 6475 | UACUCCUUU CAAGAGAA | 1114 | UCUCUUGA CUGAUGAGgnnnnnnnnCCGAA AAGGAGUA | 5270 |
| 6476 | ACUCCUUUC AAGAGAAA | 1115 | UUCUCUUG CUGAUGAGgnnnnnnnnCCGAA AAAGGAGU | 5271 |
| 6477 | CUCCUUUUC AAGAGAAA | 1116 | UUUCUCUU CUGAUGAGgnnnnnnnnCCGAA AAAAGGAG | 5272 |
| 6497 | AAAACCAUU GAAUUGU | 1117 | ACAAUUCU CUGAUGAGgnnnnnnnnCCGAA AUGGUUUU | 5273 |
| 6498 | AAACCAUUA GAAUUGUU | 1118 | AACAAUUC CUGAUGAGgnnnnnnnnCCGAA AAUGGUUU | 5274 |
| 6503 | AUUAGAAUU GUUACUCA | 1119 | UGAGUAAC CUGAUGAGgnnnnnnnnCCGAA AUUCUAAU | 5275 |
| 6506 | AGAAUUGUU ACUCAGCU | 1120 | AGCUGAGU CUGAUGAGgnnnnnnnnCCGAA ACAAUUCU | 5276 |
| 6507 | GAAUUGUUA CUCAGCUC | 1121 | GAGCUGAG CUGAUGAGgnnnnnnnnCCGAA AACAAUUC | 5277 |
| 6510 | UUGUUACUC AGCUCCUU | 1122 | AAGGAGCU CUGAUGAGgnnnnnnnnCCGAA AGUAACAA | 5278 |
| 6515 | ACUCAGCUC CUUCAAAC | 1123 | GUUUGAAG CUGAUGAGgnnnnnnnnCCGAA AGCUGAGU | 5279 |
| 6518 | CAGCUCCUU CAAACUCA | 1124 | UGAGUUUG CUGAUGAGgnnnnnnnnCCGAA AGGAGCUG | 5280 |
| 6519 | AGCUCCUUC AAACUCAG | 1125 | CUGAGUUU CUGAUGAGgnnnnnnnnCCGAA AAGGAGCU | 5281 |
| 6525 | UUCAAACUC AGGUUGU | 1126 | ACAAACCU CUGAUGAGgnnnnnnnnCCGAA AGUUUGAA | 5282 |
| 6530 | ACUCAGGUU UGUAGCAU | 1127 | AUGCUACA CUGAUGAGgnnnnnnnnCCGAA ACCUGAGU | 5283 |
| 6531 | CUCAGGUUU GUAGCAUA | 1128 | UAUGCUAC CUGAUGAGgnnnnnnnnCCGAA AACCUGAG | 5284 |
| 6534 | AGGUUUGUA GCAUACAU | 1129 | AUGUAUGC CUGAUGAGgnnnnnnnnCCGAA ACAAACCU | 5285 |
| 6539 | UGUAGCAUA CAUGAGUC | 1130 | GACUCAUG CUGAUGAGgnnnnnnnnCCGAA AUGCUACA | 5286 |
| 6547 | ACAUGAGUC CAUCCAUC | 1131 | GAUGGAUG CUGAUGAGgnnnnnnnnCCGAA ACUCAUGU | 5287 |
| 6551 | GAGUCCAUC CAUCAGUC | 1132 | GACUGAUG CUGAUGAGgnnnnnnnnCCGAA AUGGACUC | 5288 |
| 6555 | CCAUCCAUC AGUCAAAG | 1133 | CUUUGACU CUGAUGAGgnnnnnnnnCCGAA AUGGAUGG | 5289 |
| 6559 | CCAUCAGUC AAAGAAUG | 1134 | CAUUCUUU CUGAUGAGgnnnnnnnnCCGAA ACUGAUGG | 5290 |
| 6570 | AGAAUGGUU CCAUCUGG | 1135 | CCAGAUGG CUGAUGAGgnnnnnnnnCCGAA ACCAUUCU | 5291 |
| 6571 | GAAUGGUUC CAUCUGGA | 1136 | UCCAGAUG CUGAUGAGgnnnnnnnnCCGAA AACCAUUC | 5292 |
| 6575 | GGUUCCAUC UGGAGUCU | 1137 | AGACUCCA CUGAUGAGgnnnnnnnnCCGAA AUGGAACC | 5293 |
| 6582 | UCUGGAGUC UUAAUGUA GA | 1138 | UACAUUAA CUGAUGAGgnnnnnnnnCCGAA ACUCCAGA | 5294 |
| 6584 | UGGAGUCUU AAUGUAGA | 1139 | UCUACAUU CUGAUGAGgnnnnnnnnCCGAA AGACUCCA | 5295 |
| 6585 | GCAGUCUUA AUGUAGAA | 1140 | UUCUACAU CUGAUGAGgnnnnnnnnCCGAA AAGACUCC | 5296 |
| 6590 | CUUAAUGUA GAAAGAAA | 1141 | UUUCUUUC CUGAUGAGgnnnnnnnnCCGAA ACAUUAAG | 5297 |
| 6609 | UGGAGACUU AUAAUAAU | 1142 | AUUAUUAC CUGAUGAGgnnnnnnnnCCGAA AGUCUCCA | 5298 |
| 6612 | AGACUUGUA AUAAUGAG | 1143 | CUCAUUAU CUGAUGAGgnnnnnnnnCCGAA ACAAGUCU | 5299 |
| 6615 | CUUGUAAUA AUGAGCUA | 1144 | UAGCUCAU CUGAUGAGgnnnnnnnnCCGAA AUUACAAG | 5300 |
| 6623 | AAUGAGCUA GUUACAAA | 1145 | UUUGUAAC CUGAUGAGgnnnnnnnnCCGAA AGCUCAUU | 5301 |
| 6626 | GAGCUAGUU ACAAAGUG | 1146 | CACUUUGU CUGAUGAGgnnnnnnnnCCGAA ACUAGCUC | 5302 |
| 6627 | AGCUAGUUA CAAAGUGC | 1147 | GCACUUUG CUGAUGAGgnnnnnnnnCCGAA AACUAGCU | 5303 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6637 | AAAGUGCUU GUUCAUUA | 1148 | UAAUGAAC CUGAUGAGGNNNNNNNNCCGAA AGCACUUU | 5304 |
| 6640 | GUGCUUGUU CAUUAAAA | 1149 | UUUUAAUG CUGAUGAGGNNNNNNNNCCGAA ACAAGCAC | 5305 |
| 6641 | UGCUUGUUC AUUAAAAU | 1150 | AUUUUAAU CUGAUGAGGNNNNNNNNCCGAA AACAAGCA | 5306 |
| 6644 | UUGUUCAUU AAAAUAGC | 1151 | GCUAUUUU CUGAUGAGGNNNNNNNNCCGAA AUGAACAA | 5307 |
| 6645 | UGUUCAUUA AAAUAGCA | 1152 | UGCUAUUU CUGAUGAGGNNNNNNNNCCGAA AAUGAACA | 5308 |
| 6650 | AUUAAAAUA GCACUGAA | 1153 | UUCAGUGC CUGAUGAGGNNNNNNNNCCGAA AUUUUAAU | 5309 |
| 6662 | CUGAAAAUU GAAACAUG | 1154 | CAUGUUUC CUGAUGAGGNNNNNNNNCCGAA AUUUUCAG | 5310 |
| 6674 | ACAUGAAUU AACUGAUA | 1155 | UAUCAGUU CUGAUGAGGNNNNNNNNCCGAA AUUCAUGU | 5311 |
| 6675 | CAUGAAUUA ACUGAUAA | 1156 | UUAUCAGU CUGAUGAGGNNNNNNNNCCGAA AAUUCAUG | 5312 |
| 6682 | UAACUGAUA AUAUUCCA | 1157 | UGGAAUAU CUGAUGAGGNNNNNNNNCCGAA AUCAGUUA | 5313 |
| 6685 | CUGAUAAUA UUCCAAUC | 1158 | GAUUGGAA CUGAUGAGGNNNNNNNNCCGAA AUUAUCAG | 5314 |
| 6687 | GAUAAUAUU CCAAUCAU | 1159 | AUGAUUGG CUGAUGAGGNNNNNNNNCCGAA AUAUUAUC | 5315 |
| 6688 | AUAAUAUUC CAAUCAUU | 1160 | AAUGAUUG CUGAUGAGGNNNNNNNNCCGAA AAUAUUAU | 5316 |
| 6693 | AUUCCAAUC AUUGCCA | 1161 | UGGCAAAU CUGAUGAGGNNNNNNNNCCGAA AUUGGAAU | 5317 |
| 6696 | CCAAUCAUU GCCAUUU | 1162 | AAAUGGCA CUGAUGAGGNNNNNNNNCCGAA AUGAUUGG | 5318 |
| 6697 | CAAUCAUUU GCCAUUUA | 1163 | UAAAUGGC CUGAUGAGGNNNNNNNNCCGAA AAUGAUUG | 5319 |
| 6703 | UUUGCCAUU UAUGACAA | 1164 | UUGUCAUA CUGAUGAGGNNNNNNNNCCGAA AUGGCAAA | 5320 |
| 6704 | UUGCCAUUU AUGACAAA | 1165 | UUUGUCAU CUGAUGAGGNNNNNNNNCCGAA AAUGGCAA | 5321 |
| 6705 | UGCCAUUUA UGACAAAA | 1166 | UUUUGUCA CUGAUGAGGNNNNNNNNCCGAA AAAUGGCA | 5322 |
| 6719 | AAAAUGGUU GGCACUAA | 1167 | UUAGUGCC CUGAUGAGGNNNNNNNNCCGAA ACCAUUUU | 5323 |
| 6726 | UUGGCACUA ACAAAGAA | 1168 | UUCUUUGU CUGAUGAGGNNNNNNNNCCGAA AGUGCCAA | 5324 |
| 6743 | CGAGCACUU CCUUUCAG | 1169 | CUGAAAGG CUGAUGAGGNNNNNNNNCCGAA AGUGCUCG | 5325 |
| 6744 | GAGCACUUC CUUUCAGA | 1170 | UCUGAAAG CUGAUGAGGNNNNNNNNCCGAA AAGUGCUC | 5326 |
| 6747 | CACUUCCUU UCAGAGUU | 1171 | AACUCUGA CUGAUGAGGNNNNNNNNCCGAA AGGAAGUG | 5327 |
| 6748 | ACUUCCUUU CAGAGUUU | 1172 | AAACUCUG CUGAUGAGGNNNNNNNNCCGAA AAGGAAGU | 5328 |
| 6749 | CUUCCUUUC AGAGUUUC | 1173 | GAAACUCU CUGAUGAGGNNNNNNNNCCGAA AAAGGAAG | 5329 |
| 6755 | UUCAGAGUU CUGAGAU | 1174 | AUCUCAGA CUGAUGAGGNNNNNNNNCCGAA ACUCUGAA | 5330 |
| 6756 | UCAGAGUUU CUGAGAUA | 1175 | UAUCUCAG CUGAUGAGGNNNNNNNNCCGAA AACUCUGA | 5331 |
| 6757 | CAGAGUUUC UGAGAUAA | 1176 | UUAUCUCA CUGAUGAGGNNNNNNNNCCGAA AAACUCUG | 5332 |
| 6764 | UCUGAGAUA AUGUACGU | 1177 | ACGUACAU CUGAUGAGGNNNNNNNNCCGAA AUCUCAGA | 5333 |
| 6769 | GAUAAUGUA CGUAAAC | 1178 | GUUCCACG CUGAUGAGGNNNNNNNNCCGAA ACAUUAUC | 5334 |
| 6781 | GGAACAGUC UGGGUGGA | 1179 | UCCACCCA CUGAUGAGGNNNNNNNNCCGAA ACUGUUCC | 5335 |
| 6814 | GUGCAAGUC UGUGUCUU | 1180 | AAGACACA CUGAUGAGGNNNNNNNNCCGAA ACUUGCAC | 5336 |
| 6820 | GUCUGUGUC UUGUCAGU | 1181 | ACUGACAA CUGAUGAGGNNNNNNNNCCGAA ACACAGAC | 5337 |
| 6822 | CUGUGUCUU GUCAGUCC | 1182 | GGACUGAC CUGAUGAGGNNNNNNNNCCGAA AGACACAG | 5338 |
| 6825 | UGUCUUGUC AGUCCAAG | 1183 | CUUGGACU CUGAUGAGGNNNNNNNNCCGAA ACAAGACA | 5339 |
| 6829 | UUGUCAGUC CAAGAAGU | 1184 | ACUUCUUG CUGAUGAGGNNNNNNNNCCGAA ACUGACAA | 5340 |
| 6851 | CGAGAUGUU AAUUUUAG | 1185 | CUAAAAUU CUGAUGAGGNNNNNNNNCCGAA ACAUCUCG | 5341 |
| 6852 | GAGAUGUUA AUUUUAGG | 1186 | CCUAAAAU CUGAUGAGGNNNNNNNNCCGAA AACAUCUC | 5342 |
| 6855 | AUGUUAAUU UUAGGGAC | 1187 | GUCCCUAA CUGAUGAGGNNNNNNNNCCGAA AUUAACAU | 5343 |
| 6856 | UGUUAAUUU UAGGGACC | 1188 | GGUCCCUA CUGAUGAGGNNNNNNNNCCGAA AAUUAACA | 5344 |
| 6857 | GUUAAUUUU AGGGACCC | 1189 | GGGUCCCU CUGAUGAGGNNNNNNNNCCGAA AAAUUAAC | 5345 |
| 6858 | UUAAUUUUA GGGACCCG | 1190 | CGGGUCCC CUGAUGAGGNNNNNNNNCCGAA AAAAUUAA | 5346 |
| 6872 | CCGUGCCUU GUUUCCUA | 1191 | UAGGAAAC CUGAUGAGGNNNNNNNNCCGAA AGGCACGG | 5347 |
| 6875 | UGCCUUGUU UCCUAGCC | 1192 | GGCUAGGA CUGAUGAGGNNNNNNNNCCGAA ACAAGGCA | 5348 |
| 6876 | GCCUUGUUU CCUAGCCC | 1193 | GGGCUAGG CUGAUGAGGNNNNNNNNCCGAA AACAAGGC | 5349 |
| 6877 | CCUUGUUUC CUAGCCCA | 1194 | UGGGCUAG CUGAUGAGGNNNNNNNNCCGAA AAACAAGG | 5350 |
| 6880 | UGUUUCCUA GCCCACAA | 1195 | UUGUGGGC CUGAUGAGGNNNNNNNNCCGAA AGGAAACA | 5351 |
| 6901 | GCAAACAUC AAACAGAU | 1196 | AUCUGUUU CUGAUGAGGNNNNNNNNCCGAA AUGUUUGC | 5352 |
| 6910 | AAACAGAUA CUCGCUAG | 1197 | CUAGCGAG CUGAUGAGGNNNNNNNNCCGAA AUCUGUUU | 5353 |
| 6913 | CAGAUACUC GCUAGCCU | 1198 | AGGCUAGC CUGAUGAGGNNNNNNNNCCGAA AGUAUCUG | 5354 |
| 6917 | UACUCGCUA GCCUCAUU | 1199 | AAUGAGGC CUGAUGAGGNNNNNNNNCCGAA AGCGAGUA | 5355 |
| 6922 | GCUAGCCUC AUUUAAAU | 1200 | AUUUAAAU CUGAUGAGGNNNNNNNNCCGAA AGGCUAGC | 5356 |
| 6925 | AGCCUCAUU UAAAUUGA | 1201 | UCAAUUUA CUGAUGAGGNNNNNNNNCCGAA AUGAGGCU | 5357 |
| 6926 | GCCUCAUUU AAAUUGAU | 1202 | AUCAAUUU CUGAUGAGGNNNNNNNNCCGAA AAAUGAGGC | 5358 |
| 6927 | CCUCAUUUA AAUUGAUU | 1203 | AAUCAAUU CUGAUGAGGNNNNNNNNCCGAA AAAUGAGG | 5359 |
| 6931 | AUUUAAAUU GAUUAAAG | 1204 | CUUUAAUC CUGAUGAGGNNNNNNNNCCGAA AUUUAAAU | 5360 |
| 6935 | AAAUUGAUU AAGGAGG | 1205 | CCUCCUUU CUGAUGAGGNNNNNNNNCCGAA AUCAAUUU | 5361 |
| 6936 | AAUUGAUUA AAGGAGGA | 1206 | UCCUCCUU CUGAUGAGGNNNNNNNNCCGAA AAUCAAUU | 5362 |
| 6951 | GAGUGCAUC UUUGCCCG | 1207 | CGGGCAAA CUGAUGAGGNNNNNNNNCCGAA AUGCACUC | 5363 |
| 6953 | GUGCAUCUU UGGCCGAC | 1208 | GUCGGCCA CUGAUGAGGNNNNNNNNCCGAA AGAUGCAC | 5364 |
| 6954 | UGCAUCUUU GGCCGACA | 1209 | UGUCGGCC CUGAUGAGGNNNNNNNNCCGAA AAGAUGCA | 5365 |
| 6970 | AGUGGUGUA ACUGUGUG | 1210 | CACACAGU CUGAUGAGGNNNNNNNNCCGAA ACACCACU | 5366 |
| 7026 | GUGGGUGUA UGUGUGUU | 1211 | AACACACA CUGAUGAGGNNNNNNNNCCGAA ACACCCAC | 5367 |
| 7034 | AUGUGUGUU UUGUGCAU | 1212 | AUGCACAA CUGAUGAGGNNNNNNNNCCGAA ACACACAU | 5368 |
| 7035 | UGUGUGUUU UGUGCAUA | 1213 | UAUGCACA CUGAUGAGGNNNNNNNNCCGAA AACACACA | 5369 |
| 7036 | GUGUGUUUU GUGCAUAA | 1214 | UUAUGCAC CUGAUGAGGNNNNNNNNCCGAA AAACACAC | 5370 |
| 7043 | UUGUGCAUA ACUAUUUA | 1215 | UAAAUAGU CUGAUGAGGNNNNNNNNCCGAA AUGCACAA | 5371 |
| 7047 | GCAUAACUA UUUAAGGA | 1216 | UCCUUAAA CUGAUGAGGNNNNNNNNCCGAA AGUUAUGC | 5372 |
| 7049 | AUAACUAUU UAAGGAAA | 1217 | UUUCCUUA CUGAUGAGGNNNNNNNNCCGAA AUAGUUAU | 5373 |
| 7050 | UAACUAUUU AAGGAAAC | 1218 | GUUUCCUU CUGAUGAGGNNNNNNNNCCGAA AAUAGUUA | 5374 |
| 7051 | AACUAUUUA AGGAAACU | 1219 | AGUUUCCU CUGAUGAGGNNNNNNNNCCGAA AAAUAGUU | 5375 |
| 7065 | ACUGGAAUU UUAAAGUU | 1220 | AACUUUAA CUGAUGAGGNNNNNNNNCCGAA AUUCCAGU | 5376 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7066 | CUGGAAUUU UAAAGUUA | 1221 | UAACUUUA CUGAUGAGGNNNNNNNNCCGAA AAUUCCAG | 5377 |
| 7067 | UGGAAUUUU AAAGUUAC | 1222 | GUAACUUU CUGAUGAGGNNNNNNNNCCGAA AAAUUCCA | 5378 |
| 7068 | GGAAUUUUA AAGUUACU | 1223 | AGUAACUU CUGAUGAGGNNNNNNNNCCGAA AAAAUUCC | 5379 |
| 7073 | UUUAAAGUU ACUUUUAU | 1224 | AUAAAAGU CUGAUGAGGNNNNNNNNCCGAA ACUUUAAA | 5380 |
| 7074 | UUAAAGUUA CUUUUAUA | 1225 | UAUAAAAG CUGAUGAGGNNNNNNNNCCGAA AACUUUAA | 5381 |
| 7077 | AAGUUACUU UUAUACAA | 1226 | UUGUAUAA CUGAUGAGGNNNNNNNNCCGAA AGUAACUU | 5382 |
| 7078 | AGUUACUUU UAUACAAA | 1227 | UUUGUAUA CUGAUGAGGNNNNNNNNCCGAA AAGUAACU | 5383 |
| 7079 | GUUACUUUU AUACAAAC | 1228 | GUUUGUAU CUGAUGAGGNNNNNNNNCCGAA AAAGUAAC | 5384 |
| 7080 | UUACUUUUA UACAAACC | 1229 | GGUUUGUA CUGAUGAGGNNNNNNNNCCGAA AAAAGUAA | 5385 |
| 7082 | ACUUUUAUA CAAACCAA | 1230 | UUGGUUUG CUGAUGAGGNNNNNNNNCCGAA AUAAAAGU | 5386 |
| 7095 | CCAAGAAUA UAUGCUAC | 1231 | GUAGCAUA CUGAUGAGGNNNNNNNNCCGAA AUUCUUGG | 5387 |
| 7097 | AAGAAUAUA UGCUACAG | 1232 | CUGUAGCA CUGAUGAGGNNNNNNNNCCGAA AUAUUCUU | 5388 |
| 7102 | UAUAUGCUA CAGAUAUA | 1233 | UAUAUCUG CUGAUGAGGNNNNNNNNCCGAA AGCAUAUA | 5389 |
| 7108 | CUACAGAUA UAGACAG | 1234 | CUGUCUUA CUGAUGAGGNNNNNNNNCCGAA AUCUGUAG | 5390 |
| 7110 | ACAGAUAUA AGACAGAC | 1235 | GUCUGUCU CUGAUGAGGNNNNNNNNCCGAA AUAUCUGU | 5391 |
| 7124 | GACAUGGUU UGGUCCUA | 1236 | UAGGACCA CUGAUGAGGNNNNNNNNCCGAA ACCAUGUC | 5392 |
| 7125 | ACAUGGUUU GGUCCUAU | 1237 | AUAGGACC CUGAUGAGGNNNNNNNNCCGAA AACCAUGU | 5393 |
| 7129 | GGUUUGGUC CUAUAUUU | 1238 | AAAUAUAG CUGAUGAGGNNNNNNNNCCGAA ACCAAACC | 5394 |
| 7132 | UUGGUCCUA UAUUUCUA | 1239 | UAGAAAUA CUGAUGAGGNNNNNNNNCCGAA AGGACCAA | 5395 |
| 7134 | GGUCCUAUA UUUCUAGU | 1240 | ACUAGAAA CUGAUGAGGNNNNNNNNCCGAA AUAGGACC | 5396 |
| 7136 | UCCUAUAUU UCUAGUCA | 1241 | UGACUAGA CUGAUGAGGNNNNNNNNCCGAA AUAUAGGA | 5397 |
| 7137 | CCUAUAUUU CUAGUCAU | 1242 | AUGACUAG CUGAUGAGGNNNNNNNNCCGAA AAAUAUAGG | 5398 |
| 7138 | CUAUAUUUC UAGUCAUG | 1243 | CAUGACUA CUGAUGAGGNNNNNNNNCCGAA AAAUAUAG | 5399 |
| 7140 | AUAUUUCUA GUCAUGAU | 1244 | AUCAUGAC CUGAUGAGGNNNNNNNNCCGAA AGAAAUAU | 5400 |
| 7143 | UUUCUAGUC AUGAUGAA | 1245 | UUCAUCAU CUGAUGAGGNNNNNNNNCCGAA ACUAGAAA | 5401 |
| 7155 | AUGAAUGUA UUUUGUAU | 1246 | AUACAAAA CUGAUGAGGNNNNNNNNCCGAA ACAUUCAU | 5402 |
| 7157 | GAAUGUAUU UGUAUACC | 1247 | GUAUACAA CUGAUGAGGNNNNNNNNCCGAA AUACAUUC | 5403 |
| 7158 | AAUGUAUUU UGUAUACC | 1248 | GGUAUACA CUGAUGAGGNNNNNNNNCCGAA AAUACAUU | 5404 |
| 7159 | AUGUAUUUU GUAUACCA | 1249 | UGGUAUAC CUGAUGAGGNNNNNNNNCCGAA AAAUACAU | 5405 |
| 7162 | UAUUUUGUA UACCAUCU | 1250 | AGAUGGUA CUGAUGAGGNNNNNNNNCCGAA ACAAAAUA | 5406 |
| 7164 | UUUUGUAUA CCAUCUUC | 1251 | GAAGAUGG CUGAUGAGGNNNNNNNNCCGAA AUACAAAA | 5407 |
| 7169 | UAUACCAUC UUCAUAUA | 1252 | UAUAUGAA CUGAUGAGGNNNNNNNNCCGAA AUGGUAUA | 5408 |
| 7171 | UACCAUCUU CAUAUAAU | 1253 | AUUAUAUG CUGAUGAGGNNNNNNNNCCGAA AGAUGGUA | 5409 |
| 7172 | ACCAUCUUC AUAUAAUA | 1254 | UAUUAUAU CUGAUGAGGNNNNNNNNCCGAA AAGAUGGU | 5410 |
| 7175 | AUCUUCAUA UAAUACU | 1255 | GUAUUAUA CUGAUGAGGNNNNNNNNCCGAA AUGAAGAU | 5411 |
| 7177 | CUUCAUAUA AUAUACUU | 1256 | AAGUAUAU CUGAUGAGGNNNNNNNNCCGAA AUAUGAAG | 5412 |
| 7180 | CAUAUAAUA UACUUAAA | 1257 | UUUAAGUA CUGAUGAGGNNNNNNNNCCGAA AUUAUAUG | 5413 |
| 7182 | UAUAAUAUA CUUAAAA | 1258 | UUUUUAAG CUGAUGAGGNNNNNNNNCCGAA AUAUUAUA | 5414 |
| 7185 | AAUAUACUU AAAAUAUU | 1259 | AUAUUUUA CUGAUGAGGNNNNNNNNCCGAA AGUAUAUU | 5415 |
| 7186 | AUAUACUUA AAAUAUU | 1260 | AAUAUUUU CUGAUGAGGNNNNNNNNCCGAA AAGUAUAU | 5416 |
| 7192 | UUAAAAAUA UUUCUUAA | 1261 | UUAAGAAA CUGAUGAGGNNNNNNNNCCGAA AUUUUUAA | 5417 |
| 7194 | AAAAAUAUU UCUUAAUU | 1262 | AAUUAAGA CUGAUGAGGNNNNNNNNCCGAA AUAUUUUU | 5418 |
| 7195 | AAAAUAUUU CUUAAUUG | 1263 | CAAUUAAG CUGAUGAGGNNNNNNNNCCGAA AAAUAUUUU | 5419 |
| 7196 | AAAUAUUUC UUAAUUGG | 1264 | CCAAUUAA CUGAUGAGGNNNNNNNNCCGAA AAAUAUUU | 5420 |
| 7198 | AUAUUUCUU AAUUGGGA | 1265 | UCCCAAUU CUGAUGAGGNNNNNNNNCCGAA AGAAAUAU | 5421 |
| 7199 | UAUUUCUUA AUUGGGAU | 1266 | AUCCCAAU CUGAUGAGGNNNNNNNNCCGAA AAGAAAUA | 5422 |
| 7202 | UUCUUAAUU GGGAUUUG | 1267 | CAAAUCCC CUGAUGAGGNNNNNNNNCCGAA AUUAAGAA | 5423 |
| 7208 | AUUGGGAUU UGUAAUCG | 1268 | CGAUUACA CUGAUGAGGNNNNNNNNCCGAA AUCCCAAU | 5424 |
| 7209 | UUGGGAUUU GUAAUCGU | 1269 | ACGAUUAC CUGAUGAGGNNNNNNNNCCGAA AAUCCCAA | 5425 |
| 7212 | GGAUUUGUA AUCGUACC | 1270 | GGUACGAU CUGAUGAGGNNNNNNNNCCGAA ACAAAUCC | 5426 |
| 7215 | UUUGUAAUC GUACCAAC | 1271 | GUUGGUAC CUGAUGAGGNNNNNNNNCCGAA AUUACAAA | 5427 |
| 7218 | GUAAUCGUA CCAACUUA | 1272 | UAAGUUGG CUGAUGAGGNNNNNNNNCCGAA ACGAUUAC | 5428 |
| 7225 | UACCAACUU AAUUGAUA | 1273 | UAUCAAUU CUGAUGAGGNNNNNNNNCCGAA AGUUGGUA | 5429 |
| 7226 | ACCAACUUA AUUGAUAA | 1274 | UUAUCAAU CUGAUGAGGNNNNNNNNCCGAA AAGUUGGU | 5430 |
| 7229 | AACUUAAUU GAUAAACU | 1275 | AGUUUAUC CUGAUGAGGNNNNNNNNCCGAA AUUAAGUU | 5431 |
| 7233 | UAAUUGAUA AACUUGGC | 1276 | GCCAAGUU CUGAUGAGGNNNNNNNNCCGAA AUCAAUUA | 5432 |
| 7238 | GAUAAACUU GGCAACUG | 1277 | CAGUUGCC CUGAUGAGGNNNNNNNNCCGAA AGUUUAUC | 5433 |
| 7249 | CAACUGCUU UAUGUUC | 1278 | GAACAUAA CUGAUGAGGNNNNNNNNCCGAA AGCAGUUG | 5434 |
| 7250 | AACUGCUUU UAUGUUCU | 1279 | AGAACAUA CUGAUGAGGNNNNNNNNCCGAA AAGCAGUU | 5435 |
| 7251 | ACUGCUUUU AUGUUCUG | 1280 | CAGAACAU CUGAUGAGGNNNNNNNNCCGAA AAAGCAGU | 5436 |
| 7252 | CUGCUUUUA UGUUCUGU | 1281 | ACAGAACA CUGAUGAGGNNNNNNNNCCGAA AAAAGCAG | 5437 |
| 7256 | UUUUAUGUU CUGUCUCC | 1282 | GGAGACAG CUGAUGAGGNNNNNNNNCCGAA ACAUAAAA | 5438 |
| 7257 | UUUAUGUUC UGUCUCCU | 1283 | AGGAGACA CUGAUGAGGNNNNNNNNCCGAA AACAUAAA | 5439 |
| 7261 | UGUUCUGUC UCCUUCCA | 1284 | UGGAAGGA CUGAUGAGGNNNNNNNNCCGAA ACAGAACA | 5440 |
| 7263 | UUCUGUCUC CUUCCAUA | 1285 | UAUGGAAG CUGAUGAGGNNNNNNNNCCGAA AGACAGAA | 5441 |
| 7266 | UGUCUCCUU CCAUAAAU | 1286 | AUUUAUGG CUGAUGAGGNNNNNNNNCCGAA AGGAGACA | 5442 |
| 7267 | GUCUCCUUC CAUAAAUU | 1287 | AAUUUAUG CUGAUGAGGNNNNNNNNCCGAA AAGGAGAC | 5443 |
| 7271 | CCUUCCAUA AAUUUUUC | 1288 | GAAAAAUU CUGAUGAGGNNNNNNNNCCGAA AUGGAAGG | 5444 |
| 7275 | CCAUAAAUU UUUCAAAA | 1289 | UUUUGAAA CUGAUGAGGNNNNNNNNCCGAA AUUUAUGG | 5445 |
| 7276 | CAUAAAUUU UUCAAAAU | 1290 | AUUUUGAA CUGAUGAGGNNNNNNNNCCGAA AAUUUAUG | 5446 |
| 7277 | AUAAAUUUU UCAAAAUA | 1291 | UAUUUUGA CUGAUGAGGNNNNNNNNCCGAA AAAUUUAU | 5447 |
| 7278 | UAAAUUUUU CAAAAUAC | 1292 | GUAUUUUG CUGAUGAGGNNNNNNNNCCGAA AAAAUUUA | 5448 |
| 7279 | AAAUUUUUC AAAAUACU | 1293 | AGUAUUUU CUGAUGAGGNNNNNNNNCCGAA AAAAAUUU | 5449 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7285 | UUCAAAAUA CUAAUUCA | 1294 | UGAAUUAG CUGAUGAGGNNNNNNNNCCGAA AUUUUGAA | 5450 |
| 7288 | AAAAUACUA AUUCAACA | 1295 | UGUUGAAU CUGAUGAGGNNNNNNNNCCGAA AGUAUUUU | 5451 |
| 7291 | AUACUAAUU CAACAAAG | 1296 | CUUUGUUG CUGAUGAGGNNNNNNNNCCGAA AUUAGUAU | 5452 |
| 7292 | UACUAAUUC AACAAAGA | 1297 | UCUUUGUU CUGAUGAGGNNNNNNNNCCGAA AAUUAGUA | 5453 |
| 7308 | AAAAAGCUC UUUUUUUU | 1298 | AAAAAAAA CUGAUGAGGNNNNNNNNCCGAA AGCUUUUU | 5454 |
| 7310 | AAAGCUCUU UUUUUCC | 1299 | GGAAAAAA CUGAUGAGGNNNNNNNNCCGAA AGAGCUUU | 5455 |
| 7311 | AAGCUCUUU UUUUUCCU | 1300 | AGGAAAAA CUGAUGAGGNNNNNNNNCCGAA AAGAGCUU | 5456 |
| 7312 | AGCUCUUUU UUUUCCUA | 1301 | UAGGAAAA CUGAUGAGGNNNNNNNNCCGAA AAAGAGCU | 5457 |
| 7313 | GCUCUUUUU UUUCCUAA | 1302 | UUAGGAAA CUGAUGAGGNNNNNNNNCCGAA AAAAGAGC | 5458 |
| 7314 | CUCUUUUUU UUCCUAAA | 1303 | UUUAGGAA CUGAUGAGGNNNNNNNNCCGAA AAAAAGAG | 5459 |
| 7315 | UCUUUUUUU UCCUAAAA | 1304 | UUUUAGGA CUGAUGAGGNNNNNNNNCCGAA AAAAAAGA | 5460 |
| 7316 | CUUUUUUUU CCUAAAAU | 1305 | AUUUUAGG CUGAUGAGGNNNNNNNNCCGAA AAAAAAAG | 5461 |
| 7317 | UUUUUUUUC CUAAAAUA | 1306 | UAUUUUAG CUGAUGAGGNNNNNNNNCCGAA AAAAAAAA | 5462 |
| 7320 | UUUUUCCUA AAAUAAAC | 1307 | GUUUAUUU CUGAUGAGGNNNNNNNNCCGAA AGGAAAAA | 5463 |
| 7325 | CCUAAAAUA AACUCAAA | 1308 | UUUGAGUU CUGAUGAGGNNNNNNNNCCGAA AUUUUAGG | 5464 |
| 7330 | AAUAAACUC AAAUUUAU | 1309 | AUAAAUUU CUGAUGAGGNNNNNNNNCCGAA AGUUUAUU | 5465 |
| 7335 | ACUCAAAUU UAUCCUUG | 1310 | CAAGGAUA CUGAUGAGGNNNNNNNNCCGAA AUUUGAGU | 5466 |
| 7336 | CUCAAAUUU AUCCUUGU | 1311 | ACAAGGAU CUGAUGAGGNNNNNNNNCCGAA AAUUUGAG | 5467 |
| 7337 | UCAAAUUUA UCCUUGUU | 1312 | AACAAGGA CUGAUGAGGNNNNNNNNCCGAA AAAUUUGA | 5468 |
| 7339 | AAAUUUAUC CUUGUUUA | 1313 | UAAACAAG CUGAUGAGGNNNNNNNNCCGAA AUAAAUUU | 5469 |
| 7342 | UUUAUCCUU GUUUAGAG | 1314 | CUCUAAAC CUGAUGAGGNNNNNNNNCCGAA AGGAUAAA | 5470 |
| 7345 | AUCCUUGUU UAGCAGA | 1315 | CUGCUCUA CUGAUGAGGNNNNNNNNCCGAA ACAAGGAU | 5471 |
| 7346 | UCCUUGUUU AGAGCAGA | 1316 | UCUGCUCU CUGAUGAGGNNNNNNNNCCGAA AACAAGGA | 5472 |
| 7347 | CCUUGUUUA GAGCAGAG | 1317 | CUCUGCUC CUGAUGAGGNNNNNNNNCCGAA AAACAAGG | 5473 |
| 7362 | AGAAAAAUU AAGAAAAA | 1318 | UUUUUCUU CUGAUGAGGNNNNNNNNCCGAA AUUUUUCU | 5474 |
| 7363 | GAAAAAUUA AGAAAAAC | 1319 | GUUUUUCU CUGAUGAGGNNNNNNNNCCGAA AAUUUUUC | 5475 |
| 7373 | GAAAAACUU UGAAAUGG | 1320 | CCAUUUCA CUGAUGAGGNNNNNNNNCCGAA AGUUUUUC | 5476 |
| 7374 | AAAAACUUU GAAAUGGU | 1321 | ACCAUUUC CUGAUGAGGNNNNNNNNCCGAA AAGUUUUU | 5477 |
| 7383 | GAAAUGGUC UCAAAAAA | 1322 | UUUUUUGA CUGAUGAGGNNNNNNNNCCGAA ACCAUUUC | 5478 |
| 7385 | AAUGGUCUC AAAAAAUU | 1323 | AAUUUUUU CUGAUGAGGNNNNNNNNCCGAA AGACCAUU | 5479 |
| 7393 | CAAAAAAUU GCUAAAUA | 1324 | UAUUUAGC CUGAUGAGGNNNNNNNNCCGAA AUUUUUUG | 5480 |
| 7397 | AAAUUGCUA AAUAUUUU | 1325 | AAAAUAUU CUGAUGAGGNNNNNNNNCCGAA AGCAAUUU | 5481 |
| 7401 | UGCUAAAUA UUUUCAAU | 1326 | AUUGAAAA CUGAUGAGGNNNNNNNNCCGAA AUUUAGCA | 5482 |
| 7403 | CUAAAUAUU UUCAAUGG | 1327 | CCAUUGAA CUGAUGAGGNNNNNNNNCCGAA AUAUUUAG | 5483 |
| 7404 | UAAAUAUUU UCAAUGGA | 1328 | UCCAUUGA CUGAUGAGGNNNNNNNNCCGAA AAUAUUUA | 5484 |
| 7405 | AAAUAUUUU CAAUGGAA | 1329 | UUCCAUUG CUGAUGAGGNNNNNNNNCCGAA AAAUAUUU | 5485 |
| 7406 | AAUAUUUUC AAUGGAAA | 1330 | UUUCCAUU CUGAUGAGGNNNNNNNNCCGAA AAAAUAUU | 5486 |
| 7418 | GGAAAACUA AAUGUUAG | 1331 | CUAACAUU CUGAUGAGGNNNNNNNNCCGAA AGUUUUCC | 5487 |
| 7424 | CUAAAUGUU AGCUAAAC | 1332 | GCUAAACU CUGAUGAGGNNNNNNNNCCGAA ACAUUUAG | 5488 |
| 7425 | UAAAUGUUA GUUUAGCU | 1333 | AGCUAAAC CUGAUGAGGNNNNNNNNCCGAA AACAUUUA | 5489 |
| 7428 | AUGUUAGUU UAGCUGAU | 1334 | AUCAGCUA CUGAUGAGGNNNNNNNNCCGAA ACUAACAU | 5490 |
| 7429 | UGUUAGUUU AGCUGAUU | 1335 | AAUCAGCU CUGAUGAGGNNNNNNNNCCGAA AACUAACA | 5491 |
| 7430 | GUUAGUUUA GCUGAUUG | 1336 | CAAUCAGC CUGAUGAGGNNNNNNNNCCGAA AAACUAAC | 5492 |
| 7437 | UAGCUGAUU GUAUGGGG | 1337 | CCCCAUAC CUGAUGAGGNNNNNNNNCCGAA AUCAGCUA | 5493 |
| 7440 | CUGAUUGUA UGGGGUUU | 1338 | AAACCCCA CUGAUGAGGNNNNNNNNCCGAA ACAAUCAG | 5494 |
| 7447 | UAUGGGGUU UUCGAACC | 1339 | GGUUCGAA CUGAUGAGGNNNNNNNNCCGAA ACCCCAUA | 5495 |
| 7448 | AUGGGGUUU UCGAACCU | 1340 | AGGUUCGA CUGAUGAGGNNNNNNNNCCGAA AACCCCAU | 5496 |
| 7449 | UGGGGUUUU CGAACCUU | 1341 | AAGGUUCG CUGAUGAGGNNNNNNNNCCGAA AAACCCCA | 5497 |
| 7450 | GGGGUUUUC GAACCUUU | 1342 | AAAGGUUC CUGAUGAGGNNNNNNNNCCGAA AAAACCCC | 5498 |
| 7457 | UCGAACCUU UCACUUUU | 1343 | AAAAGUGA CUGAUGAGGNNNNNNNNCCGAA AGGUUCGA | 5499 |
| 7458 | CGAACCUUU CACUUUUU | 1344 | AAAAAGUG CUGAUGAGGNNNNNNNNCCGAA AAGGUUCG | 5500 |
| 7459 | GAACCUUUC ACUUUUUG | 1345 | CAAAAAGU CUGAUGAGGNNNNNNNNCCGAA AAAGGUUC | 5501 |
| 7463 | CUUUCACUU UUUGUUUG | 1346 | CAAACAAA CUGAUGAGGNNNNNNNNCCGAA AGUGAAAG | 5502 |
| 7464 | UUUCACUUU UUGUUUGU | 1347 | ACAAACAA CUGAUGAGGNNNNNNNNCCGAA AAGUGAAA | 5503 |
| 7465 | UUCACUUUU UGUUUGUU | 1348 | AACAAACA CUGAUGAGGNNNNNNNNCCGAA AAAGUGAA | 5504 |
| 7466 | UCACUUUUU GUUUGUUU | 1349 | AAACAAAC CUGAUGAGGNNNNNNNNCCGAA AAAAGUGA | 5505 |
| 7469 | CUUUUUGUU UGUUUUAC | 1350 | GUAAAACA CUGAUGAGGNNNNNNNNCCGAA ACAAAAAG | 5506 |
| 7470 | UUUUUGUUU GUUUUACC | 1351 | GGUAAAAC CUGAUGAGGNNNNNNNNCCGAA AACAAAAA | 5507 |
| 7473 | UUGUUUGUU UUACCUAU | 1352 | AUAGGUAA CUGAUGAGGNNNNNNNNCCGAA ACAAACAA | 5508 |
| 7474 | UGUUUGUUU UACCAUU | 1353 | AAUAGGUA CUGAUGAGGNNNNNNNNCCGAA AACAAACA | 5509 |
| 7475 | GUUUGUUUU ACCAUUU | 1354 | AAAUAGGU CUGAUGAGGNNNNNNNNCCGAA AAACAAAC | 5510 |
| 7476 | UUUGUUUUA CCAUUUC | 1355 | GAAAUAGG CUGAUGAGGNNNNNNNNCCGAA AAAACAAA | 5511 |
| 7480 | UUUUACCUA UUUCACAA | 1356 | UUGUGAAA CUGAUGAGGNNNNNNNNCCGAA AGGUAAAA | 5512 |
| 7482 | UUACCUAUU UCACAACU | 1357 | AGUUGUGA CUGAUGAGGNNNNNNNNCCGAA AUAGGUAA | 5513 |
| 7483 | UACCUAUUU CACAACUG | 1358 | CAGUUGUG CUGAUGAGGNNNNNNNNCCGAA AAUAGGUA | 5514 |
| 7484 | ACCUAUUUC ACAACUGU | 1359 | ACAGUUGU CUGAUGAGGNNNNNNNNCCGAA AAAUAGGU | 5515 |
| 7495 | AACUGUGUA AAUGCCAA | 1360 | UGGCAAUU CUGAUGAGGNNNNNNNNCCGAA ACACAGUU | 5516 |
| 7499 | GUGUAAAUG GCCAAUAA | 1361 | UUAUUGGC CUGAUGAGGNNNNNNNNCCGAA AUUUACAC | 5517 |
| 7506 | UUGCCAAUA AUUCCUGU | 1362 | ACAGGAAU CUGAUGAGGNNNNNNNNCCGAA AUUGGCAA | 5518 |
| 7509 | CCAAUAAUU CCUGUCCA | 1363 | UGGACAGG CUGAUGAGGNNNNNNNNCCGAA AUUAUUGG | 5519 |
| 7510 | CAAUAAUUC CUGUCCAU | 1364 | AUGGACAG CUGAUGAGGNNNNNNNNCCGAA AAUUAUUG | 5520 |
| 7515 | AUCCUGUC CAUGAAAA | 1365 | UUUUCAUG CUGAUGAGGNNNNNNNNCCGAA ACAGGAAU | 5521 |
| 7531 | AUGCAAAUU AUCCAGUG | 1366 | CACUGGAU CUGAUGAGGNNNNNNNNCCGAA AUUUGCAU | 5522 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7532 | UGCAAAUUA UCCAGUGU | 1367 | ACACUGGA CUGAUGAGGNNNNNNNNCCGAA AAUUUGCA | 5523 |
| 7534 | CAAAUUAUC CAGUGUAG | 1368 | CUACACUG CUGAUGAGGNNNNNNNNCCGAA AUAAUUUG | 5524 |
| 7541 | UCCAGUGUA GAUAUAUU | 1369 | AAUAUAUC CUGAUGAGGNNNNNNNNCCGAA ACACUGGA | 5525 |
| 7545 | GUGUAGAUA UAUUUGAC | 1370 | GUCAAAUA CUGAUGAGGNNNNNNNNCCGAA AUCUACAC | 5526 |
| 7547 | GUAGAUAUA UUUGACCA | 1371 | UGGUCAAA CUGAUGAGGNNNNNNNNCCGAA AUAUCUAC | 5527 |
| 7549 | AGAUAUAUU UGACCAUC | 1372 | GAUGGUCA CUGAUGAGGNNNNNNNNCCGAA AUAUAUCU | 5528 |
| 7550 | GAUAUAUUU GACCAUCA | 1373 | UGAUGGUC CUGAUGAGGNNNNNNNNCCGAA AAUAUAUC | 5529 |
| 7557 | UUGACCAUC ACCCUAUG | 1374 | CAUAGGGU CUGAUGAGGNNNNNNNNCCGAA AUGGUCAA | 5530 |
| 7563 | AUCACCCUA UGGAUAUU | 1375 | AAUAUCCA CUGAUGAGGNNNNNNNNCCGAA AGGGUGAU | 5531 |
| 7569 | CUAUGGAUA UUGGCUAG | 1376 | CUAGCCAA CUGAUGAGGNNNNNNNNCCGAA AUCCAUAG | 5532 |
| 7571 | AUGGAUAUU GGCUAGUU | 1377 | AACUAGCC CUGAUGAGGNNNNNNNNCCGAA AUAUCCAU | 5533 |
| 7576 | UAUGGCUA GUUUGCC | 1378 | GGCAAAAC CUGAUGAGGNNNNNNNNCCGAA AGCCAUA | 5534 |
| 7579 | UGGCUAGUU UUGCCUUU | 1379 | AAAGGCAA CUGAUGAGGNNNNNNNNCCGAA ACUAGCCA | 5535 |
| 7580 | GGCUAGUUU UGCCUUUA | 1380 | UAAAGGCA CUGAUGAGGNNNNNNNNCCGAA AACUAGCC | 5536 |
| 7581 | GCUAGUUUU GCCUUUAU | 1381 | AUAAAGGC CUGAUGAGGNNNNNNNNCCGAA AAACUAGC | 5537 |
| 7586 | UUUUGCCUU UAUUAAGC | 1382 | GCUUAAUA CUGAUGAGGNNNNNNNNCCGAA AGGCAAAA | 5538 |
| 7587 | UUUGCCUUU AUUAAGCA | 1383 | UGCUUAAU CUGAUGAGGNNNNNNNNCCGAA AAGGCAAA | 5539 |
| 7588 | UUGCCUUUA UUAAGCAA | 1384 | UUGCUUAA CUGAUGAGGNNNNNNNNCCGAA AAAGGCAA | 5540 |
| 7590 | GCCUUUAUU AAGCAAAU | 1385 | AUUUGCUU CUGAUGAGGNNNNNNNNCCGAA AUAAAGGC | 5541 |
| 7591 | CCUUUAUUA AGCAAAUU | 1386 | AAUUUGCU CUGAUGAGGNNNNNNNNCCGAA AAUAAAGG | 5542 |
| 7599 | AAGCAAAUU CAUUUCAG | 1387 | CUGAAAUG CUGAUGAGGNNNNNNNNCCGAA AUUUGCUU | 5543 |
| 7600 | AGCAAAUUC AUUUCAGC | 1388 | GCUGAAAU CUGAUGAGGNNNNNNNNCCGAA AAUUUGCU | 5544 |
| 7603 | AAAUUCAUU UCAGCCUG | 1389 | CAGGCUGA CUGAUGAGGNNNNNNNNCCGAA AUGAAUUU | 5545 |
| 7604 | AAUUCAUUU CAGCCUGA | 1390 | UCAGGCUG CUGAUGAGGNNNNNNNNCCGAA AAUGAAUU | 5546 |
| 7605 | AUUCAUUUC AGCCUGAA | 1391 | UUCAGGCU CUGAUGAGGNNNNNNNNCCGAA AAAUGAAU | 5547 |
| 7617 | CUGAAUGUC UGCCUAUA | 1392 | UAUAGGCA CUGAUGAGGNNNNNNNNCCGAA ACAUUCAG | 5548 |
| 7623 | GUCUGCCUA UAUAUUCU | 1393 | AGAAUAUA CUGAUGAGGNNNNNNNNCCGAA AGGCAGAC | 5549 |
| 7625 | CUGCCUAUA UAUUCUCU | 1394 | AGAGAAUA CUGAUGAGGNNNNNNNNCCGAA AUAGGCAG | 5550 |
| 7627 | GCCUAUAUA UUCUCUGC | 1395 | GCAGAGAA CUGAUGAGGNNNNNNNNCCGAA AUAUAGGC | 5551 |
| 7629 | CUAUAUAUU CUCUGCUC | 1396 | GAGCAGAG CUGAUGAGGNNNNNNNNCCGAA AUAUAUAG | 5552 |
| 7630 | UAUAUAUUC UCUGCUCU | 1397 | AGAGCAGA CUGAUGAGGNNNNNNNNCCGAA AAUAUAUA | 5553 |
| 7632 | UAUAUUCUC UGCUCUUU | 1398 | AAAGAGCA CUGAUGAGGNNNNNNNNCCGAA AGAAUAUA | 5554 |
| 7637 | UCUCUGCUC UUUGUAUU | 1399 | AAUACAAA CUGAUGAGGNNNNNNNNCCGAA AGCAGAGA | 5555 |
| 7639 | UCUGCUCUU UGUAUUCU | 1400 | AGAAUACA CUGAUGAGGNNNNNNNNCCGAA AGAGCAGA | 5556 |
| 7640 | CUGCUCUUU GUAUUCUC | 1401 | GAGAAUAC CUGAUGAGGNNNNNNNNCCGAA AAGAGCAG | 5557 |
| 7643 | CUCUUUGUA UUCUCCUU | 1402 | AAGGAGAA CUGAUGAGGNNNNNNNNCCGAA ACAAAGAG | 5558 |
| 7645 | CUUUGUAUU CUCCUUUG | 1403 | CAAAGGAG CUGAUGAGGNNNNNNNNCCGAA AUACAAAG | 5559 |
| 7646 | UUUGUAUUC UCCUUUGA | 1404 | UCAAAGGA CUGAUGAGGNNNNNNNNCCGAA AAUACAAA | 5560 |
| 7648 | UGUAUUCUC CUUUGAAC | 1405 | GUUCAAAG CUGAUGAGGNNNNNNNNCCGAA AGAAUACA | 5561 |
| 7651 | AUUCUCCUU UGAACCCG | 1406 | CGGGUUCA CUGAUGAGGNNNNNNNNCCGAA AGGAGAAU | 5562 |
| 7652 | UUCUCCUUU GAACCCGU | 1407 | ACGGGUUC CUGAUGAGGNNNNNNNNCCGAA AAGGAGAA | 5563 |
| 7661 | GAACCCGUU AAAACAUC | 1408 | GAUGUUUU CUGAUGAGGNNNNNNNNCCGAA ACGGGUUC | 5564 |
| 7662 | AACCCGUUA AAACAUCC | 1409 | GGAUGUUU CUGAUGAGGNNNNNNNNCCGAA AACGGGUU | 5565 |
| 7669 | UAAAACAUC CUGUGGCA | 1410 | UGCCACAG CUGAUGAGGNNNNNNNNCCGAA AUGUUUUA | 5566 |

Where "X" represents stem II region of a HH ribozyme (Hertel et al., 1992 Nucleic Acids Res. 20 3252). The length of stem II may be ≧2 base-pairs. Underlined region can be any X sequence or linker, as described herein.

TABLE III

Human flt1 VEGF Receptor-Hairpin Ribozyme and Substrate sequence

| Pos | Substrate | Seq ID No | HP Ribozyme Sequence | Seq ID No |
|---|---|---|---|---|
| 16 | CCUCUCG GCU CCUCCCCG | 1411 | CGGGGAGG AGAA GAGAGG ACCAGAGAAACACACGUUGUGGUACAUUACCUGGUA | 5567 |
| 39 | GGCGGCG GCU CGGAGCGG | 1412 | CCGCCGCG AGAA CCGCCGCC ACCAGAGAAACACACGUUGUGGUACAUUACCUGGUA | 5568 |
| 180 | GAGGACG GAC UCUGGCGG | 1413 | CCGCCAGA AGAA GUCCUC ACCAGAGAAACACACGUUGUGGUACAUUACCUGGUA | 5569 |
| 190 | UCUGGCG GCC GGGUCGUU | 1414 | AACGACCC AGAA GCCAGA ACCAGAGAAACACACGUUGUGGUACAUUACCUGGUA | 5570 |
| 278 | GGGUCCU GCU GUGCGCGC | 1415 | GCGCGCAC AGAA GGACCC ACCAGAGAAACACACGUUGUGGUACAUUACCUGGUA | 5571 |
| 290 | GCGCGCU GCU CAGCUGUC | 1416 | GACACUG AGAA GCGCGC ACCAGAGAAACACACGUUGUGGUACAUUACCUGGUA | 5572 |
| 295 | CUGCUCA GCU GUCUGCUU | 1417 | AAGCAGAC AGAA GAGCAG ACCAGAGAAACACACGUUGUGGUACAUUACCUGGUA | 5573 |
| 298 | CUCAGCU GUC UGCUUCUC | 1418 | GAGAAGCA AGAA GCUAGA ACCAGAGAAACACACGUUGUGGUACAUUACCUGGUA | 5574 |
| 302 | GCUGUCU GCU UCUCACAG | 1419 | CUGUGAGA AGAA GACAGC ACCAGAGAAACACACGUUGUGGUACAUUACCUGGUA | 5575 |
| 420 | GGAAGCA GCU CAUAAAUG | 1420 | CAUUUAUG AGAA GCUUCC ACCAGAGAAACACACGUUGUGGUACAUUACCUGGUA | 5576 |
| 486 | UAAAUCU GCC UGUGGAAG | 1421 | CUUCCACA AGAA GAUUUA ACCAGAGAAACACACGUUGUGGUACAUUACCUGGUA | 5577 |
| 537 | GAACACA GCU CAAGCAAA | 1422 | UUUGCUUG AGAA GUGUUC ACCAGAGAAACACACGUUGUGGUACAUUACCUGGUA | 5578 |
| 565 | UUCUACA GCU GCAAAUAU | 1423 | AUAUUUGC AGAA GUAGAA ACCAGAGAAACACACGUUGUGGUACAUUACCUGGUA | 5579 |
| 721 | AUUCCCU GCC GGGUUACG | 1424 | CGUAACCC AGAA GGGAAU ACCAGAGAAACACACGUUGUGGUACAUUACCUGGUA | 5580 |
| 786 | GAUCCCU GAU GGAAAACG | 1425 | CGUUUUCC AGAA GGGAUC ACCAGAGAAACACACGUUGUGGUACAUUACCUGGUA | 5581 |

TABLE III-continued

Human flt1 VEGF Receptor-Hairpin Ribozyme and Substrate sequence

| Pos | Substrate | Seq ID No | HP Ribozyme Sequence | Seq ID No |
|---|---|---|---|---|
| 863 | GGCUUCU GAC CUGUGAAG | 1426 | CUUCACAG AGAA GAAGCC ACCAGAGAAACACACGUUGUGGUACAUUACCUGGUA | 5582 |
| 1056 | UUACCCU GAU GAAAAAAA | 1427 | UUUUUUUC AGAA GGGUAA ACCAGAGAAACACACGUUGUGGUACAUUACCUGGUA | 5583 |
| 1301 | GCAAGCG GUC UUACCGGC | 1428 | GCCGGUAA AGAA GCUUGC ACCAGAGAAACACACGUUGUGGUACAUUACCUGGUA | 5584 |
| 1310 | CUUACCG GCU CUCUAUGA | 1429 | UCAUAGAG AGAA GGUAAG ACCAGAGAAACACACGUUGUGGUACAUUACCUGGUA | 5585 |
| 1389 | GAAAUCU GCU CGCUAUUU | 1430 | AAAUAGCG AGAA GAUUUC ACCAGAGAAACACACGUUGUGGUACAUUACCUGGUA | 5586 |
| 1535 | AACCCCA GAU UUACGAAA | 1431 | UUUCGUAA AGAA GGGGUU ACCAGAGAAACACACGUUGUGGUACAUUACCUGGUA | 5587 |
| 1566 | GUUUCCA GAC CCGGCUCU | 1432 | AGAGCCGG AGAA GGAAAC ACCAGAGAAACACACGUUGUGGUACAUUACCUGGUA | 5588 |
| 1572 | AGACCCG GCU CUCUACCC | 1433 | GGGUAGAG AGAA GGGUCU ACCAGAGAAACACACGUUGUGGUACAUUACCUGGUA | 5589 |
| 1604 | AAAUCCU GAC UUGUACCG | 1434 | CGGUACAA AGAA GGAUUU ACCAGAGAAACACACGUUGUGGUACAUUACCUGGUA | 5590 |
| 1824 | UGUGGCU GAC UCUAGAAU | 1435 | AUUCUAGA AGAA GCCACA ACCAGAGAAACACACGUUGUGGUACAUUACCUGGUA | 5591 |
| 1908 | UAUCACA GAU GUGCCAAA | 1436 | UUUGGCAC AGAA GUGAUA ACCAGAGAAACACACGUUGUGGUACAUUACCUGGUA | 5592 |
| 1949 | AAAUGCC GAC GGAAGGAG | 1437 | CUCCUUCC AGAA GCAUUU ACCAGAGAAACACACGUUGUGGUACAUUACCUGGUA | 5593 |
| 1973 | UGAAACU GUC UUGCACAG | 1438 | CUGUGCAA AGAA GUUUCA ACCAGAGAAACACACGUUGUGGUACAUUACCUGGUA | 5594 |
| 2275 | AUCAGCA GAU CCACCACU | 1439 | AGUGGUGG AGAA GCUGAU ACCAGAGAAACACACGUUGUGGUACAUUACCUGGUA | 5595 |
| 2321 | AGCCUCA GAU CACUUGGU | 1440 | ACCAAGUG AGAA GAGGCU ACCAGAGAAACACACGUUGUGGUACAUUACCUGGUA | 5596 |
| 2396 | GCACGCU GUU UAUUGAAA | 1441 | UUUCAAUA AGAA GCGUGC ACCAGAGAAACACACGUUGUGGUACAUUACCUGGUA | 5597 |
| 2490 | CCUCACU GUU CAAGGAAC | 1442 | GUUCCUUG AGAA GUGAGG ACCAGAGAAACACACGUUGUGGUACAUUACCUGGUA | 5598 |
| 2525 | UGGAGCU GAU CACUCUAA | 1443 | UUAGAGUG AGAA GCUCCA ACCAGAGAAACACACGUUGUGGUACAUUACCUGGUA | 5599 |
| 2625 | AAAGACU GAC UACCUAUC | 1444 | GAUAGGUA AGAA GUCUUU ACCAGAGAAACACACGUUGUGGUACAUUACCUGGUA | 5600 |
| 2652 | GGACCCA GAU GAAGUUCC | 1445 | GGAACUUC AGAA GGGUCC ACCAGAGAAACACACGUUGUGGUACAUUACCUGGUA | 5601 |
| 2684 | GUGAGCG GCU CCCUUAUG | 1446 | CAUAAGGG AGAA GCUCAC ACCAGAGAAACACACGUUGUGGUACAUUACCUGGUA | 5602 |
| 2816 | CGUGCCG GAC GUGGCUG | 1447 | CAGCCACA AGAA GGCACG ACCAGAGAAACACACGUUGUGGUACAUUACCUGGUA | 5603 |
| 2873 | AAGCUCU GAU GACUGAGC | 1448 | GCUCAGUC AGAA GAGCUU ACCAGAGAAACACACGUUGUGGUACAUUACCUGGUA | 5604 |
| 2930 | UUAACCU GCU GGGAGCCU | 1449 | AGGCUCCC AGAA GGUUAA ACCAGAGAAACACACGUUGUGGUACAUUACCUGGUA | 5605 |
| 2963 | GGCCUCU GAU GGUGAUUG | 1450 | CAAUCACC AGAA GAGGCC ACCAGAGAAACACACGUUGUGGUACAUUACCUGGUA | 5606 |
| 3157 | AGCUCCG GCU UUCAGGAA | 1451 | UUCCUGAA AGAA GGAGCU ACCAGAGAAACACACGUUGUGGUACAUUACCUGGUA | 5607 |
| 3207 | GGAUUCU GAC GGUUUCUA | 1452 | UAGAAACC AGAA GAAUCC ACCAGAGAAACACACGUUGUGGUACAUUACCUGGUA | 5608 |
| 3211 | UCUGACG GUU UCUACAAG | 1453 | CUUGUAGA AGAA GUCAGA ACCAGAGAAACACACGUUGUGGUACAUUACCUGGUA | 5609 |
| 3245 | AAGAUCU GAU UUCUUACA | 1454 | UGUAAGAA AGAA GAUCUU ACCAGAGAAACACACGUUGUGGUACAUUACCUGGUA | 5610 |
| 3256 | UCUUACA GUU UUCAAGUG | 1455 | CACUUGAA AGAA GUAAGA ACCAGAGAAACACACGUUGUGGUACAUUACCUGGUA | 5611 |
| 3287 | AGUUCCU GUC UUCCAGAA | 1456 | UUCUGGAA AGAA GGAACU ACCAGAGAAACACACGUUGUGGUACAUUACCUGGUA | 5612 |
| 3402 | GAACCCC GAU UAUGUGAG | 1457 | CUCACAUA AGAA GGGUUC ACCAGAGAAACACACGUUGUGGUACAUUACCUGGUA | 5613 |
| 3580 | UUUUGCA GUC GCCUGAGG | 1458 | CCUCAGGC AGAA GCAAAA ACCAGAGAAACACACGUUGUGGUACAUUACCUGGUA | 5614 |
| 3641 | UCUAUCA GAU CAUGCUGG | 1459 | CCAGCAUG AGAA GAUAGA ACCAGAGAAACACACGUUGUGGUACAUUACCUGGUA | 5615 |
| 3655 | CUGGACU GCU GGCACAGA | 1460 | UCUGUGCC AGAA GUCCAG ACCAGAGAAACACACGUUGUGGUACAUUACCUGGUA | 5616 |
| 3810 | AACUCCU GCC UUCUCUGA | 1461 | UCAGAGAA AGAA GGAGUU ACCAGAGAAACACACGUUGUGGUACAUUACCUGGUA | 5617 |
| 3846 | UAUUUCA GCU CCGAAGUU | 1462 | AACUUCGG AGAA GAAAUA ACCAGAGAAACACACGUUGUGGUACAUUACCUGGUA | 5618 |
| 3873 | AAGCUCU GAU GAUGUCAG | 1463 | CUGACAUC AGAA GAGCUU ACCAGAGAAACACACGUUGUGGUACAUUACCUGGUA | 5619 |
| 3995 | GCACUCU GUU GGCCUCUC | 1464 | GAGAGGCC AGAA GAGUGC ACCAGAGAAACACACGUUGUGGUACAUUACCUGGUA | 5620 |
| 4100 | CGGGGCU GUC UGAUGUCA | 1465 | UGACAUCA AGAA GCCCCG ACCAGAGAAACACACGUUGUGGUACAUUACCUGGUA | 5621 |
| 4104 | GCUGUCU GAU GUCAGCAG | 1466 | CUGCUGAC AGAA GACAGC ACCAGAGAAACACACGUUGUGGUACAUUACCUGGUA | 5622 |
| 4120 | AGGCCCA GUU UCUGCCAU | 1467 | AUGGCAGA AGAA GGGCCU ACCAGAGAAACACACGUUGUGGUACAUUACCUGGUA | 5623 |
| 4135 | CAUUCCA GCU GUGGGCAC | 1468 | GUGCCCAC AGAA GGAAUG ACCAGAGAAACACACGUUGUGGUACAUUACCUGGUA | 5624 |
| 4210 | GCGUGCU GCU CCCCGCCC | 1469 | GGGCGGGG AGAA GCACGC ACCAGAGAAACACACGUUGUGGUACAUUACCUGGUA | 5625 |
| 4217 | GCUCCCC GCC CCCAGACU | 1470 | AGUCUGGG AGAA GGGGAGC ACCAGAGAAACACACGUUGUGGUACAUUACCUGGUA | 5626 |
| 4224 | GCCCCCA GAC UACAACUC | 1471 | GAGUUGUA AGAA GGGGGC ACCAGAGAAACACACGUUGUGGUACAUUACCUGGUA | 5627 |
| 4382 | GGAGCCA GCU GCUUUUUG | 1472 | CAAAAAGC AGAA GGCUCC ACCAGAGAAACACACGUUGUGGUACAUUACCUGGUA | 5628 |
| 4385 | GCCAGCU GCU UUUUGUGA | 1473 | UCACAAAA AGAA GCUGGC ACCAGAGAAACACACGUUGUGGUACAUUACCUGGUA | 5629 |
| 4537 | CUUCCCU GCU CCAACCCC | 1474 | GGGGUUGG AGAA GGGAAG ACCAGAGAAACACACGUUGUGGUACAUUACCUGGUA | 5630 |
| 4573 | AGGACCA GUU UGAUUGAG | 1475 | CUCAAUCA AGAA GGUCCU ACCAGAGAAACACACGUUGUGGUACAUUACCUGGUA | 5631 |
| 4594 | CUGCACU GAU CACCCAAU | 1476 | AUUGGGUG AGAA GUGCAG ACCAGAGAAACACACGUUGUGGUACAUUACCUGGUA | 5632 |
| 4628 | UGGGCCA GCC CUGCAGCC | 1477 | GGCUGCAG AGAA GGCCCA ACCAGAGAAACACACGUUGUGGUACAUUACCUGGUA | 5633 |
| 4636 | CCCUGCA GCC CAAAACCC | 1478 | GGGUUUUG AGAA GCAGGG ACCAGAGAAACACACGUUGUGGUACAUUACCUGGUA | 5634 |
| 4866 | CUUCCCA GCU CUGACCCU | 1479 | AGGGUCAG AGAA GGGAAG ACCAGAGAAACACACGUUGUGGUACAUUACCUGGUA | 5635 |
| 4871 | CAGCUCU GAC CCUUCUAC | 1480 | GUAGAAGG AGAA GAGCUG ACCAGAGAAACACACGUUGUGGUACAUUACCUGGUA | 5636 |
| 4905 | AGGAGCA GAU GGACAGCG | 1481 | CGCUGUCC AGAA GCUCCU ACCAGAGAAACACACGUUGUGGUACAUUACCUGGUA | 5637 |
| 5233 | UUAUUCU GUU UUGCACAG | 1482 | CUGUGCAA AGAA GAAUAA ACCAGAGAAACACACGUUGUGGUACAUUACCUGGUA | 5638 |
| 5281 | AAAUGCA GUC CUGAGGAG | 1483 | CUCCUCAG AGAA GCAUUU ACCAGAGAAACACACGUUGUGGUACAUUACCUGGUA | 5639 |
| 5319 | GAGGGCU GAU GGAGGAAA | 1484 | UUUCCUCC AGAA GCCCUC ACCAGAGAAACACACGUUGUGGUACAUUACCUGGUA | 5640 |
| 5358 | AGACCCC GUC UCUAUACC | 1485 | GGUAUAGA AGAA GGGUCU ACCAGAGAAACACACGUUGUGGUACAUUACCUGGUA | 5641 |
| 5392 | CAACACA GUU GGGACCCA | 1486 | UGGGUCCC AGAA GUGUUG ACCAGAGAAACACACGUUGUGGUACAUUACCUGGUA | 5642 |
| 5563 | UUCUCCA GUU GGGACUCA | 1487 | UGAGUCCC AGAA GGAGAA ACCAGAGAAACACACGUUGUGGUACAUUACCUGGUA | 5643 |
| 5622 | UUCAACU GCU UUGAAACU | 1488 | AGUUUCAA AGAA GUUGAA ACCAGAGAAACACACGUUGUGGUACAUUACCUGGUA | 5644 |
| 5738 | UGGCUCU GUU UGAUGCUA | 1489 | UAGCAUCA AGAA GAGCCA ACCAGAGAAACACACGUUGUGGUACAUUACCUGGUA | 5645 |
| 5838 | UGGCUCU GUU UGAUGCUA | 1489 | UAGCAUCA AGAA GAGCCA ACCAGAGAAACACACGUUGUGGUACAUUACCUGGUA | 5645 |
| 5933 | GAUUGCU GCU UCUUGGGG | 1490 | CCCCAAGA AGAA GCAAUC ACCAGAGAAACACACGUUGUGGUACAUUACCUGGUA | 5646 |
| 6022 | UGCCUCU GUU CUUAUGUG | 1491 | CACAUAAG AGAA GAGGCA ACCAGAGAAACACACGUUGUGGUACAUUACCUGGUA | 5647 |
| 6120 | GGCAGCG GCU UUUGUGGA | 1492 | UCCACAAA AGAA GCUGCC ACCAGAGAAACACACGUUGUGGUACAUUACCUGGUA | 5648 |
| 6163 | UGGGACA GUC CUCUCCAC | 1493 | GUGGAGAG AGAA GUCCCA ACCAGAGAAACACACGUUGUGGUACAUUACCUGGUA | 5649 |
| 6270 | UGUGACA GCU GGCAAUUU | 1494 | AAAUUGCC AGAA GUCACA ACCAGAGAAACACACGUUGUGGUACAUUACCUGGUA | 5650 |
| 6412 | CUUAGCU GUU CAUGUCUU | 1495 | AAGACAUG AGAA GCUAAG ACCAGAGAAACACACGUUGUGGUACAUUACCUGGUA | 5651 |
| 6511 | UUACUCA GCU CCUUCAAA | 1496 | UUUGAAGG AGAA GAGUAA ACCAGAGAAACACACGUUGUGGUACAUUACCUGGUA | 5652 |
| 6778 | UGGAACA GUC UGGGUGGA | 1497 | UCCACCCA AGAA GUUCCA ACCAGAGAAACACACGUUGUGGUACAUUACCUGGUA | 5653 |

TABLE III-continued

Human flt1 VEGF Receptor-Hairpin Ribozyme and Substrate sequence

| Pos | Substrate | Seq ID No | HP Ribozyme Sequence | Seq ID No |
|---|---|---|---|---|
| 6826 | CUUGUCA GUC CAAGAAGU | 1498 | ACUUCUUG AGAA GACAAG ACCAGAGAAACACACGUUGUGGUACAUUACCUGGUA | 5654 |
| 7245 | GGCAACU GCU UUUAUGUU | 1499 | AACAUAAA AGAA GUUGCC ACCAGAGAAACACACGUUGUGGUACAUUACCUGGUA | 5655 |
| 7258 | AUGUUCU GUC UCCUUCCA | 1500 | UGGAAGGA AGAA GAACAU ACCAGAGAAACACACGUUGUGGUACAUUACCUGGUA | 5656 |
| 7433 | UUUAGCU GAU UGUAUGGG | 1501 | CCCAUACA AGAA GCUAAA ACCAGAGAAACACACGUUGUGGUACAUUACCUGGUA | 5657 |
| 7512 | AAUUCCU GUC CAUGAAAA | 1502 | UUUUCAUG AGAA GGAAUU ACCAGAGAAACACACGUUGUGGUACAUUACCUGGUA | 5658 |
| 7606 | CAUUUCA GCC UGAAUGUC | 1503 | GACAUUCA AGAA GAAAUG ACCAGAGAAACACACGUUGUGGUACAUUACCUGGUA | 5659 |
| 7618 | AAUGUCU GCC UAUAUAUU | 1504 | AAUAUAUA AGAA GACAUU ACCAGAGAAACACACGUUGUGGUACAUUACCUGGUA | 5660 |
| 7633 | AUUCUCU GCU CUUUGUAU | 1505 | AUACAAAG AGAA GAGAAU ACCAGAGAAACACACGUUGUGGUACAUUACCUGGUA | 5661 |

TABLE IV

Human KDR VEGF Receptor-Hammerhead Ribozyme and Substrate Sequence

| Pos | Substrate | Seq ID No | HH Ribozyme Sequence | Seq ID No |
|---|---|---|---|---|
| 21 | CUGGCCGUC GCCCUGUG | 1506 | CACAGGGC CUGAUGAGgNNNNNNNNCCGAA ACGGCCAG | 5662 |
| 33 | CUGUGGCUC UGCGUGGA | 1507 | UCCACGCA CUGAUGAGgNNNNNNNNCCGAA AGCCACAG | 5663 |
| 56 | GGCCGCCUC UGUGGGUU | 1508 | AACCCACA CUGAUGAGgNNNNNNNNCCGAA AGGCGGCC | 5664 |
| 64 | CUGUGGGUU UGCCUAGU | 1509 | ACUAGGCA CUGAUGAGgNNNNNNNNCCGAA ACCCACAG | 5665 |
| 65 | UGUGGGUUU GCCUAGUG | 1510 | CACUAGGC CUGAUGAGgNNNNNNNNCCGAA AACCCACA | 5666 |
| 70 | GUUUGCCUA GUGUUUCU | 1511 | AGAAACAC CUGAUGAGgNNNNNNNNCCGAA AGGCAAAC | 5667 |
| 75 | CCUAGUGUU UCUCUUGA | 1512 | UCAAGAGA CUGAUGAGgNNNNNNNNCCGAA ACACUAGG | 5668 |
| 76 | CUAGUGUUU CUCUUGAU | 1513 | AUCAAGAG CUGAUGAGgNNNNNNNNCCGAA AACACUAG | 5669 |
| 77 | UAGUGUUUC UCUUGAUC | 1514 | GAUCAAGA CUGAUGAGgNNNNNNNNCCGAA AAACACUA | 5670 |
| 79 | GUGUUUCUC UUGAUCUG | 1515 | CAGAUCAA CUGAUGAGgNNNNNNNNCCGAA AGAAACAC | 5671 |
| 81 | GUUUCUCUU GAUCUGCC | 1516 | GGCAGAUC CUGAUGAGgNNNNNNNNCCGAA AGAGAAAC | 5672 |
| 85 | CUCUUGAUC UGCCCAGG | 1517 | CCUGGGCA CUGAUGAGgNNNNNNNNCCGAA AUCAAGAG | 5673 |
| 96 | CCCAGGCUC AGCAUACA | 1518 | UGUAUGCU CUGAUGAGgNNNNNNNNCCGAA AGCCUGGG | 5674 |
| 102 | CUCAGCAUA CAAAAAGA | 1519 | UCUUUUUG CUGAUGAGgNNNNNNNNCCGAA AUGCUGAG | 5675 |
| 114 | AAAGACAUA CUUACAAU | 1520 | AUUGUAAG CUGAUGAGgNNNNNNNNCCGAA AUGUCUUU | 5676 |
| 117 | GACAUACUU ACAAUUAA | 1521 | UUAAUUGU CUGAUGAGgNNNNNNNNCCGAA AGUAUGUC | 5677 |
| 118 | ACAUACUUA CAAUUAAG | 1522 | CUUAAUUG CUGAUGAGgNNNNNNNNCCGAA AAGUAUGU | 5678 |
| 123 | CUUACAAUU AAGGCUAA | 1523 | UUAGCCUU CUGAUGAGgNNNNNNNNCCGAA AUUGUAAG | 5679 |
| 124 | UUACAAUUA AGGCUAAU | 1524 | AUUAGCCU CUGAUGAGgNNNNNNNNCCGAA AAUUGUAA | 5680 |
| 130 | UUAAGGCUA AUACAACU | 1525 | AGUUGUAU CUGAUGAGgNNNNNNNNCCGAA AGCCUUAA | 5681 |
| 133 | AGGCUAAUA CAACUCUU | 1526 | AAGAGUUG CUGAUGAGgNNNNNNNNCCGAA AUUAGCCU | 5682 |
| 139 | AUACAACUC UUCAAAUU | 1527 | AAUUUGAA CUGAUGAGgNNNNNNNNCCGAA AGUUGUAU | 5683 |
| 141 | ACAACUCUU CAAAUUAC | 1528 | GUAAUUUG CUGAUGAGgNNNNNNNNCCGAA AGAGUUGU | 5684 |
| 142 | CAACUCUUC AAAUUACU | 1529 | AGUAAUUU CUGAUGAGgNNNNNNNNCCGAA AAGAGUUG | 5685 |
| 147 | CUUCAAAUU ACUUGCAG | 1530 | CUGCAAGU CUGAUGAGgNNNNNNNNCCGAA AUUUGAAG | 5686 |
| 148 | UUCAAAUUA CUUGCAGG | 1531 | CCUGCAAG CUGAUGAGgNNNNNNNNCCGAA AAUUUGAA | 5687 |
| 151 | AAAUUACUU GCAGGGGA | 1532 | UCCCCUGC CUGAUGAGgNNNNNNNNCCGAA AGUAAUUU | 5688 |
| 170 | GAGGGACUU GGACUGGC | 1533 | GCCAGUCC CUGAUGAGgNNNNNNNNCCGAA AGUCCCUC | 5689 |
| 180 | GACUGGCUU UGGCCCAA | 1534 | UUGGGCCA CUGAUGAGgNNNNNNNNCCGAA AGCCAGUC | 5690 |
| 181 | ACUGGCUUU GGCCCAAU | 1535 | AUUGGGCC CUGAUGAGgNNNNNNNNCCGAA AAGCCAGU | 5691 |
| 190 | GGCCCAAUA UCAGAGUG | 1536 | ACUCUGAU CUGAUGAGgNNNNNNNNCCGAA AUUGGGCC | 5692 |
| 193 | CCAAUAAUC AGAGUGGC | 1537 | GCCACUCU CUGAUGAGgNNNNNNNNCCGAA AUUAUUGG | 5693 |
| 243 | GAUGGCCUC UUCUGUAA | 1538 | UUACAGAA CUGAUGAGgNNNNNNNNCCGAA AGGCCAUC | 5694 |
| 245 | UGGCCUCUU CUGUAAGA | 1539 | UCUUACAG CUGAUGAGgNNNNNNNNCCGAA AGAGGCCA | 5695 |
| 246 | GGCCUCUUC UGUAAGAC | 1540 | GUCUUACA CUGAUGAGgNNNNNNNNCCGAA AAGAGGCC | 5696 |
| 250 | UCUUCUGUA AGACACUC | 1541 | GAGUGUCU CUGAUGAGgNNNNNNNNCCGAA AACAGAAGA | 5697 |
| 258 | AAGACACUC ACAAUUCC | 1542 | GGAAUUGU CUGAUGAGgNNNNNNNNCCGAA AGUGUCUU | 5698 |
| 264 | CUCACAAUU CCAAAAGU | 1543 | ACUUUUGG CUGAUGAGgNNNNNNNNCCGAA AUUGUGAG | 5699 |
| 265 | UCACAAUUC CAAAAGUG | 1544 | CACUUUUG CUGAUGAGgNNNNNNNNCCGAA AAUUGUGA | 5700 |
| 276 | AAAGUGAUC GGAAAUGA | 1545 | UCAUUUCC CUGAUGAGgNNNNNNNNCCGAA AUCACUUU | 5701 |
| 296 | UGGAGCCUA CAAGUGCU | 1546 | AGCACUUG CUGAUGAGgNNNNNNNNCCGAA AGGCUCCA | 5702 |
| 305 | CAAGUGCUU CUACCGGG | 1547 | CCCGGUAG CUGAUGAGgNNNNNNNNCCGAA AGCACUUG | 5703 |
| 306 | AAGUGCUUC UACCGGGA | 1548 | UCCCGGUA CUGAUGAGgNNNNNNNNCCGAA AAGCACUU | 5704 |
| 308 | GUGCUUCUA CCGGGAAA | 1549 | UUUCCCGG CUGAUGAGgNNNNNNNNCCGAA AGAAGCAC | 5705 |
| 323 | AACUGACUU GGCCUCGG | 1550 | CCGAGGCC CUGAUGAGgNNNNNNNNCCGAA AGUCAGUU | 5706 |
| 329 | CUUGGCCUC GGUCAUUU | 1551 | AAAUGACC CUGAUGAGgNNNNNNNNCCGAA AGGCCAAG | 5707 |
| 333 | GCCUCGGUC AUUUAUGU | 1552 | ACAUAAAU CUGAUGAGgNNNNNNNNCCGAA ACCGAGGC | 5708 |
| 336 | UCGGUCAUU UAUGUCUA | 1553 | UAGACAUA CUGAUGAGgNNNNNNNNCCGAA AUGACCGA | 5709 |
| 337 | CGGUCAUUU AUGUCUAU | 1554 | AUAGACAU CUGAUGAGgNNNNNNNNCCGAA AAUGACCG | 5710 |
| 338 | GGUCAUUUA UGUCUAUG | 1555 | CAUAGACA CUGAUGAGgNNNNNNNNCCGAA AAAUGACC | 5711 |
| 342 | AUUUAUGUC UAUGUUCA | 1556 | UGAACAUA CUGAUGAGgNNNNNNNNCCGAA ACAUAAAU | 5712 |
| 344 | UUAUGUCUA UGUUCAAG | 1557 | CUUGAACA CUGAUGAGgNNNNNNNNCCGAA AGACAUAA | 5713 |
| 348 | GUCUAUGUU CAAGAUUA | 1558 | UAAUCUUG CUGAUGAGgNNNNNNNNCCGAA ACAUAGAC | 5714 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 349 | UCUAUGUUC AAGAUUAC | 1559 | GUAAUCUU CUGAUGAGGNNNNNNNNCCGAA AACAUAGA | 5715 |
| 355 | UUCAAGAUU ACAGAUCU | 1560 | AGAUCUGU CUGAUGAGGNNNNNNNNCCGAA AUCUUGAA | 5716 |
| 356 | UCAAGAUUA CAGAUCUC | 1561 | GAGAUCUG CUGAUGAGGNNNNNNNNCCGAA AAUCUUGA | 5717 |
| 362 | UUACAGAUC UCCAUUUA | 1562 | UAAAUGGA CUGAUGAGGNNNNNNNNCCGAA AUCUGUAA | 5718 |
| 364 | ACAGAUCUC CAUUUAUU | 1563 | AAUAAAUG CUGAUGAGGNNNNNNNNCCGAA AGAUCUGU | 5719 |
| 368 | AUCUCCAUU UAUUGCUU | 1564 | AAGCAAUA CUGAUGAGGNNNNNNNNCCGAA AUGGAGAU | 5720 |
| 369 | UCUCCAUUU AUUGCUUC | 1565 | GAAGCAAU CUGAUGAGGNNNNNNNNCCGAA AAUGGAGA | 5721 |
| 370 | CUCCAUUUA UUGCUUCU | 1566 | AGAAGCAA CUGAUGAGGNNNNNNNNCCGAA AAAUGGAG | 5722 |
| 372 | CCAUUUAUU GCUUCUGU | 1567 | ACAGAAGC CUGAUGAGGNNNNNNNNCCGAA AUAAAUGG | 5723 |
| 376 | UUAUUGCUU CUGUUAGU | 1568 | ACUAACAG CUGAUGAGGNNNNNNNNCCGAA AGCAAUAA | 5724 |
| 377 | UAUUGCUUC UGUUAGUG | 1569 | CACUAACA CUGAUGAGGNNNNNNNNCCGAA AAGCAAUA | 5725 |
| 381 | GCUUCUGUU AGUGACCA | 1570 | UGGUCACU CUGAUGAGGNNNNNNNNCCGAA ACAGAAGC | 5726 |
| 382 | CUUCUGUUA GUGACCAA | 1571 | UUGGUCAC CUGAUGAGGNNNNNNNNCCGAA AACAGAAG | 5727 |
| 399 | CAUGGAGUC GUGUACAU | 1572 | AUGUACAC CUGAUGAGGNNNNNNNNCCGAA ACUCCAUG | 5728 |
| 404 | AGUCGUGUA CAUUACUG | 1573 | CAGUAAUG CUGAUGAGGNNNNNNNNCCGAA ACACGACU | 5729 |
| 408 | GUGUACAUU ACUGAGAA | 1574 | UUCUCAGU CUGAUGAGGNNNNNNNNCCGAA AUGUACAC | 5730 |
| 409 | UGUACAUUA CUGAGAAC | 1575 | GUUCUCAG CUGAUGAGGNNNNNNNNCCGAA AAUGUACA | 5731 |
| 438 | GUGGUGAUU CCAUGUCU | 1576 | AGACAUGG CUGAUGAGGNNNNNNNNCCGAA AUCACCAC | 5732 |
| 439 | UGGUGAUUC CAUGUCUC | 1577 | GAGACAUG CUGAUGAGGNNNNNNNNCCGAA AAUCACCA | 5733 |
| 445 | UUCCAUGUC UCGGGUCC | 1578 | GGACCCGA CUGAUGAGGNNNNNNNNCCGAA ACAUGGAA | 5734 |
| 447 | CCAUGUCUC GGGUCCAU | 1579 | AUGGACCC CUGAUGAGGNNNNNNNNCCGAA AGACAUGG | 5735 |
| 452 | UCUCGGGUC CAUUUCAA | 1580 | UUGAAAUG CUGAUGAGGNNNNNNNNCCGAA ACCCGAGA | 5736 |
| 456 | GGGUCCAUU UCAAAUCU | 1581 | AGAUUUGA CUGAUGAGGNNNNNNNNCCGAA AUGGACCC | 5737 |
| 457 | GGUCCAUUU CAAAUCUC | 1582 | GAGAUUUG CUGAUGAGGNNNNNNNNCCGAA AAUGGACC | 5738 |
| 458 | GUCCAUUUC AAAUCUCA | 1583 | UGAGAUUU CUGAUGAGGNNNNNNNNCCGAA AAAUGGAC | 5739 |
| 463 | UUUCAAAUC UCAACGUG | 1584 | CACGUUGA CUGAUGAGGNNNNNNNNCCGAA AUUUGAAA | 5740 |
| 465 | UCAAAUCUC AACGUGUC | 1585 | GACACGUU CUGAUGAGGNNNNNNNNCCGAA AGAUUUGA | 5741 |
| 473 | CAACGUGUC ACUUUGUG | 1586 | CACAAAGU CUGAUGAGGNNNNNNNNCCGAA ACACGUUG | 5742 |
| 477 | GUGUCACUU UGUGCAAG | 1587 | CUUGCACA CUGAUGAGGNNNNNNNNCCGAA AGUGACAC | 5743 |
| 478 | UGUCACUUU GUGCAAGA | 1588 | UCUUGCAC CUGAUGAGGNNNNNNNNCCGAA AAGUGACA | 5744 |
| 488 | UGCAAGAUA CCCAGAAA | 1589 | UUUCUGGG CUGAUGAGGNNNNNNNNCCGAA AUCUUGCA | 5745 |
| 503 | AAAGAGAUU UGUUCCUG | 1590 | CAGGAACA CUGAUGAGGNNNNNNNNCCGAA AUCUCUUU | 5746 |
| 504 | AAGAGAUUU GUUCCUGA | 1591 | UCAGGAAC CUGAUGAGGNNNNNNNNCCGAA AAUCUCUU | 5747 |
| 507 | AGAUUUGUU CCUGAUGG | 1592 | CCAUCAGG CUGAUGAGGNNNNNNNNCCGAA ACAAAUCU | 5748 |
| 508 | GAUUUGUUC CUGAUGGU | 1593 | ACCAUCAG CUGAUGAGGNNNNNNNNCCGAA AACAAAUC | 5749 |
| 517 | CUGAUGGUA ACAGAAUU | 1594 | AAUUCUGU CUGAUGAGGNNNNNNNNCCGAA ACCAUCAG | 5750 |
| 525 | AACAGAAUU UCCUGGGA | 1595 | UCCCAGGA CUGAUGAGGNNNNNNNNCCGAA AUUCUGUU | 5751 |
| 526 | ACAGAAUUU CCUGGGAC | 1596 | GUCCCAGG CUGAUGAGGNNNNNNNNCCGAA AAUUCUGU | 5752 |
| 527 | CAGAAUUUC CUGGGACA | 1597 | UGUCCCAG CUGAUGAGGNNNNNNNNCCGAA AAAUUCUG | 5753 |
| 548 | GAAGGGCUU UACUAUUC | 1598 | GAAUAGUA CUGAUGAGGNNNNNNNNCCGAA AGCCCUUC | 5754 |
| 549 | AAGGGCUUU ACUAUUCC | 1599 | GGAAUAGU CUGAUGAGGNNNNNNNNCCGAA AAGCCCUU | 5755 |
| 550 | AGGGCUUUA CUAUUCCC | 1600 | GGGAAUAG CUGAUGAGGNNNNNNNNCCGAA AAAGCCCU | 5756 |
| 553 | GCUUUACUA UUCCCAGC | 1601 | GCUGGGAA CUGAUGAGGNNNNNNNNCCGAA AGUAAAGC | 5757 |
| 555 | UUUACUAUU CCCAGCUA | 1602 | UAGCUGGG CUGAUGAGGNNNNNNNNCCGAA AUAGUAAA | 5758 |
| 556 | UUACUAUUC CCAGCUAC | 1603 | GUAGCUGG CUGAUGAGGNNNNNNNNCCGAA AAUAGUAA | 5759 |
| 563 | UCCCAGCUA CAUGAUCA | 1604 | UGAUCAUG CUGAUGAGGNNNNNNNNCCGAA AGCUGGGA | 5760 |
| 570 | UACAUGAUC AGCUAUGC | 1605 | GCAUAGCU CUGAUGAGGNNNNNNNNCCGAA AUCAUGUA | 5761 |
| 575 | GAUCAGCUA UGCUGGCA | 1606 | UGCCAGCA CUGAUGAGGNNNNNNNNCCGAA AGCUGAUC | 5762 |
| 588 | GGCAUGGUC UUCUGUGA | 1607 | UCACAGAA CUGAUGAGGNNNNNNNNCCGAA ACCAUGCC | 5763 |
| 590 | CAUGGUCUU CUGUGAAG | 1608 | CUUCACAG CUGAUGAGGNNNNNNNNCCGAA AGACCAUG | 5764 |
| 591 | AUGGUCUUC UGUGAAGC | 1609 | GCUUCACA CUGAUGAGGNNNNNNNNCCGAA AAGACCAU | 5765 |
| 606 | GCAAAAAUU AAUGAUGA | 1610 | UCAUCAUU CUGAUGAGGNNNNNNNNCCGAA AUUUUUGC | 5766 |
| 607 | CAAAAAUUA AUGAUGAA | 1611 | UUCAUCAU CUGAUGAGGNNNNNNNNCCGAA AAUUUUUG | 5767 |
| 619 | AUGAAAGUU ACCAGUCU | 1612 | AGACUGGU CUGAUGAGGNNNNNNNNCCGAA ACUUUCAU | 5768 |
| 620 | UGAAAGUUA CCAGUCUA | 1613 | UAGACUGG CUGAUGAGGNNNNNNNNCCGAA AACUUUCA | 5769 |
| 626 | UUACCAGUC UAUUAUGU | 1614 | ACAUAAUA CUGAUGAGGNNNNNNNNCCGAA ACUGGUAA | 5770 |
| 628 | ACCAGUCUA UUAUGUAC | 1615 | GUACAUAA CUGAUGAGGNNNNNNNNCCGAA AGACUGGU | 5771 |
| 630 | CAGUCUAUU AUGUACAU | 1616 | AUGUACAU CUGAUGAGGNNNNNNNNCCGAA AUAGACUG | 5772 |
| 631 | AGUCUAUUA UGUACAUA | 1617 | UAUGUACA CUGAUGAGGNNNNNNNNCCGAA AAUAGACU | 5773 |
| 635 | UAUUAUGUA CAUAGUUG | 1618 | CAACUAUG CUGAUGAGGNNNNNNNNCCGAA ACAUAAUA | 5774 |
| 639 | AUGUACAUA GUUGUCGU | 1619 | ACGACAAC CUGAUGAGGNNNNNNNNCCGAA AUGUACAU | 5775 |
| 642 | UACAUAGUU GUCGUUGU | 1620 | ACAACGAC CUGAUGAGGNNNNNNNNCCGAA ACUAUGUA | 5776 |
| 645 | AUAGUUGUC GUUGUAGG | 1621 | CCUACAAC CUGAUGAGGNNNNNNNNCCGAA ACAACUAU | 5777 |
| 648 | GUUGUCGUU GUAGGGUA | 1622 | UACCCUAC CUGAUGAGGNNNNNNNNCCGAA ACGACAAC | 5778 |
| 651 | GUCGUUGUA GGGUAUAG | 1623 | CUAUACCC CUGAUGAGGNNNNNNNNCCGAA ACAACGAC | 5779 |
| 656 | UGUAGGGUA UAGGAUUU | 1624 | AAAUCCUA CUGAUGAGGNNNNNNNNCCGAA ACCCUACA | 5780 |
| 658 | UAGGGUAUA GGAUUUAU | 1625 | AUAAAUCC CUGAUGAGGNNNNNNNNCCGAA AUACCCUA | 5781 |
| 663 | UAUAGGAUU UAUGAUGU | 1626 | ACAUCAUA CUGAUGAGGNNNNNNNNCCGAA AUCCUAUA | 5782 |
| 664 | AUAGGAUUU AUGAUGUG | 1627 | CACAUCAU CUGAUGAGGNNNNNNNNCCGAA AAUCCUAU | 5783 |
| 665 | UAGGAUUUA UGAUGUGG | 1628 | CCACAUCA CUGAUGAGGNNNNNNNNCCGAA AAAUCCUA | 5784 |
| 675 | GAUGUGGUU CUGAGUCC | 1629 | GGACUCAG CUGAUGAGGNNNNNNNNCCGAA ACCACAUC | 5785 |
| 676 | AUGUGGUUC UGAGUCCG | 1630 | CGGACUCA CUGAUGAGGNNNNNNNNCCGAA AACCACAU | 5786 |
| 682 | UUCUGAGUC CGUCUCAU | 1631 | AUGAGACG CUGAUGAGGNNNNNNNNCCGAA ACUCAGAA | 5787 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 686 | GAGUCCGUC UCAUGGAA | 1632 | UUCCAUGA CUGAUGAGGNNNNNNNNCCGAA ACGGACUC | 5788 |
| 688 | GUCCGUCUC AUGGAAUU | 1633 | AAUUCCAU CUGAUGAGGNNNNNNNNCCGAA AGACGGAC | 5789 |
| 696 | CAUGGAAUU GAACUAUC | 1634 | GAUAGUUC CUGAUGAGGNNNNNNNNCCGAA AUUCCAUG | 5790 |
| 702 | AUUGAACUA UCUGUUGG | 1635 | CCAACAGA CUGAUGAGGNNNNNNNNCCGAA AGUUCAAU | 5791 |
| 704 | UGAACUAUC UGUUGGAG | 1636 | CUCCAACA CUGAUGAGGNNNNNNNNCCGAA AUAGUUCA | 5792 |
| 708 | CUAUCUGUU GGAGAAAA | 1637 | UUUUCUCC CUGAUGAGGNNNNNNNNCCGAA ACAGAUAG | 5793 |
| 720 | GAAAAGCUU GUCUUAAA | 1638 | UUUAAGAC CUGAUGAGGNNNNNNNNCCGAA AGCUUUUC | 5794 |
| 723 | AAGCUUGUC UUAAAUUG | 1639 | CAAUUUAA CUGAUGAGGNNNNNNNNCCGAA ACAAGCUU | 5795 |
| 725 | GCUUGUCUU AAAUUGUA | 1640 | UACAAUUU CUGAUGAGGNNNNNNNNCCGAA AGACAAGC | 5796 |
| 726 | CUUGUCUUA AAUUGUAC | 1641 | GUACAAUU CUGAUGAGGNNNNNNNNCCGAA AAGACAAG | 5797 |
| 730 | UCUUAAAUU GUACAGCA | 1642 | UGCUGUAC CUGAUGAGGNNNNNNNNCCGAA AUUUAAGA | 5798 |
| 733 | UAAAUUGUA CAGCAAGA | 1643 | UCUUGCUG CUGAUGAGGNNNNNNNNCCGAA ACAAUUUA | 5799 |
| 750 | ACUGAACUA AAUGUGGG | 1644 | CCCACAUU CUGAUGAGGNNNNNNNNCCGAA AGUUCAGU | 5800 |
| 762 | GUGGGGAUU GACUUCAA | 1645 | UUGAAGUC CUGAUGAGGNNNNNNNNCCGAA AUCCCCAC | 5801 |
| 767 | GAUUGACUU CAACUGGG | 1646 | CCCAGUUG CUGAUGAGGNNNNNNNNCCGAA AGUCAAUC | 5802 |
| 768 | AUUGACUUC AACUGGGA | 1647 | UCCCAGUU CUGAUGAGGNNNNNNNNCCGAA AAGUCAAU | 5803 |
| 779 | CUGGGAAUA CCCUUCUU | 1648 | AAGAAGGG CUGAUGAGGNNNNNNNNCCGAA AUUCCCAG | 5804 |
| 784 | AAUACCCUU CUUCGAAG | 1649 | CUUCGAAG CUGAUGAGGNNNNNNNNCCGAA AGGGUAUU | 5805 |
| 785 | AUACCCUUC UUCGAAGC | 1650 | GCUUCGAA CUGAUGAGGNNNNNNNNCCGAA AAGGGUAU | 5806 |
| 787 | ACCCUUCUU CGAAGCAU | 1651 | AUGCUUCG CUGAUGAGGNNNNNNNNCCGAA AGAAGGGU | 5807 |
| 788 | CCCUUCUUC GAAGCAUC | 1652 | GAUGCUUC CUGAUGAGGNNNNNNNNCCGAA AAGAAGGG | 5808 |
| 796 | CGAAGCAUC AGCAUAAG | 1653 | CUUAUGCU CUGAUGAGGNNNNNNNNCCGAA AUGCUUCG | 5809 |
| 802 | AUCAGCAUA AGAAACUU | 1654 | AAGUUUCU CUGAUGAGGNNNNNNNNCCGAA AUGCUGAU | 5810 |
| 810 | AAGAAACUU GUAAACCG | 1655 | CGGUUUAC CUGAUGAGGNNNNNNNNCCGAA AGUUUCUU | 5811 |
| 813 | AAACUUGUA AACCGAGA | 1656 | UCUCGGUU CUGAUGAGGNNNNNNNNCCGAA ACAAGUUU | 5812 |
| 825 | CGAGACCUA AAAACCCA | 1657 | UGGGUUUU CUGAUGAGGNNNNNNNNCCGAA AGGUCUCG | 5813 |
| 836 | AACCCAGUC UGGGAGUG | 1658 | CACUCCCA CUGAUGAGGNNNNNNNNCCGAA ACUGGGUU | 5814 |
| 857 | GAAGAAAUU UUUGAGCA | 1659 | UGCUCAAA CUGAUGAGGNNNNNNNNCCGAA AUUUCUUC | 5815 |
| 858 | AAGAAAUUU UUGAGCAC | 1660 | GUGCUCAA CUGAUGAGGNNNNNNNNCCGAA AAUUUCUU | 5816 |
| 859 | AGAAAUUUU UGAGCACC | 1661 | GGUGCUCA CUGAUGAGGNNNNNNNNCCGAA AAAUUUCU | 5817 |
| 860 | GAAAUUUUU GAGCACCU | 1662 | AGGUGCUC CUGAUGAGGNNNNNNNNCCGAA AAAAUUUC | 5818 |
| 869 | GAGCACCUU AACUAUAG | 1663 | CUAUAGUU CUGAUGAGGNNNNNNNNCCGAA AGGUGCUC | 5819 |
| 870 | AGCACCUUA ACUAUAGA | 1664 | UCUAUAGU CUGAUGAGGNNNNNNNNCCGAA AAGGUGCU | 5820 |
| 874 | CCUUAACUA UAGAUGGU | 1665 | ACCAUCUA CUGAUGAGGNNNNNNNNCCGAA AGUUAAGG | 5821 |
| 876 | UUAACUAUA GAUGGUGU | 1666 | ACACCAUC CUGAUGAGGNNNNNNNNCCGAA AUAGUUAA | 5822 |
| 885 | GAUGGUGUA ACCCGGAG | 1667 | CUCCGGGU CUGAUGAGGNNNNNNNNCCGAA ACACCAUC | 5823 |
| 905 | CCAAGGAUU GUACACCU | 1668 | AGGUGUAC CUGAUGAGGNNNNNNNNCCGAA AUCCUUGG | 5824 |
| 908 | AGGAUUGUA CACCUGUG | 1669 | CACAGGUG CUGAUGAGGNNNNNNNNCCGAA ACAAUCCU | 5825 |
| 923 | UGCAGCAUC CAGUGGGC | 1670 | GCCCACUG CUGAUGAGGNNNNNNNNCCGAA AUGCUGCA | 5826 |
| 956 | CAGCACAUU UGUCAGGG | 1671 | CCCUGACA CUGAUGAGGNNNNNNNNCCGAA AUGUGCUG | 5827 |
| 957 | AGCACAUUU GUCAGGGU | 1672 | ACCCUGAC CUGAUGAGGNNNNNNNNCCGAA AAUGUGCU | 5828 |
| 960 | ACAUUUGUC AGGGUCCA | 1673 | UGGACCCU CUGAUGAGGNNNNNNNNCCGAA ACAAAUGU | 5829 |
| 966 | GUCAGGGUC CAUGAAAA | 1674 | UUUUCAUG CUGAUGAGGNNNNNNNNCCGAA ACCCUGAC | 5830 |
| 979 | AAAAACCUU UUGUUGCU | 1675 | AGCAACAA CUGAUGAGGNNNNNNNNCCGAA AGGUUUUU | 5831 |
| 980 | AAAACCUUU UGUUGCUU | 1676 | AAGCAACA CUGAUGAGGNNNNNNNNCCGAA AAGGUUUU | 5832 |
| 981 | AAACCUUUU GUUGCUUU | 1677 | AAAGCAAC CUGAUGAGGNNNNNNNNCCGAA AAAGGUUU | 5833 |
| 984 | CCUUUUGUU GCUUUUGG | 1678 | CCAAAAGC CUGAUGAGGNNNNNNNNCCGAA ACAAAAGG | 5834 |
| 988 | UUGUUGCUU UUGGAAGU | 1679 | ACUUCCAA CUGAUGAGGNNNNNNNNCCGAA AGCAACAA | 5835 |
| 989 | UGUUGCUUU UGGAAGUG | 1680 | CACUUCCA CUGAUGAGGNNNNNNNNCCGAA AAGCAACA | 5836 |
| 990 | GUUGCUUUU GGAAGUGG | 1681 | CCACUUCC CUGAUGAGGNNNNNNNNCCGAA AAAGCAAC | 5837 |
| 1007 | CAUGGAAUC UCUGGUGG | 1682 | CCACCAGA CUGAUGAGGNNNNNNNNCCGAA AUUCCAUG | 5838 |
| 1009 | UGGAAUCUC UGGUGGAA | 1683 | UUCCACCA CUGAUGAGGNNNNNNNNCCGAA AGAUUCCA | 5839 |
| 1038 | GAGCGUGUC AGAAUCCC | 1684 | GGGAUUCU CUGAUGAGGNNNNNNNNCCGAA ACACGCUC | 5840 |
| 1044 | GUCAGAAUC CCUGCGAA | 1685 | UUCGCAGG CUGAUGAGGNNNNNNNNCCGAA AUUCUGAC | 5841 |
| 1055 | UGCGAAGUA CCUUGGUU | 1686 | AACCAAGG CUGAUGAGGNNNNNNNNCCGAA ACUUCGCA | 5842 |
| 1059 | AAGUACCUU GGUUACCC | 1687 | GGGUAACC CUGAUGAGGNNNNNNNNCCGAA AGGUACUU | 5843 |
| 1063 | ACCUUGGUU ACCCACCC | 1688 | GGGUGGGU CUGAUGAGGNNNNNNNNCCGAA ACCAAGGU | 5844 |
| 1064 | CCUUGGUUA CCCACCCC | 1689 | GGGGUGGG CUGAUGAGGNNNNNNNNCCGAA AACCAAGG | 5845 |
| 1080 | CCAGAAAUA AAAUGGUA | 1690 | UACCAUUU CUGAUGAGGNNNNNNNNCCGAA AUUUCUGG | 5846 |
| 1088 | AAAAUGGUA UAAAAAUG | 1691 | CAUUUUUA CUGAUGAGGNNNNNNNNCCGAA ACCAUUUU | 5847 |
| 1090 | AAUGGUAUA AAAAUGGA | 1692 | UCCAUUUU CUGAUGAGGNNNNNNNNCCGAA AUACCAUU | 5848 |
| 1101 | AAUGGAAUA CCCCUUGA | 1693 | UCAAGGGG CUGAUGAGGNNNNNNNNCCGAA AUUCCAUU | 5849 |
| 1107 | AUACCCCUU GAGUCCAA | 1694 | UUGGACUC CUGAUGAGGNNNNNNNNCCGAA AGGGGUAU | 5850 |
| 1112 | CCUUGAGUC CAAUCACA | 1695 | UGUGAUUG CUGAUGAGGNNNNNNNNCCGAA ACUCAAGG | 5851 |
| 1117 | AGUCCAAUC ACACAAUU | 1696 | AAUUGUGU CUGAUGAGGNNNNNNNNCCGAA AUUGGACU | 5852 |
| 1125 | CACACAAUU AAAGCGGG | 1697 | CCCGCUUU CUGAUGAGGNNNNNNNNCCGAA AUUGUGUG | 5853 |
| 1126 | ACACAAUUA AAGCGGGC | 1698 | CCCCGCUU CUGAUGAGGNNNNNNNNCCGAA AAUUGUGU | 5854 |
| 1140 | GGGCAUGUA CUGACGAU | 1699 | AUCGUCAG CUGAUGAGGNNNNNNNNCCGAA ACAUGCCC | 5855 |
| 1149 | CUGACGAUU AUGGAAGU | 1700 | ACUUCCAU CUGAUGAGGNNNNNNNNCCGAA AUCGUCAG | 5856 |
| 1150 | UGACGAUUA UGGAAGUG | 1701 | CACUUCCA CUGAUGAGGNNNNNNNNCCGAA AAUCGUCA | 5857 |
| 1180 | CAGGAAAUU ACACUGUC | 1702 | GACAGUGU CUGAUGAGGNNNNNNNNCCGAA AUUUCCUG | 5858 |
| 1181 | AGGAAAUUA CACUGUCA | 1703 | UGACAGUG CUGAUGAGGNNNNNNNNCCGAA AAUUUCCU | 5859 |
| 1188 | UACACUGUC AUCCUUAC | 1704 | GUAAGGAU CUGAUGAGGNNNNNNNNCCGAA ACAGUGUA | 5860 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1191 | ACUGUCAUC CUUACCAA | 1705 | UUGGUAAG CUGAUGAGGNNNNNNNNCCGAA AUGACAGU | 5861 |
| 1194 | GUCAUCCUU ACCAAUCC | 1706 | GGAUUGGU CUGAUGAGGNNNNNNNNCCGAA AGGAUGAC | 5862 |
| 1195 | UCAUCCUUA CCAAUCCC | 1707 | GGGAUUGG CUGAUGAGGNNNNNNNNCCGAA AAGGAUGA | 5863 |
| 1201 | UUACCAAUC CCAUUUCA | 1708 | UGAAAUGG CUGAUGAGGNNNNNNNNCCGAA AUUGGUAA | 5864 |
| 1206 | AAUCCCAUU UCAAAGGA | 1709 | UCCUUUGA CUGAUGAGGNNNNNNNNCCGAA AUGGGAUU | 5865 |
| 1207 | AUCCCAUUU CAAAGGAG | 1710 | CUCCUUUG CUGAUGAGGNNNNNNNNCCGAA AUGGGAU | 5866 |
| 1208 | UCCCAUUUC AAAGGAGA | 1711 | UCUCCUUU CUGAUGAGGNNNNNNNNCCGAA AAAUGGGA | 5867 |
| 1233 | CAUGUGGUC UCUCUGGU | 1712 | ACCAGAGA CUGAUGAGGNNNNNNNNCCGAA ACCACAUG | 5868 |
| 1235 | UGUGGUCUC UCUGGUUG | 1713 | CAACCAGA CUGAUGAGGNNNNNNNNCCGAA AGACCACA | 5869 |
| 1237 | UGGUCUCUC UGGUUGUG | 1714 | CACAACCA CUGAUGAGGNNNNNNNNCCGAA AGAGACCA | 5870 |
| 1242 | UCUCUGGUU GUGUAUGU | 1715 | ACAUACAC CUGAUGAGGNNNNNNNNCCGAA ACCAGAGA | 5871 |
| 1247 | GGUUGUGUA UGUCCCAC | 1716 | GUGGGACA CUGAUGAGGNNNNNNNNCCGAA ACACAACC | 5872 |
| 1251 | GUGUAUGUC CCACCCCA | 1717 | UGGGGUGG CUGAUGAGGNNNNNNNNCCGAA ACAUACAC | 5873 |
| 1263 | CCCCAGAUU GGUGAGAA | 1718 | UUCUCACC CUGAUGAGGNNNNNNNNCCGAA AUCUGGGG | 5874 |
| 1274 | UGAGAAAUC UCUAAUCU | 1719 | AGAUUAGA CUGAUGAGGNNNNNNNNCCGAA AUUUCUCA | 5875 |
| 1275 | AGAAAUCUC UAAUCUCU | 1720 | AGAGAUUA CUGAUGAGGNNNNNNNNCCGAA AGAUUUCU | 5876 |
| 1278 | AAAUCUCUA AUCUCUCC | 1721 | GGAGAGAU CUGAUGAGGNNNNNNNNCCGAA AGAGAUUU | 5877 |
| 1281 | UCUCUAAUC UCUCCUGU | 1722 | ACAGGAGA CUGAUGAGGNNNNNNNNCCGAA AUUAGAGA | 5878 |
| 1283 | UCUAAUCUC UCCUGUGG | 1723 | CCACAGGA CUGAUGAGGNNNNNNNNCCGAA AGAUUAGA | 5879 |
| 1285 | UAAUCUCUC CUGUGGAU | 1724 | AUCCACAG CUGAUGAGGNNNNNNNNCCGAA AGAGAUUA | 5880 |
| 1294 | CUGUGGAUU CCUACCAG | 1725 | CUGGUAGG CUGAUGAGGNNNNNNNNCCGAA AUCCACAG | 5881 |
| 1295 | UGUGGAUUC CUACCAGU | 1726 | ACUGGUAG CUGAUGAGGNNNNNNNNCCGAA AAUCCACA | 5882 |
| 1298 | GGAUUCCUA CCAGUACG | 1727 | CGUACUGG CUGAUGAGGNNNNNNNNCCGAA AGGAAUCC | 5883 |
| 1304 | CUACCAGUA CGGCACCA | 1728 | UGGUGCCG CUGAUGAGGNNNNNNNNCCGAA ACUGGUAG | 5884 |
| 1315 | GCACCACUC AAACGCUG | 1729 | CAGCGUUU CUGAUGAGGNNNNNNNNCCGAA AGUGGUGC | 5885 |
| 1330 | UGACAUGUA CGGUCUAU | 1730 | AUAGACCG CUGAUGAGGNNNNNNNNCCGAA ACAUGUCA | 5886 |
| 1335 | UGUACGGUC UAUGCCAU | 1731 | AUGGCAUA CUGAUGAGGNNNNNNNNCCGAA ACCGUACA | 5887 |
| 1337 | UACGGUCUA UGCCAUUC | 1732 | GAAUGGCA CUGAUGAGGNNNNNNNNCCGAA AGACCGUA | 5888 |
| 1344 | UAUGCCAUU CCUCCCCC | 1733 | GGGGGAGG CUGAUGAGGNNNNNNNNCCGAA AUGGCAUA | 5889 |
| 1345 | AUGCCAUUC CUCCCCCG | 1734 | CGGGGGAG CUGAUGAGGNNNNNNNNCCGAA AAUGGCAU | 5890 |
| 1348 | CCAUUCCUC CCCGCAU | 1735 | AUGCGGGG CUGAUGAGGNNNNNNNNCCGAA AGGAAUGG | 5891 |
| 1357 | CCCCGCAUC ACAUCCAC | 1736 | GUGGAUGU CUGAUGAGGNNNNNNNNCCGAA AUGCGGGG | 5892 |
| 1362 | CAUCACAUC CACUGGUA | 1737 | UACCAGUG CUGAUGAGGNNNNNNNNCCGAA AUGUGAUG | 5893 |
| 1370 | CCACUGGUA UUGGCAGU | 1738 | ACUGCCAA CUGAUGAGGNNNNNNNNCCGAA ACCAGUGG | 5894 |
| 1372 | ACUGGUAUU GGCAGUUG | 1739 | CAACUGCC CUGAUGAGGNNNNNNNNCCGAA AUACCAGU | 5895 |
| 1379 | UUGGCAGUU GGAGGAAG | 1740 | CUUCCUCC CUGAUGAGGNNNNNNNNCCGAA ACUGCCAA | 5896 |
| 1416 | CAAGCUGUC UCAGUGAC | 1741 | GUCACUGA CUGAUGAGGNNNNNNNNCCGAA ACAGCUUG | 5897 |
| 1418 | AGCUGUCUC AGUGACAA | 1742 | UUGUCACU CUGAUGAGGNNNNNNNNCCGAA AGACAGCU | 5898 |
| 1433 | AAACCCAUA CCCUUGUG | 1743 | CACAAGGG CUGAUGAGGNNNNNNNNCCGAA AUGGGUUU | 5899 |
| 1438 | CAUACCCUU GUGAAGAA | 1744 | UUCUUCAC CUGAUGAGGNNNNNNNNCCGAA AGGGUAUG | 5900 |
| 1466 | GGAGGACUU CCAGGGAG | 1745 | CUCCCUGG CUGAUGAGGNNNNNNNNCCGAA AGUCCUCC | 5901 |
| 1467 | GAGGACUUC CAGGGAGG | 1746 | CCUCCCUG CUGAUGAGGNNNNNNNNCCGAA AAGUCCUC | 5902 |
| 1480 | GAGGAAAUA AAAUUGAA | 1747 | UUCAAUUU CUGAUGAGGNNNNNNNNCCGAA AUUUCCUC | 5903 |
| 1485 | AAUAAAAUU GAAGUUAA | 1748 | UUAACUUC CUGAUGAGGNNNNNNNNCCGAA AUUUUAUU | 5904 |
| 1491 | AUUGAAGUU AAUAAAAA | 1749 | UUUUUAUU CUGAUGAGGNNNNNNNNCCGAA ACUUCAAU | 5905 |
| 1492 | UUGAAGUUA AUAAAAAU | 1750 | AUUUUUAU CUGAUGAGGNNNNNNNNCCGAA AACUUCAA | 5906 |
| 1495 | AAGUUAAUA AAAAUCAA | 1751 | UUGAUUUU CUGAUGAGGNNNNNNNNCCGAA AUUAACUU | 5907 |
| 1501 | AUAAAAAUC AAUUUGCU | 1752 | AGCAAAUU CUGAUGAGGNNNNNNNNCCGAA AUUUUUAU | 5908 |
| 1505 | AAAUCAAUU UGCUCUAA | 1753 | UUAGAGCA CUGAUGAGGNNNNNNNNCCGAA AUUGAUUU | 5909 |
| 1506 | AAUCAAUUU GCUCUAAU | 1754 | AUUAGAGC CUGAUGAGGNNNNNNNNCCGAA AAUUGAUU | 5910 |
| 1510 | AAUUUGCUC UAAUUGAA | 1755 | UUCAAUUA CUGAUGAGGNNNNNNNNCCGAA AGCAAAUU | 5911 |
| 1512 | UUUGCUCUA AUUGAAGG | 1756 | CCUUCAAU CUGAUGAGGNNNNNNNNCCGAA AGAGCAAA | 5912 |
| 1515 | GCUCUAAUU GAAGGAAA | 1757 | UUUCCUUC CUGAUGAGGNNNNNNNNCCGAA AUUAGAGC | 5913 |
| 1536 | AAAACUGUA AGUACCCU | 1758 | AGGGUACU CUGAUGAGGNNNNNNNNCCGAA ACAGUUUU | 5914 |
| 1540 | CUGUAAGUA CCCUUGUU | 1759 | AACAAGGG CUGAUGAGGNNNNNNNNCCGAA ACUUACAG | 5915 |
| 1545 | AGUACCCUU GUUAUCCA | 1760 | UGGAUAAC CUGAUGAGGNNNNNNNNCCGAA AGGGUACU | 5916 |
| 1548 | ACCCUUGUU AUCCAAGC | 1761 | GCUUGGAU CUGAUGAGGNNNNNNNNCCGAA ACAAGGGU | 5917 |
| 1549 | CCCUUGUUA UCCAAGCG | 1762 | CGCUUGGA CUGAUGAGGNNNNNNNNCCGAA AACAAGGG | 5918 |
| 1551 | CUUGUUAUC CAAGCGGC | 1763 | GCCGCUUG CUGAUGAGGNNNNNNNNCCGAA AUAACAAG | 5919 |
| 1568 | AAAUGUGUC AGCUUUGU | 1764 | ACAAAGCU CUGAUGAGGNNNNNNNNCCGAA ACACAUUU | 5920 |
| 1573 | UGUCAGCUU UGUACAAA | 1765 | UUUGUACA CUGAUGAGGNNNNNNNNCCGAA AGCUGACA | 5921 |
| 1574 | GUCAGCUUU GUACAAAU | 1766 | AUUUGUAC CUGAUGAGGNNNNNNNNCCGAA AAGCUGAC | 5922 |
| 1577 | AGCUUUGUA CAAAUGUG | 1767 | CACAUUUG CUGAUGAGGNNNNNNNNCCGAA ACAAAGCU | 5923 |
| 1593 | GAAGCGGUC AACAAAGU | 1768 | ACUUUGUU CUGAUGAGGNNNNNNNNCCGAA ACCGCUUC | 5924 |
| 1602 | AACAAAGUC GGGAGAGG | 1769 | CCUCUCCC CUGAUGAGGNNNNNNNNCCGAA ACUUUGUU | 5925 |
| 1623 | AGGGUGAUC UCCUUCCA | 1770 | UGGAAGGA CUGAUGAGGNNNNNNNNCCGAA AUCACCCU | 5926 |
| 1625 | GGUGAUCUC CUUCCACG | 1771 | CGUGGAAG CUGAUGAGGNNNNNNNNCCGAA AGAUCACC | 5927 |
| 1628 | GAUCUCCUU CCACGUGA | 1772 | UCACGUGG CUGAUGAGGNNNNNNNNCCGAA AGGAGAUC | 5928 |
| 1629 | AUCUCCUUC CACGUGAC | 1773 | GUCACGUG CUGAUGAGGNNNNNNNNCCGAA AAGGAGAU | 5929 |
| 1645 | CCAGGGGUC UGAAAUU | 1774 | AAUUUCAG CUGAUGAGGNNNNNNNNCCGAA ACCCCUGG | 5930 |
| 1653 | CCUGAAAUU ACUUUGCA | 1775 | UGCAAAGU CUGAUGAGGNNNNNNNNCCGAA AUUUCAGG | 5931 |
| 1654 | CUGAAAUUA CUUUGCAA | 1776 | UUGCAAAG CUGAUGAGGNNNNNNNNCCGAA AAUUUCAG | 5932 |
| 1657 | AAAUUACUU UGCAACCU | 1777 | AGGUUGCA CUGAUGAGGNNNNNNNNCCGAA AGUAAUUU | 5933 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1658 | AAUUACUUU GCAACCUG | 1778 | CAGGUUGC CUGAUGAGGNNNNNNNNCCGAA AAGUAAUU | 5934 |
| 1697 | GAGCGUGUC UUUGUGGU | 1779 | ACCACAAA CUGAUGAGGNNNNNNNNCCGAA ACACGCUC | 5935 |
| 1699 | GCGUGUCUU UGUGGUGC | 1780 | GCACCACA CUGAUGAGGNNNNNNNNCCGAA AGACACGC | 5936 |
| 1700 | CGUGUCUUU GUGGUGCA | 1781 | UGCACCAC CUGAUGAGGNNNNNNNNCCGAA AAGACACG | 5937 |
| 1721 | AGACAGAUC UACGUUUG | 1782 | CAAACGUA CUGAUGAGGNNNNNNNNCCGAA AUCUGUCU | 5938 |
| 1723 | ACAGAUCUA CGUUUGAG | 1783 | CUCAAACG CUGAUGAGGNNNNNNNNCCGAA AGAUCUGU | 5939 |
| 1727 | AUCUACGUU UGAGAACC | 1784 | GGUUCUCA CUGAUGAGGNNNNNNNNCCGAA ACGUAGAU | 5940 |
| 1728 | UCUACGUUU GAGAACCU | 1785 | AGGUUCUC CUGAUGAGGNNNNNNNNCCGAA AACGUAGA | 5941 |
| 1737 | GAGAACCUC ACAUGGUA | 1786 | UACCAUGU CUGAUGAGGNNNNNNNNCCGAA AGGUUCUC | 5942 |
| 1745 | CACAUGGUA CAAGCUUG | 1787 | CAAGCUUG CUGAUGAGGNNNNNNNNCCGAA ACCAUGUG | 5943 |
| 1752 | UACAAGCUU GGCCCACA | 1788 | UGUGGGCC CUGAUGAGGNNNNNNNNCCGAA AGCUUGUA | 5944 |
| 1765 | CACAGCCUC UGCCAAUC | 1789 | GAUUGGCA CUGAUGAGGNNNNNNNNCCGAA AGGCUGUG | 5945 |
| 1773 | CUGCCAAUC CAUGUGGG | 1790 | CCCACAUG CUGAUGAGGNNNNNNNNCCGAA AUUGGCAG | 5946 |
| 1787 | GGGAGAGUU GCCCACAC | 1791 | GUGUGGGC CUGAUGAGGNNNNNNNNCCGAA ACUCUCCC | 5947 |
| 1800 | ACACCUGUU UGCAAGAA | 1792 | UUCUUGCA CUGAUGAGGNNNNNNNNCCGAA ACAGGUGU | 5948 |
| 1801 | CACCUGUUU GCAAGAAC | 1793 | GUUCUUGC CUGAUGAGGNNNNNNNNCCGAA AACAGGUG | 5949 |
| 1811 | CAAGAACUU GGAUACUC | 1794 | GAGUAUCC CUGAUGAGGNNNNNNNNCCGAA AGUUCUUG | 5950 |
| 1816 | ACUUGGAUA CUCUUUGG | 1795 | CCAAAGAG CUGAUGAGGNNNNNNNNCCGAA AUCCAAGU | 5951 |
| 1819 | UGGAUACUC UUUGGAAA | 1796 | UUUCCAAA CUGAUGAGGNNNNNNNNCCGAA AGUAUCCA | 5952 |
| 1821 | GAUACUCUU UGGAAAUU | 1797 | AAUUUCCA CUGAUGAGGNNNNNNNNCCGAA AGAGUAUC | 5953 |
| 1822 | AUACUCUUU GGAAAUUG | 1798 | CAAUUUCC CUGAUGAGGNNNNNNNNCCGAA AAGAGUAU | 5954 |
| 1829 | UUGGAAAUU GAAUGCCA | 1799 | UGGCAUUC CUGAUGAGGNNNNNNNNCCGAA AUUUCCAA | 5955 |
| 1844 | CACCAUGUU CUCUAAUA | 1800 | UAUUAGAG CUGAUGAGGNNNNNNNNCCGAA ACAUGGUG | 5956 |
| 1845 | ACCAUGUUC UCUAAUAG | 1801 | CUAUUAGA CUGAUGAGGNNNNNNNNCCGAA AACAUGGU | 5957 |
| 1847 | CAUGUUCUC UAAUAGCA | 1802 | UGCUAUUA CUGAUGAGGNNNNNNNNCCGAA AGAACAUG | 5958 |
| 1849 | UGUUCUCUA AUAGCACA | 1803 | UGUGCUAU CUGAUGAGGNNNNNNNNCCGAA AGAGAACA | 5959 |
| 1852 | UCUCUAAUA GCACAAAU | 1804 | AUUUGUGC CUGAUGAGGNNNNNNNNCCGAA AUUAGAGA | 5960 |
| 1866 | AAUGCAUU UUGAUCAU | 1805 | AUGAUCAA CUGAUGAGGNNNNNNNNCCGAA AUGUCAUU | 5961 |
| 1867 | AUGACAUUU UGAUCAUG | 1806 | CAUGAUCA CUGAUGAGGNNNNNNNNCCGAA AAUGUCAU | 5962 |
| 1868 | UGACAUUUU GAUCAUGG | 1807 | CCAUGAUC CUGAUGAGGNNNNNNNNCCGAA AAAUGUCA | 5963 |
| 1872 | AUUUUGAUC AUGGAGCU | 1808 | AGCUCCAU CUGAUGAGGNNNNNNNNCCGAA AUCAAAAU | 5964 |
| 1881 | AUGGAGCUU AAGAAUGC | 1809 | GCAUUCUU CUGAUGAGGNNNNNNNNCCGAA AGCUCCAU | 5965 |
| 1882 | UGGAGCUUA AGAAUGCA | 1810 | UGCAUUCU CUGAUGAGGNNNNNNNNCCGAA AAGCUCCA | 5966 |
| 1892 | GAAUGCAUC CUUGCAGG | 1811 | CCUGCAAG CUGAUGAGGNNNNNNNNCCGAA AUGCAUUC | 5967 |
| 1895 | UGCAUCCUU GCAGGACC | 1812 | GGUCCUGC CUGAUGAGGNNNNNNNNCCGAA AGGAUGCA | 5968 |
| 1913 | AGGAGACUA UGUCUGCC | 1813 | GGCAGACA CUGAUGAGGNNNNNNNNCCGAA AGUCUCCU | 5969 |
| 1917 | GACUAUGUC UGCCUUGC | 1814 | GCAAGGCA CUGAUGAGGNNNNNNNNCCGAA ACAUAGUC | 5970 |
| 1923 | GUCUGCCUU GCUCAAGA | 1815 | UCUUGAGC CUGAUGAGGNNNNNNNNCCGAA AGGCAGAC | 5971 |
| 1927 | GCCUUGCUC AAGACAGG | 1816 | CCUGUCUU CUGAUGAGGNNNNNNNNCCGAA ACAAGGCC | 5972 |
| 1954 | AAAGACAUU GCGUGGUC | 1817 | GACCACGC CUGAUGAGGNNNNNNNNCCGAA AUGUCUUU | 5973 |
| 1962 | UGCGUGGUC AGGCAGCU | 1818 | AGCUGCCU CUGAUGAGGNNNNNNNNCCGAA ACCACGCA | 5974 |
| 1971 | AGGCAGCUC ACAGUCCU | 1819 | AGGACUGU CUGAUGAGGNNNNNNNNCCGAA AGCUGCCU | 5975 |
| 1977 | CUCACAGUC CUAGAGCG | 1820 | CGCUCUAG CUGAUGAGGNNNNNNNNCCGAA ACUGUGAG | 5976 |
| 1980 | ACAGUCCUA GAGCGUGU | 1821 | ACACGCUC CUGAUGAGGNNNNNNNNCCGAA AGGACUGU | 5977 |
| 2001 | CCCACGAUC ACAGGAAA | 1822 | UUUCCUGU CUGAUGAGGNNNNNNNNCCGAA AUCGUGGG | 5978 |
| 2020 | UGGAGAAUC AGACGACA | 1823 | UGUCGUCU CUGAUGAGGNNNNNNNNCCGAA AUUCUCCA | 5979 |
| 2032 | CGACAAGUA UUGGGGAA | 1824 | UUCCCCAA CUGAUGAGGNNNNNNNNCCGAA ACUUGUCG | 5980 |
| 2034 | ACAAGUAUU GGGGAAAG | 1825 | CUUUCCCC CUGAUGAGGNNNNNNNNCCGAA AUACUUGU | 5981 |
| 2046 | GAAAGCAUC GAAGUCUC | 1826 | GAGACUUC CUGAUGAGGNNNNNNNNCCGAA AUGCUUUC | 5982 |
| 2052 | AUCGAAGUC UCAUGCAC | 1827 | GUGCAUGA CUGAUGAGGNNNNNNNNCCGAA ACUUCGAU | 5983 |
| 2054 | CGAAGUCUC AUGCACGG | 1828 | CCGUGCAU CUGAUGAGGNNNNNNNNCCGAA AGACUUCG | 5984 |
| 2066 | CACGGCAUC UGGGAAUC | 1829 | GAUUCCCA CUGAUGAGGNNNNNNNNCCGAA AUGCCGUG | 5985 |
| 2074 | CUGGGAAUC CCCCUCCA | 1830 | UGGAGGGG CUGAUGAGGNNNNNNNNCCGAA AUUCCCAG | 5986 |
| 2080 | AUCCCCCUC CACAGAUC | 1831 | GAUCUGUG CUGAUGAGGNNNNNNNNCCGAA AGGGGGAU | 5987 |
| 2088 | CCACAGAUC AUGUGGUU | 1832 | AACCACAU CUGAUGAGGNNNNNNNNCCGAA AUCUGUGG | 5988 |
| 2096 | CAUGUGGUU UAAAGAUA | 1833 | UAUCUUUA CUGAUGAGGNNNNNNNNCCGAA ACCACAUG | 5989 |
| 2097 | AUGUGGUUU AAAGAUAA | 1834 | UUAUCUUU CUGAUGAGGNNNNNNNNCCGAA AACCACAU | 5990 |
| 2098 | UGUGGUUUA AAGAUAAU | 1835 | AUUAUCUU CUGAUGAGGNNNNNNNNCCGAA AAACCACA | 5991 |
| 2104 | UUAAAGAUA AUGAGACC | 1836 | GGUCUCAU CUGAUGAGGNNNNNNNNCCGAA AUCUUUAA | 5992 |
| 2115 | GAGACCCUU GUAGAAGA | 1837 | UCUUCUAC CUGAUGAGGNNNNNNNNCCGAA AGGGUCUC | 5993 |
| 2118 | ACCCUUGUA GAAGACUC | 1838 | GAGUCUUC CUGAUGAGGNNNNNNNNCCGAA ACAAGGGU | 5994 |
| 2126 | AGAAGACUC AGGCAUUG | 1839 | CAAUGCCU CUGAUGAGGNNNNNNNNCCGAA AGUCUUCU | 5995 |
| 2133 | UCAGGCAUU GUAUUGAA | 1840 | UUCAAUAC CUGAUGAGGNNNNNNNNCCGAA AUGCCUGA | 5996 |
| 2136 | GGCAUUGUA UUGAAGGA | 1841 | UCCUUCAA CUGAUGAGGNNNNNNNNCCGAA ACAAUGCC | 5997 |
| 2138 | CAUUGUAUU GAAGGAUG | 1842 | CAUCCUUC CUGAUGAGGNNNNNNNNCCGAA AUACAAUG | 5998 |
| 2160 | CGGAACCUC ACUAUCCG | 1843 | CGGAUAGU CUGAUGAGGNNNNNNNNCCGAA AGGUUCCG | 5999 |
| 2164 | ACCUCACUA UCCGCAGA | 1844 | UCUGCGGA CUGAUGAGGNNNNNNNNCCGAA AGUGAGGU | 6000 |
| 2166 | CUCACUAUC CGCAGAGU | 1845 | ACUCUGCG CUGAUGAGGNNNNNNNNCCGAA AUAGUGAG | 6001 |
| 2196 | GAAGGCCUC UACACCUG | 1846 | CAGGUGUA CUGAUGAGGNNNNNNNNCCGAA AGGCCUUC | 6002 |
| 2198 | AGGCCUCUA CACCUGCC | 1847 | GGCAGGUG CUGAUGAGGNNNNNNNNCCGAA AGAGGCCU | 6003 |
| 2220 | UGCAGUGUU CUUGGCUG | 1848 | CAGCCAAG CUGAUGAGGNNNNNNNNCCGAA ACACUGCA | 6004 |
| 2221 | GCAGUGUUC UUGGCUGU | 1849 | ACAGCCAA CUGAUGAGGNNNNNNNNCCGAA AACACUGC | 6005 |
| 2223 | AGUGUUCUU GGCUGUGC | 1850 | GCACAGCC CUGAUGAGGNNNNNNNNCCGAA AGAACACU | 6006 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 2246 | GGAGGCAUU UUUCAUAA | 1851 | UUAUGAAA CUGAUGAGGNNNNNNNNCCGAA AUGCCUCC | 6007 |
| 2247 | GAGGCAUUU UUCAUAAU | 1852 | AUUAUGAA CUGAUGAGGNNNNNNNNCCGAA AAUGCCUC | 6008 |
| 2248 | AGGCAUUUU UCAUAAUA | 1853 | UAUUAUGA CUGAUGAGGNNNNNNNNCCGAA AAAUGCCU | 6009 |
| 2249 | GGCAUUUUU CAUAAUAG | 1854 | CUAUUAUG CUGAUGAGGNNNNNNNNCCGAA AAAAUGCC | 6010 |
| 2250 | GCAUUUUUC AUAAUAGA | 1855 | UCUAUUAU CUGAUGAGGNNNNNNNNCCGAA AAAAAUGC | 6011 |
| 2253 | UUUUUCAUA AUAGAAGG | 1856 | CCUUCUAU CUGAUGAGGNNNNNNNNCCGAA AUGAAAAA | 6012 |
| 2256 | UUCAUAAUA GAAGGUGC | 1857 | GCACCUUC CUGAUGAGGNNNNNNNNCCGAA AUUAUGAA | 6013 |
| 2282 | GACGAACUU GGAAAUCA | 1858 | UGAUUUCC CUGAUGAGGNNNNNNNNCCGAA AGUUCGUC | 6014 |
| 2289 | UUGGAAAUC AUUAUUCU | 1859 | AGAAUAAU CUGAUGAGGNNNNNNNNCCGAA AUUUCCAA | 6015 |
| 2292 | GAAAUCAUU AUUCUAGU | 1860 | ACUAGAAU CUGAUGAGGNNNNNNNNCCGAA AAUGAUUC | 6016 |
| 2293 | AAAUCAUUA UUCUAGUA | 1861 | UACUAGAA CUGAUGAGGNNNNNNNNCCGAA AAUGAUUU | 6017 |
| 2295 | AUCAUUAUU CUAGUAGG | 1862 | CCUACUAG CUGAUGAGGNNNNNNNNCCGAA AUAAUGAU | 6018 |
| 2296 | UCAUUAUUC UAGUAGGC | 1863 | GCCUACUA CUGAUGAGGNNNNNNNNCCGAA AAUAAUGA | 6019 |
| 2298 | AUUAUUCUA GUAGGCAC | 1864 | GUGCCUAC CUGAUGAGGNNNNNNNNCCGAA AGAAUAAU | 6020 |
| 2301 | AUUCUAGUA GGCACGAC | 1865 | GUCGUGCC CUGAUGAGGNNNNNNNNCCGAA ACUAGAAU | 6021 |
| 2316 | ACGGUGAUU GCCAUGUU | 1866 | AACAUGGC CUGAUGAGGNNNNNNNNCCGAA AUCACCGU | 6022 |
| 2324 | UGCCAUGUU CUUCUGGC | 1867 | GCCAGAAG CUGAUGAGGNNNNNNNNCCGAA ACAUGGCA | 6023 |
| 2325 | GCCAUGUUC UUCUGGCU | 1868 | AGCCAGAA CUGAUGAGGNNNNNNNNCCGAA AACAUGGC | 6024 |
| 2327 | CAUGUUCUU CUGGCUAC | 1869 | GUAGCCAG CUGAUGAGGNNNNNNNNCCGAA AGAACAUG | 6025 |
| 2328 | AUGUUCUUC UGGCUACU | 1870 | AGUAGCCA CUGAUGAGGNNNNNNNNCCGAA AAGAACAU | 6026 |
| 2334 | UUCUGGCUA CUUCUUGU | 1871 | ACAAGAAG CUGAUGAGGNNNNNNNNCCGAA AGCCAGAA | 6027 |
| 2337 | UGGCUACUU CUUGUCAU | 1872 | AUGACAAG CUGAUGAGGNNNNNNNNCCGAA AGUAGCCA | 6028 |
| 2338 | GGCUACUUC UUGUCAUC | 1873 | GAUGACAA CUGAUGAGGNNNNNNNNCCGAA AAGUAGCC | 6029 |
| 2340 | CUACUUCUU GUCAUCAU | 1874 | AUGAUGAC CUGAUGAGGNNNNNNNNCCGAA AGAAGUAG | 6030 |
| 2343 | CUUCUUGUC AUCAUCCU | 1875 | AGGAUGAU CUGAUGAGGNNNNNNNNCCGAA ACAAGAAG | 6031 |
| 2346 | CUUGUCAUC AUCCUAGG | 1876 | CCUAGGAU CUGAUGAGGNNNNNNNNCCGAA AUGACAAG | 6032 |
| 2349 | GUCAUCAUC CUAGGGAC | 1877 | GUCCCUAG CUGAUGAGGNNNNNNNNCCGAA AUGAUGAC | 6033 |
| 2352 | AUCAUCCUA GGGACCGU | 1878 | ACGGUCCC CUGAUGAGGNNNNNNNNCCGAA AGGAUGAU | 6034 |
| 2361 | GGGACCGUU AAGCGGGC | 1879 | GCCCGCUU CUGAUGAGGNNNNNNNNCCGAA ACGGUCCC | 6035 |
| 2362 | GGACCGUUA AGCGGGCC | 1880 | GGCCCGCU CUGAUGAGGNNNNNNNNCCGAA AACGGUCC | 6036 |
| 2396 | GACAGGCUA CUUGUCCA | 1881 | UGGACAAG CUGAUGAGGNNNNNNNNCCGAA AGCCUGUC | 6037 |
| 2399 | AGGCUACUU GUCCAUCG | 1882 | CGAUGGAC CUGAUGAGGNNNNNNNNCCGAA AGUAGCCU | 6038 |
| 2402 | CUACUUGUC CAUCGUCA | 1883 | UGACGAUG CUGAUGAGGNNNNNNNNCCGAA ACAAGUAG | 6039 |
| 2406 | UUGUCCAUC GUCAUGGA | 1884 | UCCAUGAC CUGAUGAGGNNNNNNNNCCGAA AUGGACAA | 6040 |
| 2409 | UCCAUCGUC AUGGAUCC | 1885 | GGAUCCAU CUGAUGAGGNNNNNNNNCCGAA ACGAUGGA | 6041 |
| 2416 | UCAUGGAUC CAGAUGAA | 1886 | UUCAUCUG CUGAUGAGGNNNNNNNNCCGAA AUCCAUGA | 6042 |
| 2427 | GAUGAACUC CCAUUGGA | 1887 | UCCAAUGG CUGAUGAGGNNNNNNNNCCGAA AGUUCAUC | 6043 |
| 2432 | ACUCCCAUU GGAUGAAC | 1888 | GUUCAUCC CUGAUGAGGNNNNNNNNCCGAA AUGGGAGU | 6044 |
| 2443 | AUGAACAUU GUGAACGA | 1889 | UCGUUCAC CUGAUGAGGNNNNNNNNCCGAA AUGUUCAU | 6045 |
| 2458 | GACUGCCUU AUGAUGCC | 1890 | GGCAUCAU CUGAUGAGGNNNNNNNNCCGAA AGGCAGUC | 6046 |
| 2459 | ACUGCCUUA UGAUGCCA | 1891 | UGGCAUCA CUGAUGAGGNNNNNNNNCCGAA AAGGCAGU | 6047 |
| 2480 | AUGGGAAUU CCCCAGAG | 1892 | CUCUGGGG CUGAUGAGGNNNNNNNNCCGAA AUUCCCAU | 6048 |
| 2481 | UGGGAAUUC CCCAGAGA | 1893 | UCUCUGGG CUGAUGAGGNNNNNNNNCCGAA AAUUCCCA | 6049 |
| 2502 | CUGAACCUA GGUAAGCC | 1894 | GGCUUACC CUGAUGAGGNNNNNNNNCCGAA AGGUUCAG | 6050 |
| 2506 | ACCUAGGUA AGCCUCUU | 1895 | AAGAGGCU CUGAUGAGGNNNNNNNNCCGAA ACCUAGGU | 6051 |
| 2512 | GUAAGCCUC UUGGCCGU | 1896 | ACGGCCAA CUGAUGAGGNNNNNNNNCCGAA AGGCUUAC | 6052 |
| 2514 | AAGCCUCUU GGCCGUGG | 1897 | CCACGGCC CUGAUGAGGNNNNNNNNCCGAA AGAGGCUU | 6053 |
| 2528 | UGGUGCCUU UGGCCAAG | 1898 | CUUGGCCA CUGAUGAGGNNNNNNNNCCGAA AGGCACCA | 6054 |
| 2529 | GGUGCCUUU GGCCAAGA | 1899 | UCUUGGCC CUGAUGAGGNNNNNNNNCCGAA AAGGCACC | 6055 |
| 2541 | CAAGAGAUU GAAGCAGA | 1900 | UCUGCUUC CUGAUGAGGNNNNNNNNCCGAA AUCUCUUG | 6056 |
| 2555 | AGAUGCCUU UGGAAUUG | 1901 | CAAUUCCA CUGAUGAGGNNNNNNNNCCGAA AGGCAUCU | 6057 |
| 2556 | GAUGCCUUU GGAAUUGA | 1902 | UCAAUUCC CUGAUGAGGNNNNNNNNCCGAA AAGGCAUC | 6058 |
| 2562 | UUUGGAAUU GACAAGAC | 1903 | GUCUUGUC CUGAUGAGGNNNNNNNNCCGAA AUUCCAAA | 6059 |
| 2578 | CAGCAACUU GCAGGACA | 1904 | UGUCCUGC CUGAUGAGGNNNNNNNNCCGAA AGUUGCUG | 6060 |
| 2589 | AGGACAGUA GCAGUCAA | 1905 | UUGACUGC CUGAUGAGGNNNNNNNNCCGAA ACUGUCCU | 6061 |
| 2595 | GUAGCAGUC AAAAUGUU | 1906 | AACAUUUU CUGAUGAGGNNNNNNNNCCGAA ACUGCUAC | 6062 |
| 2603 | CAAAAUGUU GAAAGAAG | 1907 | CUUCUUUC CUGAUGAGGNNNNNNNNCCGAA ACAUUUUG | 6063 |
| 2632 | GUGAGCAUC GAGCUCUC | 1908 | GAGAGCUC CUGAUGAGGNNNNNNNNCCGAA AUGCUCAC | 6064 |
| 2638 | AUCGAGCUC UCAUGUCU | 1909 | AGACAUGA CUGAUGAGGNNNNNNNNCCGAA AGCUCGAU | 6065 |
| 2640 | CGAGCUCUC AUGUCUGA | 1910 | UCAGACAU CUGAUGAGGNNNNNNNNCCGAA AGAGCUCG | 6066 |
| 2645 | UCUCAUGUC UGAACUCA | 1911 | UGAGUUCA CUGAUGAGGNNNNNNNNCCGAA ACAUGAGA | 6067 |
| 2652 | UCUGAACUC AAGAUCCU | 1912 | AGGAUCUU CUGAUGAGGNNNNNNNNCCGAA AGUUCAGA | 6068 |
| 2658 | CUCAAGAUC CUCAUUCA | 1913 | UGAAUGAG CUGAUGAGGNNNNNNNNCCGAA AUCUUGAG | 6069 |
| 2661 | AAGAUCCUC AUUCAUAU | 1914 | AUAUGAAU CUGAUGAGGNNNNNNNNCCGAA AGGAUCUU | 6070 |
| 2664 | AUCCUCAUU CAUAUUGG | 1915 | CCAAUAUG CUGAUGAGGNNNNNNNNCCGAA AUGAGGAU | 6071 |
| 2665 | UCCUCAUUC AUAUUGGU | 1916 | ACCAAUAU CUGAUGAGGNNNNNNNNCCGAA AAUGAGGA | 6072 |
| 2668 | UCAUUCAUA UUGGUCAC | 1917 | GUGACCAA CUGAUGAGGNNNNNNNNCCGAA AUGAAUGA | 6073 |
| 2670 | AUUCAUAUU GGUCACCA | 1918 | UGGUGACC CUGAUGAGGNNNNNNNNCCGAA AUAUGAAU | 6074 |
| 2674 | AUAUUGGUC ACCAUCUC | 1919 | GAGAUGGU CUGAUGAGGNNNNNNNNCCGAA ACCAAUAU | 6075 |
| 2680 | GUCACCAUC UCAAUGUG | 1920 | CACAUUGA CUGAUGAGGNNNNNNNNCCGAA AUGGUGAC | 6076 |
| 2682 | CACCAUCUC AAUGUGGU | 1921 | ACCACAUU CUGAUGAGGNNNNNNNNCCGAA AGAUGGUG | 6077 |
| 2691 | AAUGUGGUC AACCUUCU | 1922 | AGAAGGUU CUGAUGAGGNNNNNNNNCCGAA ACCACAUU | 6078 |
| 2697 | GUCAACCUU CUAGGUGC | 1923 | GCACCUAG CUGAUGAGGNNNNNNNNCCGAA AGGUUGAC | 6079 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 2698 | UCAACCUUC UAGGUGCC | 1924 | GGCACCUA CUGAUGAGGNNNNNNNNCCGAA AAGGUUGA | 6080 |
| 2700 | AACCUUCUA GGUGCCUG | 1925 | CAGGCACC CUGAUGAGGNNNNNNNNCCGAA AGAAGGUU | 6081 |
| 2710 | GUGCCUGUA CCAAGCCA | 1926 | UGGCUUGG CUGAUGAGGNNNNNNNNCCGAA ACAGGCAC | 6082 |
| 2730 | GGGCCACUC AUGGUGAU | 1927 | AUCACCAU CUGAUGAGGNNNNNNNNCCGAA AGUGGCCC | 6083 |
| 2739 | AUGGUGAUU GUGGAAUU | 1928 | AAUUCCAC CUGAUGAGGNNNNNNNNCCGAA AUCACCAU | 6084 |
| 2747 | UGUGGAAUU CUGCAAAU | 1929 | AUUUGCAG CUGAUGAGGNNNNNNNNCCGAA AUUCCACA | 6085 |
| 2748 | GUGGAAUUC UGCAAAUU | 1930 | AAUUUGCA CUGAUGAGGNNNNNNNNCCGAA AAUUCCAC | 6086 |
| 2756 | CUGCAAAUU UGGAAACC | 1931 | GGUUUCCA CUGAUGAGGNNNNNNNNCCGAA AUUUGCAG | 6087 |
| 2757 | UGCAAAUUU GGAAACCU | 1932 | AGGUUUCC CUGAUGAGGNNNNNNNNCCGAA AAUUUGCA | 6088 |
| 2768 | AAACCUGUC CACUUACC | 1933 | GGUAAGUG CUGAUGAGGNNNNNNNNCCGAA ACAGGUUU | 6089 |
| 2773 | UGUCCACUU ACCUGAGG | 1934 | CCUCAGGU CUGAUGAGGNNNNNNNNCCGAA AGUGGACA | 6090 |
| 2774 | GUCCACUUA CCUGAGGA | 1935 | UCCUCAGG CUGAUGAGGNNNNNNNNCCGAA AAGUGGAC | 6091 |
| 2798 | AAAUGAAUU UGUCCCCU | 1936 | AGGGGACA CUGAUGAGGNNNNNNNNCCGAA AUUCAUUU | 6092 |
| 2799 | AAUGAAUUU GUCCCCUA | 1937 | UAGGGGAC CUGAUGAGGNNNNNNNNCCGAA AAUUCAUU | 6093 |
| 2802 | GAAUUUGUC CCCUACAA | 1938 | UUGUAGGG CUGAUGAGGNNNNNNNNCCGAA ACAAAUUC | 6094 |
| 2807 | UGUCCCCUA CAAGACCA | 1939 | UGGUCUUG CUGAUGAGGNNNNNNNNCCGAA AGGGGACA | 6095 |
| 2828 | GGCACGAUU CCGUCAAG | 1940 | CUUGACGG CUGAUGAGGNNNNNNNNCCGAA AUCGUGCC | 6096 |
| 2829 | GCACGAUUC CGUCAAGG | 1941 | CCUUGACG CUGAUGAGGNNNNNNNNCCGAA AAUCGUGC | 6097 |
| 2833 | GAUUCCGUC AAGGGAAA | 1942 | UUUCCCUU CUGAUGAGGNNNNNNNNCCGAA ACGGAAUC | 6098 |
| 2846 | GAAAGACUA CGUUGGAG | 1943 | CUCCAACG CUGAUGAGGNNNNNNNNCCGAA AGUCUUUC | 6099 |
| 2850 | GACUACGUU GGAGCAAU | 1944 | AUUGCUCC CUGAUGAGGNNNNNNNNCCGAA ACGUAGUC | 6100 |
| 2859 | GGAGCAAUC CCUGUGGA | 1945 | UCCACAGG CUGAUGAGGNNNNNNNNCCGAA AUUGCUCC | 6101 |
| 2869 | CUGUGGAUC UGAAACGG | 1946 | CCGUUUCA CUGAUGAGGNNNNNNNNCCGAA AUCCACAG | 6102 |
| 2882 | ACGGCGCUU GGACAGCA | 1947 | UGCUGUCC CUGAUGAGGNNNNNNNNCCGAA AGCGCCGU | 6103 |
| 2892 | GACAGCAUC ACCAGUAG | 1948 | CUACUGGU CUGAUGAGGNNNNNNNNCCGAA AUGCUGUC | 6104 |
| 2899 | UCACCAGUA GCCAGAGC | 1949 | GCUCUGGC CUGAUGAGGNNNNNNNNCCGAA ACUGGUGA | 6105 |
| 2909 | CCAGAGCUC AGCCAGCU | 1950 | AGCUGGCU CUGAUGAGGNNNNNNNNCCGAA AGCUCUGG | 6106 |
| 2918 | AGCCAGCUC UGGAUUUG | 1951 | CAAAUCCA CUGAUGAGGNNNNNNNNCCGAA AGCUGGCU | 6107 |
| 2924 | CUCUGGAUU UGUGGAGG | 1952 | CCUCCACA CUGAUGAGGNNNNNNNNCCGAA AUCCAGAG | 6108 |
| 2925 | UCUGGAUUU GUGGAGGA | 1953 | UCCUCCAC CUGAUGAGGNNNNNNNNCCGAA AAUCCAGA | 6109 |
| 2939 | GGAGAAGUC CCUCAGUG | 1954 | CACUGAGG CUGAUGAGGNNNNNNNNCCGAA ACUUCUCC | 6110 |
| 2943 | AAGUCCCUC AGUGAUGU | 1955 | ACAUCACU CUGAUGAGGNNNNNNNNCCGAA AGGGACUU | 6111 |
| 2952 | AGUGAUGUA GAAGAAGA | 1956 | UCUUCUUC CUGAUGAGGNNNNNNNNCCGAA ACAUCACU | 6112 |
| 2968 | AGGAAGCUC CUGAAGAU | 1957 | AUCUUCAG CUGAUGAGGNNNNNNNNCCGAA AGCUUCCU | 6113 |
| 2977 | CUGAAGAUC UGUAUAAG | 1958 | CUUAUACA CUGAUGAGGNNNNNNNNCCGAA AUCUUCAG | 6114 |
| 2981 | AGAUCUGUA UAAGGACU | 1959 | AGUCCUUA CUGAUGAGGNNNNNNNNCCGAA ACAGAUCU | 6115 |
| 2983 | AUCUGUAUA AGGACUUC | 1960 | GAAGUCCU CUGAUGAGGNNNNNNNNCCGAA AUACAGAU | 6116 |
| 2990 | UAAGGACUU CCUGACCU | 1961 | AGGUCAGG CUGAUGAGGNNNNNNNNCCGAA AGUCCUUA | 6117 |
| 2991 | AAGGACUUC CUGACCUU | 1962 | AAGGUCAG CUGAUGAGGNNNNNNNNCCGAA AAGUCCUU | 6118 |
| 2999 | CCUGACCUU GGAGCAUC | 1963 | GAUGCUCC CUGAUGAGGNNNNNNNNCCGAA AGGUCAGG | 6119 |
| 3007 | UGGAGCAUC UCAUCUGU | 1964 | ACAGAUGA CUGAUGAGGNNNNNNNNCCGAA AUGCUCCA | 6120 |
| 3009 | GAGCAUCUC AUCUGUUA | 1965 | UAACAGAU CUGAUGAGGNNNNNNNNCCGAA AGAUGCUC | 6121 |
| 3012 | CAUCUCAUC UGUUACAG | 1966 | CUGUAACA CUGAUGAGGNNNNNNNNCCGAA AUGAGAUG | 6122 |
| 3016 | UCAUCUGUU ACAGCUUC | 1967 | GAAGCUGU CUGAUGAGGNNNNNNNNCCGAA ACAGAUGA | 6123 |
| 3017 | CAUCUGUUA CAGCUUCC | 1968 | GGAAGCUG CUGAUGAGGNNNNNNNNCCGAA AACAGAUG | 6124 |
| 3023 | UUACAGCUU CCAAGUGG | 1969 | CCACUUGG CUGAUGAGGNNNNNNNNCCGAA AGCUGUAA | 6125 |
| 3024 | UACAGCUUC CAAGUGGC | 1970 | GCCACUUG CUGAUGAGGNNNNNNNNCCGAA AAGCUGUA | 6126 |
| 3034 | AAGUGGCUA AGGGCAUG | 1971 | CAUGCCCU CUGAUGAGGNNNNNNNNCCGAA AGCCACUU | 6127 |
| 3047 | CAUGGAGUU CUUGGCAU | 1972 | AUGCCAAG CUGAUGAGGNNNNNNNNCCGAA ACUCCAUG | 6128 |
| 3048 | AUGGAGUUC UUGGCAUC | 1973 | GAUGCCAA CUGAUGAGGNNNNNNNNCCGAA AACUCCAU | 6129 |
| 3050 | GGAGUUCUU GGCAUCGC | 1974 | GCGAUGCC CUGAUGAGGNNNNNNNNCCGAA AGAACUCC | 6130 |
| 3056 | CUUGGCAUC GCGAAAGU | 1975 | ACUUUCGC CUGAUGAGGNNNNNNNNCCGAA AUGCCAAG | 6131 |
| 3067 | GAAAGUGUA UCCACAGG | 1976 | CCUGUGGA CUGAUGAGGNNNNNNNNCCGAA ACACUUUC | 6132 |
| 3069 | AAGUGUAUC CACAGGGA | 1977 | UCCCUGUG CUGAUGAGGNNNNNNNNCCGAA AUACACUU | 6133 |
| 3094 | CACGAAAUA UCCUCUUA | 1978 | UAAGAGGA CUGAUGAGGNNNNNNNNCCGAA AUUUCGUG | 6134 |
| 3096 | CGAAAUAUC CUCUUAUC | 1979 | GAUAAGAG CUGAUGAGGNNNNNNNNCCGAA AUAUUUCG | 6135 |
| 3099 | AAUAUCCUC UUAUCGGA | 1980 | UCCGAUAA CUGAUGAGGNNNNNNNNCCGAA AGGAUAUU | 6136 |
| 3101 | UAUCCUCUU AUCGGAGA | 1981 | UCUCCGAU CUGAUGAGGNNNNNNNNCCGAA AGAGGAUA | 6137 |
| 3102 | AUCCUCUUA UCGGAGAA | 1982 | UUCUCCGA CUGAUGAGGNNNNNNNNCCGAA AAGAGGAU | 6138 |
| 3104 | CCUCUUAUC GGAGAAGG | 1983 | UCUUCUCC CUGAUGAGGNNNNNNNNCCGAA AUAAGAGG | 6139 |
| 3120 | AACGUGGUU AAAAUCUG | 1984 | CAGAUUUU CUGAUGAGGNNNNNNNNCCGAA ACCACGUU | 6140 |
| 3121 | ACGUGGUUA AAAUCUGU | 1985 | ACAGAUUU CUGAUGAGGNNNNNNNNCCGAA AACCACGU | 6141 |
| 3126 | GUUAAAAUC UGUGACUU | 1986 | AAGUCACA CUGAUGAGGNNNNNNNNCCGAA AUUUUAAC | 6142 |
| 3134 | CUGUGACUU UGGCUUGG | 1987 | CCAAGCCA CUGAUGAGGNNNNNNNNCCGAA AGUCACAG | 6143 |
| 3135 | UGUGACUUU GGCUUGGC | 1988 | GCCAAGCC CUGAUGAGGNNNNNNNNCCGAA AAGUCACA | 6144 |
| 3140 | CUUUGGCUU GGCCCGGG | 1989 | CCCGGGCC CUGAUGAGGNNNNNNNNCCGAA AGCCAAAG | 6145 |
| 3151 | CCCGGGAUA UUUAUAAA | 1990 | UUUAUAAA CUGAUGAGGNNNNNNNNCCGAA AUCCCGGG | 6146 |
| 3153 | CGGGAUAUU UAUAAAGA | 1991 | UCUUUAUA CUGAUGAGGNNNNNNNNCCGAA AUAUCCCG | 6147 |
| 3154 | GGGAUAUUU AUAAAGAU | 1992 | AUCUUUAU CUGAUGAGGNNNNNNNNCCGAA AAUAUCCC | 6148 |
| 3155 | GGAUAUUUA UAAAGAUC | 1993 | GAUCUUUA CUGAUGAGGNNNNNNNNCCGAA AAAUAUCC | 6149 |
| 3157 | AUAUUUAUA AAGAUCCA | 1994 | UGGAUCUU CUGAUGAGGNNNNNNNNCCGAA AUAAAUAU | 6150 |
| 3163 | AUAAAGAUC CAGAUUAU | 1995 | AUAAUCUG CUGAUGAGGNNNNNNNNCCGAA AUCUUUAU | 6151 |
| 3169 | AUCCAGAUU AUGUCAGA | 1996 | UCUGACAU CUGAUGAGGNNNNNNNNCCGAA AUCUGGAU | 6152 |

TABLE IV-continued

| Pos | Substrate | Seq ID No | HH Ribozyme Sequence (Human KDR VEGF Receptor-Hammerhead Ribozyme and Substrate Sequence) | Seq ID No |
|---|---|---|---|---|
| 3170 | UCCAGAUUA UGUCAGAA | 1997 | UUCUGACA CUGAUGAGGNNNNNNNNCCGAA AAUCUGGA | 6153 |
| 3174 | GAUUAUGUC AGAAAAGG | 1998 | CCUUUUCU CUGAUGAGGNNNNNNNNCCGAA ACAUAAUC | 6154 |
| 3190 | GAGAUGCUC GCCUCCCU | 1999 | AGGGAGGC CUGAUGAGGNNNNNNNNCCGAA AGCAUCUC | 6155 |
| 3195 | GCUCGCCUC CCUUUGAA | 2000 | UUCAAAGG CUGAUGAGGNNNNNNNNCCGAA AGGCGAGC | 6156 |
| 3199 | GCCUCCCUU UGAAAUGG | 2001 | CCAUUUCA CUGAUGAGGNNNNNNNNCCGAA AGGGAGGC | 6157 |
| 3200 | CCUCCCUUU GAAAUGGA | 2002 | UCCAUUUC CUGAUGAGGNNNNNNNNCCGAA AAGGGAGG | 6158 |
| 3225 | GAAACAAUU UUUGACAG | 2003 | CUGUCAAA CUGAUGAGGNNNNNNNNCCGAA AUUGUUUC | 6159 |
| 3226 | AAACAAUUU UUGACAGA | 2004 | UCUGUCAA CUGAUGAGGNNNNNNNNCCGAA AAUUGUUU | 6160 |
| 3227 | AACAAUUUU UGACAGAG | 2005 | CUCUGUCA CUGAUGAGGNNNNNNNNCCGAA AAAUUGUU | 6161 |
| 3228 | ACAAUUUUU GACAGAGU | 2006 | ACUCUGUC CUGAUGAGGNNNNNNNNCCGAA AAAAUUGU | 6162 |
| 3239 | CAGAGUGUA CACAAUCC | 2007 | GGAUUGUG CUGAUGAGGNNNNNNNNCCGAA ACACUCUG | 6163 |
| 3246 | UACACAAUC CAGAGUGA | 2008 | UCACUCUG CUGAUGAGGNNNNNNNNCCGAA AUUGUGUA | 6164 |
| 3258 | AGUGACGUC UGGUCUUU | 2009 | AAAGACCA CUGAUGAGGNNNNNNNNCCGAA ACGUCACU | 6165 |
| 3263 | CGUCUGGUC UUUUGGUG | 2010 | CACCAAAA CUGAUGAGGNNNNNNNNCCGAA ACCAGACG | 6166 |
| 3265 | UCUGGUCUU UUGGUGUU | 2011 | AACACCAA CUGAUGAGGNNNNNNNNCCGAA AGACCAGA | 6167 |
| 3266 | CUGGUCUUU UGGUGUUU | 2012 | AAACACCA CUGAUGAGGNNNNNNNNCCGAA AAGACCAG | 6168 |
| 3267 | UGGUCUUUU GGUGUUUU | 2013 | AAAACACC CUGAUGAGGNNNNNNNNCCGAA AAAGACCA | 6169 |
| 3273 | UUUGGUGUU UUGCUGUG | 2014 | CACAGCAA CUGAUGAGGNNNNNNNNCCGAA ACACCAAA | 6170 |
| 3274 | UUGGUGUUU UGCUGUGG | 2015 | CCACAGCA CUGAUGAGGNNNNNNNNCCGAA AACACCAA | 6171 |
| 3275 | UGGUGUUUU GCUGUGGG | 2016 | CCCACAGC CUGAUGAGGNNNNNNNNCCGAA AAACACCA | 6172 |
| 3288 | UGGGAAAUA UUUUCCUU | 2017 | AAGGAAAA CUGAUGAGGNNNNNNNNCCGAA AUUUCCCA | 6173 |
| 3290 | GGAAAUAUU UUCCUUAG | 2018 | CUAAGGAA CUGAUGAGGNNNNNNNNCCGAA AUAUUUCC | 6174 |
| 3291 | GAAAUAUUU UCCUUAGG | 2019 | CCUAAGGA CUGAUGAGGNNNNNNNNCCGAA AAUAUUUC | 6175 |
| 3292 | AAAUAUUUU CCUUAGGU | 2020 | ACCUAAGG CUGAUGAGGNNNNNNNNCCGAA AAAUAUUU | 6176 |
| 3293 | AAUAUUUUC CUUAGGUG | 2021 | CACCUAAG CUGAUGAGGNNNNNNNNCCGAA AAAAUAUU | 6177 |
| 3296 | AUUUUCCUU AGGUGCUU | 2022 | AAGCACCU CUGAUGAGGNNNNNNNNCCGAA AGGAAAAU | 6178 |
| 3297 | UUUUCCUUA GGUGCUUC | 2023 | GAAGCACC CUGAUGAGGNNNNNNNNCCGAA AAGGAAAA | 6179 |
| 3304 | UAGGUGCUU CUCCAUAU | 2024 | AUAUGGAG CUGAUGAGGNNNNNNNNCCGAA AGCACCUA | 6180 |
| 3305 | AGGUGCUUC UCCAUAUC | 2025 | GAUAUGGA CUGAUGAGGNNNNNNNNCCGAA AAGCACCU | 6181 |
| 3307 | GUGCUUCUC CAUAUCCU | 2026 | AGGAUAUG CUGAUGAGGNNNNNNNNCCGAA AGAAGCAC | 6182 |
| 3311 | UUCUCCAUA UCCUGGGG | 2027 | CCCCAGGA CUGAUGAGGNNNNNNNNCCGAA AUGGAGAA | 6183 |
| 3313 | CUCCAUAUC CUGGGGUA | 2028 | UACCCCAG CUGAUGAGGNNNNNNNNCCGAA AUAUGGAG | 6184 |
| 3321 | CCUGGGGUA AAGAUUGA | 2029 | UCAAUCUU CUGAUGAGGNNNNNNNNCCGAA ACCCCAGG | 6185 |
| 3327 | GUAAAGAUU GAUGAAGA | 2030 | UCUUCAUC CUGAUGAGGNNNNNNNNCCGAA AUCUUUAC | 6186 |
| 3338 | UGAAGAAUU UUGUAGGC | 2031 | GCCUACAA CUGAUGAGGNNNNNNNNCCGAA AUUCUUCA | 6187 |
| 3339 | GAAGAAUUU UGUAGGCG | 2032 | CGCCUACA CUGAUGAGGNNNNNNNNCCGAA AAUUCUUC | 6188 |
| 3340 | AAGAAUUUU GUAGGCGA | 2033 | UCGCCUAC CUGAUGAGGNNNNNNNNCCGAA AAAUUCUU | 6189 |
| 3343 | AAUUUUGUA GGCGAUUG | 2034 | CAAUCGCC CUGAUGAGGNNNNNNNNCCGAA ACAAAAUU | 6190 |
| 3350 | UAGGCGAUU GAAAGAAG | 2035 | CUUCUUUC CUGAUGAGGNNNNNNNNCCGAA AUCGCCUA | 6191 |
| 3364 | AAGGAACUA GAAUGAGG | 2036 | CCUCAUUC CUGAUGAGGNNNNNNNNCCGAA AGUUCCUU | 6192 |
| 3382 | CCCCUGAUU AUACUACA | 2037 | UGUAGUAU CUGAUGAGGNNNNNNNNCCGAA AUCAGGGG | 6193 |
| 3383 | CCCUGAUUA UACUACAC | 2038 | GUGUAGUA CUGAUGAGGNNNNNNNNCCGAA AAUCAGGG | 6194 |
| 3385 | CUGAUUAUA CUACACCA | 2039 | UGGUGUAG CUGAUGAGGNNNNNNNNCCGAA AUAAUCAG | 6195 |
| 3388 | AUUAUACUA CACCAGAA | 2040 | UUCUGGUG CUGAUGAGGNNNNNNNNCCGAA AGUAUAAU | 6196 |
| 3401 | AGAAAUGUA CCAGACCA | 2041 | UGGUCUGG CUGAUGAGGNNNNNNNNCCGAA ACAUUUCU | 6197 |
| 3439 | AGCCCAGUC AGAGACCC | 2042 | GGGUCUCU CUGAUGAGGNNNNNNNNCCGAA ACUGGGCU | 6198 |
| 3452 | ACCCACGUU UUCAGAGU | 2043 | ACUCUGAA CUGAUGAGGNNNNNNNNCCGAA ACGUGGGU | 6199 |
| 3453 | CCCACGUUU UCAGAGUU | 2044 | AACUCUGA CUGAUGAGGNNNNNNNNCCGAA AACGUGGG | 6200 |
| 3454 | CCACGUUUU CAGAGUUG | 2045 | CAACUCUG CUGAUGAGGNNNNNNNNCCGAA AAACGUGG | 6201 |
| 3455 | CACGUUUUC AGAGUUGG | 2046 | CCAACUCU CUGAUGAGGNNNNNNNNCCGAA AAAACGUG | 6202 |
| 3461 | UUCAGAGUU GGUGGAAC | 2047 | GUUCCACC CUGAUGAGGNNNNNNNNCCGAA ACUCUGAA | 6203 |
| 3472 | UGGAACAUU UGGGAAAU | 2048 | AUUUCCCA CUGAUGAGGNNNNNNNNCCGAA AUGUUCCA | 6204 |
| 3473 | GGAACAUUU GGGAAAUC | 2049 | GAUUUCCC CUGAUGAGGNNNNNNNNCCGAA AAUGUUCC | 6205 |
| 3481 | UGGGAAAUC UCUUGCAA | 2050 | UUGCAAGA CUGAUGAGGNNNNNNNNCCGAA AUUUCCCA | 6206 |
| 3483 | GGAAAUCUC UUGCAAGC | 2051 | GCUUGCAA CUGAUGAGGNNNNNNNNCCGAA AGAUUUCC | 6207 |
| 3485 | AAAUCUCUU GCAAGCUA | 2052 | UAGCUUGC CUGAUGAGGNNNNNNNNCCGAA AGAGAUUU | 6208 |
| 3493 | UGCAAGCUA AUGCUCAG | 2053 | CUGAGCAU CUGAUGAGGNNNNNNNNCCGAA AGCUUGCA | 6209 |
| 3499 | CUAAUGCUC AGCAGGAU | 2054 | AUCCUGCU CUGAUGAGGNNNNNNNNCCGAA AGCAUUAG | 6210 |
| 3518 | CAAAGACUA CAUUGUUC | 2055 | GAACAAUG CUGAUGAGGNNNNNNNNCCGAA AGUCUUUG | 6211 |
| 3522 | GACUACAUU GUUCUUCC | 2056 | GGAAGAAC CUGAUGAGGNNNNNNNNCCGAA AUGUAGUC | 6212 |
| 3525 | UACAUUGUU CUUCCGAU | 2057 | AUCGGAAG CUGAUGAGGNNNNNNNNCCGAA ACAAUGUA | 6213 |
| 3526 | ACAUUGUUC UUCCGAUA | 2058 | UAUCGGAA CUGAUGAGGNNNNNNNNCCGAA AACAAUGU | 6214 |
| 3528 | AUUGUUCUU CCGAUAUC | 2059 | GAUAUCGG CUGAUGAGGNNNNNNNNCCGAA AGAACAAU | 6215 |
| 3529 | UUGUUCUUC CGAUAUCA | 2060 | UGAUAUCG CUGAUGAGGNNNNNNNNCCGAA AAGAACAA | 6216 |
| 3534 | CUUCCGAUA UCAGAGAC | 2061 | GUCUCUGA CUGAUGAGGNNNNNNNNCCGAA AUCGGAAG | 6217 |
| 3536 | UCCGAUAUC AGAGACUU | 2062 | AAGUCUCU CUGAUGAGGNNNNNNNNCCGAA AUAUCGGA | 6218 |
| 3544 | CAGAGACUU UGAGCAUG | 2063 | CAUGCUCA CUGAUGAGGNNNNNNNNCCGAA AGUCUCUG | 6219 |
| 3545 | AGAGACUUU GAGCAUGG | 2064 | CCAUGCUC CUGAUGAGGNNNNNNNNCCGAA AAGUCUCU | 6220 |
| 3562 | AAGAGGAUU CUGGACUC | 2065 | GAGUCCAG CUGAUGAGGNNNNNNNNCCGAA AUCCUCUU | 6221 |
| 3563 | AGAGGAUUC UGGACUCU | 2066 | AGAGUCCA CUGAUGAGGNNNNNNNNCCGAA AAUCCUCU | 6222 |
| 3570 | UCUGGACUC UCUCUGCC | 2067 | GGCAGAGA CUGAUGAGGNNNNNNNNCCGAA AGUCCAGA | 6223 |
| 3572 | UGGACUCUC UCUGCCUA | 2068 | UAGGCAGA CUGAUGAGGNNNNNNNNCCGAA AGAGUCCA | 6224 |
| 3574 | GACUCUCUC UGCCUACC | 2069 | GGUAGGCA CUGAUGAGGNNNNNNNNCCGAA AGAGAGUC | 6225 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3580 | CUCUGCCUA CCUCACCU | 2070 | AGGUGAGG CUGAUGAGGNNNNNNNNCCGAA AGGCAGAG | 6226 |
| 3584 | GCCUACCUC ACCUGUUU | 2071 | AAACAGGU CUGAUGAGGNNNNNNNNCCGAA AGGUAGGC | 6227 |
| 3591 | UCACCUGUU UCCUGUAU | 2072 | AUACAGGA CUGAUGAGGNNNNNNNNCCGAA ACAGGUGA | 6228 |
| 3592 | CACCUGUUU CCUGUAUG | 2073 | CAUACAGG CUGAUGAGGNNNNNNNNCCGAA AACAGGUG | 6229 |
| 3593 | ACCUGUUUC CUGUAUGG | 2074 | CCAUACAG CUGAUGAGGNNNNNNNNCCGAA AAACAGGU | 6230 |
| 3598 | UUUCCUGUA UGGAGGAG | 2075 | CUCCUCCA CUGAUGAGGNNNNNNNNCCGAA ACAGGAAA | 6231 |
| 3615 | GAGGAAGUA UGUGACCC | 2076 | GGGUCACA CUGAUGAGGNNNNNNNNCCGAA ACUUCCUC | 6232 |
| 3629 | CCCCAAAUU CCAUUAUG | 2077 | CAUAAUGG CUGAUGAGGNNNNNNNNCCGAA AUUGGGG | 6233 |
| 3630 | CCCAAAUUC CAUUAUGA | 2078 | UCAUAAUG CUGAUGAGGNNNNNNNNCCGAA AAUUUGGG | 6234 |
| 3634 | AAUUCCAUU AUGACAAC | 2079 | GUUGUCAU CUGAUGAGGNNNNNNNNCCGAA AUGGAAUU | 6235 |
| 3653 | AUUCCAUUA UGACAACA | 2080 | UGUUGUCA CUGAUGAGGNNNNNNNNCCGAA AAUGGAAU | 6236 |
| 3654 | GCAGGAAUC AGUCAGUA | 2081 | UACUGACU CUGAUGAGGNNNNNNNNCCGAA AUUCCUGC | 6237 |
| 3658 | GAAUCAGUC AGUAUCUG | 2082 | CAGAUACU CUGAUGAGGNNNNNNNNCCGAA ACUGAUUC | 6238 |
| 3662 | CAGUCAGUA UCUGCAGA | 2083 | UCUGCAGA CUGAUGAGGNNNNNNNNCCGAA ACUGACUG | 6239 |
| 3664 | GUCAGUAUC UGCAGAAC | 2084 | GUUCUGCA CUGAUGAGGNNNNNNNNCCGAA AUACUGAC | 6240 |
| 3676 | AGAACAGUA AGCGAAAG | 2085 | CUUUCGCU CUGAUGAGGNNNNNNNNCCGAA ACUGUUCU | 6241 |
| 3702 | GUGAGUGUA AAAACAUU | 2086 | AAUGUUUU CUGAUGAGGNNNNNNNNCCGAA ACACUCAC | 6242 |
| 3710 | AAAAACAUU UGAAGAUA | 2087 | UAUCUUCA CUGAUGAGGNNNNNNNNCCGAA AUGUUUUU | 6243 |
| 3711 | AAAACAUUU GAAGAUAU | 2088 | AUAUCUUC CUGAUGAGGNNNNNNNNCCGAA AAUGUUUU | 6244 |
| 3718 | UUGAAGAUA UCCCGUUA | 2089 | UAACGGGA CUGAUGAGGNNNNNNNNCCGAA AUCUUCAA | 6245 |
| 3720 | GAAGAUAUC CCGUUAGA | 2090 | UCUAACGG CUGAUGAGGNNNNNNNNCCGAA AUAUCUUC | 6246 |
| 3725 | UAUCCCGUU AGAAGAAC | 2091 | GUUCUUCU CUGAUGAGGNNNNNNNNCCGAA ACGGGAUA | 6247 |
| 3726 | AUCCCGUUA GAAGAACC | 2092 | GGUUCUUC CUGAUGAGGNNNNNNNNCCGAA AACGGGAU | 6248 |
| 3741 | CCAGAAGUA AAAGUAAU | 2093 | AUUACUUU CUGAUGAGGNNNNNNNNCCGAA ACUUCUGG | 6249 |
| 3747 | GUAAAAGUA AUCCCAGA | 2094 | UCUGGGAU CUGAUGAGGNNNNNNNNCCGAA ACUUUUAC | 6250 |
| 3750 | AAAGUAAUC CCAGAUGA | 2095 | UCAUCUGG CUGAUGAGGNNNNNNNNCCGAA AUUACUUU | 6251 |
| 3778 | ACAGUGGUA UGGUUCUU | 2096 | AAGAACCA CUGAUGAGGNNNNNNNNCCGAA ACCACUGU | 6252 |
| 3783 | GGUAUGGUU CUUGCCUC | 2097 | GAGGCAAG CUGAUGAGGNNNNNNNNCCGAA ACCAUACC | 6253 |
| 3784 | GUAUGGUUC UUGCCUCA | 2098 | UGAGGCAA CUGAUGAGGNNNNNNNNCCGAA AACCAUAC | 6254 |
| 3786 | AUGGUUCUU GCCUCAGA | 2099 | UCUGAGGC CUGAUGAGGNNNNNNNNCCGAA AGAACCAU | 6255 |
| 3791 | UCUUGCCUC AGAAGAGC | 2100 | GCUCUUCU CUGAUGAGGNNNNNNNNCCGAA AGGCAAGA | 6256 |
| 3808 | UGAAAACUU UGGAAGAC | 2101 | GUCUUCCA CUGAUGAGGNNNNNNNNCCGAA AGUUUUCA | 6257 |
| 3809 | GAAAACUUU GGAAGACA | 2102 | UGUCUUCC CUGAUGAGGNNNNNNNNCCGAA AAGUUUUC | 6258 |
| 3827 | AACCAAAUU AUCUCCAU | 2103 | AUGGAGAU CUGAUGAGGNNNNNNNNCCGAA AUUUGGUU | 6259 |
| 3828 | ACCAAAUUA UCUCCAUC | 2104 | GAUGGAGA CUGAUGAGGNNNNNNNNCCGAA AAUUUGGU | 6260 |
| 3830 | CAAAUUAUC UCCAUCUU | 2105 | AAGAUGGA CUGAUGAGGNNNNNNNNCCGAA AUAAUUUG | 6261 |
| 3832 | AAUUAUCUC CAUCUUUU | 2106 | AAAAGAUG CUGAUGAGGNNNNNNNNCCGAA AGAUAAUU | 6262 |
| 3836 | AUCUCCAUC UUUUGGUG | 2107 | CACCAAAA CUGAUGAGGNNNNNNNNCCGAA AUGGAGAU | 6263 |
| 3838 | CUCCAUCUU UUGGUGGA | 2108 | UCCACCAA CUGAUGAGGNNNNNNNNCCGAA AGAUGGAG | 6264 |
| 3839 | UCCAUCUUU UGGUGGAA | 2109 | UUCCACCA CUGAUGAGGNNNNNNNNCCGAA AAGAUGGA | 6265 |
| 3840 | CCAUCUUUU GGUGGAAU | 2110 | AUUCCACC CUGAUGAGGNNNNNNNNCCGAA AAAGAUGG | 6266 |
| 3872 | CAGGGAGUC UGUGGCAU | 2111 | AUGCCACA CUGAUGAGGNNNNNNNNCCGAA ACUCCCUG | 6267 |
| 3881 | UGUGGCAUC UGAAGGCU | 2112 | AGCCUUCA CUGAUGAGGNNNNNNNNCCGAA AUGCCACA | 6268 |
| 3890 | UGAAGGCUC AAACCAGA | 2113 | UCUGGUUU CUGAUGAGGNNNNNNNNCCGAA AGCCUUCA | 6269 |
| 3908 | AAGCGGCUA CCAGUCCG | 2114 | CGGACUGG CUGAUGAGGNNNNNNNNCCGAA AGCCGCUU | 6270 |
| 3914 | CUACCAGUC GGAUAUC | 2115 | GAUAUCCG CUGAUGAGGNNNNNNNNCCGAA ACUGGUAG | 6271 |
| 3920 | GUCCGGAUA UCACUCCG | 2116 | CGGAGUGA CUGAUGAGGNNNNNNNNCCCAA AUCCGGAC | 6272 |
| 3922 | CCGGAUAUC ACUCCGAU | 2117 | AUCGGAGU CUGAUGAGGNNNNNNNNCCGAA AUAUCCGG | 6273 |
| 3926 | AUAUCACUC CGAUGACA | 2118 | UGUCAUCG CUGAUGAGGNNNNNNNNCCCAA AGUGAUAU | 6274 |
| 3950 | CACCGUGUA CUCCAGUG | 2119 | CACUGGAG CUGAUGAGGNNNNNNNNCCGAA ACACGGUG | 6275 |
| 3953 | CGUGUACUC CAGUGAGG | 2120 | CCUCACUG CUGAUGAGGNNNNNNNNCCGAA AGUACACG | 6276 |
| 3972 | GCAGAACUU UUAAAGCU | 2121 | AGCUUUAA CUGAUGAGGNNNNNNNNCCGAA AGUUCUGC | 6277 |
| 3973 | CAGAACUUU UAAAGCUG | 2122 | CAGCUUUA CUGAUGAGGNNNNNNNNCCGAA AAGUUCUG | 6278 |
| 3974 | AGAACUUUU AAAGCUGA | 2123 | UCAGCUUU CUGAUGAGGNNNNNNNNCCGAA AAAGUUCU | 6279 |
| 3975 | GAACUUUUA AAGCUGAU | 2124 | AUCAGCUU CUGAUGAGGNNNNNNNNCCGAA AAAAGUUC | 6280 |
| 3984 | AAGCUGAUA GAGAUUGG | 2125 | CCAAUCUC CUGAUGAGGNNNNNNNNCCGAA AUCAGCUU | 6281 |
| 3990 | AUAGAGAUU GGAGUGCA | 2126 | UGCACUCC CUGAUGAGGNNNNNNNNCCGAA AUCUCUAU | 6282 |
| 4006 | AAACCGGUA GCACAGCC | 2127 | GGCUGUGC CUGAUGAGGNNNNNNNNCCGAA ACCGGUUU | 6283 |
| 4020 | GCCCAGAUU CUCCAGCC | 2128 | GGCUGGAG CUGAUGAGGNNNNNNNNCCGAA AUCUGGGC | 6284 |
| 4021 | CCCAGAUUC UCCAGCCU | 2129 | AGGCUGGA CUGAUGAGGNNNNNNNNCCGAA AAUCUGGG | 6285 |
| 4023 | CAGAUUCUC CAGCUGA | 2130 | UCAGGCUG CUGAUGAGGNNNNNNNNCCGAA AGAAUCUG | 6286 |
| 4052 | ACUGAGCUC UCCUCCUG | 2131 | CAGGAGGA CUGAUGAGGNNNNNNNNCCGAA AGCUCAGU | 6287 |
| 4054 | UGAGCUCUC CUCCUGUU | 2132 | AACAGGAG CUGAUGAGGNNNNNNNNCCGAA AGAGCUCA | 6288 |
| 4057 | GCUCUCCUC CUGUUUAA | 2133 | UUAAACAG CUGAUGAGGNNNNNNNNCCGAA AGGAGAGC | 6289 |
| 4062 | CCUCCUGUU UAAAAGGA | 2134 | UCCUUUUA CUGAUGAGGNNNNNNNNCCGAA ACAGGAGG | 6290 |
| 4063 | CUCCUGUUU AAAAGGAA | 2135 | UUCCUUUU CUGAUGAGGNNNNNNNNCCGAA AACAGGAG | 6291 |
| 4064 | UCCUGUUUA AAAGGAAG | 2136 | CUUCCUUU CUGAUGAGGNNNNNNNNCCGAA AAACAGGA | 6292 |
| 4076 | GGAAGCAUC CACACCCC | 2137 | GGGGUGUG CUGAUGAGGNNNNNNNNCCGAA AUGCUUCC | 6293 |
| 4089 | CCCCAACUC CCGGACAU | 2138 | AUGUCCGG CUGAUGAGGNNNNNNNNCCGAA AGUUGGGG | 6294 |
| 4098 | CCGGACAUC ACAUGAGA | 2139 | UCUCAUGU CUGAUGAGGNNNNNNNNCCGAA AUGUCCGG | 6295 |
| 4110 | UGAGAGGUC UGCUCAGA | 2140 | UCUGAGCA CUGAUGAGGNNNNNNNNCCGAA ACCUCUCA | 6296 |
| 4115 | GGUCUGCUC AGAUUUUG | 2141 | CAAAAUCU CUGAUGAGGNNNNNNNNCCGAA AGCAGACC | 6297 |
| 4120 | GCUCAGAUU UUGAAGUG | 2142 | CACUUCAA CUGAUGAGGNNNNNNNNCCGAA AUCUGAGC | 6298 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 4121 | CUCAGAUUU UGAAGUGU | 2143 | ACACUUCA CUGAUGAG<u>GNNNNNNNN</u>CCGAA AAUCUGAG | 6299 |
| 4122 | UCAGAUUUU GAAGUGUU | 2144 | AACACUUC CUGAUGAG<u>GNNNNNNNN</u>CCGAA AAAUCUGA | 6300 |
| 4130 | UGAAGUGUU GUUCUUUC | 2145 | GAAAGAAC CUGAUGAG<u>GNNNNNNNN</u>CCGAA ACACUUCA | 6301 |
| 4133 | AGUGUUGUU CUUUCCAC | 2146 | GUGGAAAG CUGAUGAG<u>GNNNNNNNN</u>CCGAA ACAACACU | 6302 |
| 4134 | GUGUUGUUC UUUCCACC | 2147 | GGUGGAAA CUGAUGAG<u>GNNNNNNNN</u>CCGAA AACAACAC | 6303 |
| 4136 | GUUGUUCUU UCCACCAG | 2148 | CUGGUGGA CUGAUGAG<u>GNNNNNNNN</u>CCGAA AGAACAAC | 6304 |
| 4137 | UUGUUCUUU CCACCAGC | 2149 | GCUGGUGG CUGAUGAG<u>GNNNNNNNN</u>CCGAA AAGAACAA | 6305 |
| 4138 | UGUUCUUUC CACCAGCA | 2150 | UGCUGGUG CUGAUGAG<u>GNNNNNNNN</u>CCGAA AAAGAACA | 6306 |
| 4153 | CAGGAAGUA GCCGCAUU | 2151 | AAUGCGGC CUGAUGAG<u>GNNNNNNNN</u>CCGAA ACUUCCUG | 6307 |
| 4161 | AGCCGCAUU UGAUUUUC | 2152 | GAAAAUCA CUGAUGAG<u>GNNNNNNNN</u>CCGAA AAUGCGGCU | 6308 |
| 4162 | GCCGCAUUU GAUUUUCA | 2153 | UGAAAAUC CUGAUGAG<u>GNNNNNNNN</u>CCGAA AAUGCGGC | 6309 |
| 4166 | CAUUUGAUU UUCAUUUC | 2154 | GAAAUGAA CUGAUGAG<u>GNNNNNNNN</u>CCGAA AUCAAAUG | 6310 |
| 4167 | AUUUGAUUU UCAUUUCG | 2155 | CGAAAUGA CUGAUGAG<u>GNNNNNNNN</u>CCGAA AAUCAAAU | 6311 |
| 4168 | UUUGAUUUU CAUUUCGA | 2156 | UCGAAAUG CUGAUGAG<u>GNNNNNNNN</u>CCGAA AAAUCAAA | 6312 |
| 4169 | UUGAUUUUC AUUUCGAC | 2157 | GUCGAAAU CUGAUGAG<u>GNNNNNNNN</u>CCGAA AAAAUCAA | 6313 |
| 4172 | AUUUUCAUU UCGACAAC | 2158 | GUUGUCGA CUGAUGAG<u>GNNNNNNNN</u>CCGAA AUGAAAAU | 6314 |
| 4173 | UUUUCAUUU CGACAACA | 2159 | UGUUGUCG CUGAUGAG<u>GNNNNNNNN</u>CCGAA AAUGAAAA | 6315 |
| 4174 | UUUCAUUUC GACAACAG | 2160 | CUGUUGUC CUGAUGAG<u>GNNNNNNNN</u>CCGAA AAAUGAAA | 6316 |
| 4194 | AAGGACCUC GGACUGCA | 2161 | UGCAGUCC CUGAUGAG<u>GNNNNNNNN</u>CCGAA AGGUCCUU | 6317 |
| 4214 | AGCCAGCUC UUCUAGGC | 2162 | GCCUAGAA CUGAUGAG<u>GNNNNNNNN</u>CCGAA AGCUGGCU | 6318 |
| 4216 | CCAGCUCUU CUAGGCUU | 2163 | AAGCCUAG CUGAUGAG<u>GNNNNNNNN</u>CCGAA AGAGCUGG | 6319 |
| 4217 | CAGCUCUUC UAGGCUUG | 2164 | CAAGCCUA CUGAUGAG<u>GNNNNNNNN</u>CCGAA AAGAGCUG | 6320 |
| 4219 | GCUCUUCUA GGCUUGUG | 2165 | CACAAGCC CUGAUGAG<u>GNNNNNNNN</u>CCGAA AGAAGAGC | 6321 |

Where "X" represents stem II region of a HH ribozyme (Hertel et al., 1992 Nucleic Acids Res. 20 3252). The length of stem II may be >2 base-pairs.
Underlined region can be any X sequence or linker, as described herein.

TABLE V

Human KDR VEGF Receptor-Hairpin Ribozyme and Substrate Sequences

| Pos | Substrate | Seq ID No | HP Ribozyme Sequence | Seq ID No |
|---|---|---|---|---|
| 11 | AGGUGCU GCU GGCCGUCG | 2166 | CGACGGCC AGAA GCACCU ACCAGAGAAACACACGUUGUGGUACAUUACCUGGUA | 6322 |
| 18 | GCUGGCC GUC GCCCUGUG | 2167 | CACAGGGC AGAA GCCAGC ACCAGAGAAACACACGUUGUGGUACAUUACCUGGUA | 6323 |
| 51 | CCGGGCC GCC UCUGUGGG | 2168 | CCCACAGA AGAA GCCCGG ACCAGAGAAACACACGUUGUGGUACAUUACCUGGUA | 6324 |
| 86 | UUGAUCU GCC CAGGCUCA | 2169 | UGAGCCUG AGAA GAUCAA ACCAGAGAAACACACGUUGUGGUACAUUACCUGGUA | 6325 |
| 318 | GGAAACU GAC UUGGCCUC | 2170 | GAGGCCAA AGAA GUUUCC ACCAGAGAAACACACGUUGUGGUACAUUACCUGGUA | 6326 |
| 358 | GAUUACA GAU CUCCAUUU | 2171 | AAAUGGAG AGAA GUAAUC ACCAGAGAAACACACGUUGUGGUACAUUACCUGGUA | 6327 |
| 510 | UGUUCCU GAU GGUAACAG | 2172 | CUGUUACC AGAA GGAACA ACCAGAGAAACACACGUUGUGGUACAUUACCUGGUA | 6328 |
| 623 | GUUACCA GUC UAUUAUGU | 2173 | ACAUAAUA AGAA GGUAAC ACCAGAGAAACACACGUUGUGGUACAUUACCUGGUA | 6329 |
| 683 | UGAGUCC GUC UCAUGGAA | 2174 | UUCCAUGA AGAA GACUCA ACCAGAGAAACACACGUUGUGGUACAUUACCUGGUA | 6330 |
| 705 | ACUAUCU GUU GGAGAAAA | 2175 | UUUUCUCC AGAA GAUAGU ACCAGAGAAACACACGUUGUGGUACAUUACCUGGUA | 6331 |
| 833 | AAACCCA GUC UGGGAGUG | 2176 | CACUCCCA AGAA GGGUUU ACCAGAGAAACACACGUUGUGGUACAUUACCUGGUA | 6332 |
| 932 | GUGGGCU GAU GACCAAGA | 2177 | UCUUGGUC AGAA GCCCAC ACCAGAGAAACACACGUUGUGGUACAUUACCUGGUA | 6333 |
| 1142 | AUGUACU GAC GAUUAUGG | 2178 | CCAUAAUC AGAA GUACAU ACCAGAGAAACACACGUUGUGGUACAUUACCUGGUA | 6334 |
| 1259 | CACCCCA GAU UGGUGAGA | 2179 | UCUCACCA AGAA GGGGUG ACCAGAGAAACACACGUUGUGGUACAUUACCUGGUA | 6335 |
| 1332 | AUGUACG GUC UAUGCCAU | 2180 | AUGGCAUA AGAA GUACAU ACCAGAGAAACACACGUUGUGGUACAUUACCUGGUA | 6336 |
| 1376 | AUUGGCA GUU GGAGGAAG | 2181 | CUUCCUCC AGAA GCCAAU ACCAGAGAAACACACGUUGUGGUACAUUACCUGGUA | 6337 |
| 1413 | CCAAGCU GUC UCAGUGAC | 2182 | GUCACUGA AGAA GCUUGG ACCAGAGAAACACACGUUGUGGUACAUUACCUGGUA | 6338 |
| 1569 | UGUGUCA GCU UUGUACAA | 2183 | UUGUACAA AGAA GACACA ACCAGAGAAACACACGUUGUGGUACAUUACCUGGUA | 6339 |
| 1673 | ACAUGCA GCC CACUGAGC | 2184 | GCUCAGUG AGAA GCAUGU ACCAGAGAAACACACGUUGUGGUACAUUACCUGGUA | 6340 |
| 1717 | GCAGACA GAU CUACGUUU | 2185 | AAACGUAG AGAA GUCUGC ACCAGAGAAACACACGUUGUGGUACAUUACCUGGUA | 6341 |
| 1760 | GCCCACA GCC UCUGCCAA | 2186 | UUGGCAGA AGAA GUGGGC ACCAGAGAAACACACGUUGUGGUACAUUACCUGGUA | 6342 |
| 1797 | CACACCU GUU UGCAAGAA | 2187 | UUCUUGCA AGAA GGUGUG ACCAGAGAAACACACGUUGUGGUACAUUACCUGGUA | 6343 |
| 1918 | UAUGUCU GCC UUGCUCAA | 2188 | UUGAGCAA AGAA GACAUA ACCAGAGAAACACACGUUGUGGUACAUUACCUGGUA | 6344 |
| 1967 | UCAGGCA GCU CACAGUCC | 2189 | GGACUGUG AGAA GCCUGA ACCAGAGAAACACACGUUGUGGUACAUUACCUGGUA | 6345 |
| 1974 | GCUCACA GUC CUAGAGCG | 2190 | CGCUCUAG AGAA GUGAGC ACCAGAGAAACACACGUUGUGGUACAUUACCUGGUA | 6346 |
| 2021 | AGAAUCA GAC GACAAGUA | 2191 | UACUUGUC AGAA GAUUCU ACCAGAGAAACACACGUUGUGGUACAUUACCUGGUA | 6347 |
| 2084 | CUCCACA GAU CAUGUGGU | 2192 | ACCACAUG AGAA GUGGAG ACCAGAGAAACACACGUUGUGGUACAUUACCUGGUA | 6348 |
| 2418 | GGAUCCA GAU GAACUCCC | 2193 | GGGAGUUC AGAA GGAUCC ACCAGAGAAACACACGUUGUGGUACAUUACCUGGUA | 6349 |
| 2453 | AACGACU GCC UUAUGAUG | 2194 | CAUCAUAA AGAA GUCGUU ACCAGAGAAACACACGUUGUGGUACAUUACCUGGUA | 6350 |
| 2492 | GAGACCG GCU GAACCUAG | 2195 | CUAGGUUC AGAA GGUCUC ACCAGAGAAACACACGUUGUGGUACAUUACCUGGUA | 6351 |
| 2547 | UGAAGCA GAU GCCUUUGG | 2196 | CCAAAGGC AGAA GCUUCA ACCAGAGAAACACACGUUGUGGUACAUUACCUGGUA | 6352 |
| 2765 | GAAACCU GUC CACUUACC | 2197 | GGUAAGUG AGAA GGUUUC ACCAGAGAAACACACGUUGUGGUACAUUACCUGGUA | 6353 |
| 2914 | UCAGCCA GCU CUGGAUUU | 2198 | AAAUCCAG AGAA GGCUGA ACCAGAGAAACACACGUUGUGGUACAUUACCUGGUA | 6354 |
| 2993 | ACUUCCU GAC CUUGGAGC | 2199 | GCUCCAAG AGAA GGAAGU ACCAGAGAAACACACGUUGUGGUACAUUACCUGGUA | 6355 |
| 3019 | UGUUACA GCU UCCAAGUG | 2200 | CACUUGGA AGAA GUAACA ACCAGAGAAACACACGUUGUGGUACAUUACCUGGUA | 6356 |

TABLE V-continued

Human KDR VEGF Receptor-Hairpin Ribozyme and Substrate Sequences

| Pos | Substrate | Seq ID No | HP Ribozyme Sequence | Seq ID No |
|---|---|---|---|---|
| 3165 | AGAUCCA GAU UAUGUCAG | 2201 | CUGACAUA AGAA GGAUCU ACCAGAGAAACACACGUUGUGGUACAUUACCUGGUA | 6357 |
| 3378 | GGCCCCU GAU UAUACUAC | 2202 | GUAGUAUA AGAA GGGGCC ACCAGAGAAACACACGUUGUGGUACAUUACCUGGUA | 6358 |
| 3404 | UGUACCA GAC CAUGCUGG | 2203 | CCAGCAUG AGAA GGUACA ACCAGAGAAACACACGUUGUGGUACAUUACCUGGUA | 6359 |
| 3418 | CUGGACU GCU GGCACGGG | 2204 | CCCGUGCC AGAA GUCCAG ACCAGAGAAACACACGUUGUGGUACAUUACCUGGUA | 6360 |
| 3575 | UCUCUCU GCC UACCUCAC | 2205 | GUGAGGUA AGAA GAGAGA ACCAGAGAAACACACGUUGUGGUACAUUACCUGGUA | 6361 |
| 3588 | CUCACCU GUU UCCUGUAU | 2206 | AUACAGGA AGAA GGUGAG ACCAGAGAAACACACGUUGUGGUACAUUACCUGGUA | 6362 |
| 3689 | AGAGCCG GCC UGUGAGUG | 2207 | CACUCACA AGAA GGCUCU ACCAGAGAAACACACGUUGUGGUACAUUACCUGGUA | 6363 |
| 3753 | AAUCCCA GAU GACAACCA | 2208 | UGGUUGUC AGAA GGGAUU ACCAGAGAAACACACGUUGUGGUACAUUACCUGGUA | 6364 |
| 3764 | ACAACCA GAC GGACAGUG | 2209 | CACUGUCC AGAA GGUUGU ACCAGAGAAACACACGUUGUGGUACAUUACCUGGUA | 6365 |
| 3911 | GCUACCA GUC CGGAUAUC | 2210 | GAUAUCCG AGAA GGUAGC ACCAGAGAAACACACGUUGUGGUACAUUACCUGGUA | 6366 |
| 3927 | UCACUCC GAU GACACAGA | 2211 | UCUGUGUC AGAA GAGUGA ACCAGAGAAACACACGUUGUGGUACAUUACCUGGUA | 6367 |
| 4011 | UAGCACA GCC CAGAUUCU | 2212 | AGAAUCUG AGAA GUGCUA ACCAGAGAAACACACGUUGUGGUACAUUACCUGGUA | 6368 |
| 4016 | CAGCCCA GAU UCUCCAGC | 2213 | GCUGGAGA AGAA GGGCUG ACCAGAGAAACACACGUUGUGGUACAUUACCUGGUA | 6369 |
| 4025 | UUCUCCA GCC UGACACGG | 2214 | CCGUGUCA AGAA GGAGAA ACCAGAGAAACACACGUUGUGGUACAUUACCUGGUA | 6370 |
| 4059 | UCCUCCU GUU UAAAGGA | 2215 | UCCUUUUA AGAA GGAGGA ACCAGAGAAACACACGUUGUGGUACAUUACCUGGUA | 6371 |
| 4111 | GAGGUCU GCU CAGAUUUU | 2216 | AAAAUCUG AGAA GACCUC ACCAGAGAAACACACGUUGUGGUACAUUACCUGGUA | 6372 |
| 4116 | CUGCUCA GAU UUUGAAGU | 2217 | ACUUCAAA AGAA GAGCAG ACCAGAGAAACACACGUUGUGGUACAUUACCUGGUA | 6373 |
| 4195 | GACCUCG GAC UGCAGGGA | 2218 | UCCCUGCA AGAA GAGGUC ACCAGAGAAACACACGUUGUGGUACAUUACCUGGUA | 6374 |
| 4210 | GGAGCCA GCU CUUCUAGG | 2219 | CCUAGAAG AGAA GGCUCC ACCAGAGAAACACACGUUGUGGUACAUUACCUGGUA | 6375 |

TABLE VI

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 13 | GGGCGAAUU GGGUACGG | 2220 | CCGUACCC CUGAUGAGGNNNNNNNNCCGAA AUUCGCCC | 6376 |
| 18 | AAUUGGGUA CGGGACCC | 2221 | GGGUCCCG CUGAUGAGGNNNNNNNNCCGAA ACCCAAUU | 6377 |
| 31 | ACCCCCUC GAGGUCGA | 2222 | UCGACCUC CUGAUGAGGNNNNNNNNCCGAA AGGGGGGU | 6378 |
| 37 | CUCGAGGUC GACGGUAU | 2223 | AUACCGUC CUGAUGAGGNNNNNNNNCCGAA ACCUCGAG | 6379 |
| 44 | UCGACGGUA UCGAUAAG | 2224 | CUUAUCGA CUGAUGAGGNNNNNNNNCCGAA ACCGUCGA | 6380 |
| 46 | GACGGUAUC GAUAAGCU | 2225 | AGCUUAUC CUGAUGAGGNNNNNNNNCCGAA AUACCGUC | 6381 |
| 50 | GUAUCGAUA AGCUUGAU | 2226 | AUCAAGCU CUGAUGAGGNNNNNNNNCCGAA AUCGAUAC | 6382 |
| 55 | GAUAAGCUU GAUAUCGA | 2227 | UCGAUAUC CUGAUGAGGNNNNNNNNCCGAA AGCUUAUC | 6383 |
| 59 | AGCUUGAUA UCGAAUUC | 2228 | GAAUUCGA CUGAUGAGGNNNNNNNNCCGAA AUCAAGCU | 6384 |
| 61 | CUUGAUAUC GAAUUCGG | 2229 | CCGAAUUC CUGAUGAGGNNNNNNNNCCGAA AUAUCAAG | 6385 |
| 66 | UAUCGAAUU CGGGCCCA | 2230 | UGGGCCCG CUGAUGAGGNNNNNNNNCCGAA AUUCGAUA | 6386 |
| 67 | AUCGAAUUC GGGCCCAG | 2231 | CUGGGCCC CUGAUGAGGNNNNNNNNCCGAA AAUUCGAU | 6387 |
| 83 | GACUGUGUC CCGCAGCC | 2232 | GGCUGCGG CUGAUGAGGNNNNNNNNCCGAA ACACAGUC | 6388 |
| 97 | GCCGGGAUA ACCUGGCU | 2233 | AGCCAGGU CUGAUGAGGNNNNNNNNCCGAA AUCCCGGC | 6389 |
| 114 | GACCCGAUU CCGCGGAC | 2234 | GUCCGCGG CUGAUGAGGNNNNNNNNCCGAA AUCGGGUC | 6390 |
| 115 | ACCCGAUUC CGCGGACA | 2235 | UGUCCGCG CUGAUGAGGNNNNNNNNCCGAA AAUCGGGU | 6391 |
| 169 | CCCGCGCUC UCCCCGGU | 2236 | ACCGGGGA CUGAUGAGGNNNNNNNNCCGAA AGCGCGGG | 6392 |
| 171 | CGCGCUCUC CCCGGUCU | 2237 | AGACCGGG CUGAUGAGGNNNNNNNNCCGAA AGAGCGCG | 6393 |
| 178 | UCCCCGGUC UUGCGCUG | 2238 | CAGCGCAA CUGAUGAGGNNNNNNNNCCGAA ACCGGGGA | 6394 |
| 180 | CCCGGUCUU GCGCUGCG | 2239 | CGCAGCGC CUGAUGAGGNNNNNNNNCCGAA AGACCGGG | 6395 |
| 197 | GGGGCCAUA CCGCCUCU | 2240 | AGAGGCGG CUGAUGAGGNNNNNNNNCCGAA AUGGCCCC | 6396 |
| 204 | UACCGCCUC UGUGACUU | 2241 | AAGUCACA CUGAUGAGGNNNNNNNNCCGAA AGGCGGUA | 6397 |
| 212 | CUGUGACUU CUUUGCGG | 2242 | CCGCAAAG CUGAUGAGGNNNNNNNNCCGAA AGUCACAG | 6398 |
| 213 | UGUGACUUC UUUGCGGG | 2243 | CCCGCAAA CUGAUGAGGNNNNNNNNCCGAA AAGUCACA | 6399 |
| 215 | UGACUUCUU UGCGGGCC | 2244 | GGCCCGCA CUGAUGAGGNNNNNNNNCCGAA AGAAGUCA | 6400 |
| 216 | GACUUCUUU GCGGGCCA | 2245 | UGGCCCGC CUGAUGAGGNNNNNNNNCCGAA AAGAAGUC | 6401 |
| 241 | GAAGGAGUC UGUGCCUG | 2246 | CAGGCACA CUGAUGAGGNNNNNNNNCCGAA ACUCCUUC | 6402 |
| 262 | ACUGGGCUC UGUGCCCA | 2247 | UGGGCACA CUGAUGAGGNNNNNNNNCCGAA AGCCCAGU | 6403 |
| 306 | GCGCUGCUA GCUGUCGC | 2248 | GCGACAGC CUGAUGAGGNNNNNNNNCCGAA AGCAGCGC | 6404 |
| 312 | CUAGCUGUC GCUCUGUG | 2249 | CACAGAGC CUGAUGAGGNNNNNNNNCCGAA ACAGCUAG | 6405 |
| 316 | CUGUCGCUC UGUGGUUC | 2250 | GAACCACA CUGAUGAGGNNNNNNNNCCGAA AGCGACAG | 6406 |
| 323 | UCUGUGGUU CUGCGUGG | 2251 | CCACGCAG CUGAUGAGGNNNNNNNNCCGAA ACCACAGA | 6407 |
| 324 | CUGUGGUUC UGCGUGGA | 2252 | UCCACGCA CUGAUGAGGNNNNNNNNCCGAA AACCACAG | 6408 |
| 347 | AGCCGCCUC UGUGGGUU | 2253 | AACCCACA CUGAUGAGGNNNNNNNNCCGAA AGGCGGCU | 6409 |
| 355 | CUGUGGGUU UGACUGGC | 2254 | GCCAGUCA CUGAUGAGGNNNNNNNNCCGAA ACCCACAG | 6410 |
| 356 | UGUGGGUUU GACUGGCG | 2255 | CGCCAGUC CUGAUGAGGNNNNNNNNCCGAA AACCCACA | 6411 |
| 367 | CUGGCGAUU UUCCAUCCAU | 2256 | AUGGAGAA CUGAUGAGGNNNNNNNNCCGAA AUCGCCAG | 6412 |
| 368 | UGGCGAUUU UCCAUCUC | 2257 | GAUGGAGA CUGAUGAGGNNNNNNNNCCGAA AAAUCGCCA | 6413 |
| 369 | GGCGAUUUU CUCCAUCC | 2258 | GGAUGGAG CUGAUGAGGNNNNNNNNCCGAA AAAUCGCC | 6414 |
| 370 | GCGAUUUUC UCCAUCCC | 2259 | GGGAUGGA CUGAUGAGGNNNNNNNNCCGAA AAAAUCGC | 6415 |
| 372 | GAUUUUCUC CAUCCCCC | 2260 | GGGGGAUG CUGAUGAGGNNNNNNNNCCGAA AGAAAAUC | 6416 |
| 376 | UUCUCCAUC CCCCAAG | 2261 | CUUGGGGG CUGAUGAGGNNNNNNNNCCGAA AUGGAGAA | 6417 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 387 | CCCAAGCUC AGCACACA | 2262 | UGUGUGCU CUGAUGAGGNNNNNNNNCCGAA AGCUUGGG | 6418 |
| 405 | AAAGACAUA CUGACAAU | 2263 | AUUGUCAG CUGAUGAGGNNNNNNNNCCGAA AUGUCUUU | 6419 |
| 414 | CUGACAAUU UUGGCAAA | 2264 | UUUGCCAA CUGAUGAGGNNNNNNNNCCGAA AUUGUCAG | 6420 |
| 415 | UGACAAUUU UGGCAAAU | 2265 | AUUUGCCA CUGAUGAGGNNNNNNNNCCGAA AAUUGUCA | 6421 |
| 416 | GACAAUUUU GGCAAAUA | 2266 | UAUUUGCC CUGAUGAGGNNNNNNNNCCGAA AAAUUGUC | 6422 |
| 424 | UGGCAAAUA CAACCCUU | 2267 | AAGGGUUG CUGAUGAGGNNNNNNNNCCGAA AUUUGCCA | 6423 |
| 432 | ACAACCCUU CAGAUUAC | 2268 | GUAAUCUG CUGAUGAGGNNNNNNNNCCGAA AGGGUUGU | 6424 |
| 433 | CAACCCUUC AGAUUACU | 2269 | AGUAAUCU CUGAUGAGGNNNNNNNNCCGAA AAGGGUUG | 6425 |
| 438 | CUUCAGAUU ACUUGCAG | 2270 | CUGCAAGU CUGAUGAGGNNNNNNNNCCGAA AUCUGAAG | 6426 |
| 439 | UUCAGAUUA CUUGCAGG | 2271 | CCUGCAAG CUGAUGAGGNNNNNNNNCCGAA AAUCUGAA | 6427 |
| 442 | AGAUUACUU GCAGGGGA | 2272 | UCCCCUGC CUGAUGAGGNNNNNNNNCCGAA AGUAAUCU | 6428 |
| 471 | GACUGGCUU UGGCCCAA | 1534 | UUGGGCCA CUGAUGAGGNNNNNNNNCCGAA AGCCAGUC | 5690 |
| 472 | ACUGGCUUU GGCCCAAU | 1535 | AUUGGGCC CUGAUGAGGNNNNNNNNCCGAA AAGCCAGU | 5691 |
| 484 | CCAAUGCUC AGCGUGAU | 2273 | AUCACGCU CUGAUGAGGNNNNNNNNCCGAA AGCAUUGG | 6429 |
| 493 | AGCGUGAUU CUGAGGAA | 2274 | UUCCUCAG CUGAUGAGGNNNNNNNNCCGAA AUCACGCU | 6430 |
| 494 | GCGUGAUUC UGAGGAAA | 2275 | UUUCCUCA CUGAUGAGGNNNNNNNNCCGAA AAUCACGC | 6431 |
| 507 | GAAAGGGUA UUGGUGAC | 2276 | GUCACCAA CUGAUGAGGNNNNNNNNCCGAA ACCCUUUC | 6432 |
| 509 | AAGGGUAUU GGUGACUG | 2277 | CAGUCACC CUGAUGAGGNNNNNNNNCCGAA AUACCCUU | 6433 |
| 538 | GUGACAGUA UCUUCUGC | 2278 | GCAGAAGA CUGAUGAGGNNNNNNNNCCGAA ACUGUCAC | 6434 |
| 540 | GACAGUAUC UUCUGCAA | 2279 | UUGCAGAA CUGAUGAGGNNNNNNNNCCGAA AUACUGUC | 6435 |
| 542 | CAGUAUCUU CUGCAAAA | 2280 | UUUUGCAG CUGAUGAGGNNNNNNNNCCGAA AGAUACUG | 6436 |
| 543 | AGUAUCUUC UGCAAAAC | 2281 | GUUUUGCA CUGAUGAGGNNNNNNNNCCGAA AAGAUACU | 6437 |
| 555 | AAAACACUC ACCAUUCC | 2282 | GGAAUGGU CUGAUGAGGNNNNNNNNCCGAA AGUGUUUU | 6438 |
| 561 | CUCACCAUU CCCAGGGU | 2283 | ACCCUGGG CUGAUGAGGNNNNNNNNCCGAA AUGGUGAG | 6439 |
| 562 | UCACCAUUC CAGGGUG | 2284 | CACCCUGG CUGAUGAGGNNNNNNNNCCGAA AAUGGUGA | 6440 |
| 573 | AGGGUGGUU GGAAAUGA | 2285 | UCAUUUCC CUGAUGAGGNNNNNNNNCCGAA ACCACCCU | 6441 |
| 583 | GAAAUGAUA CUGGAGCC | 2286 | GGCUCCAG CUGAUGAGGNNNNNNNNCCGAA AUCAUUUC | 6442 |
| 593 | UGGAGCCUA CAAGUGCU | 1546 | AGCACUUG CUGAUGAGGNNNNNNNNCCGAA AGGCUCCA | 5702 |
| 602 | CAAGUGCUC UACCGGG | 2287 | CCCGGUAC CUGAUGAGGNNNNNNNNCCGAA AGCACUUG | 6443 |
| 605 | GUGCUCGUA CCGGGACG | 2288 | CGUCCCGG CUGAUGAGGNNNNNNNNCCGAA ACGAGCAC | 6444 |
| 615 | CGGGACGUC GACAUAGC | 2289 | GCUAUGUC CUGAUGAGGNNNNNNNNCCGAA ACGUCCCG | 6445 |
| 621 | GUCGACAUA GCCUCCAC | 2290 | GUGGAGGC CUGAUGAGGNNNNNNNNCCGAA AUGUCGAC | 6446 |
| 626 | CAUAGCCUC CACUGUUU | 2291 | AAACAGUG CUGAUGAGGNNNNNNNNCCGAA AGGCUAUG | 6447 |
| 633 | UCCACUGUU UAUGUCUA | 2292 | UAGACAUA CUGAUGAGGNNNNNNNNCCGAA ACAGUGGA | 6448 |
| 634 | CCACUGUUU AUGUCUAU | 2293 | AUAGACAU CUGAUGAGGNNNNNNNNCCGAA AACAGUGG | 6449 |
| 635 | CACUGUUUA UGUCUAUG | 2294 | CAUAGACA CUGAUGAGGNNNNNNNNCCGAA AAACAGUG | 6450 |
| 639 | GUUUAUGUC UAUGUUCG | 2295 | CGAACAUA CUGAUGAGGNNNNNNNNCCGAA ACAUAAAC | 6451 |
| 641 | UUAUGUCUA UGUUCGAG | 2296 | CUCGAACA CUGAUGAGGNNNNNNNNCCGAA AGACAUAA | 6452 |
| 645 | GUCUAUGUU CGAGAUUA | 2297 | UAAUCUCG CUGAUGAGGNNNNNNNNCCGAA ACAUAGAC | 6453 |
| 646 | UCUAUGUUC GAGAUUAC | 2298 | GUAAUCUC CUGAUGAGGNNNNNNNNCCGAA AACAUAGA | 6454 |
| 652 | UUCGAGAUU ACAGAUCA | 2299 | UGAUCUGU CUGAUGAGGNNNNNNNNCCGAA AUCUCGAA | 6455 |
| 653 | UCGAGAUUA CAGAUCAC | 2300 | GUGAUCUG CUGAUGAGGNNNNNNNNCCGAA AAUCUCGA | 6456 |
| 659 | UUACAGAUC ACCAUUCA | 2301 | UGAAUGGU CUGAUGAGGNNNNNNNNCCGAA AUCUGUAA | 6457 |
| 665 | AUCACCAUU CAUCGCCU | 2302 | AGGCGAUG CUGAUGAGGNNNNNNNNCCGAA AUGGUGAU | 6458 |
| 666 | UCACCAUUC AUCGCCUC | 2303 | GAGGCGAU CUGAUGAGGNNNNNNNNCCGAA AAUGGUGA | 6459 |
| 669 | CCAUUCAUC GCCUCUGU | 2304 | ACAGAGGC CUGAUGAGGNNNNNNNNCCGAA AUGAAUGG | 6460 |
| 674 | CAUCGCCUC UGUCAGUG | 2305 | CACUGACA CUGAUGAGGNNNNNNNNCCGAA AGGCGAUG | 6461 |
| 678 | GCCUCUGUC AGUGACCA | 2306 | UGGUCACU CUGAUGAGGNNNNNNNNCCGAA ACAGAGGC | 6462 |
| 696 | CAUGGCAUC GUGUACAU | 2307 | AUGUACAC CUGAUGAGGNNNNNNNNCCGAA AUGCCAUG | 6463 |
| 701 | CAUCGUGUA CAUCACCG | 2308 | CGGUGAUG CUGAUGAGGNNNNNNNNCCGAA ACACGAUG | 6464 |
| 705 | GUGUACAUC ACCGAGAA | 2309 | UUCUCGGU CUGAUGAGGNNNNNNNNCCGAA AUGUACAC | 6465 |
| 735 | GUGGUGAUC CCCUGCCG | 2310 | CGGCAGGG CUGAUGAGGNNNNNNNNCCGAA AUCACCAC | 6466 |
| 749 | CCGAGGGUC GAUUUCAA | 2311 | UUGAAAUC CUGAUGAGGNNNNNNNNCCGAA ACCCUCGG | 6467 |
| 753 | GGGUCGAUU UCAAACCU | 2312 | AGGUUUGA CUGAUGAGGNNNNNNNNCCGAA AUCGACCC | 6468 |
| 754 | GGUCGAUUU CAAACCUC | 2313 | GAGGUUUG CUGAUGAGGNNNNNNNNCCGAA AAUCGACC | 6469 |
| 755 | GUCGAUUUC AAACCUCA | 2314 | UGAGGUUU CUGAUGAGGNNNNNNNNCCGAA AAAUCGAC | 6470 |
| 762 | UCAAACCUC AAUGUGUC | 2315 | GACACAUU CUGAUGAGGNNNNNNNNCCGAA AGGUUUGA | 6471 |
| 770 | CAAUGUGUC UCUUUGCG | 2316 | CGCAAAGA CUGAUGAGGNNNNNNNNCCGAA ACACAUUG | 6472 |
| 772 | AUGUGUCUC UUUGCGCU | 2317 | AGCGCAAA CUGAUGAGGNNNNNNNNCCGAA AGACACAU | 6473 |
| 774 | GUGUCUCUU UGCGCUAG | 2318 | CUAGCGCA CUGAUGAGGNNNNNNNNCCGAA AGAGACAC | 6474 |
| 775 | UGUCUCUUU GCGCUAGG | 2319 | CCUAGCGC CUGAUGAGGNNNNNNNNCCGAA AAGAGACA | 6475 |
| 781 | UUUGCGCUA GGUAUCCA | 2320 | UGGAUACC CUGAUGAGGNNNNNNNNCCGAA AGCGCAAA | 6476 |
| 785 | CGCUAGGUA UCCAGAAA | 2321 | UUUCUGGA CUGAUGAGGNNNNNNNNCCGAA ACCUAGCG | 6477 |
| 787 | CUAGGUAUC CAGAAAAG | 2322 | CUUUUCUG CUGAUGAGGNNNNNNNNCCGAA AUACCUAG | 6478 |
| 800 | AAAGAGAUU GUUCCGG | 2323 | CCGGAACA CUGAUGAGGNNNNNNNNCCGAA AUCUCUUU | 6479 |
| 801 | AAGAGAUUG UUCCGGA | 2324 | UCCGGAAC CUGAUGAGGNNNNNNNNCCGAA AAUCUCUU | 6480 |
| 804 | AGAUUGUU CCGGAUGG | 2325 | CCAUCCGG CUGAUGAGGNNNNNNNNCCGAA ACAAAUCU | 6481 |
| 805 | GAUUUGUUC CGGAUGGA | 2326 | UCCAUCCG CUGAUGAGGNNNNNNNNCCGAA AACAAAUC | 6482 |
| 822 | AACAGAAUU CCUGGGA | 1595 | UCCCAGGA CUGAUGAGGNNNNNNNNCCGAA AUUCUGUU | 5751 |
| 823 | ACAGAAUUC CUGGGAC | 1596 | GUCCCAGG CUGAUGAGGNNNNNNNNCCGAA AAUUCUGU | 5752 |
| 824 | CAGAAUUCC UGGGACA | 1597 | UGUCCCAG CUGAUGAGGNNNNNNNNCCGAA AAAUUCUG | 5753 |
| 840 | AGCGAGAUA GGCUUUAC | 2327 | GUAAAGCC CUGAUGAGGNNNNNNNNCCGAA AUCUCGCU | 6483 |
| 845 | GAUAGGCUU UACUCUCC | 2328 | GGAGAGUA CUGAUGAGGNNNNNNNNCCGAA AGCCUAUC | 6484 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 846 | AUAGGCUUU ACUCUCCC | 2329 | GGGAGAGU CUGAUGAGGNNNNNNNNCCGAA AAGCCUAU | 6485 |
| 847 | UAGGCUUUA CUCUCCCC | 2330 | GGGGAGAG CUGAUGAGGNNNNNNNNCCGAA AAAGCCUA | 6486 |
| 850 | GCUUUACUC UCCCCAGU | 2331 | ACUGGGGA CUGAUGAGGNNNNNNNNCCGAA AGUAAAGC | 6487 |
| 852 | UUUACUCUC CCCAGUUA | 2332 | UAACUGGG CUGAUGAGGNNNNNNNNCCGAA AGAGUAAA | 6488 |
| 859 | UCCCCAGUU ACAUGAUC | 2333 | GAUCAUGU CUGAUGAGGNNNNNNNNCCGAA ACUGGGGA | 6489 |
| 860 | CCCCAGUUA CAUGAUCA | 2334 | UGAUCAUG CUGAUGAGGNNNNNNNNCCGAA AACUGGGG | 6490 |
| 867 | UACAUGAUC AGCUAUGC | 1605 | GCAUAGCU CUGAUGAGGNNNNNNNNCCGAA AUCAUGUA | 5761 |
| 872 | GAUCAGCUA UGCCGGCA | 2335 | UGCCGGCA CUGAUGAGGNNNNNNNNCCGAA AGCUGAUC | 6491 |
| 885 | GGCAUGGUC UUCUGUGA | 1607 | UCACAGAA CUGAUGAGGNNNNNNNNCCGAA ACCAUGCC | 5763 |
| 887 | CAUGGUCUU CUGUGAGG | 2336 | CCUCACAG CUGAUGAGGNNNNNNNNCCGAA AGACCAUG | 6492 |
| 888 | AUGGUCUUC UGUGAGGC | 2337 | GCCUCACA CUGAUGAGGNNNNNNNNCCGAA AAGACCAU | 6493 |
| 903 | GCAAAGAUC AAUGAUGA | 2338 | UCAUCAUU CUGAUGAGGNNNNNNNNCCGAA AUCUUUGC | 6494 |
| 917 | UGAAACCUA UCAGUCUA | 2339 | UAGACUGA CUGAUGAGGNNNNNNNNCCGAA AGGUUUCA | 6495 |
| 919 | AAACCUAUC AGUCUAUC | 2340 | GAUAGACU CUGAUGAGGNNNNNNNNCCGAA AUAGGUUU | 6496 |
| 923 | CUAUCAGUC UAUCAUGU | 2341 | ACAUGAUA CUGAUGAGGNNNNNNNNCCGAA ACUGAUAG | 6497 |
| 925 | AUCAGUCUA UCAUGUAC | 2342 | GUACAUGA CUGAUGAGGNNNNNNNNCCGAA AGACUGAU | 6498 |
| 927 | CAGUCUAUC AUGUACAU | 2343 | AUGUACAU CUGAUGAGGNNNNNNNNCCGAA AUAGACUG | 5772 |
| 932 | UAUCAUGUA CAUAGUUG | 2344 | CAACUAUG CUGAUGAGGNNNNNNNNCCGAA ACAUGAUA | 6499 |
| 936 | AUGUACAUA GUUGUGGU | 2345 | ACCACAAC CUGAUGAGGNNNNNNNNCCGAA AUGUACAU | 6500 |
| 939 | UACAUAGUU GUGGUUGU | 2346 | ACAACCAC CUGAUGAGGNNNNNNNNCCGAA ACUAUGUA | 6501 |
| 945 | GUUGUGGUU GUAGGAUA | 2347 | UAUCCUAC CUGAUGAGGNNNNNNNNCCGAA ACCACAAC | 6502 |
| 948 | GUGGUUGUA GGAUAUAG | 2348 | CUAUAUCC CUGAUGAGGNNNNNNNNCCGAA ACAACCAC | 6503 |
| 953 | UGUAGGAUA UAGGAUUU | 2349 | AAAUCCUA CUGAUGAGGNNNNNNNNCCGAA AUCCUACA | 6504 |
| 955 | UAGGAUAUA GGAUUUAU | 2350 | AUAAAUCC CUGAUGAGGNNNNNNNNCCGAA AUAUCCUA | 6505 |
| 960 | UAUAGGAUU UAUGAUGU | 1626 | ACAUCAUA CUGAUGAGGNNNNNNNNCCGAA AUCCUAUA | 5782 |
| 961 | AUAGGAUUU AUGAUGUG | 1627 | CACAUCAU CUGAUGAGGNNNNNNNNCCGAA AAUCCUAU | 5783 |
| 962 | UAGGAUUUA UGAUGUGA | 2351 | UCACAUCA CUGAUGAGGNNNNNNNNCCGAA AAAUCCUA | 6506 |
| 972 | GAUGUGAUU CUGAGCCC | 2352 | GGGCUCAG CUGAUGAGGNNNNNNNNCCGAA AUCACAUC | 6507 |
| 973 | AUGUGAUUC UGAGCCCC | 2353 | GGGGCUCA CUGAUGAGGNNNNNNNNCCGAA AAUCACAU | 6508 |
| 993 | CAUGAAAUU GAGCUAUC | 2354 | GAUAGCUC CUGAUGAGGNNNNNNNNCCGAA AUUUCAUG | 6509 |
| 999 | AUUGAGCUA UCUGCCGG | 2355 | CCGGCAGA CUGAUGAGGNNNNNNNNCCGAA AGCUCAAU | 6510 |
| 1001 | UGAGCUAUC UGCCGGAG | 2356 | CUCCGGCA CUGAUGAGGNNNNNNNNCCGAA AUAGCUCA | 6511 |
| 1017 | GAAAAACUU GUCUUAAA | 2357 | UUUAAGAC CUGAUGAGGNNNNNNNNCCGAA AGUUUUUC | 6512 |
| 1020 | AAACUUGUC UUAAAUUG | 2358 | CAAUUUAA CUGAUGAGGNNNNNNNNCCGAA ACAAGUUU | 6513 |
| 1022 | ACUUGUCUU AAAUUGUA | 2359 | UACAAUUU CUGAUGAGGNNNNNNNNCCGAA AGACAAGU | 6514 |
| 1023 | CUUGUCUUA AAUUGUAC | 1641 | GUACAAUU CUGAUGAGGNNNNNNNNCCGAA AAGACAAG | 5797 |
| 1027 | UCUUAAAUU GUACAGCG | 2360 | CGCUGUAC CUGAUGAGGNNNNNNNNCCGAA AUUUAAGA | 6515 |
| 1030 | UAAAUUGUA CAGCGAGA | 2361 | UCUCGCUG CUGAUGAGGNNNNNNNNCCGAA ACAAUUUA | 6516 |
| 1047 | ACAGAGCUC AAGUGGGG | 2362 | CCCCACUU CUGAUGAGGNNNNNNNNCCGAA AGCUCUGU | 6517 |
| 1059 | GUGGGGCUU GAUUUCAC | 2363 | GUGAAAUC CUGAUGAGGNNNNNNNNCCGAA AGCCCCAC | 6518 |
| 1063 | GGCUUGAUU UCACCUGG | 2364 | CCAGGUGA CUGAUGAGGNNNNNNNNCCGAA AUCAAGCC | 6519 |
| 1064 | GCUUGAUUU CACCUGGC | 2365 | GCCAGGUG CUGAUGAGGNNNNNNNNCCGAA AAUCAAGC | 6520 |
| 1065 | CUUGAUUUC ACCUGGCA | 2366 | UGCCAGGU CUGAUGAGGNNNNNNNNCCGAA AAAUCAAG | 6521 |
| 1076 | CUGGCACUC UCCACCUU | 2367 | AAGGUGGA CUGAUGAGGNNNNNNNNCCGAA AGUGCCAG | 6522 |
| 1078 | GGCACUCUC CACCUUCA | 2368 | UGAAGGUG CUGAUGAGGNNNNNNNNCCGAA AGAGUGCC | 6523 |
| 1084 | CUCCACCUU CAAAGUCU | 2369 | AGACUUUG CUGAUGAGGNNNNNNNNCCGAA AGGUGGAG | 6524 |
| 1085 | UCCACCUUC AAAGUCUC | 2370 | GAGACUUU CUGAUGAGGNNNNNNNNCCGAA AAGGUGGA | 6525 |
| 1091 | UUCAAAGUC UCAUCAUA | 2371 | UAUGAUGA CUGAUGAGGNNNNNNNNCCGAA ACUUUGAA | 6526 |
| 1093 | CAAAGUCUC AUCAUAAG | 2372 | CUUAUGAU CUGAUGAGGNNNNNNNNCCGAA AGACUUUG | 6527 |
| 1096 | AGUCUCAUC AUAAGAAG | 2373 | CUUCUUAU CUGAUGAGGNNNNNNNNCCGAA AUGAGACU | 6528 |
| 1099 | CUCAUCAUA AGAAGAUU | 2374 | AAUCUUCU CUGAUGAGGNNNNNNNNCCGAA AUGAUGAG | 6529 |
| 1107 | AAGAAGAUU GUAAACCG | 2375 | CGGUUUAC CUGAUGAGGNNNNNNNNCCGAA AUCUUCUU | 6530 |
| 1110 | AAGAUUGUA AACGGGA | 2376 | UCCCGGUU CUGAUGAGGNNNNNNNNCCGAA ACAAUCUU | 6531 |
| 1130 | GAAACCCUU UCCUGGGA | 2377 | UCCCAGGA CUGAUGAGGNNNNNNNNCCGAA AGGGUUUC | 6532 |
| 1131 | AAACCCUUU CCUGGGAC | 2378 | GUCCCAGG CUGAUGAGGNNNNNNNNCCGAA AAGGGUUU | 6533 |
| 1132 | AACCCUUUC CUGGGACU | 2379 | AGUCCCAG CUGAUGAGGNNNNNNNNCCGAA AAAGGGUU | 6534 |
| 1154 | GAAGAUGUU UUUGAGCA | 2380 | UGCUCAAA CUGAUGAGGNNNNNNNNCCGAA ACAUCUUC | 6535 |
| 1155 | AAGAUGUUU UUGAGCAC | 2381 | GUGCUCAA CUGAUGAGGNNNNNNNNCCGAA AACAUCUU | 6536 |
| 1156 | AGAUGUUUU UGAGCACC | 2382 | GGUGCUCA CUGAUGAGGNNNNNNNNCCGAA AAACAUCU | 6537 |
| 1157 | GAUGUUUUU GAGCACCU | 2383 | AGGUGCUC CUGAUGAGGNNNNNNNNCCGAA AAAACAUC | 6538 |
| 1166 | GAGCACCUU GACAAUAG | 2384 | CUAUUGUC CUGAUGAGGNNNNNNNNCCGAA AGGUGCUC | 6539 |
| 1173 | UUGACAAUA GAAAGUGU | 2385 | ACACUUUC CUGAUGAGGNNNNNNNNCCGAA AUUGUCAA | 6540 |
| 1205 | AGGGGAAUA CACCGUG | 2386 | CACAGGUG CUGAUGAGGNNNNNNNNCCGAA AUUCCCCU | 6541 |
| 1215 | ACCUGUGUA GCGUCCAG | 2387 | CUGGACGC CUGAUGAGGNNNNNNNNCCGAA ACACAGGU | 6542 |
| 1220 | UGUAGCGUC CAGUGGAC | 2388 | GUCCACUG CUGAUGAGGNNNNNNNNCCGAA ACGCUACA | 6543 |
| 1236 | CGGAUGAUC AAGAGAAA | 2389 | UUUCUCUU CUGAUGAGGNNNNNNNNCCGAA AUCAUCCG | 6544 |
| 1246 | AGAGAAAUA GAACAUUU | 2390 | AAAUGUUC CUGAUGAGGNNNNNNNNCCGAA AUUUCUCU | 6545 |
| 1253 | UAGAACAUU UGUCCGAG | 2391 | CUCGGACA CUGAUGAGGNNNNNNNNCCGAA AUGUUCUA | 6546 |
| 1254 | AGAACAUUU GUCCGAGU | 2392 | ACUCGGAC CUGAUGAGGNNNNNNNNCCGAA AAUGUUCU | 6547 |
| 1257 | ACAUUUGUC CGAGUUCA | 2393 | UGAACUCG CUGAUGAGGNNNNNNNNCCGAA ACAAAUGU | 6548 |
| 1263 | GUCCGAGUU CACACAAA | 2394 | UUUGUGUG CUGAUGAGGNNNNNNNNCCGAA ACUCGGAC | 6549 |
| 1264 | UCCGAGUUC ACACAAAG | 2395 | CUUUGUGU CUGAUGAGGNNNNNNNNCCGAA AACUCGGA | 6550 |
| 1276 | CAAAGCCUU UAUUGCU | 2396 | AGCAAUAA CUGAUGAGGNNNNNNNNCCGAA AGGCUUUG | 6551 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1277 | AAAGCCUUU UAUUGCUU | 2397 | AAGCAAUA CUGAUGAGgnnnnnnnnCCGAA AAGGCUUU | 6552 |
| 1278 | AAGCCUUUU AUUGCUUU | 2398 | AAAGCAAU CUGAUGAGgnnnnnnnnCCGAA AAAGGCUU | 6553 |
| 1279 | AGCCUUUUA UUGCUUUC | 2399 | GAAAGCAA CUGAUGAGgnnnnnnnnCCGAA AAAAGGCU | 6554 |
| 1281 | CCUUUUAUU GCUUUCGG | 2400 | CCGAAAGC CUGAUGAGgnnnnnnnnCCGAA AUAAAAGG | 6555 |
| 1285 | UUAUUGCUU UCGGUAGU | 2401 | ACUACCGA CUGAUGAGgnnnnnnnnCCGAA AGCAAUAA | 6556 |
| 1286 | UAUUGCUUU CGGUAGUG | 2402 | CACUACCG CUGAUGAGgnnnnnnnnCCGAA AAGCAAUA | 6557 |
| 1287 | AUUGCUUUC GGUAGUGG | 2403 | CCACUACC CUGAUGAGgnnnnnnnnCCGAA AAAGCAAU | 6558 |
| 1291 | CUUUCGGUA GUGGGAUG | 2404 | CAUCCCAC CUGAUGAGgnnnnnnnnCCGAA ACCGAAAG | 6559 |
| 1304 | GAUGAAAUC UUUGGUGG | 2405 | CCACCAAA CUGAUGAGgnnnnnnnnCCGAA AUUUCAUC | 6560 |
| 1306 | UGAAAUCUU UGGUGGAA | 2406 | UUCCACCA CUGAUGAGgnnnnnnnnCCGAA AGAUUUCA | 6561 |
| 1307 | GAAAUCUUU GGUGGAAG | 2407 | CUUCCACC CUGAUGAGgnnnnnnnnCCGAA AAGAUUUC | 6562 |
| 1330 | UGGGCAGUC AAGUCCGA | 2408 | UCGGACUU CUGAUGAGgnnnnnnnnCCGAA ACUGCCCA | 6563 |
| 1335 | AGUCAAGUC CGAAUCCC | 2409 | GGGAUUCG CUGAUGAGgnnnnnnnnCCGAA ACUUGACU | 6564 |
| 1341 | GUCCGAAUC CCUGUGAA | 2410 | UUCACAGG CUGAUGAGgnnnnnnnnCCGAA AUUCGGAC | 6565 |
| 1352 | UGUGAAGUA UCUCAGUU | 2411 | AACUGAGA CUGAUGAGgnnnnnnnnCCGAA ACUUCACA | 6566 |
| 1354 | UGAAGUAUC UCAGUUAC | 2412 | GUAACUGA CUGAUGAGgnnnnnnnnCCGAA AUACUUCA | 6567 |
| 1356 | AAGUAUCUC AGUUACCC | 2413 | GGGUAACU CUGAUGAGgnnnnnnnnCCGAA AGAUACUU | 6568 |
| 1360 | AUCUCAGUU ACCCAGCU | 2414 | AGCUGGGU CUGAUGAGgnnnnnnnnCCGAA ACUGAGAU | 6569 |
| 1361 | UCUCAGUUA CCCAGCUC | 2415 | GAGCUGGG CUGAUGAGgnnnnnnnnCCGAA AACUGAGA | 6570 |
| 1369 | ACCCAGCUC CUGAUAUC | 2416 | GAUAUCAG CUGAUGAGgnnnnnnnnCCGAA AGCUGGGU | 6571 |
| 1375 | CUCCUGAUA UCAAAUGG | 2417 | CCAUUUGA CUGAUGAGgnnnnnnnnCCGAA AUCAGGAG | 6572 |
| 1377 | CCUGAUAUC AAAUGGUA | 2418 | UACCAUUU CUGAUGAGgnnnnnnnnCCGAA AUAUCAGG | 6573 |
| 1385 | CAAAUGGUA CAGAAAUG | 2419 | CAUUUCUG CUGAUGAGgnnnnnnnnCCGAA ACCAUUUG | 6574 |
| 1404 | AGGCCCAUU GAGUCCAA | 2420 | UUGGACUC CUGAUGAGgnnnnnnnnCCGAA AUGGGCCU | 6575 |
| 1409 | CAUUGAGUC CAACUACA | 2421 | UGUAGUUG CUGAUGAGgnnnnnnnnCCGAA ACUCAAUG | 6576 |
| 1415 | GUCCAACUA CACAAUGA | 2422 | UCAUUGUG CUGAUGAGgnnnnnnnnCCGAA AGUUGGAC | 6577 |
| 1425 | ACAAUGAUU GUUGGCGA | 2423 | UCGCCAAC CUGAUGAGgnnnnnnnnCCGAA AUCAUUGU | 6578 |
| 1428 | AUGAUUGUU GGCGAUGA | 2424 | UCAUCGCC CUGAUGAGgnnnnnnnnCCGAA ACAAUCAU | 6579 |
| 1440 | GAUGAACUC ACCAUCAU | 2425 | AUGAUGGU CUGAUGAGgnnnnnnnnCCGAA AGUUCAUC | 6580 |
| 1446 | CUCACCAUC AUGGAAGU | 2426 | ACUUCCAU CUGAUGAGgnnnnnnnnCCGAA AUGGUGAG | 6581 |
| 1478 | AGGAAACUA CACGGUCA | 2427 | UGACCGUG CUGAUGAGgnnnnnnnnCCGAA AGUUUCCU | 6582 |
| 1485 | UACACGGUC AUCCUCAC | 2428 | GUGAGGAU CUGAUGAGgnnnnnnnnCCGAA ACCGUGUA | 6583 |
| 1488 | ACGGUCAUC CUCACCAA | 2429 | UUGGUGAG CUGAUGAGgnnnnnnnnCCGAA AUGACCGU | 6584 |
| 1491 | GUCAUCCUC ACCAACCC | 2430 | GGGUUGGU CUGAUGAGgnnnnnnnnCCGAA AGGAUGAC | 6585 |
| 1503 | AACCCCAUU UCAAUGGA | 2431 | UCCAUUGA CUGAUGAGgnnnnnnnnCCGAA AUGGGGUU | 6586 |
| 1504 | ACCCCAUUU CAAUGGAG | 2432 | CUCCAUUG CUGAUGAGgnnnnnnnnCCGAA AAUGGGGU | 6587 |
| 1505 | CCCCAUUUC AAUGGAGA | 2433 | UCUCCAUU CUGAUGAGgnnnnnnnnCCGAA AAAUGGGG | 6588 |
| 1530 | CACAUGGUC UCUCUGGU | 2434 | ACCAGAGA CUGAUGAGgnnnnnnnnCCGAA ACCAUGUG | 6589 |
| 1532 | CAUGGUCUC UCUGGUUG | 2435 | CAACCAGA CUGAUGAGgnnnnnnnnCCGAA AGACCAUG | 6590 |
| 1534 | UGGUCUCUC UGGUUGUG | 1714 | CACAACCA CUGAUGAGgnnnnnnnnCCGAA AGAGACCA | 5870 |
| 1539 | UCUCUGGUU GUGAAUGU | 2436 | ACAUUCAC CUGAUGAGgnnnnnnnnCCGAA ACCAGAGA | 6591 |
| 1548 | GUGAAUGUC CACCCCA | 2437 | UGGGGUGG CUGAUGAGgnnnnnnnnCCGAA ACAUUCAC | 6592 |
| 1560 | CCCCAGAUC GGUGAGAA | 2438 | UUCUCACC CUGAUGAGgnnnnnnnnCCGAA AUCUGGGG | 5874 |
| 1574 | GAAAGCCUU GAUCUCGC | 2439 | GCGAGAUC CUGAUGAGgnnnnnnnnCCGAA AGGCUUUC | 6593 |
| 1578 | GCCUUGAUC UCGCCUAU | 2440 | AUAGGCGA CUGAUGAGgnnnnnnnnCCGAA AUCAAGGC | 6594 |
| 1580 | CUUGAUCUC GCCUAUGG | 2441 | CCAUAGGC CUGAUGAGgnnnnnnnnCCGAA AGAUCAAG | 6595 |
| 1585 | UCUCGCCUA UGGAUUCC | 2442 | GGAAUCCA CUGAUGAGgnnnnnnnnCCGAA AGGCGAGA | 6596 |
| 1591 | CUAUGGAUU CCUACCAG | 2443 | CUGGUAGG CUGAUGAGgnnnnnnnnCCGAA AUCCAUAG | 6597 |
| 1592 | UAUGGAUUC CUACCAGU | 2444 | ACUGGUAG CUGAUGAGgnnnnnnnnCCGAA AAUCCAUA | 6598 |
| 1595 | GGAUUCCUA CCAGUAUG | 2445 | CAUACUGG CUGAUGAGgnnnnnnnnCCGAA AGGAAUCC | 6599 |
| 1601 | CUACCAGUA UGGGACCA | 2446 | UGGUCCCA CUGAUGAGgnnnnnnnnCCGAA ACUGGUAG | 6600 |
| 1619 | GCAGACAUU GACAUGCA | 2447 | UGCAUGUC CUGAUGAGgnnnnnnnnCCGAA AUGUCUGC | 6601 |
| 1632 | UGCACAGUC UACGCCAA | 2448 | UUGGCGUA CUGAUGAGgnnnnnnnnCCGAA ACUGUGCA | 6602 |
| 1634 | CACAGUCUA CGCCAACC | 2449 | GGUUGGCG CUGAUGAGgnnnnnnnnCCGAA AGACUGUG | 6603 |
| 1645 | CCAACCCUC CCUGCAC | 2450 | GUGCAGGG CUGAUGAGgnnnnnnnnCCGAA AGGGUUGG | 6604 |
| 1659 | CACCACAUC CAGUGGUA | 2451 | UACCACUG CUGAUGAGgnnnnnnnnCCGAA AUGUGGUG | 6605 |
| 1667 | CCAGUGGUA CUGGCAGC | 2452 | GCUGCCAG CUGAUGAGgnnnnnnnnCCGAA ACCACUGG | 6606 |
| 1677 | UGGCAGCUA AAGAAGC | 2453 | GCUUCUUC CUGAUGAGgnnnnnnnnCCGAA AGCUGCCA | 6607 |
| 1691 | AGCCUGCUC CUACAGAC | 2454 | GUCUGUAG CUGAUGAGgnnnnnnnnCCGAA AGCAGGCU | 6608 |
| 1694 | CUGCUCCUA CAGACCCG | 2455 | CGGGUCUG CUGAUGAGgnnnnnnnnCCGAA AGGAGCAG | 6609 |
| 1718 | AAGCCCGUA UGCUUGUA | 2456 | UACAAGCA CUGAUGAGgnnnnnnnnCCGAA ACGGGCUU | 6610 |
| 1723 | CGUAUGCUU GUAAAGAA | 2457 | UUCUUUAC CUGAUGAGgnnnnnnnnCCGAA AGCAUACG | 6611 |
| 1726 | AUGCUUGUA AAGAAUGG | 2458 | CCAUUCUU CUGAUGAGgnnnnnnnnCCGAA ACAAGCAU | 6612 |
| 1750 | UGGAGGAUU UCCAGGGG | 2459 | CCCCUGGA CUGAUGAGgnnnnnnnnCCGAA AUCCUCCA | 6613 |
| 1751 | GGAGGAUUU CCAGGGGG | 2460 | CCCCCUGG CUGAUGAGgnnnnnnnnCCGAA AAUCCUCC | 6614 |
| 1752 | GAGGAUUUC CAGGGGGA | 2461 | CCCCCCUG CUGAUGAGgnnnnnnnnCCGAA AAAUCCUC | 6615 |
| 1770 | AACAAGAUC GAAGUCAC | 2462 | GUGACUUC CUGAUGAGgnnnnnnnnCCGAA AUCUUGUU | 6616 |
| 1776 | AUCGAAGUC ACCAAAAA | 2463 | UUUUUGGU CUGAUGAGgnnnnnnnnCCGAA ACUUCGAU | 6617 |
| 1790 | AAACCAAUA UGCCCUGA | 2464 | UCAGGGCA CUGAUGAGgnnnnnnnnCCGAA AUUGGUUU | 6618 |
| 1800 | GCCCUGAUU GAAGGAAA | 2465 | UUUCCUUC CUGAUGAGgnnnnnnnnCCGAA AUCAGGGC | 6619 |
| 1821 | AAAACUGUA AGUACGCU | 2466 | AGCGUACU CUGAUGAGgnnnnnnnnCCGAA ACAGUUUU | 6620 |
| 1825 | CUGUAAGUA CGCUGGUC | 2467 | GACCAGCG CUGAUGAGgnnnnnnnnCCGAA ACUUACAG | 6621 |
| 1833 | ACGCUGGUC AUCCAAGC | 2468 | GCUUGGAU CUGAUGAGgnnnnnnnnCCGAA ACCAGCGU | 6622 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1836 | CUGGUCAUC CAAGCUGC | 2469 | GCAGCUUG CUGAUGAGGNNNNNNNNCCGAA AUGACCAG | 6623 |
| 1853 | CAACGUGUC AGCGUUGU | 2470 | ACAACGCU CUGAUGAGGNNNNNNNNCCGAA ACACGUUG | 6624 |
| 1859 | GUCAGCGUU GUACAAAU | 2471 | AUUUGUAC CUGAUGAGGNNNNNNNNCCGAA ACGCUGAC | 6625 |
| 1862 | AGCGUUGUA CAAAUGUG | 2472 | CACAUUUG CUGAUGAGGNNNNNNNNCCGAA ACAACGCU | 6626 |
| 1878 | GAAGCCAUC AACAAAGC | 2473 | GCUUUGUU CUGAUGAGGNNNNNNNNCCGAA AUGGCUUC | 6627 |
| 1905 | GAGAGGGUC AUCUCCUU | 2474 | AAGGAGAU CUGAUGAGGNNNNNNNNCCGAA ACCCUCUC | 6628 |
| 1908 | AGGGUCAUC UCCUUCCA | 2475 | UGGAAGGA CUGAUGAGGNNNNNNNNCCGAA AUGACCCU | 6629 |
| 1910 | GGUCAUCUC CUUCCAUG | 2476 | CAUGGAAG CUGAUGAGGNNNNNNNNCCGAA AGAUGACC | 6630 |
| 1913 | CAUCUCCUU CCAUGUGA | 2477 | UCACAUGG CUGAUGAGGNNNNNNNNCCGAA AGGAGAUG | 6631 |
| 1914 | AUCUCCUUC CAUGUGAU | 2478 | AUCACAUG CUGAUGAGGNNNNNNNNCCGAA AAGGAGAU | 6632 |
| 1923 | CAUGUGAUC AGGGGUCC | 2479 | GGACCCCU CUGAUGAGGNNNNNNNNCCGAA AUCACAUG | 6633 |
| 1930 | UCAGGGGUC CUGAAAUU | 2480 | AAUUUCAG CUGAUGAGGNNNNNNNNCCGAA ACCCCUGA | 6634 |
| 1938 | CCUGAAAUU ACUGUGCA | 2481 | UGCACAGU CUGAUGAGGNNNNNNNNCCGAA AUUUCAGG | 6635 |
| 1939 | CUGAAAUUA CUGUGCAA | 2482 | UUGCACAG CUGAUGAGGNNNNNNNNCCGAA AAUUUCAG | 6636 |
| 1982 | GAGUGUGUC CCUGUUGU | 2483 | ACAACAGG CUGAUGAGGNNNNNNNNCCGAA ACACACUC | 6637 |
| 1988 | GUCCCUGUU GUGCACUG | 2484 | CAGUGCAC CUGAUGAGGNNNNNNNNCCGAA ACAGGGAC | 6638 |
| 2008 | ACAGAAAUA CGUUUGAG | 2485 | CUCAAACG CUGAUGAGGNNNNNNNNCCGAA AUUUCUGU | 6639 |
| 2012 | AAAUACGUU UGAGAACC | 2486 | GGUUCUCA CUGAUGAGGNNNNNNNNCCGAA ACGUAUUU | 6640 |
| 2013 | AAUACGUUU GAGAACCU | 2487 | AGGUUCUC CUGAUGAGGNNNNNNNNCCGAA AACGUAUU | 6641 |
| 2022 | GAGAACCUC ACGUGGUA | 2488 | UACCACGU CUGAUGAGGNNNNNNNNCCGAA AGGUUCUC | 6642 |
| 2030 | CACGUGGUA CAAGCUUG | 2489 | CAAGCUUG CUGAUGAGGNNNNNNNNCCGAA ACCACGUG | 6643 |
| 2037 | UACAAGCUU GGCUCACA | 2490 | UGUGAGCC CUGAUGAGGNNNNNNNNCCGAA AGCUUGUA | 6644 |
| 2042 | GCUUGGCUC ACAGGCAA | 2491 | UUGCCUGU CUGAUGAGGNNNNNNNNCCGAA AGCCAAGC | 6645 |
| 2054 | GGCAACAUC GGUCCACA | 2492 | UGUGGACC CUGAUGAGGNNNNNNNNCCGAA AUGUUGCC | 6646 |
| 2058 | ACAUCGGUC CACAUGGG | 2493 | CCCAUGUG CUGAUGAGGNNNNNNNNCCGAA ACCGAUGU | 6647 |
| 2072 | GGGCGAAUC ACUCACAC | 2494 | GUGUGAGU CUGAUGAGGNNNNNNNNCCGAA AUUCGCCC | 6648 |
| 2076 | GAAUCACUC ACACCAGU | 2495 | ACUGGUGU CUGAUGAGGNNNNNNNNCCGAA AGUGAUUC | 6649 |
| 2085 | ACACCAGUU GCAAGAA | 2496 | UUCUUGCA CUGAUGAGGNNNNNNNNCCGAA ACUGGUGU | 6650 |
| 2086 | CACCAGUUU GCAAGAAC | 2497 | GUUCUUGC CUGAUGAGGNNNNNNNNCCGAA AACUGGUG | 6651 |
| 2096 | CAAGAACUU GGAUGCUC | 2498 | GAGCAUCC CUGAUGAGGNNNNNNNNCCGAA AGUUCUUG | 6652 |
| 2104 | UGGAUGCUC UUUGGAAA | 2499 | UUUCCAAA CUGAUGAGGNNNNNNNNCCGAA AGCAUCCA | 6653 |
| 2106 | GAUGCUCUU UGGAAACU | 2500 | AGUUUCCA CUGAUGAGGNNNNNNNNCCGAA AGAGCAUC | 6654 |
| 2107 | AUGCUCUUU GGAAACUG | 2401 | CAGUUUCC CUGAUGAGGNNNNNNNNCCGAA AAGAGCAU | 6655 |
| 2129 | CACCAUGUU UUCUAACA | 2502 | UGUUAGAA CUGAUGAGGNNNNNNNNCCGAA ACAUGGUG | 6656 |
| 2130 | ACCAUGUUU UCUAACAG | 2503 | CUGUUAGA CUGAUGAGGNNNNNNNNCCGAA AACAUGGU | 6657 |
| 2131 | CCAUGUUUU CUAACAGC | 2504 | GCUGUUAG CUGAUGAGGNNNNNNNNCCGAA AAACAUGG | 6658 |
| 2132 | CAUGUUUUC UAACAGCA | 2505 | UGCUGUUA CUGAUGAGGNNNNNNNNCCGAA AAAACAUG | 6659 |
| 2134 | UGUUUUCUA ACAGCACA | 2506 | UGUGCUGU CUGAUGAGGNNNNNNNNCCGAA AGAAAACA | 6660 |
| 2151 | AAUGACAUC UUGAUUGU | 2507 | ACAAUCAA CUGAUGAGGNNNNNNNNCCGAA AUGUCAUU | 6661 |
| 2153 | UGACAUCUU GAUUGUGG | 2508 | CCACAAUC CUGAUGAGGNNNNNNNNCCGAA AGAUGUCA | 6662 |
| 2157 | AUCUUGAUU GUGGCAUU | 2509 | AAUGCCAC CUGAUGAGGNNNNNNNNCCGAA AUCAAGAU | 6663 |
| 2165 | UGUGGCAUU UCAGAAUG | 2510 | CAUUCUGA CUGAUGAGGNNNNNNNNCCGAA AUGCCACA | 6664 |
| 2166 | GUGGCAUUU CAGAAUGC | 2511 | GCAUUCUG CUGAUGAGGNNNNNNNNCCGAA AAUGCCAC | 6665 |
| 2167 | UGGCAUUUC AGAAUGCC | 2512 | GGCAUUCU CUGAUGAGGNNNNNNNNCCGAA AAAUGCCA | 6666 |
| 2177 | GAAUGCCUC UCUGCAGG | 2513 | CCUGCAGA CUGAUGAGGNNNNNNNNCCGAA AGGCAUUC | 6667 |
| 2179 | AUGCUCUC UGCAGGAC | 2514 | GUCCUGCA CUGAUGAGGNNNNNNNNCCGAA AGAGGCAU | 6668 |
| 2198 | AGGCGACUA UGUUUGCU | 2515 | AGCAAACA CUGAUGAGGNNNNNNNNCCGAA AGUCGCCU | 6669 |
| 2202 | GACUAUGUU UGCUCUGC | 2516 | GCAGAGCA CUGAUGAGGNNNNNNNNCCGAA ACAUAGUC | 6670 |
| 2203 | ACUAUGUUU GCUCUGCU | 2517 | AGCAGAGC CUGAUGAGGNNNNNNNNCCGAA AACAUAGU | 6671 |
| 2207 | UGUUUGCUC UGCUCAAG | 2518 | CUUGAGCA CUGAUGAGGNNNNNNNNCCGAA AGCAAACA | 6672 |
| 2212 | GCUCUGCUC AAGAUAAG | 2519 | CUUAUCUU CUGAUGAGGNNNNNNNNCCGAA AGCAGAGC | 6673 |
| 2218 | CUCAAGAUA AGAAGCU | 2520 | GGUCUUCU CUGAUGAGGNNNNNNNNCCGAA AUCUGGAG | 6674 |
| 2239 | AAAGACAUU GCCUGGUC | 2521 | GACCAGGC CUGAUGAGGNNNNNNNNCCGAA AUGUCUUU | 6675 |
| 2247 | UGCCUGGUC AAACAGCU | 2522 | AGCUGUUU CUGAUGAGGNNNNNNNNCCGAA ACCAGGCA | 6676 |
| 2256 | AAACAGCUC AUCAUCCU | 2523 | AGGAUGAU CUGAUGAGGNNNNNNNNCCGAA AGCUGUUU | 6677 |
| 2259 | CAGCUCAUC AUCCUAGA | 2524 | UCUAGGAU CUGAUGAGGNNNNNNNNCCGAA AUGAGCUG | 6678 |
| 2262 | CUCAUCAUC CUAGAGCG | 2525 | CGCUCUAG CUGAUGAGGNNNNNNNNCCGAA AUGAUGAG | 6679 |
| 2265 | AUCAUCCUA GAGCGCAU | 2526 | AUGCGCUC CUGAUGAGGNNNNNNNNCCGAA AGGAUGAU | 6680 |
| 2286 | CCCAUGAUC ACCGGAAA | 2527 | UUUCCGGU CUGAUGAGGNNNNNNNNCCGAA AUCAUGGG | 6681 |
| 2296 | CCGGAAAUC UGGAGAAU | 2528 | AUUCUCCA CUGAUGAGGNNNNNNNNCCGAA AUUUCCGG | 6682 |
| 2305 | UGGAGAAUC AGACAACA | 2529 | UGUUGUCU CUGAUGAGGNNNNNNNNCCGAA AUUCUCCA | 6683 |
| 2319 | ACAACCAUU GGCGAGAC | 2530 | GUCUCGCC CUGAUGAGGNNNNNNNNCCGAA AUGGUUGU | 6684 |
| 2331 | GAGACCAUU GAAGUGAC | 2531 | GUCACUUC CUGAUGAGGNNNNNNNNCCGAA AUGGUCUC | 6685 |
| 2341 | AAGUGACUU GCCCAGCA | 2532 | UGCUGGGC CUGAUGAGGNNNNNNNNCCGAA AGUCACUU | 6686 |
| 2351 | CCCAGCAUC UGGAAAUC | 2533 | GAUUUCCA CUGAUGAGGNNNNNNNNCCGAA AUGCUGGG | 6687 |
| 2359 | CUGGAAAUC CUACCCCA | 2534 | UGGGGUAG CUGAUGAGGNNNNNNNNCCGAA AUUUCCAG | 6688 |
| 2362 | GAAAUCCUA CCCCACAC | 2535 | GUGUGGGG CUGAUGAGGNNNNNNNNCCGAA AGGAUUUC | 6689 |
| 2373 | CCACACAUU ACAUGGUU | 2536 | AACCAUGU CUGAUGAGGNNNNNNNNCCGAA AUGUGUGG | 6690 |
| 2374 | CACACAUUA CAUGGUUC | 2537 | GAACCAUG CUGAUGAGGNNNNNNNNCCGAA AAUGUGUG | 6691 |
| 2381 | UACAUGGUU CAAAGACA | 2538 | UGUCUUUG CUGAUGAGGNNNNNNNNCCGAA ACCAUGUA | 6692 |
| 2382 | ACAUGGUUC AAAGACAA | 2539 | UUGUCUUU CUGAUGAGGNNNNNNNNCCGAA AACCAUGU | 6693 |
| 2403 | ACCCUGGUA GAAGAUUC | 2540 | GAAUCUUC CUGAUGAGGNNNNNNNNCCGAA ACCAGGGU | 6694 |
| 2410 | UAGAAGAUU CAGGCAUU | 2541 | AAUGCCUG CUGAUGAGGNNNNNNNNCCGAA AUCUUCUA | 6695 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2411 | AGAAGAUUC AGGCAUUG | 2542 | CAAUGCCU CUGAUGAGGNNNNNNNNCCGAA AAUCUUCU | 6696 |
| 2418 | UCAGGCAUU GUACUGAG | 2543 | CUCAGUAC CUGAUGAGGNNNNNNNNCCGAA AUGCCUGA | 6697 |
| 2421 | GGCAUUGUA CUGAGAGA | 2544 | UCUCUCAG CUGAUGAGGNNNNNNNNCCGAA ACAAUGCC | 6698 |
| 2449 | ACCUGACUA UCCGCAGG | 2545 | CCUGCGGA CUGAUGAGGNNNNNNNNCCGAA AGUCAGGU | 6699 |
| 2451 | CUGACUAUC CGCAGGGU | 2546 | ACCCUGCG CUGAUGAGGNNNNNNNNCCGAA AUAGUCAG | 6700 |
| 2481 | GGAGGCCUC UACACCUG | 2547 | CAGGUGUA CUGAUGAGGNNNNNNNNCCGAA AGGCCUCC | 6701 |
| 2483 | AGGCCUCUA CACCUGCC | 1847 | GGCAGGUG CUGAUGAGGNNNNNNNNCCGAA AGAGGCCU | 6003 |
| 2505 | UGCAAUGUC CUUGGCUG | 2548 | CAGCCAAG CUGAUGAGGNNNNNNNNCCGAA ACAUUGCA | 6702 |
| 2508 | AAUGUCCUU GGCUGUGC | 2549 | GCACAGCC CUGAUGAGGNNNNNNNNCCGAA AGGACAUU | 6703 |
| 2532 | GAGACGCUC UUCAUAAU | 2550 | AUUAUGAA CUGAUGAGGNNNNNNNNCCGAA AGCGCUCU | 6704 |
| 2534 | GACGCUCUU CAUAAUAG | 2551 | CUAUUAUG CUGAUGAGGNNNNNNNNCCGAA AGAGCGUC | 6705 |
| 2535 | ACGCUCUUC AUAAUAGA | 2552 | UCUAUUAU CUGAUGAGGNNNNNNNNCCGAA AAGAGCGU | 6706 |
| 2538 | CUCUUCAUA AUAGAAGG | 2553 | CCUUCUAU CUGAUGAGGNNNNNNNNCCGAA AUGAAGAG | 6707 |
| 2541 | UUCAUAAUA GAAGGUGC | 1857 | GCACCUUC CUGAUGAGGNNNNNNNNCCGAA AUUAUGAA | 6013 |
| 2567 | GACCAACUU GGAAGUCA | 2554 | UGACUUCC CUGAUGAGGNNNNNNNNCCGAA AGUUGGUC | 6708 |
| 2574 | UUGGAAGUC AUUAUCCU | 2555 | AGGAUAAU CUGAUGAGGNNNNNNNNCCGAA ACUUCCAA | 6709 |
| 2577 | GAAGUCAUU AUCCUCGU | 2556 | ACGAGGAU CUGAUGAGGNNNNNNNNCCGAA AUGACUUC | 6710 |
| 2578 | AAGUCAUUA UCCUCGUC | 2557 | GACGAGGA CUGAUGAGGNNNNNNNNCCGAA AAUGACUU | 6711 |
| 2580 | GUCAUUAUC CUCGUCGG | 2558 | CCGACGAG CUGAUGAGGNNNNNNNNCCGAA AUAAUGAC | 6712 |
| 2583 | AUUAUCCUC GUCGGCAC | 2559 | GUGCCGAC CUGAUGAGGNNNNNNNNCCGAA AGGAUAAU | 6713 |
| 2586 | AUCCUCGUC GGCACUGC | 2560 | GCAGUGCC CUGAUGAGGNNNNNNNNCCGAA ACGAGGAU | 6714 |
| 2601 | GCAGUGAUU GCCAUGUU | 2561 | AACAUGGC CUGAUGAGGNNNNNNNNCCGAA AUCACUGC | 6715 |
| 2609 | UGCCAUGUU CUUCUGGC | 1867 | GCCAGAAG CUGAUGAGGNNNNNNNNCCGAA ACAUGGCA | 6023 |
| 2610 | GCCAUGUUC UUCUGGCU | 1868 | AGCCAGAA CUGAUGAGGNNNNNNNNCCGAA AACAUGGC | 6024 |
| 2612 | CAUGUUCUU CUGGCUCC | 2562 | GGAGCCAG CUGAUGAGGNNNNNNNNCCGAA AGAACAUG | 6716 |
| 2613 | AUGUUCUUC UGGCUCCU | 2563 | AGGAGCCA CUGAUGAGGNNNNNNNNCCGAA AAGAACAU | 6717 |
| 2619 | UUCUGGCUC CUUCUUGU | 2564 | ACAAGAAG CUGAUGAGGNNNNNNNNCCGAA AGCCAGAA | 6027 |
| 2622 | UGGCUCCUU CUUGUCAU | 2565 | AUGACAAG CUGAUGAGGNNNNNNNNCCGAA AGGAGCCA | 6718 |
| 2623 | GGCUCCUUC UUGUCAUU | 2566 | AAUGACAA CUGAUGAGGNNNNNNNNCCGAA AAGGAGCC | 6719 |
| 2625 | CUCCUUCUU GUCAUUGU | 2567 | ACAAUGAC CUGAUGAGGNNNNNNNNCCGAA AGAAGGAG | 6720 |
| 2628 | CUUCUUGUC AUUGUCCU | 2568 | AGGACAAU CUGAUGAGGNNNNNNNNCCGAA ACAAGAAG | 6721 |
| 2631 | CUUGUCAUU GUCCUACG | 2569 | CGUAGGAC CUGAUGAGGNNNNNNNNCCGAA AUGACAAG | 6722 |
| 2634 | GUCAUUGUC CUACGGAC | 2570 | GUCCGUAG CUGAUGAGGNNNNNNNNCCGAA ACAAUGAC | 6723 |
| 2637 | AUUGUCCUA CGGACCGU | 2571 | ACGGUCCG CUGAUGAGGNNNNNNNNCCGAA AGGACAAU | 6724 |
| 2646 | CGGACCGUU AAGCGGGC | 2572 | GCCCGCUU CUGAUGAGGNNNNNNNNCCGAA ACGGUCCG | 6725 |
| 2647 | GGACCGUUA AGCGGGCC | 1880 | GGCCCGCU CUGAUGAGGNNNNNNNNCCGAA AACGGUCC | 6036 |
| 2681 | GACAGGCUA CUUGUCUA | 2573 | UAGACAAG CUGAUGAGGNNNNNNNNCCGAA AGCCUGUC | 6726 |
| 2684 | AGGCUACUU GUCUAUUG | 2574 | CAAUAGAC CUGAUGAGGNNNNNNNNCCGAA AGUAGCCU | 6727 |
| 2687 | CUACUUGUC UAUUGUCA | 2575 | UGACAAUA CUGAUGAGGNNNNNNNNCCGAA ACAAGUAG | 6728 |
| 2689 | ACUUGUCUA UUGUCAUG | 2576 | CAUGACAA CUGAUGAGGNNNNNNNNCCGAA AGACAAGU | 6729 |
| 2691 | UUGUCUAUU GUCAUGGA | 2577 | UCCAUGAC CUGAUGAGGNNNNNNNNCCAA AUAGACAA | 6730 |
| 2694 | UCUAUUGUC AUGGAUCC | 2578 | GGAUCCAU CUGAUGAGGNNNNNNNNCCGAA ACAAUAGA | 6731 |
| 2701 | UCAUGGAUC CAGAUGAA | 1886 | UUCAUCUG CUGAUGAGGNNNNNNNNCCGAA AUCCAUGA | 6042 |
| 2711 | AGAUGAAUU GCCCUUGG | 2579 | CCAAGGGC CUGAUGAGGNNNNNNNNCCGAA AUUCAUCU | 6732 |
| 2717 | AUUGCCCUU GGAUGAGC | 2580 | GCUCAUCC CUGAUGAGGNNNNNNNNCCGAA AGGGCAAU | 6733 |
| 2738 | UGAACGCUU GCCUUAUG | 2581 | CAUAAGGC CUGAUGAGGNNNNNNNNCCGAA AGCGUUCA | 6734 |
| 2743 | GCUUGCCUU AUGAUGCC | 2582 | GGCAUCAU CUGAUGAGGNNNNNNNNCCGAA AGGCAAGC | 6735 |
| 2744 | CUUGCCUUA UGAUGCCA | 2583 | UGGCAUCA CUGAUGAGGNNNNNNNNCCGAA AAGGCAAG | 6736 |
| 2765 | GUGGGAAUU CCCCAGGG | 2584 | CCCUGGGG CUGAUGAGGNNNNNNNNCCGAA AUUCCCAC | 6737 |
| 2766 | UGGGAAUUC CCCAGGGA | 2585 | UCCCUGGG CUGAUGAGGNNNNNNNNCCGAA AAUUCCCA | 6738 |
| 2787 | CUGAAACUA GGAAAACC | 2586 | GGUUUUCC CUGAUGAGGNNNNNNNNCCGAA AGUUUCAG | 6739 |
| 2797 | GAAAACCUC UUGGCCGC | 2587 | GCGGCCAA CUGAUGAGGNNNNNNNNCCGAA AGGUUUUC | 6740 |
| 2799 | AAACCUCUU GGCCGCGG | 2588 | CCGCGGCC CUGAUGAGGNNNNNNNNCCGAA AGAGGUUU | 6741 |
| 2813 | CGGUGCCUU CGGCCAAG | 2589 | CUUGGCCG CUGAUGAGGNNNNNNNNCCGAA AGGCACCG | 6742 |
| 2814 | GGUGCCUUC GGCCAAGU | 2590 | ACUUGGCC CUGAUGAGGNNNNNNNNCCGAA AAGGCACC | 6743 |
| 2826 | CAAGUGAUU GAGGCAGA | 2591 | UCUGCCUC CUGAUGAGGNNNNNNNNCCGAA AUCACUUG | 6744 |
| 2839 | CAGACGCUU UUGGAAUU | 2592 | AAUUCCAA CUGAUGAGGNNNNNNNNCCGAA AGCGUCUG | 6745 |
| 2840 | AGACGCUUU UGGAAUUG | 2593 | CAAUUCCA CUGAUGAGGNNNNNNNNCCGAA AAGCGUCU | 6746 |
| 2841 | GACGCUUUU GGAAUUGA | 2594 | UCAAUUCC CUGAUGAGGNNNNNNNNCCGAA AAAGCGUC | 6747 |
| 2847 | UUUGGAAUU GACAAGAC | 1903 | GUCUUGUC CUGAUGAGGNNNNNNNNCCGAA AUUCCAAA | 6059 |
| 2863 | CAGCGACUU GCAAAACA | 2595 | UGUUUUGC CUGAUGAGGNNNNNNNNCCGAA AGUCGCUG | 6748 |
| 2874 | AAAACAGUA GCCGUCAA | 2596 | UUGACGGC CUGAUGAGGNNNNNNNNCCGAA ACUGUUUU | 6749 |
| 2880 | GUAGCCGUC AAGAUGUU | 2597 | AACAUCUU CUGAUGAGGNNNNNNNNCCGAA ACGGCUAC | 6750 |
| 2888 | CAAGAUGUU GAAAGAAG | 2598 | CUUCUUUC CUGAUGAGGNNNNNNNNCCGAA ACAUCUUG | 6751 |
| 2917 | GCGAGCAUC GAGCCCUC | 2599 | GAGGGCUC CUGAUGAGGNNNNNNNNCCGAA AUGCUCGC | 6752 |
| 2925 | CGAGCCCUC AUGUCUGA | 2600 | UCAGACAU CUGAUGAGGNNNNNNNNCCGAA AGGGCUCG | 6753 |
| 2930 | CCUCAUGUC UGAACUCA | 2601 | UGAGUUCA CUGAUGAGGNNNNNNNNCCGAA ACAUGAGG | 6754 |
| 2937 | UCUGAACUC AAGAUCCU | 1912 | AGGAUCUU CUGAUGAGGNNNNNNNNCCGAA AGUUCAGA | 6068 |
| 2943 | CUCAAGAUC CUCAUCCA | 2602 | UGGAUGAG CUGAUGAGGNNNNNNNNCCGAA AUCUUGAG | 6755 |
| 2946 | AAGAUCCUC AUCCACAU | 2603 | AUGUGGAU CUGAUGAGGNNNNNNNNCCGAA AGGAUCUU | 6756 |
| 2949 | AUCCUCAUC CACAUUGG | 2604 | CCAAUGUG CUGAUGAGGNNNNNNNNCCGAA AUGAGGAU | 6757 |
| 2955 | AUCCACAUU GGUCACCA | 2605 | UGGUGACC CUGAUGAGGNNNNNNNNCCGAA AUGUGGAU | 6758 |
| 2959 | ACAUUGGUC ACCAUCUC | 2606 | GAGAUGGU CUGAUGAGGNNNNNNNNCCGAA ACCAAUGU | 6759 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2965 | GUCACCAUC UCAAUGUG | 1920 | CACAUUGA CUGAUGAGGNNNNNNNNCCGAA AUGGUGAC | 6076 |
| 2967 | CACCAUCUC AAUGUGGU | 1921 | ACCACAUU CUGAUGAGGNNNNNNNNCCGAA AGAUGGUG | 6077 |
| 2982 | GUGAACCUC CUAGGCGC | 2607 | GCGCCUAG CUGAUGAGGNNNNNNNNCCGAA AGGUUCAC | 6760 |
| 2985 | AACCUCCUA GGCGCCUG | 2608 | CAGGCGCC CUGAUGAGGNNNNNNNNCCGAA AGGAGGUU | 6761 |
| 3013 | GAGGGCCUC UCAUGGUG | 2609 | CACCAUGA CUGAUGAGGNNNNNNNNCCGAA AGGCCCUC | 6762 |
| 3015 | GGGCCUCUC AUGGUGAU | 2610 | AUCACCAU CUGAUGAGGNNNNNNNNCCGAA AGAGGCCC | 6763 |
| 3024 | AUGGUGAUU GUGGAAUU | 1928 | AAUUCCAC CUGAUGAGGNNNNNNNNCCGAA AUCACCAU | 6084 |
| 3032 | UGUGCAAUU CUGCAAGU | 2611 | ACUUGCAG CUGAUGAGGNNNNNNNNCCGAA AUUCCACA | 6764 |
| 3033 | GUGGAAUUC UGCAAGUU | 2612 | AACUUGCA CUGAUGAGGNNNNNNNNCCGAA AAUUCCAC | 6765 |
| 3041 | CUGCAACUU UGGAAACC | 2613 | GGUUUCCA CUGAUGAGGNNNNNNNNCCGAA ACUUGCAG | 6766 |
| 3042 | UGCAAGUUU GGAAACCU | 2614 | AGGUUUCC CUGAUGAGGNNNNNNNNCCGAA AACUUGCA | 6767 |
| 3051 | GGAAACCUA UCAACUUA | 2615 | UAAGUUGA CUGAUGAGGNNNNNNNNCCGAA AGGUUUCC | 6768 |
| 3053 | AAACCUAUC AACUUACU | 2616 | AGUAAGUU CUGAUGAGGNNNNNNNNCCGAA AUAGGUUU | 6769 |
| 3058 | UAUCAACUU ACUUACGG | 2617 | CCGUAAGU CUGAUGAGGNNNNNNNNCCGAA AGUUGAUA | 6770 |
| 3059 | AUCAACUUA CUUACGGG | 2618 | CCCGUAAG CUGAUGAGGNNNNNNNNCCGAA AAGUUGAU | 6771 |
| 3062 | AACUUACUU ACGGGCA | 2619 | UGCCCCGU CUGAUGAGGNNNNNNNNCCGAA AGUAACUU | 6772 |
| 3063 | ACUUACUUA CGGGGCAA | 2620 | UUGCCCCG CUGAUGAGGNNNNNNNNCCGAA AAGUAAGU | 6773 |
| 3083 | AAAUGAAUU UGUUCCCU | 2621 | AGGGAACA CUGAUGAGGNNNNNNNNCCGAA AUUCAUUU | 6774 |
| 3084 | AAUGAAUUU GUUCCCUA | 2622 | UAGGGAAC CUGAUGAGGNNNNNNNNCCGAA AAUUCAUU | 6775 |
| 3087 | GAAUUUGUU CCCUAUAA | 2623 | UUAUAGGG CUGAUGAGGNNNNNNNNCCGAA ACAAAUUC | 6776 |
| 3088 | AAUUUGUUC CCUAUAAG | 2624 | CUUAUAGG CUGAUGAGGNNNNNNNNCCGAA AACAAAUU | 6777 |
| 3092 | UGUUCCCUA UAAGAGCA | 2625 | UGCUCUUA CUGAUGAGGNNNNNNNNCCGAA AGGGAACA | 6778 |
| 3094 | UUCCCUAUA AGAGCAAA | 2626 | UUUGCUCU CUGAUGAGGNNNNNNNNCCGAA AUAGGGAA | 6779 |
| 3113 | GGCACGCUU CCGCCAGG | 2627 | CCUGGCGG CUGAUGAGGNNNNNNNNCCGAA AGCGUGCC | 6780 |
| 3114 | GCACGCUUC CGCCAGGG | 2628 | CCCUGGCG CUGAUGAGGNNNNNNNNCCGAA AAGCGUGC | 6781 |
| 3131 | CAAGGACUA CGUUGGGG | 2629 | CCCCAACG CUGAUGAGGNNNNNNNNCCGAA AGUCCUUG | 6782 |
| 3135 | GACUACGUU GGGGAGCU | 2630 | AGCUCCCC CUGAUGAGGNNNNNNNNCCGAA ACGUAGUC | 6783 |
| 3144 | GGGGAGCUC UCCGUGGA | 2631 | UCCACGGA CUGAUGAGGNNNNNNNNCCGAA AGCUCCCC | 6784 |
| 3146 | GGAGCUCUC CGUGGAUC | 2632 | GAUCCACG CUGAUGAGGNNNNNNNNCCGAA AGAGCUCC | 6785 |
| 3154 | CCGUGGAUC UGAAAAGA | 2633 | UCUUUUCA CUGAUGAGGNNNNNNNNCCGAA AUCCACGG | 6786 |
| 3167 | AAGACGCUU GGACAGCA | 2634 | UGCUGUCC CUGAUGAGGNNNNNNNNCCGAA AGCGUCUU | 6787 |
| 3177 | GACAGCAUC ACCAGCAG | 2635 | CUGCUGGU CUGAUGAGGNNNNNNNNCCGAA AUGCUGUC | 6788 |
| 3194 | CCAGAGCUC UGCCAGCU | 2636 | AGCUGGCA CUGAUGAGGNNNNNNNNCCGAA AGCUCUGG | 6789 |
| 3203 | UGCCAGCUC AGGCUUUG | 2637 | CAAAGCCU CUGAUGAGGNNNNNNNNCCGAA AGCUGGCA | 6790 |
| 3209 | CUCAGGCUU UCUUGAGG | 2638 | CCUCAACA CUGAUGAGGNNNNNNNNCCGAA AGCCUGAA | 6791 |
| 3210 | UCAGGCUUU GUUGAGGA | 2639 | UCCUCAAC CUGAUGAGGNNNNNNNNCCGAA AAGCCUGA | 6792 |
| 3213 | GGCUUUGUU GAGGAGAA | 2640 | UUCUCCUC CUGAUGAGGNNNNNNNNCCGAA ACAAAGCC | 6793 |
| 3224 | GGAGAAAUC GCUCAGUG | 2641 | CACUGAGC CUGAUGAGGNNNNNNNNCCGAA AUUUCUCC | 6794 |
| 3228 | AAAUCGCUC AGUGAUGU | 2642 | ACAUCACU CUGAUGAGGNNNNNNNNCCGAA AGCGAUUU | 6795 |
| 3237 | AGUGAUGUA GAGGAAGA | 2643 | UCUUCCUC CUGAUGAGGNNNNNNNNCCGAA ACAUCACU | 4658 |
| 3253 | AAGAAGCUU CUGAAGAA | 2644 | UUCUUCAG CUGAUGAGGNNNNNNNNCCGAA AGCUUCUU | 6796 |
| 3254 | AGAAGCUUC UGAAGAAC | 2645 | GUUCUUCA CUGAUGAGGNNNNNNNNCCGAA AAGCUUCU | 6797 |
| 3266 | AGAACUGUA CAAGGACU | 2646 | AGUCCUUG CUGAUGAGGNNNNNNNNCCGAA ACAGUUCU | 6798 |
| 3275 | CAAGGACUU CCUGACCU | 2647 | AGGUCAGG CUGAUGAGGNNNNNNNNCCGAA AGUCCUUG | 6799 |
| 3276 | AAGGACUUC CUGACCUU | 1962 | AAGGUCAG CUGAUGAGGNNNNNNNNCCGAA AAGUCCUU | 6118 |
| 3284 | CCUGACCUU GGAGCAUC | 1963 | GAUGCUCC CUGAUGAGGNNNNNNNNCCGAA AGGUCAGG | 6119 |
| 3292 | UGGAGCAUC UCAUCUGU | 1964 | ACAGAUGA CUGAUGAGGNNNNNNNNCCGAA AUGCUCCA | 6120 |
| 3294 | GAGCAUCUC AUCUGUUA | 1965 | UAACAGAU CUGAUGAGGNNNNNNNNCCGAA AGAUGCUC | 6121 |
| 3297 | CAUCUCAUC UGUUACAG | 1966 | CUGUAACA CUGAUGAGGNNNNNNNNCCGAA AUGAGAUG | 6122 |
| 3301 | UCAUCUGUU ACAGCUUC | 1967 | GAAGCGUU CUGAUGAGGNNNNNNNNCCGAA ACAGAUGA | 6123 |
| 3302 | CAUCUGUUA CAGCUUCC | 1968 | GGAAGCUG CUGAUGAGGNNNNNNNNCCGAA AACAGAUG | 6124 |
| 3308 | UUACAGCUU CCAAGUGG | 1969 | CCACUUGG CUGAUGAGGNNNNNNNNCCGAA AGCUGUAA | 6125 |
| 3309 | UACAGCUUC CAAGUGGC | 1970 | GCCACUUG CUGAUGAGGNNNNNNNNCCGAA AAGCUGUA | 6126 |
| 3319 | AAGUGGCUA AGGGCAUG | 1971 | CAUGCCCU CUGAUGAGGNNNNNNNNCCGAA AGCCACUU | 6127 |
| 3332 | CAUGGAGUU CUUGGCAU | 1972 | AUGCCAAG CUGAUGAGGNNNNNNNNCCGAA ACUCCAUG | 6128 |
| 3333 | AUGGAGUUC UUGGCAUC | 1973 | GAUGCCAA CUGAUGAGGNNNNNNNNCCGAA AACUCCAU | 6129 |
| 3335 | GGAGUUCUU GGCAUCAA | 2648 | UUGAUGCC CUGAUGAGGNNNNNNNNCCGAA AGAACUCC | 6800 |
| 3341 | CUUGGCAUC AAGGAAGU | 2649 | ACUUCCUU CUGAUGAGGNNNNNNNNCCGAA AUGCCAAG | 6801 |
| 3352 | GGAAGUGUA UCCACAGG | 2650 | CCUGUGGA CUGAUGAGGNNNNNNNNCCGAA ACACUUCC | 6802 |
| 3354 | AAGUGUAUC CACAGGAU | 1977 | UCCCUGUG CUGAUGAGGNNNNNNNNCCGAA AUACACUU | 6133 |
| 3381 | CGAAACAUU CUCCUAUC | 2651 | GAUAGGAG CUGAUGAGGNNNNNNNNCCGAA AUGUUUCG | 6803 |
| 3382 | GAAACAUUC UCCUAUCG | 2652 | CGAUAGGA CUGAUGAGGNNNNNNNNCCGAA AAUGUUUC | 6804 |
| 3384 | AACAUUCUC CUAUCGGA | 2653 | UCCGAUAG CUGAUGAGGNNNNNNNNCCGAA AGAAUGUU | 6805 |
| 3387 | AUUCUCCUA UCGGAGAA | 2654 | UUCUCCGA CUGAUGAGGNNNNNNNNCCGAA AGGAGAAU | 6806 |
| 3389 | UCUCCUAUC GGAGAAGA | 2655 | UCUUCUCC CUGAUGAGGNNNNNNNNCCGAA AUAGGAGA | 6807 |
| 3405 | AAUGUGGUU AAGAUCUG | 2656 | CAGAUCUU CUGAUGAGGNNNNNNNNCCGAA ACCACAUU | 6808 |
| 3406 | AUGUGGUUA AGAUCUGU | 2657 | ACAGAUCU CUGAUGAGGNNNNNNNNCCGAA AACCACAU | 6809 |
| 3411 | GUUAAGAUC UGUGACUU | 2658 | AAGUCACA CUGAUGAGGNNNNNNNNCCGAA AUCUUAAC | 6810 |
| 3419 | CUGUGACUU CGGCUUGG | 2659 | CCAAGCCG CUGAUGAGGNNNNNNNNCCGAA AGUCACAG | 6811 |
| 3420 | UGUGACUUC GGCUUGGC | 2660 | GCCAAGCC CUGAUGAGGNNNNNNNNCCGAA AAGUCACA | 6144 |
| 3425 | CUUCGGCUU GGCCCGGG | 2661 | CCCGGGCC CUGAUGAGGNNNNNNNNCCGAA AGCCGAAG | 6812 |
| 3438 | CGGGACAUU UAUAAAGA | 2662 | UCUUUAUA CUGAUGAGGNNNNNNNNCCGAA AUGUCCCG | 6813 |
| 3439 | GGGACAUUU AUAAAGAC | 2663 | GUCUUUAU CUGAUGAGGNNNNNNNNCCGAA AAUGUCCC | 6814 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3440 | GGACAUUUA UAAAGACC | 2664 | GGUCUUUA CUGAUGAGGNNNNNNNNCCGAA AAAUGUCC | 6815 |
| 3442 | ACAUUUAUA AAGACCCG | 2665 | CGGGUCUU CUGAUGAGGNNNNNNNNCCGAA AUAAAUGU | 6816 |
| 3454 | ACCCGGAUU AUGUCAGA | 2666 | UCUGACAU CUGAUGAGGNNNNNNNNCCGAA AUCCGGGU | 6817 |
| 3455 | CCCGGAUUA UGUCAGAA | 2667 | UUCUGACA CUGAUGAGGNNNNNNNNCCGAA AAUCCGGG | 6818 |
| 3459 | GAUUAUGUC AGAAAAGG | 1998 | CCUUUUCU CUGAUGAGGNNNNNNNNCCGAA ACAUAAUC | 6154 |
| 3480 | GCCCGACUC CCUUUGAA | 2668 | UUCAAAGG CUGAUGAGGNNNNNNNNCCGAA AGUCGGGC | 6819 |
| 3484 | GACUCCCUU UGAAGUGG | 2669 | CCACUUCA CUGAUGAGGNNNNNNNNCCGAA AGGGAGUC | 6820 |
| 3485 | ACUCCCUUU GAAGUGGA | 2670 | UCCACUUC CUGAUGAGGNNNNNNNNCCGAA AAGGGAGU | 6821 |
| 3510 | GAAACCAUU UUUGACAG | 2671 | CUGUCAAA CUGAUGAGGNNNNNNNNCCGAA AUGGUUUC | 6822 |
| 3511 | AAACCAUUU UUGACAGA | 2672 | UCUGUCAA CUGAUGAGGNNNNNNNNCCGAA AAUGGUUU | 6823 |
| 3512 | AACCAUUUU UGACAGAG | 2673 | CUCUGUCA CUGAUGAGGNNNNNNNNCCGAA AAAUGGUU | 6824 |
| 3513 | ACCAUUUUU GACAGAGU | 2674 | ACUCUGUC CUGAUGAGGNNNNNNNNCCGAA AAAAUGGU | 6825 |
| 3522 | GACAGAGUA UACACAAU | 2675 | AUUGUGUA CUGAUGAGGNNNNNNNNCCGAA ACUCUGUC | 6826 |
| 3524 | CAGAGUAUA CACAAUUC | 2676 | GAAUUGUG CUGAUGAGGNNNNNNNNCCGAA AUACUCUG | 6827 |
| 3531 | UACACAAUU CAGAGCGA | 2677 | UCGCUCUG CUGAUGAGGNNNNNNNNCCGAA AUUGUGUA | 6828 |
| 3532 | ACACAAUUC AGAGCGAU | 2678 | AUCGCUCU CUGAUGAGGNNNNNNNNCCGAA AAUUGUGU | 6829 |
| 3548 | UGUGUGGUC UUUCGGUG | 2679 | CACCGAAA CUGAUGAGGNNNNNNNNCCGAA ACCACACA | 6830 |
| 3550 | UGUGGUCUU UCGGUGUG | 2680 | CACACCGA CUGAUGAGGNNNNNNNNCCGAA AGACCACA | 6831 |
| 3551 | GUGGUCUUU CGGUGUGU | 2681 | ACACACCG CUGAUGAGGNNNNNNNNCCGAA AAGACCAC | 6832 |
| 3552 | UGGUCUUUC GGUGUGUU | 2682 | AACACACC CUGAUGAGGNNNNNNNNCCGAA AAAGACCA | 6833 |
| 3560 | CGGUGUGUU GCUCUGGG | 2683 | CCCAGAGC CUGAUGAGGNNNNNNNNCCGAA ACACACCG | 6834 |
| 3564 | GUGUUGCUC UGGGAAAU | 2684 | AUUUCCCA CUGAUGAGGNNNNNNNNCCGAA AGCAACAC | 6835 |
| 3573 | UGGGAAAUA UUUUCCUU | 2017 | AAGGAAAA CUGAUGAGGNNNNNNNNCCGAA AUUUCCCA | 6173 |
| 3575 | GGAAAUAUU UUCCUUAG | 2018 | CUAAGGAA CUGAUGAGGNNNNNNNNCCGAA AUAUUUCC | 6174 |
| 3576 | GAAAUAUUU UCCUUAGG | 2019 | CCUAAGGA CUGAUGAGGNNNNNNNNCCGAA AAUAUUUC | 6175 |
| 3577 | AAAUAUUUU CCUUAGGU | 2020 | ACCUAAGG CUGAUGAGGNNNNNNNNCCGAA AAAUAUUU | 6176 |
| 3578 | AAUAUUUUC CUUAGGUG | 2021 | CACCUAAG CUGAUGAGGNNNNNNNNCCGAA AAAAUAUU | 6177 |
| 3581 | AUUUUCCUU AGGUGCCU | 2685 | AGGCACCU CUGAUGAGGNNNNNNNNCCGAA AGGAAAAU | 6836 |
| 3582 | UUUUCCUUA GGUGCCUC | 2686 | GAGGCACC CUGAUGAGGNNNNNNNNCCGAA AAGGAAAA | 6837 |
| 3590 | AGGUGCCUC CCCAUACC | 2687 | GGUAUGGG CUGAUGAGGNNNNNNNNCCGAA AGGCACCU | 6838 |
| 3596 | CUCCCCAUA CCCUGGGG | 2688 | CCCCAGGG CUGAUGAGGNNNNNNNNCCGAA AUGGGGAG | 6839 |
| 3606 | CCUGGGGUC AAGAUUGA | 2689 | UCAAUCUU CUGAUGAGGNNNNNNNNCCGAA ACCCCAGG | 6185 |
| 3612 | GUCAAGAUU GAUGAAGA | 2690 | UCUUCAUC CUGAUGAGGNNNNNNNNCCGAA AUCUUGAC | 6840 |
| 3623 | UGAAGAAUU UUGUAGGA | 2691 | UCCUACAA CUGAUGAGGNNNNNNNNCCGAA AUUCUUCA | 6841 |
| 3624 | GAAGAAUUU UGUAGGAG | 2692 | CUCCUACA CUGAUGAGGNNNNNNNNCCGAA AAUUCUUC | 6842 |
| 3625 | AAGAAUUUU GUAGGAGA | 2693 | UCUCCUAC CUGAUGAGGNNNNNNNNCCGAA AAAUUCUU | 6843 |
| 3628 | AAUUUUGUA GGAGAUUG | 2694 | CAAUCUCC CUGAUGAGGNNNNNNNNCCGAA ACAAAAUU | 6844 |
| 3635 | UAGGAGAUU GAAAGAAG | 2695 | CUUCUUUC CUGAUGAGGNNNNNNNNCCGAA AUCUCCUA | 6845 |
| 3649 | AAGGAACUA GAAUGCGG | 2696 | CCGCAUUC CUGAUGAGGNNNNNNNNCCGAA AGUUCCUU | 6846 |
| 3661 | UGCGGGCUC CUGACUAC | 2697 | GUAGUCAG CUGAUGAGGNNNNNNNNCCGAA AGCCCGCA | 6847 |
| 3668 | UCCUGACUA CACUACCC | 2698 | GGGUAGUG CUGAUGAGGNNNNNNNNCCGAA AGUCAGGA | 6848 |
| 3673 | ACUACACUA CCCCAGAA | 2699 | UUCUGGGG CUGAUGAGGNNNNNNNNCCGAA AGUGUAGU | 6849 |
| 3686 | AGAAAUGUA CCAGACCA | 2041 | UGGUCUGG CUGAUGAGGNNNNNNNNCCGAA ACAUUUCU | 6197 |
| 3734 | GAGACCCUC GUUUCAG | 2700 | CUGAAAAC CUGAUGAGGNNNNNNNNCCGAA AGGGUCUC | 6850 |
| 3737 | ACCCUCGUU UUCAGAGU | 2701 | ACUCUGAA CUGAUGAGGNNNNNNNNCCGAA ACGAGGGU | 6851 |
| 3738 | CCCUCGUUU UCAGAGUU | 2702 | AACUCUGA CUGAUGAGGNNNNNNNNCCGAA AACGAGGG | 6852 |
| 3739 | CCUCGUUUU CAGAGUUG | 2703 | CAACUCUG CUGAUGAGGNNNNNNNNCCGAA AAACGAGG | 6853 |
| 3740 | CUCGUUUUC AGAGUUGG | 2704 | CCAACUCU CUGAUGAGGNNNNNNNNCCGAA AAAACGAG | 6854 |
| 3746 | UUCAGAGUU GGUGGAGC | 2705 | GCUCCACC CUGAUGAGGNNNNNNNNCCGAA ACUCUGAA | 6855 |
| 3757 | UGGAGCAUU UGGGAAAC | 2706 | GUUUCCCA CUGAUGAGGNNNNNNNNCCGAA AUGCUCCA | 6856 |
| 3758 | GGAGCAUUU GGGAAACC | 2707 | GGUUUCCC CUGAUGAGGNNNNNNNNCCGAA AAUGCUCC | 6857 |
| 3768 | GGAAACCUC CUGCAAGC | 2708 | GCUUGCAG CUGAUGAGGNNNNNNNNCCGAA AGGUUUCC | 6858 |
| 3803 | CAAAGACUA UAUUGUUC | 2709 | GAACAAUA CUGAUGAGGNNNNNNNNCCGAA AGUCUUUG | 6859 |
| 3805 | AAGACUAUA UUGUUCUU | 2710 | AAGAACAA CUGAUGAGGNNNNNNNNCCGAA AUAGUCUU | 6860 |
| 3807 | GACUAUAUU GUUCUUCC | 2711 | GGAAGAAC CUGAUGAGGNNNNNNNNCCGAA AUAUAGUC | 6861 |
| 3810 | UAUAUUGUU CUUCCAAU | 2712 | AUUGGAAG CUGAUGAGGNNNNNNNNCCGAA ACAAUAUA | 6862 |
| 3811 | AUAUUGUUC UUCCAAUG | 2713 | CAUUGGAA CUGAUGAGGNNNNNNNNCCGAA AACAAUAU | 6863 |
| 3813 | AUUGUUCUU CCAAUGUC | 2714 | GACAUUGG CUGAUGAGGNNNNNNNNCCGAA AGAACAAU | 6864 |
| 3814 | UUGUUCUUC CAAUGUCA | 2715 | UGACAUUG CUGAUGAGGNNNNNNNNCCGAA AAGAACAA | 6865 |
| 3821 | UCCAAUGUC AGAGACAC | 2716 | GUGUCUCU CUGAUGAGGNNNNNNNNCCGAA ACAUUGGA | 6866 |
| 3847 | AAGAGGAUU CUGGACUC | 2065 | GAGUCCAG CUGAUGAGGNNNNNNNNCCGAA AUCCUCUU | 6221 |
| 3848 | AGAGGAUUC UGGACUCU | 2066 | AGAGUCCA CUGAUGAGGNNNNNNNNCCGAA AAUCCUCU | 6222 |
| 3855 | UCUGGACUC UCCCUGCC | 2717 | GGCAGGGA CUGAUGAGGNNNNNNNNCCGAA AGUCCAGA | 6867 |
| 3857 | UGGACUCUC CCUGCCUA | 2718 | UAGGCAGG CUGAUGAGGNNNNNNNNCCGAA AGAGUCCA | 6868 |
| 3865 | CCCUGCCUA CCUCACCU | 2719 | AGGUGAGG CUGAUGAGGNNNNNNNNCCGAA AGGCAGGG | 6869 |
| 3869 | GCCUACCUC ACCUGUUU | 2071 | AAACAGGU CUGAUGAGGNNNNNNNNCCGAA AGGUAGGC | 6227 |
| 3876 | UCACCUGUU UCCUGUAU | 2072 | AUACAGGA CUGAUGAGGNNNNNNNNCCGAA ACAGGUGA | 6228 |
| 3877 | CACCUGUUU CCUGUAUG | 2073 | CAUACAGG CUGAUGAGGNNNNNNNNCCGAA AACAGGUG | 6229 |
| 3878 | ACCUGUUUC CUGUAUGG | 2074 | CCAUACAG CUGAUGAGGNNNNNNNNCCGAA AAACAGGU | 6230 |
| 3883 | UUUCCUGUA UGGAGGAA | 2720 | UUCCUCCA CUGAUGAGGNNNNNNNNCCGAA ACAGGAAA | 6870 |
| 3914 | CCCCAAAUU CCAUUAUG | 2077 | CAUAAUGG CUGAUGAGGNNNNNNNNCCGAA AUUUGGGG | 6233 |
| 3915 | CCCAAAUUC CAUUAUGA | 2078 | UCAUAAUG CUGAUGAGGNNNNNNNNCCGAA AAUUUGGG | 6234 |
| 3919 | AAUUCCAUU AUGACAAC | 2079 | GUUGUCAU CUGAUGAGGNNNNNNNNCCGAA AUGGAAUU | 6235 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3920 | AUUCCAUUA UGACAACA | 2080 | UGUUGUCA CUGAUGAGGNNNNNNNNCCGAA AAUGGAAU | 6236 |
| 3939 | GCAGGAAUC AGUCAUUA | 2721 | UAAUGACU CUGAUGAGGNNNNNNNNCCGAA AUUCCUGC | 6871 |
| 3943 | GAAUCAGUC AUUAUCUC | 2722 | GAGAUAAU CUGAUGAGGNNNNNNNNCCGAA ACUGAUUC | 6872 |
| 3946 | UCAGUCAUU AUCUCCAG | 2723 | CUGGAGAU CUGAUGAGGNNNNNNNNCCGAA AUGACUGA | 6873 |
| 3947 | CAGUCAUUA UCUCCAGA | 2724 | UCUGGAGA CUGAUGAGGNNNNNNNNCCGAA AAUGACUG | 6874 |
| 3949 | GUCAUUAUC UCCAGAAC | 2725 | GUUCUGGA CUGAUGAGGNNNNNNNNCCGAA AUAAUGAC | 6875 |
| 3951 | CAUUAUCUC CAGAACAG | 2726 | CUGUUCUG CUGAUGAGGNNNNNNNNCCGAA AGAUAAUG | 6876 |
| 3961 | AGAACAGUA AGCGAAAG | 2085 | CUUUCGCU CUGAUGAGGNNNNNNNNCCGAA ACUGUUCU | 6241 |
| 3987 | GUGAGUGUA AAAACAUU | 2086 | AAUGUUUU CUGAUGAGGNNNNNNNNCCGAA ACACUCAC | 6242 |
| 3995 | AAAAACAUU UGAAGAUA | 2087 | UAUCUUCA CUGAUGAGGNNNNNNNNCCGAA AUGUUUUU | 6243 |
| 3996 | AAAACAUUU GAAGAUAU | 2088 | AUAUCUUC CUGAUGAGGNNNNNNNNCCGAA AAUGUUUU | 6244 |
| 4003 | UUGAAGAUA UCCCAUUG | 2727 | CAAUGGGA CUGAUGAGGNNNNNNNNCCGAA AUCUUCAA | 6877 |
| 4005 | GAAGAUAUC CCAUUGGA | 2728 | UCCAAUGG CUGAUGAGGNNNNNNNNCCGAA AUAUCUUC | 6878 |
| 4010 | UAUCCCAUU GGAGGAAC | 2729 | GUUCCUCC CUGAUGAGGNNNNNNNNCCGAA AUGGGAUA | 6879 |
| 4026 | CCAGAAGUA AAAGUGAU | 2730 | AUCACUUU CUGAUGAGGNNNNNNNNCCGAA ACUUCUGG | 6880 |
| 4035 | AAAGUGAUC CCAGAUGA | 2731 | UCAUCUGG CUGAUGAGGNNNNNNNNCCGAA AUCACUUU | 6881 |
| 4068 | GGGAUGGUC CUUGCAUC | 2732 | GAUGCAAG CUGAUGAGGNNNNNNNNCCGAA ACCAUCCC | 6882 |
| 4071 | AUGGUCCUU GCAUCAGA | 2733 | UCUGAUGC CUGAUGAGGNNNNNNNNCCGAA AGGACCAU | 6883 |
| 4076 | CCUUGCAUC AGAAGAGC | 2734 | GCUCUUCU CUGAUGAGGNNNNNNNNCCGAA AUGCAAGG | 6884 |
| 4093 | UGAAAACUC UGGAAGAC | 2735 | GUCUUCCA CUGAUGAGGNNNNNNNNCCGAA AGUUUUCA | 6257 |
| 4112 | GAACAAAUU AUCUCCAU | 2736 | AUGGAGAU CUGAUGAGGNNNNNNNNCCGAA AUUUGUUC | 6885 |
| 4113 | AACAAAUUA UCUCCAUC | 2737 | GAUGGAGA CUGAUGAGGNNNNNNNNCCGAA AAUUUGUU | 6886 |
| 4115 | CAAAUUAUC UCCAUCUU | 2105 | AAGAUGGA CUGAUGAGGNNNNNNNNCCGAA AUAAUUUG | 6261 |
| 4117 | AAUUAUCUC CAUCUUUU | 2106 | AAAAGAUG CUGAUGAGGNNNNNNNNCCGAA AGAUAAUU | 6262 |
| 4121 | AUCUCCAUC UUUUGGUG | 2107 | CACCAAAA CUGAUGAGGNNNNNNNNCCGAA AUGGAGAU | 6263 |
| 4123 | CUCCAUCUU UUGGUGGA | 2108 | UCCACCAA CUGAUGAGGNNNNNNNNCCGAA AGAUGGAG | 6264 |
| 4124 | UCCAUCUUU UGGUGGAA | 2109 | UUCCACCA CUGAUGAGGNNNNNNNNCCGAA AAGAUGGA | 6265 |
| 4125 | CCAUCUUUU GGUGGAAU | 2110 | AUUCCACC CUGAUGAGGNNNNNNNNCCGAA AAAGAUGG | 6266 |
| 4144 | UGCCCAGUA AAAGCAGG | 2738 | CCUGCUUU CUGAUGAGGNNNNNNNNCCGAA ACUGGGCA | 6887 |
| 4157 | CAGGGAGUC UGUGGCCU | 2739 | AGGCCACA CUGAUGAGGNNNNNNNNCCGAA ACUCCCUG | 6888 |
| 4166 | UGUGGCCUC GGAAGGCU | 2740 | AGCCUUCC CUGAUGAGGNNNNNNNNCCGAA AGGCCACA | 6889 |
| 4175 | GGAAGGCUC CAACCAGA | 2741 | UCUGGUUG CUGAUGAGGNNNNNNNNCCGAA AGCCUUCC | 6890 |
| 4193 | CAGUGGCUA CCAGUCUG | 2742 | CAGACUGG CUGAUGAGGNNNNNNNNCCGAA AGCCACUG | 6891 |
| 4199 | CUACCAGUC UGGGUAUC | 2743 | GAUACCCA CUGAUGAGGNNNNNNNNCCGAA ACUGGUAG | 6892 |
| 4205 | GUCUGGGUA UCACUCAG | 2744 | CUGAGUGA CUGAUGAGGNNNNNNNNCCGAA ACCCAGAC | 6893 |
| 4207 | CUGGGUAUC ACUCAGAU | 2745 | AUCUGAGU CUGAUGAGGNNNNNNNNCCGAA AUACCCAG | 6894 |
| 4211 | GUAUCACUC AGAUGACA | 2746 | UGUCAUCU CUGAUGAGGNNNNNNNNCCGAA AGUGAUAC | 6895 |
| 4235 | CACCGUGUA CUCCAGCG | 2747 | CGCUGGAG CUGAUGAGGNNNNNNNNCCGAA ACACGGUG | 6896 |
| 4238 | CGUGUACUC CAGCGACG | 2748 | CGUCGCUG CUGAUGAGGNNNNNNNNCCGAA AGUACACG | 6897 |
| 4257 | GCAGGACUU UUAAAGAU | 2749 | AUCUUUAA CUGAUGAGGNNNNNNNNCCGAA AGUCCUGC | 6898 |
| 4258 | CAGGACUUU UAAAGAUG | 2750 | CAUCUUUA CUGAUGAGGNNNNNNNNCCGAA AAGUCCUG | 6899 |
| 4259 | AGGACUUUU AAAGAUGG | 2751 | CCAUCUUU CUGAUGAGGNNNNNNNNCCGAA AAAGUCCU | 6900 |
| 4260 | GGACUUUUA AAGAUGGU | 2752 | ACCAUCUU CUGAUGAGGNNNNNNNNCCGAA AAAAGUCC | 6901 |
| 4281 | GCUGCAGUU CACGCUGA | 2753 | UCAGCGUG CUGAUGAGGNNNNNNNNCCGAA ACUGCAGC | 6902 |
| 4282 | CUGCAGUUC ACGCUGAC | 2754 | GUCAGCGU CUGAUGAGGNNNNNNNNCCGAA AACUGCAG | 6903 |
| 4292 | CGCUGACUC AGGGACCA | 2755 | UGGUCCCU CUGAUGAGGNNNNNNNNCCGAA AGUCAGCG | 6904 |
| 4311 | CUGCAGCUC ACCUCCUG | 2756 | CAGGAGGU CUGAUGAGGNNNNNNNNCCGAA AGCUGCAG | 6905 |
| 4316 | GCUCACCUC CUGUUUAA | 2757 | UUAAACAG CUGAUGAGGNNNNNNNNCCGAA AGGUGAGC | 6906 |
| 4321 | CCUCCUGUU AAAUGGA | 2758 | UCCAUUUA CUGAUGAGGNNNNNNNNCCGAA ACAGGAGG | 6907 |
| 4322 | CUCCUGUUU AAAUGGAA | 2759 | UUCCAUUU CUGAUGAGGNNNNNNNNCCGAA AACAGGAG | 6908 |
| 4323 | UCCUGUUUA AAUGGAAG | 2760 | CUUCCAUU CUGAUGAGGNNNNNNNNCCGAA AAACAGGA | 6909 |
| 4336 | GAAGUGGUC CUGUCCCG | 2761 | CGGGACAG CUGAUGAGGNNNNNNNNCCGAA ACCACUUC | 6910 |
| 4341 | GGUCCUGUC CCGGCUCC | 2762 | GGAGCCGG CUGAUGAGGNNNNNNNNCCGAA ACAGGACC | 6911 |
| 4348 | UCCCGGCUC CGCCCCCA | 2763 | UGGGGGCG CUGAUGAGGNNNNNNNNCCGAA AGCCGGGA | 6912 |
| 4360 | CCCCAACUC UGGAAAU | 2764 | AUUUCCAG CUGAUGAGGNNNNNNNNCCGAA AGUGGGG | 6913 |
| 4369 | CUGGAAAUC ACGAGAGA | 2765 | UCUCUCGU CUGAUGAGGNNNNNNNNCCGAA AUUUCCAG | 6914 |
| 4387 | GUGCUGCUU AGAUUUUC | 2766 | GAAAAUCU CUGAUGAGGNNNNNNNNCCGAA AGCAGCAC | 6915 |
| 4388 | UGCUGCUUA GAUUUUCA | 2767 | UGAAAAUC CUGAUGAGGNNNNNNNNCCGAA AAGCAGCA | 6916 |
| 4392 | GCUUAGAUU UCAAGUG | 2768 | CACUUGAA CUGAUGAGGNNNNNNNNCCGAA AUCUAAGC | 6917 |
| 4393 | CUUAGAUUU UCAAGUGU | 2769 | ACACUUGA CUGAUGAGGNNNNNNNNCCGAA AAUCUAAG | 6918 |
| 4394 | UUAGAUUUU CAAGUGUU | 2770 | AACACUUG CUGAUGAGGNNNNNNNNCCGAA AAAUCUAA | 6919 |
| 4395 | UAGAUUUUC AAGUGUUG | 2771 | CAACACUU CUGAUGAGGNNNNNNNNCCGAA AAAAUCUA | 6920 |
| 4402 | UCAAGUGUU GUUCUUUC | 2772 | GAAAGAAC CUGAUGAGGNNNNNNNNCCGAA ACACUUGA | 6921 |
| 4405 | AGUGUUGUU CUUCCAC | 2146 | GUGGAAAG CUGAUGAGGNNNNNNNNCCGAA ACAACACU | 6302 |
| 4406 | GUGUUGUUC UUUCCACC | 2147 | GGUGGAAA CUGAUGAGGNNNNNNNNCCGAA AACAACAC | 6303 |
| 4408 | GUUGUUCUU UCCACCAC | 2773 | GUGGUGGA CUGAUGAGGNNNNNNNNCCGAA AGAACAAC | 6922 |
| 4409 | UUGUUCUUU CCACCACC | 2774 | GGUGGUGG CUGAUGAGGNNNNNNNNCCGAA AAGAACAA | 6923 |
| 4410 | UGUUCUUUC CACCACCC | 2775 | GGGUGGUG CUGAUGAGGNNNNNNNNCCGAA AAAGAACA | 6924 |
| 4425 | CCGGAAGUA GCCACAUU | 2776 | AAUGUGGC CUGAUGAGGNNNNNNNNCCGAA ACUUCCGG | 6925 |
| 4433 | AGCCACAUU UGAUUUUC | 2777 | GAAAAUCA CUGAUGAGGNNNNNNNNCCGAA AUGUGGCU | 6926 |
| 4434 | GCCACAUUU GAUUUUCA | 2778 | UGAAAAUC CUGAUGAGGNNNNNNNNCCGAA AAUGUGGC | 6927 |
| 4438 | CAUUUGAUU UUCAUUUU | 2779 | AAAAUGAA CUGAUGAGGNNNNNNNNCCGAA AUCAAAUG | 6928 |
| 4439 | AUUUGAUUU UCAUUUUU | 2780 | AAAAAUGA CUGAUGAGGNNNNNNNNCCGAA AAUCAAAU | 6929 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4440 | UUUGAUUUU CAUUUUUG | 2781 | CAAAAAUG CUGAUGAGGNNNNNNNNCCGAA AAAUCAAA | 6930 |
| 4441 | UUGAUUUUC AUUUUUGG | 2782 | CCAAAAAU CUGAUGAGGNNNNNNNNCCGAA AAAAUCAA | 6931 |
| 4444 | AUUUUCAUU UUUGGAGG | 2783 | CCUCCAAA CUGAUGAGGNNNNNNNNCCGAA AUGAAAAU | 6932 |
| 4445 | UUUUCAUUU UUGGAGGA | 2784 | UCCUCCAA CUGAUGAGGNNNNNNNNCCGAA AAUGAAAA | 6933 |
| 4446 | UUUCAUUUU UGGAGGAG | 2785 | CUCCUCCA CUGAUGAGGNNNNNNNNCCGAA AAAUGAAA | 6934 |
| 4447 | UUCAUUUUU GGAGGAGG | 2786 | CCUCCUCC CUGAUGAGGNNNNNNNNCCGAA AAAAUGAA | 6935 |
| 4461 | AGGGACCUC AGACUGCA | 2787 | UGCAGUCU CUGAUGAGGNNNNNNNNCCGAA AGGUCCCU | 6936 |
| 4477 | AAGGAGCUU GUCCUCAG | 2788 | CUGAGGAC CUGAUGAGGNNNNNNNNCCGAA AGCUCCUU | 6937 |
| 4480 | GAGCUUGUC CUCAGGGC | 2789 | GCCCUGAG CUGAUGAGGNNNNNNNNCCGAA ACAAGCUC | 6938 |
| 4483 | CUUGUCCUC AGGGCAUU | 2790 | AAUGCCCU CUGAUGAGGNNNNNNNNCCGAA AGGACAAG | 6939 |
| 4491 | CAGGGCAUU UCCAGAGA | 2791 | UCUCUGGA CUGAUGAGGNNNNNNNNCCGAA AUGCCCUG | 6940 |
| 4492 | AGGGCAUUU CCAGAGAA | 2792 | UUCUCUGG CUGAUGAGGNNNNNNNNCCGAA AAUGCCCU | 6941 |
| 4493 | GGGCAUUUC CAGAGAAG | 2793 | CUUCUCUG CUGAUGAGGNNNNNNNNCCGAA AAAUGCCC | 6942 |
| 4528 | GAAUGUGUU GACUCUAC | 2794 | GUAGAGUC CUGAUGAGGNNNNNNNNCCGAA ACACAUUC | 6943 |
| 4530 | UGUUGACUC UACUCUCU | 2795 | AGAGAGUA CUGAUGAGGNNNNNNNNCCGAA AGUCAACA | 6944 |
| 4532 | UUGACUCUA CUCUCUUU | 2796 | AAAGAGAG CUGAUGAGGNNNNNNNNCCGAA AGAGUCAA | 6945 |
| 4535 | ACUCUACUC UCUUUCC | 2797 | GGAAAAGA CUGAUGAGGNNNNNNNNCCGAA AGUAGAGU | 6946 |
| 4537 | UCUACUCUC UUUUCCAU | 2798 | AUGGAAAA CUGAUGAGGNNNNNNNNCCGAA AGAGUAGA | 6947 |
| 4539 | UACUCUCUU UUCCAUUC | 2799 | GAAUGGAA CUGAUGAGGNNNNNNNNCCGAA AGAGAGUA | 6948 |
| 4540 | ACUCUCUUU UCCAUUCA | 2800 | UGAAUGGA CUGAUGAGGNNNNNNNNCCGAA AAGAGAGU | 6949 |
| 4541 | CUCUCUUUU CCAUUCAU | 2801 | AUGAAUGG CUGAUGAGGNNNNNNNNCCGAA AAAGAGAG | 6950 |
| 4542 | UCUCUUUUC CAUUCAUU | 2802 | AAUGAAUG CUGAUGAGGNNNNNNNNCCGAA AAAAGAGA | 6951 |
| 4546 | UUUUCCAUU CAUUUAAA | 2803 | UUUAAAUG CUGAUGAGGNNNNNNNNCCGAA AUGGAAAA | 6952 |
| 4547 | UUUCCAUUC AUUUAAAA | 2804 | UUUUAAAU CUGAUGAGGNNNNNNNNCCGAA AAUGGAAA | 6953 |
| 4550 | CCAUUCAUU UAAAAGUC | 2805 | GACUUYUA CUGAUGAGGNNNNNNNNCCGAA AUGAAUGG | 6954 |
| 4551 | CAUUCAUUU AAAAGUCC | 2806 | GGACUUUU CUGAUGAGGNNNNNNNNCCGAA AAUGAAUG | 6955 |
| 4552 | AUUCAUUUA AAAGUCCU | 2807 | AGGACUUU CUGAUGAGGNNNNNNNNCCGAA AAAUGAAU | 6956 |
| 4558 | UUAAAAGUC CUAUAUAA | 2808 | UUAUAUAG CUGAUGAGGNNNNNNNNCCGAA ACUUUUAA | 6957 |
| 4561 | AAAGUCCUA UAUAAUGU | 2809 | ACAUUAUA CUGAUGAGGNNNNNNNNCCGAA AGGACUUU | 6958 |
| 4563 | AGUCCUAUA UAAUGUGC | 2810 | GCACAUUA CUGAUGAGGNNNNNNNNCCGAA AUAGGACU | 6959 |
| 4565 | UCCUAUAUA AUGUGCCC | 2811 | GGGCACAU CUGAUGAGGNNNNNNNNCCGAA AUAUAGGA | 6960 |
| 4583 | GCUGUGGUC UCACUACC | 2812 | GGUAGUGA CUGAUGAGGNNNNNNNNCCGAA ACCACAGC | 6961 |
| 4585 | UGUGGUCUC ACUACCAG | 2813 | CUGGUAGU CUGAUGAGGNNNNNNNNCCGAA AGACCACA | 6962 |
| 4589 | GUCUCACUA CCAGUUAA | 2814 | UUAACUGG CUGAUGAGGNNNNNNNNCCGAA AGUGAGAC | 6963 |
| 4595 | CUACCAGUU AAAGCAAA | 2815 | UUUGCUUU CUGAUGAGGNNNNNNNNCCGAA ACUGGUAG | 6964 |
| 4596 | UACCAGUUA AAGCAAAA | 2816 | UUUUGCUU CUGAUGAGGNNNNNNNNCCGAA AACUGGUA | 696S |
| 4609 | AAAAGACUU UCAAACAC | 2817 | GUGUUUGA CUGAUGAGGNNNNNNNNCCGAA AGUCUUUU | 6966 |
| 4610 | AAAGACUUU CAAACACG | 2818 | CGUGUUUG CUGAUGAGGNNNNNNNNCCGAA AAGUCUUU | 6967 |
| 4611 | AAGACUUUC AAACACGU | 2819 | ACGUGUUU CUGAUGAGGNNNNNNNNCCGAA AAAGUCUU | 6968 |
| 4625 | CGUGGACUC UGUCCUCC | 2820 | GGAGGACA CUGAUGAGGNNNNNNNNCCGAA AGUCCACG | 6969 |
| 4629 | GACUCUGUC CUCCAAGA | 2821 | UCUUGGAG CUGAUGAGGNNNNNNNNCCGAA ACAGAGUC | 6970 |
| 4632 | UCUGUCCUC CAAGAAGU | 2822 | ACUUCUUG CUGAUGAGGNNNNNNNNCCGAA AGGACAGA | 6971 |
| 4654 | CGGCACCUC UGUGAAAC | 2823 | GUUUCACA CUGAUGAGGNNNNNNNNCCGAA AGGUGCCG | 6972 |
| 4668 | AACUGGAUC GAAUGGGC | 2824 | GCCCAUUC CUGAUGAGGNNNNNNNNCCGAA AUCCAGUU | 6973 |
| 4683 | GCAAUGCUU UGUGUGUU | 2825 | AACACACA CUGAUGAGGNNNNNNNNCCGAA AGCAUUGC | 6974 |
| 4684 | CAAUGCUUU GUGUGUUG | 2826 | CAACACAC CUGAUGAGGNNNNNNNNCCGAA AAGCAUUG | 6975 |
| 4691 | UUGUGUGUU GAGGAUGG | 2827 | CCAUCCUC CUGAUGAGGNNNNNNNNCCGAA ACACACAA | 6976 |
| 4709 | UGAGAUGUC CCAGGGCC | 2828 | GGCCCUGG CUGAUGAGGNNNNNNNNCCGAA ACAUCUCA | 6977 |
| 4722 | GGCCGAGUC UGUCUACC | 2829 | GGUAGACA CUGAUGAGGNNNNNNNNCCGAA ACUCGGCC | 6978 |
| 4726 | GAGUCUGUC UACCUUGG | 2830 | CCAAGGUA CUGAUGAGGNNNNNNNNCCGAA ACAGACUC | 6979 |
| 4728 | GUCUGUCUA CCUUGGAG | 2831 | CUCCAAGG CUGAUGAGGNNNNNNNNCCGAA AGACAGAC | 6980 |
| 4732 | GUCUACCUU GGAGGCUU | 2832 | AAGCCUCC CUGAUGAGGNNNNNNNNCCGAA AGGUAGAC | 6981 |
| 4740 | UGGAGGCUU UGUGGAGG | 2833 | CCUCCACA CUGAUGAGGNNNNNNNNCCGAA AGCCUCCA | 6982 |
| 4741 | GGAGGCUUU GUGGAGGA | 2834 | UCCUCCAC CUGAUGAGGNNNNNNNNCCGAA AAGCCUCC | 6983 |
| 4758 | UGCGGGCUA UGAGCCAA | 2835 | UUGGCUCA CUGAUGAGGNNNNNNNNCCGAA AGCCCGCA | 6984 |
| 4771 | CCAAGUGUU AAGUGUGG | 2836 | CCACACUU CUGAUGAGGNNNNNNNNCCGAA ACACUUGG | 6985 |
| 4772 | CAAGUGUUA AGUGUGGG | 2837 | CCCACACU CUGAUGAGGNNNNNNNNCCGAA AACACUUG | 6986 |
| 4811 | GCGCAAGUC GCUCGGAG | 2838 | CUCCGAGC CUGAUGAGGNNNNNNNNCCGAA ACUUGCGC | 6987 |
| 4815 | AAGUCGCUC GGAGAGCG | 2839 | CGCUCUCC CUGAUGAGGNNNNNNNNCCGAA AGCGACUU | 6988 |
| 4826 | AGAGCGGUU GGAGCCUG | 2840 | CAGGCUCC CUGAUGAGGNNNNNNNNCCGAA ACCGCUCU | 6989 |
| 4844 | AGAUGCAUU GUGCUGGC | 2841 | GCCAGCAC CUGAUGAGGNNNNNNNNCCGAA AUGCAUCU | 6990 |
| 4854 | UGCUGGCUC UGGUGGAG | 2842 | CUCCACCA CUGAUGAGGNNNNNNNNCCGAA AGCCAGCA | 6991 |
| 4870 | GGUGGGCUU GUGGCCUG | 2843 | CAGGCCAC CUGAUGAGGNNNNNNNNCCGAA AGCCCACC | 6992 |
| 4880 | UGGCCUGUC AGGAAACG | 2844 | CGUUUCCU CUGAUGAGGNNNNNNNNCCGAA ACAGGCCA | 6993 |
| 4908 | GGCAGGGUU UGGUUUUG | 2845 | CAAAACCA CUGAUGAGGNNNNNNNNCCGAA ACCCUGCC | 6994 |
| 4909 | GCAGGGUUU GGUUUUGG | 2846 | CCAAAACC CUGAUGAGGNNNNNNNNCCGAA AACCCUGC | 6995 |
| 4913 | GGUUUGGUU UUGGAAGG | 2847 | CCUUCCAA CUGAUGAGGNNNNNNNNCCGAA ACCAAACC | 6996 |
| 4914 | GUUUGGUUU UGGAAGGU | 2848 | ACCUUCCA CUGAUGAGGNNNNNNNNCCGAA AACCAAAC | 6997 |
| 4915 | UUUGGUUUU GGAAGGUU | 2849 | AACCUUCC CUGAUGAGGNNNNNNNNCCGAA AAACCAAA | 6998 |
| 4923 | UGGAAGGUU UGCGUGCU | 2850 | AGCACGCA CUGAUGAGGNNNNNNNNCCGAA ACCUUCCA | 6999 |
| 4924 | GGAAGGUUU GCGUGCUC | 2851 | GAGCACGC CUGAUGAGGNNNNNNNNCCGAA AACCUUCC | 7000 |
| 4932 | UGCGUGCUC UUCACAGU | 2852 | ACUGUGAA CUGAUGAGGNNNNNNNNCCGAA AGCACGCA | 7001 |
| 4934 | CGUGCUCUU CACAGUCG | 2853 | CGACUGUG CUGAUGAGGNNNNNNNNCCGAA AGAGCACG | 7002 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4935 | GUGCUCUUC ACAGUCGG | 2854 | CCGACUGU CUGAUGAGGNNNNNNNNCCGAA AAGAGCAC | 7003 |
| 4941 | UUCACAGUC GGGUUACA | 2855 | UGUAACCC CUGAUGAGGNNNNNNNNCCGAA ACUGUGAA | 7004 |
| 4946 | AGUCGGGUU ACAGGCGA | 2856 | UCGCCUGU CUGAUGAGGNNNNNNNNCCGAA ACCCGACU | 7005 |
| 4947 | GUCGGGUUA CAGGCGAG | 2857 | CUCGCCUG CUGAUGAGGNNNNNNNNCCGAA AACCCGAC | 7006 |
| 4957 | AGGCGAGUU CCCUGUGG | 2858 | CCACAGGG CUGAUGAGGNNNNNNNNCCGAA ACUCGCCU | 7007 |
| 4958 | GGCGAGUUC CCUGUGGC | 2859 | GCCACAGG CUGAUGAGGNNNNNNNNCCGAA AACUCGCC | 7008 |
| 4969 | UGUGGCGUU UCCUACUC | 2860 | GAGUAGGA CUGAUGAGGNNNNNNNNCCGAA ACGCCACA | 7009 |
| 4970 | GUGGCGUUU CCUACUCC | 2861 | GGAGUAGG CUGAUGAGGNNNNNNNNCCGAA AACGCCAC | 7010 |
| 4971 | UGGCGUUUC CUACUCCU | 2862 | AGGAGUAG CUGAUGAGGNNNNNNNNCCGAA AAACGCCA | 7011 |
| 4974 | CGUUUCCUA CUCCUAAU | 2863 | AUUAGGAG CUGAUGAGGNNNNNNNNCCGAA AGGAAACG | 7012 |
| 4977 | UUCCUACUC CUAAUGAG | 2864 | CUCAUUAG CUGAUGAGGNNNNNNNNCCGAA AGUAGGAA | 7013 |
| 4980 | CUACUCCUA AUGAGAGU | 2865 | ACUCUCAU CUGAUGAGGNNNNNNNNCCGAA AGGAGUAG | 7014 |
| 4989 | AUGAGAGUU CCUUCCGG | 2866 | CCGGAAGG CUGAUGAGGNNNNNNNNCCGAA ACUCUCAU | 7015 |
| 4990 | UGAGAGUUC CUUCCGGA | 2867 | UCCGGAAG CUGAUGAGGNNNNNNNNCCGAA AACUCUCA | 7016 |
| 4993 | GAGUUCCUU CCGGACUC | 2868 | GAGUCCGG CUGAUGAGGNNNNNNNNCCGAA AGGAACUC | 7017 |
| 4994 | AGUUCCUUC CGGACUCU | 2869 | AGAGUCCG CUGAUGAGGNNNNNNNNCCGAA AAGGAACU | 7018 |
| 5001 | UCCGGACUC UUACGUGU | 2870 | ACACGUAA CUGAUGAGGNNNNNNNNCCGAA AGUCCGGA | 7019 |
| 5003 | CGGACUCUU ACGUGUCU | 2871 | AGACACGU CUGAUGAGGNNNNNNNNCCGAA AGAGUCCG | 7020 |
| 5004 | GGACUCUUA CGUGUCUC | 2872 | GAGACACG CUGAUGAGGNNNNNNNNCCGAA AAGAGUCC | 7021 |
| 5010 | UUACGUGUC UCCUGGCC | 2873 | GGCCAGGA CUGAUGAGGNNNNNNNNCCGAA ACACGUAA | 7022 |
| 5012 | ACGUGUCUC CUGGCCUG | 2874 | CAGGCCAG CUGAUGAGGNNNNNNNNCCGAA AGACACGU | 7023 |
| 5046 | AUGCAGCUU GCUCCUUC | 2875 | GAAGGAGC CUGAUGAGGNNNNNNNNCCGAA AAGCUGCAU | 7024 |
| 5050 | AGCUUGCUC CUUCCUCA | 2876 | UGAGGAAG CUGAUGAGGNNNNNNNNCCGAA AGCAAGCU | 7025 |
| 5053 | UUGCUCCUU CCUCAUCU | 2877 | AGAUGAGG CUGAUGAGGNNNNNNNNCCGAA AGGAGCAA | 7026 |
| 5054 | UGCUCCUUC CUCAUCUC | 2878 | GAGAUGAG CUGAUGAGGNNNNNNNNCCGAA AAGGAGCA | 7027 |
| 5057 | UCCUUCCUC AUCUCUCA | 2879 | UGAGAGAU CUGAUGAGGNNNNNNNNCCGAA AGGAAGGA | 7028 |
| 5060 | UUCCUCAUC UCUCAGGC | 2880 | GCCUGAGA CUGAUGAGGNNNNNNNNCCGAA AUGAGGAA | 7029 |
| 5062 | CCUCAUCUC UCAGGCUG | 2881 | CAGCCUGA CUGAUGAGGNNNNNNNNCCGAA AGAUGAGG | 7030 |
| 5064 | UCAUCUCUC AGGCUGUG | 2882 | CACAGCCU CUGAUGAGGNNNNNNNNCCGAA AGAGAUGA | 7031 |
| 5076 | CUGUGCCUU AAUUCAGA | 2883 | UCUGAAUU CUGAUGAGGNNNNNNNNCCGAA AGGCACAG | 7032 |
| 5077 | UGUGCCUUA AUUCAGAA | 2884 | UUCUGAAU CUGAUGAGGNNNNNNNNCCGAA AAGGCACA | 7033 |
| 5080 | GCCUUAAUU CAGAACAC | 2885 | GUGUUCUG CUGAUGAGGNNNNNNNNCCGAA AUUAAGGC | 7034 |
| 5081 | CCUUAAUUC AGAACACC | 2886 | GGUGUUCU CUGAUGAGGNNNNNNNNCCGAA AAUUAAGG | 7035 |
| 5105 | AGGAACGUC GGCAGAGG | 2887 | CCUCUGCC CUGAUGAGGNNNNNNNNCCGAA ACGUUCCU | 7036 |
| 5116 | CAGAGGCUC CUGACGGG | 2888 | CCCGUCAG CUGAUGAGGNNNNNNNNCCGAA AGCCUCUG | 7037 |
| 5135 | CGAAGAAUU GUGAGAAC | 2889 | GUUCUCAC CUGAUGAGGNNNNNNNNCCGAA AUUCUUCG | 7038 |
| 5156 | CAGAAACUC AGGGUUUC | 2890 | GAAACCCU CUGAUGAGGNNNNNNNNCCGAA AGUUUCUG | 7039 |
| 5162 | CUCAGGGUU UCUGCUGG | 2891 | CCAGCAGA CUGAUGAGGNNNNNNNNCCGAA ACCCUGAG | 7040 |
| 5163 | UCAGGGUUU CUGCUGGG | 2892 | CCCAGCAG CUGAUGAGGNNNNNNNNCCGAA AACCCUGA | 7041 |
| 5164 | CAGGGUUUC UGCUGGGU | 2893 | ACCCAGCA CUGAUGAGGNNNNNNNNCCGAA AAACCCUG | 7042 |
| 5203 | UGGCAGGUC UGAGGGUU | 2894 | AACCCUCA CUGAUGAGGNNNNNNNNCCGAA ACCUGCCA | 7043 |
| 5211 | CUGAGGGUU CUCUGUCA | 2895 | UGACAGAG CUGAUGAGGNNNNNNNNCCGAA ACCCUCAG | 7044 |
| 5212 | UGAGGGUUC UCUGUCAA | 2896 | UUGACAGA CUGAUGAGGNNNNNNNNCCGAA AACCCUCA | 7045 |
| 5214 | AGGGUUCUC UGUCAAGU | 2897 | ACUUGACA CUGAUGAGGNNNNNNNNCCGAA AGAACCCU | 7046 |
| 5218 | UUCUCUGUC AAGUGGCG | 2898 | CGCCACUU CUGAUGAGGNNNNNNNNCCGAA ACAGAGAA | 7047 |
| 5229 | GUGGCGGUA AAGGCUCA | 2899 | UGAGCCUU CUGAUGAGGNNNNNNNNCCGAA ACCGCCAC | 7048 |
| 5226 | UAAAGGCUC AGGCAGGU | 2900 | ACCAGCCU CUGAUGAGGNNNNNNNNCCGAA AGCCUUUA | 7049 |
| 5247 | GCUGGUGUU CUUCCUCU | 2901 | AGAGGAAG CUGAUGAGGNNNNNNNNCCGAA ACACCAGC | 7050 |
| 5248 | CUGGUGUUC UUCCUCUA | 2902 | UAGAGGAA CUGAUGAGGNNNNNNNNCCGAA AACACCAG | 7051 |
| 5250 | GGUGUUCUU CCUCUAUC | 2903 | GAUAGAGG CUGAUGAGGNNNNNNNNCCGAA AGAACACC | 7052 |
| 5251 | GUGUUCUUC CUCUAUCU | 2904 | AGAUAGAG CUGAUGAGGNNNNNNNNCCGAA AAGAACAC | 7053 |
| 5254 | UUCUUCCUC UAUCUCCA | 2905 | UGGAGAUA CUGAUGAGGNNNNNNNNCCGAA AGGAAGAA | 7054 |
| 5256 | CUUCCUCUA UCUCCACU | 2906 | AGUGGAGA CUGAUGAGGNNNNNNNNCCGAA AGAGGAAG | 7055 |
| 5258 | UCCUCUAUC UCCACUCC | 2907 | GGAGUGGA CUGAUGAGGNNNNNNNNCCGAA AUAGGAGA | 7056 |
| 5260 | CUCUAUCUC CACUCCUG | 2908 | CAGGAGUG CUGAUGAGGNNNNNNNNCCGAA AGAUAGAG | 7057 |
| 5265 | UCUCCACUC CUGUCAGG | 2909 | CCUGACAG CUGAUGAGGNNNNNNNNCCGAA AGUGGAGA | 7058 |
| 5270 | ACUCCUGUC AGGCCCCC | 2910 | GGGGGCCU CUGAUGAGGNNNNNNNNCCGAA ACAGGAGU | 7059 |
| 5283 | CCCCAAGUC UCAGUAU | 2911 | AUACUGAG CUGAUGAGGNNNNNNNNCCGAA ACUUGGGG | 7060 |
| 5286 | CAAGUCCUC AGUAUUUU | 2912 | AAAAUACU CUGAUGAGGNNNNNNNNCCGAA AGGACUUG | 7061 |
| 5290 | UCCUCAGUA UUUUAGCU | 2913 | AGCUAAAA CUGAUGAGGNNNNNNNNCCGAA ACUGAGGA | 7062 |
| 5292 | CUCAGUAUU UUAGCUUU | 2914 | AAAGCUAA CUGAUGAGGNNNNNNNNCCGAA AUACUGAG | 7063 |
| 5293 | UCAGUAUUU UAGCUUUG | 2915 | CAAAGCUA CUGAUGAGGNNNNNNNNCCGAA AAUACUGA | 7064 |
| 5294 | CAGUAUUUU AGCUUUGU | 2916 | ACAAAGCU CUGAUGAGGNNNNNNNNCCGAA AAAUACUG | 7065 |
| 5295 | AGUAUUUUA GCUUUGUG | 2917 | CACAAAGC CUGAUGAGGNNNNNNNNCCGAA AAAAUACU | 7066 |
| 5299 | UUUUAGCUU UGUGGCUU | 2918 | AAGCCACA CUGAUGAGGNNNNNNNNCCGAA AGCUAAAA | 7067 |
| 5300 | UUUAGCUUU GUGGCUUC | 2919 | GAAGCCAC CUGAUGAGGNNNNNNNNCCGAA AAGCUAAA | 7068 |
| 5307 | UUGUGGCUU CCUGAUGG | 2920 | CCAUCAGG CUGAUGAGGNNNNNNNNCCGAA AGCCACAA | 7069 |
| 5308 | UGUGGCUUC CUGAUGGC | 2921 | GCCAUCAG CUGAUGAGGNNNNNNNNCCGAA AAGCCACA | 7070 |
| 5325 | AGAAAAAUC UUAAUUGG | 2922 | CCAAUUAA CUGAUGAGGNNNNNNNNCCGAA AUUUUUCU | 7071 |
| 5327 | AAAAAUCUU AAUGGUU | 2923 | AACCAAUU CUGAUGAGGNNNNNNNNCCGAA AGAUUUUU | 7072 |
| 5328 | AAAAUCUUA AUGGUUG | 2924 | CAACCAAU CUGAUGAGGNNNNNNNNCCGAA AAGAUUUU | 7073 |
| 5331 | AUCUUAAUU GGUUGGUU | 2925 | AACCAACC CUGAUGAGGNNNNNNNNCCGAA AUUAAGAU | 7074 |
| 5335 | UAAUUGGUU GGUUUGCU | 2926 | AGCAAACC CUGAUGAGGNNNNNNNNCCGAA ACCAAUUA | 7075 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 5339 | UGGUUGGUU UGCUCUCC | 2927 | GGAGAGCA CUGAUGAGGNNNNNNNNCCGAA ACCAACCA | 7076 |
| 5340 | GGUUGGUUU GCUCUCCA | 2928 | UGGAGAGC CUGAUGAGGNNNNNNNNCCGAA AACCAACC | 7077 |
| 5344 | GGUUUGCUC UCCAGAUA | 2929 | UAUCUGGA CUGAUGAGGNNNNNNNNCCGAA AGCAAACC | 7078 |
| 5346 | UUUGCUCUC CAGAUAAU | 2930 | AUUAUCUG CUGAUGAGGNNNNNNNNCCGAA AGAGCAAA | 7079 |
| 5352 | CUCCAGAUA AUCACUAG | 2931 | CUAGUGAU CUGAUGAGGNNNNNNNNCCGAA AUCUGGAG | 7080 |
| 5355 | CAGAUAAUC ACUAGCCA | 2932 | UGGCUAGU CUGAUGAGGNNNNNNNNCCGAA AUUAUCUG | 7081 |
| 5359 | UAAUCACUA GCCAGAUU | 2933 | AAUCUGGC CUGAUGAGGNNNNNNNNCCGAA AGUGAUUA | 7082 |
| 5367 | AGCCAGAUU UCGAAAUU | 2934 | AAUUUCGA CUGAUGAGGNNNNNNNNCCGAA AUCUGGCU | 7083 |
| 5368 | GCCAGAUUU CGAAAUUA | 2935 | UAAUUUCG CUGAUGAGGNNNNNNNNCCGAA AAUCUGGC | 7084 |
| 5369 | CCAGAUUUC GAAAUUAC | 2936 | GUAAUUUC CUGAUGAGGNNNNNNNNCCGAA AAAUCUGG | 7085 |
| 5375 | UUCGAAAUU ACUUUUUA | 2937 | UAAAAAGU CUGAUGAGGNNNNNNNNCCGAA AUUUCGAA | 7086 |
| 5376 | UCGAAAUUA CUUUUUAG | 2938 | CUAAAAAG CUGAUGAGGNNNNNNNNCCGAA AAUUUCGA | 7087 |
| 5379 | AAAUUACUU UUUAGCCG | 2939 | CGGCUAAA CUGAUGAGGNNNNNNNNCCGAA AGUAAUUU | 7088 |
| 5380 | AAUUACUUU UUAGCCGA | 2940 | UCGGCUAA CUGAUGAGGNNNNNNNNCCGAA AAGUAAUU | 7089 |
| 5381 | AUUACUUUU UAGCCGAG | 2941 | CUCGGCUA CUGAUGAGGNNNNNNNNCCGAA AAAGUAAU | 7090 |
| 5382 | UUACUUUUU AGCCGAGG | 2942 | CCUCGGCU CUGAUGAGGNNNNNNNNCCGAA AAAAGUAA | 7091 |
| 5383 | UACUUUUUA GCCGAGGU | 2943 | ACCUCGGC CUGAUGAGGNNNNNNNNCCGAA AAAAAGUA | 7092 |
| 5392 | GCCGAGGUU AUGAUAAC | 2944 | GUUAUCAU CUGAUGAGGNNNNNNNNCCGAA ACCUCGGC | 7093 |
| 5393 | CCGAGGUUA UGAUAACA | 2945 | UGUUAUCA CUGAUGAGGNNNNNNNNCCGAA AACCUCGG | 7094 |
| 5398 | GUUAUGAUA ACAUCUAC | 2946 | GUAGAUGU CUGAUGAGGNNNNNNNNCCGAA AUCAUAAC | 7095 |
| 5403 | GAUAACAUC UACUGUAU | 2947 | AUACAGUA CUGAUGAGGNNNNNNNNCCGAA AUGUUAUC | 7096 |
| 5405 | UAACAUCUA CUGUAUCC | 2948 | GGAUACAG CUGAUGAGGNNNNNNNNCCGAA AGAGUUA | 7097 |
| 5410 | UCUACUGUA UCCUUUAG | 2949 | CUAAAGGA CUGAUGAGGNNNNNNNNCCGAA ACAGUAGA | 7098 |
| 5412 | UACUGUAUC CUUUAGAA | 2950 | UUCUAAAG CUGAUGAGGNNNNNNNNCCGAA AUACAGUA | 7099 |
| 5415 | UGUAUCCUU UAGAAUUU | 2951 | AAAUUCUA CUGAUGAGGNNNNNNNNCCGAA AGGAUACA | 7100 |
| 5416 | GUAUCCUUU AGAAUUUU | 2952 | AAAAUUCU CUGAUGAGGNNNNNNNNCCGAA AAGGAUAC | 7101 |
| 5417 | UAUCCUUUA GAAUUUUA | 2953 | UAAAAUUC CUGAUGAGGNNNNNNNNCCGAA AAAGGAUA | 7102 |
| 5422 | UUUAGAAUU UUAACCUA | 2954 | UAGGUUAA CUGAUGAGGNNNNNNNNCCGAA AUUCUAAA | 7103 |
| 5423 | UUAGAAUUU UAACCUAU | 2955 | AUAGGUUA CUGAUGAGGNNNNNNNNCCGAA AAUUCUAA | 7104 |
| 5424 | UAGAAUUUU AACCUAUA | 2956 | UAUAGGUU CUGAUGAGGNNNNNNNNCCGAA AAAUUCUA | 7105 |
| 5425 | AGAAUUUUA ACCUAUAA | 2957 | UUAUAGGU CUGAUGAGGcsCCGUUAGGCCGAA AAAAUUCU | 7106 |
| 5430 | UUUAACCUA UAAAACUA | 2958 | UAGUUUUA CUGAUGAGGNNNNNNNNCCGAA AGGUUAAA | 7107 |
| 5432 | UAACCUAUA AAACUAUG | 2959 | CAUAGUUU CUGAUGAGGNNNNNNNNCCGAA AUAGGUUA | 7108 |
| 5438 | AUAAACUA UGUCUACU | 2960 | AGUAGACA CUGAUGAGGNNNNNNNNCCGAA AGUUUUAU | 7109 |
| 5442 | AACUAUGUC UACUGGUU | 2961 | AACCAGUA CUGAUGAGGNNNNNNNNCCGAA ACAUAGUU | 7110 |
| 5444 | CUAUGUCUA CUGGUUUC | 2962 | GAAACCAG CUGAUGAGGNNNNNNNNCCGAA AGACAUAG | 7111 |
| 5450 | CUACUGGUU UCUGCCUG | 2963 | CAGGCAGA CUGAUGAGGNNNNNNNNCCGAA ACCAGUAG | 7112 |
| 5451 | UACUGGUUU CUGCCUGU | 2964 | ACAGGCAG CUGAUGAGGNNNNNNNNCCGAA AACCAGUA | 7113 |
| 5452 | ACUGGUUUC UGCCUGUG | 2965 | CACAGGCA CUGAUGAGGNNNNNNNNCCGAA AAACCAGU | 7114 |

Where "X" represents stem II region of a HH ribozyme (Hertel et al., 1992 Nucleic Acids Res. 20 3252). The length of stem II may be ≥ 2 base-pairs.
Underlined region can be any X sequence or linker, as described herein.

TABLE VII

Mouse flt-1 VEGF Receptor-Hairpin Ribozyme and Substrate Sequence 5

| Pos | Substrate | Seq ID No | HP Ribozyme | Seq ID No |
|---|---|---|---|---|
| 74 | GGGCCCA GAC UGUGUCCC | 2966 | GGGACACA AGAA GGGCCC ACCAGAGAAACACACGUUGUGGUACAUUACCUGGUA | 7115 |
| 88 | UCCCGCA GCC GGGAUAAC | 2967 | GUUAUCCC AGAA GCGGGA ACCAGAGAAACACACGUUGUGGUACAUUACCUGGUA | 7116 |
| 105 | CCUGGCU GAC CCGAUUCC | 2968 | GGAAUCGG AGAA AGCCAGG ACCAGAGAAACACACGUUGUGGUACAUUACCUGGUA | 7117 |
| 110 | CUGACCC GAU UCCGCGGA | 2969 | UCCGCGGA AGAA GGUCAG ACCAGAGAAACACACGUUGUGGUACAUUACCUGGUA | 7118 |
| 125 | GGACACC GCU GACAGCCG | 2970 | CGGCUGUC AGAA GUGUCC ACCAGAGAAACACACGUUGUGGUACAUUACCUGGUA | 7119 |
| 132 | GCUGACA GCC GCGGCUGG | 2971 | CCAGCCGC AGAA GUCAGC ACCAGAGAAACACACGUUGUGGUACAUUACCUGGUA | 7120 |
| 138 | AGCCGCG GCU GGAGCCAG | 2972 | CUGGCUCC AGAA GCGGCU ACCAGAGAAACACACGUUGUGGUACAUUACCUGGUA | 7121 |
| 175 | CUCCCCG GUC UUGCGCUG | 2973 | CAGCGCAA AGAA GGGGAG ACCAGAGAAACACACGUUGUGGUACAUUACCUGGUA | 7122 |
| 199 | CCAUACC GCC UCUGUGAC | 2974 | GUCACAGA AGAA GGUAUGG ACCAGAGAAACACACGUUGUGGUACAUUACCUGGUA | 7123 |
| 309 | GCUAGCU GUC GCUCUGUG | 2975 | CACAGAGC AGAA GCUAGC ACCAGAGAAACACACGUUGUGGUACAUUACCUGGUA | 7124 |
| 342 | CCGAGCC GCC UCUGUGGG | 2976 | CCCACAGA AGAA GCUCGG ACCAGAGAAACACACGUUGUGGUACAUUACCUGGUA | 7125 |
| 434 | CCCUUCA GAU UACUUGCA | 2977 | UGCAAGUA AGAA GAAGGG ACCAGAGAAACACACGUUGUGGUACAUUACCUGGUA | 7126 |
| 630 | CUCCACU GUU UAUGUCUA | 2978 | UAGACAUA AGAA GUGGAG ACCAGAGAAACACACGUUGUGGUACAUUACCUGGUA | 7127 |
| 655 | GAUUACA GAU CACCAUUC | 2979 | GAAUGGUG AGAA GUAAUC ACCAGAGAAACACACGUUGUGGUACAUUACCUGGUA | 7128 |
| 739 | AUCCCCU GCC GAGGGUCG | 2980 | CGACCCUC AGAA GGGGAU ACCAGAGAAACACACGUUGUGGUACAUUACCUGGUA | 7129 |
| 807 | UGUUCCG GAU GGAAACAG | 2981 | CUGUUUCC AGAA GGAACA ACCAGAGAAACACACGUUGUGGUACAUUACCUGGUA | 7130 |
| 920 | CCUAUCA GUC UAUCAUGU | 2982 | ACAUGAUA AGAA GAUAGG ACCAGAGAAACACACGUUGUGGUACAUUACCUGGUA | 7131 |
| 1002 | GCUAUCU GCC GGAGAAAA | 2983 | UUUUCUCC AGAA GAUAGC ACCAGAGAAACACACGUUGUGGUACAUUACCUGGUA | 7132 |
| 1229 | GUGGACG GAU GAUCAAGA | 2984 | UCUUGAUC AGAA GUCCAC ACCAGAGAAACACACGUUGUGGUACAUUACCUGGUA | 7133 |
| 1365 | UUACCCA GCU CCUGAUAU | 2985 | AUAUCAGG AGAA GGGUAA ACCAGAGAAACACACGUUGUGGUACAUUACCUGGUA | 7134 |

TABLE VII-continued

Mouse flt-1 VEGF Receptor-Hairpin Ribozyme and Substrate Sequence 5

| Pos | Substrate | Seq ID No | HP Ribozyme | Seq ID No |
|---|---|---|---|---|
| 1556 | CACCCCA GAU CGGUGAGA | 2986 | UCUCACCG AGAA GGGGUG ACCAGAGAAACACACGUUGUGGUACAUUACCUGGUA | 7135 |
| 1629 | AUGCACA GUC UACGCCAA | 2987 | UUGGCGUA AGAA GUGCAU ACCAGAGAAACACACGUUGUGGUACAUUACCUGGUA | 7136 |
| 1687 | GAAGCCU GCU CCUACAGA | 2988 | UCUGUAGG AGAA GGCUUC ACCAGAGAAACACACGUUGUGGUACAUUACCUGGUA | 7137 |
| 1696 | UCCUACA GAC CCGGCCAA | 2989 | UUGGCCGG AGAA GUAGGA ACCAGAGAAACACACGUUGUGGUACAUUACCUGGUA | 7138 |
| 1796 | AUGCCCU GAU UGAAGGAA | 2990 | UUCCUUCA AGAA GGGCAU ACCAGAGAAACACACGUUGUGGUACAUUACCUGGUA | 7139 |
| 1950 | GCAACCU GCU GCCCAGCC | 2991 | GGCUGGGC AGAA GGUUGC ACCAGAGAAACACACGUUGUGGUACAUUACCUGGUA | 7140 |
| 1953 | ACCUGCU GCC CAGCCAAC | 2992 | GUUGGCUG AGAA GCAGGU ACCAGAGAAACACACGUUGUGGUACAUUACCUGGUA | 7141 |
| 1985 | UGUCCCU GUU GUGCACUG | 2993 | CAGUGCAC AGAA GGGACA ACCAGAGAAACACACGUUGUGGUACAUUACCUGGUA | 7142 |
| 2055 | AACAUCG GUC CACAUGGG | 2994 | CCCAUGUG AGAA GAUGUU ACCAGAGAAACACACGUUGUGGUACAUUACCUGGUA | 7143 |
| 2082 | CACACCA GUU UGCAAGAA | 2995 | UUCUUGCA AGAA GGUGUG ACCAGAGAAACACACGUUGUGGUACAUUACCUGGUA | 6343 |
| 2208 | UUGCUCU GCU CAAGAUAA | 2996 | UUAUCUUG AGAA GAGCAA ACCAGAGAAACACACGUUGUGGUACAUUACCUGGUA | 7144 |
| 2252 | UCAAACA GCU CAUCAUCC | 2997 | GGAUGAUG AGAA GUUUGA ACCAGAGAAACACACGUUGUGGUACAUUACCUGGUA | 7145 |
| 2444 | GGAACCU GAC UAUCCGCA | 2998 | UGCGGAUA AGAA GGUUCC ACCAGAGAAACACACGUUGUGGUACAUUACCUGGUA | 7146 |
| 2639 | UCCUACG GAC CGUUAAGC | 2999 | GCUUAACG AGAA GUAGGA ACCAGAGAAACACACGUUGUGGUACAUUACCUGGUA | 7147 |
| 2703 | GGAUCCA GCU GAAUUGCC | 3000 | GGCAAUUC AGAA GGAUCC ACCAGAGAAACACACGUUGUGGUACAUUACCUGGUA | 7148 |
| 2777 | GGGACCG GCU GAAACUAG | 3001 | CUAGUUUC AGAA GGUCCC ACCAGAGAAACACACGUUGUGGUACAUUACCUGGUA | 7149 |
| 2832 | UGAGGCA GAC GCUUUGG | 3002 | CCAAAGC AGAA GCCUCA ACCAGAGAAACACACGUUGUGGUACAUUACCUGGUA | 7150 |
| 3199 | UCUGCCA GCU CAGGCUUU | 3003 | AAAGCCUG AGAA GGCAGA ACCAGAGAAACACACGUUGUGGUACAUUACCUGGUA | 7151 |
| 3278 | ACUUCCU GAC CUUGGAGC | 2199 | GCUCCAAG AGAA GGAAGU ACCAGAGAAACACACGUUGUGGUACAUUACCUGGUA | 6355 |
| 3304 | UGUUACA GCU UCCAAGUG | 2200 | CACUUGGA AGAA GUAACA ACCAGAGAAACACACGUUGUGGUACAUUACCUGGUA | 6356 |
| 3421 | GACUUCG GCU UGGCCCGG | 3004 | CCGGGCCA AGAA GAAGUC ACCAGAGAAACACACGUUGUGGUACAUUACCUGGUA | 7152 |
| 3450 | AGACCCG GAU UAUGUCAG | 3005 | CUGACAUA AGAA GGGUCU ACCAGAGAAACACACGUUGUGGUACAUUACCUGGUA | 7153 |
| 3475 | GAUGCCU GAC UCCCUUUG | 3006 | CAAAGGGA AGAA GGCAUC ACCAGAGAAACACACGUUGUGGUACAUUACCUGGUA | 7154 |
| 3663 | GGCUCCU GAC UACACUG | 3007 | GUAGUGUA AGAA GGAGCC ACCAGAGAAACACACGUUGUGGUACAUUACCUGGUA | 7155 |
| 3689 | UGUACCA GAC CAUGCUGG | 2203 | CCAGCAUG AGAA GGUACA ACCAGAGAAACACACGUUGUGGUACAUUACCUGGUA | 6359 |
| 3703 | CUGGACU GCU GGCAUGAG | 3008 | CUCAUGCC AGAA GUCCAG ACCAGAGAAACACACGUUGUGGUACAUUACCUGGUA | 7156 |
| 3860 | UCUCCCU GCC UACCUCAC | 3009 | GUGAGGUA AGAA GGGAGA ACCAGAGAAACACACGUUGUGGUACAUUACCUGGUA | 7157 |
| 3873 | CUCACCU GUU UCCUGUAU | 2206 | AUACAGGA AGAA GGUGAG ACCAGAGAAACACACGUUGUGGUACAUUACCUGGUA | 6362 |
| 4038 | GAUCCCA GAU GACAGCCA | 3010 | UGGCUGUC AGAA GGGAUC ACCAGAGAAACACACGUUGUGGUACAUUACCUGGUA | 7158 |
| 4181 | CCAACCA GAC CAGUGGCU | 3011 | AGCCACUG AGAA GGUUGG ACCAGAGAAACACACGUUGUGGUACAUUACCUGGUA | 7159 |
| 4196 | GCUACCA GUC UGGGUAUC | 3012 | GAUACCCA AGAA GGUAGC ACCAGAGAAACACACGUUGUGGUACAUUACCUGGUA | 7160 |
| 4212 | UCACUCA GAC GACACAGA | 3013 | UCUGUGUC AGAA GAGUGA ACCAGAGAAACACACGUUGUGGUACAUUACCUGGUA | 6367 |
| 4278 | UGCUGCA GUU CACGCUGA | 3014 | UCAGCGUG AGAA GCAGCA ACCAGAGAAACACACGUUGUGGUACAUUACCUGGUA | 7161 |
| 4287 | UCACGCU GAC UCAGGGAC | 3015 | GUCCCUGA AGAA GCGUGA ACCAGAGAAACACACGUUGUGGUACAUUACCUGGUdUA | 7162 |
| 4307 | CACUGCA GCU CACCUCCU | 3016 | AGGAGGUG AGAA GCAGUG ACCAGAGAAACACACGUUGUGGUACAUUACCUGGUA | 7163 |
| 4318 | ACCUCCU GCU UAAAUGGA | 3017 | UCCAUUUA AGAA GGAGGU ACCAGAGAAACACACGUUGUGGUACAUUACCUGGUA | 7164 |
| 4338 | UGGUCCU GUC CCGGCUCC | 3018 | GGAGCCGG AGAA GGACCA ACCAGAGAAACACACGUUGUGGUACAUUACCUGGUA | 7165 |
| 4344 | UGUCCCG GCU CCGCCCCC | 3019 | GGGGGCGG AGAA GGGACA ACCAGAGAAACACACGUUGUGGUACAUUACCUGGUA | 7166 |
| 4349 | CGGCUCC GCC CCCAACUC | 3020 | GAGUUGGG AGAA GAGCCG ACCAGAGAAACACACGUUGUGGUACAUUACCUGGUA | 7167 |
| 4383 | AGGUGCU GCU UAGAUUUU | 3021 | AAAAUCUA AGAA GCACCU ACCAGAGAAACACACGUUGUGGUACAUUACCUGGUA | 7168 |
| 4462 | GACCUCA GAC UGCAAGGA | 3022 | UCCUUGCA AGAA GAGGUC ACCAGAGAAACACACGUUGUGGUACAUUACCUGGUA | 7169 |
| 4574 | GUGCCCU GCU GUGGUCUC | 3023 | GAGACCAC AGAA GGGCAC ACCAGAGAAACACACGUUGUGGUACAUUACCUGGUA | 7170 |
| 4626 | GGACUCU GUC CUCCAAGA | 3024 | UCUUGGAG AGAA GAGUCC ACCAGAGAAACACACGUUGUGGUACAUUACCUGGUA | 7171 |
| 4723 | CGAGUCU GUC UACCUUGG | 3025 | CCAAGGUA AGAA GACUCG ACCAGAGAAACACACGUUGUGGUACAUUACCUGGUA | 7172 |
| 4823 | GAGAGCG GUU GGAGCCUG | 3026 | CAGGCUCC AGAA GCUCUC ACCAGAGAAACACACGUUGUGGUACAUUACCUGGUA | 7173 |
| 4836 | GCCUGCA GAU GCAUUGUG | 3027 | CACAAUGC AGAA GCAGGC ACCAGAGAAACACACGUUGUGGUACAUUACCUGGUA | 7174 |
| 4896 | AAAGGCG GCC GGCAGGGU | 3028 | ACCCUGCC AGAA GCCUUU ACCAGAGAAACACACGUUGUGGUACAUUACCUGGUA | 7175 |
| 4938 | CUUCACA GUC GGGUUACA | 3029 | UGUAACCC AGAA GUGAAG ACCAGAGAAACACACGUUGUGGUACAUUACCUGGUA | 7176 |
| 4996 | CCUUCCG GAC UCUUACGU | 3030 | ACGUAAGA AGAA GGAAGG ACCAGAGAAACACACGUUGUGGUACAUUACCUGGUA | 7177 |
| 5042 | UGAUGCA GAC UGCUCCUU | 3031 | AAGGAGCA AGAA GCAUCA ACCAGAGAAACACACGUUGUGGUACAUUACCUGGUA | 7178 |
| 5118 | GGCUCCU GAC GGGGCCGA | 3032 | UCGGCCCC AGAA GGAGCC ACCAGAGAAACACACGUUGUGGUACAUUACCUGGUA | 7179 |
| 5165 | GGUUUCU GCU GGGUGGAG | 3033 | CUCCACCC AGAA GAAACC ACCAGAGAAACACACGUUGUGGUACAUUACCUGGUA | 7180 |
| 5310 | GCUUCCU GAU GGCAGAAA | 3034 | UUUCUGCC AGAA GGAAGC ACCAGAGAAACACACGUUGUGGUACAUUACCUGGUA | 7181 |
| 5363 | CUAGCCA GAU UUCGAAAU | 3035 | AUUUCGAA AGAA GGCUAG ACCAGAGAAACACACGUUGUGGUACAUUACCUGGUA | 7182 |
| 5453 | GGUUUCU GCC UGUGUGCU | 3036 | AGCACACA AGAA GAAACC ACCAGAGAAACACACGUUGUGGUACAUUACCUGGUA | 7183 |

TABLE VIII

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 17 | GGCCGCGUC UUGCUCAC | 3037 | GUGAGCAA CUGAUGAGNNNNNNNNCCGAA ACGCGGCC | 7184 |
| 19 | CCGCGUCUU GCUCACCA | 3038 | UGGUGAGC CUGAUGAGNNNNNNNNCCGAA AGACGCGG | 7185 |
| 23 | GUCUUGCUC ACCAUGGU | 3039 | ACCAUGGU CUGAUGAGNNNNNNNNCCGAA AGCAAGAC | 7186 |
| 32 | ACCAUGGUC AGCUGCUG | 3040 | CAGCAGCU CUGAUGAGNNNNNNNNCCGAA ACCAUGGU | 7187 |
| 53 | ACCGCGGUC UUGCCUUA | 3041 | UAAGGCAA CUGAUGAGNNNNNNNNCCGAA ACCGCGGU | 7188 |
| 55 | CGCGUCUUU GCCUUACG | 3042 | CGUAAGGC CUGAUGAGNNNNNNNNCCGAA AGACCGCG | 7189 |
| 60 | UCUUGCCUU ACGCGCUG | 3043 | CAGCGCGU CUGAUGAGNNNNNNNNCCGAA AGGCAAGA | 7190 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 61 | CUUGCCUUA CGCGCUGC | 3044 | GCAGCGCG CUGAUGAGGNNNNNNNNNCCGAA AAGGCAAG | 7191 |
| 71 | GCGCUGCUC GGGUGUCU | 3045 | AGACACCC CUGAUGAGGNNNNNNNNNCCGAA AGCAGCGC | 7192 |
| 78 | UCGGGUGUC UGCUUCUC | 3046 | GAGAAGCA CUGAUGAGGNNNNNNNNNCCGAA ACACCCGA | 7193 |
| 83 | UGUCUGCUU CUCACAGG | 25 | ACUGUGAG CUGAUGAGGNNNNNNNNNCCGAA AGCAGACA | 4181 |
| 84 | GUCUGCUUC UCACAGGA | 26 | UCCUGUGA CUGAUGAGGNNNNNNNNNCCGAA AAGCAGAC | 4182 |
| 86 | CUGCUUCUC ACAGGAUA | 3047 | UAUCCUGU CUGAUGAGGNNNNNNNNNCCGAA AGAAGCAG | 7194 |
| 94 | CACAGGAUA UGGCUCAG | 3048 | CUGAGCCA CUGAUGAGGNNNNNNNNNCCGAA AUCCUGUG | 7195 |
| 100 | AUAUGGCUC AGGGUCGA | 3049 | UCGACCCU CUGAUGAGGNNNNNNNNNCCGAA AGCCAUAU | 7196 |
| 106 | CUCAGGGUC GAAGUUAA | 3050 | UUAACUUC CUGAUGAGGNNNNNNNNNCCGAA ACCCUGAG | 7197 |
| 112 | GUCGAAGUU AAAAGUGC | 3051 | GCAGUUUU CUGAUGAGGNNNNNNNNNCCGAA ACUUCGAC | 7198 |
| 113 | UCGAAGUUA AAAGUGCC | 3052 | GGCACUUU CUGAUGAGGNNNNNNNNNCCGAA AACUUCGA | 7199 |
| 132 | AACUGAGUU AUAAAGGC | 37 | GCCUUUUA CUGAUGAGGNNNNNNNNNCCGAA ACUCAGUU | 4193 |
| 133 | ACUGAGUUU AAAAGGCA | 38 | UGCCUUUU CUGAUGAGGNNNNNNNNNCCGAA AACUCAGU | 4194 |
| 134 | CUGAGUUUC AAAGGCAC | 39 | GUGCCUUU CUGAUGAGGNNNNNNNNNCCGAA AAACUCAG | 4195 |
| 152 | CAGCAUGUC AUGCAAGC | 3053 | GCUUGCAU CUGAUGAGGNNNNNNNNNCCGAA ACAUGCUG | 7200 |
| 171 | GCCAGACUC UCUUUCUC | 3054 | GAGAAAGA CUGAUGAGGNNNNNNNNNCCGAA AGUCUGGC | 7201 |
| 173 | CAGACUCUC UUUCUCAA | 3055 | UUGAGAAA CUGAUGAGGNNNNNNNNNCCGAA AGAGUCUG | 7202 |
| 175 | GACUCUCUU UCUCAAGU | 3056 | ACUUGAGA CUGAUGAGGNNNNNNNNNCCGAA AGAGAGUC | 7203 |
| 176 | ACUCUCUUU CUCAAGUG | 3057 | CACUUGAG CUGAUGAGGNNNNNNNNNCCGAA AAGAGAGU | 7204 |
| 177 | CUCUCUUUC UCAAGUGC | 3058 | GCACUUGA CUGAUGAGGNNNNNNNNNCCGAA AAAGAGAG | 7205 |
| 179 | CUCUUUCUC AAGUGCAG | 3059 | CUGCACUU CUGAUGAGGNNNNNNNNNCCGAA AGAAAGAG | 7206 |
| 205 | AGCCCACUC AUGGUCUC | 3060 | GAGACCAU CUGAUGAGGNNNNNNNNNCCGAA AGUGGGCU | 7207 |
| 211 | CUCAUGGUC UCUGCCCA | 3061 | UGGGCAGA CUGAUGAGGNNNNNNNNNCCGAA ACCAUGAG | 7208 |
| 213 | CAUGGUCUC UGCCCACG | 3062 | CGUGGGCA CUGAUGAGGNNNNNNNNNCCGAA AGACCAUG | 7209 |
| 254 | CUGAGCAUC ACUCCCCC | 3063 | GGGGGAGU CUGAUGAGGNNNNNNNNNCCGAA AUGCUCAG | 7210 |
| 258 | GCAUCACUC CCCCAUCG | 3064 | CGAUGGGG CUGAUGAGGNNNNNNNNNCCGAA AGUGAUGC | 7211 |
| 265 | UCCCCCAUC GGCCUGUG | 3065 | CACAGGCC CUGAUGAGGNNNNNNNNNCCGAA AUGGGGGA | 7212 |
| 282 | GGAGGGAUA ACAGGCAA | 3066 | UUGCCUGU CUGAUGAGGNNNNNNNNNCCGAA AUCCCUCC | 7213 |
| 292 | CAGGCAAUU CUGCAGCA | 3067 | UGCUGCAG CUGAUGAGGNNNNNNNNNCCGAA AUUGCCUG | 7214 |
| 293 | AGGCAAUUC UGCAGCAC | 3068 | GUGCUGCA CUGAUGAGGNNNNNNNNNCCGAA AAGGUCCU | 7215 |
| 304 | CAGCACCUU GACCUUGG | 3069 | CCAAGGUC CUGAUGAGGNNNNNNNNNCCGAA AGGUGCUG | 7216 |
| 310 | CUUGACCUU GGACACGG | 3070 | GGCUCUGG CUGAUGAGGNNNNNNNNNCCGAA AGGUCAAG | 7217 |
| 341 | ACGGGCCUA UACACCUG | 3071 | CAGGUGUA CUGAUGAGGNNNNNNNNNCCGAA AGGCCCGU | 7218 |
| 343 | GGGCUCUA CACCUGUA | 3072 | UACAGGUG CUGAUGAGGNNNNNNNNNCCGAA AGAGGCCC | 7219 |
| 351 | ACACCUGA GAUACCUC | 3073 | GAGGUAUC CUGAUGAGGNNNNNNNNNCCGAA ACAGGUGU | 7220 |
| 355 | CUGUAGAUA CCUCCCUA | 3074 | UAGGGAGG CUGAUGAGGNNNNNNNNNCCGAA AUCUACAG | 7221 |
| 359 | AGAUACCUC CCUACAUC | 3075 | GAUGUAGG CUGAUGAGGNNNNNNNNNCCGAA AGGUAUCU | 7222 |
| 363 | ACCUCCCUA CAUCUACU | 3076 | AGUAGAUG CUGAUGAGGNNNNNNNNNCCGAA AGGGAGGU | 7223 |
| 367 | CCCUACAUC UACUUCGA | 3077 | UCGAAGUA CUGAUGAGGNNNNNNNNNCCGAA AUGUAGGG | 7224 |
| 369 | CUACAUCUA CUUCGAAG | 3078 | CUUCGAAG CUGAUGAGGNNNNNNNNNCCGAA AGAUGUAG | 7225 |
| 372 | CAUCUACUU CGAAGAAA | 3079 | UUUCUUCG CUGAUGAGGNNNNNNNNNCCGAA AGUAGAUG | 7226 |
| 373 | AUCUACUUC GAAGAAAA | 3080 | UUUUCUUC CUGAUGAGGNNNNNNNNNCCGAA AAGUAGAU | 7227 |
| 394 | AGCGGAAUC UUCAAUCU | 3081 | AGAUUGAA CUGAUGAGGNNNNNNNNNCCGAA AUUCCGCU | 7228 |
| 396 | CGGAAUCUU CAAUCUAC | 3082 | GUAGAUUG CUGAUGAGGNNNNNNNNNCCGAA AGAUUCCG | 7229 |
| 397 | GGAAUCUUC AAUCUACA | 3083 | UGUAGAUU CUGAUGAGGNNNNNNNNNCCGAA AAGAUUCC | 7230 |
| 401 | UCUUCAAUC UACAUAUU | 3084 | AAUAUGUA CUGAUGAGGNNNNNNNNNCCGAA AUUGAAGA | 7231 |
| 403 | UUCAAUCUA CAUAUUUG | 3085 | CAAAUAUG CUGAUGAGGNNNNNNNNNCCGAA AGAUUGAA | 7232 |
| 407 | AUCUACAUA UUUGUUAG | 3086 | CUAACAAA CUGAUGAGGNNNNNNNNNCCGAA AUGUAGAU | 7233 |
| 409 | CUACAUAUU UGUUAGUG | 3087 | CACUAACA CUGAUGAGGNNNNNNNNNCCGAA AUAUGUAG | 7234 |
| 410 | UACAUAUUU GUUAGUGA | 3088 | UCACUAAC CUGAUGAGGNNNNNNNNNCCGAA AAUAUGUA | 7235 |
| 413 | AUAUUUGUU AGUGAUGC | 3089 | GCAUCACU CUGAUGAGGNNNNNNNNNCCGAA ACAAAUAU | 7236 |
| 414 | UAUUUGUUA GUGAUGCA | 3090 | UGCAUCAC CUGAUGAGGNNNNNNNNNCCGAA AACAAAUA | 7237 |
| 429 | CAGGGAGUC UUUCAUA | 3091 | UAUGCCCG CUGAUGAGGNNNNNNNNNCCGAA ACUCCCUG | 7238 |
| 432 | GGAGUCCUU UCAUAGAG | 3092 | CUCUAUGA CUGAUGAGGNNNNNNNNNCCGAA AGGACUCC | 7239 |
| 433 | GAGUCCUUU CAUAGAGA | 3093 | UCUCUAUG CUGAUGAGGNNNNNNNNNCCGAA AACCACUC | 7240 |
| 434 | AGUCCUUUC AUAGAGAU | 3094 | AUCUCUAU CUGAUGAGGNNNNNNNNNCCGAA AAAGGACU | 7241 |
| 437 | CCUUUCAUA GAGAUGCA | 3095 | UGCAUCUC CUGAUGAGGNNNNNNNNNCCGAA AUGAAAGG | 7242 |
| 455 | ACUGACAUA CCCAAACU | 3096 | AGUUUGGG CUGAUGAGGNNNNNNNNNCCGAA AUGUCAGU | 7243 |
| 464 | CCCAAACUU GUGCACAU | 3097 | AUGUGCAC CUGAUGAGGNNNNNNNNNCCGAA AGUUUGGG | 7244 |
| 491 | AGACAGCUC AUCAUCCC | 3098 | GGGAUGAU CUGAUGAGGNNNNNNNNNCCGAA AGCUGUCU | 7245 |
| 494 | CAGCUCAUC AUCCCCUG | 3099 | CAGGGGAU CUGAUGAGGNNNNNNNNNCCGAA AUGAGCUG | 7246 |
| 497 | CUCAUCAUC CCCUGCCG | 3100 | CGGCAGGG CUGAUGAGGNNNNNNNNNCCGAA AUGAUGAG | 7247 |
| 514 | GGUGACGUC ACCCAACG | 3101 | CGUUGGGU CUGAUGAGGNNNNNNNNNCCGAA ACGUCACC | 7248 |
| 524 | CCCAACGUU ACAGUCAC | 3102 | GUGACUGU CUGAUGAGGNNNNNNNNNCCGAA ACGUUGGG | 7249 |
| 530 | GUCACAGUC ACCCUAAA | 3103 | UUUAGGGU CUGAUGAGGNNNNNNNNNCCGAA ACUGUGAC | 7250 |
| 536 | GUCACCCUA AAAAAGUU | 3104 | AACUUUUU CUGAUGAGGNNNNNNNNNCCGAA AGGGUGAC | 7251 |
| 544 | AAAAAGUU UCCAUUUG | 3105 | CAAAUGGA CUGAUGAGGNNNNNNNNNCCGAA ACUUUUUU | 7252 |
| 545 | AAAAAGUUU CCAUUUGA | 3106 | UCAAAUGG CUGAUGAGGNNNNNNNNNCCGAA AACUUUUU | 7253 |
| 546 | AAAAGUUUC CAUUUGAU | 3107 | AUCAAAUG CUGAUGAGGNNNNNNNNNCCGAA AAACUUUU | 7254 |
| 550 | GUUUCCAUU UGAUACUC | 3108 | GAGUAUCA CUGAUGAGGNNNNNNNNNCCGAA AUGGAAAC | 7255 |
| 551 | UUUCCAUUU GAUACUCU | 3109 | AGAGUAUC CUGAUGAGGNNNNNNNNNCCGAA AAUGGAAA | 7256 |
| 555 | CAUUUGAUA CUCUUACC | 3110 | GGUAAGAG CUGAUGAGGNNNNNNNNNCCGAA AUCAAAUG | 7257 |
| 558 | UUGAUACUC UUACCCCU | 3111 | AGGGGUAA CUGAUGAGGNNNNNNNNNCCGAA AGUAUCAA | 7258 |

TABLE VIII-continued

Mouse *flt*-1 VEGF Receptor-Hammerhead Ribozyme and Substrate Sequence

| Pos | Substrate | Seq ID No | HH Ribozyme Sequence | Seq ID No |
|---|---|---|---|---|
| 560 | GAUACUCUU ACCCCUGA | 3112 | UCAGGGGU CUGAUGAGGNNNNNNNNCCGAA AGAGUAUC | 7259 |
| 561 | AUACUCUUA CCCCUGAU | 3113 | AUCAGGGG CUGAUGAGGNNNNNNNNCCGAA AAGAGUAU | 7260 |
| 581 | CAAAGAAUA ACAUGGGA | 3114 | UCCCAUGU CUGAUGAGGNNNNNNNNCCGAA AUUCUUUG | 7261 |
| 594 | GGGACAGUA GGAGAGGC | 3115 | GCCUCUCC CUGAUGAGGNNNNNNNNCCGAA ACUGUCCC | 7262 |
| 604 | GAGAGGCUU UAUAAUAG | 3116 | CUAUUAUA CUGAUGAGGNNNNNNNNCCGAA AGCCUCUC | 7263 |
| 605 | AGAGGCUUU AUAAUAGC | 3117 | GCUAUUAU CUGAUGAGGNNNNNNNNCCGAA AAGCCUCU | 7264 |
| 606 | GAGGCUUUA UAAUAGCA | 3118 | UGCUAUUA CUGAUGAGGNNNNNNNNCCGAA AAAGCCUC | 7265 |
| 608 | GGCUUUAUA AUAGCAAA | 3119 | UUUGCUAU CUGAUGAGGNNNNNNNNCCGAA AUAAAGCC | 7266 |
| 611 | UUUAUAAUA GCAAAUGC | 3120 | GCAUUUGC CUGAUGAGGNNNNNNNNCCGAA AUUAUAAA | 7267 |
| 625 | UGCAACGUA CAAAGAGA | 3121 | UCUCUUUG CUGAUGAGGNNNNNNNNCCGAA ACGUUGCA | 7268 |
| 635 | AAAGAGAUA GGACUGCU | 3122 | AGCAGUCC CUGAUGAGGNNNNNNNNCCGAA AUCUCUUU | 7269 |
| 662 | GCCACCGUC AACGGGCA | 3123 | UGCCCGUU CUGAUGAGGNNNNNNNNCCGAA ACGGUGGC | 7270 |
| 676 | GCACCUGUA CCAGACAA | 3124 | UUGUCUGG CUGAUGAGGNNNNNNNNCCGAA ACAGGUGC | 7271 |
| 688 | GACAAACUA UCUGACCC | 3125 | GGGUCAGA CUGAUGAGGNNNNNNNNCCGAA AGUUUGUC | 7272 |
| 690 | CAAACUAUC UGACCCAU | 3126 | AUGGGUCA CUGAUGAGGNNNNNNNNCCGAA AUAGUUUG | 7273 |
| 699 | UGACCCAUC GGCAGACC | 3127 | GGUCUGCC CUGAUGAGGNNNNNNNNCCGAA AUGGGUCA | 7274 |
| 711 | AGACCAAUA CAAUCCUA | 3128 | UAGGAUUG CUGAUGAGGNNNNNNNNCCGAA AUUGGUCU | 7275 |
| 716 | AAUACAAUC CUAGAUGU | 3129 | ACAUCUAG CUGAUGAGGNNNNNNNNCCGAA AUUGUAUU | 7276 |
| 719 | ACAAUCCUA GAUGUCCA | 3130 | UGGACAUC CUGAUGAGGNNNNNNNNCCGAA AGGAUUGU | 7277 |
| 725 | CUAGAUGUC CAAAUACG | 3131 | CGUAUUUG CUGAUGAGGNNNNNNNNCCGAA ACAUCUAG | 7278 |
| 731 | GUCCAAAUA CGCCCGCC | 3132 | GGCGGGCG CUGAUGAGGNNNNNNNNCCGAA AUUUGGAC | 7279 |
| 758 | AGACUGCUC CACGGGCA | 3133 | UGCCCGUG CUGAUGAGGNNNNNNNNCCGAA AGCAGUCU | 7280 |
| 771 | GGCAGACUC UUGUCCUC | 3134 | GAGGACAA CUGAUGAGGNNNNNNNNCCGAA AGUCUGCC | 7281 |
| 773 | CAGACUCUU GUCCUCAA | 3135 | UUCAGGAC CUGAUGAGGNNNNNNNNCCGAA AGAGUCUG | 7282 |
| 776 | ACUCUUGUC CUCAACUG | 3136 | CAGUUGAG CUGAUGAGGNNNNNNNNCCGAA ACAAGAGU | 7283 |
| 779 | CUUGCCUC AACUGCAC | 3137 | GUGCAGUU CUGAUGAGGNNNNNNNNCCGAA AGGACAAG | 7284 |
| 803 | ACGGAGCUC AAUACGAG | 3138 | CUCGUAUU CUGAUGAGGNNNNNNNNCCGAA AGCUCCGU | 7285 |
| 807 | AGCUCAAUA CGAGGGUG | 3139 | CACCCUCG CUGAUGAGGNNNNNNNNCCGAA AUUGAGCU | 7286 |
| 831 | GCUGGAAUU ACCCUGGU | 3140 | ACCAGGGU CUGAUGAGGNNNNNNNNCCGAA AUUCCAGC | 7287 |
| 832 | CUGGAAUUA CCCUGGUA | 3141 | UACCAGGG CUGAUGAGGNNNNNNNNCCGAA AAUUCCAG | 7288 |
| 840 | ACCCUGGUA AAGCAACU | 3142 | AGUUGCUU CUGAUGAGGNNNNNNNNCCGAA ACCAGGGU | 7289 |
| 849 | AAGCAACUA AGAGAGCA | 3143 | UGCUCUCU CUGAUGAGGNNNNNNNNCCGAA AGUUGCUU | 7290 |
| 859 | GAGAGCAUC UAUAAGGC | 3144 | GCCUUAUA CUGAUGAGGNNNNNNNNCCGAA AUGCUCUC | 7291 |
| 861 | GAGCAUCUA UAAGGCAG | 3145 | CUGCCUUA CUGAUGAGGNNNNNNNNCCGAA AGAUGCUC | 7292 |
| 863 | GCAUCUAUA AGGCAGCG | 3146 | CGCUGCCU CUGAUGAGGNNNNNNNNCCGAA AUAGAUGC | 7293 |
| 875 | CAGCGGAUU GACCGGAG | 3147 | CUCCGGUC CUGAUGAGGNNNNNNNNCCGAA AUCCGCUG | 7294 |
| 888 | GGAGCCAUU CCCACAAC | 3148 | GUUGUGGG CUGAUGAGGNNNNNNNNCCGAA AUGGCUCC | 7295 |
| 889 | GAGCCAUUC CCACAACA | 3149 | UGUUGUGG CUGAUGAGGNNNNNNNNCCGAA AAUGGCUC | 7296 |
| 904 | CAAUGUGUU CCACAGUG | 3150 | CACUGUGG CUGAUGAGGNNNNNNNNCCGAA ACACAUUG | 7297 |
| 905 | AAUGUGUUC CACAGUGU | 3151 | ACACUGUG CUGAUGAGGNNNNNNNNCCGAA AACACAUU | 7298 |
| 914 | CACAGUGUU CUUAAGAU | 3152 | AUCUUAAG CUGAUGAGGNNNNNNNNCCGAA ACACUGUG | 7299 |
| 915 | ACAGUGUUC UUAAGAUC | 3153 | GAUCUUAA CUGAUGAGGNNNNNNNNCCGAA AACACUGU | 7300 |
| 917 | AGUGUUCUU AAGAUCAA | 3154 | UUGAUCUU CUGAUGAGGNNNNNNNNCCGAA AGAACACU | 7301 |
| 918 | GUGUUCUUA AGAUCAAC | 3155 | GUUGAUCU CUGAUGAGGNNNNNNNNCCGAA AAGAACAC | 7302 |
| 923 | CUUAAGAUC AACAAUGU | 3156 | ACAUUGUU CUGAUGAGGNNNNNNNNCCGAA AUCUUAAG | 7303 |
| 953 | AAGGGGCUC UACACCUG | 3157 | CAGGUGUA CUGAUGAGGNNNNNNNNCCGAA AGCCCCUU | 7304 |
| 955 | GGGGCUCUA CACCUGUC | 3158 | GACAGGUG CUGAUGAGGNNNNNNNNCCGAA AGAGCCCC | 7305 |
| 963 | ACACCUGUC GCGUGAAG | 3159 | CUUCACGC CUGAUGAGGNNNNNNNNCCGAA ACAGGUGU | 7306 |
| 979 | GAGUGGGUC CUCGUUCC | 3160 | GGAACGAG CUGAUGAGGNNNNNNNNCCGAA ACCCACUC | 7307 |
| 982 | UGGGUCCUC GUUCCAGU | 3161 | ACUGGAAC CUGAUGAGGNNNNNNNNCCGAA AGGACCCA | 7308 |
| 985 | GUCCUCGUU CCAGUCUU | 3162 | AAGACUGG CUGAUGAGGNNNNNNNNCCGAA ACGAGGAC | 7309 |
| 986 | UCCUCGUUC CAGUCUUU | 3163 | AAAGACUG CUGAUGAGGNNNNNNNNCCGAA AACGAGGA | 7310 |
| 991 | GUUCCAGUC UUUCAACA | 3164 | UGUUGAAA CUGAUGAGGNNNNNNNNCCGAA ACUGGAAC | 7311 |
| 993 | UCCAGUCUU UCAACACC | 3165 | GGUGUUGA CUGAUGAGGNNNNNNNNCCGAA AGACUGGA | 7312 |
| 994 | CCAGUCUUU CAACACCU | 3166 | AGGUGUUG CUGAUGAGGNNNNNNNNCCGAA AAGACUGG | 7313 |
| 995 | CAGUCUUUC AACACCUC | 3167 | GAGGUGUU CUGAUGAGGNNNNNNNNCCGAA AAAGACUG | 7314 |
| 1003 | CAACACCUC CGUGCAUG | 3168 | CAUGCACG CUGAUGAGGNNNNNNNNCCGAA AGGUGUUG | 7315 |
| 1015 | GCAUGUGUA UCAAAAAG | 3169 | CUUUUUGA CUGAUGAGGNNNNNNNNCCGAA ACACAUGC | 7316 |
| 1027 | AAAAGGAUU CAUCAGUG | 3170 | CACUGAUG CUGAUGAGGNNNNNNNNCCGAA AUCCUUUU | 7317 |
| 1028 | AAAGGAUUC AUCAGUGU | 3171 | ACACUGAU CUGAUGAGGNNNNNNNNCCGAA AAUCCUUU | 7318 |
| 1031 | GGAUUCAUC AGUGUGAA | 3172 | UUCACACU CUGAUGAGGNNNNNNNNCCGAA AUGAAUCC | 7319 |
| 1044 | UGAAACAUC GGAAGCAG | 3173 | CUGCUUCC CUGAUGAGGNNNNNNNNCCGAA AUGUUUCA | 7320 |
| 1084 | AAGACGGUC CUAUCGGC | 3174 | GCCGAUAG CUGAUGAGGNNNNNNNNCCGAA ACCGUCUU | 7321 |
| 1087 | ACGGUCCUA UCGGCUGU | 3175 | ACAGCCGA CUGAUGAGGNNNNNNNNCCGAA AGGACCGU | 7322 |
| 1089 | GGUCCUAUC GGCUGUCC | 3176 | GGACAGCC CUGAUGAGGNNNNNNNNCCGAA AUAGGACC | 7323 |
| 1096 | UCGGCUGUC CAUGAAAG | 3177 | CUUUCAUG CUGAUGAGGNNNNNNNNCCGAA ACAGCCGA | 7324 |
| 1114 | GAAGGCCUU CCCCUCCC | 3178 | GGGAGGGG CUGAUGAGGNNNNNNNNCCGAA AGGCCUUC | 7325 |
| 1115 | AAGGCCUUC CCCUCCCC | 3179 | GGGGAGGG CUGAUGAGGNNNNNNNNCCGAA AAGGCCUU | 7326 |
| 1120 | CUUCCCCUC CCCAGAAA | 3180 | UUUCUGGG CUGAUGAGGNNNNNNNNCCGAA AGGGGAAG | 7327 |
| 1130 | CCAGAAAUC GUAUGGUU | 3181 | AACCAUAC CUGAUGAGGNNNNNNNNCCGAA AUUUCUGG | 7328 |
| 1133 | GAAAUCGUA UGGUUAAA | 3182 | UUUAACCA CUGAUGAGGNNNNNNNNCCGAA ACGAUUUC | 7329 |
| 1138 | CGUAUGGUU AAAAGAUG | 3183 | CAUCUUUU CUGAUGAGGNNNNNNNNCCGAA ACCAUACG | 7330 |
| 1139 | GUAUGGUUA AAAGAUGG | 210 | CCAUCUUU CUGAUGAGGNNNNNNNNCCGAA AACCAUAC | 4366 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1150 | AGAUGGCUC GCCUGCAA | 3184 | UUGCAGGC CUGAUGAGGNNNNNNNNCCGAA AGCCAUCU | 7331 |
| 1162 | UGCAACAUU GAAGUCUG | 3185 | CAGACUUC CUGAUGAGGNNNNNNNNCCGAA AUGUUGCA | 7332 |
| 1168 | AUUGAAGUC UGCUCGCU | 3186 | AGCGAGCA CUGAUGAGGNNNNNNNNCCGAA ACUUCAAU | 7333 |
| 1173 | AGUCUGCUC GCUAUUUG | 3187 | CAAAUAGC CUGAUGAGGNNNNNNNNCCGAA AGCAGACU | 7334 |
| 1177 | UGCUCGCUA UUUGGUAC | 3188 | GUACCAAA CUGAUGAGGNNNNNNNNCCGAA AGCGAGCA | 7335 |
| 1179 | CUCGCUAUU UGGUACAU | 3189 | AUGUACCA CUGAUGAGGNNNNNNNNCCGAA AUAGCGAG | 7336 |
| 1180 | UCGCUAUUU GGUACAUG | 3190 | CAUGUACC CUGAUGAGGNNNNNNNNCCGAA AAUAGCGA | 7337 |
| 1184 | UAUUUGGUA CAUGGCUA | 3191 | UAGCCAUG CUGAUGAGGNNNNNNNNCCGAA ACCAAAUA | 7338 |
| 1192 | ACAUGGCUA CUCAUUAA | 3192 | UUAAUGAG CUGAUGAGGNNNNNNNNCCGAA AGCCAUGU | 7339 |
| 1195 | UGGCUACUC AUUAAUUA | 3193 | UAAUUAAU CUGAUGAGGNNNNNNNNCCGAA AGUAGCCA | 7340 |
| 1198 | CUACUCAUU AAUUAUCA | 3194 | UGAUAAUU CUGAUGAGGNNNNNNNNCCGAA AUGAGUAG | 7341 |
| 1199 | UACUCAUUA AUUAUCAA | 3195 | UUGAUAAU CUGAUGAGGNNNNNNNNCCGAA AAUGAGUA | 7342 |
| 1202 | UCAUUAAUU AUCAAAGA | 3196 | UCUUUGAU CUGAUGAGGNNNNNNNNCCGAA AUUAAUGA | 7343 |
| 1203 | CAUUAAUUA UCAAAGAU | 3197 | AUCUUUGA CUGAUGAGGNNNNNNNNCCGAA AAUUAAUG | 7344 |
| 1205 | UUAAUUAUC AAAGAUGU | 3198 | ACAUCUUU CUGAUGAGGNNNNNNNNCCGAA AUAAUUAA | 7345 |
| 1237 | AGGGGACUA UACGAUCU | 3199 | AGAUCGUA CUGAUGAGGNNNNNNNNCCGAA AGUCCCCU | 7346 |
| 1239 | GGGACUAUA CGAUCUUG | 3200 | CAAGAUCG CUGAUGAGGNNNNNNNNCCGAA AUAGUCCC | 7347 |
| 1244 | UAUACGAUC UUGCUGGG | 3201 | CCCAGCAA CUGAUGAGGNNNNNNNNCCGAA AUCGUAUA | 7348 |
| 1246 | UACGAUCUU GCUGGGCA | 3202 | UGCCCAGC CUGAUGAGGNNNNNNNNCCGAA AGAUCGUA | 7349 |
| 1256 | CUGGGCAUA AAGCAGUC | 3203 | GACUGCUU CUGAUGAGGNNNNNNNNCCGAA AUGCCCAG | 7350 |
| 1264 | AAAGCAGUC AAGGCUAU | 3204 | AUAGCCUU CUGAUGAGGNNNNNNNNCCGAA ACUGCUUU | 7351 |
| 1271 | UCAAGGCUA UUUAAAAA | 3205 | UUUUUAAA CUGAUGAGGNNNNNNNNCCGAA AGCCUUGA | 7352 |
| 1273 | AAGGCUAUU UAAAAACC | 3206 | GGUUUUUA CUGAUGAGGNNNNNNNNCCGAA AUAGCCUU | 7353 |
| 1274 | AGGCUAUUU AAAAACCU | 3207 | AGGUUUUU CUGAUGAGGNNNNNNNNCCGAA AAUAGCCU | 7354 |
| 1275 | GGCUAUUUA AAAACCUC | 3208 | GAGGUUUU CUGAUGAGGNNNNNNNNCCGAA AAAUAGCC | 7355 |
| 1283 | AAAAACCUC ACUGCCAC | 237 | GUGGCAGU CUGAUGAGGNNNNNNNNCCGAA AGGUUUUU | 4393 |
| 1293 | CUGCCACUC UCAUUGUA | 3209 | UACAAUGA CUGAUGAGGNNNNNNNNCCGAA AGUGGCAG | 7356 |
| 1295 | GCCACUCUC AUUGUAAA | 3210 | UUUACAAU CUGAUGAGGNNNNNNNNCCGAA AGAGUGGC | 7357 |
| 1298 | ACUCUCAUU GUAAACGA | 3211 | ACGUUUAC CUGAUGAGGNNNNNNNNCCGAA AUGAGAGU | 7358 |
| 1301 | CUCAUUGUA AACGUGAA | 3212 | UUCACGUU CUGAUGAGGNNNNNNNNCCGAA ACAAUGAG | 7359 |
| 1314 | UGAAACCUC AGAUCUAC | 3213 | GUAGAUCU CUGAUGAGGNNNNNNNNCCGAA AGGUUUCA | 7360 |
| 1319 | CCUCAGAUC UACGAAAA | 3214 | UUUUCGUA CUGAUGAGGNNNNNNNNCCGAA AUCUGAGG | 7361 |
| 1321 | UCAGAUCUA CGAAAAGU | 3215 | ACUUUUCG CUGAUGAGGNNNNNNNNCCGAA AGAUCUGA | 7362 |
| 1330 | CGAAAAGUC CGUCUCCU | 3216 | AGGACACG CUGAUGAGGNNNNNNNNCCGAA ACUUUUCG | 7363 |
| 1336 | GUCCGUGUC CUCGCUUC | 3217 | GAAGCGAG CUGAUGAGGNNNNNNNNCCGAA ACACGGAC | 7364 |
| 1339 | CGUGUCCUC GCUUCCAA | 3218 | UUGGAAGC CUGAUGAGGNNNNNNNNCCGAA AGGACACG | 7365 |
| 1343 | UCCUCGCUU CCAAGCCC | 3219 | GGGCUUGG CUGAUGAGGNNNNNNNNCCGAA AGCGACCA | 7366 |
| 1344 | CCUCGCUUC CAAGCCCA | 3220 | UGGGCUUG CUGAUGAGGNNNNNNNNCCGAA AAGCGAGG | 7367 |
| 1356 | GCCCACCUC UCUAUCCG | 3221 | CGGAUAGA CUGAUGAGGNNNNNNNNCCGAA AGGUGGGC | 7368 |
| 1358 | CCACCUCUC UAUCCGCU | 3222 | AGCGGAUA CUGAUGAGGNNNNNNNNCCGAA AGAGGUGG | 7369 |
| 1360 | ACCUCUCUA UCCGCUGG | 3223 | CCAGCGGA CUGAUGAGGNNNNNNNNCCGAA AGAGAGGU | 7370 |
| 1362 | CUCUCUAUC CGCUGGGC | 3224 | GCCCAGCG CUGAUGAGGNNNNNNNNCCGAA AUAGAGAG | 7371 |
| 1382 | AGACAAGUC CUCACUUG | 3225 | CAAGUGAG CUGAUGAGGNNNNNNNNCCGAA ACUUGUCU | 7372 |
| 1385 | CAAGUCCUC ACUUGCAC | 3226 | GUGCAAGU CUGAUGAGGNNNNNNNNCCGAA AGGACUUG | 7373 |
| 1389 | UCCUCACUU GCACCGUG | 3227 | CACGGUGC CUGAUGAGGNNNNNNNNCCGAA AGUGAGGA | 7374 |
| 1399 | CACCGUGUA UGGCAUCC | 3228 | GGAUGCCA CUGAUGAGGNNNNNNNNCCGAA AGAGGGUG | 7375 |
| 1406 | UAUGGCAUG CCUCGGCC | 3229 | GGCCGAGG CUGAUGAGGNNNNNNNNCCGAA AUGCCAUA | 7376 |
| 1410 | GCAUCCCUC GGCCAACA | 3230 | UGUUGGCC CUGAUGAGGNNNNNNNNCCGAA AGGGAUGC | 7377 |
| 1421 | CCAACAAUC ACGUGGCU | 3231 | AGCCACGU CUGAUGAGGNNNNNNNNCCGAA AUUCUUGG | 7378 |
| 1430 | ACGUGGCUC UGGCACCC | 3232 | GGGUGCCA CUGAUGAGGNNNNNNNNCCGAA AGCCACGU | 7379 |
| 1443 | ACCCCUGUC ACCACAAU | 3233 | AUUGUGGU CUGAUGAGGNNNNNNNNCCGAA ACAGGGGU | 7380 |
| 1452 | ACCACAAUC ACUCCAAA | 3234 | UUUGGAGU CUGAUGAGGNNNNNNNNCCGAA AUUGUGGU | 7381 |
| 1456 | CAAUCACUC CAAAGAAA | 3235 | UUUCUUUG CUGAUGAGGNNNNNNNNCCGAA AGUGAUUG | 7382 |
| 1468 | AGAAACCUA UGACUUCU | 3236 | AGAAGUCA CUGAUGAGGNNNNNNNNCCGAA ACCUUUCU | 7383 |
| 1474 | GUAUGACUU CUGCACUG | 3237 | CAGUGCAG CUGAUGAGGNNNNNNNNCCGAA AGUCAUAC | 7384 |
| 1475 | UAUGACUUC UGCACUGA | 3238 | UCAGUGCA CUGAUGAGGNNNNNNNNCCGAA AAGUCAUA | 7385 |
| 1495 | UGAAGAAUC CUUUAUCC | 3239 | GGAUAAAG CUGAUGAGGNNNNNNNNCCGAA AUUCUUCA | 7386 |
| 1498 | AGAAUCCUU UAUCCUGG | 3240 | CCAGGAUA CUGAUGAGGNNNNNNNNCCGAA AGGAUUCA | 7387 |
| 1499 | GAAUCCUUU AUCCUGGA | 3241 | UCCAGGAU CUGAUGAGGNNNNNNNNCCGAA AAGGAUUC | 7388 |
| 1500 | AAUCCUUUA UCCUGGAU | 3242 | AUCCAGGA CUGAUGAGGNNNNNNNNCCGAA AAACCAUU | 7389 |
| 1502 | UCCUUUAUC CUGGAUCC | 3243 | GGAUCCAG CUGAUGAGGNNNNNNNNCCGAA AUAAAGGA | 7390 |
| 1509 | UCCUGGAUC CCAGCAGC | 3244 | GCUGCUGG CUGAUGAGGNNNNNNNNCCGAA AUCCAGGA | 7391 |
| 1522 | CAGCAACUU AGGAAACA | 3245 | UGUUUCCU CUGAUGAGGNNNNNNNNCCGAA AGUUGCUG | 7392 |
| 1523 | AGCAACUUA CCAAACAG | 3246 | CUGUUUCC CUGAUGAGGNNNNNNNNCCGAA AAGUUGCU | 7393 |
| 1535 | AACAGAAUU GAGAGCAU | 280 | AUGCUCUC CUGAUGAGGNNNNNNNNCCGAA AUUCUGUU | 4436 |
| 1544 | GAGAGCAUC UCUCAGCG | 3247 | CGCUGAGA CUGAUGAGGNNNNNNNNCCGAA AUGCUCUC | 7394 |
| 1546 | GAGCAUCUC UCAGCGCA | 3248 | UGCGCUCA CUGAUGAGGNNNNNNNNCCGAA AGAUGCUC | 7395 |
| 1548 | GCAUCUCUC AGCGCAUG | 3249 | CAUGCGCU CUGAUGAGGNNNNNNNNCCGAA AGAGAUGC | 7396 |
| 1562 | AUGACGGUC AUAGAAGG | 3250 | CCUUCUAU CUGAUGAGGNNNNNNNNCCGAA ACCGUCAU | 7397 |
| 1565 | ACGGUCAUA GAAGGAAC | 3251 | GUUCCUUC CUGAUGAGGNNNNNNNNCCGAA AUGACCGU | 7398 |
| 1578 | GAACAAAUA AGACGGUU | 3252 | AACCGUCU CUGAUGAGGNNNNNNNNCCGAA AUUUGUUC | 7399 |
| 1586 | AAGACGGUU AGCACAUU | 3253 | AAUGUGCU CUGAUGAGGNNNNNNNNCCGAA ACCGUCUU | 7400 |
| 1587 | AGACGGUUA GCACAUUG | 3254 | CAAUGUGC CUGAUGAGGNNNNNNNNCCGAA AACCGUCU | 7401 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1594 | UAGCACAUU GGUGGUGG | 3255 | CCACCACC CUGAUGAGGNNNNNNNNCCGAA AUGUGCUA | 7402 |
| 1609 | GGCUGACUC UCAGACCC | 3256 | GGGUCUGA CUGAUGAGGNNNNNNNNCCGAA AGUCAGCC | 7403 |
| 1611 | CUGACUCUC AGACCCCU | 3257 | AGGGGUCU CUGAUGAGGNNNNNNNNCCGAA AGAGUCAG | 7404 |
| 1625 | CCUGGAAUC UACAGCUG | 3258 | CAGCUGUA CUGAUGAGGNNNNNNNNCCGAA AUUCCAGG | 7405 |
| 1627 | UGGAAUCUA CAGCUGCC | 3259 | GGCAGCUG CUGAUGAGGNNNNNNNNCCGAA AGAUUCCA | 7406 |
| 1642 | CCGGGCCUU CAAUAAAA | 3260 | UUUUAUUG CUGAUGAGGNNNNNNNNCCGAA AGGCCCGG | 7407 |
| 1643 | CGGGCCUUC AAUAAAAU | 3261 | AUUUUAUU CUGAUGAGGNNNNNNNNCCGAA AAGGCCCG | 7408 |
| 1647 | CCUUCAAUA AAAUAGGG | 3262 | CCCUAUUU CUGAUGAGGNNNNNNNNCCGAA AUUCAAGG | 7409 |
| 1652 | AAUAAAAUA GGGACUGU | 3263 | ACAGUCCC CUGAUGAGGNNNNNNNNCCGAA AUUUUAUU | 7410 |
| 1673 | AGAAACAUA AAAUUUUA | 3264 | UAAAAUUU CUGAUGAGGNNNNNNNNCCGAA AUGUUUCU | 7411 |
| 1678 | CAUAAAAUU UUAUGUCA | 3265 | UGACAUAA CUGAUGAGGNNNNNNNNCCGAA AUUUUAUG | 7412 |
| 1679 | AUAAAAUUU UAUGUCAC | 3266 | GUGACAUA CUGAUGAGGNNNNNNNNCCGAA AAUUUUAU | 7413 |
| 1680 | UAAAAUUUU AUGUCACA | 3267 | UGUGACAU CUGAUGAGGNNNNNNNNCCGAA AAAUUUUA | 7414 |
| 1681 | AAAAUUUUA UGUCACAG | 3268 | CUGUGACA CUGAUGAGGNNNNNNNNCCGAA AAAAUUUU | 7415 |
| 1685 | UUUUAUGUC ACAGAUGU | 3269 | ACAUCUGU CUGAUGAGGNNNNNNNNCCGAA ACAUAAAA | 7416 |
| 1705 | GAAUGGCUU UCACGUUU | 3270 | AAACGUCA CUGAUGAGGNNNNNNNNCCGAA AGCCAUUC | 7417 |
| 1706 | AAUGGCUUU CACGUUUC | 3271 | GAAACGUG CUGAUGAGGNNNNNNNNCCGAA AAGCCAUU | 7418 |
| 1707 | AUGGCUUUC ACGUUUCC | 3272 | GGAAACGU CUGAUGAGGNNNNNNNNCCGAA AAAGCCAU | 7419 |
| 1712 | UUUCACGUU UCCUUGGA | 3273 | UCCAAGGA CUGAUGAGGNNNNNNNNCCGAA ACGUGAAA | 7420 |
| 1713 | UUCACGUUU CCUUGGAA | 3274 | UUCCAAGG CUGAUGAGGNNNNNNNNCCGAA AACGUCAA | 7421 |
| 1714 | UCACGUUUC CUUGGAAA | 3275 | UUUCCAAG CUGAUGAGGNNNNNNNNCCGAA AAACGUGA | 7422 |
| 1717 | CGUUUCCUU GGAAAAGA | 3276 | UCUUUUCC CUGAUGAGGNNNNNNNNCCGAA AGGAAACG | 7423 |
| 1756 | GAAACUGUC CUGUGUGG | 3277 | CCACACAG CUGAUGAGGNNNNNNNNCCGAA ACAGUUUC | 7424 |
| 1766 | UGUGUGGUC AAUAAAUU | 3278 | AAUUUAUU CUGAUGAGGNNNNNNNNCCGAA ACCACACA | 7425 |
| 1770 | UGGUCAAUA AAUUCCUG | 3279 | CA55AAUU CUGAUGAGGNNNNNNNNCCGAA AUUGACCA | 7426 |
| 1774 | CAAUAAAUU CCUGUACA | 3280 | UGUACAGG CUGAUGAGGNNNNNNNNCCGAA AUUUAUUG | 7427 |
| 1775 | AAUAAAUUC CUGUACAG | 3281 | CUGUACAG CUGAUGAGGNNNNNNNNCCGAA AAUUUAUU | 7428 |
| 1780 | AUUCCUGUA CAGAGACA | 3282 | UGUCUCUG CUGAUGAGGNNNNNNNNCCGAA ACAGGAAU | 7429 |
| 1790 | AGAGACAUU ACCUGGAC | 3283 | AUCCAGGU CUGAUGAGGNNNNNNNNCCGAA AUGUCUCU | 7430 |
| 1791 | GAGACAUUA CCUGGAUU | 3284 | AAUCCAGG CUGAUGAGGNNNNNNNNCCGAA AAUGUCUC | 7431 |
| 1799 | ACCUGGAUU CUGCUACG | 3285 | CGUAGCAG CUGAUGAGGNNNNNNNNCCGAA AUCCAGGU | 7432 |
| 1800 | CCUGGAUUC UGCUACGG | 3286 | CCGUAGCA CUGAUGAGGNNNNNNNNCCGAA AAUCCAGG | 7433 |
| 1805 | AUUCUGCUA CGGACACU | 3287 | ACUGUCCG CUGAUGAGGNNNNNNNNCCGAA AGCAGAAU | 7434 |
| 1814 | CGGACAGUU AACAACAG | 3288 | CUGUUGUU CUGAUGAGGNNNNNNNNCCGAA ACUGUCCG | 7435 |
| 1815 | GGACAGUUA ACAACAGA | 3289 | UCUGUUGU CUGAUGAGGNNNNNNNNCCGAA AACUGUCC | 7436 |
| 1836 | UGCACCAUA GUAUCAGC | 3290 | GCUGAUAC CUGAUGAGGNNNNNNNNCCGAA AUGGUGCA | 7437 |
| 1839 | ACCAUAGUA UCAGCAAG | 3291 | CUUGCUGA CUGAUGAGGNNNNNNNNCCGAA ACUAUGGU | 7438 |
| 1841 | CAUAGUAUC AGCAAGCA | 3292 | UGCUUGCU CUGAUGAGGNNNNNNNNCCGAA AUACUAUG | 7439 |
| 1866 | CCACCACUC AAGAUUAC | 3293 | GUAAUCUU CUGAUGAGGNNNNNNNNCCGAA AGUGGUGG | 7440 |
| 1872 | CUCAAGAUU ACUCCAUC | 3294 | GAUGGAGU CUGAUGAGGNNNNNNNNCCGAA AUCUUGAG | 7441 |
| 1873 | UCAAGAUUA CUCCAUCA | 3295 | UGAUGGAG CUGAUGAGGNNNNNNNNCCGAA AAUCUUGA | 7442 |
| 1876 | AGAUUACUC CAUCACUC | 3296 | GAGUGAUG CUGAUGAGGNNNNNNNNCCGAA AGUAAGCU | 7443 |
| 1880 | UACUCCUAC ACUCUGAA | 3297 | UUCAGAGU CUGAUGAGGNNNNNNNNCCGAA AUGGAGUA | 7444 |
| 1884 | CCAUCACUC UGAACCUU | 3298 | AAGGUUCA CUGAUGAGGNNNNNNNNCCGAA AGUGAUGG | 7445 |
| 1892 | CUGAACCUU GUCAUCAA | 3299 | UUGAUGAC CUGAUGAGGNNNNNNNNCCGAA AGGUUCAG | 7446 |
| 1895 | AACCUUGUC AUCAAGAA | 3300 | UUCUUGAU CUGAUGAGGNNNNNNNNCCGAA ACAAGGUU | 7447 |
| 1898 | CUUGUCAUC AAGAACGU | 3301 | ACGUUCUU CUGAUGAGGNNNNNNNNCCGAA AUGACAAG | 7448 |
| 1909 | GAACGUGUC UCUAGAAG | 3302 | CUUCUAGA CUGAUGAGGNNNNNNNNCCGAA ACACGUUC | 7449 |
| 1911 | ACGUGUCUC UAGAAGAC | 3303 | GUCUUCUA CUGAUGAGGNNNNNNNNCCGAA AGACACGU | 7450 |
| 1913 | GUGUCUCUA GAAGACUC | 3304 | GAGUCUUC CUGAUGAGGNNNNNNNNCCGAA AGAGACAC | 7451 |
| 1921 | AGAAGACUC GGGCACCU | 3305 | AGGUGCCC CUGAUGAGGNNNNNNNNCCGAA AGUCUUCU | 7452 |
| 1930 | GGGCACCUA UGCGUGCA | 3306 | UGCACGCA CUGAUGAGGNNNNNNNNCCGAA AGGUGCCC | 7453 |
| 1952 | AGGAACAUA UACACAGG | 3307 | CCUGUGUA CUGAUGAGGNNNNNNNNCCGAA AUGUUCCU | 7454 |
| 1954 | GAACAUAUA CACAGGGG | 3308 | CCCCUGUG CUGAUGAGGNNNNNNNNCCGAA AUAUGUUC | 7455 |
| 1970 | GAAGACAUC CUUCGGAA | 3309 | UUCCGAAG CUGAUGAGGNNNNNNNNCCGAA AUGUCUUC | 7456 |
| 1973 | GACAUCCUU CGGAAGAC | 3310 | GUCUUCCG CUGAUGAGGNNNNNNNNCCGAA AGGAUGUC | 7457 |
| 1974 | ACAUCCUUC GGAAGACA | 3311 | UGUCUUCC CUGAUGAGGNNNNNNNNCCGAA AAGGAUGU | 7458 |
| 1988 | ACAGAAGUU C7GUUAG | 3312 | CUAACGAG CUGAUGAGGNNNNNNNNCCGAA ACUUCUGU | 7459 |
| 1989 | CAGAAGUUC UCGUUAGA | 3313 | UCUAACGA CUGAUGAGGNNNNNNNNCCGAA AACUUCUG | 7460 |
| 1991 | GAAGUUCUC GUUAGAGA | 3314 | UCUCUAAC CUGAUGAGGNNNNNNNNCCGAA AGAACUUC | 7461 |
| 1994 | GUUCUCGUU AGAGAUUC | 3315 | GAAUCUCU CUGAUGAGGNNNNNNNNCCGAA ACGAGAAC | 7462 |
| 1995 | UUCUCGUUA GAGAUUCG | 3316 | CGAAUCUC CUGAUGAGGNNNNNNNNCCGAA AACGACAA | 7463 |
| 2001 | UUAGAGAUU CGGAAGCG | 3317 | CGCUUCCG CUGAUGAGGNNNNNNNNCCGAA AUCUCUAA | 7464 |
| 2002 | UAGAGAUUC GGAAGCGC | 3318 | GCGCUUCC CUGAUGAGGNNNNNNNNCCGAA AAUCUCUA | 7465 |
| 2021 | CACCUGCUU CAAAACCU | 3319 | AGGUUUUG CUGAUGAGGNNNNNNNNCCGAA AGCAGGUG | 7466 |
| 2022 | ACCUGCUUC AAAACCUC | 3320 | GAGGUUUU CUGAUGAGGNNNNNNNNCCGAA AAGCAGGU | 7467 |
| 2030 | CAAAACCUC AGUGACUA | 3321 | UAGUCACU CUGAUGAGGNNNNNNNNCCGAA AGGUUUUG | 7468 |
| 2038 | CAGUGACUA CGACCUCU | 3322 | AGACCUCG CUGAUGAGGNNNNNNNNCCGAA AGUCACUG | 7469 |
| 2045 | UACGAGGUC UCCAUCAG | 3323 | CUGAUGGA CUGAUGAGGNNNNNNNNCCGAA ACCUCGUA | 7470 |
| 2047 | CGAGGUCUC CAUCAGUG | 3324 | CACUGAUG CUGAUGAGGNNNNNNNNCCGAA AGACCUCG | 7471 |
| 2051 | GUCUCCAUC AGUGGCUC | 3325 | GAGCCACU CUGAUGAGGNNNNNNNNCCGAA AUGGAGAC | 7472 |
| 2059 | CAGUGGCUC UACGACCU | 3326 | AGGUCGUA CUGAUGAGGNNNNNNNNCCGAA AGCCACUG | 7473 |
| 2061 | GUGGCUCUA CGACCUUA | 3327 | UAAGGUCG CUGAUGAGGNNNNNNNNCCGAA AGAGCCAC | 7474 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 2068 | UACGACCUU AGACUGUC | 3328 | GACAGUAU CUGAUGAGGNNNNNNNNCCGAA AGGUCGUA | 7475 |
| 2069 | ACGACCUUA GACUGUCA | 3329 | UGACAGUC CUGAUGAGGNNNNNNNNCCGAA AAGGUCGU | 7476 |
| 2076 | UAGACUGUC AAGCUAGA | 3330 | UCUAGCUU CUGAUGAGGNNNNNNNNCCGAA ACAGUCUA | 7477 |
| 2082 | GUCAAGCUA GAGGUGUC | 3331 | GACACCUC CUGAUGAGGNNNNNNNNCCGAA AGCUUGAC | 7478 |
| 2090 | AGAGGUGUC CCCGCGCC | 3332 | GGCGCGGG CUGAUGAGGNNNNNNNNCCGAA ACACCUCU | 7479 |
| 2100 | CCGCGCCUC AGAUCACU | 3333 | AGUGAUCU CUGAUGAGGNNNNNNNNCCGAA AGGCGCGG | 7480 |
| 2105 | CCUCAGAUC ACUUGGUU | 378 | AACCAAGU CUGAUGAGGNNNNNNNNCCGAA AUCUGAGG | 4534 |
| 2109 | AGAUCACUU GGUUCAAA | 3334 | UUUGAACC CUGAUGAGGNNNNNNNNCCGAA AGUGAUCU | 7481 |
| 2113 | CACUUGGUU CAAAACA | 3335 | UGUUUUG CUGAUGAGGNNNNNNNNCCGAA ACCAAGUG | 7482 |
| 2114 | ACUUGGUUC AAAAACAA | 3336 | UUGUUUUU CUGAUGAGGNNNNNNNNCCGAA AACCAAGU | 4537 |
| 2132 | CACAAAAUA CAACAAGA | 383 | UCUUGUUG CUGAUGAGGNNNNNNNNCCGAA AUUUUGUG | 4539 |
| 2150 | CCGGGAAUU AUUUUAGG | 3337 | CCUAAAAU CUGAUGAGGNNNNNNNNCCGAA AUUCCCGG | 7483 |
| 2151 | CGGGAAUUA UUUUAGGA | 3338 | UCCUAAAA CUGAUGAGGNNNNNNNNCCGAA AAUUCCCG | 7484 |
| 2153 | GGAAUUAUU UUAGGACC | 386 | GGUCCUAA CUGAUGAGGNNNNNNNNCCGAA AUAAUUCC | 4542 |
| 2154 | GAAUUAUUU UAGGACCA | 387 | UGGUCCUA CUGAUGAGGNNNNNNNNCCGAA AAUAAUUC | 4543 |
| 2155 | AAUUAUUUU AGGACCAG | 388 | CUGGUCCU CUGAUGAGGNNNNNNNNCCGAA AAAUAAUU | 4544 |
| 2156 | AUUAUUUUA GGACCAGG | 389 | CCUGGUCC CUGAUGAGGNNNNNNNNCCGAA AAAAUAAU | 4545 |
| 2179 | CACGCUAUU UAUUGAAA | 390 | UUUCAAUA CUGAUGAGGNNNNNNNNCCGAA ACAGCGUG | 4546 |
| 2180 | ACGCUGUUU AUUGAAAG | 391 | CUUUCAAU CUGAUGAGGNNNNNNNNCCGAA AACAGCGU | 4547 |
| 2181 | CGCUGUUUA UUGAAAGA | 392 | UCUUUCAA CUGAUGAGGNNNNNNNNCCGAA AAACAGCG | 4548 |
| 2183 | CUGUUUAUU GAAAGAGU | 393 | ACUCUUUC CUGAUGAGGNNNNNNNNCCGAA AUAAACAG | 4549 |
| 2192 | GAAAGAGUC ACAGAGGA | 3339 | UCCUCUGU CUGAUGAGGNNNNNNNNCCGAA ACUCUUUC | 7485 |
| 2213 | GAGGGUGUC UAUAGGUG | 3340 | CACCUAUA CUGAUGAGGNNNNNNNNCCGAA ACACCCUC | 7486 |
| 2215 | GGGUGUCUA UAGGUGCC | 3341 | GGCACCUA CUGAUGAGGNNNNNNNNCCGAA AGACACCC | 7487 |
| 2217 | GUGUCUAUA GGUGCCGA | 3342 | UCGGCACC CUGAUGAGGNNNNNNNNCCGAA AUAGACAC | 7488 |
| 2263 | CGCAGCCUA CCUCACCG | 3343 | CGGUGAGG CUGAUGAGGNNNNNNNNCCGAA AGGCUGCG | 7489 |
| 2267 | GCCUACCUC ACCGUGCA | 3344 | UGCACGGU CUGAUGAGGNNNNNNNNCCGAA AGGUAGGC | 7490 |
| 2284 | AGGAACCUC AGACAAGU | 3345 | ACUUGUCU CUGAUGAGGNNNNNNNNCCGAA AGGUUCCU | 7491 |
| 2293 | AGACAAGUC AAACCUGG | 3346 | CCAGGUUU CUGAUGAGGNNNNNNNNCCGAA ACUUGUCU | 7492 |
| 2309 | GAGCUGAUC ACGCUCAC | 3347 | GUGAGCGU CUGAUGAGGNNNNNNNNCCGAA AUCAGCUC | 7493 |
| 2315 | AUCACGCUC ACGUGCAC | 3348 | GUGCACGU CUGAUGAGGNNNNNNNNCCGAA AGCGUGAU | 7494 |
| 2342 | GCGACCCUC UUUUGGCU | 3349 | AGCCAAAA CUGAUGAGGNNNNNNNNCCGAA AGGGUCGC | 7495 |
| 2344 | GACCCUCUU UUGGCUCC | 3350 | GGAGCCAA CUGAUGAGGNNNNNNNNCCGAA AGAGGGUC | 7496 |
| 2345 | ACCCUCUUU UGGCUCCU | 3351 | AGGAGCCA CUGAUGAGGNNNNNNNNCCGAA AAGAGGGU | 7497 |
| 2346 | CCCUCUUUU GGCUCCUU | 3352 | AAGGAGCC CUGAUGAGGNNNNNNNNCCGAA AAAGAGGG | 7498 |
| 2351 | UUUUGGCUC CUUCUAAC | 3353 | GUUAGAAG CUGAUGAGGNNNNNNNNCCGAA AGCCAAAA | 7499 |
| 2354 | UGGCUCCUU CUAACUCU | 3354 | AGAGUUAG CUGAUGAGGNNNNNNNNCCGAA AGGAGCCA | 7500 |
| 2355 | GGCUCCUUC UAACUCUC | 3355 | GAGAGUUA CUGAUGAGGNNNNNNNNCCGAA AAGGAGCC | 7501 |
| 2357 | CUCCUUCUA ACUCUCUU | 3356 | AAGAGAGU CUGAUGAGGNNNNNNNNCCGAA AGAAGGAG | 7502 |
| 2361 | UUCUAACUC UCUUCAUC | 3357 | GAUGAAGA CUGAUGAGGNNNNNNNNCCGAA AGUUAGAA | 7503 |
| 2363 | CUAACUCUC UUCAUCAG | 3358 | CUGAUGAA CUGAUGAGGNNNNNNNNCCGAA AGAGUUAG | 7504 |
| 2365 | AACUCUCUU CAUCAGAA | 3359 | UUCUGAUG CUGAUGAGGNNNNNNNNCCGAA AGAGACUU | 7505 |
| 2366 | ACUCUCUUC AUCAGAAA | 3360 | UUUCUGAU CUGAUGAGGNNNNNNNNCCGAA AAGAGAGU | 7506 |
| 2369 | CUCUUCAUC AGAAACU | 3361 | AGUUUCU CUGAUGAGGNNNNNNNNCCGAA AUGAAGAG | 7507 |
| 2386 | GAAGCGGUC UUCUUCCG | 3362 | CGGAAGAA CUGAUGAGGNNNNNNNNCCGAA ACCGCUUC | 7508 |
| 2388 | AGCGGUCUU CUUCCGAA | 3363 | UUCGGAAG CUGAUGAGGNNNNNNNNCCGAA AGACCGCU | 7509 |
| 2389 | GCGGUCUUC UUCCGAAG | 3364 | CUUCGGAA CUGAUGAGGNNNNNNNNCCGAA AAGACCGC | 7510 |
| 2391 | GGUCUUCUU CCGAAGUC | 3365 | UACUUCGG CUGAUGAGGNNNNNNNNCCGAA AGAAGACC | 7511 |
| 2392 | GUCUUCUUC CGAAGUAA | 3366 | UUACUUCG CUGAUGAGGNNNNNNNNCCGAA AAGAAGAC | 7512 |
| 2399 | UCCGAAGUA AACACAGA | 3367 | UCUGUCUU CUGAUGAGGNNNNNNNNCCGAA ACUUCGGA | 7513 |
| 2410 | GACAGACUA CCUGUCAA | 3368 | UUGACAGG CUGAUGAGGNNNNNNNNCCGAA AGUCUGUC | 7514 |
| 2416 | CUACCUGUC AAUCAUUA | 3369 | UAAUGAUU CUGAUGAGGNNNNNNNNCCGAA ACAGGUAG | 7515 |
| 2420 | CUGUCAAUC AUUAUGGA | 3370 | UCCAUCCU CUGAUGAGGNNNNNNNNCCGAA AUUGACAG | 7516 |
| 2423 | UCAAUCAUU AUGGACCC | 3371 | GGGUCCAU CUGAUGAGGNNNNNNNNCCGAA AUGAUUGA | 7517 |
| 2424 | CAAUCAUUA UGGACCCA | 3372 | UGGGUCCA CUGAUGAGGNNNNNNNNCCGAA AAUGAUUG | 7518 |
| 2441 | GAUGAAGUU CCCUGGA | 3373 | UCCAGGGG CUGAUGAGGNNNNNNNNCCGAA ACUUCAUC | 7519 |
| 2442 | AUGAAGUUC CCUGGAU | 3374 | AUCCAGGG CUGAUGAGGNNNNNNNNCCGAA AACUUCAU | 7520 |
| 2473 | GCUGCCCUA UGAUGCCA | 3375 | UGGCAUCA CUGAUGAGGNNNNNNNNCCGAA AGGGCAGC | 7521 |
| 2494 | GUGGGAGUU UGCACGGG | 3376 | CCCGUGCA CUGAUGAGGNNNNNNNNCCGAA ACUCCCAC | 7522 |
| 2495 | UGGGAGUUU GCACGGGA | 3377 | UCCCGUGC CUGAUGAGGNNNNNNNNCCGAA AACUCCCA | 7523 |
| 2516 | CUGAAACUA GGCAAAUC | 3378 | GAUUUGCC CUGAUGAGGNNNNNNNNCCGAA AGUUUCAG | 7524 |
| 2524 | AGGCAAAUC GCUCGGAA | 3379 | UUCCGAGC CUGAUGAGGNNNNNNNNCCGAA AUUUGCCU | 7525 |
| 2528 | AAAUCGCUC GGAAGAGG | 3380 | CCUCUUCC CUGAUGAGGNNNNNNNNCCGAA AGCGAUUU | 7526 |
| 2541 | GAGGGGCUU UUGGGAAA | 3381 | UUUCCCAA CUGAUGAGGNNNNNNNNCCGAA AGCCCCUC | 7527 |
| 2542 | AGGGGCUUU UGGGAAAG | 3382 | CUUUCCCA CUGAUGAGGNNNNNNNNCCGAA AAGCCCCU | 7528 |
| 2543 | GGGGCUUUU GGGAAAGU | 3383 | ACUUUCCC CUGAUGAGGNNNNNNNNCCGAA AAAGCCCC | 7529 |
| 2552 | GGGAAAGUC GUUCAAGC | 3384 | GCUUGAAC CUGAUGAGGNNNNNNNNCCGAA ACUUUCCC | 7530 |
| 2555 | AAACUCGUC CAAGCCUC | 3385 | GAGGCUUG CUGAUGAGGNNNNNNNNCCGAA ACGACUUU | 7531 |
| 2556 | AAGUCGUUC AAGCCUCU | 3386 | AGAGGCUU CUGAUGAGGNNNNNNNNCCGAA AACGACUU | 7532 |
| 2563 | UCAAGCCUC UGCAUUUG | 3387 | CAAAUGCA CUGAUGAGGNNNNNNNNCCGAA AGGCUUGA | 7533 |
| 2569 | CUCUGCAUU UGGCAUUA | 3388 | UAAUGCCA CUGAUGAGGNNNNNNNNCCGAA AUGCAGAG | 7534 |
| 2570 | UCUGCAUUU GGCAUUAA | 3389 | UUAAUGCC CUGAUGAGGNNNNNNNNCCGAA AAUCCAGA | 7535 |
| 2576 | UUUGGCAUU AAGAAAUC | 457 | GAUUUCUU CUGAUGAGGNNNNNNNNCCGAA AUCGCAAA | 4613 |

TABLE VIII-continued

Mouse *flt*-1 VEGF Receptor-Hammerhead Ribozyme and Substrate Sequence

| Pos | Substrate | Seq ID No | HH Ribozyme Sequence | Seq ID No |
|---|---|---|---|---|
| 2577 | UUGGCAUUA AGAAAUCA | 458 | UGAUUUCU CUGAUGAGGNNNNNNNNCCGAA AAUGCCAA | 4614 |
| 2584 | UAAGAAAUC ACCCACCU | 3390 | AGGUGGGU CUGAUGAGGNNNNNNNNCCGAA AUUUCUUA | 7536 |
| 2617 | GAAGAUGUU GAAAGAGG | 3391 | CCUCUUUC CUGAUGAGGNNNNNNNNCCGAA ACAUCUUC | 7537 |
| 2644 | CAGUGAGUA CAAAGCUC | 3392 | GAGCUUUG CUGAUGAGGNNNNNNNNCCGAA ACUCACUG | 7538 |
| 2652 | ACAAAGCUC UGUUGACC | 3393 | GGUCAACA CUGAUGAGGNNNNNNNNCCGAA AGCUUUGU | 7539 |
| 2666 | ACCGAACUC AAGAUCUU | 3394 | AAGAUCUU CUGAUGAGGNNNNNNNNCCGAA AGUUCGGU | 7540 |
| 2672 | CUCAAGAUC UUGACCCA | 3395 | UGGGUCAA CUGAUGAGGNNNNNNNNCCGAA AUCUUGAG | 7541 |
| 2674 | CAAGAUCUU GACCCACA | 3396 | UGUGGGUC CUGAUGAGGNNNNNNNNCCGAA AGAUCUUG | 7542 |
| 2684 | ACCCACAUC GGCCAUCA | 3397 | UGAUGGCC CUGAUGAGGNNNNNNNNCCGAA AUCUGGGU | 7543 |
| 2691 | UCGGCGAUC AUCUGAAU | 3398 | AUUCAGAU CUGAUGAGGNNNNNNNNCCGAA AUCGCCGA | 7544 |
| 2694 | GCCAUCAUC UGAAUGUG | 3399 | CACAUUCA CUGAUGAGGNNNNNNNNCCGAA AUGGUGGC | 7545 |
| 2705 | AAUGUGGUU AACCUCCU | 3400 | AGGAGGUU CUGAUGAGGNNNNNNNNCCGAA ACCACAUU | 7546 |
| 2706 | AUGUGGUUA ACCUCCUG | 3401 | ACGGAGGU CUGAUGAGGNNNNNNNNCCGAA ACCAACAU | 7547 |
| 2711 | GUUAACCUC CUGGGAGC | 3402 | GCUCCCAG CUGAUGAGGNNNNNNNNCCGAA AACCUAAC | 7548 |
| 2742 | GAGGGCCUC UGACGGUG | 470 | CACCAUCA CUGAUGAGGNNNNNNNNCCGAA AGGCCCUC | 4626 |
| 2753 | AUGGUGAUC GUGGAAUA | 3403 | UAUUCCAC CUGAUGAGGNNNNNNNNCCGAA AUCACCAU | 7549 |
| 2761 | CGUGGAAUA CUGCAAAU | 3404 | AUUUGCAG CUGAUGAGGNNNNNNNNCCGAA AUCACACG | 7550 |
| 2770 | CUGCAAAUA CGGAAACC | 3405 | GGUUUCCG CUGAUGAGGNNNNNNNNCCGAA AUUCGCAG | 7551 |
| 2782 | AAACCUGUC CAACUACC | 3406 | GGUAGUUG CUGAUGAGGNNNNNNNNCCGAA AUUUGUUU | 7552 |
| 2788 | GUCCAACUA CCUCAAGA | 3407 | UCUUGAGG CUGAUGAGGNNNNNNNNCCGAA ACAGGGAC | 7553 |
| 2792 | AACUACCUC AAGAGCAA | 479 | UUGCUCUU CUGAUGAGGNNNNNNNNCCGAA AGUUAGUU | 4635 |
| 2809 | ACGUGACUU AUUCUGUC | 3408 | GACAGAAU CUGAUGAGGNNNNNNNNCCGAA AGGUACGU | 7554 |
| 2810 | CGUCACUUA CCGUGUCU | 3409 | AGACAGAA CUGAUGAGGNNNNNNNNCCGAA AGUCCACG | 7555 |
| 2812 | UGACUUAUU CUGUCUCA | 3410 | UGAGACAG CUGAUGAGGNNNNNNNNCCGAA AUAAGUCA | 7556 |
| 2813 | GACUUAUUC UGUCUCAA | 3411 | UUGAGACA CUGAUGAGGNNNNNNNNCCGAA AUAAAGUC | 7557 |
| 2817 | UAUUCUGUC UCAACAAG | 3412 | CUUGUUGA CUGAUGAGGNNNNNNNNCCGAA ACAGAAUA | 7558 |
| 2819 | UUCUGUCUC AACAUGGA | 3413 | UCCUUGUU CUGAUGAGGNNNNNNNNCCGAA ACAGAGAA | 7559 |
| 2836 | CGCAGCCUU GCAUAUGG | 3414 | CCAUAUGC CUGAUGAGGNNNNNNNNCCGAA AGGCUGCG | 7560 |
| 2841 | CCUUGCAUA UGGAGCUC | 3415 | GAGCUCCA CUGAUGAGGNNNNNNNNCCGAA AUGCAAGG | 7561 |
| 2849 | AUGGAGCUC AAGAAAGA | 3416 | UCUUUCUU CUGAUGAGGNNNNNNNNCCGAA AGCUCCAU | 7562 |
| 2900 | CCCCGCCUA GACAGUGU | 3417 | AGAGUGUC CUGAUGAGGNNNNNNNNCCGAA AGGCGGGG | 7563 |
| 2909 | GACAGUGUC AGCAGCUC | 3418 | GAGCUGCU CUGAUGAGGNNNNNNNNCCGAA ACACUGUC | 7564 |
| 2917 | CAGCAGCUC AAGUGUCA | 3419 | UGACACUU CUGAUGAGGNNNNNNNNCCGAA AGCUGCUG | 7565 |
| 2924 | UCAAGUGUC ACCAGCUC | 3420 | GAGCUGGU CUGAUGAGGNNNNNNNNCCGAA ACACUUGA | 7566 |
| 2932 | CACCAGCUC CAGCUUCC | 3421 | GGAAGCUG CUGAUGAGGNNNNNNNNCCGAA AGCUGGUG | 7567 |
| 2938 | CUCCAGCUU CCCUGAAG | 3422 | CUUCAGGG CUGAUGAGGNNNNNNNNCCGAA AGCUGGAG | 7568 |
| 2939 | UCCAGCUUC CCUGAAGA | 3423 | UCUUCAGG CUGAUGAGGNNNNNNNNCCGAA AAGCUGGA | 7569 |
| 2982 | ACGAGGAUU ACAGUGAG | 3424 | CUCACUGU CUGAUGAGGNNNNNNNNCCGAA AUCCUCGU | 7570 |
| 2983 | CGAGGAUUA CAGUGAGA | 3425 | UCUCACUG CUGAUGAGGNNNNNNNNCCGAA AAUCCUCG | 7571 |
| 2993 | AGUGAGAUC UCCAAGCA | 3426 | UGCUUGGA CUGAUGAGGNNNNNNNNCCGAA AUCUCACU | 7572 |
| 2995 | UGAGAUCUC CAAGCAGC | 3427 | GCUGCUUG CUGAUGAGGNNNNNNNNCCGAA AGAUCUCA | 7573 |
| 3008 | CAGCCCCUC ACCAUGGA | 3428 | UCCAUGGU CUGAUGAGGNNNNNNNNCCGAA AGGGGCUG | 7574 |
| 3026 | GACCUGAUU UCCUACAG | 3429 | GUCUAGGA CUGAUGAGGNNNNNNNNCCGAA AUCAGGUC | 7575 |
| 3027 | ACCUGAUUU CCUACAGU | 3430 | ACUGUAGG CUGAUGAGGNNNNNNNNCCGAA AAUCAGGU | 7576 |
| 3028 | CCUGAUUUC CUACAGUU | 3431 | AACUGUAG CUGAUGAGGNNNNNNNNCCGAA AAAUCAGG | 7577 |
| 3031 | GAUUUCCUA CAGUUCC | 3432 | GGAAACUG CUGAUGAGGNNNNNNNNCCGAA AGGAAAUC | 7578 |
| 3036 | CCUACAGUU UCCAAGUG | 3433 | CACUUGGA CUGAUGAGGNNNNNNNNCCGAA ACUGUAGG | 7579 |
| 3037 | CUACAGUUU CCAAGUGG | 3434 | CCACUUGG CUGAUGAGGNNNNNNNNCCGAA AACUGUAG | 7580 |
| 3038 | UACAGUUUC CAAGUGGC | 3435 | GCCACUUG CUGAUGAGGNNNNNNNNCCGAA AAACUGUA | 4675 |
| 3061 | CAUGGAGUU UCUGUCCU | 3436 | AGGACAGA CUGAUGAGGNNNNNNNNCCGAA ACUCCAUG | 7581 |
| 3062 | AUGGAGUUU CUGUCCUC | 3437 | GAGGACAG CUGAUGAGGNNNNNNNNCCGAA AACUCCAU | 7582 |
| 3063 | UGGAGUUUC UGUCCUCC | 3438 | GGAGGACA CUGAUGAGGNNNNNNNNCCGAA AAACUCCA | 7583 |
| 3067 | GUUUUUGUC CUCCAGAA | 3439 | UUCUGGAG CUGAUGAGGNNNNNNNNCCGAA ACAGAAAC | 7584 |
| 3070 | UCUGUCCUC CAGAAAGU | 3440 | ACUUUCUG CUGAUGAGGNNNNNNNNCCGAA AGGACAGA | 7585 |
| 3083 | AAGUGCAUU CAUCGGGU | 526 | UCCCGAUG CUGAUGAGGNNNNNNNNCCGAA AUGCACUU | 4682 |
| 3084 | AGUGCAUUC AUCGGGAC | 527 | GUCCCGAU CUGAUGAGGNNNNNNNNCCGAA AAUGCACU | 4683 |
| 3087 | GCAUUCAUC GGGACCUG | 528 | CAGGUCCC CUGAUGAGGNNNNNNNNCCGAA AUGAAUGC | 4684 |
| 3110 | AGAAACAUC CUUUUAUC | 3441 | GAUAAAAG CUGAUGAGGNNNNNNNNCCGAA AUGUUUCU | 4685 |
| 3113 | AACAUCCUU UUAUCUGA | 3442 | UCAGAUAA CUGAUGAGGNNNNNNNNCCGAA AGGAUGUU | 7586 |
| 3114 | ACAUCCUUU UAUCUGAG | 3443 | CUCAGAUA CUGAUGAGGNNNNNNNNCCGAA AAGGAUGU | 7587 |
| 3115 | CAUCCUUUU AUCUGAGA | 3444 | UCUCAGAU CUGAUGAGGNNNNNNNNCCGAA AAAGGAUG | 7588 |
| 3116 | AUCCUUUUA UCUGAGAA | 3445 | UUCUCAGA CUGAUGAGGNNNNNNNNCCGAA AAAAGGAU | 7589 |
| 3118 | CCUUUUAUC UGAGAACA | 3446 | UGUUCUCA CUGAUGAGGNNNNNNNNCCGAA AUAAAAGG | 7590 |
| 3140 | GUGAAGAUU UGCGACUU | 3447 | AAGUCGCA CUGAUGAGGNNNNNNNNCCGAA AUCUUCAC | 7591 |
| 3141 | UGAAGAUUU GCGACUUU | 3448 | AAAGUCGC CUGAUGAGGNNNNNNNNCCGAA AAUCUUCA | 7592 |
| 3148 | UUGCGACUU UGGCCUGG | 3449 | CCAGGCCA CUGAUGAGGNNNNNNNNCCGAA AGUCGCAA | 7593 |
| 3149 | UGCGACUUU GGCCUGGC | 3450 | GCCAGGCC CUGAUGAGGNNNNNNNNCCGAA AAGUCGCA | 7594 |
| 3165 | CCCGGGAUA UUUAUAAG | 542 | CUUAUAAA CUGAUGAGGNNNNNNNNCCGAA AUCCCGGG | 4698 |
| 3167 | CGGGAUAUU UAUAAGAA | 543 | UUCUUAUA CUGAUGAGGNNNNNNNNCCGAA AUAUCCCG | 4699 |
| 3168 | GGGAUAUUU AUAAGAAC | 544 | GUUCUUAU CUGAUGAGGNNNNNNNNCCGAA AAUAUCCC | 4700 |
| 3169 | GGAUAUUUA UAAGAACC | 545 | GGUUCUUA CUGAUGAGGNNNNNNNNCCGAA AAAUAUCC | 4701 |
| 3171 | AUAUUUAUA AGAACCCU | 3451 | AGGGUUCU CUGAUGAGGNNNNNNNNCCGAA AUAAAUAU | 7595 |
| 3183 | ACCCUGAUU AUGUGAGG | 3452 | CCUCACAU CUGAUGAGGNNNNNNNNCCGAA AUCAGGGU | 7596 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 3184 | CCCUGUAAU UGUGAGGA | 3453 | UCCUCACA CUGAUGAGGNNNNNNNNCCGAA AAUCAGGG | 7597 |
| 3201 | GAGGAGAUA CUCGACUU | 3454 | AAGUCGAG CUGAUGAGGNNNNNNNNCCGAA AUCUCCUC | 7598 |
| 3204 | GAGAUACUC GACUUCCC | 3455 | GGGAAGUC CUGAUGAGGNNNNNNNNCCGAA AGUAUCUC | 7599 |
| 3209 | ACUCGACUU CCCCUAAA | 3456 | UUUAGGGG CUGAUGAGGNNNNNNNNCCGAA AGUCGAGU | 7600 |
| 3210 | CUCGACUUC CCCUAAAA | 3457 | UUUUAGGG CUGAUGAGGNNNNNNNNCCGAA AAGUCGAG | 7601 |
| 3215 | CUUCCCCUA AAAUGGAU | 3458 | AUCCAUUU CUGAUGAGGNNNNNNNNCCGAA AGGGGAAG | 7602 |
| 3228 | GGAUGGCUC CUGAAUCC | 3459 | GGAUUCAG CUGAUGAGGNNNNNNNNCCGAA AGCCAUCC | 7603 |
| 3235 | UCCAGAAUC CAUCUUUG | 3460 | CAAAGAUG CUGAUGAGGNNNNNNNNCCGAA AUUCAGGA | 7604 |
| 3239 | GAAUCCAUC UUUGACAA | 3461 | UUGUCAAA CUGAUGAGGNNNNNNNNCCGAA AUGGAUUC | 7605 |
| 3241 | AUCCAUCUU UGACAAGG | 3462 | CCUUGUCA CUGAUGAGGNNNNNNNNCCGAA AGAUGGAU | 7606 |
| 3242 | UCCAUCUUU GACAAGGU | 3463 | ACCUUGUC CUGAUGAGGNNNNNNNNCCGAA AAGAUGGA | 7607 |
| 3251 | GACAAGGUC UACAGCAC | 3464 | GUGCUGUA CUGAUGAGGNNNNNNNNCCGAA ACCUUGUC | 7608 |
| 3253 | CAAGGUCUA CAGCACCA | 3465 | UGGUGCUG CUGAUGAGGNNNNNNNNCCGAA AGACCUUG | 7609 |
| 3277 | UGUGUGGUC CUAUGGCG | 3466 | CGCCAUAG CUGAUGAGGNNNNNNNNCCGAA ACCACACA | 7610 |
| 3280 | GUGGUCCUA UGGCGUGU | 3467 | ACACGCCA CUGAUGAGGNNNNNNNNCCGAA AGGACCAC | 7611 |
| 3289 | UGGCGUGUU GCUGUGGG | 3468 | CCCACAGC CUGAUGAGGNNNNNNNNCCGAA ACACGCCA | 7612 |
| 3302 | UGGGAGAUC UUCUCCUU | 3469 | AAGGAGAA CUGAUGAGGNNNNNNNNCCGAA AUCUCCCA | 7613 |
| 3304 | GGAGAUCUU CUCCUCAG | 3470 | CUAAGGAG CUGAUGAGGNNNNNNNNCCGAA AGAUCUCC | 7614 |
| 3305 | GAGAUCUUC UCCUUCAG | 3471 | CCUAAGGA CUGAUGAGGNNNNNNNNCCGAA AAGAUCUC | 7615 |
| 3307 | GAUCUCUCU CUUAGGGG | 3472 | CCCCUAAG CUGAUGAGGNNNNNNNNCCGAA AGAAGAUC | 7616 |
| 3310 | CUUCUCCUU AGGGGUU | 3473 | AACCCCCU CUGAUGAGGNNNNNNNNCCGAA AGGAGAAG | 7617 |
| 3311 | UUCUCCUUA GGGGUUC | 3474 | GAACCCCC CUGAUGAGGNNNNNNNNCCGAA AAGGAGAA | 7618 |
| 3318 | UAGGGGGUU CUCCAUAC | 3475 | GUAUGGAG CUGAUGAGGNNNNNNNNCCGAA ACCCCCUA | 7619 |
| 3319 | AGGGGGUUC UCCAUACC | 3476 | GGUAUGGA CUGAUGAGGNNNNNNNNCCGAA AACCCCCU | 7620 |
| 3321 | GGGGUUCUC CAUACCCA | 3477 | UGGGUAUG CUGAUGAGGNNNNNNNNCCGAA AGAACCCC | 7621 |
| 3325 | UUCUCCAUA CCCAGGAG | 3478 | CUCCUGGG CUGAUGAGGNNNNNNNNCCGAA AUGGAGAA | 7622 |
| 3352 | UGAAGACUU CUGUAGCC | 3479 | GGCUGCAG CUGAUGAGGNNNNNNNNCCGAA AGUCUUCA | 7623 |
| 3353 | GAAGACUUC UGCAGCCG | 3480 | CGGCUGCA CUGAUGAGGNNNNNNNNCCGAA AAGUCUUC | 7624 |
| 3397 | CCCGGAGUA UGCCACAC | 3481 | GUGUGGCA CUGAUGAGGNNNNNNNNCCGAA AGUCCGGG | 7625 |
| 3413 | CCUGAAAUC UACCAAAU | 3482 | AUUUGGUA CUGAUGAGGNNNNNNNNCCGAA AUUUCAGG | 7626 |
| 3415 | UGAAAUCUA CCAAAUCA | 3483 | UGAUUUGG CUGAUGAGGNNNNNNNNCCGAA AGAUUUCA | 7627 |
| 3422 | UACCAAAUC AUGUUGGA | 3484 | UCCAACAU CUGAUGAGGNNNNNNNNCCGAA AUUUGGUA | 7628 |
| 3427 | AAUCAUGUU GGAUUGCU | 3485 | AGCAAUCC CUGAUGAGGNNNNNNNNCCGAA AGAUGAUU | 7629 |
| 3432 | UGUUGGAUU GCUGGCAC | 3486 | GUGCCAGC CUGAUGAGGNNNNNNNNCCGAA AUCCAACA | 7630 |
| 3466 | GCCCCGGUU UGCUGAAC | 3487 | GUUCAGCA CUGAUGAGGNNNNNNNNCCGAA ACCGGGGC | 7631 |
| 3467 | CCCCGGUUU GCUGAACU | 3488 | AGUUCAGC CUGAUGAGGNNNNNNNNCCGAA AACCGGGG | 7632 |
| 3476 | GCUGAACUU GUGGAGAA | 3489 | UUCUCCAC CUGAUGAGGNNNNNNNNCCGAA ACUUCAGC | 7633 |
| 3488 | GAGAAACUU GGUGACCU | 3490 | AGGUCACC CUGAUGAGGNNNNNNNNCCGAA AGUUUCUC | 7634 |
| 3500 | GACCUGCUU CAAGCCAA | 3491 | UUGGCUUG CUGAUGAGGNNNNNNNNCCGAA AGCAGGUC | 7635 |
| 3501 | ACCUGCUUC AAGCCAAC | 3492 | GUUGGCUU CUGAUGAGGNNNNNNNNCCGAA AAGCAGGU | 7636 |
| 3512 | GCCAACGUC CAACAGGA | 3493 | UCCUGUUG CUGAUGAGGNNNNNNNNCCGAA ACGUUGGC | 7637 |
| 3531 | GGAAAGAUU ACAUCCCC | 3494 | GGGGAUGU CUGAUGAGGNNNNNNNNCCGAA AUCUUUCC | 7638 |
| 3532 | GAAAGAUUA CAUCCCCC | 3495 | GGGGGAUG CUGAUGAGGNNNNNNNNCCGAA AAUCUUUC | 7639 |
| 3536 | GAUUACAUC CCCCUCAA | 3496 | UUGAGGGG CUGAUGAGGNNNNNNNNCCGAA AUGUAAUC | 7640 |
| 3542 | AUCCCCCUC AAUGCCAU | 3497 | AUGGCAUU CUGAUGAGGNNNNNNNNCCGAA AGGGGGAU | 7641 |
| 3551 | AAUGCCAUA CUGACUAG | 3498 | CUAGUCAG CUGAUGAGGNNNNNNNNCCGAA AUGGCAUU | 7642 |
| 3558 | UACAGACUA GAAACAGU | 3499 | ACUGUUUC CUGAUGAGGNNNNNNNNCCGAA AGUCAGUA | 7643 |
| 3567 | GAAACAGUA GCUUCACA | 3500 | UGUGAAGC CUGAUGAGGNNNNNNNNCCGAA ACUGUUUC | 7644 |
| 3571 | CAGUAGCUU CACAUACU | 3501 | AGUAUGUG CUGAUGAGGNNNNNNNNCCGAA AGCUACUG | 7645 |
| 3572 | AGUAGCUUC ACAUACUC | 3502 | GAGUAUGU CUGAUGAGGNNNNNNNNCCGAA AAGCUACU | 7646 |
| 3577 | CUUCACAUA CUCGACCC | 3503 | GGGUCGAG CUGAUGAGGNNNNNNNNCCGAA AUGUGAAG | 7647 |
| 3580 | CACAUACUC GACCCCA | 3504 | UGGGGGUC CUGAUGAGGNNNNNNNNCCGAA AGUCUGUG | 7648 |
| 3592 | CCCCACCUU CUCUGAGG | 3505 | CCUCAGAG CUGAUGAGGNNNNNNNNCCGAA AGGUGGGG | 7649 |
| 3593 | CCCACCUUC UCUGAGGA | 3506 | UCCUCAGA CUGAUGAGGNNNNNNNNCCGAA AAGGUGGG | 7650 |
| 3595 | CACCUUCUC UGAGGACC | 3507 | GGUCCUCA CUGAUGAGGNNNNNNNNCCGAA AGAAGGUG | 7651 |
| 3605 | GAGGACCUU UUCAAGGA | 3508 | UCCUUGAA CUGAUGAGGNNNNNNNNCCGAA AGGUCCUC | 7652 |
| 3606 | AGGACCUUU UCAAGGAC | 3509 | GUCCUUGA CUGAUGAGGNNNNNNNNCCGAA AAGGUCCU | 7653 |
| 3607 | GGACCUUUU CAAGGACG | 3510 | CGUCCUUG CUGAUGAGGNNNNNNNNCCGAA AAAGGUCC | 7654 |
| 3608 | GACCUUUUC AAGGACGG | 3511 | CCGUCCUU CUGAUGAGGNNNNNNNNCCGAA AAAAGGUC | 7655 |
| 3619 | GGACGGCUU UGCAGAUC | 3512 | GAUCUGCA CUGAUGAGGNNNNNNNNCCGAA AGCCGUCC | 7656 |
| 3620 | GACGGCUUU GCAGAUCC | 3513 | GGAUCUGC CUGAUGAGGNNNNNNNNCCGAA AAGCCGUC | 7657 |
| 3627 | UUGCAGAUC CACAUUUU | 3514 | AAAAUGUG CUGAUGAGGNNNNNNNNCCGAA AUCUGCAA | 7658 |
| 3633 | AUCCACAUU UUCAUUCC | 3515 | GGAAUGAA CUGAUGAGGNNNNNNNNCCGAA AUGUGGAU | 7659 |
| 3634 | UCCACAUUU UCAUUCCG | 3516 | CGGAAUGA CUGAUGAGGNNNNNNNNCCGAA AAUGUGGA | 7660 |
| 3635 | CCACAUUUU CAUUCCGG | 3517 | CCGGAAUG CUGAUGAGGNNNNNNNNCCGAA AAAUGUGG | 7661 |
| 3636 | CACAUUUUC AUUCCGGA | 3518 | UCCGGAAU CUGAUGAGGNNNNNNNNCCGAA AAAAUGUG | 7662 |
| 3639 | AUUUUCAUU CCGGAAGC | 3519 | GCUUCCGG CUGAUGAGGNNNNNNNNCCGAA AUGAAAAU | 7663 |
| 3640 | UUUUCAUUC CGGAAGCU | 3520 | AGCUUCCG CUGAUGAGGNNNNNNNNCCGAA AAUGAAAA | 7664 |
| 3649 | CGGAAGCUC UGAUGAUG | 3521 | CAUCAUCA CUGAUGAGGNNNNNNNNCCGAA AGCUUCCG | 7665 |
| 3664 | UGUGAGAUA UGUAAACG | 3522 | CGUUUACA CUGAUGAGGNNNNNNNNCCGAA AUCUCACA | 7666 |
| 3668 | AGAUAUGUA AACGCUUU | 3523 | AAAGCGUU CUGAUGAGGNNNNNNNNCCGAA ACAUAUCU | 7667 |
| 3675 | UAAACGCUU UCAAAUUC | 3524 | GAAUUUGA CUGAUGAGGNNNNNNNNCCGAA AGCGUUUA | 7668 |
| 3676 | AAACGCUUU CAAAUUCA | 3525 | UGAAUUUG CUGAUGAGGNNNNNNNNCCGAA AAGCGUUU | 7669 |

TABLE VIII-continued

Mouse *flt*-1 VEGF Receptor-Hammerhead Ribozyme and Substrate Sequence

| Pos | Substrate | Seq ID No | HH Ribozyme Sequence | Seq ID No |
|---|---|---|---|---|
| 3677 | AACGCUUUC AAAUUCAU | 3526 | AUGAAUUU CUGAUGAGGNNNNNNNNCCGAA AAAGCGUU | 7670 |
| 3682 | UUUCAAAUU CAUGAGCC | 3527 | GGCUCAUG CUGAUGAGGNNNNNNNNCCGAA AUUUGAAA | 7671 |
| 3683 | UUCAAAUUC AUGAGCCU | 3528 | AGGCUCAU CUGAUGAGGNNNNNNNNCCGAA AAUUUGAA | 7672 |
| 3701 | GAAAGAAUC AAAACCUU | 637 | AAGGUUUU CUGAUGAGGNNNNNNNNCCGAA AUUCUUUC | 4793 |
| 3709 | CAAAACCUU UGAGGAGC | 3529 | GCUCCUCA CUGAUGAGGNNNNNNNNCCGAA AGGUUUUG | 7673 |
| 3710 | AAAACCUUU GAGGAGCU | 3530 | AGCUCCUC CUGAUGAGGNNNNNNNNCCGAA AAGGUUUU | 7674 |
| 3719 | GAGGAGCUU UCACCGAA | 3531 | UUCGGUGA CUGAUGAGGNNNNNNNNCCGAA AGCUCCUC | 7675 |
| 3720 | AGGAGCUUU CACCGAAC | 3532 | GUUCGGUG CUGAUGAGGNNNNNNNNCCGAA AAGCUCCU | 7676 |
| 3721 | GGAGCUUUC ACCGAACU | 3533 | AGUUCGGU CUGAUGAGGNNNNNNNNCCGAA AAAGCUCC | 7677 |
| 3730 | ACCGAACUC CACCUCCA | 3534 | UGGAGGUG CUGAUGAGGNNNNNNNNCCGAA AGUUCGGU | 7678 |
| 3736 | CUCCACCUC CAUGUUUG | 3535 | CAAACAUG CUGAUGAGGNNNNNNNNCCGAA AGGUGGAG | 7679 |
| 3742 | CUCCAUGUU UGAGGACU | 3536 | AGUCCUCA CUGAUGAGGNNNNNNNNCCGAA ACAUGGAG | 7680 |
| 3743 | UCCAUGUUU GAGGACUA | 3537 | UAGUCCUC CUGAUGAGGNNNNNNNNCCGAA AACAUGGA | 7681 |
| 3751 | UGAGGACUA UCAGCUGG | 3538 | CCAGCUGA CUGAUGAGGNNNNNNNNCCGAA AGUCCUCA | 7682 |
| 3753 | AGGACUAUC AGCUGGAC | 3539 | GUCCAGCU CUGAUGAGGNNNNNNNNCCGAA AUAGUCCU | 7683 |
| 3765 | UGGACACUA GCACUCUG | 3540 | CAGAGUGC CUGAUGAGGNNNNNNNNCCGAA AGUGUCCA | 7684 |
| 3771 | CUAGCACUC UGCUGGGC | 3541 | GCCCAGCA CUGAUGAGGNNNNNNNNCCGAA AGUGCUAG | 7685 |
| 3781 | GCUGGGCUC CCCCUUGC | 3542 | GCAAGGGG CUGAUGAGGNNNNNNNNCCGAA AGCCCAGC | 7686 |
| 3787 | CUCCCCCUU GCUGAAGC | 3543 | GCUUCAGC CUGAUGAGGNNNNNNNNCCGAA AGGGGGAG | 7687 |
| 3799 | GAAGCGGUU CACCUGGA | 3544 | UCCAGGUG CUGAUGAGGNNNNNNNNCCGAA ACCGCUUC | 7688 |
| 3800 | AAGCGGUUC ACCUGGAC | 3545 | GUCCAGGU CUGAUGAGGNNNNNNNNCCGAA AACCGCUU | 7689 |
| 3829 | CAAGGCCUC CAUGAAGA | 3546 | UCUUCAUG CUGAUGAGGNNNNNNNNCCGAA AGGCCUUG | 7690 |
| 3839 | AUGAAGAUA GACUUGAG | 3547 | CUCAAGUC CUGAUGAGGNNNNNNNNCCGAA AUCUUCAU | 7691 |
| 3844 | GAUAGACUU GAGAAUAG | 3548 | CUAUUCUC CUGAUGAGGNNNNNNNNCCGAA AGUCUAUC | 7692 |
| 3851 | UUGAGAAUA GCGAGUAA | 3549 | UUACUCGC CUGAUGAGGNNNNNNNNCCGAA AUUCUCAA | 7693 |
| 3858 | UAGCGAGUA AAAGCAAG | 3550 | CUUGCUUU CUGAUGAGGNNNNNNNNCCGAA ACUCGCUA | 7694 |
| 3878 | GCGGGACUU UCCGAUCU | 3551 | AGAUCGGA CUGAUGAGGNNNNNNNNCCGAA AGUCCCGC | 7695 |
| 3879 | CGGGACUUU CCGAUCUG | 3552 | CAGAUCGG CUGAUGAGGNNNNNNNNCCGAA AAGUCCCG | 7696 |
| 3880 | GGGACUUUC CGAUCUGC | 3553 | GCAGAUCG CUGAUGAGGNNNNNNNNCCGAA AAAGUCCC | 7697 |
| 3885 | UUUCCGAUC UGCCGAGG | 3554 | CCUCGGCA CUGAUGAGGNNNNNNNNCCGAA AUCGGAAA | 7698 |
| 3901 | GCCCAGCUU CUGCUUCU | 3555 | AGAAGCAG CUGAUGAGGNNNNNNNNCCGAA AGCUGGGC | 7699 |
| 3902 | CCCAGCUUC UGCUUCUC | 3556 | GAGAAGCA CUGAUGAGGNNNNNNNNCCGAA AAGCUGGG | 7700 |
| 3907 | CUUCUGCUU CUCCAGCU | 3557 | AGCUGGAG CUGAUGAGGNNNNNNNNCCGAA AGCAGAAG | 7701 |
| 3908 | UUCUGCUUC UCCAGCUG | 3558 | CAGCUGGA CUGAUGAGGNNNNNNNNCCGAA AAGCAGAA | 7702 |
| 3910 | CUGCUUCUC CAGCUGUG | 3559 | CACAGCUG CUGAUGAGGNNNNNNNNCCGAA AGAAGCAG | 7703 |
| 3926 | GGCCACAUC AGGCCCGU | 3560 | ACGGGCCU CUGAUGAGGNNNNNNNNCCGAA AUGUGGCC | 7704 |
| 3949 | CGAUGAAUC UGAGCUGG | 3561 | CCAGCUCA CUGAUGAGGNNNNNNNNCCGAA AUUCAUCG | 7705 |
| 3967 | AAAGGAGUC CUGCUGUU | 3562 | AACAGCAG CUGAUGAGGNNNNNNNNCCGAA ACUCCUUU | 7706 |
| 3975 | CCUGCUGUU CUCCACCC | 3563 | GGGUGGAG CUGAUGAGGNNNNNNNNCCGAA ACAGCAGG | 7707 |
| 3976 | CUGCUGUUC UCCACCCC | 3564 | GGGGUGGA CUGAUGAGGNNNNNNNNCCGAA AACAGCAG | 7708 |
| 3978 | GCUGUUCUC CACCCCCA | 3565 | UGGGGGUG CUGAUGAGGNNNNNNNNCCGAA AGAACAGC | 7709 |
| 3991 | CCCAGACUA CAACUCCG | 3566 | CGGAGUUG CUGAUGAGGNNNNNNNNCCGAA AGUCUGGG | 7710 |
| 3997 | CUACAACUC CGUGGUGU | 3567 | ACACCACG CUGAUGAGGNNNNNNNNCCGAA AGUUGUAG | 7711 |
| 4006 | CGUGGUGUU GUACUCCU | 3568 | AGGAGUAC CUGAUGAGGNNNNNNNNCCGAA ACACCACG | 7712 |
| 4009 | GGUGUUGUA CUCCUCCC | 3569 | GGGAGGAG CUGAUGAGGNNNNNNNNCCGAA ACAACACC | 7713 |
| 4012 | GUUGUACUC CUCCCCGC | 3570 | GCGGGGAG CUGAUGAGGNNNNNNNNCCGAA AGUACAAC | 7714 |
| 4015 | GUACUCCUC CCCGCCCG | 3571 | CGGGCGGG CUGAUGAGGNNNNNNNNCCGAA AGGAGUAC | 7715 |
| 4027 | GCCCGCCUA AAGCUUCU | 3572 | AGAAGCUU CUGAUGAGGNNNNNNNNCCGAA AGGCGGGC | 7716 |
| 4033 | CUAAAGCUU CUCACCAG | 3573 | CUGGUGAG CUGAUGAGGNNNNNNNNCCGAA AGCUUUAG | 7717 |
| 4034 | UAAAGCUUC UCACCAGC | 3574 | GCUGGUGA CUGAUGAGGNNNNNNNNCCGAA AAGCUUUA | 7718 |
| 4036 | AAGCUUCUC ACCAGCCC | 3575 | GGGCUGGU CUGAUGAGGNNNNNNNNCCGAA AGAAGCUU | 7719 |
| 4066 | CUGACAGUA UUAUACAU | 3576 | AUGUAUAA CUGAUGAGGNNNNNNNNCCGAA ACUGUCAG | 7720 |
| 4068 | GACAGUAUU AUACAUCU | 3577 | AGAUGUAU CUGAUGAGGNNNNNNNNCCGAA AUACUGUC | 7721 |
| 4069 | ACAGUAUUA UACAUCUA | 3578 | UAGAUGUA CUGAUGAGGNNNNNNNNCCGAA AAUACUGU | 7722 |
| 4071 | AGUAUUAUA CAUCUAUG | 3579 | CAUAGAUG CUGAUGAGGNNNNNNNNCCGAA AUAAUACU | 7723 |
| 4075 | UUAUACAUC UAUGAGUU | 3580 | AACUCAUA CUGAUGAGGNNNNNNNNCCGAA AUGUAUAA | 7724 |
| 4077 | AUACAUCUA UGAGUUUA | 3581 | UAAACUCA CUGAUGAGGNNNNNNNNCCGAA AGAUGUAU | 7725 |
| 4083 | CUAUGAGUU UACACCUA | 3582 | UAGGUGUA CUGAUGAGGNNNNNNNNCCGAA ACUCAUAG | 7726 |
| 4084 | UAUGAGUUU ACACCUAU | 3583 | AUAGGUGU CUGAUGAGGNNNNNNNNCCGAA AACUCAUA | 7727 |
| 4085 | AUGAGUUUA CACCUAUU | 3584 | AAUAGGUG CUGAUGAGGNNNNNNNNCCGAA AAACUCAU | 7728 |
| 4091 | UUACACCUA UUCCGCUC | 3585 | GAGCGGAA CUGAUGAGGNNNNNNNNCCGAA AGGUGUAA | 7729 |
| 4093 | ACACCUAUU CCGCUCCA | 3586 | UGGAGCGG CUGAUGAGGNNNNNNNNCCGAA AUAGGUGU | 7730 |
| 4094 | CACCUAUUC CGCUCCAC | 3587 | GUGGAGCG CUGAUGAGGNNNNNNNNCCGAA AAUAGGUG | 7731 |
| 4099 | AUUCCGCUC CACAGGAG | 3588 | CUCCUGUG CUGAUGAGGNNNNNNNNCCGAA AGCGGAAU | 7732 |
| 4117 | CAGCUGCUU UUCGUGAC | 3589 | GUCACGAA CUGAUGAGGNNNNNNNNCCGAA AGCAGCUG | 7733 |
| 4118 | AGCUGCUUU UCGUGACC | 3590 | GGUCACGA CUGAUGAGGNNNNNNNNCCGAA AAGCAGCU | 7734 |
| 4119 | GCUGCUUUU CGUGACCU | 3591 | AGGUCACG CUGAUGAGGNNNNNNNNCCGAA AAAGCAGC | 7735 |
| 4120 | CUGCUUUUC GUGACCUU | 3592 | AAGGUCAC CUGAUGAGGNNNNNNNNCCGAA AAAAGCAG | 7736 |
| 4128 | CGUGACCUU UAAUCGUG | 3593 | CACGAUUA CUGAUGAGGNNNNNNNNCCGAA AGGUCACG | 7737 |
| 4129 | GUGACCUUU AAUCGUGC | 3594 | GCACGAUU CUGAUGAGGNNNNNNNNCCGAA AAGGUCAC | 7738 |
| 4130 | UGACCUUUA AUCGUGCU | 3595 | AGCACGAU CUGAUGAGGNNNNNNNNCCGAA AAAGGUCA | 7739 |
| 4133 | CCUUUAAUC GUGCUUUU | 3596 | AAAAGCAC CUGAUGAGGNNNNNNNNCCGAA AUUAAAGG | 7740 |
| 4139 | AUCGUGCUU UUUGUUU | 3597 | AAACAAAA CUGAUGAGGNNNNNNNNCCGAA AGCACGAU | 7741 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4140 | UCGUGCUUU UUUGUUUU | 3598 | AAAACAAA CUGAUGAGGNNNNNNNNCCGAA AAGCACGA | 7742 |
| 4141 | CGUGCUUUU UUGUUUUU | 3599 | AAAAACAA CUGAUGAGGNNNNNNNNCCGAA AAGCACG | 7743 |
| 4142 | GUGCUUUUU UGUUUUUU | 3600 | AAAAAACA CUGAUGAGGNNNNNNNNCCGAA AAAAGCAC | 7744 |
| 4143 | UGCUUUUUU GUUUUUUG | 3601 | CAAAAAAC CUGAUGAGGNNNNNNNNCCGAA AAAAAGCA | 7745 |
| 4146 | UUUUUUGUU UUUUGUUU | 3602 | AAACAAAA CUGAUGAGGNNNNNNNNCCGAA ACAAAAAA | 7746 |
| 4147 | UUUUUGUUU UUUGUUUU | 3603 | AAAACAAA CUGAUGAGGNNNNNNNNCCGAA AACAAAAA | 7747 |
| 4148 | UUUUGUUUU UUGUUUUG | 3604 | CAAAACAA CUGAUGAGGNNNNNNNNCCGAA AAACAAAA | 7748 |
| 4149 | UUUGUUUUU UGUUUUGU | 3605 | ACAAAACA CUGAUGAGGNNNNNNNNCCGAA AAACAAA | 7749 |
| 4150 | UUGUUUUUU GUUUUGUU | 3606 | AACAAAAC CUGAUGAGGNNNNNNNNCCGAA AAAAACAA | 7750 |
| 4153 | UUUUUUGUU UUUGUUUGU | 3607 | ACAAACAA CUGAUGAGGNNNNNNNNCCGAA ACAAAAAA | 7751 |
| 4154 | UUUUUGUUU UGUUUGUU | 3608 | AACAAACA CUGAUGAGGNNNNNNNNCCGAA AACAAAAA | 7752 |
| 4155 | UUUUGUUUU GUUUGUUG | 3609 | CAACAAAC CUGAUGAGGNNNNNNNNCCGAA AAACAAAA | 7753 |
| 4158 | UGUUUGUU UGUUGUUG | 3610 | CAACAACA CUGAUGAGGNNNNNNNNCCGAA ACAAACA | 7754 |
| 4159 | GUUUUGUU GUUGUUGC | 3611 | GCAACAAC CUGAUGAGGNNNNNNNNCCGAA AACAAAAC | 7755 |
| 4162 | UUGCUUGUU GUUGCUGU | 3612 | ACAGCAAC CUGAUGAGGNNNNNNNNCCGAA ACAAACAA | 7756 |
| 4165 | UUUGUUGUU GCUGUUUU | 3613 | AAAACAGC CUGAUGAGGNNNNNNNNCCGAA ACAACAAA | 7757 |
| 4171 | GUUGCUGUU UUGACUAA | 3614 | UUAGUCAA CUGAUGAGGNNNNNNNNCCGAA ACAGCAAC | 7758 |
| 4172 | UUGCUGUUU UGACUAAC | 3615 | GUUAGUCA CUGAUGAGGNNNNNNNNCCGAA AACAGCAA | 7759 |
| 4173 | UGCUGUUUU GACUAACA | 3616 | UGUUAGUC CUGAUGAGGNNNNNNNNCCGAA AAACAGCA | 7760 |
| 4178 | UUUUGACUA ACAAGAAU | 737 | AUUCUUGU CUGAUGAGGNNNNNNNNCCGAA AGUCAAAA | 4893 |
| 4189 | AAGAAUGUA ACCCCAGU | 3617 | ACUGGGGU CUGAUGAGGNNNNNNNNCCGAA ACAUUCUU | 7761 |
| 4198 | ACCCCAGUU AGUGACGU | 3618 | ACGUCACU CUGAUGAGGNNNNNNNNCCGAA ACUGGGGU | 7762 |
| 4199 | CCCCAGUUA GUGACGUG | 3619 | CACGUCAC CUGAUGAGGNNNNNNNNCCGAA AACUGGGG | 7763 |
| 4216 | UGAAGAAUA CUAUUGUU | 3620 | AACAAUAG CUGAUGAGGNNNNNNNNCCGAA AUUCUUCA | 7764 |
| 4219 | AGAAUACUA UUGUUAGA | 3621 | UCUAACAA CUGAUGAGGNNNNNNNNCCGAA AGUAUUCU | 7765 |
| 4221 | AAUACUAUU GUUAGAGA | 3622 | UCUCUAAC CUGAUGAGGNNNNNNNNCCGAA AUAGUAUU | 7766 |
| 4224 | ACUAUUGUU AGAGAAAU | 3623 | AUUUCUCU CUGAUGAGGNNNNNNNNCCGAA ACAAUAGU | 7767 |
| 4225 | CUAUUGUUA GAGAAAUC | 3624 | GAUUUCUC CUGAUGAGGNNNNNNNNCCGAA AACAAUAG | 7768 |
| 4233 | AGAGAAAUC CCCCCGC | 3625 | GCGGGGGG CUGAUGAGGNNNNNNNNCCGAA AUUUCUCU | 7769 |
| 4249 | CAAAGCCUC AGGGUAAC | 3626 | GUUACCCU CUGAUGAGGNNNNNNNNCCGAA AGGCUUUG | 7770 |
| 4255 | CUCAGGGUA ACCUGGAC | 3627 | GUCCAGGU CUGAUGAGGNNNNNNNNCCGAA ACCCUGAG | 7771 |
| 4282 | AGGUGCCUC UGGCGACC | 3628 | GGUCGCCA CUGAUGAGGNNNNNNNNCCGAA AGGCACCU | 7772 |
| 4323 | CCCACCCUC CCUGCAGC | 3629 | GCUGCAGG CUGAUGAGGNNNNNNNNCCGAA AGGGUGGG | 7773 |
| 4341 | GUGGGACUA GAGGCAGU | 3630 | ACUGCCUC CUGAUGAGGNNNNNNNNCCGAA AGUCCCAC | 7774 |
| 4350 | GAGGCAGUA AGCCCAUU | 3631 | AAUGGGCU CUGAUGAGGNNNNNNNNCCGAA ACUGCCUC | 7775 |
| 4358 | AAGCCCAUU AGCUCAUG | 3632 | CAUGAGCU CUGAUGAGGNNNNNNNNCCGAA AUGGGCUU | 7776 |
| 4359 | AGCCCAUUA GCUCAUGG | 3633 | CCAUGAGC CUGAUGAGGNNNNNNNNCCGAA AAUGGGCU | 7777 |
| 4363 | CAUUAGCUC AUGGCUGC | 3634 | GCAGCCAU CUGAUGAGGNNNNNNNNCCGAA AGCUAAUG | 7778 |
| 4387 | GACCUGCUC UGUCUCUC | 3635 | GAGAGACA CUGAUGAGGNNNNNNNNCCGAA AGCAGGUC | 7779 |
| 4391 | UGCUCUGUC UCUCUUAU | 3636 | AUAAGAGA CUGAUGAGGNNNNNNNNCCGAA ACAGAGCA | 7780 |
| 4393 | CUCUGUCUC UCUUAUGG | 3637 | CCAUAAGA CUGAUGAGGNNNNNNNNCCGAA AGACAGAG | 7781 |
| 4395 | CUGUCUCUC UUAUGGAG | 3638 | CUCCAUAA CUGAUGAGGNNNNNNNNCCGAA AGAGACAG | 7782 |
| 4397 | GUCUCUCUU AUGGAGGA | 3639 | UCCUCCAU CUGAUGAGGNNNNNNNNCCGAA AGAGAGAC | 7783 |
| 4398 | UCUCUCUUA UGGAGGAA | 3640 | UUCCUCCA CUGAUGAGGNNNNNNNNCCGAA AAGAGAGA | 7784 |
| 4445 | AAAAGGCUU UGGGAUGC | 3641 | GCAUCCCA CUGAUGAGGNNNNNNNNCCGAA AGCCUUUU | 7785 |
| 4446 | AAAGGCUUU GGGAUGCG | 3642 | CGCAUCCC CUGAUGAGGNNNNNNNNCCGAA AAGCCUUU | 7786 |
| 4456 | GGAUGCGUC CGUCCUGU | 3643 | ACAGGACG CUGAUGAGGNNNNNNNNCCGAA ACGCAUCC | 7787 |
| 4460 | GCGUCCGUC CUGUGGAG | 3644 | CUCCACAG CUGAUGAGGNNNNNNNNCCGAA ACGGACGC | 7788 |
| 4487 | AGGGGGCUC CGCUAUGC | 3645 | GCAUAGCG CUGAUGAGGNNNNNNNNCCGAA AGCCCCCU | 7789 |
| 4492 | GCUCCGCUA UGCCACUU | 3646 | AAGUGGCA CUGAUGAGGNNNNNNNNCCGAA AGCGGAGC | 7790 |
| 4500 | AUGCCACUU CAGUGACU | 3647 | AGUCACUG CUGAUGAGGNNNNNNNNCCGAA AGUGGCAU | 7791 |
| 4501 | UGCCACUUC AGUGACUU | 3648 | AAGUCACU CUGAUGAGGNNNNNNNNCCGAA AAGUGGCA | 7792 |
| 4509 | CAGUGACUU CUCACUCC | 3649 | GGAGUGAG CUGAUGAGGNNNNNNNNCCGAA AGUCACUG | 7793 |
| 4510 | AGUGACUUC UCACUCCU | 3650 | AGGAGUGA CUGAUGAGGNNNNNNNNCCGAA AAGUCACU | 7794 |
| 4512 | UGACUUCUC ACUCCUGG | 3651 | CCAGGAGU CUGAUGAGGNNNNNNNNCCGAA AGAAGUCA | 7795 |
| 4516 | UUCUCACUC CUGGCCUC | 3652 | GAGGCCAG CUGAUGAGGNNNNNNNNCCGAA AGUGAGAA | 7796 |
| 4524 | CCUGGCCUC CGCUGUUU | 3653 | AAACAGCG CUGAUGAGGNNNNNNNNCCGAA AGGCCAGG | 7797 |
| 4531 | UCCGCUGUU UCGGGCCC | 3654 | GGGCCCGA CUGAUGAGGNNNNNNNNCCGAA ACAGCGGA | 7798 |
| 4532 | CCGCUGUUU CGGGCCCC | 3655 | GGGGCCCG CUGAUGAGGNNNNNNNNCCGAA AACAGCGG | 7799 |
| 4533 | CGCUGUUUC GGGCCCCG | 3656 | GGGGGCCC CUGAUGAGGNNNNNNNNCCGAA AAACAGCG | 7800 |
| 4543 | GGCCCCCUU CCAAGAGG | 3657 | CCUCUUGG CUGAUGAGGNNNNNNNNCCGAA AGGGGGCC | 7801 |
| 4544 | GCCCCCUUC CAAGAGGU | 3658 | ACCUCUUG CUGAUGAGGNNNNNNNNCCGAA AAGGGGGC | 7802 |
| 4553 | CAAGAGGUA UCAGAGCA | 3659 | UGCUCUGA CUGAUGAGGNNNNNNNNCCGAA ACCUCUUG | 7803 |
| 4555 | AGAGGUAUC AGAGCAGA | 3660 | UCUGCUCU CUGAUGAGGNNNNNNNNCCGAA AUACCUCU | 7804 |
| 4577 | AGGGACGUU UCCUAGAC | 3661 | GUCUAGGA CUGAUGAGGNNNNNNNNCCGAA ACGUCCCU | 7805 |
| 4578 | GGGACGUUU CCUAGACC | 3662 | GGUCUAGG CUGAUGAGGNNNNNNNNCCGAA AACGUCCC | 7806 |
| 4579 | GGACGUUUC CUAGACCA | 3663 | UGGUCUAG CUGAUGAGGNNNNNNNNCCGAA AAACGUCC | 7807 |
| 4582 | CGUUUCCUA GACCAGGG | 3664 | CCCUGGUC CUGAUGAGGNNNNNNNNCCGAA AGGAAACG | 7808 |
| 4598 | GCACAUGUU CUCGGGAA | 3665 | UUCCCGAG CUGAUGAGGNNNNNNNNCCGAA ACAUGUGC | 7809 |
| 4599 | CACAUGUUC UCGGGAAC | 3666 | GUUCCCGA CUGAUGAGGNNNNNNNNCCGAA AACAUGUG | 7810 |
| 4601 | CAUGUUCUC GGGAACCA | 3667 | UGGUUCCC CUGAUGAGGNNNNNNNNCCGAA AGAACAUG | 7811 |
| 4614 | ACCACAGUU AAUCUUAA | 3668 | UUAAGAUU CUGAUGAGGNNNNNNNNCCGAA ACUGUGGU | 7812 |
| 4615 | CCACAGUUA AUCUUAAA | 3669 | UUUAAGAU CUGAUGAGGNNNNNNNNCCGAA AACUGUGG | 7813 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4618 | CAGUUAAUC UUAAAUCU | 3670 | AGAUUUAA CUGAUGAGGNNNNNNNNCCGAA AUUAACUG | 7814 |
| 4620 | GUUAAUCUU AAAUCUUU | 3671 | AAAGAUUU CUGAUGAGGNNNNNNNNCCGAA AGAUUAAC | 7815 |
| 4621 | UUAAUCUUA AAUCUUUU | 3672 | AAAAGAUU CUGAUGAGGNNNNNNNNCCGAA AAGAUUAA | 7816 |
| 4625 | UCUUAAAUC UUUUCCCG | 3673 | CGGGAAAA CUGAUGAGGNNNNNNNNCCGAA AUUUAAGA | 7817 |
| 4627 | UUAAAUCUU UUCCCGGG | 3674 | CCCGGGAA CUGAUGAGGNNNNNNNNCCGAA AGAUUUAA | 7818 |
| 4628 | UAAAUCUUU UCCCGGGA | 3675 | UCCCGGGA CUGAUGAGGNNNNNNNNCCGAA AAGAUUUA | 7819 |
| 4629 | AAAUCUUUU CCCGGGAG | 3676 | CUCCCGGG CUGAUGAGGNNNNNNNNCCGAA AAAGAUUU | 7820 |
| 4630 | AAUCUUUUC CCGGGAGU | 3677 | ACUCCCGG CUGAUGAGGNNNNNNNNCCGAA AAAAGAUU | 7821 |
| 4639 | CCGGGAGUC UUCUGUUG | 3678 | CAACAGAA CUGAUGAGGNNNNNNNNCCGAA ACUCCCGG | 7822 |
| 4641 | GGGAGUCUU CUGUUGUC | 3679 | GACAACAG CUGAUGAGGNNNNNNNNCCGAA AGACUCCC | 7823 |
| 4642 | GGAGUCUUC UGUUGUCU | 3680 | AGACAACA CUGAUGAGGNNNNNNNNCCGAA AAGACUCC | 7824 |
| 4646 | UCUUCUGUU GUCUGUUU | 3681 | AAACAGAC CUGAUGAGGNNNNNNNNCCGAA ACAGAAGA | 7825 |
| 4649 | UCUGUUGUC UGUUUACC | 3682 | GGUAAACA CUGAUGAGGNNNNNNNNCCGAA ACAACAGA | 7826 |
| 4653 | UUGUCUGUU UACCAUCC | 3683 | GGAUGGUA CUGAUGAGGNNNNNNNNCCGAA ACAGACAA | 7827 |
| 4654 | UGUCUGUUU ACCAUCCA | 3684 | UGGAUGGU CUGAUGAGGNNNNNNNNCCGAA AACAGACA | 7828 |
| 4655 | GUCUGUUUA CCAUCCAA | 3685 | UUGGAUGG CUGAUGAGGNNNNNNNNCCGAA AAACAGAC | 7829 |
| 4660 | UUUACCAUC CAAAGCAU | 3686 | AUGCUUUG CUGAUGAGGNNNNNNNNCCGAA AUGGUAAA | 7830 |
| 4669 | CAAAGCAUA UUUAACAU | 3687 | AUGUUAAA CUGAUGAGGNNNNNNNNCCGAA AUGCUUUG | 7831 |
| 4671 | AAGCAUAUU UAACAUGU | 3688 | ACAUGUUA CUGAUGAGGNNNNNNNNCCGAA AUAUGCUU | 7832 |
| 4672 | AGCAUAUUU AACAUGUG | 3689 | CACAUGUU CUGAUGAGGNNNNNNNNCCGAA AAUAUGCU | 7833 |
| 4673 | GCAUAUUUA ACAUGUGU | 3690 | ACACAUGU CUGAUGAGGNNNNNNNNCCGAA AAAUAUGC | 7834 |
| 4682 | ACAUGUGUC AGUGGGGG | 3691 | CCCCCACU CUGAUGAGGNNNNNNNNCCGAA ACACAUGU | 7835 |
| 4698 | GUGGCGCUU GGCUUCUG | 3692 | CAGAAGCC CUGAUGAGGNNNNNNNNCCGAA AGCGCCAC | 7836 |
| 4703 | GCUUGGCUU CUGAGGCC | 3693 | GGCCUCAG CUGAUGAGGNNNNNNNNCCGAA AGCCAAGC | 7837 |
| 4704 | CUUGGCUUC UGAGGCCA | 3694 | UGGCCUCA CUGAUGAGGNNNNNNNNCCGAA AAGCCAAG | 7838 |
| 4720 | AGAGCCAUC AUCAGUUC | 3695 | GAACUGAU CUGAUGAGGNNNNNNNNCCGAA AUGGCUCU | 7839 |
| 4723 | GCCAUCAUC AGUUCCUC | 3696 | GAGGAACU CUGAUGAGGNNNNNNNNCCGAA AUGAUGGC | 7840 |
| 4727 | UCAUCAGUU CCUCUAGU | 3697 | ACUAGAGG CUGAUGAGGNNNNNNNNCCGAA ACUGAUGA | 7841 |
| 4728 | CAUCAGUUC CUCUAGUG | 3698 | CACUAGAG CUGAUGAGGNNNNNNNNCCGAA AACUGAUG | 7842 |
| 4731 | CAGUUCCUC UAGUGAGA | 3699 | UCUCACUA CUGAUGAGGNNNNNNNNCCGAA AGGAACUG | 7843 |
| 4733 | GUUCCUCUA GUGAGAUG | 3700 | CAUCUCAC CUGAUGAGGNNNNNNNNCCGAA AGAGGAAC | 7844 |
| 4745 | AGAUGCAUU GAGGUCAU | 3701 | AUGACCUC CUGAUGAGGNNNNNNNNCCGAA AUGCAUCU | 7845 |
| 4751 | AUUGAGGUC AUACCCAA | 3702 | UUGGGUAU CUGAUGAGGNNNNNNNNCCGAA ACCUCAAU | 7846 |
| 4754 | GAGGUCAUA CCCAAGCU | 3703 | AGCUUGGG CUGAUGAGGNNNNNNNNCCGAA AUGACCUC | 7847 |
| 4763 | CCCAAGCUU GCAGGCCU | 3704 | AGGCCUGC CUGAUGAGGNNNNNNNNCCGAA AGCUUGGG | 7848 |
| 4777 | CCUGACCUU CGCAUACU | 3705 | AGUAUGCG CUGAUGAGGNNNNNNNNCCGAA AGGUCAGG | 7849 |
| 4778 | CUGACCUUC GCAUACUG | 3706 | CAGUAUGC CUGAUGAGGNNNNNNNNCCGAA AAGGUCAG | 7850 |
| 4783 | CUUCGCAUA CUGCUCAC | 3707 | GUGAGCAG CUGAUGAGGNNNNNNNNCCGAA AUGCGAAG | 7851 |
| 4789 | AUACUGCUC ACGGGGAG | 3708 | CUCCCCGU CUGAUGAGGNNNNNNNNCCGAA AGCAGUAU | 7852 |
| 4799 | CGGGGAGUU AAGUGGUC | 3709 | GACCACUU CUGAUGAGGNNNNNNNNCCGAA ACUCCCCG | 7853 |
| 4800 | GGGGAGUUA AGUGGUCC | 3710 | GGACCACU CUGAUGAGGNNNNNNNNCCGAA AACUCCCC | 7854 |
| 4807 | UAAGUGGUC CAGUUUGG | 3711 | CCAAACUG CUGAUGAGGNNNNNNNNCCGAA ACCACUUA | 7855 |
| 4812 | GGUCCAGUU UGGCCUAG | 3712 | CUAGGCCA CUGAUGAGGNNNNNNNNCCGAA ACUGGACC | 7856 |
| 4813 | GUCCAGUUU GGCCUAGU | 3713 | ACUAGGCC CUGAUGAGGNNNNNNNNCCGAA AACUGGAC | 7857 |
| 4819 | UUUGGCCUA GUAAGGUU | 3714 | AACCUUAC CUGAUGAGGNNNNNNNNCCGAA AGGCCAAA | 7858 |
| 4822 | GGCCUAGUA AGGUUGCC | 3715 | GGCAACCU CUGAUGAGGNNNNNNNNCCGAA ACUAGGCC | 7859 |
| 4827 | AGUAAGGUU GCCUACUG | 3716 | CAGUAGGC CUGAUGAGGNNNNNNNNCCGAA ACCUUACU | 7860 |
| 4832 | GGUUGCCUA CUGAUGGG | 3717 | CCCAUCAG CUGAUGAGGNNNNNNNNCCGAA AGGCAACC | 7861 |
| 4843 | GAUGGGCUC AAAAGCCA | 3718 | UGGCUUUU CUGAUGAGGNNNNNNNNCCGAA AGCCCAUC | 7862 |
| 4855 | AGCCACAUU UUAAACAG | 3719 | CUGUUUAA CUGAUGAGGNNNNNNNNCCGAA AUGUGGCU | 7863 |
| 4856 | GCCACAUUU UAAACAGG | 3720 | CCUGUUUA CUGAUGAGGNNNNNNNNCCGAA AAUGUGGC | 7864 |
| 4857 | CCACAUUUU AAACAGGU | 3721 | ACCUGUUU CUGAUGAGGNNNNNNNNCCGAA AAAUGUGG | 7865 |
| 4858 | CACAUUUUA AACAGGUU | 3722 | AACCUGUU CUGAUGAGGNNNNNNNNCCGAA AAAAUGUG | 7866 |
| 4866 | AAACAGGUU UAUCUCA | 3723 | UGAGAUAA CUGAUGAGGNNNNNNNNCCGAA ACCUGUUU | 7867 |
| 4867 | AACAGGUUU AUCUCAA | 3724 | UUGAGAUA CUGAUGAGGNNNNNNNNCCGAA AACCUGUU | 7868 |
| 4868 | ACAGGUUUA UCUCAAG | 3725 | CUUGAGAU CUGAUGAGGNNNNNNNNCCGAA AAACCUGU | 7869 |
| 4869 | CAGGUUUAU CUCAAGU | 3726 | ACUUGAGA CUGAUGAGGNNNNNNNNCCGAA AAAACCUG | 7870 |
| 4871 | GGUUUAUCU CAAGUAU | 3727 | AUACUUGA CUGAUGAGGNNNNNNNNCCGAA AUAAACC | 7871 |
| 4873 | UUUUAUCUC AAGUAUUA | 3728 | UAAUACUU CUGAUGAGGNNNNNNNNCCGAA AGAUAAAA | 7872 |
| 4878 | UCUCAAGUA UUAAUAUA | 3729 | UAUAUUAA CUGAUGAGGNNNNNNNNCCGAA ACUUGAGA | 7873 |
| 4880 | UCAAGUAUU AAUAUAUA | 3730 | UAUAUAUU CUGAUGAGGNNNNNNNNCCGAA AUACUUGA | 7874 |
| 4881 | CAAGUAUUA AUAUAUAG | 3731 | CUAUAUAU CUGAUGAGGNNNNNNNNCCGAA AAUACUUG | 7875 |
| 4884 | GUAUUAAUA UAUAGACA | 3732 | UGUCUAUA CUGAUGAGGNNNNNNNNCCGAA AUUAAUAC | 7876 |
| 4886 | AUUAAUAUA UAGACAAG | 3733 | CUUGUCUA CUGAUGAGGNNNNNNNNCCGAA AUAUUAAU | 7877 |
| 4888 | UAAAUAUAUA GACAAGAC | 3734 | GUCUUGUC CUGAUGAGGNNNNNNNNCCGAA AUAUAUUA | 7878 |
| 4900 | AAGCACUU AUGCAUUA | 3735 | UAAUGCAU CUGAUGAGGNNNNNNNNCCGAA AGUGCUU | 7879 |
| 4901 | AGACACUUA UGCAUUAU | 3736 | AUAAUGCA CUGAUGAGGNNNNNNNNCCGAA AAGUGUCU | 7880 |
| 4907 | UUAUGCAUU AUCCUGUU | 3737 | AACAGGAU CUGAUGAGGNNNNNNNNCCGAA AUGCAUAA | 7881 |
| 4908 | UAUGCAUUA UCCUGUUU | 3738 | AAACAGGA CUGAUGAGGNNNNNNNNCCGAA AAUGCAUA | 7882 |
| 4910 | UGCAUUAUC CUGUUUUA | 3739 | UAAAACAG CUGAUGAGGNNNNNNNNCCGAA AUAAUGCA | 7883 |
| 4915 | UAUCCUGUU UUAUAUAU | 3740 | AUAUAUAA CUGAUGAGGNNNNNNNNCCGAA ACAGGAUA | 7884 |
| 4916 | AUCCUGUUU UAUAUAUC | 3741 | GAUAUAUA CUGAUGAGGNNNNNNNNCCGAA AACAGGAU | 7885 |
| 4917 | UCCUGUUUU AUAUAUCC | 3742 | GGAUAUAU CUGAUGAGGNNNNNNNNCCGAA AAACAGGA | 7886 |

TABLE VIII-continued

Mouse *flt*-1 VEGF Receptor-Hammerhead Ribozyme and Substrate Sequence

| Pos | Substrate | Seq ID No | HH Ribozyme Sequence | Seq ID No |
|---|---|---|---|---|
| 4918 | CCUGUUUUA UAUAUCCA | 3743 | UGGAUAUA CUGAUGAGGNNNNNNNNCCGAA AAAACAGG | 7887 |
| 4920 | UGUUUUAUA UAUCCAAU | 3744 | AUUGGAUA CUGAUGAGGNNNNNNNNCCGAA AUAAAACA | 7888 |
| 4922 | UUUUAUAUA UCCAAUGA | 3745 | UCAUUGGA CUGAUGAGGNNNNNNNNCCGAA AUAUAAAA | 7889 |
| 4924 | UUAUAUAUC CAAUGAAU | 3746 | AUUCAUUG CUGAUGAGGNNNNNNNNCCGAA AUAUAUAA | 7890 |
| 4933 | CAAUGAAUA UAACUGGG | 3747 | CCCAGUUA CUGAUGAGGNNNNNNNNCCGAA AUUCAUUG | 7891 |
| 4935 | AUGAAUAUA ACUGGGGC | 3748 | GCCCCAGU CUGAUGAGGNNNNNNNNCCGAA AUAUUCAU | 7892 |
| 4948 | GGGCGAGUU AAGAGUCA | 3749 | UGACUCUU CUGAUGAGGNNNNNNNNCCGAA ACUCGCCC | 7893 |
| 4949 | GGCGAGUUA AGAGUCAU | 3750 | AUGACUCU CUGAUGAGGNNNNNNNNCCGAA AACUCGCC | 7894 |
| 4955 | UUAAGAGUC AUGGUCUA | 3751 | UAGACCAU CUGAUGAGGNNNNNNNNCCGAA ACUCUUAA | 7895 |
| 4961 | GUCAUGGUC UAGAAAAG | 3752 | CUUUUCUA CUGAUGAGGNNNNNNNNCCGAA ACCAUGAC | 7896 |
| 4963 | CAUGGUCUA GAAAAGGG | 3753 | CCCUUUUC CUGAUGAGGNNNNNNNNCCGAA AGACCAUG | 7897 |
| 4974 | AAAGGGGUU UCUCUGUA | 3754 | UACAGAGA CUGAUGAGGNNNNNNNNCCGAA ACCCCUUU | 7898 |
| 4975 | AAGGGGUUU CUCUGUAC | 3755 | GUACAGAG CUGAUGAGGNNNNNNNNCCGAA AACCCCUU | 7899 |
| 4976 | AGGGGUUUC UCUGUACC | 3756 | GGUACAGA CUGAUGAGGNNNNNNNNCCGAA AAACCCCU | 7900 |
| 4978 | GGGUUUCUC UGUACCCA | 3757 | UGGGUACA CUGAUGAGGNNNNNNNNCCGAA AGAAACCC | 7901 |
| 4982 | UUCUCUGUA CCCAAAUC | 3758 | GAUUUGGG CUGAUGAGGNNNNNNNNCCGAA ACAGAGAA | 7902 |
| 4990 | ACCCAAAUC GGGCUGGU | 3759 | ACCAGCCC CUGAUGAGGNNNNNNNNCCGAA AUUUGGGU | 7903 |
| 4999 | GGGCUGGUU GGACCAAG | 3760 | CUUGGUCC CUGAUGAGGNNNNNNNNCCGAA ACCAGCCC | 7904 |
| 5029 | AGAGUGGUU GUCCCAGC | 3761 | GCUGGGAC CUGAUGAGGNNNNNNNNCCGAA ACCACUCU | 7905 |
| 5032 | GUGGUUGUC CCAGCUAU | 3762 | AUAGCUGG CUGAUGAGGNNNNNNNNCCGAA ACAACCAC | 7906 |
| 5039 | UCCCAGCUA UAGUUACU | 3763 | AGUAACUA CUGAUGAGGNNNNNNNNCCGAA AGCUGGGA | 7907 |
| 5041 | CCAGCUAUA GUUACUAA | 3764 | UUAGUAAC CUGAUGAGGNNNNNNNNCCGAA AUAGCUGG | 7908 |
| 5044 | GCUAUAGUU ACUAAACU | 3765 | AGUUUAGU CUGAUGAGGNNNNNNNNCCGAA ACUAUAGC | 7909 |
| 5045 | CUAUAGUUA CUAAACUA | 3766 | UAGUUUAG CUGAUGAGGNNNNNNNNCCGAA AACUAUAG | 7910 |
| 5048 | UAGUUACUA AACUACUC | 3767 | GAGUAGUU CUGAUGAGGNNNNNNNNCCGAA AGUAACUA | 7911 |
| 5053 | ACUAAACUA CUCACCCA | 3768 | UGGGUGAG CUGAUGAGGNNNNNNNNCCGAA AGUUUAGU | 7912 |
| 5056 | AAACUACUC ACCCAAAG | 3769 | CUUUGGGU CUGAUGAGGNNNNNNNNCCGAA AGUAGUUU | 7913 |
| 5066 | CCCAAAGUU GGGACCUC | 3770 | GAGGUCCC CUGAUGAGGNNNNNNNNCCGAA ACUUUGGG | 7914 |
| 5074 | UGGGACCUC ACUGGCUU | 3771 | AAGCCAGU CUGAUGAGGNNNNNNNNCCGAA AGGUCCCA | 7915 |
| 5082 | CACUGGCUU CUCUUUAC | 3772 | GUAAAGAG CUGAUGAGGNNNNNNNNCCGAA AGCCAGUG | 7916 |
| 5083 | ACUGGCUUC UCUUUACU | 3773 | AGUAAAGA CUGAUGAGGNNNNNNNNCCGAA AAGCCAGU | 7917 |
| 5085 | UGGCUUCUC UUUACUUC | 3774 | GAAGUAAA CUGAUGAGGNNNNNNNNCCGAA AGAAGCCA | 7918 |
| 5087 | GCUUCUCUU UACUUCAU | 3775 | AUGAAGUA CUGAUGAGGNNNNNNNNCCGAA AGAGAAGC | 7919 |
| 5088 | CUUCUCUUU ACUUCAUC | 3776 | GAUGAAGU CUGAUGAGGNNNNNNNNCCGAA AAGAGAAG | 7920 |
| 5089 | UUCUCUUUA CUUCAUCA | 3777 | UGAUGAAG CUGAUGAGGNNNNNNNNCCGAA AAAGAGAA | 7921 |
| 5092 | UCUUUACUU CAUCAUGG | 3778 | CCAUGAUG CUGAUGAGGNNNNNNNNCCGAA AGUAAAGA | 7922 |
| 5093 | CUUUACUUC AUCAUGGA | 3779 | UCCAUGAU CUGAUGAGGNNNNNNNNCCGAA AAGUAAAG | 7923 |
| 5096 | UACUUCAUC AUGGAUUU | 3780 | AAAUCCAU CUGAUGAGGNNNNNNNNCCGAA AUGAAGUA | 7924 |
| 5103 | UCAUGGAUU UCACCAUC | 3781 | GAUGGUGA CUGAUGAGGNNNNNNNNCCGAA AUCCAUGA | 7925 |
| 5104 | CAUGGAUUU CACCAUCC | 3782 | GGAUGGUG CUGAUGAGGNNNNNNNNCCGAA AAUCCAUG | 7926 |
| 5105 | AUGGAUUUC ACCAUCCC | 3783 | GGGAUGGU CUGAUGAGGNNNNNNNNCCGAA AAAUCCAU | 7927 |
| 5111 | UUCACCAUC CCAAGGCA | 3784 | UGCCUUGG CUGAUGAGGNNNNNNNNCCGAA AUGGUGAA | 7928 |
| 5122 | AAGGCAGUC UGAGAGGA | 3785 | UCCUCUCA CUGAUGAGGNNNNNNNNCCGAA ACUGCCUU | 7929 |
| 5134 | GAGGAGCUA AAGAGUAU | 3786 | AUACUCUU CUGAUGAGGNNNNNNNNCCGAA AGCUCCUC | 7930 |
| 5141 | UAAAGAGUA UCAGCCCA | 3787 | UGGGCUGA CUGAUGAGGNNNNNNNNCCGAA ACUCUUUA | 7931 |
| 5143 | AAGAGUAUC AGCCCAUA | 3788 | UAUGGGCU CUGAUGAGGNNNNNNNNCCGAA AUACUCUU | 7932 |
| 5151 | CAGCCCAUA UUUAUUAA | 3789 | UUAAUAAA CUGAUGAGGNNNNNNNNCCGAA AUGGGCUG | 7933 |
| 5153 | GCCCAUAUU UAUUAAGC | 3790 | GCUUAAUA CUGAUGAGGNNNNNNNNCCGAA AUAUGGGC | 7934 |
| 5154 | CCCAUAUUU AUUAAGCA | 3791 | UGCUUAAU CUGAUGAGGNNNNNNNNCCGAA AAUAUGGG | 7935 |
| 5155 | CCAUAUUUA UUAAGCAC | 3792 | GUGCUUAA CUGAUGAGGNNNNNNNNCCGAA AAAUAUGG | 7936 |
| 5157 | AUAUUUAUU AAGCACUU | 3793 | AAGUGCUU CUGAUGAGGNNNNNNNNCCGAA AUAAAUAU | 7937 |
| 5158 | UAUUUAUUA AGCACUUU | 3794 | AAAGUGCU CUGAUGAGGNNNNNNNNCCGAA AAUAAAUA | 7938 |
| 5165 | UAAGCACUU UAUGCUCC | 3795 | GGAGCAUA CUGAUGAGGNNNNNNNNCCGAA AGUGCUUA | 7939 |
| 5166 | AAGCACUUU AUGCUCCU | 3796 | AGGAGCAU CUGAUGAGGNNNNNNNNCCGAA AAGUGCUU | 7940 |
| 5167 | AGCACUUUA UGCUCCUU | 3797 | AAGGAGCA CUGAUGAGGNNNNNNNNCCGAA AAAGUGCU | 7941 |
| 5172 | UUUAUGCUC CUUGGCAC | 3798 | GUGCCAAG CUGAUGAGGNNNNNNNNCCGAA AGCAUAAA | 7942 |
| 5175 | AUGCUCCUU GGCACAGC | 3799 | GCUGUGCC CUGAUGAGGNNNNNNNNCCGAA AGGAGCAU | 7943 |
| 5195 | UGAUGUGUA AUUUAUGC | 3800 | GCAUAAAU CUGAUGAGGNNNNNNNNCCGAA ACACAUCA | 7944 |
| 5198 | UGUGUAAUU UAUGCAAG | 3801 | CUUGCAUA CUGAUGAGGNNNNNNNNCCGAA AUUACACA | 7945 |
| 5199 | GUGUAAUUU AUGCAAGC | 3802 | GCUUGCAU CUGAUGAGGNNNNNNNNCCGAA AAUUACAC | 7946 |
| 5200 | UGUAAUUUA UGCAAGCU | 3803 | AGCUUGCA CUGAUGAGGNNNNNNNNCCGAA AAAUUACA | 7947 |
| 5209 | UGCAAGCUC CUCUCCA | 3804 | UGGAGAGG CUGAUGAGGNNNNNNNNCCGAA AGCUUGCA | 7948 |
| 5213 | AGCUCCUC UCCAGCUA | 3805 | UAGCUGGA CUGAUGAGGNNNNNNNNCCGAA AGGGAGCU | 7949 |
| 5215 | CUCCCUCUC CAGCUAGG | 3806 | CCUAGCUG CUGAUGAGGNNNNNNNNCCGAA AGAGGGAG | 7950 |
| 5221 | CUCCAGCUA GGACUCAG | 3807 | CUGAGUCC CUGAUGAGGNNNNNNNNCCGAA AGCUGGAG | 7951 |
| 5227 | CUAGGACUC AGGAUAUU | 3808 | AAUAUCCU CUGAUGAGGNNNNNNNNCCGAA AGUCCUAG | 7952 |
| 5233 | CUCAGGAUA UUAGUCAA | 3809 | UUGACUAA CUGAUGAGGNNNNNNNNCCGAA AUCCUGAG | 7953 |
| 5235 | CAGGAUAUU AGUCAAUG | 3810 | CAUUGACU CUGAUGAGGNNNNNNNNCCGAA AUAUCCUG | 7954 |
| 5236 | AGGAUAUUA GUCAAUGA | 3811 | UCAUUGAC CUGAUGAGGNNNNNNNNCCGAA AAUAUCCU | 7955 |
| 5239 | AUAUUAGUC AAUGAGCC | 3812 | GGCUCAUU CUGAUGAGGNNNNNNNNCCGAA ACUAAUAU | 5095 |
| 5250 | UGAGCCAUC AAAAGGAA | 3813 | UUCCUUUU CUGAUGAGGNNNNNNNNCCGAA AUGGCUCA | 7956 |
| 5273 | AAAAACCUA UCUUAUUU | 3814 | AAAUAAGA CUGAUGAGGNNNNNNNNCCGAA AGGUUUUU | 7957 |
| 5275 | AAACCUAUC UUAUUUUC | 3815 | GAAAAUAA CUGAUGAGGNNNNNNNNCCGAA AUAGGUUU | 7958 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5277 | ACCUAUCUU AUUUUCAU | 3816 | AUGAAAAU CUGAUGAGGNNNNNNNNCCGAA AGAUAGGU | 7959 |
| 5278 | CCUAUCUUA UUUUCAUC | 3817 | GAUGAAAA CUGAUGAGGNNNNNNNNCCGAA AAGAUAGG | 7960 |
| 5280 | UAUCUUAUU UUCAUCUG | 3818 | CAGAUGAA CUGAUGAGGNNNNNNNNCCGAA AUAAGAUA | 7961 |
| 5281 | AUCUUAUUU UCAUCUGU | 3819 | ACAGAUGA CUGAUGAGGNNNNNNNNCCGAA AAUAAGAU | 7962 |
| 5282 | UCUUAUUUU CAUCUGUU | 3820 | AACAGAUG CUGAUGAGGNNNNNNNNCCGAA AAAUAAGA | 7963 |
| 5283 | CUUAUUUUC AUCUGUUU | 3821 | AAACAGAU CUGAUGAGGNNNNNNNNCCGAA AAAAUAAG | 7964 |
| 5286 | AUUUUCAUC UGUUUCAU | 3822 | AUGAAACA CUGAUGAGGNNNNNNNNCCGAA AUGAAAAU | 7965 |
| 5290 | UCAUCUGUU UCAUACCU | 3823 | AGGUAUGA CUGAUGAGGNNNNNNNNCCGAA ACAGAUGA | 7966 |
| 5291 | CAUCUGUUU CAUACCUU | 3824 | AAGGUAUG CUGAUGAGGNNNNNNNNCCGAA AACAGAUG | 7967 |
| 5292 | AUCUGUUUC AUACCUUG | 3825 | CAAGGUAU CUGAUGAGGNNNNNNNNCCGAA AAACAGAU | 7968 |
| 5295 | UGUUUCAUA CCUUGUCU | 3826 | AGACAAGG CUGAUGAGGNNNNNNNNCCGAA AUGAAACA | 7969 |
| 5299 | UCAUACCUU GUCUGGGG | 3827 | CCCCAGAC CUGAUGAGGNNNNNNNNCCGAA AGGUAUGA | 7970 |
| 5302 | UACCUUGUC UGGGGUCU | 3828 | AGACCCCA CUGAUGAGGNNNNNNNNCCGAA ACAAGGUA | 7971 |
| 5309 | UCUGGGGUC UAAUGACG | 3829 | CGUCAUUA CUGAUGAGGNNNNNNNNCCGAA ACCCCAGA | 7972 |
| 5311 | UGGGGUCUA AUGACGAU | 3830 | AUCGUCAU CUGAUGAGGNNNNNNNNCCGAA AGACCCCA | 7973 |
| 5331 | AACAGGGUA GACAUGGG | 3831 | CCCAUGUC CUGAUGAGGNNNNNNNNCCGAA ACCCUGUU | 7974 |
| 5350 | GACAGGGUA GAAAAGGG | 3832 | CCCUUUUC CUGAUGAGGNNNNNNNNCCGAA ACCCUGUC | 7975 |
| 5367 | UGCCCGCUC UUUGGGGU | 3833 | ACCCCAAA CUGAUGAGGNNNNNNNNCCGAA AGCGGGCA | 7976 |
| 5369 | CCCGCUCUU UGGGGUCU | 3834 | AGACCCCA CUGAUGAGGNNNNNNNNCCGAA AGAGCGGG | 7977 |
| 5370 | CCGCUCUUU GGGGUCUA | 3835 | UAGACCCC CUGAUGAGGNNNNNNNNCCGAA AAGAGCGG | 7978 |
| 5376 | UUUGGGGUC UAGAGAUG | 3836 | CAUCUCUA CUGAUGAGGNNNNNNNNCCGAA ACCCCAAA | 7979 |
| 5378 | UGGGGUCUA GAGAUGAG | 3837 | CUCAUCUC CUGAUGAGGNNNNNNNNCCGAA AGACCCCA | 7980 |
| 5395 | CCCUGGGUC UCUAAAAU | 3838 | AUUUUAGA CUGAUGAGGNNNNNNNNCCGAA ACCCAGGG | 7981 |
| 5397 | CUGGGUCUC UAAAAUGG | 3839 | CCAUUUUA CUGAUGAGGNNNNNNNNCCGAA AGACCCAG | 7982 |
| 5399 | GGGUCUCUA AAAUGGCU | 3840 | AGCCAUUU CUGAUGAGGNNNNNNNNCCGAA AGAGACCC | 7983 |
| 5408 | AAAUGGCUC UCUUAGAA | 3841 | UUCUAAGA CUGAUGAGGNNNNNNNNCCGAA AGCCAUUU | 7984 |
| 5410 | AUGGCUCUC UUAGAAGU | 3842 | ACUUCUAA CUGAUGAGGNNNNNNNNCCGAA AGAGCCAU | 7985 |
| 5412 | GGCUCUCUU AGAAGUUG | 3843 | CAACUUCU CUGAUGAGGNNNNNNNNCCGAA AGAGAGCC | 7986 |
| 5413 | GCUCUCUUA GAAGUUGU | 3844 | ACAACUUC CUGAUGAGGNNNNNNNNCCGAA AAGAGAGC | 7987 |
| 5419 | UUAGAAGUU GUAUGUGC | 3845 | GCACAUAC CUGAUGAGGNNNNNNNNCCGAA ACUUCUAA | 7988 |
| 5422 | GAAGUUGUA UGUGCAAA | 3846 | UUUGCACA CUGAUGAGGNNNNNNNNCCGAA ACAACUUC | 7989 |
| 5432 | GUGCAAAUU AUGGUCUG | 3847 | CAGACCAU CUGAUGAGGNNNNNNNNCCGAA AUUUGCAC | 7990 |
| 5433 | UGCAAAUUA UGGUCUGU | 3848 | ACAGACCA CUGAUGAGGNNNNNNNNCCGAA AAUUUGCA | 7991 |
| 5438 | AUUAUGGUC UGUGUGCU | 3849 | AGCACACA CUGAUGAGGNNNNNNNNCCGAA ACCAUAAU | 7992 |
| 5447 | UGUGUGCUU AGGUCGUG | 3850 | CACGACCU CUGAUGAGGNNNNNNNNCCGAA AGCACACA | 7993 |
| 5448 | GUGUGCUUA GGUCGUGC | 3851 | GCACGACC CUGAUGAGGNNNNNNNNCCGAA AAGCACAC | 7994 |
| 5452 | GCUUAGGUC GUGCACAC | 3852 | GUGUGCAC CUGAUGAGGNNNNNNNNCCGAA ACCUAAGC | 7995 |
| 5475 | GAGCCGGUC ACAGCUGG | 3853 | CCAGCUGU CUGAUGAGGNNNNNNNNCCGAA ACCGGCUC | 7996 |
| 5497 | CGAUGAAUA GCUGCUUU | 3854 | AAAGCAGC CUGAUGAGGNNNNNNNNCCGAA AUUCAUCG | 7997 |
| 5504 | UAGCUGCUU UGGGAGAG | 3855 | CUCUCCCA CUGAUGAGGNNNNNNNNCCGAA AGCAGCUA | 7998 |
| 5505 | AGCUGCUUU GGGAGAGC | 3856 | GCUCUCCC CUGAUGAGGNNNNNNNNCCGAA AAGCAGCU | 7999 |
| 5524 | AGCAUGCUA GCCACUUA | 3857 | UAAGUGGC CUGAUGAGGNNNNNNNNCCGAA AGCAUGCU | 8000 |
| 5531 | UAGCCACUU AAUUCUCU | 3858 | AGAGAAUU CUGAUGAGGNNNNNNNNCCGAA AGUGGCUA | 8001 |
| 5532 | AGCCACUUA AUUCUCUG | 3859 | CAGAGAAU CUGAUGAGGNNNNNNNNCCGAA AAGUGGCU | 8002 |
| 5535 | CACUUAAUU CUCUGACC | 3860 | GGUCAGAG CUGAUGAGGNNNNNNNNCCGAA AUUAAGUG | 8003 |
| 5536 | ACUUAAUUC UCUGACCG | 3861 | CGGUCAGA CUGAUGAGGNNNNNNNNCCGAA AAUUAAGU | 8004 |
| 5538 | UUAAUUCUC UGACCGGG | 3862 | CCCGGUCA CUGAUGAGGNNNNNNNNCCGAA AGAAUUAA | 8005 |
| 5554 | GCCAGCAUC AUGGGUAC | 3863 | GUACCCAU CUGAUGAGGNNNNNNNNCCGAA AUGCUGGC | 8006 |
| 5561 | UCAUGGGUA CCUGCUCC | 3864 | GGAGCAGG CUGAUGAGGNNNNNNNNCCGAA ACCCAUGA | 8007 |
| 5568 | UACCUGCUC CCUGUGUU | 3865 | ACACAGGG CUGAUGAGGNNNNNNNNCCGAA AGCAGGUA | 8008 |
| 5577 | CCCUGUGUA CCCCAUCC | 3866 | GGAUGGGG CUGAUGAGGNNNNNNNNCCGAA ACACAGGG | 8009 |
| 5584 | UACCCCAUC CUUAAGGU | 3867 | ACCUUAAG CUGAUGAGGNNNNNNNNCCGAA AUGGGGUA | 8010 |
| 5587 | CCCAUCCUU AAGGUUUU | 3868 | AAAACCUU CUGAUGAGGNNNNNNNNCCGAA AGGAUGGG | 8011 |
| 5588 | CCAUCCUUA AGGUUUUC | 3869 | GAAAACCU CUGAUGAGGNNNNNNNNCCGAA AAGGAUGG | 8012 |
| 5593 | CUUAAGGUU UUCUGUCU | 3870 | AGACAGAA CUGAUGAGGNNNNNNNNCCGAA ACCUUAAG | 8013 |
| 5594 | UUAAGGUUU UCUGUCUG | 3871 | CAGACAGA CUGAUGAGGNNNNNNNNCCGAA AACCUUAA | 8014 |
| 5595 | UAAGGUUUU CUGUCUGA | 3872 | UCAGACAG CUGAUGAGGNNNNNNNNCCGAA AAACCUUA | 8015 |
| 5596 | AAGGUUUUC UGUCUGAU | 3873 | AUCAGACA CUGAUGAGGNNNNNNNNCCGAA AAAACCUU | 8016 |
| 5600 | UUUUCUGUC UGAUGAGA | 3874 | UCUCAUCA CUGAUGAGGNNNNNNNNCCGAA ACAGAAAA | 8017 |
| 5627 | AGUGCAAUC CCCACUGA | 3875 | UCAGUGGG CUGAUGAGGNNNNNNNNCCGAA AUUGCACU | 8018 |
| 5660 | CUGUGGCUC UUGGUGCA | 3876 | UGCACCAA CUGAUGAGGNNNNNNNNCCGAA AGCCACAG | 8019 |
| 5662 | GUGGCUCUU GGUGCACU | 3877 | AGUGCACC CUGAUGAGGNNNNNNNNCCGAA AGAGCCAC | 8020 |
| 5671 | GGUGCACUC ACCAGCCA | 3878 | UGGCUGGU CUGAUGAGGNNNNNNNNCCGAA AGUGCACC | 8021 |
| 5685 | CCAGGACUA GACAAGUA | 3879 | UACUUGUC CUGAUGAGGNNNNNNNNCCGAA AGUCCUGG | 8022 |
| 5693 | AGACAAGUA GGAAAGGG | 3880 | CCCUUUCC CUGAUGAGGNNNNNNNNCCGAA ACUUGUCU | 8023 |
| 5704 | AAAGGGCUU CUAGCCAC | 3881 | GUGGCUAG CUGAUGAGGNNNNNNNNCCGAA AGCCCUUU | 8024 |
| 5705 | AAGGGCUUC UAGCCACA | 3882 | UGUGGCUA CUGAUGAGGNNNNNNNNCCGAA AAGCCCUU | 8025 |
| 5707 | GGGCUUCUA GCCACACU | 3883 | AGUGUGGC CUGAUGAGGNNNNNNNNCCGAA AGAAGCCC | 8026 |
| 5731 | AAGAAAAUC AGGUAGGG | 3884 | CCCUACCU CUGAUGAGGNNNNNNNNCCGAA AUUUUCUU | 8027 |
| 5736 | AAUCAGGUA GGGCUGGC | 3885 | GCCAGCCC CUGAUGAGGNNNNNNNNCCGAA ACCUGAUU | 8028 |
| 5754 | AAAGACAUC UUUGUCCA | 3886 | UGGACAAA CUGAUGAGGNNNNNNNNCCGAA AUGUCUUU | 8029 |
| 5756 | AGACAUCUU UGUCCAUU | 3887 | AAUGGACA CUGAUGAGGNNNNNNNNCCGAA AGAUGUCU | 8030 |
| 5757 | GACAUCUUU GUCCAUUC | 3888 | GAAUGGAC CUGAUGAGGNNNNNNNNCCGAA AAGAUGUC | 8031 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5760 | AUCUUUGUC CAUUCGCA | 3889 | UGCGAAUG CUGAUGAG<u>GNNNNNNNN</u>CCGAA ACAAAGAU | 8032 |
| 5764 | UUGUCCAUU CGCAAAAG | 3890 | CUUUUGCG CUGAUGAG<u>GNNNNNNNN</u>CCGAA AUGGACAA | 8033 |
| 5765 | UGUCCAUUC GCAAAAGC | 3891 | GCUUUUGC CUGAUGAG<u>GNNNNNNNN</u>CCGAA AAUGGACA | 8034 |
| 5775 | CAAAAGCUC UUGUCGGC | 3892 | GCCGACAA CUGAUGAG<u>GNNNNNNNN</u>CCGAA AGCUUUUG | 8035 |
| 5777 | AAAGCUCUU GUCGGCUG | 3893 | CAGCCGAC CUGAUGAG<u>GNNNNNNNN</u>CCGAA AGAGCUUU | 8036 |
| 5780 | GCUCUUGUC GGCUGCAG | 3894 | CUGCAGCC CUGAUGAG<u>GNNNNNNNN</u>CCGAA ACAAGAGC | 8037 |
| 5794 | CAGUGUGUA AGUCAGGC | 3895 | GCCUGACU CUGAUGAG<u>GNNNNNNNN</u>CCGAA ACACACUG | 8038 |
| 5798 | GUGUAAGUC AGGCGAUG | 3896 | CAUCGCCU CUGAUGAG<u>GNNNNNNNN</u>CCGAA ACUUACAC | 8039 |
| 5818 | CAGAGGCUA CCAGAGAA | 3897 | UUCUCUGG CUGAUGAG<u>GNNNNNNNN</u>CCGAA AGCCUCUG | 8040 |
| 5852 | CCUGAGGUU UCUCAUCC | 3898 | GGAUGAGA CUGAUGAG<u>GNNNNNNNN</u>CCGAA ACCUCAGG | 8041 |
| 5853 | CUGAGGUUU CUCAUCCA | 3899 | UGGAUGAG CUGAUGAG<u>GNNNNNNNN</u>CCGAA AACCUCAG | 8042 |
| 5854 | UGAGGUUUC UCAUCCAG | 3900 | CUGGAUGA CUGAUGAG<u>GNNNNNNNN</u>CCGAA AAACCUCA | 8043 |
| 5856 | AGGUUUCUC AUCCAGAU | 3901 | AUCUGGAU CUGAUGAG<u>GNNNNNNNN</u>CCGAA AGAAACCU | 8044 |
| 5859 | UUUCUCAUC CAGAUAUC | 3902 | GAUAUCUG CUGAUGAG<u>GNNNNNNNN</u>CCGAA AUGAGAAA | 8045 |
| 5865 | AUCCAGAUA UCCAGCAA | 3903 | UUGCUGGA CUGAUGAG<u>GNNNNNNNN</u>CCGAA AUCUGGAU | 8046 |
| 5867 | CCAGAUAUC CAGCAAUU | 3904 | AAUUGCUG CUGAUGAG<u>GNNNNNNNN</u>CCGAA AUAUCUGG | 8047 |
| 5875 | CCAGCAAUU GGGGGUG | 3905 | CACCCCCC CUGAUGAG<u>GNNNNNNNN</u>CCGAA AUUGCUGG | 8048 |
| 5896 | AAGACCAUA GAUGGUCC | 3906 | GGACCAUC CUGAUGAG<u>GNNNNNNNN</u>CCGAA AUGGUCUU | 8049 |
| 5903 | UAGAUGGUC CUGUAUUA | 3907 | UAAUACAG CUGAUGAG<u>GNNNNNNNN</u>CCGAA ACCAUCUA | 8050 |
| 5908 | GGUCCUGUA UUAUUCCG | 3908 | CGGAAUAA CUGAUGAG<u>GNNNNNNNN</u>CCGAA ACAGGACC | 8051 |
| 5910 | UCCUGUAUU AUUCCGAU | 3909 | AUCGGAAU CUGAUGAG<u>GNNNNNNNN</u>CCGAA AUACAGGA | 8052 |
| 5911 | CCUGUAUUA UUCCGAUU | 3910 | AAUCGGAA CUGAUGAG<u>GNNNNNNNN</u>CCGAA AAUACAGG | 8053 |
| 5913 | UGUAUUAUU CCGAUUUU | 3911 | AAAAUCGG CUGAUGAG<u>GNNNNNNNN</u>CCGAA AUAAUACA | 8054 |
| 5914 | GUAUUAUUC CGAUUUUA | 3912 | UAAAAUCG CUGAUGAG<u>GNNNNNNNN</u>CCGAA AAUAAUAC | 8055 |
| 5919 | AUUCCGAUU UUAAUAAU | 3913 | AUUAUUAA CUGAUGAG<u>GNNNNNNNN</u>CCGAA AUCGGAAU | 8056 |
| 5920 | UUCCGAUUU UAAUAAUC | 3914 | GAUUAUUA CUGAUGAG<u>GNNNNNNNN</u>CCGAA AAUCGGAA | 8057 |
| 5921 | UCCGAUUUU AAUAAUCU | 3915 | AGAUUAUU CUGAUGAG<u>GNNNNNNNN</u>CCGAA AAAUCGGA | 8058 |
| 5922 | CCGAUUUUA AUAAUCUA | 3916 | UAGAUUAU CUGAUGAG<u>GNNNNNNNN</u>CCGAA AAAAUCGG | 8059 |
| 5925 | AUUUUAAUA AUCUAAUU | 3917 | AAUUAGAU CUGAUGAG<u>GNNNNNNNN</u>CCGAA AUUAAAAU | 8060 |
| 5928 | UUAAUAAUC UAAUUCGU | 3918 | ACGAAUUA CUGAUGAG<u>GNNNNNNNN</u>CCGAA AUUAUUAA | 8061 |
| 5930 | AAUAAUCUA AUUCGUGA | 3919 | UCACGAAU CUGAUGAG<u>GNNNNNNNN</u>CCGAA AGAUUAUU | 8062 |
| 5933 | AAUCUAAUU CGUGAUCA | 3920 | UGAUCACG CUGAUGAG<u>GNNNNNNNN</u>CCGAA AUUAGAUU | 8063 |
| 5934 | AUCUAAUUC GUGAUCAU | 3921 | AUGAUCAC CUGAUGAG<u>GNNNNNNNN</u>CCGAA AAUUAGAU | 8064 |
| 5940 | UUCGUGAUC AUUAAGAG | 3922 | CUCUUAAU CUGAUGAG<u>GNNNNNNNN</u>CCGAA AUCACGAA | 8065 |
| 5943 | GUGAUCAUU AAGAGACU | 3923 | AGUCUCUU CUGAUGAG<u>GNNNNNNNN</u>CCGAA AUGAUCAC | 8066 |
| 5944 | UGAUCAUUA AGAGACUU | 3924 | AAGUCUCU CUGAUGAG<u>GNNNNNNNN</u>CCGAA AAUGAUCA | 8067 |
| 5952 | AAGAGACUU UAGUAAAU | 3925 | AUUUACUA CUGAUGAG<u>GNNNNNNNN</u>CCGAA AGUCUCUU | 8068 |
| 5953 | AGAGACUUU AGUAAAUG | 3926 | CAUUUACU CUGAUGAG<u>GNNNNNNNN</u>CCGAA AAGUCUCU | 8069 |
| 5954 | GAGACUUUA GUAAAUGU | 3927 | ACAUUUAC CUGAUGAG<u>GNNNNNNNN</u>CCGAA AAAGUCUC | 8070 |
| 5957 | ACUUUAGUA AAUGUCCC | 3928 | GGGACAUU CUGAUGAG<u>GNNNNNNNN</u>CCGAA ACUAAAGU | 8071 |
| 5963 | GUAAAUGUC CCUUUUCC | 3929 | GGAAAAGG CUGAUGAG<u>GNNNNNNNN</u>CCGAA ACAUUUAC | 8072 |
| 5967 | AUGUCCCUU UUCCCACA | 3930 | UGUGGGAA CUGAUGAG<u>GNNNNNNNN</u>CCGAA AGGGACAU | 8073 |
| 5968 | UGUCCCUUU UCCCACAA | 3931 | UUGUGGGA CUGAUGAG<u>GNNNNNNNN</u>CCGAA AAGGGACA | 8074 |
| 5969 | GUCCCUUUU CCCACAAA | 3932 | UUUGUGGG CUGAUGAG<u>GNNNNNNNN</u>CCGAA AAAGGGAC | 8075 |
| 5970 | UCCCUUUUC CCACAAAA | 3933 | UUUUGUGG CUGAUGAG<u>GNNNNNNNN</u>CCGAA AAAAGGGA | 8076 |
| 5981 | ACAAAAGUA AAGAAAAG | 3934 | CUUUUCUU CUGAUGAG<u>GNNNNNNNN</u>CCGAA ACUUUUGU | 8077 |
| 5992 | GAAAAGCUA UCGGGAUU | 3935 | AAUCCCGA CUGAUGAG<u>GNNNNNNNN</u>CCGAA AGCUUUUC | 8078 |
| 5994 | AAAGCUAUC GGGAUUCU | 3936 | AGAAUCCC CUGAUGAG<u>GNNNNNNNN</u>CCGAA AUAGCUUU | 8079 |
| 6000 | AUCGGGAUU CUCUGGUU | 3937 | AACCAGAG CUGAUGAG<u>GNNNNNNNN</u>CCGAA AUCCCGAU | 8080 |
| 6001 | UCGGGAUUC UCUGGUUC | 3938 | GAACCAGA CUGAUGAG<u>GNNNNNNNN</u>CCGAA AAUCCCGA | 8081 |
| 6003 | GGGAUUCUC UGGUUCUG | 3939 | CAGAACCA CUGAUGAG<u>GNNNNNNNN</u>CCGAA AGAAUCCC | 8082 |
| 6008 | UCUCUGGUU CUGCUUAA | 3940 | UUAAGCAG CUGAUGAG<u>GNNNNNNNN</u>CCGAA ACCAGAGA | 8083 |
| 6009 | CUCUGGUUC UGCUUAAA | 3941 | UUUAAGCA CUGAUGAG<u>GNNNNNNNN</u>CCGAA AACCAGAG | 8084 |
| 6014 | GUUCUGCUU AAAGACUU | 3942 | AAGUCUUU CUGAUGAG<u>GNNNNNNNN</u>CCGAA AGCAGAAC | 8085 |
| 6015 | UUCUGCUUA AAGACUUA | 3943 | UAGUCUUU CUGAUGAG<u>GNNNNNNNN</u>CCGAA AAGCAGAA | 8086 |
| 6022 | UAAAGACUU AGCUUUGG | 3944 | CCAAAGCU CUGAUGAG<u>GNNNNNNNN</u>CCGAA AGUCUUUA | 8087 |
| 6023 | AAAGACUUA GCUUUGGA | 3945 | UCCAAAGC CUGAUGAG<u>GNNNNNNNN</u>CCGAA AAGUCUUU | 8088 |
| 6027 | ACUUAGCUU UGGAGCCU | 3946 | AGGCUCCA CUGAUGAG<u>GNNNNNNNN</u>CCGAA AGCUAAGU | 8089 |
| 6028 | CUUAGCUUU GGAGCCUA | 3947 | UAGGCUCC CUGAUGAG<u>GNNNNNNNN</u>CCGAA AAGCUAAG | 8090 |
| 6036 | UGGAGCCUA UGAAAGUU | 3948 | AACUUUCA CUGAUGAG<u>GNNNNNNNN</u>CCGAA AGGCUCCA | 8091 |
| 6044 | AUGAAAGUU GAUCAGCC | 3949 | GGCUGAUC CUGAUGAG<u>GNNNNNNNN</u>CCGAA ACUUUCAU | 8092 |

Where "X" represents stem II region of a HH ribozyme (Hertel et al., 1992 Nucleic Acids Res. 20 3252). The length of stem II may be ≧2 base-pairs.
Underlined region can be any X sequence or linker, as described herein.

TABLE IX

Mouse flt1 VEGF Receptor-Hairpin Ribozyme and Substrate Sequence

| Pos | Substrate | Seq ID No | HP Ribozyme | Seq ID No |
|---|---|---|---|---|
| 33 | AUGGUCA GCU GCUGGGAC | 3950 | GUCCCAGC AGAA GACCAU ACCAGAGAAACACACGUUGUGGUACAUUACCUGGUA | 8093 |
| 36 | GUCAGCU GCU GGGACACC | 3951 | GGUGUCCC AGAA GCUGAC ACCAGAGAAACACACGUUGUGGUACAUUACCUGGUA | 8094 |
| 50 | CACCGCG GCU UUGCCUUA | 3952 | UAAGGCAA AGAA GCGGUG ACCAGAGAAACACACGUUGUGGUACAUUACCUGGUA | 8095 |
| 67 | ACGCGCU GCU CGGGUGUC | 3953 | GACACCCG AGAA GCGCGU ACCAGAGAAACACACGUUGUGGUACAUUACCUGGUA | 8096 |
| 79 | GGUGUCU GCU UCUCACAG | 3954 | CUGUGAGA AGAA GACACC ACCAGAGAAACACACGUUGUGGUACAUUACCUGGUA | 8097 |
| 166 | CAGGCCA GAC UCUCUUUC | 3955 | GAAAGAGA AGAA GGCCUG ACCAGAGAAACACACGUUGUGGUACAUUACCUGGUA | 8098 |
| 197 | GGAGGCA GCC CACUCAUG | 3956 | CAUGAGUG AGAA GCCUCC ACCAGAGAAACACACGUUGUGGUACAUUACCUGGUA | 8099 |
| 214 | GGUCUCU GCC CACGACCG | 3957 | CGGUCGUG AGAA GAGACC ACCAGAGAAACACACGUUGUGGUACAUUACCUGGUA | 8100 |
| 266 | CCCAUCG GCC UGUGGGAG | 3958 | CUCCCACA AGAA GAUGGG ACCAGAGAAACACACGUUGUGGUACAUUACCUGGUA | 8101 |
| 487 | GAAGACA GCU CAUCAUCC | 3959 | GGAUGAUG AGAA GUCUUC ACCAGAGAAACACACGUUGUGGUACAUUACCUGGUA | 8102 |
| 501 | AUCCCCU GCU GGGUGACG | 3960 | CGUCACCC AGAA GGGGAU ACCAGAGAAACACACGUUGUGGUACAUUACCUGGUA | 8103 |
| 566 | UACCCCU GAU GGGCAAAG | 3961 | CUUUGCCC AGAA GGGGUA ACCAGAGAAACACACGUUGUGGUACAUUACCUGGUA | 8104 |
| 640 | UAGGACU GCU GAACUGCG | 3962 | CGCAGUUC AGAA GUCCUA ACCAGAGAAACACACGUUGUGGUACAUUACCUGGUA | 8105 |
| 691 | ACUAUCU GAC CCAUCGGC | 3963 | GCCGAUGG AGAA GAUAGU ACCAGAGAAACACACGUUGUGGUACAUUACCUGGUA | 8106 |
| 703 | AUCGGCA GCC CAAUACAA | 3964 | UUGUAUUG AGAA GCCGAU ACCAGAGAAACACACGUUGUGGUACAUUACCUGGUA | 8107 |
| 736 | UACGCCC GCC GAGCCCAG | 3965 | CUGGGCUC AGAA GGCGUA ACCAGAGAAACACACGUUGUGGUACAUUACCUGGUA | 8108 |
| 754 | UGAGACU GCU CCACGGGC | 3966 | GCCCGUGG AGAA GUCUCA ACCAGAGAAACACACGUUGUGGUACAUUACCUGGUA | 8109 |
| 766 | ACGGGCA GAC UCUUGUCC | 3967 | GGACAAGA AGAA GCCCGU ACCAGAGAAACACACGUUGUGGUACAUUACCUGGUA | 8110 |
| 871 | GGCAGCG GAU UGACCGGA | 3968 | UCCGGUCA AGAA GCUGCC ACCAGAGAAACACACGUUGUGGUACAUUACCUGGUA | 8111 |
| 960 | UACACCU GUC GCGUGAAG | 3969 | CUUCACGC AGAA GGUGUA ACCAGAGAAACACACGUUGUGGUACAUUACCUGGUA | 8112 |
| 988 | CGUUCCA GUC UUUCAACA | 3970 | UGUUGAAA AGAA GGAACG ACCAGAGAAACACACGUUGUGGUACAUUACCUGGUA | 8113 |
| 1051 | GGAAGCA GCC GGUGCAGG | 3971 | CCUGCACC AGAA GCUUCC ACCAGAGAAACACACGUUGUGGUACAUUACCUGGUA | 8114 |
| 1081 | GAAGACG GUC CUAUCGGC | 3972 | GCCGAUAG AGAA GUCUUC ACCAGAGAAACACACGUUGUGGUACAUUACCUGGUA | 8115 |
| 1090 | CCUAUCG GCU GUCCAUGA | 3973 | UCAUGGAC AGAA GAUAGG ACCAGAGAAACACACGUUGUGGUACAUUACCUGGUA | 8116 |
| 1093 | AUCGGCU GUC CAUGAAAG | 3974 | CUUUCAUG AGAA GCCGAU ACCAGAGAAACACACGUUGUGGUACAUUACCUGGUA | 8117 |
| 1169 | GAAGUCU GCU CGCUAUUU | 3975 | AAAUAGCG AGAA GACUUC ACCAGAGAAACACACGUUGUGGUACAUUACCUGGUA | 8118 |
| 1315 | AACCUCA GAU CUACGAAA | 3976 | UUUCGUAG AGAA GAGGUU ACCAGAGAAACACACGUUGUGGUACAUUACCUGGUA | 8119 |
| 1363 | UCUAUCC GCU GGGCAGCA | 3977 | UGCUGCCC AGAA GAUAGA ACCAGAGAAACACACGUUGUGGUACAUUACCUGGUA | 8120 |
| 1604 | GGUGGCU GAC UCUCAGAC | 3978 | GUCUGAGA AGAA GCCACC ACCAGAGAAACACACGUUGUGGUACAUUACCUGGUA | 8121 |
| 1612 | ACUCUCA GAC CCCUGGAA | 3979 | UUCCAGGG AGAA GAGAGU ACCAGAGAAACACACGUUGUGGUACAUUACCUGGUA | 8122 |
| 1629 | AUCUACA GCU GCCGGGCC | 3980 | GGCCCGGC AGAA GUAGAU ACCAGAGAAACACACGUUGUGGUACAUUACCUGGUA | 8123 |
| 1632 | UACAGCU GCC GGGCCUUC | 3981 | GAAGGCCC AGAA GCUGUA ACCAGAGAAACACACGUUGUGGUACAUUACCUGGUA | 8124 |
| 1688 | UGUCACA GAU GUGCCGAA | 3982 | UUCGGCAC AGAA GUGACA ACCAGAGAAACACACGUUGUGGUACAUUACCUGGUA | 8125 |
| 1730 | GAUGCCA GCC GAAGGAGA | 3983 | UCUCCUUC AGAA GGCAUC ACCAGAGAAACACACGUUGUGGUACAUUACCUGGUA | 8126 |
| 1753 | UGAAACU GUC CUGUGUGG | 3984 | CCACACAG AGAA GUUUCA ACCAGAGAAACACACGUUGUGGUACAUUACCUGGUA | 8127 |
| 2017 | CACACCU GCU UCAAAACC | 3985 | GGUUUUGA AGAA GGUGUG ACCAGAGAAACACACGUUGUGGUACAUUACCUGGUA | 8128 |
| 2101 | CGCCUCA GAU CACUUGGU | 3986 | ACCAAGUG AGAA GAGGCG ACCAGAGAAACACACGUUGUGGUACAUUACCUGGUA | 8129 |
| 2176 | GCACGCU GUU UAUUGAAA | 1441 | UUUCAAUA AGAA GCGUGC ACCAGAGAAACACACGUUGUGGUACAUUACCUGGUA | 5597 |
| 2258 | AAGCGCA GCC UACCUCAC | 3987 | GUGAGGUA AGAA GCGCUU ACCAGAGAAACACACGUUGUGGUACAUUACCUGGUA | 8130 |
| 2305 | UGGAGCU GAU CACGCUCA | 3988 | UGAGCGUG AGAA GCUCCA ACCAGAGAAACACACGUUGUGGUACAUUACCUGGUA | 8131 |
| 2383 | UGAAGCG GUC UUCUUCCG | 3989 | CGGAAGAA AGAA GCUUCA ACCAGAGAAACACACGUUGUGGUACAUUACCUGGUA | 8132 |
| 2405 | AAAGACA GAC UACCUGUC | 3990 | GACAGGUA AGAA GUCUUU ACCAGAGAAACACACGUUGUGGUACAUUACCUGGUA | 8133 |
| 2432 | GGACCCA GAU GAAGUUCC | 1445 | GGAACUUC AGAA GGGUCC ACCAGAGAAACACACGUUGUGGUACAUUACCUGGUA | 5601 |
| 2464 | GUGAACG GCU GCCCUAUG | 3991 | CAUAGGGC AGAA GUUCAC ACCAGAGAAACACACGUUGUGGUACAUUACCUGGUA | 8134 |
| 2467 | AACGGCU GCC CUAUGAUG | 3992 | CAUCAUAG AGAA GCCGUU ACCAGAGAAACACACGUUGUGGUACAUUACCUGGUA | 8135 |
| 2592 | CCCACCU GCC GGACUGUG | 3993 | CACAGUCC AGAA GGUGGG ACCAGAGAAACACACGUUGUGGUACAUUACCUGGUA | 8136 |
| 2596 | CCUGCCG GAC UGUGGCUG | 3994 | CAGCCACA AGAA GGCAGG ACCAGAGAAACACACGUUGUGGUACAUUACCUGGUA | 8137 |
| 2653 | AAGCUCU GAU GACCGAAC | 3995 | GUUCGGUC AGAA GAGCUU ACCAGAGAAACACACGUUGUGGUACAUUACCUGGUA | 8138 |
| 2743 | GGCCUCU GAU GGUGAUCG | 3996 | CGAUCACC AGAA GAGGCC ACCAGAGAAACACACGUUGUGGUACAUUACCUGGUA | 8139 |
| 2779 | GAAACCU GUC CAACUACC | 3997 | GGUAGUUG AGAA GGUUUC ACCAGAGAAACACACGUUGUGGUACAUUACCUGGUA | 8140 |
| 2814 | UUAUUCU GUC UCAACAAG | 3998 | CUUGUUGA AGAA GAAUAA ACCAGAGAAACACACGUUGUGGUACAUUACCUGGUA | 8141 |
| 2831 | GGACGCA GCC UUGCAUAU | 3999 | AUAUGCAA AGAA GCGUCC ACCAGAGAAACACACGUUGUGGUACAUUACCUGGUA | 8142 |
| 2895 | AAGCCCC GCC UAGACAGU | 4000 | ACUGUCUA AGAA GGGGCU ACCAGAGAAACACACGUUGUGGUACAUUACCUGGUA | 8143 |
| 2913 | GUCAGCA GCU CAAGUGUC | 4001 | GACACUUG AGAA GCUGAC ACCAGAGAAACACACGUUGUGGUACAUUACCUGGUA | 8144 |
| 2928 | GUCACCA GCU CCAGCUUC | 4002 | GAAGCUGG AGAA GGUGAC ACCAGAGAAACACACGUUGUGGUACAUUACCUGGUA | 8145 |
| 2934 | AGCUCCA GCU UCCCUGAA | 4003 | UUCAGGGA AGAA GGAGCU ACCAGAGAAACACACGUUGUGGUACAUUACCUGGUA | 8146 |
| 3001 | CCAAGCA GCC CCUCACCA | 4004 | UGGUGAGG AGAA GCUUGG ACCAGAGAAACACACGUUGUGGUACAUUACCUGGUA | 8147 |
| 3022 | AAGACCU GAU UUCCUACA | 4005 | UGUAGGAA AGAA GGUCUU ACCAGAGAAACACACGUUGUGGUACAUUACCUGGUA | 8148 |
| 3033 | UCCUACA GUU UCCAAGUG | 4006 | CACUUGGA AGAA GUAGGA ACCAGAGAAACACACGUUGUGGUACAUUACCUGGUA | 8149 |
| 3064 | AGUUUCU GUC CUCCAGAA | 4007 | UUCUGGAG AGAA GAAACU ACCAGAGAAACACACGUUGUGGUACAUUACCUGGUA | 8150 |
| 3179 | GAACCCU GUC UAUGUGAG | 4008 | CUCACAUA AGAA GGGUUC ACCAGAGAAACACACGUUGUGGUACAUUACCUGGUA | 5613 |
| 3357 | UUCUGCA GCC GCCUGAAG | 4009 | CUUCAGGC AGAA GCAGAA ACCAGAGAAACACACGUUGUGGUACAUUACCUGGUA | 8151 |
| 3360 | UGCAGCC GCC UGAGGAA | 4010 | UUCCUUCA AGAA GCUGCA ACCAGAGAAACACACGUUGUGGUACAUUACCUGGUA | 8152 |
| 3379 | GCAUGCG GAU GAGAACCC | 4011 | GGGUUCUC AGAA GCAUGC ACCAGAGAAACACACGUUGUGGUACAUUACCUGGUA | 8153 |
| 3463 | GGCCCCG GUU UGCUGAAC | 4012 | GUUCAGCA AGAA GGGGCC ACCAGAGAAACACACGUUGUGGUACAUUACCUGGUA | 8154 |
| 3496 | GUGACCU GCU UCAAGCCA | 4013 | UGGCUUGA AGAA GGUCAC ACCAGAGAAACACACGUUGUGGUACAUUACCUGGUA | 8155 |
| 3553 | CCAUACU GAC UAGAAACA | 4014 | UGUUUCUA AGAA GUAUGG ACCAGAGAAACACACGUUGUGGUACAUUACCUGGUA | 8156 |
| 3615 | AAGGACG GCU UUGCAGAU | 4015 | AUCUGCAA AGAA GUCCUU ACCAGAGAAACACACGUUGUGGUACAUUACCUGGUA | 8157 |
| 3623 | CUUUGCA GAU CCACAUUU | 4016 | AAAUGUGG AGAA GCAAAG ACCAGAGAAACACACGUUGUGGUACAUUACCUGGUA | 8158 |
| 3650 | AAGCUCU GAU GAUGUGAG | 4017 | CUCACAUC AGAA GAGCUU ACCAGAGAAACACACGUUGUGGUACAUUACCUGGUA | 8159 |
| 3754 | ACUAUCA GCU GGACACUA | 4018 | UAGUGUCC AGAA GAUAGU ACCAGAGAAACACACGUUGUGGUACAUUACCUGGUA | 8160 |
| 3772 | GCACUCU GCU GGGCUCCC | 4019 | GGGAGCCC AGAA GAGUGC ACCAGAGAAACACACGUUGUGGUACAUUACCUGGUA | 8161 |
| 3796 | UGAAGCU GUU CACCUGGA | 4020 | UCCAGGUG AGAA GCUUCA ACCAGAGAAACACACGUUGUGGUACAUUACCUGGUA | 8162 |
| 3881 | ACUUUCC GAU CUGCCGAG | 4021 | CUCGGCAG AGAA GAAAGU ACCAGAGAAACACACGUUGUGGUACAUUACCUGGUA | 8163 |

TABLE IX-continued

Mouse flt1 VEGF Receptor-Hairpin Ribozyme and Substrate Sequence

| Pos | Substrate | Seq ID No | HP Ribozyme | Seq ID No |
|---|---|---|---|---|
| 3886 | CCGAUCU GCC GAGGCCCA | 4022 | UGGGCCUC AGAA GAUCGG ACCAGAGAAACACACGUUGUGGUACAUUACCUGGUA | 8164 |
| 3897 | AGGCCCA GCU UCUGCUUC | 4023 | GAAGCAGA AGAA GGGCCU ACCAGAGAAACACACGUUGUGGUACAUUACCUGGUA | 8165 |
| 3903 | AGCUUCU GCU UCUCCAGC | 4024 | GCUGGAGA AGAA GAAGCU ACCAGAGAAACACACGUUGUGGUACAUUACCUGGUA | 8166 |
| 3912 | UUCUCCA GCU GUGGCCAC | 4025 | GUGGCCAC AGAA GGAGAA ACCAGAGAAACACACGUUGUGGUACAUUACCUGGUA | 8167 |
| 3969 | GAGUCCU GCU GUUCUCCA | 4026 | UGGAGAAC AGAA GGACUC ACCAGAGAAACACACGUUGUGGUACAUUACCUGGUA | 8168 |
| 3972 | UCCUGCU GUU CUCCACCC | 4027 | GGGUGGAG AGAA GCAGGA ACCAGAGAAACACACGUUGUGGUACAUUACCUGGUA | 8169 |
| 3986 | ACCCCCA GAC UACAACUC | 4028 | GAGUUGUA AGAA GGGGGU ACCAGAGAAACACACGUUGUGGUACAUUACCUGGUA | 8170 |
| 4018 | CCUCCCC GCC CGCCUAAA | 4029 | UUUAGGCG AGAA GGGAGG ACCAGAGAAACACACGUUGUGGUACAUUACCUGGUA | 8171 |
| 4022 | CCCGCCC GCC UAAAGCUU | 4030 | AAGCUUUA AGAA GGCGGG ACCAGAGAAACACACGUUGUGGUACAUUACCUGGUA | 8172 |
| 4040 | CUCACCA GCC CCGACAAC | 4031 | GUUGUCGG AGAA GGUGAG ACCAGAGAAACACACGUUGUGGUACAUUACCUGGUA | 8173 |
| 4053 | ACAACCA GCC CCUGACAG | 4032 | CUGUCAGG AGAA GGUUGU ACCAGAGAAACACACGUUGUGGUACAUUACCUGGUA | 8174 |
| 4095 | CUAUUCC GCU CCACAGGA | 4033 | UCCUGUGG AGAA GGAAUAG ACCAGAGAAACACACGUUGUGGUACAUUACCUGGUA | 8175 |
| 4110 | GGAGCCA GCU GCUUUCG | 4034 | CGAAAAGC AGAA GGCUCC ACCAGAGAAACACACGUUGUGGUACAUUACCUGGUA | 8176 |
| 4113 | GCCAGCU GCU UUUCGUGA | 4035 | UCACGAAA AGAA GCUGGC ACCAGAGAAACACACGUUGUGGUACAUUACCUGGUA | 8177 |
| 4168 | UGUUGCU GCU UUGACUAA | 4036 | UUAGUCAA AGAA GCAACA ACCAGAGAAACACACGUUGUGGUACAUUACCUGGUA | 8178 |
| 4290 | GGCGACC GCC CGCCCACC | 4037 | GGUGGGCG AGAA GUCGCC ACCAGAGAAACACACGUUGUGGUACAUUACCUGGUA | 8179 |
| 4294 | ACCGCCC GCC CACCGGCC | 4038 | GGCCGGUG AGAA GGCGGU ACCAGAGAAACACACGUUGUGGUACAUUACCUGGUA | 8180 |
| 4329 | CCCUGCA GCU GUGGGACU | 4039 | AGUCCCAC AGAA GCAGGG ACCAGAGAAACACACGUUGUGGUACAUUACCUGGUA | 8181 |
| 4378 | AUGCACU GAC CUGCUCUG | 4040 | CAGAGCAG AGAA GUGCAU ACCAGAGAAACACACGUUGUGGUACAUUACCUGGUA | 8182 |
| 4383 | CUGACCU GCU CUGUCUCU | 4041 | AGAGACAG AGAA GGUCAG ACCAGAGAAACACACGUUGUGGUACAUUACCUGGUA | 8183 |
| 4388 | CUGCUCU GUC UCUCUUAU | 4042 | AUAAGAGA AGAA GAGCAG ACCAGAGAAACACACGUUGUGGUACAUUACCUGGUA | 8184 |
| 4457 | UGCGUCC GUC CUGUGGAG | 4043 | CUCCACAG AGAA GACGCA ACCAGAGAAACACACGUUGUGGUACAUUACCUGGUA | 8185 |
| 4525 | GGCCUCC GCU GUUUCGGG | 4044 | CCCGAAAC AGAA GAGGCC ACCAGAGAAACACACGUUGUGGUACAUUACCUGGUA | 8186 |
| 4528 | CUCCGCU GCU UCGGGCCC | 4045 | GGGCCCGA AGAA GCGGAG ACCAGAGAAACACACGUUGUGGUACAUUACCUGGUA | 8187 |
| 4643 | GUCUUCU GUU GUCUGUUU | 4046 | AAACAGAC AGAA GAAGAC ACCAGAGAAACACACGUUGUGGUACAUUACCUGGUA | 8188 |
| 4650 | GUUGUCU GUU UACCAUCC | 4047 | GGAUGGUA AGAA GACAAC ACCAGAGAAACACACGUUGUGGUACAUUACCUGGUA | 8189 |
| 4724 | AUCAUCA GUU CCUCUAGU | 4048 | ACUAGAGG AGAA GAUGAU ACCAGAGAAACACACGUUGUGGUACAUUACCUGGUA | 8190 |
| 4771 | CAGGCCU GAC CUUCGCAU | 4049 | AUGCGAAG AGAA GGCCUG ACCAGAGAAACACACGUUGUGGUACAUUACCUGGUA | 8191 |
| 4785 | GCAUACU GCU CACGGGGA | 4050 | UCCCCGUG AGAA GUAUGC ACCAGAGAAACACACGUUGUGGUACAUUACCUGGUA | 8192 |
| 4809 | UGGUCCA GUU UGGCCUAG | 4051 | CUAGGCCA AGAA GGACCA ACCAGAGAAACACACGUUGUGGUACAUUACCUGGUA | 8193 |
| 4834 | GCCUACU GAU GGGCUCAA | 4052 | UUGAGCCC AGAA GUAGGC ACCAGAGAAACACACGUUGUGGUACAUUACCUGGUA | 8194 |
| 4912 | UUAUCCU GUU UUAUAUAU | 4053 | AUAUAUAA AGAA GGAUAA ACCAGAGAAACACACGUUGUGGUACAUUACCUGGUA | 8195 |
| 5119 | CAAGGCA GUC UGAGAGGA | 4054 | UCCUCUCA AGAA GCCUUG ACCAGAGAAACACACGUUGUGGUACAUUACCUGGUA | 8196 |
| 5144 | AGUAUCA GCC CAUAUUUA | 4055 | UAAAUAUG AGAA GAUACU ACCAGAGAAACACACGUUGUGGUACAUUACCUGGUA | 8197 |
| 5287 | UUCAUCU GUU UCAUACCU | 4056 | AGGUAUGA AGAA GAUGAA ACCAGAGAAACACACGUUGUGGUACAUUACCUGGUA | 8198 |
| 5363 | GGUGCCC GCU CUUUGGGG | 4057 | CCCCAAAG AGAA GGCACC ACCAGAGAAACACACGUUGUGGUACAUUACCUGGUA | 8199 |
| 5462 | CACACCU GCC GGAGCCGG | 4058 | CCGGCUCC AGAA GGUGUG ACCAGAGAAACACACGUUGUGGUACAUUACCUGGUA | 8200 |
| 5478 | GGUCACA GCU GGGCAGAC | 4059 | GUCUGCCC AGAA GUGACC ACCAGAGAAACACACGUUGUGGUACAUUACCUGGUA | 8201 |
| 5486 | CUGGGCA GAC GAUGAAUA | 4060 | UAUUCAUC AGAA GCCCAG ACCAGAGAAACACACGUUGUGGUACAUUACCUGGUA | 8202 |
| 5500 | AAUAGCU GCU UUGGGAGA | 4061 | UCUCCCAA AGAA GCUAUU ACCAGAGAAACACACGUUGUGGUACAUUACCUGGUA | 8203 |
| 5539 | AUUCUCU GCU CGGGCCAG | 4062 | CUGGCCCG AGAA GAGAAU ACCAGAGAAACACACGUUGUGGUACAUUACCUGGUA | 8204 |
| 5564 | GGUACCU GCU CCCCUGUG | 4063 | CACAGGGG AGAA GGUACC ACCAGAGAAACACACGUUGUGGUACAUUACCUGGUA | 8205 |
| 5597 | GUUUUCU GUC UGAUGAGA | 4064 | UCUCAUCA AGAA GAAAAC ACCAGAGAAACACACGUUGUGGUACAUUACCUGGUA | 8206 |
| 5601 | UCUGUCU GAU GAGACUGG | 4065 | CCAGUCUC AGAA GACAGA ACCAGAGAAACACACGUUGUGGUACAUUACCUGGUA | 8207 |
| 5639 | UGAGACA GCC UGCAGCCC | 4066 | GGGCUGCA AGAA GUCUCA ACCAGAGAAACACACGUUGUGGUACAUUACCUGGUA | 8208 |
| 5646 | GCCUGCA GCC CACUGUGG | 4067 | CCACAGUG AGAA GCAGGC ACCAGAGAAACACACGUUGUGGUACAUUACCUGGUA | 8209 |
| 5781 | CUUGUCG GCU GCAGUGUG | 4068 | CACACUGC AGAA GACAAG ACCAGAGAAACACACGUUGUGGUACAUUACCUGGUA | 8210 |
| 5829 | AGAAACG GAU GAGAACAG | 4069 | CUGUUCUC AGAA GUUUCU ACCAGAGAAACACACGUUGUGGUACAUUACCUGGUA | 8211 |
| 5842 | AACAGCA GCC UGAGGUUU | 4070 | AAACCUCA AGAA GCUGUU ACCAGAGAAACACACGUUGUGGUACAUUACCUGGUA | 8212 |
| 5915 | UUAUUCC GAU UUUAAUAA | 4071 | UUAUUAAA AGAA GGAAUAA ACCAGAGAAACACACGUUGUGGUACAUUACCUGGUA | 8213 |
| 6010 | UGGUUCU GCU UAAAGACU | 4072 | AGUCUUUA AGAA GAACCA ACCAGAGAAACACACGUUGUGGUACAUUACCUGGUA | 8214 |

TABLE X

Homologous Hammerhead Ribozyme Target Sites Between Human flt-1 and KDR RNA

| nt. Position | flt-1 Target Sequence | Seq ID No | nt. Position | KDR Target Sequence | Seq ID No |
|---|---|---|---|---|---|
| 3388 | CCGGGAU A UUUAUAA | 4073 | 3151 | CCGGGAUAUUUAUAA | 4073 |
| 2174 | AAUGUAU A CACAGGG | 4074 | 3069 | AgUGUAUcCACAGGG | 4116 |
| 2990 | UGCAAAU A UGGAAAU | 4075 | 2756 | UGCAAAUuUGGAAAc | 4117 |
| 2693 | CUCCCUU A UGAUGCC | 4076 | 2459 | CUgCCUUAUGAUGCC | 4118 |
| 2981 | GUUGAAU A CUGCAAA | 4077 | 2747 | GUgGAAUuCUGCAAA | 4119 |
| 1359 | UAUGGUU A AAAGAUG | 4078 | 2097 | UgUGGUUuAAAGAUa | 4120 |
| 3390 | GGGAUAU U UAUAAGA | 4079 | 3153 | GGGAUUUUAUAAag | 4121 |
| 3391 | GGAUAUU U AUAAGAA | 4080 | 3154 | GGAUAUUUAUAAagA | 4122 |
| 2925 | ACGUGGU U AACCUGC | 4081 | 2691 | AuGUGGUcAACCUuC | 4123 |
| 7140 | UAUUUCU A GUCAUGA | 4082 | 2340 | UAcUUCUuGUCAUcA | 4124 |
| 1785 | CAAUAAU A GAAGGAA | 4083 | 1515 | CucUAAUuGAAGGAA | 4125 |
| 2731 | GAGACUU A AACUGGG | 4084 | 768 | uuGACUUcAACUGGG | 4126 |

TABLE X-continued

Homologous Hammerhead Ribozyme Target Sites Between Human flt-1 and KDR RNA

| nt. Position | flt-1 Target Sequence | Seq ID No | nt. Position | KDR Target Sequence | Seq ID No |
|---|---|---|---|---|---|
| 3974 | GAUGACU A CCAGGGC | 4085 | 1466 | GAgGACUuCCAGGGa | 4127 |
| 6590 | UUAAUGU A GAAAGAA | 4086 | 2603 | aaAAUGUuGAAAGAA | 4128 |
| 6705 | GCCAUUU A UGACAAA | 4087 | 3227 | aCaAUUUuUGACAgA | 4129 |
| 974 | GUCAAAU U ACUUAGA | 4088 | 147 | uUCAAAUUACUUgcA | 4130 |
| 1872 | AUAAAGU U GGGACUG | 4089 | 1602 | AcAAAGUcGGGAgaG | 4131 |
| 2333 | ACUUGGU U UAAAAAC | 4090 | 1088 | AaaUGGUaUAAAAAu | 4132 |
| 2775 | AAGUGGU U CAAGCAU | 4091 | 1745 | AcaUGGUaCAAGCuU | 4133 |
| 3533 | UUCUCCU U AGGUGGG | 4092 | 3296 | UUuUCCUUAGGUGcu | 4134 |
| 3534 | UCUCCUU A GGUGGGU | 4093 | 3297 | UUUCCUUAGGUGcuU | 4135 |
| 3625 | GUACUCU A CUCCUGA | 4094 | 4054 | GagCUCUcCUCCUGu | 4136 |
| 1814 | AGCACCU U GGUUGUG | 4095 | 1059 | AGuACCUUGGUUacc | 4137 |
| 2744 | GGCAAAU C ACUUGGA | 4096 | 147 | uuCAAAUuACUUGcA | 4130 |
| 2783 | CAAGCAU C AGCAUUU | 4097 | 796 | gAAGCAUCAGCAUaa | 4138 |
| 3613 | GAGAGCU C CUGAGUA | 4098 | 2968 | GgaAGCUCCUGAagA | 4139 |
| 4052 | AAGGCCU C GCUCAAG | 4099 | 1923 | ucuGCCUuGCUCAAG | 4140 |
| 5305 | UCUCCAU A UCAAAAC | 4100 | 456 | ggUCCAUuUCAAAuC | 4141 |
| 7158 | AUGUAUU U UGUAUAC | 4101 | 631 | gUcUAUUaUGUAcAu | 4142 |
| 1836 | CUAGAAU U UCUGGAA | 4102 | 1007 | aUgGAAUcUCUGGug | 4143 |
| 2565 | CUCUCUU C UGGCUCC | 4103 | 2328 | uguUCUUCUGGCUaC | 4144 |
| 4250 | CUGUACU C CACCCCA | 4104 | 3388 | uUaUACUaCACCagA | 4145 |
| 7124 | ACAUGGU U UGGUCCU | 4105 | 3778 | cagUGGUaUGGUuCU | 4146 |
| 436 | AUGGUCU U UGCCUGA | 4106 | 1337 | AcGGUCUaUGCCauu | 4147 |
| 2234 | GCACCAU A CCUCCUG | 4107 | 1344 | augCCAUuCCUCCcc | 4148 |
| 2763 | GGGCUUU U GGAAAAG | 4108 | 990 | uuGCUUUUGGAAguG | 4149 |
| 4229 | CCAGACU A CAACUCG | 4109 | 767 | auuGACUuCAACUgG | 4150 |
| 5301 | GUUUUCU C CAUAUCA | 4110 | 3307 | ugcUUCUCCAUAUCc | 4151 |
| 6015 | AGAAUGU A UGCCUCU | 4111 | 1917 | AcuAUGUcUGCCUug | 4152 |
| 6095 | AUUCCCU A GUGAGCC | 4112 | 1438 | AUaCCCUuGUGAaga | 4153 |
| 6236 | UGUUGUU C CUCUUCU | 4113 | 76 | UagUGUUcCUCUUga | 4154 |
| 5962 | GCUUCCU U UUAUCCA | 4114 | 3099 | auaUCCUcUUAUCgg | 4155 |
| 7629 | UAUAUAU U CUCUGCU | 4115 | 3096 | gAaAUAUcCUCUuaU | 4156 |

Lowercase letters are used to represent sequence variance between flt-1 and KDR RNA

SEQUENCE LISTING

The patent contains a lengthy "Sequence Listing" section. A copy of the "Sequence Listing" is available in electronic form from the USPTO web site (http://seqdata.uspto.gov/sequence.html?DocID=5732822B9). An electronic copy of the "Sequence Listing" will also be available from the USPTO upon request and payment of the fee set forth in 37 CFR 1.19(b)(3).

What is claimed is:

1. An enzymatic nucleic acid molecule, comprising a sequence complementary to any of the substrate sequences identified as SEQ ID NO:1597, 1641, 1892, 2086, or 2119.

2. The enzymatic nucleic acid molecule of claim 1, wherein said enzymatic nucleic acid molecule is a ribozyme.

3. The enzymatic nucleic acid molecule of claim 2, wherein said enzymatic nucleic acid molecule is in a hammerhead motif.

4. The enzymatic nucleic acid molecule of claim 2, wherein said enzymatic nucleic acid molecule is in a hairpin, hepatitis Delta virus, group I intron, VS nucleic acid or RNase P nucleic acid motif.

5. The enzymatic nucleic acid molecule of claim 1, wherein said enzymatic nucleic acid molecule comprises between 12 and 100 bases complementary to the RNA of KDR receptor.

6. The enzymatic nucleic acid molecule of claim 5, wherein said enzymatic nucleic acid molecule comprises between 14 and 24 bases complementary to the RNA of KDR receptor.

7. A mammalian cell comprising the enzymatic nucleic acid molecule of claim 1, wherein said mammalian cell is not a living human.

8. The mammalian cell of claim 7, wherein said mammalian cell is a human cell.

9. An expression vector comprising nucleic acid sequence encoding one or more of the enzymatic nucleic acid molecules of claim 1.

10. A mammalian cell comprising an expression vector of claim 9, wherein said mammalian cell is not a living human.

11. The mammalian cell of claim 10, wherein said mammalian cell is a human cell.

12. An enzymatic nucleic acid molecule comprising any ribozyme sequence identified as SEQ ID NO:5753, 5797, 6048, 6242, or 6275.

* * * * *